US012768841B2

(12) United States Patent
Reed et al.

(10) Patent No.: US 12,768,841 B2
(45) Date of Patent: Oct. 20, 2026

(54) COMPOSITIONS AND METHODS FOR POLYPEPTIDE ANALYSIS

(71) Applicant: Quantum-Si Incorporated, Guilford, CT (US)

(72) Inventors: Brian Reed, Madison, CT (US); Manjula Pandey, Guilford, CT (US); David Kamber, Guilford, CT (US); Kenneth Skinner, Cambridge, MA (US)

(73) Assignee: Quantum-Si Incorporated, Branford, CT (US)

( * ) Notice: Subject to any disclaimer, the term of this patent is extended or adjusted under 35 U.S.C. 154(b) by 752 days.

(21) Appl. No.: 18/145,815

(22) Filed: Dec. 22, 2022

(65) Prior Publication Data

US 2023/0213527 A1 Jul. 6, 2023

Related U.S. Application Data

(60) Provisional application No. 63/395,325, filed on Aug. 4, 2022, provisional application No. 63/293,054, filed on Dec. 22, 2021.

(51) Int. Cl.
*G01N 33/68* (2006.01)

(52) U.S. Cl.
CPC ..... *G01N 33/6818* (2013.01); *G01N 33/6893* (2013.01); *G01N 2440/10* (2013.01);
(Continued)

(58) Field of Classification Search
CPC ........... G01N 2440/10; G01N 2440/12; G01N 2440/14; G01N 2440/18; G01N 2800/102;
(Continued)

(56) References Cited

U.S. PATENT DOCUMENTS

| | | | |
|---|---|---|---|
| 4,548,904 | A | 10/1985 | Kent et al. |
| 5,591,646 | A | 1/1997 | Hudson et al. |

(Continued)

FOREIGN PATENT DOCUMENTS

| | | | |
|---|---|---|---|
| AU | 2003282832 | A1 | 5/2004 |
| AU | 2009251881 | A1 | 12/2009 |

(Continued)

OTHER PUBLICATIONS

Invitation to Pay Additional Fees for Application No. PCT/US2022/082302, mailed Mar. 30, 2023.

(Continued)

*Primary Examiner* — Jennifer Wecker
(74) *Attorney, Agent, or Firm* — Wolf, Greenfield & Sacks, P.C.

(57) ABSTRACT

Aspects of the application relate to methods and systems for obtaining information regarding multiple amino acids in a polypeptide based on binding interactions between the polypeptide and one or more amino acid recognizers. Kinetic signature information may be obtained from a series of signal pulses indicative of a series of binding events between one or more amino acid recognizers and an amino acid of a polypeptide (e.g., a terminal amino acid, an internal amino acid). The kinetic signature information (e.g., pulse duration, interpulse duration, recognition segment (RS) duration, intersegment duration) may be used to determine one or more chemical characteristics (e.g., identity, modification) of multiple amino acids of the polypeptide.

18 Claims, 59 Drawing Sheets
(49 of 59 Drawing Sheet(s) Filed in Color)

Specification includes a Sequence Listing.

(52) U.S. Cl.
CPC ..... *G01N 2440/12* (2013.01); *G01N 2440/14* (2013.01); *G01N 2440/18* (2013.01); *G01N 2800/102* (2013.01); *G01N 2800/2821* (2013.01); *G01N 2800/32* (2013.01)

(58) Field of Classification Search
CPC ....... G01N 2800/2821; G01N 2800/32; G01N 33/574; G01N 33/6818; G01N 33/6893
See application file for complete search history.

(56) References Cited

U.S. PATENT DOCUMENTS

| | | | |
|---|---|---|---|
| 5,707,804 | A | 1/1998 | Mathies et al. |
| 5,851,840 | A | 12/1998 | Sluka et al. |
| 6,153,442 | A | 11/2000 | Pirio et al. |
| 6,248,518 | B1 | 6/2001 | Parkhurst et al. |
| 6,255,083 | B1 | 7/2001 | Williams |
| 6,762,048 | B2 | 7/2004 | Williams |
| 6,787,308 | B2 | 9/2004 | Balasubramanian et al. |
| 6,846,638 | B2 | 1/2005 | Shipwash |
| 6,869,764 | B2 | 3/2005 | Williams et al. |
| 6,936,702 | B2 | 8/2005 | Williams et al. |
| 7,052,847 | B2 | 5/2006 | Korlach et al. |
| 7,056,661 | B2 | 6/2006 | Korlach et al. |
| 7,229,799 | B2 | 6/2007 | Williams |
| 7,361,466 | B2 | 4/2008 | Korlach et al. |
| 7,968,702 | B2 | 6/2011 | Wegener et al. |
| 8,034,623 | B2 | 10/2011 | Oh et al. |
| 8,084,734 | B2 | 12/2011 | Vertes et al. |
| 8,153,375 | B2 | 4/2012 | Travers et al. |
| 8,192,961 | B2 | 6/2012 | Williams |
| 8,252,910 | B2 | 8/2012 | Korlach et al. |
| 8,257,954 | B2 | 9/2012 | Clark et al. |
| 8,309,330 | B2 | 11/2012 | Travers et al. |
| 8,354,252 | B2 | 1/2013 | Wegener et al. |
| 8,420,366 | B2 | 4/2013 | Clark et al. |
| 8,455,193 | B2 | 6/2013 | Travers et al. |
| 8,530,154 | B2 | 9/2013 | Williams |
| 8,581,179 | B2 | 11/2013 | Franzen |
| 8,586,006 | B2 | 11/2013 | Hood |
| 8,846,881 | B2 | 9/2014 | Korlach et al. |
| 8,906,614 | B2 | 12/2014 | Wegener et al. |
| 8,927,212 | B2 | 1/2015 | Kong et al. |
| 8,980,584 | B2 | 3/2015 | Williams |
| 9,062,091 | B2 | 6/2015 | Bjornson et al. |
| 9,238,822 | B2 | 1/2016 | Baum et al. |
| 9,404,146 | B2 | 8/2016 | Travers et al. |
| 9,435,810 | B2 | 9/2016 | Havranek et al. |
| 9,464,107 | B2 | 10/2016 | Wegener et al. |
| 9,542,527 | B2 | 1/2017 | Travers et al. |
| 9,551,031 | B2 | 1/2017 | Korlach et al. |
| 9,551,660 | B2 | 1/2017 | Kong et al. |
| 9,566,335 | B1 | 2/2017 | Emili et al. |
| 9,582,640 | B2 | 2/2017 | Travers et al. |
| 9,600,626 | B2 | 3/2017 | Travers et al. |
| 9,625,469 | B2 | 4/2017 | Marcotte et al. |
| 9,678,080 | B2 | 6/2017 | Bjornson et al. |
| 9,719,073 | B2 | 8/2017 | Emig et al. |
| 9,759,658 | B2 | 9/2017 | Rothberg et al. |
| 9,845,501 | B2 | 12/2017 | Williams |
| 9,879,319 | B2 | 1/2018 | Korlach et al. |
| 9,885,657 | B2 | 2/2018 | Rothberg et al. |
| 9,910,956 | B2 | 3/2018 | Travers et al. |
| 9,957,291 | B2 | 5/2018 | Sebo et al. |
| 10,023,605 | B2 | 7/2018 | Bjornson et al. |
| 10,048,208 | B2 | 8/2018 | Rothberg et al. |
| 10,066,258 | B2 | 9/2018 | Kong et al. |
| 10,138,291 | B2 | 11/2018 | Chhabra et al. |
| 10,150,872 | B2 | 12/2018 | Zheng et al. |
| 10,161,002 | B2 | 12/2018 | Korlach et al. |
| 10,246,742 | B2 | 4/2019 | Rothberg et al. |
| 10,481,162 | B2 | 11/2019 | Emili et al. |
| 10,544,449 | B2 | 1/2020 | Shen et al. |
| 10,545,153 | B2 | 1/2020 | Marcotte et al. |
| 10,551,624 | B2 | 2/2020 | Rothberg et al. |
| 10,570,445 | B2 | 2/2020 | Kong et al. |
| 10,676,788 | B2 | 6/2020 | Shen et al. |
| 10,745,750 | B2 | 8/2020 | Korlach et al. |
| 10,787,573 | B2 | 9/2020 | Zheng et al. |
| 10,845,308 | B2 | 11/2020 | Rothberg et al. |
| 11,162,952 | B2 | 11/2021 | Marcotte et al. |
| 11,237,326 | B2 | 2/2022 | Rothberg et al. |
| 11,268,963 | B2 | 3/2022 | Emili |
| 11,573,238 | B2 | 2/2023 | Callewaert et al. |
| 11,802,878 | B2 | 10/2023 | Emili et al. |
| 11,959,920 | B2 | 4/2024 | Reed et al. |
| 12,000,835 | B2 | 6/2024 | Reed et al. |
| 12,019,076 | B2 | 6/2024 | Callewaert et al. |
| 12,055,548 | B2 | 8/2024 | Reed et al. |
| 12,065,466 | B2 | 8/2024 | Reed et al. |
| 12,174,196 | B2 | 12/2024 | Reed et al. |
| 12,259,391 | B2 | 3/2025 | Reed et al. |
| 12,360,114 | B2 | 7/2025 | Reed et al. |
| 12,422,438 | B2 | 9/2025 | Callewaert et al. |
| 12,618,845 | B2 | 5/2026 | Reed et al. |
| 2004/0175822 | A1 | 9/2004 | Timperman |
| 2005/0042633 | A1 | 2/2005 | Williams |
| 2005/0266456 | A1 | 12/2005 | Williams et al. |
| 2006/0014212 | A1 | 1/2006 | Benkovic et al. |
| 2007/0072196 | A1 | 3/2007 | Xu et al. |
| 2007/0219367 | A1 | 9/2007 | Shchepinov et al. |
| 2007/0231925 | A1 | 10/2007 | Chhabra et al. |
| 2008/0085840 | A1 | 4/2008 | Buzby |
| 2008/0299565 | A1 | 12/2008 | Schneider et al. |
| 2009/0028832 | A1 | 1/2009 | Chung et al. |
| 2009/0061447 | A1 | 3/2009 | Schneider et al. |
| 2009/0105341 | A1 | 4/2009 | Stanton |
| 2009/0263802 | A1 | 10/2009 | Drmanac |
| 2010/0009872 | A1 | 1/2010 | Eid et al. |
| 2010/0029494 | A1 | 2/2010 | Cherkasov et al. |
| 2010/0035254 | A1 | 2/2010 | Williams |
| 2010/0255518 | A1* | 10/2010 | Goix ................. G01N 15/1459 436/15 |
| 2011/0003343 | A1 | 1/2011 | Nikiforov et al. |
| 2011/0281776 | A1 | 11/2011 | Eshoo et al. |
| 2012/0178676 | A1 | 7/2012 | Barrack et al. |
| 2012/0322692 | A1 | 12/2012 | Pham et al. |
| 2013/0316912 | A1 | 11/2013 | Bjornson et al. |
| 2015/0087526 | A1 | 3/2015 | Hesselberth |
| 2017/0037462 | A1 | 2/2017 | Turner et al. |
| 2017/0052194 | A1 | 2/2017 | Havranek et al. |
| 2017/0136433 | A1 | 5/2017 | Sun et al. |
| 2017/0204401 | A1 | 7/2017 | Brevnova et al. |
| 2017/0212126 | A1 | 7/2017 | Emili et al. |
| 2017/0336419 | A1 | 11/2017 | Tran et al. |
| 2017/0356921 | A1* | 12/2017 | Van Roosmalen .... C07K 16/18 |
| 2018/0172906 | A1 | 6/2018 | Rothberg et al. |
| 2018/0211003 | A1 | 7/2018 | Travers et al. |
| 2018/0299460 | A1 | 10/2018 | Emili |
| 2018/0326412 | A1 | 11/2018 | Rothberg et al. |
| 2018/0346507 | A1 | 12/2018 | Sebo et al. |
| 2018/0372752 | A1 | 12/2018 | Emili et al. |
| 2019/0010183 | A1 | 1/2019 | Bjornson et al. |
| 2019/0024168 | A1 | 1/2019 | Rothberg et al. |
| 2019/0025511 | A1 | 1/2019 | Rothberg et al. |
| 2019/0234966 | A1 | 8/2019 | Steen et al. |
| 2019/0249153 | A1 | 8/2019 | Kamtekar et al. |
| 2020/0141944 | A1 | 5/2020 | Emili et al. |
| 2020/0148727 | A1 | 5/2020 | Tullman et al. |
| 2020/0209249 | A1 | 7/2020 | Reed et al. |
| 2020/0209253 | A1 | 7/2020 | Reed et al. |
| 2020/0209254 | A1 | 7/2020 | Reed et al. |
| 2020/0209255 | A1 | 7/2020 | Reed et al. |
| 2020/0209256 | A1 | 7/2020 | Reed et al. |
| 2020/0209257 | A1* | 7/2020 | Reed ...................... C07K 19/00 |
| 2020/0217853 | A1 | 7/2020 | Estandian et al. |
| 2020/0219590 | A1 | 7/2020 | Reed et al. |
| 2020/0231956 | A1 | 7/2020 | Callewaert et al. |
| 2020/0395099 | A1 | 12/2020 | Meyer et al. |
| 2020/0400677 | A1 | 12/2020 | Boyden et al. |
| 2021/0071162 | A1 | 3/2021 | Franzetti et al. |
| 2021/0139973 | A1 | 5/2021 | Dyer et al. |
| 2021/0148921 | A1 | 5/2021 | Reed et al. |
| 2021/0148922 | A1 | 5/2021 | Dyer et al. |

(56) References Cited

U.S. PATENT DOCUMENTS

| | | | |
|---|---|---|---|
| 2021/0364527 | A1 | 11/2021 | Reed et al. |
| 2021/0396762 | A1 | 12/2021 | Chee et al. |
| 2022/0186297 | A1 | 6/2022 | Reed et al. |
| 2022/0214354 | A1 | 7/2022 | Callewaert et al. |
| 2022/0227889 | A1 | 7/2022 | Gunderson et al. |
| 2022/0291226 | A1 | 9/2022 | Boyden et al. |
| 2023/0016396 | A1 | 1/2023 | Gunderson et al. |
| 2023/0021352 | A1 | 1/2023 | Callewaert et al. |
| 2023/0032607 | A1 | 2/2023 | Feng et al. |
| 2023/0054691 | A1 | 2/2023 | Chee et al. |
| 2023/0076975 | A1 | 3/2023 | Anslyn et al. |
| 2023/0104998 | A1 | 4/2023 | Estandian et al. |
| 2023/0221329 | A1 | 7/2023 | Callewaert et al. |
| 2024/0192221 | A1 | 6/2024 | Emili et al. |
| 2024/0272169 | A1 | 8/2024 | Reed et al. |
| 2024/0272170 | A1 | 8/2024 | Reed et al. |
| 2024/0295562 | A1 | 9/2024 | Reed et al. |
| 2024/0302380 | A1 | 9/2024 | Marcotte et al. |
| 2024/0337661 | A1 | 10/2024 | Estandian et al. |
| 2024/0344122 | A1 | 10/2024 | Dyer et al. |
| 2024/0409995 | A1 | 12/2024 | Estandian et al. |
| 2025/0130238 | A1 | 4/2025 | Reed et al. |
| 2025/0147035 | A1 | 5/2025 | Reed |
| 2025/0179123 | A1 | 6/2025 | Reed et al. |
| 2025/0283886 | A1 | 9/2025 | Reed et al. |
| 2025/0314657 | A1 | 10/2025 | Reed et al. |
| 2025/0369978 | A1 | 12/2025 | Pandey et al. |
| 2026/0016481 | A1 | 1/2026 | Reed |

FOREIGN PATENT DOCUMENTS

| | | | |
|---|---|---|---|
| AU | 2013226090 | A1 | 9/2014 |
| AU | 2014296288 | A1 | 2/2016 |
| EP | 3008094 | A1 | 4/2016 |
| JP | 2007-319063 | A | 12/2007 |
| JP | 2019-531715 | A | 11/2019 |
| KR | 101778174 | B1 | 9/2017 |
| WO | WO 2005/044836 | A2 | 5/2005 |
| WO | WO 2007/070572 | A2 | 6/2007 |
| WO | WO 2007/120805 | A2 | 10/2007 |
| WO | WO 2008/045148 | A2 | 4/2008 |
| WO | WO 2010/065322 | A1 | 6/2010 |
| WO | WO 2010/115016 | A2 | 10/2010 |
| WO | WO 2013/130683 | A2 | 9/2013 |
| WO | WO 2015/017529 | A3 | 2/2015 |
| WO | WO 2016/069124 | A1 | 5/2016 |
| WO | WO 2016/164530 | A1 | 10/2016 |
| WO | WO 2017/024049 | A1 | 2/2017 |
| WO | WO 2017/063093 | A1 | 4/2017 |
| WO | WO 2017/192633 | A1 | 11/2017 |
| WO | WO 2018/045186 | A1 | 3/2018 |
| WO | WO 2019/040825 | A1 | 2/2019 |
| WO | WO 2019/063827 | A1 | 4/2019 |
| WO | WO 2020/102741 | A1 | 5/2020 |
| WO | WO 2020/201350 | A1 | 10/2020 |
| WO | WO 2021/236983 | A2 | 11/2021 |
| WO | WO 2022/125973 | A1 | 6/2022 |
| WO | WO 2023/122769 | A2 | 6/2023 |
| WO | WO 2024/031031 | A2 | 2/2024 |
| WO | WO 2024/086832 | A1 | 4/2024 |
| WO | WO 2025/101639 | A3 | 5/2025 |
| WO | WO 2025/147658 | A1 | 7/2025 |

OTHER PUBLICATIONS

International Search Report and Written Opinion for Application No. PCT/US2022/082302, mailed Jun. 23, 2023.

Choi et al., Structural basis for the recognition of N-end rule substrates by the UBR box of ubiquitin ligases. Nat Struct Mol Biol. Oct. 2010;17(10):1175-81. doi: 10.1038/nsmb.1907. Epub Sep. 12, 2010.

Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.

Munoz-Escobar et al., Bound Waters Mediate Binding of Diverse Substrates to a Ubiquitin Ligase. Structure. May 2, 2017;25(5):719-729.e3. doi: 10.1016/j.str.2017.03.004. Epub Apr. 6, 2017.

Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.

Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.

Stein et al., Structural Basis of an N-Degron Adaptor with More Stringent Specificity. Structure. Feb. 2, 2016;24(2):232-42. doi: 10.1016/j.str.2015.12.008. Epub Jan. 21, 2016.

Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.

Swaminathan et al., A theoretical justification for single molecule peptide sequencing. PLoS Comput Biol. Feb. 25, 2015;11(2):e1004080. doi: 10.1371/journal.pcbi.1004080.

Tullman et al., Engineering ClpS for selective and enhanced N-terminal amino acid binding. Appl Microbiol Biotechnol. Mar. 2019;103(6):2621-2633. doi: 10.1007/s00253-019-09624-2. Epub Jan. 24, 2019.

Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.

Extended European Search Report for Application No. EP 22912756.8, dated Dec. 8, 2025.

International Preliminary Report on Patentability for Application No. PCT/US2022/082302, mailed Jul. 4, 2024.

[No Author Listed], aminopeptidase [Thermus aquaticus]. NCBI Reference Sequence: WP_053768123.1. GenBank. Jun. 8, 2016. https://www.ncbi.nlm.nih.gov/protein/927055022?sat=51&satkey=55916985 (Last accessed Jun. 19, 2023). 1 page.

Aksel et al., High-density and scalable protein arrays for single-molecule proteomics studies. bioRxiv. May 2, 2022:2022-05. 33 pages.

Altschul et al., Basic local alignment search tool. Journal of molecular biology. Oct. 5, 1990;215(3):403-10.

Arima et al., Change in substrate preference of Streptomyces aminopeptidase through modification of the environment around the substrate binding site. Appl Environ Microbiol. Dec. 2006;72(12):7962-7. doi: 10.1128/AEM.01460-06. Epub Oct. 6, 2006.

Astruc et al., Dendrimers designed for functions: from physical, photophysical, and supramolecular properties to applications in sensing, catalysis, molecular electronics, photonics, and nanomedicine. Chem Rev. Apr. 14, 2010;110(4):1857-959. doi: 10.1021/cr900327d.

Borgo et al., Computer-aided design of a catalyst for Edman degradation utilizing substrate-assisted catalysis. Protein Sci. Apr. 2015;24(4):571-579. https://doi.org/10.1002/pro.2633. Epub Dec. 16, 2014.

Boutureira et al., Advances in chemical protein modification. Chem Rev. Mar. 11, 2015;115(5):2174-95. doi: 10.1021/cr500399p. Epub Feb. 20, 2015.

Callahan et al. Strategies for Development of a Next-Generation Protein Sequencing Platform. Trends Biochem Sci. Jan. 2020;45(1):76-89. doi: 10.1016/j.tibs.2019.09.005. Epub Oct. 30, 2019.

Chen et al., Effect of linker for immobilization of glutathione on BSA-assembled controlled pore glass beads. Bulletin of the Korean Chemical Society. 2004;25(9):1366-70.

Chin et al., Addition of p-azido-L-phenylalanine to the genetic code of *Escherichia coli*. J Am Chem Soc. Aug. 7, 2002;124(31):9026-7. doi: 10.1021/ja027007w.

Costa et al., Fusion tags for protein solubility, purification and immunogenicity in *Escherichia coli:* the novel Fh8 system. Front Microbiol. Feb. 19, 2014;5:63. doi: 10.3389/fmicb.2014.00063.

(56) References Cited

OTHER PUBLICATIONS

De Gents et al., Molecular basis for the preferential cleft recognition by dromedary heavy-chain antibodies. Proc Natl Acad Sci U S A. Mar. 21, 2006;103(12):4586-91. doi: 10.1073/pnas.0505379103. Epub Mar. 13, 2006.
Drag et al., Aminopeptidase fingerprints, an integrated approach for identification of good substrates and optimal inhibitors. J Biol Chem. Jan. 29, 2010;285(5):3310-8. doi: 10.1074/jbc.M109.060418. Epub Nov. 30, 2009.
Egertson et al., A theoretical framework for proteome-scale single-molecule protein identification using multi-affinity protein binding reagents. BioRxiv. Oct. 12, 2021:2021-10. 29 pages.
Erbse et al., ClpS is an essential component of the N-end rule pathway in *Escherichia coli*. Nature. Feb. 9, 2006;439(7077):753-6.
Fonovic et al., Proteomics evaluation of chemically cleavable activity-based probes. Molecular & Cellular Proteomics. Oct. 1, 2007;6(10):1761-70.
Garcia-Guerrero et al. Crystal structure and mechanism of human carboxypeptidase O: Insights into its specific activity for acidic residues. PNAS. Apr. 24, 2018;115(17):E3932-E3939. doi: 10.1073/pnas.1803685115. Epub Apr. 10, 2018.
GenPept, Accession No. WP_052275729, Jun. 18, 2019, obtained from <https://www.ncbi.nlm.nih.gov/protein/WP_052275729.1?report=genbank&log$=protalign&blast_rank=1&RID=4G0PWKS0013> [obtained on Jun. 11, 2025].
Gilboa et al., Interactions of Streptomyces griseus aminopeptidase with amino acid reaction products and their implications toward a catalytic mechanism. Proteins. Sep. 1, 2001;44(4):490-504. doi: 10.1002/prot.1115.
Guo et al., Crystal structure of the heterodimeric complex of the adaptor, ClpS, with the N-domain of the AAA+ chaperone, ClpA. Journal of Biological Chemistry. Nov. 29, 2002;277(48):46753-62.
Gurupriya et al., Proteases and Protease Inhibitors in Male Reproduction. In: Proteases in Physiology and Pathology. Chakraborti et al., Eds. 2017:195-216. https://doi.org/10.1007/978- 981-10-2513-6_10.
Hafok-Peters et al., Enzymatic cleavage directly on the probe tip for mass spectrometric identification of peptides. Biomedical & environmental mass spectrometry. Mar. 1990;19(3):159-63.
Hamaguchi et al., Aptamer beacons for the direct detection of proteins. Anal Biochem. Jul. 15, 2001;294(2):126-31. doi: 10.1006/abio.2001.5169.
Harris et al., Single-molecule DNA sequencing of a viral genome. Science. Apr. 4, 2008;320(5872):106-9.
Hawkins et al., Detection, identification, and quantification of oxidative protein modifications. J Biol Chem. Dec. 20, 2019;294(51):19683-19708. doi: 10.1074/jbc.REV119.006217. Epub Oct. 31, 2019.
Henikoff et al., Amino acid substitution matrices from protein blocks. Proceedings of the National Academy of Sciences. Nov. 15, 1992;89(22):10915-9.
Higgins et al., Fast and sensitive multiple sequence alignments on a microcomputer. Bioinformatics. Apr. 1, 1989;5(2):151-3.
Kim, Probing structures of membrane proteins and their inhibitors. 2005 (Doctoral dissertation, University of Oxford), 258 pages.
Kimple et al., Overview of affinity tags for protein purification. Curr Protoc Protein Sci. Sep. 24, 2013;73:9.9.1-9.9.23. doi: 10.1002/0471140864.ps0909s73. Author Manuscript, 26 pages.
Kosobokova et al., Overview of Fusion Tags for Recombinant Proteins. Biochemistry (Mosc). Mar. 2016;81(3):187-200. doi: 10.1134/S0006297916030019.
Minagawa et al., Isolation and characterization of a thermostable aminopeptidase (aminopeptidase T) from Thermus aquaticus YT-1, an extremely thermophilic bacterium. Agricultural and biological chemistry. Jul. 1, 1988;52(7):1755-63.
Needleman et al., A general method applicable to the search for similarities in the amino acid sequence of two proteins. J Mol Biol. Mar. 1970;48(3):443-53. doi: 10.1016/0022-2836(70)90057-4.
Pearson et al., Improved tools for biological sequence comparison. PNAS. Apr. 1, 1988;85(8):2444-8. https://doi.org/10.1073/pnas.85.8.2444.
Ramazi et al., Posttranslational modifications in proteins: resources, tools and prediction methods. Database (Oxford). Apr. 7, 2021;2021:baab012. doi: 10.1093/database/baab012.
Ray et al., Peptide nucleic acid (PNA): its medical and biotechnical applications and promise for the future. The FASEB Journal. Jun. 2000;14(9):1041-60.
Reed et al., Real-time dynamic single-molecule protein sequencing on an integrated semiconductor device, bioRxiv, Jan. 10, 2022, DOI: 10.1101/2022.01.04.475002. Retrieved from the Internet: URL:https://www.biorxiv.org/content/10.1101/2022.01.04.475002v2.full.pdf (37 pages).
Reiland et al., Binding of inhibitory aromatic amino acids to *Streptomyces griseus* aminopeptidase. Acta Crystallogr D Biol Crystallogr. Oct. 2004;60(Pt 10):1738-46. doi: 10.1107/S0907444904018281. Epub Sep. 23, 2004.
Roman-Hernandez et al., Molecular basis of substrate selection by the N-end rule adaptor protein ClpS. Proceedings of the National Academy of Sciences. Jun. 2, 2009;106(22):8888-93.
Roy et al., SPR-Measured Dissociation Kinetics of PROTAC Ternary Complexes Influence Target Degradation Rate. ACS Chem Biol. Mar. 15, 2019;14(3):361-368. doi: 10.1021/acschembio.9b00092. Epub Feb. 22, 2019.
Samyn et al., A case study of de novo sequence analysis of N-sulfonated peptides by MALDI TOF/TOF mass spectrometry. J Am Soc Mass Spectrom. Dec. 2004;15(12):1838-52. doi: 10.1016/j.jasms.2004.08.010.
Schuenemann et al., Structural basis of N-end rule substrate recognition in *Escherichia coli* by the ClpAP adaptor protein ClpS. EMBO reports. May 2009;10(5):508-14.
Slade et al., Chemical and biological methods to detect post-translational modifications of arginine. Biopolymers. Feb. 2014;101(2):133-43. doi: 10.1002/bip.22256.
Smith et al., Comparison of biosequences. Adv Appl Math. Dec. 1981;2(4):482-9. https://doi.org/10.1016/0196-8858(81)90046-4.
Smith et al., The Human Proteoform Project: Defining the human proteome. Sci Adv. Nov. 12, 2021;7(46):eabk0734. doi: 10.1126/sciadv.abk0734. Epub Nov. 12, 2021.
Steinhardt et al., Rational design of a trispecific antibody targeting the HIV-1 Env with elevated anti-viral activity. Nat Commun. Feb. 28, 2018;9(1):877. 12 pages. doi: 10.1038/s41467-018-03335-4.
Swaminathan et al. A theoretical justification for single molecule peptide sequencing. PLoS Comput Biol. Feb. 25, 2015;11(2):e1004080. doi: 10.1371/journal.pcbi.1004080. eCollection Feb. 2015.
Tasaki et al., The substrate recognition domains of the N-end rule pathway. Journal of Biological Chemistry. Jan. 16, 2009;284(3):1884-95.
Thakur et al., Real-time measurement of protein-protein interactions at single-molecule resolution using a biological nanopore. Nat. Biotechnol. Jan. 2019; 37(1):96-101.
Third Party Observation for European Application No. 19817882.4 mailed Dec. 20, 2021.
Tullman et al., A ClpS-based N-terminal amino acid binding reagent with improved thermostability and selectivity. Biochemical Engineering Journal. Feb. 15, 2020;154:107438.
Uniprot Accession No. A0A0K1RWM1, ATP-dependent Clp protease adapter protein CLPS, XP55836295, Nov. 11, 2015. 4 pages.
Van Vught et al., Site-specific functionalization of proteins and their applications to therapeutic antibodies. Comput Struct Biotechnol J. Feb. 14, 2014;9:e201402001. doi: 10.5936/csbj.201402001.
Wagner et al., Specificity of Aeromonas aminopeptidase toward amino acid amides and dipeptides. J Biol Chem. Feb. 25, 1972;247(4):1208-10.
Wang et al., The molecular basis of N-end rule recognition. Molecular cell. Nov. 7, 2008;32(3):406-14.
Witze et al., Mapping protein post-translational modifications with mass spectrometry. Nat Methods. Oct. 2007;4(10):798-806. doi: 10.1038/nmeth1100.

(56) References Cited

OTHER PUBLICATIONS

Xu et al., PTMD: A Database of Human Disease-associated Post-translational Modifications. Genomics Proteomics Bioinformatics. Aug. 2018;16(4):244-251. doi: 10.1016/j.gpb.2018.06.004. Epub Sep. 21, 2018.
Yao et al. Single-molecule protein sequencing through fingerprinting: computational assessment. Phys Biol. Aug. 12, 2015;12(5):055003. doi: 10.1088/1478-3975/12/5/055003.
Yu et al., Synthetic fusion protein design and applications. Biotechnol Adv. Jan.-Feb. 2015;33(1):155-164. doi: 10.1016/j.biotechadv.2014.11.005. Epub Nov. 18, 2014.
Bartlam et al., Crystal structure of an acylpeptide hydrolase/esterase from Aeropyrum pernix K1. Structure. Aug. 2004;12(8):1481-8. doi: 10.1016/j.str.2004.05.019.
Jones et al., Genetic relationship between acylpeptide hydrolase and acylase, two hydrolytic enzymes with similar binding but different catalytic specificities. Proc Natl Acad Sci U S A. Mar. 15, 1991;88(6):2194-8. doi: 10.1073/pnas.88.6.2194.
Kiss-Szemán et al., Cryo-EM structure of acylpeptide hydrolase reveals substrate selection by multimerization and a multi-state serine-protease triad. Chem Sci. May 18, 2022;13(24):7132-7142. doi: 10.1039/d2sc02276a.
Zhang et al., The conserved N-terminal helix of acylpeptide hydrolase from archaeon Aeropyrum pernix K1 is important for its hyperthermophilic activity. Biochim Biophys Acta. Sep. 2008;1784(9):1176-83. doi: 10.1016/j.bbapap.2008.05.011. Epub Jun. 6, 2008.

* cited by examiner

Bin 0: 12.71
Bin 1: 48.42
Intensity: 48.42
Bin ratio (Bin 0 / Bin 1): 0.26

Bin 0: 61.63
Bin 1: 101.23
Intensity: 101.23
Bin Ratio (Bin 0 / Bin 1): 0.61

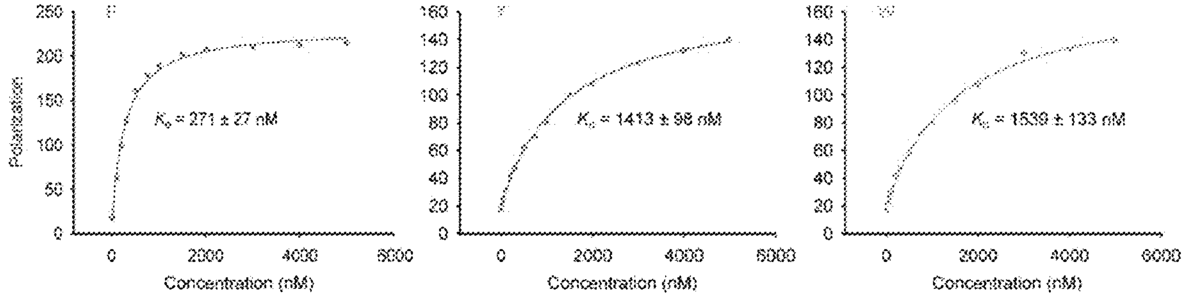
FIG. 7A
| Peptide | $k_{off}$ ($s^{-1}$) | SD |
|---|---|---|
| FAKLK(FITC)DEESILKQ | 1.80 | 0.13 |
| YAKLK(FITC)DEESILKQ | 4.70 | 0.51 |
| WAKLK(FITC)DEESILKQ | 10.07 | 1.48 |
FIG. 7B
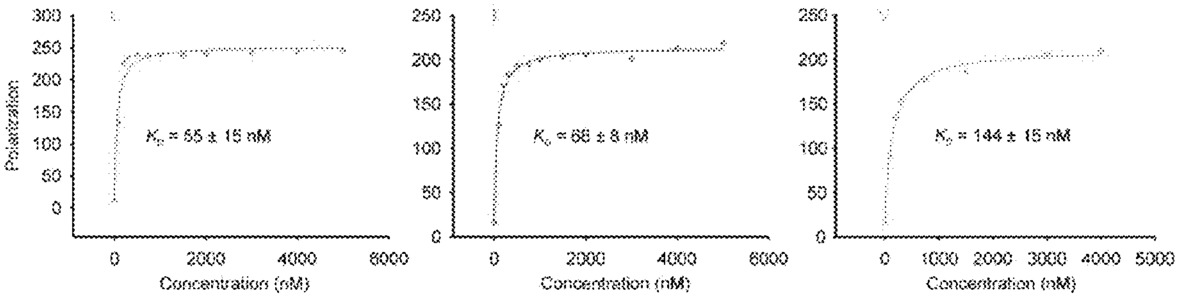
FIG. 7C L recognition segment duration

RLYFIAYPDDD

R RS mean PD = 0.9 s
L RS mean PD = 2.45 s

RLpYFIAYPDDD

R RS mean PD = 0.45 s
L RS mean PD = 3.4 s

RLIFAKAYPDDD

Mean pulse duration:

F = 1.4 sec

A = 1.3 sec

RLIFAK{acetyl}AYPDDD

Mean pulse duration:

F = 1.8 sec

A = 2.2 sec

Variant A21G

Variant E22G

Variant F19P

COMPOSITIONS AND METHODS FOR POLYPEPTIDE ANALYSIS

RELATED APPLICATIONS

This application claims priority under 35 U.S.C. § 119(e) to U.S. Provisional Patent Application No. 63/293,054, filed Dec. 22, 2021, and U.S. Provisional Patent Application No. 63/395,325, filed Aug. 4, 2022, each of which is hereby incorporated by reference in its entirety.

REFERENCE TO AN ELECTRONIC SEQUENCE LISTING

The contents of the electronic sequence listing (R070870150WO00-SEQ-MKN.xml; Size: 908,570 bytes; and Date of Creation: Dec. 21, 2022) are herein incorporated by reference in their entirety.

BACKGROUND

Measurements of the proteome provide deep and valuable insight into key biological processes. In adjacent fields, like genomics, advances in DNA sequencing technology have proven extremely valuable in improving understanding of the progression of complex human disease. Applying similar approaches to proteomics has been challenging for a number of reasons, including the large number of different proteins and even larger number of proteoforms, the wide dynamic range of protein abundance in cells and biological fluids, and the inability to copy or amplify proteins. Accordingly, improved approaches are needed.

SUMMARY

Methods and systems for determining chemical characteristics of polypeptides are generally described.

In some aspects, the application provides a method for determining chemical characteristics of a polypeptide. In some embodiments, the method comprises contacting a polypeptide with one or more amino acid recognizers. In certain embodiments, the one or more amino acid recognizers comprise a first set of one or more amino acid recognizers that bind to the polypeptide. In some embodiments, the method comprises detecting a first series of signal pulses indicative of a first series of binding events between the first set of one or more amino acid recognizers and the polypeptide. In some embodiments, the method comprises determining at least one chemical characteristic of a first set of at least two amino acids of the polypeptide based on at least one characteristic of the first series of signal pulses.

In some aspects, the application provides a device comprising at least one processor and at least one non-transitory computer-readable storage medium having instructions encoded thereon that, when executed by the at least one processor, cause the at least one processor to perform a method for determining chemical characteristics of a polypeptide. In some embodiments, the method comprises detecting a first series of signal pulses indicative of a first series of binding events between a first set of one or more amino acid recognizers and the polypeptide. In some embodiments, the method comprises determining at least one chemical characteristic of at least two amino acids of the polypeptide based on at least one characteristic of the first series of signal pulses.

In some aspects, the application provides at least one non-transitory computer-readable storage medium having instructions encoded thereon that, when executed by at least one processor, cause the at least one processor to perform a method for determining chemical characteristics of a polypeptide. In some embodiments, the method comprises detecting a first series of signal pulses indicative of a first series of binding events between a first set of one or more amino acid recognizers and the polypeptide. In some embodiments, the method comprises determining at least one chemical characteristic of at least two amino acids of the polypeptide based on at least one characteristic of the first series of signal pulses.

In some aspects, the application provides a method comprising obtaining data during a degradation process of a polypeptide. In some embodiments, the method comprises analyzing the data to determine portions of the data, each portion corresponding to at least one amino acid of the polypeptide. In certain embodiments, at least a first portion of the data corresponds to a first amino acid and comprises a first plurality of signal pulses indicative of a series of binding events between a first type of amino acid recognizer and the first amino acid. In certain embodiments, a second portion of the data corresponds to a second amino acid and does not comprise signal pulses indicative of binding events between any type of amino acid recognizer and the second amino acid. In some embodiments, the method comprises determining at least one chemical characteristic of the first amino acid and/or the second amino acid based on at least one characteristic of the first portion of the data and at least one characteristic of the second portion of the data. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

In some aspects, the application provides a method for determining chemical characteristics of a polypeptide. In some embodiments, the method comprises detecting a first series of signal pulses indicative of a first series of binding events between a first set of one or more amino acid recognizers and a polypeptide. In some embodiments, the method comprises determining at least one characteristic of the first series of signal pulses. In some embodiments, the method comprises comparing the at least one characteristic of the first series of signal pulses with known characteristics of a plurality of amino acid segments that comprise at least two amino acids. In some embodiments, the method comprises determining at least one chemical characteristic of at least two amino acids of the polypeptide based on the comparing. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

In some aspects, the application provides a method comprising obtaining data during a degradation process of a polypeptide. In some embodiments, the method comprises analyzing the data to determine at least three portions of the data, each portion corresponding to an amino acid of the polypeptide and comprising a plurality of signal pulses indicative of a series of binding events between one or more amino acid recognizers and the amino acid. In some embodiments, the method comprises determining one or more characteristics of each of the at least three portions of the data. In some embodiments, the method comprises identifying the polypeptide based on the order of the at least three portions of the data and the one or more characteristics of each of the at least three portions of the data. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

In some aspects, the application provides a method for determining at least one chemical characteristic of an amino acid of a polypeptide. In some embodiments, the method comprises detecting a first series of signal pulses indicative of a series of binding events between one or more amino acid recognizers and a first amino acid of the polypeptide. In some embodiments, the method comprises determining at least one chemical characteristic of a second amino acid of the polypeptide based on at least one characteristic of the first series of signal pulses. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

In some aspects, the application provides a method for determining at least one chemical characteristic of an amino acid of a polypeptide. In some embodiments, the method comprises detecting a first series of signal pulses indicative of a series of binding events between a first set of one or more amino acid recognizers and a first amino acid of the polypeptide. In some embodiments, the method comprises detecting a second series of signal pulses indicative of a series of binding events between a second set of one or more amino acid recognizers and a second amino acid of the polypeptide. In some embodiments, the method comprises determining at least one chemical characteristic of the second amino acid of the polypeptide based on at least one characteristic of the first series of signal pulses and at least one characteristic of the second series of signal pulses. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

In some aspects, the application provides a method of identifying a disease or disorder in a subject. In some embodiments, the method comprises digesting a protein in a sample from the subject to produce a plurality of polypeptides. In some embodiments, the method comprises contacting a polypeptide of the plurality of polypeptides with one or more amino acid recognizers and a cleaving agent. In some embodiments, the method comprises detecting one or more series of signal pulses indicative of binding events between the one or more amino acid recognizers and the polypeptide as amino acids are progressively cleaved from a terminus of the polypeptide by the cleaving agent. In some embodiments, the method comprises determining at least one chemical characteristic of the polypeptide based on at least one characteristic of the one or more series of signal pulses. In certain embodiments, the at least one chemical characteristic is indicative of a modification of the protein. In certain embodiments, the modification of the protein is indicative of the disease or disorder in the subject. In some embodiments, there is provided at least one non-transitory computer-readable medium having instructions encoded thereon that, when executed by at least one process, cause the at least one processor to perform the method. In some embodiments, there is provided a device comprising at least one processor and the at least one non-transitory computer-readable medium.

The details of certain embodiments of the disclosure are set forth in the Detailed Description. Other features, objects, and advantages of the disclosure will be apparent from the Examples, Drawings, and Claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying Drawings, which constitute a part of this specification, illustrate several embodiments of the disclosure and, together with the accompanying description, serve to explain the principles of the disclosure.

FIGS. 2A-2C show example traces demonstrating single-molecule N-terminal recognition by PS610 (FIG. 2A), PS961 (FIG. 2B), and PS691 (FIG. 2C); scatter plots of the number of pulses per recognition segment (RS) v. RS mean pulse duration (PD) are displayed for each peptide in FIGS. 2A-2C, with median PD indicated. FIG. 2D shows example traces from dynamic sequencing of the synthetic peptide FAAWAAYAAAADDD (SEQ ID NO: 813); median PD is indicated above each RS. FIGS. 2E-2G show dynamic sequencing of the synthetic peptide LAQFASIAAYASDDD (SEQ ID NO: 793) using PS610 and PS961. FIG. 2E shows example traces. FIG. 2F shows a scatter plot of RS mean PD v. bin ratio illustrating discrimination of recognizers by bin ratio and NAAs by pulse duration. FIG. 2G shows a scatter plot of the number of pulses per RS v. RS mean PD, grouped by the amino acid label assigned to the RS.

FIGS. 3A-3E show dynamic sequencing of the peptide DQQRLIFAG (SEQ ID NO: 794). FIG. 3A shows an example trace of DQQRLIFAG (SEQ ID NO: 794). FIG. 3B shows a scatter plot of RS mean PD v. bin ratio. FIG. 3C shows additional example traces of dynamic sequencing of DQQRLIFAG (SEQ ID NO: 794). FIG. 3D shows distributions of the duration of each RS and non-recognition segment (NRS) acquired during sequencing, with mean durations indicated. FIG. 3E shows kinetic signature plots summarizing the characteristic sequencing behavior of DQQRLIFAG (SEQ ID NO: 794) peptide. FIGS. 3F-3G show dynamic sequencing of the synthetic peptides DQQIASSRLAASFAAQQYPDDD (SEQ ID NO: 795) (top), RLAFSALGAADDD (SEQ ID NO: 796) (middle), and EFIAWLV (SEQ ID NO: 797) (bottom). FIG. 3F shows example traces for each peptide. FIG. 3G shows corresponding kinetic signature plots of DQQIASSRLAASFAAQQY (SEQ ID NO: 856), RLAFSAL (SEQ ID NO: 857), and EFIAWLV (SEQ ID NO: 797).

FIGS. 4A-4B show dynamic sequencing of synthetic peptides that differ by a single amino acid: RLAFAYPDDD (SEQ ID NO: 798) (top), RLIFAYPDDD (SEQ ID NO: 799) (middle), RLVFAYPDDD (SEQ ID NO: 800) (bottom). FIG. 4A shows example traces. FIG. 4B shows scatter plots of RS mean PD v. bin ratio. FIGS. 4C-4D show detection of oxidized methionine using the peptide RLMFAYPDDD (SEQ ID NO: 801). FIG. 4C shows distributions of mean PD for leucine; labels indicate populations with leucine followed by methionine (LM) or methionine sulfoxide (LMo). FIG. 4D shows example traces in which methionine is recognized by PS961 and leucine exhibits long PD (top, RLMFAYPDDD (SEQ ID NO: 801)), or in which methionine is not recognized due to oxidation and leucine exhibits short PD (bottom, RLMoFAYPDDD (SEQ ID NO: 858)). FIG. 4E shows scatter plots of RS mean PD v. bin ratio for runs in which oxidation was not controlled (top) or in which methionine was fully oxidized (bottom).

FIG. 5A shows example traces from sequencing a mixture of the peptides DQQRLIFAG (SEQ ID NO: 794) and RLAFSALGAADDD (SEQ ID NO: 796) on the same chip; the chip window indicates the location of reaction chambers producing a sequencing readout for each peptide. FIG. 5B shows example traces from the dynamic sequencing of two peptides, DQQRLIFAGK (SEQ ID NO: 802) (top) and EFIAWLVK (SEQ ID NO: 803) (bottom), isolated from the recombinant human proteins ubiquitin and GLP-1, respectively. FIG. 5C shows a diagram illustrating identification of the protein ubiquitin as a match to the kinetic signature from DQQRLIFAGK (SEQ ID NO: 802) peptide in an in silico digest of the human proteome based on kinetic information. SEQ ID NOs: 804 (IVNFSRLIFHHLK), 805 (DIRLIFSNAK), 806 (GQSRLIFTYGLTNSGK), 807 (DQQRLLIFAGK), and 808 (DEHCLRLIFLK) are shown.

FIG. 6A shows an exploded view of the compact benchtop instrument designed to support the custom semiconductor chip and protein sequencing assay. FIG. 6B shows that the chip achieves electronic rejection by discarding photoelectrons from the pulsed laser before shifting to collect fluorescence photoelectrons from bound NAA recognizers; the timing of the rejection and collection windows cycles between two modes (Bin 1 and Bin 0, example waveforms shown) in alternate frames to provide a bin ratio estimate of the fluorescence lifetime of the dye. FIG. 6C shows that the chip achieves >10,000-fold attenuation of incident laser light within 1 ns from initiation of a rejection mode. FIG. 6D shows example pulses for dyes with short and long fluorescence lifetime, illustrating the difference in signal collection in Bin 0 and Bin 1. FIG. 6E shows distributions of mean RS bin ratio collected for three dyes with different fluorescence lifetime. FIG. 6F shows dye channel identification accuracy increases with the number of pulses captured per RS.

FIGS. 7A-7H show an example of recognizer properties. FIGS. 7A-7E show recognizer kinetic characterization using polarization assays (Example 1, Methods). FIGS. 7A-7B show affinity ($K_D$) (FIG. 7A) and off-rate ($k_{off}$) (FIG. 7B) of PS610 for peptides with N-terminal phenylalanine, tyrosine, and tryptophan. In FIG. 7B, SEQ ID NOs: 809 (FAKLK(FITC)DEESILKQ), 810 (YAKLK(FITC)DEESILKQ), and 811 (WAKLK(FITC)DEESILKQ) are shown. FIG. 7C shows affinity of PS961 for peptides with N-terminal leucine, isoleucine, and valine. FIGS. 7D-7E show affinity of PS691 for a peptide with N-terminal arginine (FIG. 7D) and single-point polarization data measured for peptides with N-terminal arginine, lysine, and histidine using 2000 nM PS691 (FIG. 7E). FIG. 7F shows binding energy was calculated using a computational model (Example 1, Methods) for peptides of initial sequence LAX and LXA, where X=all 20 amino acids; boxplots show the fraction of total binding energy contributed by the amino acid at position 1 (P1), position 2 (P2), and position 3 (P3), with an exponentially decreasing trend from P1 to P3 ($R^2$>0.97). FIG. 7G shows RS mean PD determined in single-molecule assays for LXA and LAX peptides using PS961 and for FXA and FAX peptides using PS610. FIG. 7H shows the non-polar solvation energy term from the computational binding model with PS961 exhibits high correlation with actual RS mean PD values observed in single-molecule assays with peptides containing N-terminal leucine and varying amino acids at the P2 position. Peptides LVFA (SEQ ID NO: 859), LIFA (SEQ ID NO: 860), LVAR (SEQ ID NO: 861), LAFA (SEQ ID NO: 862), LQAR (SEQ ID NO: 863), LDAA (SEQ ID NO: 864), LCAR (SEQ ID NO: 865), LGAA (SEQ ID NO: 866), LMFA (SEQ ID NO: 867), LSAR (SEQ ID NO: 868), and LEFA (SEQ ID NO: 869) are shown.

FIGS. 8A-8B show interpulse duration (IPD) decreases with increasing recognizer concentration. Scatter plots of RS mean PD v. RS mean IPD are displayed for PS961 binding to LIF (FIG. 8A) and IFA (FIG. 8B) in dynamic sequencing assays at a concentration of 125 nM (orange) or 250 nM (blue); median IPD values are indicated. Recognizer concentration did not affect RS mean PD. FIG. 8C shows single exponential decay curves fit to the RS duration distributions for arginine, leucine, isoleucine, and phenylalanine acquired from dynamic sequencing of the synthetic peptide DQQRLIFAG (SEQ ID NO: 794). FIGS. 8D-8E show that increasing the aminopeptidase concentrations in dynamic sequencing runs of the synthetic peptide DQQRLIFAG (SEQ ID NO: 794) resulted in decreased NRS (FIG. 8D) and RS (FIG. 8E) durations; median RS duration values are indicated.

FIG. 9A shows kinetic signature plots for three peptides: RLAFAYPDDD (SEQ ID NO: 798) (top), RLIFAYPDDD (SEQ ID NO: 799) (middle), and RLVFAYPDDD (SEQ ID NO: 800) (bottom). FIGS. 9B-9C show incomplete RS information observed in dynamic sequencing of RLIFAYPDDD (SEQ ID NO: 799) peptide. FIG. 9B shows percentage of reads and example traces of each type of observed deletion of one or more RSs in traces beginning with arginine and ending with tyrosine recognition. RLIFY (SEQ ID NO: 812) is shown. FIG. 9C shows percentage of reads and example traces of each type of observed truncation of one or more RSs in traces beginning with arginine. RLIFY (SEQ ID NO: 812) is shown. FIG. 9D shows affinity of PS961 for a peptide with N-terminal methionine measured a polarization assay (Example 1, Methods). FIG. 9E shows binding energy prediction for peptides with N-terminal methionine and methionine sulfoxide (Mo) from computational modeling with PS961 (Example 1, Methods). FIG. 9F shows kinetic signature plots for DQQRLIFAG (SEQ ID NO: 794, residues 1-7 shown) and RLAFSALGAADDD (SEQ ID NO: 796, residues 1-7 shown) peptides mixed and run on the same chip. FIG. 9G shows kinetic signature plots for DQQRLIFAGK (SEQ ID NO: 802, residues 1-7 shown) and EFIAWLVK (SEQ ID NO: 803, residues 1-6 shown) peptides obtained from digestion of recombinant human ubiquitin and GLP-1.

FIGS. 10A-10C show heatmaps of predicted pulse durations for PS961 binding tripeptide targets having leucine (FIG. 10A), isoleucine (FIG. 10B), or valine (FIG. 10C) at the N-terminal position. FIGS. 10D-10F show heatmaps of predicted pulse durations for PS610 binding tripeptide targets having phenylalanine (FIG. 10D), tyrosine (FIG. 10E), or tryptophan (FIG. 10F) at the N-terminal position. FIG. 10G shows a heatmap of predicted pulse durations for PS1122 binding tripeptide targets having arginine at the N-terminal position. FIG. 10H shows plots demonstrating high correlation of predicted pulse durations with actual pulse durations from on-chip experiments for PS961 (left plot) and PS610 (right plot). FIGS. 10I-10K show the results from an analysis of the human proteome. FIGS. 10L-10M show the results from an analysis of the *E. coli* proteome.

FIG. 11A shows different arginine PTMs, including symmetric dimethylarginine (SDMA), asymmetric dimethylarginine (ADMA), and citrullinated arginine. FIG. 11B shows an exemplary workflow for collecting samples, preparing libraries of digested peptides, loading on a chip, and conducting on-chip sequencing and data analysis. FIG. 11C shows sequencing data demonstrating that kinetic signatures distinguish peptides containing arginine, ADMA, and SDMA. FIG. 11C-A shows example protein sequencing traces for three synthetic P38MAPKa-derived peptides containing arginine, ADMA, or SDMA at position 2. Full length peptide sequences are indicated for each example trace: YRELRLLK (SEQ ID NO: 834) (top), YRADMAELRKKL (SEQ ID NO: 894) (middle), $YR_{SDMA}$ELRLLK (SEQ ID NO: 895) (bottom). FIG. 11C-B shows the distribution of recognition segment (RS) mean pulse duration (PD) for RSs corresponding to the initial 4-residue sequence of each peptide: YREL (SEQ ID NO: 814) (left), YRADMAEL (SEQ ID NO: 815) (middle), and YRSDMAEL (SEQ ID NO: 816) (right). Median values are indicated for each distribution. FIG. 11C-C shows interpulse duration (IPD) for arginine v. ADMA detection by PS621. FIG. 11D shows sequencing data demonstrating that kinetic signatures distinguish peptides containing arginine and citrulline. FIG. 11D-A shows example protein sequencing traces for two synthetic peptides containing arginine or citrulline at position 2: peptide sequence LRLAFAYPDDDK (SEQ ID NO: 817) (QP707) and citrullinated peptide sequence LRCitLAFAYPDDDK (SEQ ID NO: 818) (QP789). Full length peptide sequences are indicated for each example trace. FIG. 11D-B shows the distribution of RS mean PD for RSs corresponding to the initial 5-residue sequence of each peptide: LRLAF (SEQ ID NO: 819) (left) and LCitLAF (SEQ ID NO: 820) (right). Median values are indicated for each distribution.

FIG. 12A shows an example method for determining chemical characteristics of a polypeptide. FIG. 12B shows an example method for determining chemical characteristics of a polypeptide where one or more amino acids of the polypeptide are unrecognizable. FIG. 12C shows an example method for determining chemical characteristics of a polypeptide. FIG. 12D shows an example method for identifying a protein from which a polypeptide originated based on a pulse pattern including at least three recognition segments. FIG. 12E shows an example method of characterizing an amino acid based on a pulse pattern emitted by one or more recognizers bound to a first amino acid. FIG. 12F shows an example method for determining at least one chemical characteristic of an amino acid of a polypeptide. FIG. 12G shows an example method for identifying a disease or disorder in a subject based on at least one chemical characteristic of a polypeptide.

FIGS. 14A-14B show results from sequencing reactions using the recognizers PS691, PS610, and PS961 for the peptides: RLTFIAYPDDD (SEQ ID NO: 821) (FIG. 14A); and RLpTFIAYPDDD (SEQ ID NO: 822), where pT is phosphothreonine (FIG. 14B). FIG. 14C shows recognition segment (RS) durations for leucine recognition in the sequencing reactions of FIGS. 14A (left panel) and 14B (right panel).

FIG. 17A illustrates an example of a β-amyloid variant. FIG. 17B illustrates an example workflow for β-amyloid variant detection. FIGS. 17C-17G illustrate examples of pulse patterns of β-amyloid wild type LVFFAE (SEQ ID NO: 827) versus variants (LVFFAK (SEQ ID NO: 828), LVFFGK (SEQ ID NO: 829), LVFFAG (SEQ ID NO: 830), LVPFAE (SEQ ID NO: 831)).

FIG. 18A shows a plot of bin ratio v. pulse duration for the peptide fragment VRFLEQQNK (SEQ ID NO: 841). FIG. 18B shows a plot of bin ratio v. pulse duration for the peptide fragment VCitFLEQQNK (SEQ ID NO: 842), where Cit is citrulline.

FIGS. 19A and 19B show example traces, and FIGS. 19C and 19D show example plots of intensity v. bin ratio.

FIGS. 20A and 20B show example traces, and FIGS. 20C and 20D show example plots of intensity v. bin ratio.

In FIG. 21A, kinetic signatures from each of 5 clusters of traces from cerebral dopamine neurotrophic factor (CDNF) sequencing were mapped to a database of predicted kinetic signatures for more than 300,000 peptides derived from in silico Lys-C digestion of about 20,000 human proteins, and candidate matching peptides are shown for each cluster. FIG. 21B shows matching peptides for each kinetic signature aligned to the full-length sequence of human CDNF protein.

DETAILED DESCRIPTION

Figure 1:
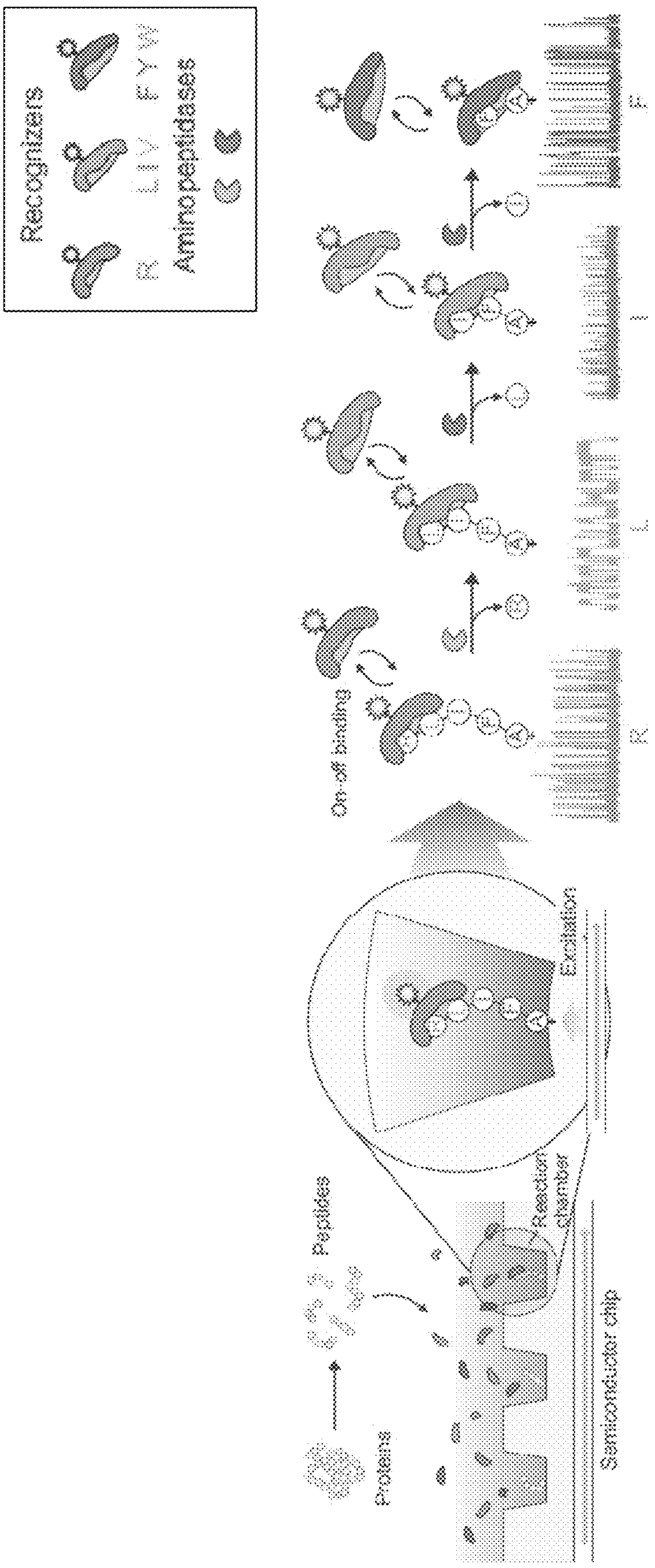
FIG. 1 shows an example overview of real-time dynamic protein sequencing. Protein samples are digested into polypeptides, immobilized in nanoscale reaction chambers, and incubated with a mixture of freely-diffusing N-terminal amino acid (NAA) recognizers and cleaving agents (e.g., aminopeptidases) that carry out the sequencing process. The labeled recognizers bind on and off to the polypeptide when one of their cognate NAAs is exposed at the N-terminus, thereby producing characteristic pulsing patterns. The NAA is cleaved by a cleaving agent, exposing the next amino acid for recognition. The temporal order of NAA recognition and the kinetics of binding enable polypeptide identification and are sensitive to features that modulate binding kinetics, such as post-translational modifications (PTMs).

Aspects of the application relate to methods and systems for obtaining information regarding multiple amino acids in a polypeptide based on binding interactions between the polypeptide and one or more amino acid recognizers. For example, kinetic signature information may be obtained from a series of signal pulses indicative of a series of binding events between one or more amino acid recognizers and an amino acid of a polypeptide (e.g., a terminal amino acid, an internal amino acid). The kinetic signature information (e.g., pulse duration, interpulse duration, recognition segment (RS) duration, intersegment duration) may be used to determine one or more chemical characteristics (e.g., identity, modification) of multiple amino acids of the polypeptide.

Protein characterization has a number of important applications, including determination of the presence or absence of a protein (e.g., a disease-relevant protein) in a biological sample, identification of an unknown protein in a biological sample, and identification of a protein responsible for biological activity in an isolated protein fraction. However, conventional methods of characterizing proteins, such as mass spectrometry and affinity-based methods, often face substantial challenges, including the inability to identify unknown proteins and/or differentiate unmodified proteins from proteins with post-translational modifications (PTMs). In contrast, methods and systems described herein may provide accurate characterization of a wide range of proteins. In some aspects, methods and systems described herein use single molecule protein sequencing to identify and/or otherwise characterize proteins based on the kinetic signature of binding between recognizers and polypeptide fragments of the proteins. This approach provides the resolution needed to differentiate between polypeptides with similar sequences or physicochemical properties.

Kinetic signature information can be beneficial for mapping peptides to their proteins of origin at least because the kinetic signature information associated with one amino acid may provide information about the chemical characteristics of multiple amino acids. In some cases, when amino acid recognizers bind to a polypeptide, they contact not just one amino acid, but one or more upstream and/or downstream amino acids. This contact with one or more upstream and/or downstream amino acids can influence kinetic signature information (e.g., pulse duration, interpulse duration, recognition segment duration, intersegment duration). This sensitivity of kinetic signature information to upstream and/or downstream amino acids can provide a wealth of information on peptide sequence composition and can facilitate mapping peptides to the proteome. In some embodiments, recognizers may bind to a terminal amino acid of a polypeptide and one or more downstream amino acids. In some embodiments, recognizers may bind to an internal amino acid of a polypeptide and one or more upstream and/or downstream amino acids. In this manner, the recognizers may directly or indirectly sense all 20 amino acids found in the human body (i.e., the building blocks of the human proteome), and this information can be encoded in the average pulse duration, interpulse duration, recognition segment (RS) duration, and/or intersegment duration. Additionally, adjacent visible residues in a polypeptide can be represented on average by immediately adjacent RSs (i.e., a consensus gap between two RSs may only occur if there is at least one invisible amino acid between them).

As described herein, signal pulses from a dye-labeled first type of amino acid recognizer that binds to an amino acid, such as the terminal amino acid or an internal amino acid of a polypeptide, may be used to determine one or more chemical characteristics of multiple amino acids of the polypeptide. The inventors have recognized that such techniques are advantageous. For example, such techniques may allow for determining chemical characteristics of amino acids which are unrecognized. Such amino acids may be unrecognizable by any amino acid recognizers present in a reaction chamber, in some instances. Such techniques may also save time, require fewer amino acid recognizers, and/or require less signal collection. Accordingly, obtaining information regarding multiple amino acids based on fewer series of signal pulses and/or using fewer recognizers is advantageous.

In some embodiments, kinetic signature information obtained from a first series of binding events between one or more amino acid recognizers and a first amino acid of a polypeptide (e.g., a terminal amino acid, an internal amino acid) may be used to determine one or more chemical characteristics of at least 1, 2, 3, 4, 5, 6, 7, 8, 9, 10, 15, 20, 25, 50, 100, or more amino acids of the polypeptide. In certain embodiments, kinetic signature information obtained from the first series of binding events may be used to determine one or more chemical characteristics of 1 amino acid, 2 amino acids, 3 amino acids, 4 amino acids, 5 amino acids, 10 amino acids, 15 amino acids, 20 amino acids, 50 amino acids, or 100 amino acids. In certain embodiments, kinetic signature information obtained from the first series of binding events may be used to determine one or more chemical characteristics of 1-2 amino acids, 1-3 amino acids, 1-4 amino acids, 1-5 amino acids, 1-10 amino acids, 1-15 amino acids, 1-20 amino acids, 1-50 amino acids, 1-100 amino acids, 2-3 amino acids, 2-4 amino acids, 2-5 amino acids, 2-10 amino acids, 2-15 amino acids, 2-20 amino acids, 2-50 amino acids, 2-100 amino acids, 3-5 amino acids, 3-10 amino acids, 3-15 amino acids, 3-20 amino acids, 3-50 amino acids, 3-100 amino acids, 5-10 amino acids, 5-15 amino acids, 5-20 amino acids, 5-50 amino acids, 5-100 amino acids, 10-20 amino acids, 10-50 amino acids, 10-100 amino acids, 20-50 amino acids, 20-100 amino acids, or 50-100 amino acids.

In some embodiments, kinetic signature information obtained from a first series of binding events between one or more amino acid recognizers and a first amino acid of a polypeptide (e.g., a terminal amino acid, an internal amino acid) may be used to determine one or more chemical characteristics of at least a second amino acid of the polypeptide. In certain embodiments, the first amino acid is a terminal amino acid and the second amino acid is downstream of the first amino acid. In certain embodiments, the first amino acid is an internal amino acid and the second amino acid is upstream or downstream of the first amino acid. In some instances, the second amino acid is proximate to the first amino acid. In some cases, for example, the second amino acid is separated from the first amino acid by 10 amino acids or fewer, 5 amino acids or fewer, 4 amino acids or fewer, 3 amino acids or fewer, 2 amino acids or fewer, 1 amino acid or fewer, or 0 amino acids (i.e., the first and second amino acids are immediately adjacent). In some cases, the second amino acid is separated from the first amino acid by at least 1 amino acid, at least 2 amino acids, at least 3 amino acids, at least 4 amino acids, at least 5 amino acids, or at least 10 amino acids. In some cases, the second amino acid is separated from the first amino acid by 1-2 amino acids, 1-3 amino acids, 1-4 amino acids, 1-5 amino acids 1-10 amino acids, 2-3 amino acids, 2-4 amino acids, 2-5 amino acids, 2-10 amino acids, 3-5 amino acids, 3-10 amino acids, or 5-10 amino acids.

In some embodiments, kinetic signature information obtained from a first series of binding events between one or more amino acid recognizers and a first amino acid of a polypeptide (e.g., a terminal amino acid, an internal amino acid) may be used to determine one or more chemical characteristics of at least a second amino acid and a third amino acid of the polypeptide. In certain embodiments, the first amino acid is a terminal amino acid and the second and third amino acids are downstream of the first amino acid. In certain embodiments, the first amino acid is an internal amino acid and the second and third amino acids are independently upstream or downstream of the first amino acid. In some instances, the second amino acid and/or third amino acid are proximate to the first amino acid. In some cases, for example, the second amino acid and/or third amino acid are separated from the first amino acid by 10 amino acids or fewer, 5 amino acids or fewer, 4 amino acids or fewer, 3 amino acids or fewer, 2 amino acids or fewer, 1 amino acid or fewer, or 0 amino acids (i.e., the first amino acid is immediately adjacent to the second amino acid and/or the third amino acid). In some cases, the second amino acid and/or the third amino acid are separated from the first amino acid by at least 1 amino acid, at least 2 amino acids, at least 3 amino acids, at least 4 amino acids, at least 5 amino acids, or at least 10 amino acids. In some cases, the second amino acid and/or the third amino acid are separated from the first amino acid by 1-2 amino acids, 1-3 amino acids, 1-4 amino acids, 1-5 amino acids 1-10 amino acids, 2-3 amino acids, 2-4 amino acids, 2-5 amino acids, 2-10 amino acids, 3-5 amino acids, 3-10 amino acids, or 5-10 amino acids. In certain cases, the second amino acid is proximate to the third amino acid. The second amino acid may be adjacent or non-adjacent to the third amino acid. In some embodiments, the second amino acid is separated from the third amino acid by 10 amino acids or fewer, 5 amino acids or fewer, 4 amino acids or fewer, 3 amino acids or fewer, 2 amino acids or fewer, 1 amino acid or fewer, or 0 amino acids (i.e., the second amino acid is immediately adjacent to the third amino acid). In some cases, the second amino acid is separated from the third amino acid by at least 1 amino acid, at least 2 amino acids, at least 3 amino acids, at least 4 amino acids, at least 5 amino acids, or at least 10 amino acids. In some cases, the second amino acid is separated from the third amino acid by 1-2 amino acids, 1-3 amino acids, 1-4 amino acids, 1-5 amino acids 1-10 amino acids, 2-3 amino acids, 2-4 amino acids, 2-5 amino acids, 2-10 amino acids, 3-5 amino acids, 3-10 amino acids, or 5-10 amino acids.

In some embodiments, the determined one or more chemical characteristics comprise an identity of a first amino acid, a second amino acid, and/or a third amino acid of a polypeptide. In some embodiments, the determined one or more chemical characteristics comprise a modification (e.g., a post-translational modification, a mutation, a bond to a binding component) of a first amino acid, a second amino acid, and/or a third amino acid of a polypeptide. In certain embodiments, the determined one or more chemical characteristics may be used to identify the first amino acid, the second amino acid, and/or the third amino acid. In certain embodiments, the identified amino acids may be used to identify a protein from which the polypeptide originated.

In some aspects, compositions, methods, and systems of the disclosure may be utilized in a dynamic peptide sequencing reaction. In this technique, structural information for polypeptides can be determined by evaluating single-molecule binding interactions between amino acid recognizers and a polypeptide while amino acids are progressively cleaved from a terminal end of the polypeptide. FIG. 1 shows an example of a dynamic peptide sequencing reaction in which individual on-off binding events give rise to signal pulses of a signal output. As shown at left, a protein sample may be fragmented into polypeptides, which are immobilized in reaction chambers of an array, where the immobilized polypeptides are exposed to one or more amino acid recognizers and one or more cleaving agents (e.g., aminopeptidases). As shown at right, an amino acid recognizer reversibly binds a terminal end of the polypeptide, and a detectable signal is produced while the recognizer is bound to the polypeptide. As the on-off binding of recognizers generally occurs at a faster rate than amino acid cleavage, the binding events preceding amino acid cleavage give rise to a series of pulses in a signal output which can be used to determine structural information about amino acids of the polypeptide.

Compositions, systems, and methods for performing dynamic polypeptide sequencing and analyzing data obtained therefrom are described more fully in PCT International Publication No. WO2020102741A1, filed Nov. 15, 2019, and PCT International Publication No. WO2021236983A2, filed May 20, 2021, each of which is incorporated by reference in its entirety.

As used herein, in some embodiments, the term "bond" or "bonds" refers to any non-covalent interaction (e.g., a hydrogen bond, a van der Waals interaction, an aromatic interaction, an electrostatic interaction) or covalent interaction between specified binding components or any plurality thereof, and the terms "bind," "binding," "bound," and like terms refer to the formation and/or existence of any such bonds. As an illustrative example, a binding event between an amino acid recognizer and an amino acid may comprise the formation of one or more non-covalent or covalent interactions between the amino acid recognizer and the amino acid.

In some embodiments, the terminology includes identifying one or more amino acids of a polypeptide. As used herein, in some embodiments, "identifying," "determining the identity," and like terms, in reference to an amino acid, include determination of an express identity of an amino acid as well as determination of a probability of an express identity of an amino acid. For example, in some embodiments, an amino acid is identified by determining a probability (e.g., from 0% to 100%) that the amino acid is of a specific type, or by determining a probability for each of a plurality of specific types. Accordingly, in some embodiments, the terms "amino acid sequence," "polypeptide sequence," and "protein sequence" as used herein may refer to the polypeptide or protein material itself and is not restricted to the specific sequence information (e.g., the succession of letters representing the order of amino acids from one terminus to another terminus) that biochemically characterizes a specific polypeptide or protein.

Exemplary Techniques for Obtaining Information Regarding Amino Acids

As described herein, the inventors have developed techniques for obtaining information regarding multiple amino acids in a polypeptide based on a series of signal pulses indicative of a series of binding events between one or more amino acid recognizers and an amino acid of the polypeptide. FIGS. 12A-12G show example methods for determining and using kinetic signature information to characterize polypeptides.

The methods described herein may be implemented by a system. For example, in some embodiments, the system comprises at least one non-transitory computer-readable medium having instructions encoded thereon that, when executed, cause a processor to perform one or more of the methods described herein. In some embodiments, the system further comprises the processor. The system may comprise any of the components of the integrated device described herein.

The methods may facilitate obtaining information regarding multiple amino acids. For example, a polypeptide comprising a chain of amino acids may be used with the techniques described herein. The chain of amino acids may comprise at least one amino acid to which a dye-labeled recognizer binds. In some embodiments, the chain of amino acids comprises a terminal amino acid and one or more downstream amino acids (e.g., amino acids at position 1, 2, 3, 4, and/or 5 relative to the polypeptide terminus). In some embodiments, one or more amino acid recognizers may bind to the terminal amino acid. In some embodiments, the one or more amino acid recognizers may bind to one or more amino acids downstream of the terminal amino acid in addition to the terminal amino acid of the peptide. In some embodiments, the one or more amino acid recognizers may bind to an internal amino acid and one or more amino acids upstream or downstream of the internal amino acid.

The polypeptide may comprise any number of amino acids. In some embodiments, the polypeptide comprises at least 5 amino acids, at least 10 amino acids, at least 15 amino acids, at least 20 amino acids, at least 50 amino acids, or at least 100 amino acids. In some embodiments, the polypeptide comprises 5-10, 5-15, 5-20, 5-50, 5-100, 10-15, 10-20, 10-50, 10-100, 15-20, 15-50, 15-100, 20-50, 20-100, or 50-100 amino acids.

In some embodiments, to obtain information regarding the chain of amino acids, a sample comprising at least a portion (e.g., all or a fragment thereof) of the polypeptide may be loaded onto an integrated device, such as the integrated device described herein. In particular, the polypeptide may be loaded into a reaction chamber of the integrated device. In some cases, the polypeptide may be bound to the surface of the chamber via a covalent or non-covalent bond (e.g., a streptavidin-biotin bond, a click chemistry bond) which immobilizes the polypeptide in the chamber.

In some embodiments, multiple polypeptides may be loaded onto the integrated device and multiple chambers of the integrated device may receive one or more of the polypeptides. The techniques described herein for obtaining information regarding polypeptides may be performed in a parallel manner (e.g., concurrently, simultaneously).

Figure 12A:
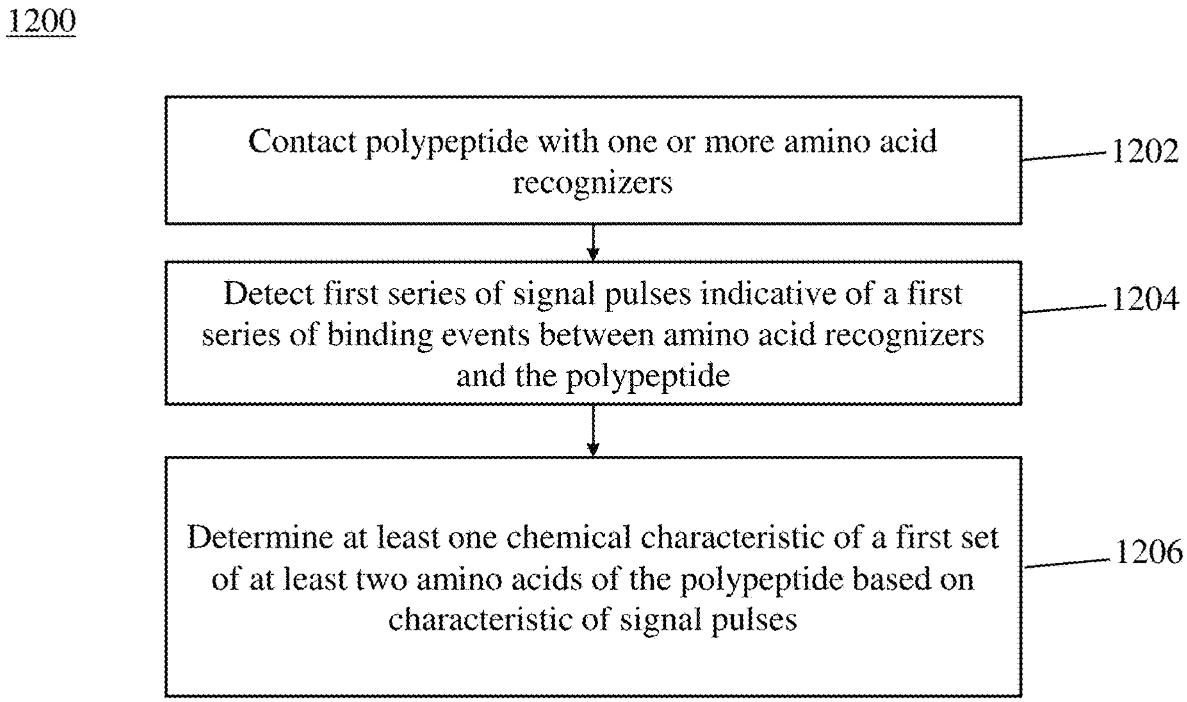
FIGS. 12A-12G show example methods for using kinetic signature information.

FIG. 12A shows an example method 1200 for determining chemical characteristics of a polypeptide. In some embodiments, method 1200 may begin at act 1202. In some embodiments, one or more additional or alternative acts may be performed prior to act 1202, such as any of the loading steps described herein.

At act 1202, a polypeptide may be contacted with one or more amino acid recognizers. As described herein, the polypeptide may comprise a plurality of amino acids. In some embodiments, the polypeptide comprises a first amino acid (e.g., a terminal amino acid, an internal amino acid) to which the one or more amino acid recognizers may bind, and at least one other (e.g., upstream, downstream) amino acid (e.g., a second amino acid).

The one or more amino acid recognizers may comprise a first set of one or more amino acid recognizers that bind to the polypeptide. In some embodiments, the first set of one or more amino acid recognizers may bind to an amino acid of the polypeptide and, in some embodiments, to one or more additional amino acids. In certain embodiments, the first set of one or more amino acid recognizers may bind to a terminal amino acid of the polypeptide and, in some embodiments, to one or more downstream amino acids. In certain embodiments, the first set of one or more amino acid recognizers may bind to an internal amino acid of the polypeptide and, in some embodiments, to one or more upstream and/or downstream amino acids. At least one (and, in some embodiments, each) of the one or more amino acid recognizers may be labeled with a fluorescent dye that emits emission light when excited with excitation light, as described herein. In some cases, the one or more amino acid recognizers comprise a plurality of types of amino acid recognizers. In certain cases, each type of amino acid recognizer may only bind to certain amino acids. As an illustrative example, a first type of amino acid recognizer may preferentially bind to leucine, isoleucine, and valine. As another illustrative example, a second type of amino acid recognizer may preferentially bind to phenylalanine, tyrosine, and tryptophan. As another illustrative example, a third type of amino acid recognizer may preferentially bind to arginine. In some embodiments, the first set of one or more amino acid recognizers comprises one type of amino acid recognizer. In some embodiments, the first set of one or more amino acid recognizers comprises two or more types of amino acid recognizers. In some embodiments, each type of recognizer is labeled with a unique dye and/or a unique number of dyes. Accordingly, the emission light from the dye-labeled amino acid recognizers may be used to obtain information about (e.g., identify) the amino acid to which the dye-labeled amino acid recognizer is bound, and in some embodiments, about one or more additional amino acids.

In some embodiments, contacting the polypeptide with the one or more amino acid recognizers comprises introducing the one or more amino acid recognizers onto the device (e.g., by loading a solution comprising the one or more amino acid recognizers onto the integrated device comprising the polypeptide). The one or more amino acid recognizers may periodically bind to the polypeptide (e.g., to at least one amino acid of the polypeptide). The rate at which the one or more amino acid recognizers bind to the polypeptide is referred to herein as the binding rate. In some embodiments, the one or more amino acid recognizers may be labeled with (e.g., conjugated to) fluorescent dyes that may become excited when the one or more recognizers are bound to or in the vicinity of an amino acid of the polypeptide. Therefore, periodic signals emitted by the fluorescent dyes may be characteristic of the binding rate of the amino acid recognizers.

At act 1204, a first series of signal pulses may be detected. For example, the integrated device may comprise one or more photodetection regions which detect light emitted by the reaction chambers, and more specifically, by the excited fluorescent dyes therein. As described herein, the fluorescent dyes which label the one or more amino acid recognizers may become excited with excitation light (e.g., from at least one light source such as a pulsed laser). When excited, electrons of the fluorescent dyes absorb energy from excitation light and move to a higher energy level. After a period of time, the electrons return to the ground state. When returning to the ground state, the electrons emit energy in the form of photons. The emitted photons (also referred to herein as emission light or signals) may be detected by the integrated device described herein. The signal pulses detected by the integrated device include information characteristic of the sample that the fluorescent dye is bound to (e.g., pulse duration, interpulse duration, recognition segment duration, intersegment duration, cleavage rate, cleavage time, intensity, wavelength, fluorescence lifetime, whether an amino acid is recognized). In particular, the signal pulses include information characteristic of a fluorescent dye. Each type of amino acid recognizer may be conjugated to a unique combination of one or more fluorescent dyes. Accordingly, the signal pulses may correlate to one or more amino acids and may be used to obtain information regarding the sample.

The first series of signal pulses detected at act 1204 may be indicative of a first series of binding events between a first set of one or more dye-labeled amino acid recognizers and at least one amino acid of the polypeptide. As described herein, the one or more dye-labeled amino acid recognizers may periodically bind to an amino acid (e.g., the terminal amino acid, an internal amino acid) and may emit signals when bound to the amino acid. Accordingly, the first series of signal pulses may be indicative of a series of binding events between the one or more dye-labeled amino acid recognizers and the amino acid, and in some embodiments, one or more upstream and/or downstream amino acids.

At act 1206, at least one chemical characteristic of the polypeptide may be determined based on at least one characteristic of the first series of signal pulses detected at act 1204. In some embodiments, determining at least one chemical characteristic of the polypeptide comprises determining at least one chemical characteristic of a first set of at least two amino acids of the polypeptide. In some embodiments, the at least two amino acids include the amino acid to which the one or more amino acid recognizers is bound and one or more other amino acids (e.g., one or more upstream and/or downstream amino acids). In some embodiments, the at least two amino acids include the terminal amino acid and one or more downstream amino acids.

As described herein, at least one characteristic of the series of signal pulses may be determined. Examples of the at least one characteristic include, but are not limited to, intensity, fluorescence lifetime, wavelength, pulse duration, interpulse duration, recognition segment duration, intersegment duration, cleavage rate, cleavage time, absence of signal pulses, and whether an amino acid is recognized. In some embodiments, the at least one characteristic of the series of signal pulses comprises an average characteristic of the series of signal pulses.

In some embodiments, the at least one characteristic of the series of signal pulses comprises intensity (e.g., average intensity of the series of signal pulses). Intensity may be determined based on an amount of charge carriers detected in the photodetection region which receives the emission light from the fluorescent labels. In some embodiments, emission light from a particular fluorescent label may have a characteristic intensity such that analyzing intensity information of emission light may facilitate identification of one or more chemical characteristics of the polypeptide.

In some embodiments, the at least one characteristic of the series of signal pulses comprises wavelength (e.g., average wavelength of the series of signal pulses). Wavelength of the emission light may be determined in any suitable manner, for example by using one or more optical filters and/or photodetection regions disposed at different depths. In some embodiments, emission light from a particular fluorescent label may have a characteristic wavelength such that analyzing wavelength information of emission light may facilitate identification of one or more chemical characteristics of the polypeptide.

In some embodiments, the at least one characteristic of the series of signal pulses comprises fluorescence lifetime (e.g., average fluorescence lifetime of the series of signal pulses). In some embodiments, fluorescent labels, when excited by incident excitation light, fluoresce with a characteristic lifetime (e.g., a characteristic emission decay time period), such that analyzing the lifetime information of emission light may facilitate identification of one or more chemical characteristics of the polypeptide. Fluorescence lifetime, also referred to herein as simply "lifetime", is a measure of the time which a fluorescent dye spends in the excited state before returning to a ground state and emitting a photon. In some embodiments, fluorescence lifetime information and/or other timing characteristics described herein may be obtained through techniques for time binning charge carriers generated by photons incident on a photodetection region (e.g., a photodiode).

In some embodiments, the at least one characteristic of the series of signal pulses comprises pulse duration (e.g., average pulse duration), also referred to herein as pulse width. Pulse duration refers to the interval of time measured across a pulse. In some embodiments, pulse width is measured at the full width half maximum of a pulse. As described herein, dye-labeled amino acid recognizers periodically bind and unbind to the polypeptide (e.g., to an amino acid of the polypeptide). When bound, the dye-labeled amino acid recognizers may become excited and emit emission light. The average duration of respective signal pulses emitted by the dye-labeled amino acid recognizers comprise the pulse duration of the fluorescent label. In certain embodiments, for example, at least one characteristic of a first series of signal pulses comprises a first pulse duration, and the first pulse duration comprises an average duration of respective pulses of the first series of signal pulses.

In some embodiments, the at least one characteristic of the series of signal pulses comprises interpulse duration (e.g., average interpulse duration). Interpulse duration, also referred to herein as interpulse width, refers to the interval of time between adjacent pulses. As described herein, dye-labeled amino acid recognizers periodically bind and unbind to the polypeptide (e.g., to an amino acid of the polypeptide). When bound, the dye-labeled amino acid recognizers may become excited and emit emission light. The average durations between signal pulses emitted by the fluorescent label comprise the interpulse duration of the fluorescent label. In certain embodiments, for example, at least one characteristic of a first series of signal pulses comprises a first interpulse duration, and the first interpulse duration comprises an average duration between respective pulses of the first series of signal pulses.

In some embodiments, the at least one characteristic of the series of signal pulses comprises recognition segment (RS) duration. A recognition segment generally refers to a series of signal pulses indicative of a series of binding events between a type of amino acid recognizer (e.g., one or more molecules of the type of amino acid recognizer) and one or more amino acids of a polypeptide. In some cases, for example, a first recognition segment comprises a first series of signal pulses indicative of a series of binding events between a first set of one or more amino acid recognizers and a first amino acid of a polypeptide (and, in some cases, one or more additional amino acids). In some cases, a second recognition segment comprises a second series of signal pulses indicative of a series of binding events between a second set of one or more amino acid recognizers and a second amino acid of the polypeptide (and, in some cases, one or more additional amino acids). A recognition segment duration generally refers to a length of time during which a series of signal pulses is received (i.e., a duration of the recognition segment). In some cases, for example, the first recognition segment may have a first recognition segment duration comprising a length of time during which the first series of signal pulses is received. In some cases, the second recognition segment may have a second recognition segment duration comprising a length of time during which the second series of signal pulses is received.

In some embodiments, the at least one characteristic of the series of signal pulses comprises an intersegment duration. Intersegment duration generally refers to a duration of time between two recognition segments. In certain embodiments, for example, a first intersegment duration comprises a length of time between a first recognition segment and a second recognition segment. The first and second recognition segments may have different characteristics, as described herein, which may allow the recognition segments to be distinguished from each other.

In some embodiments, the at least one characteristic of the series of signal pulses comprises a cleavage rate (e.g., an average cleavage rate) and/or a cleavage time. In some embodiments, for example, a terminal amino acid of the polypeptide disposed in the reaction chamber is cleaved from the polypeptide. In certain embodiments, cleaving the terminal amino acid is performed by exposing the polypeptide to a cleaving agent (e.g., one or more aminopeptidases). In some embodiments, the cleaving agent may be included in the same solution as the amino acid recognizers. Cleavage of an amino acid (e.g., a terminal amino acid) from the polypeptide may be referred to as a cleavage event. A cleavage rate may refer to a number of cleavage events per unit time. A cleavage time may refer to a length of time between cleavage events. In some embodiments, cleavage events may be determined by observing a change from a recognition segment to another recognition segment (e.g., based on different characteristics of the recognition segments), a change from a recognition segment to a non-recognition segment (i.e., a segment during which signal pulses are not received), and/or a change from a non-recognition segment to a recognition segment.

In some embodiments, the at least one characteristic comprises an absence of signal pulses at one or more reference time points. As an illustrative example, a polypeptide may have an expected sequence comprising a first amino acid to which a first amino acid recognizer preferentially binds. In certain embodiments, the expected series of binding events between the first amino acid and the first amino acid recognizer may not occur, and there may be an absence of signal pulses at one or more reference time points. In some cases, the absence of signal pulses may indicate the presence of a modification (e.g., a post-translational modification of the first amino acid, a mutation relative to a wild type protein, a bond to a binding component).

One or more of the characteristics of the series of signal pulses may be used to determine at least one chemical characteristic of a first set of at least two amino acids of the polypeptide. In some embodiments, the first set of at least two amino acids includes the terminal amino acid and at least one downstream amino acid of the polypeptide. In some embodiments, the first set of at least two amino acids includes an internal amino acid and at least one upstream and/or downstream amino acid of the polypeptide. In some embodiments, the at least two amino acids of the polypeptide comprise the amino acid to which the dye-labeled recognizers bind and at least one other amino acid (e.g., one or more upstream and/or downstream amino acids). In some embodiments, the first set of at least two amino acids does not consist of a terminal amino acid and a penultimate amino acid of the polypeptide (i.e., a terminal amino acid and an immediately adjacent amino acid). In some embodiments, the at least two amino acids comprise at least three amino acids, at least four amino acids, at least five amino acids, at least ten amino acids, at least fifteen amino acids, at least twenty amino acids, at least fifty amino acids, or at least one hundred amino acids. In some embodiments, the at least two amino acids comprise two amino acids, three amino acids, four amino acids, five amino acids, ten amino acids, fifteen amino acids, twenty amino acids, fifty amino acids, one hundred amino acids, etc. In some embodiments, the at least two amino acids comprise 2-3 amino acids, 2-4 amino acids, 2-5 amino acids, 2-10 amino acids, 2-15 amino acids, 2-20 amino acids, 2-50 amino acids, 2-100 amino acids, 3-5 amino acids, 3-10 amino acids, 3-15 amino acids, 3-20 amino acids, 3-50 amino acids, 3-100 amino acids, 5-10 amino acids, 5-15 amino acids, 5-20 amino acids, 5-50 amino acids, 5-100 amino acids, 10-15 amino acids, 10-20 amino acids, 10-50 amino acids, 10-100 amino acids, 20-50 amino acids, 20-100 amino acids, or 50-100 amino acids.

In some embodiments, the at least one chemical characteristic comprises an identity of an amino acid (e.g., an identity of one or more of the first set of at least two amino acids). In some embodiments, the at least one chemical characteristic may be used to determine an identity of one or more of the first set of at least two amino acids.

In some embodiments, the at least one chemical characteristic comprises a structural characteristic of an amino acid, including a structural characteristic of one or more of the first set of at least two amino acids (e.g., whether the amino acid comprises a modification, what type of modification the amino acid comprises). In some embodiments, the modification comprises a post-translational modification, an unnatural modification, an oxidative modification, a cross-linking modification, and/or a chemical modification. In some embodiments, the modification comprises one or more mutations relative to a wild type protein. In some embodiments, the modification comprises one or more insertions relative to a wild type protein. In some embodiments, the modification comprises one or more deletions relative to a wild type protein. In some embodiments, the modification comprises a covalent or non-covalent bond to a binding component (e.g., a nucleic acid, a linker, an antibody). In some embodiments, the modification affects the at least one characteristic of the first series of signal pulses (e.g., pulse duration, interpulse duration, recognition segment duration, intersegment duration, cleavage rate, cleavage time, intensity, wavelength, fluorescence lifetime, absence of signal pulses, whether an amino acid is recognized). The impact of the modification on the at least one characteristic of the first series of signal pulses allows the modification to be identified based on the first series of signal pulses.

Accordingly, in some embodiments, determining at least one chemical characteristic of a polypeptide comprises identifying one or more amino acids of a polypeptide. In some embodiments, identifying an amino acid comprises determining which of the naturally-occurring 20 amino acids is present. In some embodiments, the identity of an amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, determining at least one chemical characteristic of a first set of at least two amino acids of the polypeptide comprises identifying at least one (and, in some embodiments, each) amino acid of the first set of at least two amino acids.

In some embodiments, determining at least one chemical characteristic of a polypeptide comprises determining a subset of potential amino acids that can be present in the polypeptide. In some embodiments, this can be accomplished by determining that an amino acid is not one or more specific amino acids (and therefore could be any of the other amino acids). In some embodiments, this can be accomplished by determining which of a specified subset of amino acids (e.g., based on size, charge, hydrophobicity, post-translational modification, binding properties) could be in the polypeptide (e.g., using a recognizer that binds to a specified subset of two or more amino acids). In some embodiments, determining at least one chemical characteristic of a first set of at least two amino acids of the polypeptide comprises determining that at least one (and, in some embodiments, each) amino acid of the first set of at least two amino acids is not one or more specific amino acids.

In some embodiments, determining at least one chemical characteristic of a polypeptide comprises determining that an amino acid of the polypeptide comprises a post-translational modification. The post-translational modification may affect the series of signals emitted by a dye-labeled amino acid recognizer bound to the polypeptide (e.g., to a terminal amino acid and/or an internal amino acid). In some embodiments, the series of signals emitted by the dye-labeled amino acid recognizer may be impacted by the post-translational modification even if the post-translational modification is to an amino acid which does not bind to the dye-labeled amino acid recognizer. In some embodiments, a post-translational modification of an amino acid to which a dye-labeled recognizer binds and/or a post-translational modification of one or more upstream or downstream amino acids may cause at least one characteristic of a series of signal pulses (e.g., pulse duration, interpulse duration, recognition segment duration, intersegment duration, cleavage rate, cleavage time, intensity, wavelength, fluorescence lifetime, absence of signal pulses) to change (e.g., increase, decrease) relative to an unmodified amino acid. Non-limiting examples of post-translational modifications include acetylation (e.g., acetylated lysine), ADP-ribosylation, caspase cleavage, citrullination, formylation, N-linked glycosylation (e.g., glycosylated asparagine), 0-linked glycosylation (e.g., glycosylated serine, glycosylated threonine), hydroxylation, methylation (e.g., methylated lysine, methylated arginine), myristoylation (e.g., myristoylated glycine), neddylation, nitration (e.g., nitrated tyrosine), chlorination (e.g., chlorinated tyrosine), oxidation/reduction (e.g., oxidized cysteine, oxidized methionine), carbonylation (e.g., carbonylated lysine, carbonylated proline, carbonylated arginine, carbonylated threonine), palmitoylation (e.g., palmitoylated cysteine), phosphorylation, prenylation (e.g., prenylated cysteine), S-nitrosylation (e.g., S-nitrosylated cysteine, S-nitrosylated methionine), sulfation (e.g., sulfated tyrosine), glycation (e.g., glycated lysine), sumoylation (e.g., sumoylated lysine), and ubiquitination (e.g., ubiquitinated lysine).

In some embodiments, determining at least one chemical characteristic of a polypeptide comprises determining that an arginine residue of the polypeptide comprises a post-translational modification. For example, as described herein, amino acid recognizers of the disclosure are capable of distinguishing between different arginine modifications, including symmetric dimethylarginine (SDMA), asymmetric dimethylarginine (ADMA), and citrulline (also referred to as citrullinated arginine). In some embodiments, determining at least one chemical characteristic of a first set of at least two amino acids of the polypeptide comprises determining that at least one amino acid of the first set of at least two amino acids is a post-translationally modified arginine (e.g., SDMA, ADMA, citrulline).

In some embodiments, determining at least one chemical characteristic of a polypeptide comprises determining that an amino acid of the polypeptide comprises a phosphorylated side chain. For example, in some embodiments, determining at least one chemical characteristic of a polypeptide comprises determining that the polypeptide comprises a phosphorylated threonine (e.g., phospho-threonine). In some embodiments, determining at least one chemical characteristic of a polypeptide comprises determining that the polypeptide comprises a phosphorylated tyrosine (e.g., phospho-tyrosine). In some embodiments, determining at least one chemical characteristic of a polypeptide comprises determining that the polypeptide comprises a phosphorylated serine (e.g., phospho-serine). In some embodiments, determining at least one chemical characteristic of a first set of at least two amino acids of the polypeptide comprises determining that at least one (and, in some embodiments, each) amino acid of the first set of at least two amino acids comprises a phosphorylated side chain. In certain embodiments, determining at least one chemical characteristic of a first set of at least two amino acids of the polypeptide comprises determining that at least one (and, in some embodiments, each) amino acid of the first set of at least two amino acids is a phosphorylated threonine, a phosphorylated tyrosine, and/or a phosphorylated serine.

In some embodiments, determining at least one chemical characteristic of a polypeptide comprises determining that the polypeptide comprises a chemically modified variant of an amino acid, an unnatural amino acid, and/or a proteinogenic amino acid (e.g., selenocysteine, pyrrolysine). Examples of unnatural amino acids include, without limitation, 2-naphthyl-alanine, statine, homoalanine, a-amino acid, β2-amino acid, β3-amino acid, γ-amino acid, 3-pyridyl-alanine, 4-fluorophenyl-alanine, cyclohexyl-alanine, N-alkyl amino acid, peptoid amino acid, homo-cysteine, penicillamine, 3-nitro-tyrosine, homo-phenyl-alanine, t-leucine, hydroxy-proline, 3-Abz, 5-F-tryptophan, and azabicyclo-[2.2.1]heptane. In certain embodiments, determining at least one chemical characteristic of a first set of at least two amino acids of the polypeptide comprises determining that at least one (and, in some embodiments, each) amino acid of the first set of at least two amino acids is a chemically modified variant of an amino acid, an unnatural amino acid, and/or a proteinogenic amino acid.

In some embodiments, determining at least one chemical characteristic of a polypeptide comprises determining that an amino acid of the polypeptide comprises an oxidative modification. For example, as described herein, amino acid recognizers of the disclosure are capable of distinguishing between oxidized methionine and its unmodified variant. In some embodiments, the oxidative modification comprises an oxidatively-damaged side chain of an amino acid. In some embodiments, the oxidatively-damaged side chain comprises a cysteine-derived product (e.g., disulfide, sulfinic acid, sulfonic acid, sulfenic acid, S-nitrosocysteine), a tyrosine-derived product (e.g., di-tyrosine, 3,4-dihydroxyphenylalanine, 3-chlorotyrosine, 3-nitrotyrosine), a histidine-derived product (e.g., 2-oxohistidine, 4-hydroxy-2-oxohistidine, di-histidine, asparagine, aspartic acid, urea), a methionine-derived product (e.g., sulfoxide, sulfone), a tryptophan-derived product (e.g., di-tryptophan, N-formylkynurenine, kynurenine, 2-oxo-tryptophan oxindolylalanine, 6-nitrotryptophan, hydroxytryptophan), a phenylalanine-derived product (e.g., meta-tyrosine, ortho-tyrosine), or a generic side-chain product (e.g., alcohol, hydroperoxide, aldehyde/ketone carbonyl). Examples of oxidatively damaged amino acids are known in the art, see, e.g., Hawkins, C. L., Davies, M. J. Detection, identification, and quantification of oxidative protein modifications. J Biol Chem. 2019 Dec. 20; 294(51):19683-19708. In certain embodiments, determining at least one chemical characteristic of a first set of at least two amino acids of the polypeptide comprises determining that at least one (and, in some embodiments, each) amino acid of the first set of at least two amino acids comprises an oxidative modification.

In some embodiments, determining at least one chemical characteristic of a polypeptide comprises determining that an amino acid of the polypeptide comprises a side chain characterized by one or more biochemical properties. For example, an amino acid may comprise a nonpolar aliphatic side chain, a positively charged side chain, a negatively charged side chain, a nonpolar aromatic side chain, or a polar uncharged side chain at physiological pH. Non-limiting examples of an amino acid comprising a nonpolar aliphatic side chain include alanine, glycine, valine, leucine, methionine, and isoleucine. Non-limiting examples of an amino acid comprising a positively charged side chain includes lysine, arginine, and histidine. Non-limiting examples of an amino acid comprising a negatively charged side chain include aspartate and glutamate. Non-limiting examples of an amino acid comprising a nonpolar, aromatic side chain include phenylalanine, tyrosine, and tryptophan. Non-limiting examples of an amino acid comprising a polar uncharged side chain include serine, threonine, cysteine, proline, asparagine, and glutamine.

In some embodiments, determining at least one chemical characteristic of a polypeptide comprises identifying one or more mutations relative to a wild type protein. Non-limiting examples of mutations include substitutions, insertions, and deletions. In certain embodiments, the one or more mutations comprise two or more, three or more, four or more, five or more, ten or more, fifteen or more, or twenty or more mutations. In certain embodiments, the one or more mutations comprise 2-3, 2-4, 2-5, 2-10, 2-15, 2-20, 3-4, 3-5, 3-10, 3-15, 3-20, 5-10, 5-15, 5-20, 10-15, 10-20, or 15-20 mutations. In some cases, determining at least one chemical characteristic of a first set of at least two amino acids of the polypeptide comprises determining that at least one (and, in some embodiments, each) amino acid of the first set of at least two amino acids has been mutated relative to a wild type protein.

In some embodiments, determining at least one chemical characteristic of a polypeptide comprises determining that at least one amino acid is bound (e.g., via a covalent or non-covalent interaction) to a binding component. Non-limiting examples of suitable binding components include a nucleic acid (e.g., DNA, RNA), a linker, and an antibody. In some instances, one or more amino acids of a polypeptide may be bound to a nucleic acid via one or more non-covalent interactions. In some instances, one or more amino acids of a polypeptide may be bound to a linker via one or more covalent interactions. In certain embodiments, determining at least one chemical characteristic of a first set of at least two amino acids of the polypeptide comprises determining that at least one (and, in some embodiments, each) amino acid of the first set of at least two amino acids is covalently or non-covalently bound to a binding component.

In some embodiments, one or more characteristics of a first series of signal pulses indicative of a first series of binding events between a first set of one or more amino acid recognizers and a first amino acid of a polypeptide (e.g., a terminal amino acid, an internal amino acid) may be impacted by one or more chemical characteristics of the polypeptide. In certain instances, one or more modifications of one or more amino acids (e.g., post-translational modifications, mutations, bonds to binding components) may promote a covalent or non-covalent interaction between one or more amino acid recognizers and the first amino acid (e.g., through electrostatic attraction, pi stacking, hydrogen bond formation, etc.), thereby increasing pulse duration. In certain instances, one or more modifications of one or more amino acids (e.g., post-translational modifications, mutations, presence of binding components) may discourage a covalent or non-covalent interaction between one or more amino acid recognizers and the first amino acid (e.g., through electrostatic repulsion, steric hindrance, etc.), thereby decreasing pulse duration.

In some embodiments, determining at least one chemical characteristic of the polypeptide may comprise comparing at least one characteristic of the series of signal pulses with known characteristics of known amino acid segments. For example, FIGS. 10A-10G illustrate known pulse durations for various amino acid segments. In illustrated embodiments, known pulse durations are shown for various tripeptide segments. Using a table such as those shown in FIGS. 10A-10G and determined characteristic(s) (e.g., pulse duration) from a series of signal pulses may allow for identification of an amino acid segment (e.g., a tripeptide segment, a tetrapeptide segment). A table of known characteristics of amino acid segments may be constructed by theoretical means, by simulation, empirically, or any combination thereof. The amino acid segments may have any length. In some embodiments, a table comprises known characteristics of amino acid segments having three amino acids, four amino acids, five amino acids, ten amino acids, fifteen amino acids, or twenty amino acids. In some embodiments, a table comprises known characteristics of amino acid segments having 3-4, 3-5, 3-10, 3-15, 3-20, 4-5, 4-10, 4-15, 4-20, 5-10, 5-15, 5-20, 10-15, 10-20, or 15-20 amino acids.

In some embodiments, a protein from which the polypeptide originated may be identified. For example, as described herein, the techniques may include identifying one of more of the amino acids of an amino acid segment (e.g., a tripeptide segment, a tetrapeptide segment). Based on the identified amino acids, a protein from which the polypeptide originated may be identified. For example, identifying the protein from which the polypeptide originated may comprise comparing the identified amino acids of the amino acid segment to known information. In some embodiments, identifying a protein from which the polypeptide originated may comprise identifying a pattern in the amino acid segment(s) also present in a candidate matching protein. The pattern may be unique to the candidate matching protein relative to other candidate matching proteins. Accordingly, the techniques described herein may allow for identifying a protein from which a polypeptide originated based on identifying only a portion of the amino acids of the polypeptide. In some embodiments, identifying a polypeptide comprises identifying a protein from which a polypeptide originated. In some embodiments, identifying a polypeptide comprises identifying a pattern of amino acids present in the polypeptide and identifying a candidate matching polypeptide comprising the pattern of amino acids.

The polypeptides described herein may be of any type. In some embodiments, the polypeptide comprises a fragment of a protein. In some embodiments, the polypeptide is derived from a biological source. In certain embodiments, the polypeptide is derived from digestion of one or more proteins present in a biological sample (e.g., a human sample, a non-human animal sample, a plant sample). In some embodiments, the polypeptide is a recombinant polypeptide. In some embodiments, the polypeptide is a synthetic polypeptide.

In some embodiments, a protein is present in a biological sample (e.g., blood, plasma, tissue, saliva, urine, or other biological source). In certain cases, the biological sample is obtained from a human subject or a non-human animal subject. In certain cases, the biological sample is obtained from a plant, fungus, virus, or bacterium. The protein may be a wild type or mutant protein. In some embodiments, the protein is a recombinant protein. In some embodiments, the protein is a synthetic protein.

In some embodiments, a protein is digested (e.g., by an enzymatic or chemical reagent) to produce a plurality of polypeptides. Non-limiting examples of suitable reagents for enzymatic and/or chemical digestion include Lys-C, Arg-C, Asp-N, Lys-N, trypsin, chemotrypsin, BNPS-Skatole, CNBr, caspase, formic acid, glutamyl endopeptidase, hydroxylamine, iodosobenzoic acid, neutrophil elastase, pepsin, proline-endopeptidase, proteinase K, staphylococcal peptidase I, thermolysin, and thrombin.

In some embodiments, a solution comprising a mixture of polypeptides may be introduced onto the integrated device. In some embodiments, a reaction chamber may receive at least one polypeptide. In some embodiments, a reaction chamber may receive at least two polypeptides (which may be different polypeptides). In some embodiments, a first polypeptide and a second polypeptide are disposed in different reaction chambers. Respective series of signals from each of the polypeptides may be obtained and used to obtain the at least one chemical characteristic of the amino acids described herein.

It should be appreciated that determining the at least one chemical characteristic of the first set of at least two amino acids may be based on multiple series of signal pulses, in some embodiments. For example, one or more amino acids of the at least two amino acids may be identified and/or otherwise characterized, as described herein, based on a first series of signal pulses (e.g., a series of signal pulses indicative of a series of binding events between one or more amino acid recognizers and a first amino acid) and at least one additional series of signal pulses (e.g., a series of signal pulses indicative of a series of binding events between one or more amino acid recognizers and a second amino acid). In some embodiments, the first series of signal pulses may be obtained when the one or more amino acids are in a first position in the chain of amino acids of the polypeptide (e.g., a position other than the terminal position) and the second series of signal pulses may be obtained when the one or more amino acids are in a second position in the chain of amino acids of the polypeptide (e.g., in the terminal position) different than the first position. In some embodiments, one or more additional series of signal pulses may be used to identify and/or otherwise characterize the at least two amino acids. Such techniques for multi-sampling the same amino acid(s) may ensure greater accuracy in identifying and/or otherwise characterizing the at least two amino acids.

In some embodiments, a method for determining chemical characteristics of a polypeptide (e.g., method 1200) further comprises detecting a second series of signal pulses indicative of a second series of binding events between a second set of one or more amino acid recognizers and the polypeptide. In some embodiments, the method further comprises determining at least one chemical characteristic of a second set of at least two amino acids of the polypeptide based on at least one characteristic of the second series of signal pulses. In certain embodiments, the method further comprises identifying the polypeptide based on the at least one chemical characteristic of the second set of at least two amino acids of the polypeptide. In certain embodiments, the method further comprises identifying the polypeptide based on at least one chemical characteristic of the first set of at least two amino acids and at least one chemical characteristic of the second set of at least two amino acids.

In certain embodiments, the second set of at least two amino acids of the polypeptide comprises at least one amino acid of the first set of at least two amino acids. As an illustrative example, a first set of at least two amino acids may comprise a first amino acid (e.g., a terminal amino acid), a second amino acid, and a third amino acid, and a second set of at least two amino acids may comprise the second amino acid, the third amino acid, and a fourth amino acid.

The at least one characteristic of the second series of signal pulses may comprise any characteristic described herein (e.g., pulse duration, interpulse duration, recognition segment duration, intersegment duration, cleavage rate, cleavage time, whether an amino acid is recognized). In some embodiments, the at least one characteristic of the second series of signal pulses comprises a second recognition segment duration (e.g., a length of time during which the second series of signal pulses is received).

In some embodiments, the at least one characteristic of the second series of signal pulses is based in part on at least one characteristic of the first series of signal pulses. In certain embodiments, the at least one characteristic of the second series of signal pulses comprises a first intersegment duration. In some cases, the first intersegment duration comprises a length of time between a first recognition segment during which the first series of signal pulses is received and a second recognition segment during which the second series of signal pulses is received. In certain embodiments, the at least one characteristic of the second series of signal pulses comprises an average of the first recognition segment duration and the second recognition segment duration. In certain embodiments, the at least one characteristic of the second series of signal pulses comprises an average of the first intersegment duration and a second intersegment duration. In some instances, the second intersegment duration comprises a length of time between the second recognition segment and a third recognition segment during which a third series of signal pulses indicative of a third series of binding events between a third set of one or more amino acid recognizers and the polypeptide is received.

The at least one chemical characteristic of the second set of at least two amino acids may comprise any chemical characteristic described herein. In certain embodiments, determining the at least one chemical characteristic of the second set of at least two amino acids comprises identifying at least one (and, in some cases, each) amino acid of the second set of at least two amino acids. In certain embodiments, determining the at least one chemical characteristic of the second set of at least two amino acids comprises identifying a modification of at least one (and, in some cases, each) amino acid of the second set of at least two amino acids. In some instances, the modification comprises a post-translational modification, an unnatural modification, an oxidative modification, a crosslinking modification, and/or a chemical modification. In some instances, the modification comprises one or more mutations relative to a wild type protein. In some instances, the modification comprises a covalent or non-covalent bond between the at least one amino acid and a binding component (e.g., a nucleic acid, a linker, an antibody).

As described herein, the inventors have recognized characteristics of signal pulses are impacted by not only the amino acid to which a dye-labeled amino acid recognizer is bound, but also by one or more upstream and/or downstream amino acids, which may or may not be bound to the dye-labeled amino acid recognizer. Accordingly, in some embodiments, signals from one or more series of signal pulses may be used to determine chemical characteristics regarding a number of amino acids greater than the number of series of signal pulses used. In some embodiments, at least one of the amino acids may be unrecognized (e.g., unrecognizable) by any amino acid recognizers present in a reaction chamber, meaning no signal pulses which would otherwise result from a dye-labeled amino acid recognizer bound to the amino acid are obtained. Although at least one of the amino acids is unrecognized, information regarding the amino acid may still be obtained from other series of signal pulses.

Figure 12B:
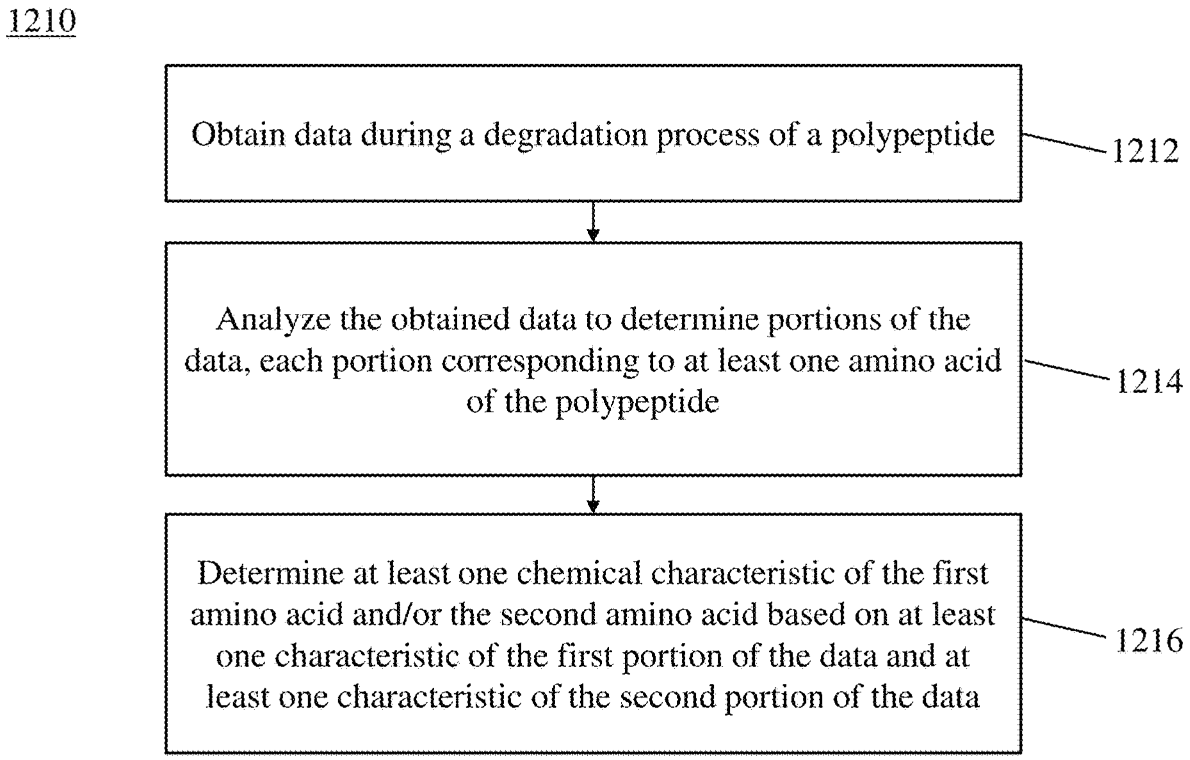

FIG. 12B shows an example method 1210 for determining chemical characteristics of a polypeptide where one or more amino acids of the polypeptide are unrecognizable. Method 1210 may begin at act 1212 wherein data is obtained during a degradation process of a polypeptide. In some embodiments, the data may comprise at least one series of signal pulses indicative of a series of binding events between the polypeptide and one or more amino acid recognizers. In some embodiments, the series of binding events may be between the one or more amino acid recognizers and at least one amino acid of the polypeptide (e.g., a terminal amino acid exposed at a terminus of the polypeptide, an internal amino acid). The data may be obtained according to any of the techniques described herein.

At act 1214, the obtained data may be analyzed to determine portions of the data. Each of the determined portions of the data may comprise a recognition segment, as described herein. For example, each of the determined portions of the data may correspond to an amino acid of the polypeptide during the degradation process (e.g., an amino acid exposed at a terminus of the polypeptide during the degradation process). The data may comprise at least one recognition segment and at least one non-recognition segment (e.g., a period of time where a series of pulse segments is expected to be received but is not, due to, for example, an amino acid at the terminus of the polypeptide being unrecognized). In some embodiments, the data may comprise a first portion corresponding to a first amino acid of the polypeptide. In certain embodiments, the first portion of the data may comprise a first plurality of signal pulses indicative of a series of binding events between a first type of amino acid recognizer and the first amino acid. In some embodiments, the data may comprise a second portion corresponding to a second amino acid of the polypeptide. In certain embodiments, the second portion of the data may not comprise signal pulses indicative of binding events between any type of amino acid recognizer and the second amino acid (e.g., due to the second amino acid being unrecognizable by the one or more amino acid recognizers).

At act 1216, at least one chemical characteristic of the first amino acid and/or the second amino acid may be determined based on at least one characteristic of the first portion of the data and at least one characteristic of the second portion of the data. The at least one characteristic of the respective portions of the data may comprise any of the characteristics described herein (e.g., pulse duration, interpulse duration, recognition segment duration, intersegment duration, cleavage rate, cleavage time, intensity, wavelength, fluorescence lifetime, absence of signal pulses, whether an amino acid is recognized). In some embodiments, the at least one characteristic of the second portion of the data comprises a duration of the second portion of data (e.g., a duration in which there is a lack of signal pulses). The at least one chemical characteristic of the respective amino acids may comprise any of the chemical characteristics described herein (e.g., identity, structural modification, presence of a binding component). In certain embodiments, the at least one chemical characteristic of the first amino acid and/or the second amino acid comprises an identity of the first amino acid and/or the second amino acid. In certain embodiments, the at least one chemical characteristic comprises a modification (e.g., a post-translational modification, a mutation, a bond to a binding component) of the first amino acid and/or the second amino acid. In some embodiments, act 1216 comprises determining at least one chemical characteristic of each of the first amino acid and the second amino acid.

Figure 12C:
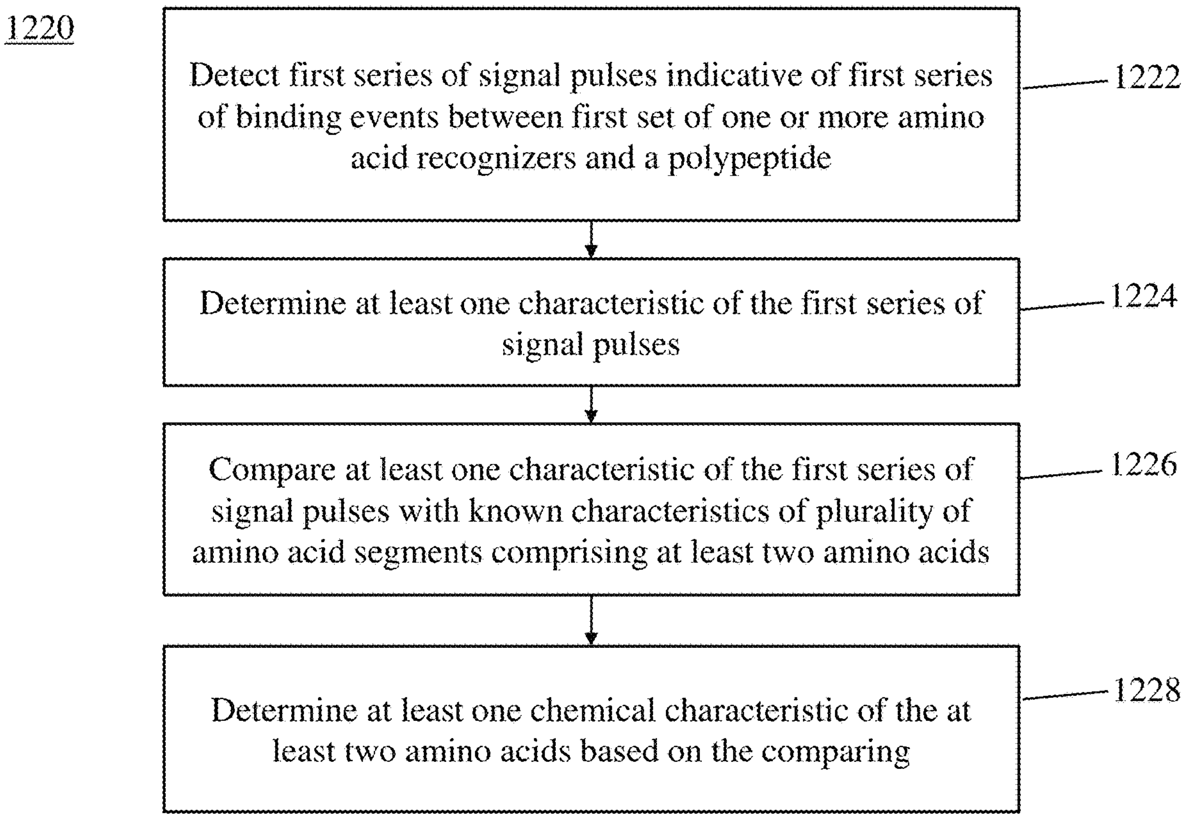

As described herein, the techniques described herein may be used for identifying characteristics of amino acids based on known information. FIG. 12C shows an example method 1220 for determining chemical characteristics of a polypeptide. Method 1220 may begin at act 1222 where a first series of signal pulses is detected. The first series of signal pulses may be indicative of a first series of binding events between a first set of one or more amino acid recognizers and the polypeptide. In some embodiments, the first series of signal pulses are indicative of a first series of binding events between the first set of one or more amino acid recognizers and an amino acid of the polypeptide (e.g., a terminal amino acid, an internal amino acid).

At act 1224, at least one characteristic of the first series of signal pulses may be determined. For example, any of the characteristics of signal pulses described herein (e.g., pulse duration, interpulse duration, recognition segment duration, intersegment duration, cleavage rate, cleavage time, intensity, wavelength, fluorescence lifetime, absence of signal pulses, whether an amino acid is recognized) may be determined at act 1224.

At act 1226, the at least one characteristic of the first series of signal pulses may be compared with known characteristics of a plurality of amino acid segments that comprise at least two amino acids. For example, the "heat maps" shown in FIGS. 10A-10G illustrate known pulse durations for different known tripeptide segments. Act 1226 may be performed using a table such as those shown in FIGS. 10A-10G to compare at least one characteristic of the first series of signal pulses with known characteristics of a plurality of amino acid segments (e.g., tripeptide segments, tetrapeptide segments). The table of known characteristics of a plurality of amino acid segments may be constructed by theoretical means, by simulation, empirically, or any combination thereof. The amino acid segments of the plurality of amino acid segments may have any suitable length. In some embodiments, one or more (and, in some cases, all) of the amino acid segments of the plurality of amino acid segments have a length of at least three amino acids, at least four amino acids, at least five amino acids, at least ten amino acids, at least fifteen amino acids, or at least twenty amino acids. In some embodiments, one or more (and, in some cases, all) of the amino acid segments of the plurality of amino acid segments have a length of three amino acids, four amino acids, five amino acids, ten amino acids, fifteen amino acids, or twenty amino acids. In some embodiments, one or more of the at least two amino acids of the amino acid segments are contiguous. In some embodiments, one or more of the at least two amino acids of the amino acid segments are non-contiguous (e.g., separated by one or more amino acids).

At act 1228, at least one chemical characteristic of at least two amino acids of the polypeptide may be determined based on the comparing. For example, any of the chemical characteristics described herein may be determined (e.g., identities of the amino acids, identities or presence of modifications). In some embodiments, determining at least one chemical characteristic of the at least two amino acids comprises identifying at least one (and, in some cases, both) of the at least two amino acids. In some embodiments, determining at least one chemical characteristic of the at least two amino acids comprises identifying a modification (e.g., a post-translational modification, a mutation, a bond to a binding component) of at least one (and, in some cases, both) of the at least two amino acids. The comparing may be performed according to any of the techniques described herein. For example, the comparing may be performed using an algorithm or by manual comparison. In some embodiments, the method may further comprise identifying a protein from which the polypeptide originated based on the determined chemical characteristics.

In some embodiments, additional series of signal pulses may be obtained. For example, the method may further comprise detecting a second series of signal pulses indicative of a second series of binding events between a second set of one or more amino acid recognizers and the polypeptide. In certain embodiments, the second series of signal pulses may be indicative of a second series of binding events between the second set of one or more amino acid recognizers and a subsequent amino acid of the polypeptide (e.g., a second amino acid which becomes the terminal amino acid after cleaving the initial terminal amino acid). In some embodiments, at least one characteristic of the second series of signal pulses may be determined and compared to known characteristics of the plurality of amino acid segments. The at least one chemical characteristic of the amino acids may be determined based on the respective one or more characteristics of the first series of signal pulses and the second series of signal pulses.

Figure 12D:
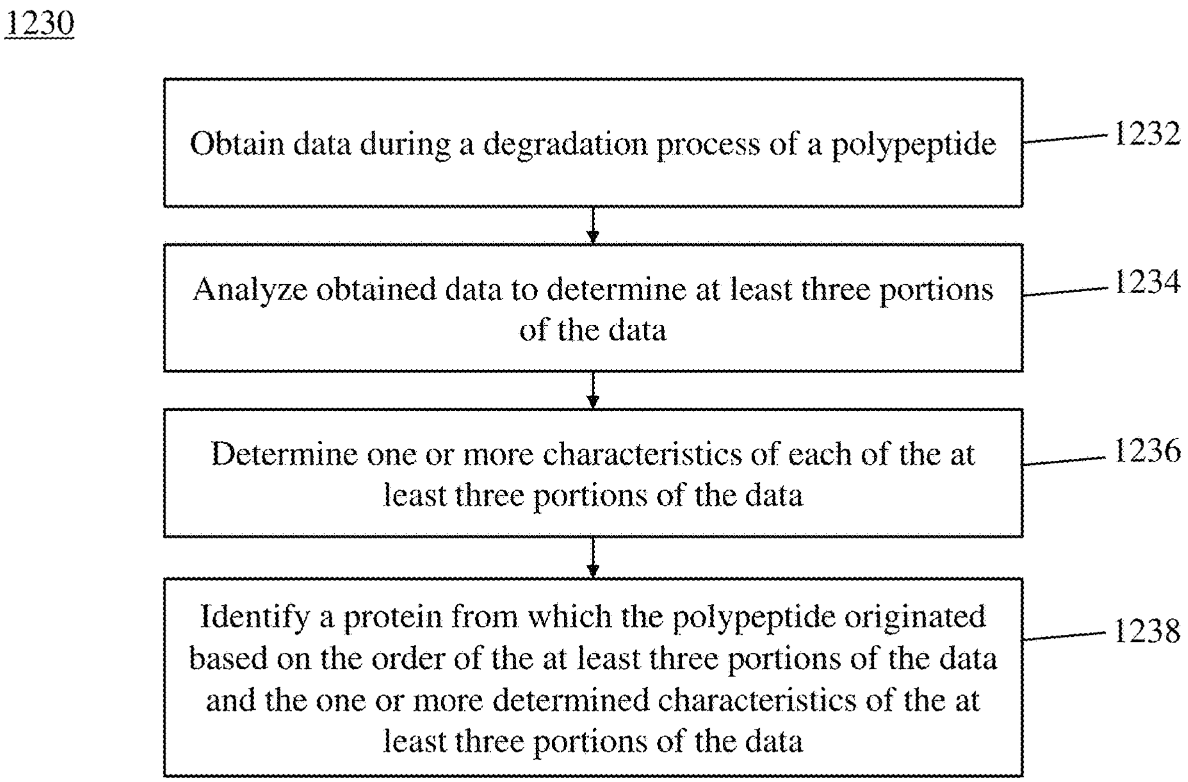

FIG. 12D shows an example method 1230 for identifying a protein from which a polypeptide originated based on a pulse pattern including at least three recognition segments. Method 1230 may begin at 1232 where data is obtained during a degradation process of the polypeptide. The data may comprise series of signal pulses indicative of respective binding events with at least three amino acids (e.g., at least three recognition segments).

At act 1234, the data may be analyzed to determine at least three portions of the data. In some embodiments, each portion corresponds to an amino acid of the polypeptide and comprises a plurality of signal pulses indicative of a series of binding events between one or more amino acid recognizers and the amino acid. For example, in certain embodiments, a first portion of the data comprises a first recognition segment and corresponds to a first amino acid. In some embodiments, the first portion of the data comprises a plurality of signal pulses indicative of a series of binding events between one or more amino acid recognizers and the first amino acid. In certain embodiments, a second portion of the data comprises a second recognition segment and corresponds to a second amino acid. In some embodiments, the second portion of the data comprises a plurality of signal pulses indicative of a series of binding events between one or more amino acid recognizers and the second amino acid. In certain embodiments, a third portion of the data comprises a third recognition segment and corresponds to a third amino acid. In some embodiments, the third portion of the data comprises a plurality of signal pulses indicative of a series of binding events between one or more amino acid recognizers and the third amino acid. In some cases, the first amino acid is an amino acid exposed at the terminal of the polypeptide during the degradation process. In some cases, the first amino acid is an internal amino acid.

At act 1236, one or more characteristics of each of the at least three portions of the data may be determined. The one or more characteristics may comprise any of the characteristics described herein (e.g., pulse duration, interpulse duration, recognition segment duration, intersegment duration, cleavage rate, cleavage time, intensity, wavelength, fluorescence lifetime, absence of signal pulses, whether an amino acid is recognized, etc.).

At act 1238, a protein from which the polypeptide originated may be identified based on the order of the at least three portions of the data and the one or more characteristics of each of the at least three portions of the data. For example, the one or more characteristics of the at least three portions of the data may be used to identify at least three amino acids of the polypeptide. The identities of the at least three amino acids may be used, according to the techniques described herein, for example, to identify a protein from which the polypeptide originated. In some embodiments, the at least three portions of the data comprise at least four portions, at least five portions, at least six portions, at least seven portions, at least eight portions, at least nine portions, at least ten portions, at least fifteen portions, at least twenty portions, or at least fifty portions of the data. In certain embodiments, the at least three portions of the data comprise 3-4 portions, 3-5 portions, 3-10 portions, 3-15 portions, 3-20 portions, 3-50 portions, 5-10 portions, 5-15 portions, 5-20 portions, 5-50 portions, 10-15 portions, 10-20 portions, 10-50 portions, or 20-50 portions of the data.

Figure 12E:
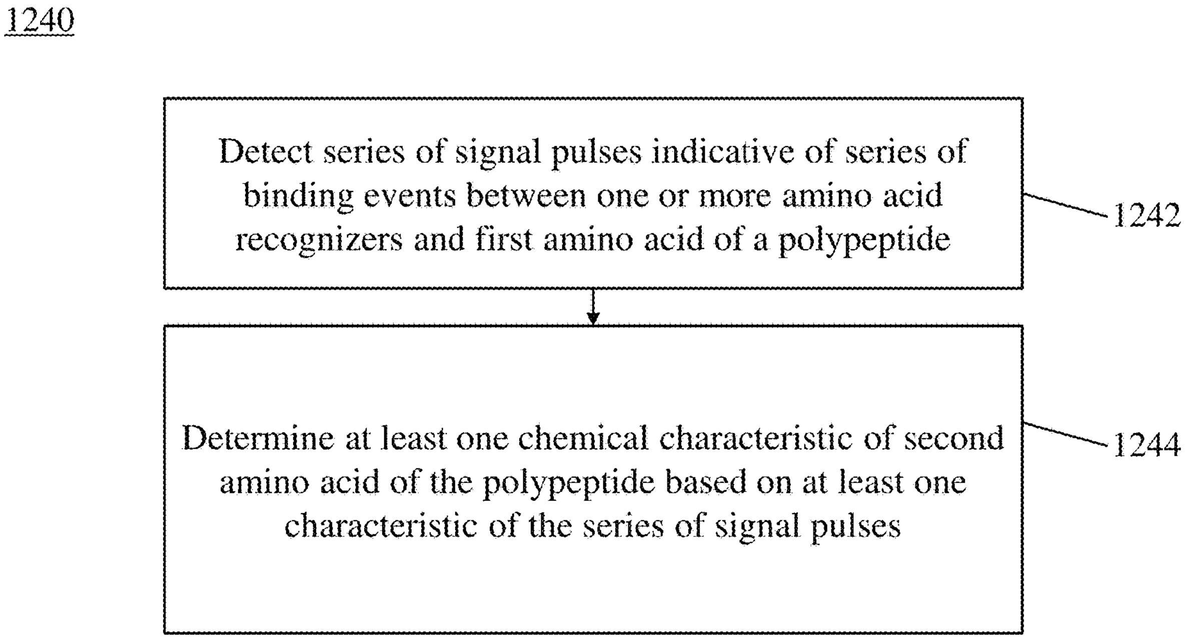

FIG. 12E shows an example method 1240 of characterizing a second amino acid based on a pulse pattern emitted by one or more amino acid recognizers bound to a first amino acid. The method 1240 may begin at act 1242 where a series of signal pulses indicative of a series of binding events between one or more amino acid recognizers and a first amino acid of a polypeptide is detected. Detecting the series of signal pulses may be performed in accordance with any of the techniques described herein.

At act 1244, at least one characteristic of the series of signal pulses may be used to determine at least one chemical characteristic of a second amino acid of the polypeptide. The at least one characteristic of the series of signal pulses may be any characteristic described herein (e.g., pulse duration, interpulse duration, recognition segment duration, intersegment duration, cleavage rate, cleavage time, intensity, wavelength, fluorescence lifetime, absence of signal pulses, whether an amino acid is recognized). The at least one chemical characteristic of the second amino acid may be any chemical characteristic described herein. Accordingly, signals obtained based on binding of one or more amino acid recognizers to a first amino acid of a polypeptide may be used to identify (or otherwise characterize) a second amino acid of the polypeptide. The inventors have recognized that such a technique is especially beneficial in instances where the second amino acid is unrecognizable (e.g., by the one or more amino acid recognizers).

In some embodiments, determining the at least one chemical characteristic of the second amino acid comprises identifying the second amino acid. In some embodiments, determining the at least one chemical characteristic of the second amino acid comprises identifying a modification of the second amino acid (e.g., a post-translational modification, a mutation, a bond to a binding component).

The polypeptide may comprise a chain of amino acids including the first and second amino acids. In some embodiments, the second amino acid is downstream of the first amino acid. In some embodiments, the second amino acid is upstream of the first amino acid. In some embodiments, the second amino acid is contiguous (e.g., adjacent) to the first amino acid. In some embodiments, the second amino acid is separated from the first amino acid in the chain of amino acids by at least one amino acid (e.g., a third amino acid). In some embodiments, the second amino acid is separated from the first amino acid by at least five amino acids, at least ten amino acids, at least fifteen amino acids, or at least 20 amino acids. In some embodiments, the second amino acid is separated from the first amino acid by five amino acids or fewer.

Figure 12F:
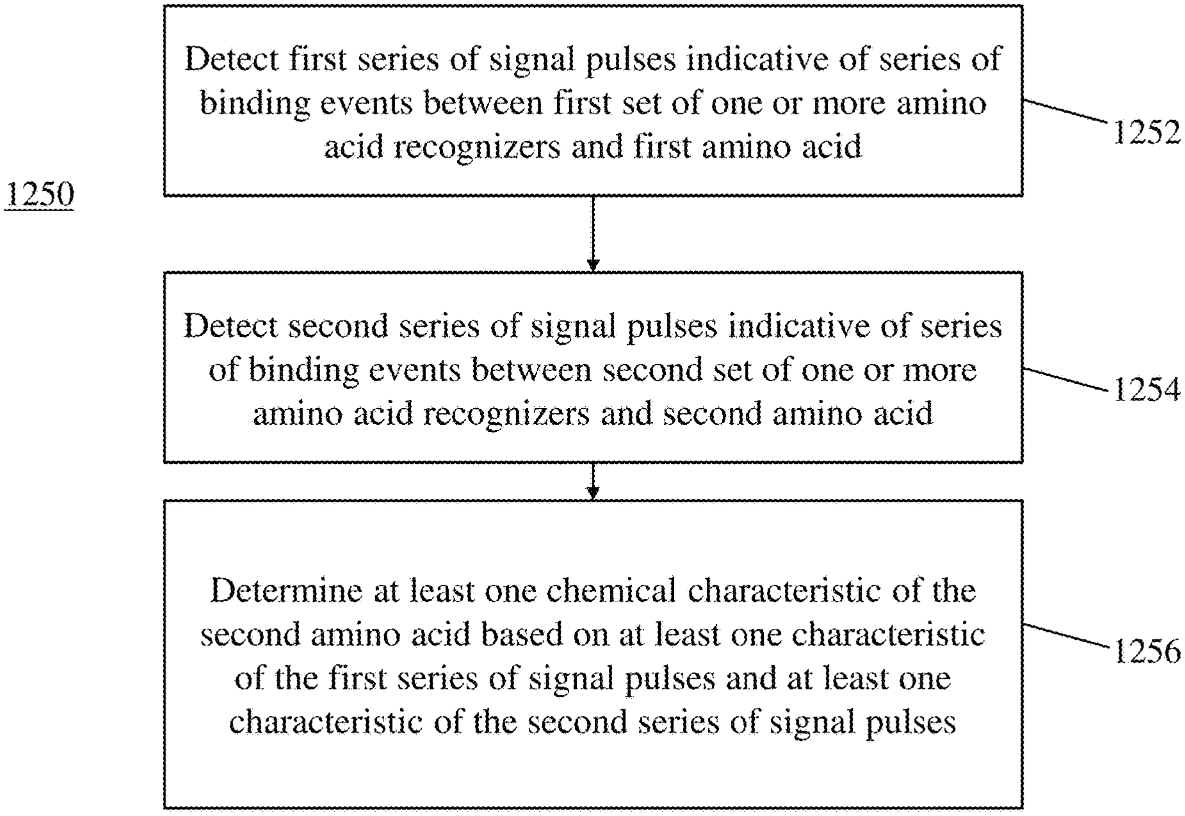

FIG. 12F shows an example method 1250 for determining at least one chemical characteristic of an amino acid of a polypeptide. Method 1250 may begin at act 1252 where a first series of signal pulses indicative of a first series of binding events between a first set of one or more amino acid recognizers and a first amino acid of a polypeptide are detected. Detecting the first series of signal pulses may be performed in accordance with any of the techniques described herein.

At act 1254, a second series of signal pulses indicative of a second series of binding events between a second set of amino acid recognizers and a second amino acid of the polypeptide may be detected. Detecting the second series of signal pulses may be performed in accordance with any of the techniques described herein.

At act 1256, at least chemical characteristic of the second amino acid may be determined based on at least one characteristic of the first series of signal pulses and at least one characteristic of the second series of signal pulses. As described herein, the inventors have recognized that multi-sampling of signal pulses for an amino acid may be advantageous. For example, multi-sampling may advantageously enhance accuracy of identification and/or other characterization of an amino acid. At act 1256, at least one chemical characteristic of the second amino acid may be determined based on at least one characteristic from each of two signal pulses. The at least one characteristic of the respective series of signal pulses may be the same, in some embodiments, or different, in other embodiments. The characteristic of the series of signal pulses may be any of the characteristics described herein, including but not limited to pulse duration, interpulse duration, recognition segment duration, intersegment duration, cleavage rate, cleavage time, intensity, wavelength, fluorescence lifetime, absence of signal pulses, whether an amino acid is recognized, or any other characteristic.

In some embodiments, additional series of signal pulses may be used. For example, in some embodiments, a third series of signal pulses indicative of a series of binding events between a third set of one or more amino acid recognizers and a third amino acid of the polypeptide may be detected. Determining the at least one chemical characteristic of the second amino acid may be based on at least one characteristic of each of the first, second, and third series of signal pulses.

Figure 12G:
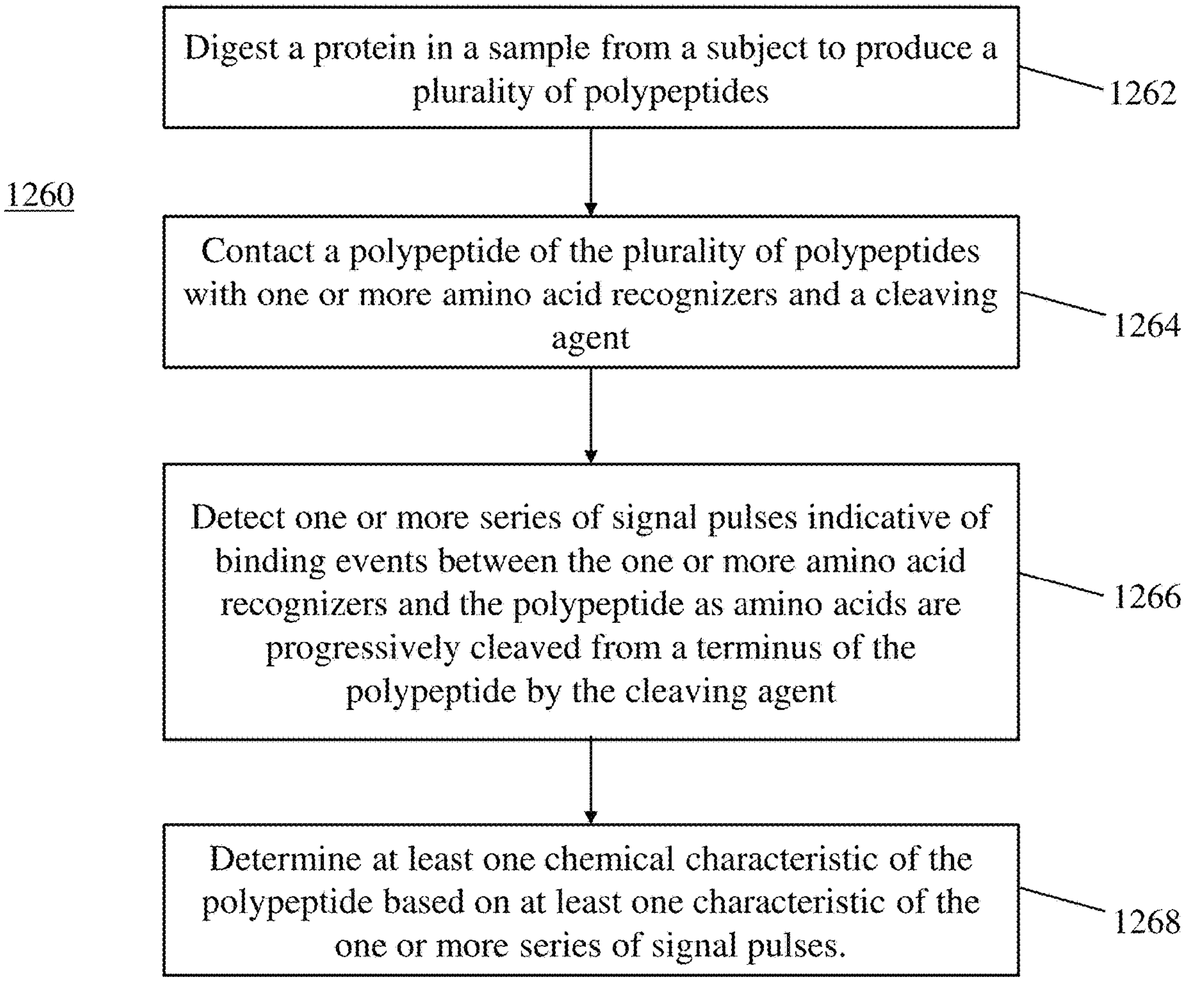

FIG. 12G shows an example method 1260 of identifying a disease or disorder in a subject. In some embodiments, the subject is a human subject. In some embodiments, the subject is a non-human animal subject.

The method 1260 may begin at act 1262 where a protein in a sample from a subject may be digested to produce a plurality of polypeptides. The protein may be any protein. Examples of a protein of interest include, but are not limited to, vimentin and a β-amyloid protein. Digesting the protein may be performed in accordance with any of the enzymatic and/or chemical techniques described herein.

At act 1264, a polypeptide of the plurality of polypeptides may be contacted with one or more amino acid recognizers and a cleaving agent. The amino acid recognizers may be any amino acid recognizers described herein. The cleaving agent may be any cleaving agent described herein.

At act 1266, one or more series of signal pulses indicative of binding events between one or more amino acid recognizers and the polypeptide are detected as amino acids are progressively cleaved from a terminus of the polypeptide by the cleaving agent. Detecting the series of signal pulses may be performed in accordance with any of the techniques described herein.

At act 1268, at least one characteristic of the one or more series of signal pulses may be used to determine at least one chemical characteristic of the polypeptide. The at least one characteristic of the one or more series of signal pulses may comprise any characteristic described herein. In some embodiments, the at least one characteristic comprises pulse duration, interpulse duration, recognition segment duration, intersegment duration, cleavage rate, cleavage time, intensity, wavelength, fluorescence lifetime, whether an amino acid is recognized). In some embodiments, the at least one characteristic comprises an absence of signal pulses at one or more reference time points.

The at least one chemical characteristic may comprise any chemical characteristic described herein. In certain embodiments, the at least one chemical characteristic is indicative of a modification of the protein. In some embodiments, the modification is a post-translational modification. The post-translational modification may be any post-translational modification described herein. In certain embodiments, the post-translational modification comprises citrullination of at least one amino acid. In some instances, the at least one amino acid comprises arginine. In certain embodiments, the post-translational modification comprises methylation (e.g., demethylation) of at least one amino acid. In some instances, the at least one amino acid comprises arginine and/or lysine. In certain embodiments, the post-translational modification comprises phosphorylation of at least one amino acid. In some instances, the at least one amino acid comprises threonine, tyrosine, and/or serine. In certain embodiments, the post-translational modification comprises acetylation of at least one amino acid. In some instances, the at least one amino acid comprises lysine. In certain embodiments, the post-translational modification comprises oxidation of at least one amino acid. In some instances, the at least one amino acid comprises methionine and/or cysteine. In some embodiments, the modification comprises one or more mutations relative to a wild type protein.

In some embodiments, the modification of the protein is indicative of a disease or disorder in the subject. Non-limiting examples of diseases or disorders include a cardiovascular disease, an autoimmune disease, a cancer, and/or a neurodegenerative disease. In certain embodiments, the disease or disorder comprises an autoimmune disease. Non-limiting examples of autoimmune diseases include rheumatoid arthritis, Crohn's disease, lupus, and multiple sclerosis. In certain embodiments, the disease or disorder comprises a cancer. Non-limiting examples of cancers include lung cancer, breast cancer, prostate cancer, skin cancer, brain cancer, oral cancer, gastrointestinal cancer, and colorectal cancer. In certain embodiments, the disease or disorder comprises a neurodegenerative disease. A non-limiting example of a neurodegenerative disease is Alzheimer's disease.

Amino Acid Recognizers

In some aspects, the techniques described herein can be performed using any amino acid recognizer known in the art. See, for example, PCT International Publication No. WO2020102741A1, filed Nov. 15, 2019, and PCT International Publication No. WO2021236983A2, filed May 20, 2021, which describe amino acid recognizers (e.g., recognition molecules) in detail, the relevant contents of which are incorporated by reference in their entirety.

In some embodiments, an amino acid recognizer of the disclosure comprises an amino acid binding protein having an amino acid sequence selected from Table 1. Table 1 herein provides a list of example sequences of amino acid binding proteins. It should be appreciated that these sequences and other examples described herein are meant to be non-limiting, and amino acid recognizers in accordance with the disclosure can include any homologs, variants, or fragments thereof minimally containing domains or subdomains responsible for amino acid recognition.

In some embodiments, the amino acid binding protein has an amino acid sequence that is at least 80% identical to an amino acid sequence selected from Table 1. In some embodiments, an amino acid binding protein has at least 40%, at least 50%, at least 60%, at least 70%, at least 80%, at least 85%, at least 90%, at least 95%, at least 98%, or higher, amino acid sequence identity to an amino acid sequence selected from Table 1. In some embodiments, an amino acid binding protein has 25-50%, 50-60%, 60-70%, 70-80%, 80-90%, 90-95%, 95-99%, 40-100%, 50-100%, 60-100%, 70-100%, 80-100%, 90-100%, or 95-100% amino acid sequence identity to an amino acid sequence selected from Table 1.

For the purposes of comparing two or more amino acid sequences, the percentage of "sequence identity" between a first amino acid sequence and a second amino acid sequence (also referred to herein as "amino acid identity") may be calculated by: dividing [the number of amino acid residues in the first amino acid sequence that are identical to the amino acid residues at the corresponding positions in the second amino acid sequence] by [the total number of amino acid residues in the first amino acid sequence] and multiplying by [100], in which each deletion, insertion, substitution or addition of an amino acid residue in the second amino acid sequence compared to the first amino acid sequence is considered as a difference at a single amino acid residue (position). Alternatively, the degree of sequence identity between two amino acid sequences may be calculated using a known computer algorithm (e.g., by the local homology algorithm of Smith and Waterman (1970) Adv. Appl. Math. 2:482c, by the homology alignment algorithm of Needleman and Wunsch, J. Mol. Biol. (1970) 48:443, by the search for similarity method of Pearson and Lipman. Proc. Natl. Acad. Sci. USA (1998) 85:2444, or by computerized implementations of algorithms available as Blast, Clustal Omega, or other sequence alignment algorithms) and, for example, using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Additionally, or alternatively, two or more sequences may be assessed for the identity between the sequences. The terms "identical" or percent "identity" in the context of two or more amino acid sequences refer to two or more sequences or subsequences that are the same. Two sequences are "substantially identical" if two sequences have a specified percentage of amino acid residues that are the same (e.g., at least 80%, 85%, 90%, 95%, 96%, 97%, 98%, 99%, 99.5%, 99.6%, 99.7%, 99.8%, or 99.9% identical) over a specified region or over the entire sequence, when compared and aligned for maximum correspondence over a comparison window, or designated region as measured using one of the above sequence comparison algorithms or by manual alignment and visual inspection. Optionally, the identity exists over a region that is at least about 25, 50, 75, or 100 amino acids in length, or over a region that is 100 to 150, 150 to 200, 100 to 200, or 200 or more, amino acids in length.

Additionally, or alternatively, two or more sequences may be assessed for the alignment between the sequences. The terms "alignment" or percent "alignment" in the context of two or more amino acid sequences refer to two or more sequences or subsequences that are the same. Two sequences are "substantially aligned" if two sequences have a specified percentage of amino acid residues that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the above sequence comparison algorithms or by manual alignment and visual inspection. Optionally, the alignment exists over a region that is at least about 25, 50, 75, or 100 amino acids in length, or over a region that is 100 to 150, 150 to 200, 100 to 200, or 200 or more amino acids in length.

In some embodiments, the amino acid binding protein comprises a modified amino acid binding protein and includes one or more amino acid deletions, additions, or mutations relative to a sequence set forth in Table 1. In some embodiments, a modified amino acid binding protein includes a deletion, addition, or mutation of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids (which may or may not be consecutive amino acids) relative to a sequence set forth in Table 1.

Devices and Systems

Methods in accordance with the disclosure, in some aspects, may be performed using a system that permits single-molecule analysis. The system may include an integrated device and an instrument configured to interface with the integrated device. The integrated device may include an array of pixels, where individual pixels include a reaction chamber and at least one photodetector. The reaction chambers of the integrated device may be formed on or through a surface of the integrated device and be configured to receive a sample placed on the surface of the integrated device. Collectively, the reaction chambers may be considered as an array of reaction chambers. The plurality of reaction chambers may have a suitable size and shape such that at least a portion of the reaction chambers receive a single sample (e.g., a single molecule, such as a polypeptide). In some embodiments, the number of samples within a reaction chamber may be distributed among the reaction chambers of the integrated device such that some reaction chambers contain one sample while others contain zero, two or more samples.

Excitation light is provided to the integrated device from one or more light sources external to the integrated device. Optical components of the integrated device may receive the excitation light from the light source and direct the light towards the array of reaction chambers of the integrated device and illuminate an illumination region within the reaction chamber. In some embodiments, a reaction chamber may have a configuration that allows for the sample to be retained in proximity to a surface of the reaction chamber, which may ease delivery of excitation light to the sample and detection of emission light from the sample. A sample positioned within the illumination region may emit emission light in response to being illuminated by the excitation light. For example, the sample may be labeled with a fluorescent label, which emits light in response to achieving an excited state through the illumination of excitation light. Emission light emitted by a sample may then be detected by one or more photodetectors within a pixel corresponding to the reaction chamber with the sample being analyzed. When performed across the array of reaction chambers, which may range in number between approximately 10,000 pixels to 1,000,000 pixels according to some embodiments, multiple samples can be analyzed in parallel.

The integrated device may include an optical system for receiving excitation light and directing the excitation light among the reaction chamber array. The optical system may include one or more grating couplers configured to couple excitation light to other optical components of the integrated device and direct the excitation light to the other optical components. For example, the optical system may include optical components that direct the excitation light from the grating coupler(s) towards the reaction chamber array. Such optical components may include optical splitters, optical combiners, and waveguides. In some embodiments, one or more optical splitters may couple excitation light from a grating coupler and deliver excitation light to at least one of the waveguides. According to some embodiments, the optical splitter may have a configuration that allows for delivery of excitation light to be substantially uniform across all the waveguides such that each of the waveguides receives a substantially similar amount of excitation light. Such embodiments may improve performance of the integrated device by improving the uniformity of excitation light received by reaction chambers of the integrated device. Examples of suitable components, e.g., for coupling excitation light to a reaction chamber and/or directing emission light to a photodetector, to include in an integrated device are described in U.S. patent application Ser. No. 14/821,688, filed Aug. 7, 2015, titled "INTEGRATED DEVICE FOR PROBING, DETECTING AND ANALYZING MOLECULES," and U.S. patent application Ser. No. 14/543,865, filed Nov. 17, 2014, titled "INTEGRATED DEVICE WITH EXTERNAL LIGHT SOURCE FOR PROBING, DETECTING, AND ANALYZING MOLECULES," both of which are incorporated by reference in their entirety. Examples of suitable grating couplers and waveguides that may be implemented in the integrated device are described in U.S. patent application Ser. No. 15/844,403, filed Dec. 15, 2017, titled "OPTICAL COUPLER AND WAVEGUIDE SYSTEM," which is incorporated by reference in its entirety.

Additional photonic structures may be positioned between the reaction chambers and the photodetectors and configured to reduce or prevent excitation light from reaching the photodetectors, which may otherwise contribute to signal noise in detecting emission light. In some embodiments, metal layers which may act as a circuitry for the integrated device, may also act as a spatial filter. Examples of suitable photonic structures may include spectral filters, a polarization filters, and spatial filters and are described in U.S. patent application Ser. No. 16/042,968, filed Jul. 23, 2018, titled "OPTICAL REJECTION PHOTONIC STRUCTURES," and U.S. Provisional Patent Application No. 63/124,655, filed Dec. 11, 2020, titled "INTEGRATED CIRCUIT WITH IMPROVED CHARGE TRANSFER EFFICIENCY AND ASSOCIATED TECHNIQUES," both of which are incorporated by reference in their entirety.

Components located off of the integrated device may be used to position and align an excitation source to the integrated device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference. Additional examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety.

The photodetector(s) positioned with individual pixels of the integrated device may be configured and positioned to detect emission light from the pixel's corresponding reaction chamber. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. In some embodiments, a reaction chamber and its respective photodetector(s) may be aligned along a common axis. In this manner, the photodetector(s) may overlap with the reaction chamber within the pixel.

Characteristics of the detected emission light may provide an indication for identifying the label associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, such characteristics can be any one or a combination of two or more of luminescence lifetime, luminescence intensity, brightness, absorption spectra, emission spectra, luminescence quantum yield, wavelength (e.g., peak wavelength), and signal characteristics (e.g., pulse duration, interpulse durations, change in signal magnitude).

In some embodiments, a photodetector may have a configuration that allows for the detection of one or more timing characteristics associated with a sample's emission light (e.g., luminescence lifetime). The photodetector may detect a distribution of photon arrival times after a pulse of excitation light propagates through the integrated device, and the distribution of arrival times may provide an indication of a timing characteristic of the sample's emission light (e.g., a proxy for luminescence lifetime). In some embodiments, the one or more photodetectors provide an indication of the probability of emission light emitted by the label (e.g., luminescence intensity). In some embodiments, a plurality of photodetectors may be sized and arranged to capture a spatial distribution of the emission light. Output signals from the one or more photodetectors may then be used to distinguish a label from among a plurality of labels, where the plurality of labels may be used to identify a sample within the sample. In some embodiments, a sample may be excited by multiple excitation energies, and emission light and/or timing characteristics of the emission light emitted by the sample in response to the multiple excitation energies may distinguish a label from a plurality of labels.

In operation, parallel analyses of samples within the reaction chambers are carried out by exciting some or all of the samples within the chambers using excitation light and detecting signals from sample emission with the photodetectors. Emission light from a sample may be detected by a corresponding photodetector and converted to at least one electrical signal. The electrical signals may be transmitted along conducting lines in the circuitry of the integrated device, which may be connected to an instrument interfaced with the integrated device. The electrical signals may be subsequently processed and/or analyzed. Processing or analyzing of electrical signals may occur on a suitable computing device either located on or off the instrument.

The instrument may include a user interface for controlling operation of the instrument and/or the integrated device. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or integrated device, such as proper alignment and/or information obtained by readout signals from the photodetectors on the integrated device. In some embodiments, the user interface may provide feedback using a speaker to provide audible feedback. In some embodiments, the user interface may include indicator lights and/or a display screen for providing visual feedback to a user.

In some embodiments, the instrument may include a computer interface configured to connect with a computing device. The computer interface may be a USB interface, a FireWire interface, or any other suitable computer interface. A computing device may be any general purpose computer, such as a laptop or desktop computer. In some embodiments, a computing device may be a server (e.g., cloud-based server) accessible over a wireless network via a suitable computer interface. The computer interface may facilitate communication of information between the instrument and the computing device. Input information for controlling and/or configuring the instrument may be provided to the computing device and transmitted to the instrument via the computer interface. Output information generated by the instrument may be received by the computing device via the computer interface. Output information may include feedback about performance of the instrument, performance of the integrated device, and/or data generated from the readout signals of the photodetector.

In some embodiments, the instrument may include a processing device configured to analyze data received from one or more photodetectors of the integrated device and/or transmit control signals to the excitation source(s). In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof). In some embodiments, the processing of data from one or more photodetectors may be performed by both a processing device of the instrument and an external computing device. In other embodiments, an external computing device may be omitted and processing of data from one or more photodetectors may be performed solely by a processing device of the integrated device.

According to some embodiments, the instrument that is configured to analyze samples based on luminescence emission characteristics may detect differences in luminescence lifetimes and/or intensities between different luminescent molecules (e.g., fluorescent molecules), and/or differences between lifetimes and/or intensities of the same luminescent molecules in different environments. The inventors have recognized and appreciated that differences in luminescence emission lifetimes can be used to discern between the presence or absence of different luminescent molecules and/or to discern between different environments or conditions to which a luminescent molecule is subjected. In some cases, discerning luminescent molecules based on lifetime (rather than emission wavelength, for example) can simplify aspects of the system. As an example, wavelength-discriminating optics (such as wavelength filters, dedicated detectors for each wavelength, dedicated pulsed optical sources at different wavelengths, and/or diffractive optics) may be reduced in number or eliminated when discerning luminescent molecules based on lifetime. In some cases, a single pulsed optical source operating at a single characteristic wavelength may be used to excite different luminescent molecules that emit within a same wavelength region of the optical spectrum but have measurably different lifetimes. An analytic system that uses a single pulsed optical source, rather than multiple sources operating at different wavelengths, to excite and discern different luminescent molecules emitting in a same wavelength region can be less complex to operate and maintain, more compact, and may be manufactured at lower cost.

Although analytic systems based on luminescence lifetime analysis may have certain benefits, the amount of information obtained by an analytic system and/or detection accuracy may be increased by allowing for additional detection techniques. For example, some embodiments of the systems may additionally be configured to discern one or more properties of a sample based on luminescence wavelength and/or luminescence intensity. In some implementations, luminescence intensity may be used additionally or alternatively to distinguish between different luminescent labels. For example, some luminescent labels may emit at significantly different intensities or have a significant difference in their probabilities of excitation (e.g., at least a difference of about 35%) even though their decay rates may be similar. By referencing binned signals to measured excitation light, it may be possible to distinguish different luminescent labels based on intensity levels.

According to some embodiments, different luminescence lifetimes may be distinguished with a photodetector that is configured to time-bin luminescence emission events following excitation of a luminescent label. The time binning may occur during a single charge-accumulation cycle for the photodetector. A charge-accumulation cycle is an interval between read-out events during which photo-generated carriers are accumulated in bins of the time-binning photodetector. Examples of a time-binning photodetector are described in U.S. patent application Ser. No. 14/821,656, filed Aug. 7, 2015, titled "INTEGRATED DEVICE FOR TEMPORAL BINNING OF RECEIVED PHOTONS," which is incorporated herein by reference. In some embodiments, a time-binning photodetector may generate charge carriers in a photon absorption/carrier generation region and directly transfer charge carriers to a charge carrier storage bin in a charge carrier storage region. In such embodiments, the time-binning photodetector may not include a carrier travel/capture region. Such a time-binning photodetector may be referred to as a "direct binning pixel." Examples of time-binning photodetectors, including direct binning pixels, are described in U.S. patent application Ser. No. 15/852,571, filed Dec. 22, 2017, titled "INTEGRATED PHOTODETECTOR WITH DIRECT BINNING PIXEL," which is incorporated herein by reference.

In some embodiments, different numbers of fluorophores of the same type may be linked to different reagents in a sample, so that each reagent may be identified based on luminescence intensity. For example, two fluorophores may be linked to a first labeled recognition molecule and four or more fluorophores may be linked to a second labeled recognition molecule. Because of the different numbers of fluorophores, there may be different excitation and fluorophore emission probabilities associated with the different recognition molecules. For example, there may be more emission events for the second labeled recognition molecule during a signal accumulation interval, so that the apparent intensity of the bins is significantly higher than for the first labeled recognition molecule.

The inventors have recognized and appreciated that distinguishing biological or chemical samples based on fluorophore decay rates and/or fluorophore intensities may enable a simplification of the optical excitation and detection systems. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each reaction chamber to detect emission from different fluorophores. The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

According to an aspect of the present disclosure, an exemplary integrated device may be configured to perform single-molecule analysis in combination with an instrument as described above. It should be appreciated that the exemplary integrated device described herein is intended to be illustrative and that other integrated device configurations may be configured to perform any or all techniques described herein.

Figure 13:
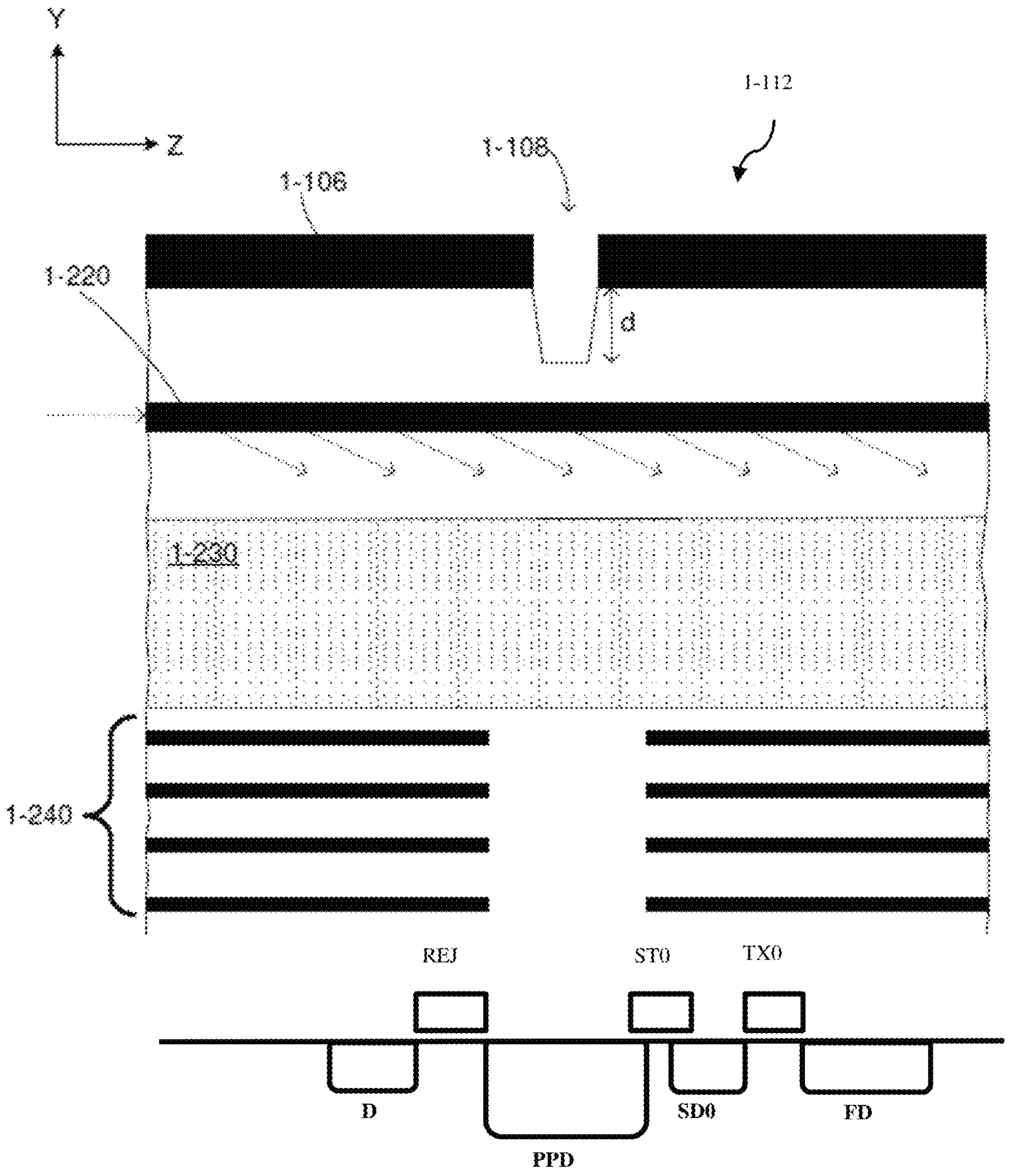
FIG. 13 shows an example schematic of a pixel of an integrated device.

FIG. 13 illustrates a cross-sectional view of a pixel 1-112 of an integrated device 1-102. Pixel 1-112 includes a photodetection region, which may be a pinned photodiode (PPD), and a charge storage region, which may be a storage diode (SD0). In some embodiments, a photodetection region and charge storage regions may be formed in semiconductor material of a pixel by doping regions of the semiconductor material. For example, the photodetection region and charge storage regions can be formed using a same conductivity type (e.g., n-type doping or p-type doping).

During operation of pixel 1-112, excitation light may illuminate reaction chamber 1-108 causing incident photons, including fluorescence emissions from a sample, to flow along the optical axis to photodetection region PPD. As shown in FIG. 13, pixel 1-112 may include a waveguide 1-220 configured to optically (e.g., evanescently) couple excitation light from a grating coupler of the integrated device (not shown) to the reaction chamber 1-108. In response, a sample in the reaction chamber 1-108 may emit fluorescent light toward photodetection region PPD. In some embodiments, pixel 1-112 may also include one or more photonic structures 1-230, which may include one or more optical rejection structures such as a spectral filter, a polarization filter, and/or a spatial filter. For example, the photonic structures 1-230 may be configured to reduce the amount of excitation light that reaches the photodetection region PPD and/or increase the amount of fluorescent emissions that reach the photodetection region PPD. Also shown in pixel 1-112, pixel 1-112 may include one or more metal layers 1-240, which may be configured as a filter and/or may carry control signals from a control circuit configured to control transfer gates, as described further herein.

In some embodiments, pixel 1-112 may include one or more transfer gates configured to control operation of pixel 1-112 by applying an electrical bias to one or more semiconductor regions of pixel 1-112 in response to one or more control signals. For example, when transfer gate ST0 induces a first electrical bias at the semiconductor region between photodetection region PPD and storage region SD0, a transfer path (e.g., charge transfer channel) may be formed in the semiconductor region. Charge carriers (e.g., photoelectrons) generated in photodetection region PPD by the incident photons may flow along the transfer path to storage region SD0. In some embodiments, the first electrical bias may be applied during a collection period during which charge carriers from the sample are selectively directed to storage region SD0. Alternatively, when transfer gate ST0 provides a second electrical bias at the semiconductor region between photodetection region PPD and storage region SD0, charge carriers from photodetection region PPD may be blocked from reaching storage region SD0 along the transfer path. In some embodiments, drain gate REJ may provide a channel to drain D to draw noise charge carriers generated in photodetection region PPD by the excitation light away from photodetection region PPD and storage region SD0, such as during a rejection period before fluorescent emission photons from the sample reach photodetection region PPD. In some embodiments, during a readout period, transfer gate ST0 may provide the second electrical bias and transfer gate TX0 may provide an electrical bias to cause charge carriers stored in storage region SD0 to flow to the readout region, which may be a floating diffusion (FD) region, for processing.

It should be appreciated that, in accordance with various embodiments, transfer gates described herein may include semiconductor material(s) and/or metal, and may include a gate of a field effect transistor (FET), a base of a bipolar junction transistor (BJT), and/or the like.

In some embodiments, operation of pixel 1-112 may include one or more collection sequences, each collection sequence including one or more rejection (e.g., drain) periods and one or more collection periods. In one example, a collection sequence performed in accordance with one or more pulses of an excitation light source may begin with a rejection period, such as to discard charge carriers generated in pixel 1-112 (e.g., in photodetection region PD) responsive to excitation photons from the light source. For instance, the excitation photons may arrive at pixel 1-112 prior to the arrival of fluorescence emission photons from the reaction chamber. Transfer gates for the charge storage regions may be biased to have low conductivity in the charge transfer channels coupling the charge storage regions to the photodetection region, blocking transfer and accumulation of charge carriers in the charge storage regions. A drain gate for the drain region may be biased to have high conductivity in a drain channel between the photodetection region and the drain region, facilitating draining of charge carriers from the photodetection region to the drain region. Transfer gates for any charge storage regions coupled to the photodetection region may be biased to have low conductivity between the photodetection region and the charge storage regions, such that charge carriers are not transferred to or accumulated in the charge storage regions during the rejection period.

Following the rejection period, a collection period may occur in which charge carriers generated responsive to the incident photons are transferred to one or more charge storage regions. During the collection period, the incident photons may include fluorescent emission photons, resulting in accumulation of fluorescent emission charge carriers in the charge storage region(s). For instance, a transfer gate for one of the charge storage regions may be biased to have high conductivity between the photodetection region and the charge storage region, facilitating accumulation of charge carriers in the charge storage region. Any drain gates coupled to the photodetection region may be biased to have low conductivity between the photodetection region and the drain region such that charge carriers are not discarded during the collection period.

Some embodiments may include multiple rejection and/or collection periods in a collection sequence, such as a second rejection period and second collection period following a first rejection period and a collection period, where each pair of rejection and collection periods is conducted in response to a pulse of excitation light. In one example, charge carriers generated in the photodetection region during each collection period of a collection sequence (e.g., in response to a plurality of pulses of excitation light) may be aggregated in a single charge storage region. In some embodiments, charge carriers aggregated in the charge storage region may be read out for processing prior to the next collection sequence. Alternatively or additionally, in some embodiments, charge carriers aggregated in a first charge storage region during a first collection sequence may be transferred to a second charge storage region sequentially coupled to the first charge storage region and read out simultaneously with the next collection sequence. In some embodiments, a processing circuit configured to read out charge carriers from one or more pixels may be configured to determine one or more of luminescence intensity information, luminescence lifetime information, luminescence spectral information, and/or any other mode of luminescence information associated with performing techniques described herein.

In some embodiments, a first collection sequence may include transferring, to a charge storage region at a first time following each excitation pulse, charge carriers generated in the photodetection response in response to the excitation pulse, and a second collection sequence may include transferring, to the charge storage region at a second time following each excitation pulse, charge carriers generated in the photodetection response in response to the excitation pulse. For example, the number of charge carriers aggregated after the first and second times may indicate luminance lifetime information of the received light.

As described further herein, pixels of an integrated device may be controlled to perform one or more collection sequences using one or more control signals from a control circuit of the integrated circuit, such as by providing the control signal(s) to drain and/or transfer gates of the pixel(s) of the integrated circuit. In some embodiments, charge carriers may be read out from the FD region of each pixel during a readout pixel associated with each pixel and/or a row or column of pixels for processing. In some embodiments, FD regions of the pixels may be read out using correlated double sampling (CDS) techniques.

Sequence Information

TABLE 1

Non-limiting example sequences of amino acid binding proteins.

| Name | SEQ ID NO. | Sequence |
|---|---|---|
| PS557 | 1 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDRLLARSKGSMKASIEAEE |
| PS621 | 2 | MHSKFSHAGRICGAKFKVGEPIYRCKECSFDDTCVLCVNCFNPKDHTGHHVYTTICTEFN NGICDCGDKEAWNHTLFCKAEEG |
| Ntaq1sf | 3 | MNGLSAQHERIAPARHECVYTSCYCEENVWKLCEHIKTSKRCPLGDVYAVFISNERKMVP IWKQKSGRGEEPVIWDYHVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKT |
| PS579 | 4 | MSDSPVDLKPKPKVKPKLERPKLYKVMLLNDDYTTAFFVTKVLKAVFRMSEDTGRRVMMT AHRFGSAVVVVCERDIAETKAKEATDLGKEAGFPLMFTTEPEE |
| PS580 | 5 | MSDSPVDLKPKPKVKPKLERPKLYKVMLLNDDYTTMRFVTLVLKAVFRMSEDTGRRVMMT AHRFGSAVVVVCERDIAETKAKEATDLGKEAGFPLMFTTEPEE |

TABLE 1-continued

Non-limiting example sequences of amino acid binding proteins.

| Name | SEQ ID NO. | Sequence |
|---|---|---|
| PS581 | 6 | MLSATRRALQLFHSLFPIPRMGDSAAKIVSPQEALPGRKEPLVVAAKHHVNGNRTVEPFP EGTQMAVFGMGCFWGAERKFWTLKGVYSTQVGFAGGYTPNPTYKEVCSGKTGHAEVVRVV FQPEHISFEELLKVFWENHDPTQGMRQGNDHGSQYRSAIYPTSAEHVGAALKSKEDYQKV LSEHGFGLITTDIREGQTFYYAEDYHQQYLSKDPDGYCGLGGTGVSCPLGIKK |
| PS582 | 7 | MLSATRRALQLFHSLFPIPRMGDSAAKIVSPQEALPGRKEPLVVAAKHHVNGNRTVEPFP EGTQMAVFGMGSFWGAERKFWTLKGVYSTQVGFAGGYTPNPTYKEVCSGKTGHAEVVRVV FQPEHISFEELLKVFWENHDPTQGMRQGNDHGSQYRSAIYPTSAEHVGAALKSKEDYQKV LSEHGFGLITTDIREGQTFYYAEDYHQQYLSKDPDGYCGLGGTGVSCPLGIKK |
| PS585 | 8 | MAFPARGKTAPKNEVRRQPPYNVILLNDDDTTYRYVIEMLQKIFGFPPEKGFQIAEEVDR TGRVILLTTSKEHAELKQDQVHSYGPDPYLGRPCSGSMTCVIEPAV |
| PS586 | 9 | MAFPARGKTAPKNEVRRQPPYNVILLDDDDHTYRYVIEMLQKIFGFPPEKGFQIAEEVDR TGRVILLTTSKEHAELKQDQVHSYGPDPYLGRPCSGSMTCVIEPAV |
| PS587 | 10 | MAFPARGKTAPKNEVRRQPPYNVILLKDDDHTYRYVIEMLQKIFGFPPEKGFQIAEEVDR TGRVILLTTSKEHAELKQDQVHSYGPDPYLGRPCSGSMTCVIEPAV |
| PS588 | 11 | MAFPARGKTAPKNEVRRQPPYNVILLNKDDHTYRYVIEMLQKIFGFPPEKGFQIAEEVDR TGRVILLTTSKEHAELKQDQVHSYGPDPYLGRPCSGSMTCVIEPAV |
| PS589 | 12 | MAFPARGKTAPKNEVRRQPPYNVILLNDDDHTYRYVIEMLQKIFGFPPEKGFQIAEEVHR TGRVILLTTSKEHAELKQDQVHSYGPDPYLGRPCSGSMTCVIEPAV |
| PS590 | 13 | MAFPARGKTAPKNEVRRQPPYNVILLNDDNHTYRYVIEMLQKIFGFPPEKGFQIAEEVDR TGRVILLTTSKEHAELKQDQVHSYGPDPYLGRPCSGSMTCVIEPAV |
| PS591 | 14 | MGSVHKHTGRNCGRKFKIGEPLYRCHECGCDDTCVLCIHCFNPKDHVKHHVCTDICTEFT SGICDCGDEEAWNSPLHCKAEEQ |
| PS594 | 15 | MTSLNIMGRKFILERAKRNDNIEEIYTSAYVSLPSSTDTRLPHFKAKEEDCDVYEEGTNL VGKNAKYTYRSLGRHLDFLRPGLRFGGSQSSKYTYYTVEVKIDTVNLPLYKDSRSLDPHV TGTFTIKNLTPVLDKVVTLFEGYVINYNQFPLCSLHWPAEETLDPYMAQRESDCSHWKRF GHFGSDNWSLTERNFGQYNHESAEFMNQRYIYLKWKERFLLDDEEQENQMLDDNHHLEGA SFEGFYYVCLDQLTGSVEGYYYHPACELFQKLELVPTNCDALNTYSSGFEIA |
| PS595 | 16 | MGSSHHHHHHHHHHSSGLVPRGSHMQIFVKTLTGKTITLEVEPSDTIENVKAKIQDKEGI PPDQQRLIFAGKQLEDGRTLSDYNIQKESTLHLVLRLRGGMASVVEYKGLKAGYYCGYCE SREGKTSCGMWAHSMTVQDYQDLIDRGWRRSGKYVYKPVMDQTCCPQYTIRCHPLQFQPS KSHKKVLKKMLKFLAKGEISKGNCEDEPMDSTVEDAVDGDFALINKLDIKCDLKTLSDLK GSIESEEKEKEKSIKKEGSKEFIHPQSIEEKLGSGEPSHPIKVHIGPKPGKGADLSKPPC RKAREMRKERQRLKRMQQASAAASEAQGQPVCLLPKAKSNQPKSLEDLIFQSLPENASHK LEVRLVPASFEDPEFNSSFNQSFSLYTKYQVAIHQEAPEICEKSEFTRFLCSSPLEAEHP ADGPECGYGSFHQQYWLDGKIIAVGVLDILPYCVSSVYLYYDPDYSFLSLGVYSALREIA FTRQLHEKTSQLSYYYMGFYIHSCPKMRYKGQYRPSDLLCPETYVWVPIEQCLPSLDNSK YCRFNQDPEAEDEGRSKELDRLRVFHRRSAMPYGVYKNHQEDPSEEAGVLEYANLVGQKC SERMLLFRH |
| PS630 | 17 | MSEPMTLPAIPQPRLKERTQRQPPYNVILLNDDDKSYEYVAAMLQVLFGYPPEKGYQMAK EVDSTGRVILLTTTREHAELKQEQIHAFGPDPNQARNSGSMKAVIEPAV |
| PS631 | 18 | MSEPMTLPAIPQPRLKERTQRQPPYNVILLNDDDKSYEYVIAMLQVLFGYPPEKGYQMAK EVDSTGRVILLTTTREHAELKQEQIHAFGPDPNQARNSGSMKAVIEPAV |
| PS632 | 19 | MSEPMTLPAIPQPRLKERTQRQPPYNVIILNDDDKSFEYVAAMLQVLFGYPPEKGYQMAK EIDSTGRVIMLTTTREHAELKQEQIHAFGPDPNQARNSGSMKAVIEPAV |
| PS633 | 20 | MSEPMTLPAIPQPRLKERTQRQPPYNVIILNDDDKSFEYVAALLQVLFGYPPEKGYQMAK EIDSTGRVIMLTTTREHAELKQEQIHAFGPDPNQARNSGSMKAVIEPAV |
| PS634 | 21 | MSEPMTLPAIPQPRLKERTQRQPPYNVIVLNDDDKSFEYVAAMLQVLFGYPPEKGYQVAK EIDSTGRVITLTTTREHAELKQEQIHAFGPDPNQARNSGSMKAVIEPAV |
| PS635 | 22 | MPTAASATESAIEDTPAPARPEVDGRTKPKRQPRYHVVQWNDDRHTYQYTVVMFQSLFGH PPERGYRLAKESDTQGRIIVLTTTREHAELKRDQIHAFGYDRLLARDKGSYKASIEAEE |
| PS636 | 23 | HHHHHHHHHHDYDIPTTENLYFQGMPTAASATESAIEDTPAPARPEVDGRTKPKRQPRYH VVLWNDDDHTYQYVVVMLQSLFGHPPERGYRLAKEVDTQGRVIVLTTTREHAELKRDQIH AFGYDRLLARSKGSMKASIEAEE |
| PS642 | 24 | MPTAASATESAIEDTPAPARPEVDGRTKPKRQPRYHVVQWNDDRHTYQYTVVMFQSLFGH PPERGYRLAKESDTQGRIIVLTTTREHAELKRDQIHAFGYDPLQSGDKGSYKASIEAEE |

TABLE 1-continued

Non-limiting example sequences of amino acid binding proteins.

| Name | SEQ ID NO. | Sequence |
|---|---|---|
| PS643 | 25 | MPTAASATESAIEDTPAPARPEVDGRTKPKRQPRYHVVAWNDDRHTYQYTVVMFQSLFGH PPERGYRLAKEQDTQGRIIVLTTTREHAELKRDQIHAFGYDPLQSGDKGSYKASIEAEE |
| PS644 | 26 | MPTAASATESAIEDTPAPARPEVDGRTKPKRQPRYHVVAWNDDRHTYQYTVVMFQSLFGH PPERGYRLAKEQDTQGRIIVLTTTREHAELKRDQIHAFGYDPLQSGDKGSYKASIEAEE |
| PS645 | 27 | MPTAASATESAIEDTPAPARPEVDGRTKPKRQPRYHVVSWNDDKHTYQWTVVMFQSLFGH PPERGYRLAKERDTQGRIIVLTTTREHAELKRDQIHAFGYDPLQSGDKGSMKASIEAEE |
| PS646 | 28 | MKMYNIPTPTMAQVIMVDDPITTTEFVISALRDFFDKSLEEAKALTSSIHRDGEGVCGVY PYDIARHRAAWVRDKAKALEFPLKLLVEEIK |
| PS647 | 29 | MKMYNIPTPTMAQVIMVDDPINTYEFTISALRDFFDKSLEEAKALASSIDRDGEGVCGVY PYDIARHRAAWVRDKAKALEFPEKLLVEEIK |
| PS648 | 30 | MKMYNIPTPTMAQVIMVDDPINTKEFTISALRDFFDKSLEEAKALASSIDRDGEGVCGVY PYDIARHRAAWVRDKAKALEFPEKLLVEEIK |
| PS649 | 31 | MKMYNIPTPTMAQVIRVDDPSMTNEFGISALRDFFDKSLEEAKALASSIDRDGEGVCGVY PYDIARHRAAWVRDKAKALEFPSKLLVEEIK |
| PS650 | 32 | MKMYNIPTPTMAQVIRVDDPSMTYEFGISALRDFFDKSLEEAKALASSIDRDGEGVCGVY PYDIARHRAAWVRDKAKALEFPSKLLVEEIK |
| PS657 | 33 | MPQERQQVTRKHYPNYKVIFLNSDFYTFQHLVALMMKYIPNMTSDRAWEISNQIHYEGQA IVWVGPQEQAELYHEQFLRAGLTMAPLEPE |
| PS658 | 34 | MTSTLRARPARDTDLQHRPYPHYRIITLDDDVMTFQHMANSYVTFLPGMTRDQMWAMSQQ DDGEGSMVVWTGPQEQAELYHVQLGNHGQTNIPLEPV |
| PS659 | 35 | MTSTLRARPARDTDLQHRPYPHYRIIVLDDDVMTFQHMANSFVTFLPGMTRDQMWAMSQQ DEGEGSMVVWTGPQEQAELYHVQLGNHGQTNIPLEPV |
| PS660 | 36 | MTSTLRARPARDTDLQHRPYPHYRIIVLDDDVMTFQHLANSFVTFLPGMTRDQMWAMSQQ DDGEGSMVVWTGPQEQAELYHVQLGNHGQTNIPLEPV |
| PS661 | 37 | MTSTLRARPARDTDLQHRPYPHYRIIVLDDDVMTFQHMANSFVTFLPGMTRDQMWAMSQQ DDGEGSMVVWTGPQEQAELYHVQLGNHGQTNIPLEPV |
| PS662 | 38 | MTSTLRARPARDTDLQHRPYPHYRIILLDSDVITFQLTANAFVTFLPGMTRDQMWAKIQQ SDGEGSCVVWTGPQEQAELYHVQLGNQGLTEIPLEPV |
| PS663 | 39 | MVSIGAATVACAEGRPIFSGYFDWLAAMPETVTVPRTRLRPKTERPKLHKVIEVNQDYIP WEFWVTFFKGEFHMSEDQAQRKMIAGDRRGVYVVAVFTRDVAETKATRFSDHGRAKGYPT QMTTEPEE |
| PS664 | 40 | MGQTVEKPRVEGPGTGLGGSWRVITRNNDHYTRDHWARTIARFIPGVSLERAHEWSKVIH TTGRKWYTGHKEAAEHYWQQFKGSGLESMPLEQG |
| PS665 | 41 | MTLSVALGPDTQESTQTGTAVSTDTLTAPDIPWNLVDWNDPVNLMSYISYVFQSYFGYSE TKANKLMMEQDKKGRSIVAHGSKEQVEQHAVALHGYGNWATVEKATGGNSGGGKSGGPGK GKGKRG |
| PS666 | 42 | MSGTVVESKPRNSTQLAPRWKVIYHDNPVTTFDFTTGMFRRVFAKPPGEARRMTREAHDT GSVLVDVLALEQAEFRRDQMHSLARAEGFPQTLTLEPAD |
| PS667 | 43 | MSGTVVESKPRNSTQLAPRWKVIYHDQPVTTFDFTTGLFRRVFAKPPGEARRMTREAHDT GSVLVDVLALEQAEFRRDQMHSLARAEGFPQTLTLEPAD |
| PS668 | 44 | MSDSPVDLKPKPKVKPKLERPSMYKVITVNDDYTPMEFTIDHLQKFFSYDVERATQLMLA SDYQGKAICGVFTAEVAETKVAMMNKSARENEHPELCTLEKAE |
| PS669 | 45 | MSDSPVDLKPKPKVKPKLERPSMYKVITVNDDYTPMEFTIDHLQKFFSYDVERATQLMLA SEYQGKAICGVFTAEVAETKVAMMNKSARENEHPELCTLEKAE |
| PS670 | 46 | MHSKFNHAGRICGAKHRVGEPMYRCKECSFDDTCTLCVNCFNPKDHVGHHVYTSICTEFK NGICDCGDKEAWNHELNCKGAED |
| PS671 | 47 | MHSKFNHAGRICGAKFRVGEPLYRCKECSFDDTCVLCVNCFNPKDHVGHHVYTSICTEFL NGICDCGDKEAWNHELNCKGAED |
| PS672 | 48 | MHSKFNHAGRICGAKFRVGEPLYKCKECSFDDTCVLCVNCFNPKDHVGHHVYTMICTEFL NGICDCGDKEAWNHELNCKGAED |

TABLE 1-continued

Non-limiting example sequences of amino acid binding proteins.

| Name | SEQ ID NO. | Sequence |
|---|---|---|
| PS673 | 49 | MAFPARGKTAPKNEVRRQPPYNVIMLNDDDHTWRYAMELFQKIFGFPPEKGFQIVEEMDR TGRVILLTTSKEHAELKQDQMHSYGPDPYLGRPCSGSMTCVIEPAV |
| PS674 | 50 | MAFPARGKTAPKNEVRRQPPYNVIILNDDDHTWRYLMEMFQKIFGFPPEKGFQIIEEIDR TGRAILLTTSKEHAELKQDQLHSYGPDPYLGRPCSGSMTVVIEPAV |
| PS675 | 51 | MAFPARGKTAPKNEVRRQPPYNVILLNDDDHTWRYIMEMFQKIFGFPPEKGFQITEEIDR TGRAILLTTSKEHAELKQDQTHSYGPDPYLGRPCSGSMTMVIEPAV |
| PS676 | 52 | MAFPARGKTAPKNEVRRQPPYNVIILNDDDMTWRYLMEAFQKIFGFPPEKGFQIIEEIDR TGRAILLTTSKEHAELKQDQMHSYGPDPYLGRPCSGSMTMVIEPAV |
| PS677 | 53 | MSGTVVESKPRNSTQLAPRWKVIMHDQPVITFDFTLGMFRRVFAKPPGEARRITREAHDT GSVLVDVLALEQAEFRRDQMHSLARAEGFPLTMTLEPAD |
| PS678 | 54 | MAFPARGKTAPKNEVRRQPPYNVIILNDDDHTYRYFIEMFQKIFGFPPEKGFQYTEEMDR TGRLILLTTSKEHAELKQDQLHSYGPDPYLGRPCSGSVTWIEPAV |
| PS679 | 55 | MAFPARGKTAPKNEVRRQPPYNVIILNDDDHTYRYFLEMFQKIFGFPPEKGFQYAEEIDR TGRLILLTTSKEHAELKQDQMHSYGPDPYLGRPCSGSITCVIEPAV |
| PS680 | 56 | MAFPARGKTAPKNEVRRQPPYNVIILNDDDHTYRYFIEMFQKIFGFPPEKGFQIVEEIDR TGRYILLTTSKEHAELKQDQLHSYGPDPYLGRPCSGSITCVIEPAV |
| PS681 | 57 | MAFPARGKTAPKNEVRRQPPYNVIMLNDDDHTYRYFIELFQKIFGFPPEKGFQIIEEIDR TGRAILLTTSKEHAELKQDQIHSYGPDPYLGRPCSGSITCVIEPAV |
| PS682 | 58 | MAFPARGKTAPKNEVRRQPPYNVIILNDDDHTYRYFLEMFQKIFGFPPEKGFQYVEEIDR TGRIILLTTSKEHAELKQDQMHSYGPDPYLGRPCSGSITCVIEPAV |
| PS683 | 59 | MPTAASATESAIEDTPAPARPEVDGRTKPKRQPRYHVVIWNDDDHTYQYFVVMFQSLFGH PPERGYRIVKEIDTQGRYIVLTTTREHAELKRDQLHAFGYDRLLARSKGSIKASIEAEE |
| PS684 | 60 | MPTAASATESAIEDTPAPARPEVDGRTKPKRQPRYHVVYWNDDDHTYQYFVVLFQSLFGH PPERGYRIVKEIDTQGRYIVLTTTREHAELKRDQTHAFGYDRLLARSKGSIKISIEAEE |
| PS685 | 61 | MPTAASATESAIEDTPAPARPEVDGRTKPKRQPRYHVVMWNDDDHTYQYFVVLLQSLFGH PPERGYRIVKEIDTQGRYIVLTTTREHAELKRDQIHAFGYDRLLARSKGSIKVSIEAEE |
| PS686 | 62 | MPTAASATESAIEDTPAPARPEVDGRTKPKRQPRYHVVFWNDDDHTYQYFVVLFQSLFGH PPERGYRIAKEIDTQGRYIVLTTTREHAELKRDQVHAFGYDRLLARSKGSIKISIEAEE |
| PS687 | 63 | MPTAASATESAIEDTPAPARPEVDGRTKPKRQPRYHVVIWNDDDHTYQYFVVTFQSLFGH PPERGYRIAKEIDTQGRYIVLTTTREHAELKRDQWHAFGYDRLLARSKGSIKCSIEAEE |
| PS688 | 64 | MHSKFSHAGRICGAKFKVGEPAYRCKECSFDDTCILCVNCFNPKDHTGHHVYTMICTEFL NGICDCGDKEAWNHTLFCKAEEG |
| PS689 | 65 | MHSKFSHAGRICGAKFKVGEPAYLCKECSFDDTCILCVNCFNPKDHTGHHVYTMICTEFL NGICDCGDKEAWNHTLFCKAEEG |
| PS710 | 66 | MSDSPVDLKPKPKVKPKLERPKLYKVMFLNDDYTPMSYIIVFFKAVFRMSEDTGRRKMMT AHRFGSMVVVVCERDIAETKAKEFTDHGKEAGFPIMMTTEPEE |
| PS711 | 67 | MSDSPVDLKPKPKVKPKLERPKLYKVMFLDDDYTPMSYIIVFFKAVFRMSEDTGRRKMMT AHRFGSMVVVVCERDIAETKAKEFTDHGKEAGFPIQMTTEPEE |
| PS712 | 68 | MIAEPICMQGEGDGEDGGTNRGTSVITRVKPKTKRPNLYRVLTLDDDYTPMEFMIHMFER FFQKDREAATRLMLLVHQHGVAECGVFTYEVAETKVSQMMDWARQHQHPFQMVMEKK |
| PS713 | 69 | MPQERQQVTRKHYPNYKVILLDMDFMTFAFMSAVLMKYIPNMTSDRSTELIRQAHYEGQT IVWVGPQEQAELYHEQFLRSGLQNMPLEPE |
| PS714 | 70 | MASAPSTTLDKSTQVVKKTYPNYKVIFLDSDLLTMDFLANVMIKYIPDMTTDRAWEKAYQ MHYQGQFIVWTGPQEQAELYHQQFRREGLENIPLEAA |
| PS715 | 71 | MTSTLRARPARDTDLQHRPYPHYRIITLDNDVNTFQKIANVHVTFLPGMTRDQMWAKMQQ VDGEGSVVVWTGPQEQAELYHVQFGNQGLKNIPLEPV |
| PS716 | 72 | MATETIERPRTRDPGSGLGGHWLVIMLDNDHMTFDLISKVLARVIPGVTVDDAYRFTYQM HQRGQVIIWRGPKEPAEHYWEQLQDVGLDNAPLERH |
| PS717 | 73 | MAFPARGKTAPKNEVRRQPPYNVIILNSDDHTYRYFMEMFQKIFGFPPEKGFQYMEEIDR TGRIILLTTSKEHAELKQDQSHSYGPDPYLGRPCSGSITMVIEPAV |

TABLE 1-continued

Non-limiting example sequences of amino acid binding proteins.

| Name | SEQ ID NO. | Sequence |
|---|---|---|
| PS718 | 74 | MGQTVEKPRVEGPGTGLGGSWRVISRDNDHYTFDEWVRIIARFIPGVSLERAHEWMKVLHTTGRMVVYTGHKEAAEHYWQQLKGAGFQSVPLEQG |
| PS719 | 75 | MVSIGAATVACAEGRPIFSGYFDWLAAMPETVTVPRTRLRPKTERPKLYKVIFVDDDFVPFEFIIRMFKAEFRMSEDQAAEKMMRAHQRGVQVVAVFTRDVAETKATRFTDWGRAKGYPLIMTTEPEE |
| PS720 | 76 | MVSIGAATVACAEGRPIFSGYFDWLAAMPETVTVPRTRLRPKTERPKLHKVIFVDQDYIPFEFIITMFKGEFHMSEDQAQRKLITAHRRGVYVVAVFTRDVAETKATRFSDAGRAKGYPLQVTTEPEE |
| PS721 | 77 | MTLSVALGPDTQESTQTGTAVSTDTLTAPDIPWNLVFWDDPVTLMSRIIYFFQSYFGYSETKAYKIVMEAHKKGRSIVAHGSKEQVEQHAVAFHGLGLWTTVEKATGGNSGGGKSGGPGKGKGKRG |
| PS722 | 78 | MSDTITLPGRPEVERDERTRRQPPYNVITHDKDDITFAYFIVMYNQLFGYPPEKGYEKLKEIHLNGRAIVLTTSKEHAELKRDQMHAWGPDPFSSKDCKGSISASIEPAY |
| PS723 | 79 | MPTAASATESAIEDTPAPARPEVDGRTKPKRQPRYHVVIWNDDDWTYQYYVVMFQSLFGHPPERGYRLMKELDTQGRFIVLTTTREHAELKRDQIHAFGYDRLLARSKGSIKASIEAEE |
| PS724 | 80 | MSSPSSLDDVQVSTSRAKPANETRTRKQPPYAVIFEDQDHVTHLWFYEMFMKVCGHAPEKGFVKSQQIHTQGKVMVWSGTLELAELKRDQFRGFGPDNYAPAPVTFPPGMTIEPLP |
| PS725 | 81 | MSGTVVESKPRNSTQLAPRWKVIFHDNPVTTFAFIIGMFRRVFAKPPGEAREMLRRAHDTGSVLVDVLALEQAEFRRDQFHSEARAEGFPSTMTLEPAD |
| PS726 | 82 | MHHHHHHHHHHDYDIPTTENLYFQGMHSKFSHAGRICGAKFKVGEPIYRCKECSFDDTCVLCVNCFNPKDHTGHHVYTTICTEFNNGICDCGDKEAWNHTLFCKAEE |
| PS727 | 83 | MSDSPVDLKPKPKVKPKLERPKLYKVMFLNQDYVPMSFIVVMFKAVFRMSEDTGRKKMMHAHRFGSVVVVVCERDIAETKAKEFTDYGKEAGFPVMMTTEPEE |
| PS728 | 84 | MTLSVALGPDTQESTQTGTAVSTDTLTAPDIPWNLVMWNQPVLLWSYMVYLFQSYFGYSETKTNKMVMEAHKKGRSIVAHGSKEQVEQHAVAMHGRGLWATVEKATGGNSGGGKSGGPGKGKGKRG |
| PS729 | 85 | MSDTITLPGRPEVERDERTRRQPPYNVITHNQDDITWEYFRVMYNQLFGYPPEKGYEKLKEIHLNGRIIVLTTSKEHAELKRDQMHAWGPDPFSSKDCKGSVSNSIEPAY |
| PS730 | 86 | MSDTITLPGRPEVERDERTRRQPPYNVIIHNTDDLTWEYFKVMFNQLFGYPPEKGYEKLKEIHLNGRAIVLTTSKEHAELKRDQMHAWGPDPFSSKDCKGSVSASIEPAY |
| PS731 | 87 | MPTAASATESAIEDTPAPARPEVDGRTKPKRQPRYHVVTWNTDDWTHQYYVVMYQSLFGHPPERGYRLTKEMDTQGRCIVLTTTREHAELKRDQMHAFGYDRLLARSKGSTKVSIEAEE |
| PS732 | 88 | MPTAASATESAIEDTPAPARPEVDGRTKPKRQPRYHVVMWNTDDWTYQYIIVMMQSLFGHPPERGYRMVKEMDTQGRTIVLTTTREHAELKRDQMHAFGYDRLLARSKGSIKNSIEAEE |
| PS733 | 89 | MSSPSSLDDVQVSTSRAKPANETRTRKQPPYAVIFENQDHVTILWFWEMFMKVCGHAPEKGFVKSQQIHTQGKVMVWSGTLELAELKRDQFRGFGPDNYAPRPVTFPPGMTIEPLP |
| PS734 | 90 | MSSPSSLDDVQVSTSRAKPANETRTRKQPPYAVIMENLDHITLLWMWEMFMKVCGHAPEKGFVKSQQNHTQGKVMVWSGTLELAELKRDQMRGWGPDNYAPRPVTFPPGFTIEPLP |
| PS735 | 91 | MSGTVVESKPRNSTQLAPRWKVIYHDQPVTTFDFIIGMFRRVFAKPPGEAREMTRRAHDTGSVLVDVLALEQAEFRRDQFHSEARAEGFPSTMTLEPAD |
| PS736 | 92 | MSGTVVESKPRNSTQLAPRWKVIYHDQPVMTFDFIIGLFRRVFAKPPGEARTITRIAHDTGSVLVDVLALEQAEFRRDQFHSEARAEGFPATMTLEPAD |
| PS737 | 93 | MSDSPVDLKPKPKVKPKLERPKLYKVMFLNQDYTPMSFIVVMFKAVFRMSEDTGRKKMMHAHRFGSVVVVVCERDIAETKAKEFTDYGKEAGFPSMMTTEPEE |
| PS738 | 94 | MIAEPICMQGEGDGEDGGTNRGTSVITRVKPKTKRPNLYRVLWLNHDYIPMEFMVHMFERFFQKDREAATRYMLLVHQHGVAECGVFTYEVAETKVSQLMDWARQHQHPFQVVMEKK |
| PS739 | 95 | MIAEPICMQGEGDGEDGGTNRGTSVITRVKPKTKRPNLYRVLWLNHDYIPMEFMVHMFERFFQKDREAATRIMLEVHQHGVSECGVFTYEVAETKVSQLMDFARQHQHPFQVVMEKK |
| PS740 | 96 | MPQERQQVTRKHYPNYKVIMLNNDFHTFQFMSAVMMKYIPNMTSDRSWEKVNQVHYEGQTIVWVGPQEQAELYHEQFLRSGLTNMPLEPE |
| PS741 | 97 | MPQERQQVTRKHYPNYKVIMLNDDFWTFQFLAAVIMKYIPNMTSDRVWEITNQVHYEGQSIVWVGPQEQAELYHEQFLREGFLHVPLEPE |

TABLE 1-continued

| Non-limiting example sequences of amino acid binding proteins. | | |
|---|---|---|
| Name | SEQ ID NO. | Sequence |
| PS742 | 98 | MASAPSTTLDKSTQVVKKTYPNYKVILLNNDLITRDKLANVLIKYIPDMTTDRAWERINQ MHYQGQFIVWTGPQEQAELYHQQFRREGMQNIPLEAA |
| PS743 | 99 | MASAPSTTLDKSTQVVKKTYPNYKVIMLNNDLLTRDEIANVFIKYIPDMTTDRMWEMTNQ MHYQGQLIVWTGPQEQAELYHQQFRREGLLNVPLEAA |
| PS744 | 100 | MTSTLRARPARDTDLQHRPYPHYRIITLDNDVITFQELVNYYVTFLPGMTRDQIWAKMQQ VDGEGSAVVWTGPQEQAELYHVQLGNQGLFNCPLEPV |
| PS745 | 101 | MTSTLRARPARDTDLQHRPYPHYRIITLDMDVNTFQEIANYYVTFLPGMTRDQMWAWMQQ VDGEGSVVVWTGPQEQAELYHVQLGNQGLYNIPLEPV |
| PS746 | 102 | MATETIERPRTRDPGSGLGGHWLVIHLNSDHFTFDEHAKWLARVIPGVTVDDAYRFTDQM HQRGQMIVWRGPKEPAEHYWEQLQDVGLSQSPLERH |
| PS747 | 103 | MATETIERPRTRDPGSGLGGHWLVIMLNSDHFTFDEFSKWLARVIPGVTVDDAYRFTDQM HQRGQVIVWRGPKEPAEHYWEQFQDIGLSQVPLERH |
| PS748 | 104 | MAFPARGKTAPKNEVRRQPPYNVIILNSDDHTYRYYMEMFQKIFGFPPEKGFQYMEEIDR TGRIILLTTSKEHAELKQDQLHSYGPDPYLGRPCSGSITCVIEPAV |
| PS749 | 105 | MAFPARGKTAPKNEVRRQPPYNVIILNSDDHTYRYFMEMFQKIFGFPPEKGFQYMEEIDR TGRIILLTTSKEHAELKQDQLHSYGPDPYLGRPCSGSITCVIEPAV |
| PS750 | 106 | MGQTVEKPRVEGPGTGLGGSWRVIMRNTDHITKDEFARSIARFIPGVSLERAHEKIKVMH TTGRFVVYTGHKEAAEHYWQQFKGSGVQVMPLEQG |
| PS751 | 107 | MGQTVEKPRVEGPGTGLGGSWRVIMRNDDHHTKDKFARMIARFIPGVSLERAHEKIKVLH TTGRMVVYTGHKEAAEHYWQQMKGAGVQNVPLEQG |
| PS752 | 108 | MVSIGAATVACAEGRPIFSGYFDWLAAMPETVTVPRTRLRPKTERPKLYKVIFVNRDFIP MEFIIRMFKAEFRMSEDQAARKMMYAHQRGVYVVAVFTRDVAETKATRFTDWGRAKGYPL LMTTEPEE |
| PS753 | 109 | MVSIGAATVACAEGRPIFSGYFDWLAAMPETVTVPRTRLRPKTERPKLYKVIFVNRDFIP MEFIIRMFKAEFRMSEDQAATKMMLAHQRGVQVVAVFTRDVAETKATRFTDWGRAKGYPL LMTTEPEE |
| PS754 | 110 | MVSIGAATVACAEGRPIFSGYFDWLAAMPETVTVPRTRLRPKTERPKLHKVIFVNQDYIP WEFIVTLFKGEFHMSEDQAQRKMIIAHRRGVYVVAVFTRDVAETKATRTSDWGRAKGYPL QFTTEPEE |
| PS755 | 111 | MVSIGAATVACAEGRPIFSGYFDWLAAMPETVTVPRTRLRPKTERPKLHKVIFVNKDYIP WEFIVTMFKGEFHMSEDQAQRKMIIAHRRGVYVVAVFTRDVAETKATRFSDWGRAKGYPL QMTTEPEE |
| PS756 | 112 | MVSIGAATVACAEGRPIFSGYFDWLAAMPETVTVPRTRLRPKTERPPLHKVILVNRDFIP MEFIIRMLKAEFRTTGDEAQRKMIYAHMKGSYVVAVFTREIAESKATRFTEWARAEGFPM LMTTEPEE |
| PS757 | 113 | MVSIGAATVACAEGRPIFSGYFDWLAAMPETVTVPRTRLRPKTERPPLHKVILVNQDFIP WEFMIRFLKAEFRTTGDEAQKKMISAHMKGSHVVAVFTREIAESKATRMTEWARAEGFPL LFTTEPEE |
| PS758 | 114 | MTLSVALGPDTQESTQTGTAVSTDTLTAPDIPWNLVIWNLPVLLWSFIVYLFQSYFGYSE TKANKIVMEMHKKGRSIVAHGSKEQVEQHAVAFHGRGLWTTVEKATGGNSGGGKSGGPGK GKGKRG |
| PS759 | 115 | MPTAASATESAIEDTPAPARPEVDGRTKPKRQPRYHVVLWNDDDHTHQYVVVMLQSLFGH PPERGYRLAKEVDTQGRVIVLTTTREHAELKRDQIHAFGYDRLLARSKGSMKASIEAEE |
| PS760 | 116 | MPTAASATESAIEDTPAPARPEVDGRTKPKRQPRYHVVLWNDDDHTYQYVVMMLQSLFGH PPERGYRLAKEVDTQGRVIVLTTTREHAELKRDQIHAFGYDRLLARSKGSMKASIEAEE |
| PS761 | 117 | MPTAASATESAIEDTPAPARPEVDGRTKPKRQPRYHVVLWNDDDHTHQYVVMMLQSLFGH PPERGYRLAKEVDTQGRVIVLTTTREHAELKRDQIHAFGYDRLLARSKGSMKASIEAEE |
| PS762 | 118 | MPTAASATESAIEDTPAPARPEVDGRTKPKRQPRYHVVLWDDDDHTYQYVVVMLQSLFGH PPERGYRLAKEVDTQGRVIVLTTTREHAELKRDQIHAFGYDRLLARSKGSMKASIEAEE |
| PS763 | 119 | MPTAASATESAIEDTPAPARPEVDGRTKPKRQPRYHVVLWDYDDHTYQYVVVMLQSLFGH PPERGYRLAKEVDTQGRVIVLTTTREHAELKRDQIHAFGYDRLLARSKGSMKASIEAEE |

TABLE 1-continued

| Name | SEQ ID NO. | Sequence |
|---|---|---|
| | | Non-limiting example sequences of amino acid binding proteins. |
| PS764 | 120 | MPTAASATESAIEDTPAPARPEVDGRTKPKRQPRYHVVLWDYDDHTYQYVVVMLQSLFGHPPERGYRLAKELDTQGRVIVLTTTREHAELKRDQIHAFGYDRLLARSKGSMKASIEAEE |
| PS765 | 121 | MPTAASATESAIEDTPAPARPEVDGRTKPKRQPRYHVVLWNDEDHTYQYVVVMLQSLFGHPPERGYRLAKEVDTQGRVIVLTTTREHAELKRDQIHAFGYDRLLARSKGSMKASIEAEE |
| PS766 | 122 | MPTAASATESAIEDTPAPARPEVDGRTKPKRQPRYHVVLWNYDDHTYQYVVVMLQSLFGHPPERGYRLAKEVDTQGRVIVLTTTREHAELKRDQIHAFGYDRLLARSKGSMKASIEAEE |
| PS767 | 123 | MTLSVALGPDTQESTQTGTAVSTDTLTAPDIPWNLVIWDDPVNLMSYVSYVFQSYFGYSETKANKLMMEVHKKGRSIVAHGSKEQVEQHAVAMHGYGLWATVEKATGGNSGGGKSGGPGKGKGKRG |
| PS768 | 124 | MSDTITLPGRPEVERDERTRRQPPYNVILHDDDDHTFEYVIVMLNQLFGYPPEKGYEMAKEVHLNGRVIVLTTSKEHAELKRDQIHAFGPDPFSSKDCKGSMSASIEPAY |
| PS769 | 125 | MPTAASATESAIEDTPAPARPEVDGRTKPKRQPRYHVVLWDDDDHTYQYVVVMLQSLFGHPPERGYRLAKEVDTQGRVIVLTTTREHAELKRDQIHAFGYDRLLARSKGSMKASIEAEE |
| PS770 | 126 | MSSPSSLDDVQVSTSRAKPANETRTRKQPPYAVIVEDDDHHTFLYVIEALMKVCGHAPEKGFVLAQQIHTQGKAMVWSGTLELAELKRDQLRGFGPDNYAPRPVTFPLGVTIEPLP |
| PS771 | 127 | MSGTVVESKPRNSTQLAPRWKVIVHDDPVTTFDFVLGVLRRVFAKPPGEARRITREAHDTGSALVDVLALEQAEFRRDQAHSLARAEGFPLTLTLEPAD |
| PS772 | 128 | MSDSPVDLKPKPKVKPKLERPKLYKVMLLDDDYTPMSFVTVVLKAVFRMSEDTGRRVMMTAHRFGSAVVVVCERDIAETKAKEATDLGKEAGFPLMFTTEPEE |
| PS773 | 129 | MIAEPICMQGEGDGEDGGTNRGTSVITRVKPKTKRPNLYRVLLLDDDYTPMEFVIHILERFFQKDREAATRIMLHVHQHGVGECGVFTYEVAETKVSQVMDFARQHQHPLQCVMEKK |
| PS774 | 130 | MPQERQQVTRKHYPNYKVIVLDDDFNTFQHVAACLMKYIPNMTSDRAWELTNQVHYEGQAIVWVGPQEQAELYHEQLLRAGLTMAPLEPE |
| PS775 | 131 | MASAPSTTLDKSTQVVKKTYPNYKVIVLDDDLNTFDHVANCLIKYIPDMTTDRAWELTNQVHYQGQAIVWTGPQEQAELYHQQLRREGLTMAPLEAA |
| PS776 | 132 | MATETIERPRTRDPGSGLGGHWLVIVLDDDHNTFDHVAKTLARVIPGVTVDDGYRFADQIHQRGQAIVWRGPKEPAEHYWEQLQDAGLSMAPLERH |
| PS777 | 133 | MAFPARGKTAPKNEVRRQPPYNVILLDDDDHTYRYVIEMLQKIFGFPPEKGFQIAEEVDRTGRVILLTTSKEHAELKQDQVHSYGPDPYLGRPCSGSMTCVIEPAV |
| PS778 | 134 | MGQTVEKPRVEGPGTGLGGSWRVIVRDDDHNTFDHVARTLARFIPGVSLERGHEIAKVIHTTGRAVVYTGHKEAAEHYWQQLKGAGLTMAPLEQG |
| PS779 | 135 | MVSIGAATVACAEGRPIFSGYFDWLAAMPETVTVPRTRLRPKTERPKLYKVILVDDDFTPREFVVRVLKAEFRMSEDQAAKVMMTAHQRGVCVVAVFTRDVAETKATRATDAGRAKGYPLLFTTEPEE |
| PS780 | 136 | MVSIGAATVACAEGRPIFSGYFDWLAAMPETVTVPRTRLRPKTERPKLHKVILVDDDYTPREFVVTVLKGEFHMSEDQAQRVMITAHRRGVCVVAVFTRDVAETKATRASDAGRAKGYPLQFTTEPEE |
| PS781 | 137 | MVSIGAATVACAEGRPIFSGYFDWLAAMPETVTVPRTRLRPKTERPPLHKVILVDDDFTPREFVVRLLKAEFRTTGDEAQRIMITAHMKGSCVVAVFTREIAESKATRATETARAEGFPLLFTTEPEE |
| PS782 | 138 | MTLSVALGPDTQESTQTGTAVSTDTLTAPDIPWNLVIWDDPVNLMSYVSYVFQSYFGYSETKANKLMMEVDKKGRSIVAHGSKEQVEQHAVAMHGYGLWATVEKATGGNSGGGKSGGPGKGKGKRG |
| PS783 | 139 | MSDTITLPGRPEVERDERTRRQPPYNVILHDDDDHTFEYVIVMLNQLFGYPPEKGYEMAKEVDLNGRVIVLTTSKEHAELKRDQIHAFGPDPFSSKDCKGSMSASIEPAY |
| PS784 | 140 | MSSPSSLDDVQVSTSRAKPANETRTRKQPPYAVIVEDDDHHTFLYVIEALMKVCGHAPEKGFVLAQQIDTQGKAMVWSGTLELAELKRDQLRGFGPDNYAPRPVTFPLGVTIEPLP |
| PS785 | 141 | MSGTVVESKPRNSTQLAPRWKVIVHDDPVTTFDFVLGVLRRVFAKPPGEARRITREADDTGSALVDVLALEQAEFRRDQAHSLARAEGFPLTLTLEPAD |
| PS786 | 142 | MSDSPVDLKPKPKVKPKLERPKLYKVMLLDDDYTPMSFVTVVLKAVFRMSEDTGRRVMMTADRFGSAVVVVCERDIAETKAKEATDLGKEAGFPLMFTTEPEE |

TABLE 1-continued

Non-limiting example sequences of amino acid binding proteins.

| Name | SEQ ID NO. | Sequence |
|---|---|---|
| PS787 | 143 | MIAEPICMQGEGDGEDGGTNRGTSVITRVKPKTKRPNLYRVLLLDDDYTPMEFVIHILER FFQKDREAATRIMLHVDQHGVGECGVFTYEVAETKVSQVMDFARQHQHPLQCVMEKK |
| PS788 | 144 | MPQERQQVTRKHYPNYKVIVLDDDFNTFQHVAACLMKYIPNMTSDRAWELTNQVDYEGQA IVWVGPQEQAELYHEQLLRAGLTMAPLEPE |
| PS789 | 145 | MASAPSTTLDKSTQVVKKTYPNYKVIVLDDDLNTFDHVANCLIKYIPDMTTDRAWELTNQ VDYQGQAIVWTGPQEQAELYHQQLRREGLTMAPLEAA |
| PS790 | 146 | MATETIERPRTRDPGSGLGGHWLVIVLDDDHNTFDHVAKTLARVIPGVTVDDGYRFADQI DQRGQAIVWRGPKEPAEHYWEQLQDAGLSMAPLERH |
| PS791 | 147 | MGQTVEKPRVEGPGTGLGGSWRVIVRDDDHNTFDHVARTLARFIPGVSLERGHEIAKVID TTGRAVVYTGHKEAAEHYWQQLKGAGLTMAPLEQG |
| PS792 | 148 | MVSIGAATVACAEGRPIFSGYFDWLAAMPETVTVPRTRLRPKTERPKLYKVILVDDDFTP REFVVRVLKAEFRMSEDQAAKVMMTADQRGVCVVAVFTRDVAETKATRATDAGRAKGYPL LFTTEPEE |
| PS793 | 149 | MVSIGAATVACAEGRPIFSGYFDWLAAMPETVTVPRTRLRPKTERPKLHKVILVDDDYTP REFVVTVLKGEFHMSEDQAQRVMITADRRGVCVVAVFTRDVAETKATRASDAGRAKGYPL QFTTEPEE |
| PS794 | 150 | MVSIGAATVACAEGRPIFSGYFDWLAAMPETVTVPRTRLRPKTERPPLHKVILVDDDFTP REFVVRLLKAEFRTTGDEAQRIMITADMKGSCVVAVFTREIAESKATRATETARAEGFPL LFTTEPEE |
| PS795 | 151 | MPTAASATESAIEDTPAPARPEVDGRTKPKRQPRYHVVLWDDDDHTYQYVVVMLRSLFGH PPERGYRLAKEVDTQGRVIVLTTTREHAELKRDQIHAFGYDRLLARSKGSMKASIEAEE |
| PS796 | 152 | MPTAASATESAIEDTPAPARPEVDGRTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS797 | 153 | MPTAASATESAIEDTPAPARPEVDGRTKPKRQPRYHVVLWDDDDHTYQYVVVMLQSLFGH PPERGYRLAKEMDTLGRVIVLTTTREHAELKRDQIHAFGYDRLLARSKGSMKASIEAEE |
| PS798 | 154 | MPTAASATESAIEDTPAPARPEVDGRTKPKRQPRYHVVLWNDDDHTYQYVVVMLQSLFGH PPERGYRLAKEMDTLGRVIVLTTTREHAELKRDQIHAFGYDRLLARSKGSMKASIEAEE |
| PS799 | 155 | MPTAASATESAIEDTPAPARPEVDGRTKPKRQPRYHVVLWNDDYHTYQYVVVMLQSLFGH PPERGYRLAKEVDTQGRVIVLTTTREHAELKRDQIHAFGYDRLLARSKGSMKASIEAEE |
| PS800 | 156 | MPTAASATESAIEDTPAPARPEVDGRTKPKRQPRYHVVLWNDNYHTYQYVVVMLQSLFGH PPERGYRLAKEVDTQGRVIVLTTTREHAELKRDQIHAFGYDRLLARSKGSMKASIEAEE |
| PS801 | 157 | MPTAASATESAIEDTPAPARPEVDGRTKPKRQPRYHVVLWNDDDHTYQYVVVMLQSLFGH PPKRGYRLAKEVDTQGRVIVLTTTREHAELKRDQIHAFGYDRLLARSKGSMKASIEAEE |
| PS802 | 158 | MPTAASATESAIEDTPAPARPEVDGRTKPKRQPRYHVVLWNDDDHTYQYVVVMLQSLFGH SPERGYRLAKEVDTQGRVIVLTTTREHAELKRDQIHAFGYDRLLARSKGSMKASIEAEE |
| PS803 | 159 | MPTAASATESAIEDTPAPARPEVDGRTKPKRQPRYHVVLWNDDDHTYQYVVVMLQSLFGH PRERGYRLAKEVDTQGRVIVLTTTREHAELKRDQIHAFGYDRLLARSKGSMKASIEAEE |
| PS804 | 160 | MPTAASATESAIEDTPAPARPEVDGRTKPKRQPRYHVVLWNDADHTYQYVVVMLQSLFGH PPERGYRLAKEVDTQGRVIVLTTTREHAELKRDQIHAFGYDRLLARSKGSMKASIEAEE |
| PS805 | 161 | MPTAASATESAIEDTPAPARPEVDGRTKPKRQPRYHVVLWNDDDHTYQYVVVMLQSLFGH PPERGFRLAKEVDTQGRVIVLTTTREHAELKRDQIHAFGYDRLLARSKGSMKASIEAEE |
| PS806 | 162 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDRLLAHSKGSMKASIEAEE |
| PS807 | 163 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDRLLAGSKGSMKASIEAEE |
| PS808 | 164 | MPTAASATESAIEDTPAPARPEVDGRTKPKRQPRYHVVLWNDDDHTYQYVVVMLRSLFGH PPERGYRLAKEVDTQGRVIVLTTTREHAELKRDQIHAFGYDRLLARSKGSMKASIEAEE |
| PS809 | 165 | MPTAASATESAIEDTPAPARPEVDGRTKPKRQPRYHVVLWNDDDHTYQYVVVMLQSLFGH PPERGYRLAKEMDTQGRVIVLTTTREHAELKRDQIHAFGYDRLLARSKGSMKASIEAEE |
| PS810 | 166 | MPTAASATESAIEDTPAPARPEVDSRTKPKRQPRYHVVNWNDDDLTCQYLVVMLQSLFGH PPERGYRLAKEVDTQGRVIVLTTTREHAELKRDQIHAFGYDRLLARSKGSIKASIEAEE |

TABLE 1-continued

Non-limiting example sequences of amino acid binding proteins.

| Name | SEQ ID NO. | Sequence |
|---|---|---|
| PS811 | 167 | MPTAASATESAIEDTPAPARPEVDSRTKPKRQPRYHVVNWNDDDLTCQYMVVMLQSLFGH PPERGYRLAKEVDTQGRVIVLTTTREHAELKRDQIHAFGYDRLLARSKGSTKASIEAEE |
| PS812 | 168 | MPTAASATESAIEDTPAPARPEVDGRTKPKRQPRYHVVNWNDDDPTRQYMVVMLQSLFGH PPERGYRLAKETDTQGRVIVLTTTREHAELKRDQIHAFGYDRLLARSKGSTKASIEAEE |
| PS813 | 169 | MPTAASATESAIEDTPAPARPEVDGRTKPKRQPRYHVVNWNDDDPTRQYLVVMLQSLFGH PPERGYRLAKETDTQGRVIVLTTTREHAELKRDQIHAFGYDRLLARSKGSTKASIEAEE |
| PS814 | 170 | MPTAASATESAIEDTPAPARPEVDGRTKPKRQPRYHVVLWNDDDHTYQYVVVMLQSLFGH PPKRGYRLAKEVDTQGRVIVLTTTREHAELKRDQIHAFGYDRLLARSKGSMKASIEAEE |
| PS815 | 171 | MPTAASATESAIEDTPAPARPEVDGRTKPKRQPRYHVVLWNDDDHTYQYVVVMLQSLFGH PPERGYRLAKEMDTQGRVIVLTTTREHAELKRDQIHAFGYDRLLARSKGSMKASIEAEE |
| PS816 | 172 | MPTAASATESAIEDTPAPARPEVDGRTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS817 | 173 | MPTAASATESAIEDTPAPARPEVDGRTKPKRQPRYHVVLWDDDDHTYQYVVVMLQSLFGH PPKRGYRLAKEVDTQGRVIVLTTTREHAELKRDQIHAFGYDRLLARSKGSMKASIEAEE |
| PS818 | 174 | MPTAASATESAIEDTPAPARPEVDGRTKPKRQPRYHVVLWNDDDHTYQYVVVMLQSLFGH PPKRGYRLAKEMDTQGRVIVLTTTREHAELKRDQIHAFGYDRLLARSKGSMKASIEAEE |
| PS819 | 175 | MPTAASATESAIEDTPAPARPEVDGRTKPKRQPRYHVVLWDDDDHTYQYVVVMLQSLFGH PPKRGYRLAKEMDTQGRVIVLTTTREHAELKRDQIHAFGYDRLLARSKGSMKASIEAEE |
| PS820 | 176 | MPTAASGTESAIEDTPAPARPEVDGRTKPKRQPRYHVVLWDDDDHTYQYVVVMLRSLFGH PPERGYRLAKEVDTQGRVIVLTTTREHAELKRDQIHAFGYDRLLARSKGSMKASIEAEE |
| PS821 | 177 | MPTAASGTESAIEDTPAPARPEVDGRTKPKRQPRYHVVLWDDDDHTYQYVVVMLRSLFGH PPERGYRLAKEMDTQGRVIVLTTTREHAELKRDQIHAFGYDRLLARSKGSMKASIEAEE |
| PS822 | 178 | MPTAASGTESAIEDTPAPARPEVDGRTKPKRQPRYHVVLWDDDDHTYQYVVVMLRSLFGH PPKRGYRLAKEMDTQGRVIVLTTTREHAELKRDQIHAFGYDRLLARSKGSMKASIEAEE |
| PS823 | 179 | MPTAASATESAFEDTPAPARPEVDGRTKPKRQPRYHVVLWDDDDHTYQYVVVMLRSLFGH PPERGYRLAKEVDTQGRVIVLTTTREHAELKRDQIHAFGYDRLLARSKGSMKASIEAEE |
| PS824 | 180 | MPTAASATESAFEDTPAPARPEVDGRTKPKRQPRYHVVLWDDDDHTYQYVVVMLRSLFGH PPERGYRLAKEMDTQGRVIVLTTTREHAELKRDQIHAFGYDRLLARSKGSMKASIEAEE |
| PS825 | 181 | MPTAASATESAFEDTPAPARPEVDGRTKPKRQPRYHVVLWDDDDHTYQYVVVMLRSLFGH PPKRGYRLAKEVDTQGRVIVLTTTREHAELKRDQIHAFGYDRLLARSKGSMKASIEAEE |
| PS826 | 182 | MPTAASATESAFEDTPAPARPEVDGRTKPKRQPRYHVVLWDDDDHTYQYVVVMLRSLFGH PPKRGYRLAKEMDTQGRVIVLTTTREHAELKRDQIHAFGYDRLLARSKGSMKASIEAEE |
| PS827 | 183 | MPTAASATESAIEDTPAPARPEVDGRTKPKRQPRYHVVLWNDDDHTYQYVVVMLQSLFGH PRERGYRLAKEVDTLGRVIVLTTTREHAELKRDQIHAFGYDRLLARSKGSMKASIEAEE |
| PS828 | 184 | MPTAASATESAIEDTPAPARPEVDGRTKPKRQPRYHVVLWDDDDHTYQYVVVMLQSLFGH PRERGYRLAKEVDTLGRVIVLTTTREHAELKRDQIHAFGYDRLLARSKGSMKASIEAEE |
| PS829 | 185 | MPTAASATESAIEDTPAPARPEVDGRTKPKRQPRYHVVLWDDDDHTYQYVVVMLQSLFGH PRERGYRLAKEMDTLGRVIVLTTTREHAELKRDQIHAFGYDRLLARSKGSMKASIEAEE |
| PS830 | 186 | MPTAASATESAIEDTPAPARPEVDGRTKPKRQPRYHVVLWDDDDHTYQYVVVMLQSLFGH PRKRGYRLAKEMDTLGRVIVLTTTREHAELKRDQIHAFGYDRLLARSKGSMKASIEAEE |
| PS831 | 187 | MPTAASATESAIEDTPAPARPEVDGRTKPKRQPRYHVVLWNDDDHTYQYVVVMLQSLFGH PRKRGYRLAKEMDTLGRVIVLTTTREHAELKRDQIHAFGYDRLLARSKGSMKASIEAEE |
| PS832 | 188 | MPTAASATESAIEDTPAPARPVVDGRTKPKRQPRYHVVLWDDDDHTYQYVVVMLQSLFGH PPERGYRLAKEVDTQGRVIVLTTTREHAELKRDQIHAFGYDRLLARSKGSMKASIEAEE |
| PS833 | 189 | MPTAASATESAIEDTPAPARPVVDGRTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS834 | 190 | MPTAASATESAIEDTPAPARPVVDGRTKPKRQPRYHVVLWDDDDHTYQYVVVMLQSLFGH PPKRGYRLAKEMDTQGRVIVLTTTREHAELKRDQIHAFGYDRLLARSKGSMKASIEAEE |
| PS835 | 191 | MPTAASATESAIEDTPAPARPVVDGRTKPKRQPRYHVVLWDDDDHTYQYVVVMLQSLFGH PPKRGYRLAKEVDTQGRVIVLTTTREHAELKRDQIHAFGYDRLLARSKGSMKASIEAEE |

TABLE 1-continued

Non-limiting example sequences of amino acid binding proteins.

| Name | SEQ ID NO. | Sequence |
|---|---|---|
| PS836 | 192 | MPTAASATESAIEDTPAPARPEVDGRTKPKRQPRYHVVLWNDDDHTYQYVVVMLQSLFGH PRERGYRLAKEVDTQGRVIVLTTTREHAELKRDQIHAFGYDRLLARSKGSMKASIEAEE |
| PS837 | 193 | MPTAASATESAIEDTPAPARPEVDGRTKPKRQPRYHVVLWDDDDHTYQYVVVMLQSLFGH PRERGYRLAKEVDTQGRVIVLTTTREHAELKRDQIHAFGYDRLLARSKGSMKASIEAEE |
| PS838 | 194 | MPTAASATESAIEDTPAPARPEVDGRTKPKRQPRYHVVLWDDDDHTYQYVVVMLQSLFGH PRERGYRLAKEMDTQGRVIVLTTTREHAELKRDQIHAFGYDRLLARSKGSMKASIEAEE |
| PS839 | 195 | MPTAASATESAIEDTPAPARPEVDGRTKPKRQPRYHVVLWDDDDHTYQYVVVMLQSLFGH PRKRGYRLAKEMDTQGRVIVLTTTREHAELKRDQIHAFGYDRLLARSKGSMKASIEAEE |
| PS840 | 196 | MPTAASATESAIEDTPAPARPEVDGRTKPKRQPRYHVVLWNDDDHTYQYVVVMLQSLFGH PRKRGYRLAKEVMDTQGRVIVLTTTREHAELKRDQIHAFGYDRLLARSKGSMKASIEAEE |
| PS841 | 197 | MPTAASATESAIEDTPAPARPEVDGRTKPKRQPRYHVVLWNDDDHTYQYVVVMLQSLFGH SPKRGYRLAKEVDTQGRVIVLTTTREHAELKRDQIHAFGYDRLLARSKGSMKASIEAEE |
| PS842 | 198 | MPTAASATESAIEDTPAPARPEVDGRTKPKRQPRYHVVLWDDDDHTYQYVVVMLQSLFGH SPKRGYRLAKEVDTQGRVIVLTTTREHAELKRDQIHAFGYDRLLARSKGSMKASIEAEE |
| PS843 | 199 | MPTAASATESAIEDTPAPARPEVDGRTKPKRQPRYHVVLWDDDDHTYQYVVVMLQSLFGH SPKRGYRLAKEMDTQGRVIVLTTTREHAELKRDQIHAFGYDRLLARSKGSMKASIEAEE |
| PS844 | 200 | MPTAASATESAIEDTPAPARPEVDGRTKPKRQPRYHVVLWNDDDHTYQYVVVMLQSLFGH SPKRGYRLAKEMDTQGRVIVLTTTREHAELKRDQIHAFGYDRLLARSKGSMKASIEAEE |
| PS845 | 201 | MPTAASATESAIEDTPAPARPEVDGRTKPKRQPRYHVVLWNDDDHTYQYVVVMLRSLFGH PPERGYRLAKEVDTQGRVIVLTTTREHAELKRDQIHAFGYDRLLARSKGSMKASIEAEE |
| PS846 | 202 | MPTAASATESAIEDTPAPARPEVDGRTKPKRQPRYHVVLWDDDDHTYQYVVVMLRSLFGH PPERGYRLAKEVDTQGRVIVLTTTREHAELKRDQIHAFGYDRLLARSKGSMKASIEAEE |
| PS847 | 203 | MPTAASATESAIEDTPAPARPEVDGRTKPKRQPRYHVVLWDDDDHTYQYVVVMLRSLFGH PPERGYRLAKEMDTQGRVIVLTTTREHAELKRDQIHAFGYDRLLARSKGSMKASIEAEE |
| PS848 | 204 | MPTAASATESAIEDTPAPARPEVDGRTKPKRQPRYHVVLWDDDDHTYQYVVVMLRSLFGH PPKRGYRLAKEMDTQGRVIVLTTTREHAELKRDQIHAFGYDRLLARSKGSMKASIEAEE |
| PS849 | 205 | MPTAASATESAIEDTPAPARPEVDGRTKPKRQPRYHVVLWNDDDHTYQYVVVMLRSLFGH PPKRGYRLAKEMDTQGRVIVLTTTREHAELKRDQIHAFGYDRLLARSKGSMKASIEAEE |
| PS850 | 206 | MPTAASATESAIEDTPAPARPEVDGRTKPKHQPRYHVVLWNDDDHTYQYVVVMLRSLFGH PPERGYRLAKEVDTQGRVIVLTTTREHAELKRDQIHAFGYDRLLARSKGSMKASIEAEE |
| PS851 | 207 | MPTAASATESAIEDTPAPARPEVDGRTKPKHQPRYHVVLWDDDDHTYQYVVVMLRSLFGH PPERGYRLAKEVDTQGRVIVLTTTREHAELKRDQIHAFGYDRLLARSKGSMKASIEAEE |
| PS852 | 208 | MPTAASATESAIEDTPAPARPEVDGRTKPKHQPRYHVVLWDDDDHTYQYVVVMLRSLFGH PPERGYRLAKEMDTQGRVIVLTTTREHAELKRDQIHAFGYDRLLARSKGSMKASIEAEE |
| PS853 | 209 | MPTAASATESAIEDTPAPARPEVDGRTKPKHQPRYHVVLWDDDDHTYQYVVVMLRSLFGH PPKRGYRLAKEMDTQGRVIVLTTTREHAELKRDQIHAFGYDRLLARSKGSMKASIEAEE |
| PS854 | 210 | MPTAASATESAIEDTPAPARPEVDGRTKPKHQPRYHVVLWNDDDHTYQYVVVMLRSLFGH PPKRGYRLAKEMDTQGRVIVLTTTREHAELKRDQIHAFGYDRLLARSKGSMKASIEAEE |
| PS855 | 211 | MPTAASATESAIEDTPAPARPEVDGRTKPKRQPRYHVVLWNDDDHTYQYVVVMLQSLFGH PPERGYRMAKEVDTQGRVIVLTTTREHAELKRDQIHAFGYDRLLARSKGSMKASIEAEE |
| PS856 | 212 | MPTAASATESAIEDTPAPARPEVDGRTKPKRQPRYHVVLWDDDDHTYQYVVVMLQSLFGH PPERGYRMAKEVDTQGRVIVLTTTREHAELKRDQIHAFGYDRLLARSKGSMKASIEAEE |
| PS857 | 213 | MPTAASATESAIEDTPAPARPEVDGRTKPKRQPRYHVVLWDDDDHTYQYVVVMLQSLFGH PPERGYRMAKEMDTQGRVIVLTTTREHAELKRDQIHAFGYDRLLARSKGSMKASIEAEE |
| PS858 | 214 | MPTAASATESAIEDTPAPARPEVDGRTKPKRQPRYHVVLWDDDDHTYQYVVVMLQSLFGH PPKRGYRMAKEMDTQGRVIVLTTTREHAELKRDQIHAFGYDRLLARSKGSMKASIEAEE |
| PS859 | 215 | MPTAASATESAIEDTPAPARPEVDGRTKPKRQPRYHVVLWNDDDHTYQYVVVMLQSLFGH PPKRGYRMAKEMDTQGRVIVLTTTREHAELKRDQIHAFGYDRLLARSKGSMKASIEAEE |
| PS860 | 216 | MPTAASATESAIEDTPAPARPEVDGRTKPKRQPRYHVVLWNDDDHTYQYVVVMLQSLLGH PPERGYRLAKEMDTQGRVIVLTTTREHAELKRDQIHAFGYDRLLARSKGSMKASIEAEE |

TABLE 1-continued

Non-limiting example sequences of amino acid binding proteins.

| Name | SEQ ID NO. | Sequence |
|---|---|---|
| PS861 | 217 | MPTAASATESAIEDTPAPARPEVDGRTKPKRQPRYHVVLWDDDDHTYQYVVVMLQSLLGH PPERGYRLAKEMDTQGRVIVLTTTREHAELKRDQIHAFGYDRLLARSKGSMKASIEAEE |
| PS862 | 218 | MPTAASATESAIEDTPAPARPEVDGRTKPKRQPRYHVVLWDDDDHTYQYVVVMLQSLLGH PPKRGYRLAKEMDTQGRVIVLTTTREHAELKRDQIHAFGYDRLLARSKGSMKASIEAEE |
| PS863 | 219 | MPTAASATESAIEDTPAPARPEVDGRTKPKRQPRYHVVLWNDDDHTYQYVVVMLQSLLGH PPKRGYRLAKEMDTQGRVIVLTTTREHAELKRDQIHAFGYDRLLARSKGSMKASIEAEE |
| PS864 | 220 | MPTAASATESAIEDTPAPARPEVDGRTKPKRQPRYHVVLWNDDDHTYQYVVVMLQSLFGH PPGRGYRLAKEVDTQGRVIVLTTTREHAELKRDQIHAFGYDRLLARSKGSMKASIEAEE |
| PS865 | 221 | MPTAASATESAIEDTPAPARPEVDGRTKPKRQPRYHVVLWDDDDHTYQYVVVMLQSLFGH PPGRGYRLAKEVDTQGRVIVLTTTREHAELKRDQIHAFGYDRLLARSKGSMKASIEAEE |
| PS866 | 222 | MPTAASATESAIEDTPAPARPEVDGRTKPKRQPRYHVVLWDDDDHTYQYVVVMLQSLFGH PPGRGYRLAKEMDTQGRVIVLTTTREHAELKRDQIHAFGYDRLLARSKGSMKASIEAEE |
| PS867 | 223 | MPTAASATESAIEDTPAPARPEVDGRTKPKRQPRYHVVLWNDDDHTYQYVVVMLQSLFGH PPGRGYRLAKEMDTQGRVIVLTTTREHAELKRDQIHAFGYDRLLARSKGSMKASIEAEE |
| PS868 | 224 | MPTAASATESAIEDTPAPARPEVDGRTKPKRQPRYHVVLWNDDDHTYQYVVVMLQSLFGH PPGRGYRLAKEVDTQGRVIVLTTTREHAELKRDQIHAFGYDRLLARSKGSMKASIEAEE |
| PS869 | 225 | MPTAASATESAIEDTPAPARPEVDGRTKPKRQPRYHVVLWDDDDHTYQYVVVMLQSLFGH PPGRGYRLAKEVDTQGRVIVLTTTREHAELKRDQIHAFGYDRLLAHSKGSMKASIEAEE |
| PS870 | 226 | MPTAASATESAIEDTPAPARPEVDGRTKPKRQPRYHVVLWDDDDHTYQYVVVMLQSLFGH PPGRGYRLAKEMDTQGRVIVLTTTREHAELKRDQIHAFGYDRLLAHSKGSMKASIEAEE |
| PS871 | 227 | MPSAAPAKPKTKRQSRTQGMPPYNVVLLDDDDHTYGYVIEMLRKVFGHPPEKGFELATEV DKNGRVIVMTTNLEVAELKRDEVHAFGPDPLMPRSKGSMSAVVERAG |
| PS872 | 228 | MPSAAPAKPKTKRQSRTQGMPPYNVVLLDDDDHTYGYVIEMLNKVFGHPPEKGFELATEM DKNGRVIVMTTNLEVAELKRDEVHAFGPDPLMPRSKGSMSAVVERAG |
| PS873 | 229 | MPSAAPAKPKTKRQSRTQGMPPYNVVLLDDDDHTYGYVIEMLRKVFGHPPEKGFELATEM DKNGRVIVMTTNLEVAELKRDEVHAFGPDPLMPRSKGSMSAVVERAG |
| PS874 | 230 | MPSAAPAKPKTKRQSRTQGMPPYNVVLLDDDDHTYGYVIEMLNKVFGHPREKGFELATEV DKLGRVIVMTTNLEVAELKRDEVHAFGPDPLMPRSKGSMSAVVERAG |
| PS875 | 231 | MPSAAPAKPKTKRQSRTQGMPPYNVVLLDDDDHTYGYVIEMLRKVFGHPREKGFELATEM DKLGRVIVMTTNLEVAELKRDEVHAFGPDPLMPRSKGSMSAVVERAG |
| PS876 | 232 | MPSAAPAKPVTKRQSRTQGMPPYNVVLLDDDDHTYGYVIEMLNKVFGHPPEKGFELATEV DKNGRVIVMTTNLEVAELKRDEVHAFGPDPLMPRSKGSMSAVVERAG |
| PS877 | 233 | MPSAAPAKPVTKRQSRTQGMPPYNVVLLDDDDHTYGYVIEMLRKVFGHPPEKGFELATEM DKNGRVIVMTTNLEVAELKRDEVHAFGPDPLMPRSKGSMSAVVERAG |
| PS878 | 234 | MPSAAPAKPKTKRQSRTQGMPPYNVVLLDDDDHTYGYVIEMLNKVFGHPREKGFELATEV DKNGRVIVMTTNLEVAELKRDEVHAFGPDPLMPRSKGSMSAVVERAG |
| PS879 | 235 | MPSAAPAKPKTKRQSRTQGMPPYNVVLLDDDDHTYGYVIEMLRKVFGHPREKGFELATEV DKNGRVIVMTTNLEVAELKRDEVHAFGPDPLMPRSKGSMSAVVERAG |
| PS880 | 236 | MPSAAPAKPKTKRQSRTQGMPPYNVVLLDDDDHTYGYVIEMLRKVFGHPREKGFELATEM DKNGRVIVMTTNLEVAELKRDEVHAFGPDPLMPRSKGSMSAVVERAG |
| PS881 | 237 | MPSAAPAKPKTKRQSRTQGMPPYNVVLLDDDDHTYGYVIEMLNKVFGHSPEKGFELATEV DKNGRVIVMTTNLEVAELKRDEVHAFGPDPLMPRSKGSMSAVVERAG |
| PS882 | 238 | MPSAAPAKPKTKRQSRTQGMPPYNVVLLDDDDHTYGYVIEMLRKVFGHSPEKGFELATEM DKNGRVIVMTTNLEVAELKRDEVHAFGPDPLMPRSKGSMSAVVERAG |
| PS883 | 239 | MPSAAPAKPKTKRQSRTQHMPPYNVVLLDDDDHTYGYVIEMLRKVFGHPPEKGFELATEV DKNGRVIVMTTNLEVAELKRDEVHAFGPDPLMPRSKGSMSAVVERAG |
| PS884 | 240 | MPSAAPAKPKTKRQSRTQHMPPYNVVLLDDDDHTYGYVIEMLRKVFGHPPEKGFELATEM DKNGRVIVMTTNLEVAELKRDEVHAFGPDPLMPRSKGSMSAVVERAG |
| PS885 | 241 | MPSAAPAKPKTKRQSRTQGMPPYNVVLLDDDDHTYGYVIEMLNKVFGHPPEKGFEMATEV DKNGRVIVMTTNLEVAELKRDEVHAFGPDPLMPRSKGSMSAVVERAG |

TABLE 1-continued

Non-limiting example sequences of amino acid binding proteins.

| Name | SEQ ID NO. | Sequence |
|---|---|---|
| PS886 | 242 | MPSAAPAKPKTKRQSRTQGMPPYNVVLLDDDDHTYGYVIEMLRKVFGHPPEKGFEMATEM DKNGRVIVMTTNLEVAELKRDEVHAFGPDPLMPRSKGSMSAVVERAG |
| PS887 | 243 | MPSAAPAKPKTKRQSRTQGMPPYNVVLLDDDDHTYGYVIEMLNKVLGHPPEKGFELATEM DKNGRVIVMTTNLEVAELKRDEVHAFGPDPLMPRSKGSMSAVVERAG |
| PS888 | 244 | MPSAAPAKPKTKRQSRTQGMPPYNVVLLDDDDHTYGYVIEMLRKVLGHPPEKGFELATEM DKNGRVIVMTTNLEVAELKRDEVHAFGPDPLMPRSKGSMSAVVERAG |
| PS889 | 245 | MPSAAPAKPKTKRQSRTQGMPPYNVVLLDDDDHTYGYVIEMLNKVFGHPPGKGFELATEV DKNGRVIVMTTNLEVAELKRDEVHAFGPDPLMPRSKGSMSAVVERAG |
| PS890 | 246 | MPSAAPAKPKTKRQSRTQGMPPYNVVLLDDDDHTYGYVIEMLRKVFGHPPGKGFELATEM DKNGRVIVMTTNLEVAELKRDEVHAFGPDPLMPRSKGSMSAVVERAG |
| PS891 | 247 | MPSAAPAKPKTKRQSRTQGMPPYNVVLLDDDDHTYGYVIEMLNKVFGHPPGKGFELATEV DKNGRVIVMTTNLEVAELKRDEVHAFGPDPLMPHSKGSMSAVVERAG |
| PS892 | 248 | MPSAAPAKPKTKRQSRTQGMPPYNVVLLDDDDHTYGYVIEMLRKVFGHPPGKGFELATEM DKNGRVIVMTTNLEVAELKRDEVHAFGPDPLMPHSKGSMSAVVERAG |
| PS896 | 249 | MPTAASATESAIEDTPAPARPEVDGRTKPKRQPRYHVVLWDDDDHTYQYVVVMLQSLFGH PPKRGYRLAKEMDTLGRVIVLTTTREHAELKRDQIHAFGYDRLLARSKGSMKASIEAEE |
| PS897 | 250 | MPTAASATESAIEDTPAPARPEVDGRTKPKRQPRYHVVNWNDDDPTRQYTVVMLQSLFGH PPERGYRLAKETRTQGRVIVLTTTREHAELKRDQIHAFGYDRLLARSKGSTKASIEAEE |
| PS898 | 251 | MPTAASATESAIEDTPAPARPEVDSRTKPKRQPRYHVVNWNDDDLTCQYTVVMLQSLFGH PPERGYRLAKEVDTQGRVIVLTTTREHAELKRDQIHAFGYDRLLARSKGSHKASIEAEE |
| PS899 | 252 | MPTAASATESAIEDTPAPARPEVDGRTKPKRQPRYHVVSWNDDDHTSQYTVVMLQSLFGH PPERGYRLAKELHTQGRVIVLTTTREHAELKRDQIHAFGYDRLLARSKGSPKASIEAEE |
| PS900 | 253 | MPTAASATESAIEDTPAPARPEVDGRTKPKRQPRYHVVLWNDDDHTYQYVVVMLQSLFGH PPKRGYRMAKEVDTQGRVIVLTTTREHAELKRDQIHAFGYDRLLARSKGSMKASIEAEE |
| PS901 | 254 | MPTAASATESAIEDTPAPARPEVDGRTKPKRQPRYHVVLWNDDDHTYQYVVVMLQSLFGH PRKRGYRLAKEVDTQGRVIVLTTTREHAELKRDQIHAFGYDRLLARSKGSMKASIEAEE |
| PS902 | 255 | MPTAASATESAIEDTPAPARPEVDGRTKPKRQPRYHVVLWNDDDHTYQYVVVMLQSLFGH PPGRGYRLAKEVDTQGRVIVLTTTREHAELKRDQIHAFGYDRLLAHSKGSMKASIEAEE |
| PS903 | 256 | MPTAASATESAIEDTPAPARPEVDGRTKPKRQPRYHVVLWNDDDHTYQYVVVMLQSLFGH PPKRGYRLAKEVDTQGRVIVLTTTREHAELKRDQIHAFGYDRLLAHSKGSMKASIEAEE |
| PS904 | 257 | MPTAASATESAIEDTPAPARPEVDGRTKPKRQPRYHVVLWNDDDHTYQYVVVMLQSLFGH PPRRGYRLAKEVDTQGRVIVLTTTREHAELKRDQIHAFGYDRLLARSKGSMKASIEAEE |
| PS905 | 258 | MPTAASATESAIEDTPAPARPEVDGRTKPKRQPRYHVVLWNDDDHTYQYVVVMLQSLFGH PPDRGYRLAKEVDTQGRVIVLTTTREHAELKRDQIHAFGYDRLLARSKGSMKASIEAEE |
| PS906 | 259 | MPTAASATESAIEDTPAPARPEVDGRTKPKRQPRYHVVLWDDDDHTYQYVVVMLQSLFGH PPKRGYRLAKEVDTQGRVIVLTTTREHAELKRDQIHAFGYDRLLAHSKGSMKASIEAEE |
| PS907 | 260 | MPTAASATESAIEDTPAPARPEVDGRTKPKRQPRYHVVLWDDDDHTYQYVVVMLQSLFGH PPKRGYRLAKEMDTQGRVIVLTTTREHAELKRDQIHAFGYDRLLAHSKGSMKASIEAEE |
| PS908 | 261 | MPTAASATESAIEDTPAPARPEVDGRTKPKRQPRYHVVLWNDDDHTYQYVVVMLRSLFGH PPERGYRLAKEVDTQGRVIVLTTTREHAELKRDQIHAFGYDRLLAHSKGSMKASIEAEE |
| PS909 | 262 | MPTAASATESAIEDTPAPARPEVDGRTKPKRQPRYHVVLWNDNYHTYQYVVVMLQSLFGH PPERGYRLAKEVDTQGRVIVLTTTREHAELKRDQIHAFGYDRLLAHSKGSMKASIEAEE |
| PS910 | 263 | MPTAASATESAIEDTPAPARPEVDGRTKPKRQPRYHVVLWNDNDHTYQYVVVMLQSLFGH PPERGYRLAKEVDTQGRVIVLTTTREHAELKRDQIHAFGYDRLLAHSKGSMKASIEAEE |
| PS911 | 264 | MPTAASATESAIEDTPAPARPEVDGRTKPKRQPRYHVVLWDDNYHTYQYVVVMLQSLFGH PPERGYRLAKEVDTQGRVIVLTTTREHAELKRDQIHAFGYDRLLAHSKGSMKASIEAEE |
| PS912 | 265 | MPTAASATESAIEDTPAPARPEVDGRTKPKRQPRYHVVLWDDDDHTYQYVVVMLQSLFGH PPERGYRLAKEVDTQGRVIVLTTTREHAELKRDQIHAFGYDRLLAHSKGSMKASIEAEE |
| PS913 | 266 | MPSAAPAKPKTKRQSRTQGMPPYNVVLLDDDDHTYGYVIEMLNKVFGHPPKKGFELATEV DKNGRVIVMTTNLEVAELKRDEVHAFGPDPLMPRSKGSMSAVVERAG |

TABLE 1-continued

Non-limiting example sequences of amino acid binding proteins.

| Name | SEQ ID NO. | Sequence |
|---|---|---|
| PS914 | 267 | MPSAAPAKPKTKRQSRTQGMPPYNVVLLDDDDHTYGYVIEMLNKVFGHPPEKGFELATEV DKNGRVIVMTTNLEVAELKRDEVHAFGPDPLMPHSKGSMSAVVERAG |
| PS915 | 268 | MPSAAPAKPKTKRQSRTQGMPPYNVVLLDDDDHTYGYVIEMLNKVFGHPPKKGFELATEV DKNGRVIVMTTNLEVAELKRDEVHAFGPDPLMPHSKGSMSAVVERAG |
| PS916 | 269 | MPSAAPAKPKTKRQSRTQGMPPYNVVLLDDDDHTYGYVIEMLNKVFGHPPEKGFELATEM DKLGRVIVMTTNLEVAELKRDEVHAFGPDPLMPRSKGSMSAVVERAG |
| PS917 | 270 | MPSAAPAKPKTKRQSRTQGMPPYNVVLLDDNYHTYGYVIEMLNKVFGHPPEKGFELATEV DKNGRVIVMTTNLEVAELKRDEVHAFGPDPLMPRSKGSMSAVVERAG |
| PS918 | 271 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDPLMPRSKGSMSAVVEAEE |
| PS919 | 272 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDPLMPRSKGSMSASIEAEE |
| PS920 | 273 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGPDPLMPRSKGSMSAVVERAG |
| PS921 | 274 | MPTAASATESAFEDTPAPARPVVDGRTKPKHQPRYHVVLWDDDDHTYQYVVVMLRSLFGH PRERGYRMAKEMDTLGRVIVLTTTREHAELKRDQIHAFGYDRLLARSKGSMKASIEAEE |
| PS922 | 275 | MPTAASATESAFEDTPAPARPVVDGRTKPKRQPRYHVVLWDDDDHTYQYVVVMLRSLFGH PRERGYRMAKEMDTLGRVIVLTTTREHAELKRDQIHAFGYDRLLARSKGSMKASIEAEE |
| PS923 | 276 | MPTAASATESAFEDTPAPARPEVDGRTKPKRQPRYHVVLWDDDDHTYQYVVVMLRSLFGH PRERGYRMAKEMDTLGRVIVLTTTREHAELKRDQIHAFGYDRLLARSKGSMKASIEAEE |
| PS924 | 277 | MPTAASATESAFEDTPAPARPEVDGRTKPKRQPRYHVVLWDDDDHTYQYVVVMLRSLFGH PRERGYRMAKEMDTQGRVIVLTTTREHAELKRDQIHAFGYDRLLARSKGSMKASIEAEE |
| PS925 | 278 | MPTAASATESAIEDTPAPARPVVDGRTKPKHQPRYHVVLWDDDDHTYQYVVVMLRSLFGH PRERGYRMAKEMDTLGRVIVLTTTREHAELKRDQIHAFGYDRLLARSKGSMKASIEAEE |
| PS926 | 279 | MPTAASATESAIEDTPAPARPVVDGRTKPKHQPRYHVVLWDDDDHTYQYVVVMLQSLFGH PRERGYRMAKEMDTLGRVIVLTTTREHAELKRDQIHAFGYDRLLARSKGSMKASIEAEE |
| PS927 | 280 | MPTAASATESAIEDTPAPARPVVDGRTKPKHQPRYHVVLWDDDDHTYQYVVVMLQSLFGH PPERGYRMAKEMDTLGRVIVLTTTREHAELKRDQIHAFGYDRLLARSKGSMKASIEAEE |
| PS928 | 281 | MPTAASATESAFEDTPAPARPEVDGRTKPKRQPRYHVVLWDDDDHTYQYVVVMLRSLFGH PPERGYRMAKEMDTQGRVIVLTTTREHAELKRDQIHAFGYDRLLARSKGSMKASIEAEE |
| PS929 | 282 | MPTAASATESAIEDTPAPARPEVDGRTKPKRQPRYHVVLWDDDDHTYQYVVVMLQSLFGH PRERGYRMAKEMDTLGRVIVLTTTREHAELKRDQIHAFGYDRLLARSKGSMKASIEAEE |
| PS930 | 283 | MPTAASATESAIEDTPAPARPEVDGRTKPKHQPRYHVVLWDDDDHTYQYVVVMLRSLFGH PPERGYRMAKEMDTQGRVIVLTTTREHAELKRDQIHAFGYDRLLARSKGSMKASIEAEE |
| PS931 | 284 | MPTAASATESAIEDTPAPARPVVDGRTKPKHQPRYHVVLWDDDDHTYQYVVVMLQSLFGH PPERGYRMAKEMDTQGRVIVLTTTREHAELKRDQIHAFGYDRLLARSKGSMKASIEAEE |
| PS932 | 285 | MPTAASATESAIEDTPAPARPVVDGRTKPKRQPRYHVVLWDDDDHTYQYVVVMLQSLFGH PPERGYRMAKEMDTQGRVIVLTTTREHAELKRDQIHAFGYDRLLARSKGSMKASIEAEE |
| PS933 | 286 | MPTAASATESAIEDTPAPARPEVDGRTKPKRQPRYHVVLWDDDDHTYQYVVVMLRSLFGH PPERGYRMAKEMDTQGRVIVLTTTREHAELKRDQIHAFGYDRLLARSKGSMKASIEAEE |
| PS934 | 287 | MPTAASATESAIEDTPAPARPEVDGRTKPKRQPRYHVVLWDDDDHTYQYVVVMLQSLFGH PRERGYRMAKEMDTQGRVIVLTTTREHAELKRDQIHAFGYDRLLARSKGSMKASIEAEE |
| PS935 | 288 | MPTAASATESAIEDTPAPARPEVDGRTKPKRQPRYHVVLWDDDDHTYQYVVVMLQSLFGH PPERGYRMAKEMDTLGRVIVLTTTREHAELKRDQIHAFGYDRLLARSKGSMKASIEAEE |
| PS936 | 289 | MPTAASATESAIEDTPAPARPEVDGRTKPKRQPRYHVVLWDDDDHTYQYVVVMLRSLFGH PPERGYRMAKEMDTQGRVIVLTTTREHAELKRDQIHAFGYDRLLARSKGSMKASIEAEE |
| PS937 | 290 | MPTAASATESAFEDTPAPARPEVDGRTKPKRQPRYHVVLWDDDDHTYQYVVVMLQSLFGH PPERGYRMAKEMDTQGRVIVLTTTREHAELKRDQIHAFGYDRLLARSKGSMKASIEAEE |
| PS938 | 291 | MPTAASATESAIEDTPAPARPEVDGRTKPKHQPRYHVVLWDDDDHTYQYVVVMLQSLFGH PPERGYRMAKEMDTQGRVIVLTTTREHAELKRDQIHAFGYDRLLARSKGSMKASIEAEE |

TABLE 1-continued

Non-limiting example sequences of amino acid binding proteins.

| Name | SEQ ID NO. | Sequence |
|---|---|---|
| PS939 | 292 | MPTAASATESAFEDTPAPARPVVDGRTKPKHQPRYHVVLWDDDDHTYQYVVVMLRSLFGH PRERGYRLAKEMDTLGRVIVLTTTREHAELKRDQIHAFGYDRLLARSKGSMKASIEAEE |
| PS940 | 293 | MPTAASATESAFEDTPAPARPVVDGRTKPKRQPRYHVVLWDDDDHTYQYVVVMLRSLFGH PRERGYRLAKEMDTLGRVIVLTTTREHAELKRDQIHAFGYDRLLARSKGSMKASIEAEE |
| PS941 | 294 | MPTAASATESAFEDTPAPARPEVDGRTKPKRQPRYHVVLWDDDDHTYQYVVVMLRSLFGH PRERGYRLAKEMDTLGRVIVLTTTREHAELKRDQIHAFGYDRLLARSKGSMKASIEAEE |
| PS942 | 295 | MPTAASATESAFEDTPAPARPEVDGRTKPKRQPRYHVVLWDDDDHTYQYVVVMLRSLFGH PRERGYRLAKEMDTQGRVIVLTTTREHAELKRDQIHAFGYDRLLARSKGSMKASIEAEE |
| PS943 | 296 | MPTAASATESAIEDTPAPARPVVDGRTKPKHQPRYHVVLWDDDDHTYQYVVVMLRSLFGH PRERGYRLAKEMDTLGRVIVLTTTREHAELKRDQIHAFGYDRLLARSKGSMKASIEAEE |
| PS944 | 297 | MPTAASATESAIEDTPAPARPVVDGRTKPKHQPRYHVVLWDDDDHTYQYVVVMLQSLFGH PRERGYRLAKEMDTLGRVIVLTTTREHAELKRDQIHAFGYDRLLARSKGSMKASIEAEE |
| PS945 | 298 | MPTAASATESAIEDTPAPARPVVDGRTKPKHQPRYHVVLWDDDDHTYQYVVVMLQSLFGH PPERGYRLAKEMDTLGRVIVLTTTREHAELKRDQIHAFGYDRLLARSKGSMKASIEAEE |
| PS946 | 299 | MPTAASATESAIEDTPAPARPVVDGRTKPKHQPRYHVVLWDDDDHTYQYVVVMLQSLFGH PPERGYRLAKEMDTQGRVIVLTTTREHAELKRDQIHAFGYDRLLARSKGSMKASIEAEE |
| PS947 | 300 | MPTAASATESAFEDTPAPARPEVDGRTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS948 | 301 | MPTAASATESAIEDTPAPARPEVDGRTKPKHQPRYHVVLWDDDDHTYQYVVVMLQSLFGH PPERGYRLAKEMDTQGRVIVLTTTREHAELKRDQIHAFGYDRLLARSKGSMKASIEAEE |
| PS949 | 302 | MPTAASATESAFEDTPAPARPVVDGRTKPKHQPRYHVVLWDDNYHTYQYVVVMLRSLFGH PRERGYRMAKEMDTLGRVIVLTTTREHAELKRDQIHAFGYDRLLAHSKGSMKASIEAEE |
| PS950 | 303 | MPTAASATESAIEDTPAPARPEVDGRTKPKRQPRYHVVLWDDNYHTYQYVVVMLQSLFGH PPERGYRMAKEMDTQGRVIVLTTTREHAELKRDQIHAFGYDRLLAHSKGSMKASIEAEE |
| PS951 | 304 | MPTAASATESAIEDTPAPARPEVDGRTKPKRQPRYHVVLWDDDYHTYQYVVVMLQSLFGH PPERGYRMAKEMDTQGRVIVLTTTREHAELKRDQIHAFGYDRLLAHSKGSMKASIEAEE |
| PS952 | 305 | MPTAASATESAIEDTPAPARPEVDGRTKPKRQPRYHVVLWDDDDHTYQYVVVMLQSLFGH PPERGYRMAKEMDTQGRVIVLTTTREHAELKRDQIHAFGYDRLLAHSKGSMKASIEAEE |
| PS953 | 306 | MPTAASATESAIEDTPAPARPEVDGRTKPKRQPRYHVVLWDDDYHTYQYVVVMLQSLFGH PPERGYRMAKEMDTQGRVIVLTTTREHAELKRDQIHAFGYDRLLARSKGSMKASIEAEE |
| PS954 | 307 | MPTAASATESAIEDTPAPARPEVDGRTKPKRQPRYHVVLWDDNDHTYQYVVVMLQSLFGH PPERGYRMAKEMDTQGRVIVLTTTREHAELKRDQIHAFGYDRLLARSKGSMKASIEAEE |
| PS955 | 308 | MPTAASATESAFEDTPAPARPVVDGRTKPKHQPRYHVVLWDDDDHTYQYVVVMLRSLFGH PRERGYRLAKEMDTLGRVIVLTTTREHAELKRDQIHAFGYDRLLARSKGSMKASIEAEE |
| PS956 | 309 | MPTAASATESAIEDTPAPARPEVDGRTKPKHQPRYHVVLWDDDDHTYQYVVVMLRSLFGH PPERGYRLAKEMDTLGRVIVLTTTREHAELKRDQIHAFGYDRLLARSKGSMKASIEAEE |
| PS957 | 310 | MPTAASATESAIEDTPAPARPEVDGRTKPKHQPRYHVVLWDDDDHTYQYVVVMLRSLFGH PRERGYRLAKEMDTQGRVIVLTTTREHAELKRDQIHAFGYDRLLARSKGSMKASIEAEE |
| PS958 | 311 | MPTAASATESAIEDTPAPARPVVDGRTKPKHQPRYHVVLWDDDDHTYQYVVVMLRSLFGH PPERGYRLAKEMDTQGRVIVLTTTREHAELKRDQIHAFGYDRLLARSKGSMKASIEAEE |
| PS959 | 312 | MHHHHHHHHHHDYDIPTTENLYFQGMPTAASATESAIEDTPAPARPEVDGRTKPKHQPRY HVVLWDDDDHTYQYVVVMLRSLFGHPPERGYRLAKEMDTQGRVIVLTTTREHAELKRDQI HAFGYDRLLARSKGSMKASIEAEE |
| PS960 | 313 | MPTAASATESAIEDTPAPARPEVDGRTKPKRQPRYHVVLWDDDDHTYQYVVVMLRSLFGI PPERGYRLAKEMDTQGRVIVLTTTREHAELKRDQIHAFGYDRLLARSKGSMKASIEAEE |
| PS961 | 314 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS962 | 315 | MPTAASATESAIEDTPAPARPEVDGRTKPKRQPRYHVVLWDDDDHTYQYVVVMLRSLFGH PYARGYRLAKEMDTQGRVIVLTTTREHAELKRDQIHAFGRDRLLARSKGSMKASIEAEE |
| PS963 | 316 | MPTAASATESAIEDTPAPARPEVDGRTKPKRQPRYHVVLWDDDDHTYQYVVVMLRSLFGH PPARGYRLAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS964 | 317 | MPTAASATESAIEDTPAPARPEVDGRTKPKRQPRYHVVLWDDDDHTYQYVVVMLRSLFGH PPWRGYRLAKEMDTQGRVIVLTTTREHAELKRDQIHAFGYDRLLAHSKGSMKASIEAEE |
| PS965 | 318 | MPTAASATESAIEDTPAPARPEVDGRTKPKRQPRYHVVLWDDDDHTYQYVVVMLQSLFGH PPSRGYRMAKEMDTQGRVIVLTTTREHAELKRDQIHAFGYDRLLAHSKGSMKASIEAEE |
| PS966 | 319 | MPTAASATESAIEDTPAPARPEVDGRTKPKRQPRYHVVLWDDDDHTYQYVVVMLQSLFGH PPARGYRLAKEMDTQGRVIVLTTTREHAELKRDQIHAFGYDRLLAHSKGSMKASIEAEE |
| PS967 | 320 | MPTAASATESAIEDTPAPARPEVDGRTKPKRQPRYHVVLWDDDDHTYQYVVVMLRSLFGH PPARGYRLAKEMDTQGRVIVLTTTREHAELKRDQIHAFGRDRLLARSKGSMKASIEAEE |
| PS968 | 321 | MPTAASATESAIEDTPAPARPEVDGRTKPKRQPRYHVVLWNDDDHTYQYVVVMLRSLFGH PPERGYRLAKEMDTQGRVIVLTTTREHAELKRDQIHAFGRDRLLARSKGSMKASIEAEE |
| PS969 | 322 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLAHSKGSMKASIEAEE |
| PS970 | 323 | MPTAASATESAIEDTPAPARPEVDGRTKPKRQPRYHVVLWNDDDHTYQYVVVMLRSLFGH PPSRGYRLAKEMDTQGRVIVLTTTREHAELKRDQIHAFGYDRLLARSKGSMKASIEAEE |
| PS971 | 324 | MPTAASATESAIEDTPAPARPEVDGRTKPKHQPRYHVVLWDDDDHTYQYVVVMLRSLFGH PPERGYRLAKEMDTQGRVIVLTTTREHAELKRDQIHAFGYDRLLAHSKGSMKASIEAEE |
| PS972 | 325 | MPTAASATESAIEDTPAPARPEVDGRTKPKHQPRYHVVLWDDDDHTYQYVVVMLHSLFGH PPERGYRLAKEMDTQGRVIVLTTTREHAELKRDQIHAFGYDRLLAHSKGSMKASIEAEE |
| PS973 | 326 | MPTAASATESAIEDTPAPARPEVDGRTKPKHQPRYHVVLWDDDDHTYQYLVVMLRSLFGH PPERGYRLAKEMDTQGRVIVLTTTREHAELKRDQIHAFGYDRLLARSKGSMKASIEAEE |
| PS974 | 327 | MPTAASATESAIEDTPAPARPEVDGRTKPKHQPRYHVVLWDDDDHTYQYIVVMLRSLFGH PPERGYRLAKEMDTQGRVIVLTTTREHAELKRDQIHAFGYDRLLARSKGSMKASIEAEE |
| PS975 | 328 | MPTAASATESAIEDTPAPARPEVDGRTKPKHQPRYHVVLWDDDDHTYQYVVVMLRSLFGH PPERGYRLAKEFDTQGRVIVLTTTREHAELKRDQIHAFGYDRLLARSKGSMKASIEAEE |
| PS976 | 329 | MPTAASATESAIEDTPAPARPEVDGRTKPKHQPRYHVVLWDDNYHTYQYVVVMLRSLFGH PPERGYRLAKEMDTQGRVIVLTTTREHAELKRDQIHAFGYDRLLARSKGSMKASIEAEE |
| PS978 | 330 | MPTAASATESAIEDTPAPARPEVDGRTKPKRQPRYHVVLWDDDDHTYQYVVVMLHSLFGH PPERGYRLAKEMDTQGRVIVLTTTREHAELKRDQIHAFGYDRLLARSKGSMKASIEAEE |
| PS979 | 331 | MPTAASGTESAIEDTPAPARPEVDGRTKPKRQPRYHVVLWDDDDHTYQYVVEMLRSLFGH PPERGYRLAKEMDTQGRVIVLTTTREHAELKRDQIHAFGYDRLLARSKGSMKASIEAEE |
| PS980 | 332 | MPTAASATESAFEDTPAPARPEVDGRTKPKRQPRYHVVLWDDDDHTYQYVVVMLRSLFGH PTERGYRLAKEMDTQGRVIVLTTTREHAELKRDQIHAFGYDRLLARSKGSMKASIEAEE |
| PS981 | 333 | MPTAASATESAIEDTPAPARPEVDGRTKPKRQPRYHVVLWDDDDHTYQYVVVMLRSLFGH PPDRGYRLAKEMDTQGRVIVLTTTREHAELKRDQIHAFGYDRLLARSKGSMKASIEAEE |
| PS982 | 334 | MPTAASATESAIEDTPAPARPEVDGRTKPKRQPRYHVVLWDDDDHTYQYVVVMLQSLLGH PPERGYRLAKEMDTQGRVIVLTTTREHAELKRDQIHAFGYDRLLARSKGSMKASIEAEE |
| PS983 | 335 | MPTAASATESAIEDTPAPARPEMDGRTKPKRQPRYHVVLWDDDDHTYQYVVVMLRSLFGH PPERGYRLAKEMDTQGRVIVLTTTREHAELKRGQIHAFGYDRLLARSKGSMKASIEAEE |
| PS984 | 336 | MPTAASATESAIEDTPAPARPEVDGRTKPKRQPRYYVVLWDDDDHTYQYVVVMLRSLFGH PPERGYRLAKEMDTQGRVIVLTTTREHAELKRDQIHAFGYDRLLARSKGSMKASIEAEE |
| PS985 | 337 | MPTAASATESAIEDTPAPARPEVDGRTKPKRQTRYHVVLWDDDDHTYQYVVVMLQSLFGH PPERGYRLAKEMDTQGRVIVLTTTREHAELKRDQIHAFGYDRLLARSKGSMKASIEAEE |
| PS986 | 338 | MPTAASATESAIEDTPAPARPEVDGRTVPKRQPRYHVVLWDDDDHTYQYVVVMLQSLFGH PPERGYHLAKEMDTQGRVIVLTTTREHAELKRDQIHAFGYDRLLARSKGSMKASIEAEE |
| PS987 | 339 | MPTAASATESAIEDTPAPARPEVDGRTKPKRQPRYHVVLWDDDDHTYQYVVVMLQSLFGH PPERGYRLAKEMDTQGRVVVLTTTREHAELKRDQIHAFGYDRLLARSKGSMKASIEAEE |
| PS988 | 340 | MPTAASATESAIEDTPAPARPEVDGRTVPKRQPRYHVVLWDDDDHTYQYVVVMLQSLFGH PPERGYRMAKEMDTQGRVIVLTTTREHAELKRDQIHAFGYDRLLARSKGSMKASIEAEE |
| PS989 | 341 | MPTAASATESAIEDTPAPARPEVDGRTKPRRQPRYHVVLWDDDDHTYQYVVVMLRSLFGH PPERGYRLAKEMDTQGRVIVLTTTREHAELKRDQIHAFGYDRLLARSKGSMKASIEAEE |

TABLE 1-continued

Non-limiting example sequences of amino acid binding proteins.

| Name | SEQ ID NO. | Sequence |
|---|---|---|
| PS990 | 342 | MPTAASATESAIEDTPAPARPEVDGRTVPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS991 | 343 | MPTAASATESAFEDTPAPARPEVDGRTKPIRQPRYHVVLWDDDDHTYQYVVVMLRSLFGH PPERGYRLAKEMDTQGRVIVLTTTREHAELKRDQIHAFGYDRLLARSKGSMKASIEAEE |
| PS992 | 344 | MPTAASATESAIEDTPAPARPEVDGRTKPKRQPRCHVVLWDDDDHTYQYVVVMLRSLFGH PPERGYRLAKEMDTQGRVIVLTTTREHAELKRDQIHAFGYDRLLARSKGSMKASIEAEE |
| PS993 | 345 | MPTAASATESAIEDTPAPARSEVDGRTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS994 | 346 | MPTAASATESAIEDTPAPARPEVDGRTKPERQPRYHVVLWDDDDHTYQYVVVMLQSLFGH PPERGYRLAKEMDTQGRVIVLTTTREHAELKRDQIHAFGYDRLLARSKGSMKASIEAEE |
| PS995 | 347 | MPTAASATESAIEDTPAPARPEVDGCTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS996 | 348 | MPTAASATESAIEDTPAPARPEVDGSTKPKRQPRYHVVLWDDDDHTYQYVVVMLQSLFGH PPERGYRLAKEMDTQGRVIVLTTTREHAELKRDQIHAFGYDRLLARSKGSMKASIEAEE |
| PS997 | 349 | MPTAASATESAIEDTPAPARPEMDGRTKPKRQPRYHVVLWDDDDHTYQYVVVMLRSLFGH PPERGYRLAKEMDTQGRVIVLTTTREHAELKRDQIHAVGYDRLLARSKGSMKASIEAEE |
| PS998 | 350 | MPTAASATESAIEDTPAPARPEVDGRTKPKRHPRYHVVLWDDDDHTYQYVVVMLQSLFGH SPKRGYCLAKEMDTQGRVIVLTTTREHAELKRDQIHAFGYDRLLARSKGSMKASIEAEE |
| PS999 | 351 | MPTAASATESAFEDTPAPARPEVDGRTKPKRQPRYHVVLWDDDDHTYQYVVVMLRSLFGY PPERGYRLAKEMDTQGRVIVLTTTREHAELKRDQIHAFGYDRLLARSKGSMKASIEAEE |
| PS1000 | 352 | MPTAASATESAIEDTPAPARPVVDGRTKPKRQPRYHVVLWDDDDHTYQYVVVMLRSLFGH PPERGYRLAKEMDTQGRVIVLTTTREHAELKRDQIHAFGYDRLLARSKGSMKASIEAEE |
| PS1001 | 353 | MPTAASATESAFEDTPAPARPEVDGRTKPKRQPRYHVVLWDDDDHTYQYVVVMLRTLFGH PPERGYRLAKEMDTQGRVIVLTTTREHAELKRDQIHAFGYDRLLARSKGSMKASIEAEE |
| PS1002 | 354 | MPTAASATESAIEDTPAPARPEVDGRTKPKHQPRYHVVLWDDDDHTYQYVVVMLRDLFGH PPERGYRLAKEMDTQGRVIVLTTTREHAELKRDQIHAFGYDRLLARSKGSMKASIEAEE |
| PS1003 | 355 | MPTAASATESAIEDTPAPARPEVDGRTKPKHQPRYHVVLWDDDDHTYQYVVVMLRSLFGH PKQRGYRLAKEMDTQGRVIVLTTTREHAELKRDQIHAFGYDRLLARSKGSMKASIEAEE |
| PS1004 | 356 | MPTAASATESAIEDTPAPARPVVDGRTKPKHQPRYHVVLWDDDDHTYQYVVVMLRSLFGH PQRRGYRLAKEMDTQGRVIVLTTTREHAELKRDQIHAFGYDRLLARSKGSMKASIEAEE |
| PS1005 | 357 | MPTAASATESAIEDTPAPARPVVDGRTKPKRQPRYHVVLWDDDDHTYQYVVVMLLSLFGH PSERGYRLAKEMDTQGRVIVLTTTREHAELKRDQIHAFGYDRLLARSKGSMKASIEAEE |
| PS1006 | 358 | MPTAASATESAFEDTPAPARPEVDGRTKPKHQPRYHVVLWDDDDHTYQYVVVMLRSLFGH PPERGYRLAKEMDTQGRVIVLTTTREHAELKRDQIHAFGYDRLLARSKGSMKASIEAEE |
| PS1007 | 359 | MPTAASATESAIEDTPAPARPEVDGRTKPKHQPRYHVVLWDDDDHTYQYVVVMLRYLFGH PPERGYRLAKEMDTQGRVIVLTTTREHAELKRDQIHAFGYDRLLARSKGSMKASIEAEE |
| PS1008 | 360 | MPTAASATESAIEDTPALARPEVDGRTKPKHQPRYHVVLWDDDDHTYQYVVVMLLSLFGH PPERGYRLAKEMDTQGRVIVLTTTREHAELKRDQIHAFGYDRLLARSKGSMKASIEAEE |
| PS1009 | 361 | MPTAASATESAIEDTPAPARPVVDGRTKPKRQPRYHVVLWDDHDHTYQYVVVMLRSLFGH PPERGYRLAKEMDTQGRVIVLTTTREHAELKRDQIHAFGYDRLLARSKGSMKASIEAEE |
| PS1010 | 362 | MPTAASATESAIEDTPAPARPEVDGRTKPKRQPRYHVVLWDDDDHTYQYVVVMLRSLFGH PPERGYRKAKELDTQGRVIVLTTTREHAELKRDQIHAFGYDRLLARSKGSMKASIEAEE |
| PS1011 | 363 | MPTAASATESAIEDTPAPARPEVDGRTKPKRQPRYHVVLWDDDDHTYQYVVVMLRSLFGH PPERGYRLAKELVTQGRVIVLTTTREHAELKRDQIHAFGYDRLLARSKGSMKASIEAEE |
| PS1012 | 364 | MPTAASATESAIEDTPAPARPEVDGRTKPKRQPRYHVVLWDDDDHTYQYVVVMLRTLFGH PPSRGYRMAKEMDTQGRVIVLTTTREHAELKRDQIHAFGRDRLLARSKGSMKASIEAEE |
| PS1013 | 365 | MPTAASATESAIEDTPAPARPEVDGRTKPKRQPRYHVVLWDDDDHTYQYVVVMLRDLFGH PPSRGYRMAKEMDTQGRVIVLTTTREHAELKRDQIHAFGRDRLLARSKGSMKASIEAEE |
| PS1014 | 366 | MPTAASATESAIEDTPAPARPEVDGRTKPKRQPRYHVVLWDDDDHTYQYVVVMLRYLFGH PPSRGYRMAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1015 | 367 | MPTAASATESAIEDTPAPARPEVDGRTKPKRQPRYHVVLWDDDDHTYQYVVVMLRSLFGH PKQRGYRMAKEMDTQGRVIVLTTTREHAELKRDQIHAFGRDRLLARSKGSMKASIEAEE |
| PS1016 | 368 | MPTAASATESAFEDTPAPARPEVDGRTKPKHQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1017 | 369 | MPTAASATESAIEDTPAPARPEVDGRTKPKRQPRYHVVLWDDDDHTYQYVVVMLRSLFGH PQRRGYRMAKEMDTQGRVIVLTTTREHAELKRDQIHAFGRDRLLARSKGSMKASIEAEE |
| PS1018 | 370 | MPTAASATESAIEDTPAPARPVVDGRTKPKHQPRYHVVLWDDDDHTYQYVVVMLRSLFGH PQRRGYRMAKEMDTQGRVIVLTTTREHAELKRDQIHAFGRDRLLARSKGSMKASIEAEE |
| PS1019 | 371 | MPTAASATESAIEDTPAPARPEVDGRTKPKRQPRYHVVLWDDDDHTYQYVVVMLRSLFGH PRSRGYRMAKEMDTQGRVIVLTTTREHAELKRDQIHAFGRDRLLARSKGSMKASIEAEE |
| PS1020 | 372 | MPTAASATESAFEDIPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1021 | 373 | MPTATSATESAIEDTPAPARPEVDGRTKPKRQPHYHVVLWDDDDHTYQYVVVMLRSLFGH PPSRGYRMAKEMDTQGRVIVLTTTREHAELKRDQIHAFGRDRLLARSKGSMKASIEAEE |
| PS1022 | 374 | MPTAASATESAIEDTPAPARPEVDGRTKPKRQPRYHVVLWDDDDHTYQYVVVMLRSLFGH PRERGYRLAKEMDTQGRVIVLTTTREHAELKRDQIHAFGYDRLLARSKGSMKASIEAEE |
| PS1023 | 375 | MPTAASATESAFEDIPAPARPEVDGRTKPKRQPRYHVVLWDDDDHTYQYVVVMLRSLFGH PPERGYRLAKEMDTQGRVIVLTTTREHAELKRDQIHAFGYDRLLARSKGSMKASIEAEE |
| PS1024 | 376 | MPTATSATESAIEDTPAPARPEVDGRTKPKRQPHYHVVLWDDDDHTYQYVVVMLRSLFGH PPERGYRLAKEMDTQGRVIVLTTTREHAELKRDQIHAFGYDRLLARSKGSMKASIEAEE |
| PS1025 | 377 | MPTAASATESAIEDTPAPARPEVDGRTKPKKQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1026 | 378 | MPTAASATESAIEDTPAPARPEVDGRTKPKRQPRYHVVLWDDDDHTYQYVVVMLRSLFGF PPSRGYRMAKEMDTQGRVIVLTTTREHAELKRDQIHAFGRDRLLARSKGSMKASIEAEE |
| PS1027 | 379 | MPTAASATESAIEDIPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1028 | 380 | MPTAASATESAIEDTPAPARPEVDGRTKPKRQPRYHVVLWDDDDHTYQYVVVMFRSLFGH PPSRGYRMAKEMDTQGRVIVLTTTREHAELKRDQIHAFGRDRLLARSKGSMKASIEAEE |
| PS1029 | 381 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHALGRDRLLARSKGSMKASIEAEE |
| PS1030 | 382 | MPTAASATESAIEDTPAPARPEVDGRTKPKRQPRYHVVLWDDDDHTYQYVVVMLRSLFGH PPSRGYRMAKEMDTQGRVIVLTTTNEHAELKRDQIHAFGRDRLLARSKGSMKASIEAEE |
| PS1031 | 383 | MPTAASATESAIEDTPAPARPEVDGRTKPKRQPRYHVVLWDDDDHTYQYVVVMFRSLFGH PPSRGYRMAKEMDTQGRVIVLTTTREHAELKRDQIHALGRDRLLARSKGSMKASIEAEE |
| PS1032 | 384 | MPTAASATESAIEDTPAPARPEVDGRTKPKRQPRYHVVLWDDDDHTYQYVVVMLRSLFGH PPSRGYRMAKEMDTQGVVIVLTTTREHAELKRDQIHAFGRDRLLARSKGSMKASIEAEE |
| PS1033 | 385 | MPTAASATESAIEDTPAPARPEVDGRTKPKRQPRYHVVLWDDDDHTYQYVVVMLRSLFGH PPSRGYRMAKEMRTQGRVIVLTTTREHAELKRDQIHAFGRDRLLARSKGSMKASIEAEE |
| PS1034 | 386 | MPTAASATESAIEDTPAPARPEVDGRTKPKRQPRYHVVLWDDDDHTYQYVVVMLRSLFGH PPSRGYRMAKEMDTQGRVIPLTTTREHAELKRDQIHAFGRDRLLARSKGSMKASIEAEE |
| PS1035 | 387 | MPTAASATESAIEDTPAPARPEVDGRTKPKRQPRYHVVNWDDDDHTYQYVVVMLRSLFGH PPSRGYRMAKEMDTQGRVIVLTTTREHAELKRDQIHAFGRDRLLARSKGSMKASIEAEE |
| PS1036 | 388 | MPTAASATESAIEDTPAPARPEVDGRTKPKRQPRYHVVLWDDDDHTYQYVVVMLRSLFGH PPSRGYRMAKEMDTQGRVIVLTTTTEHAELKRDQIHAFGRDRLLARSKGSMKASIEAEE |
| PS1038 | 389 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEEG SAGSAAGSGEFMPTAASATESAIEDTPAPARPEVDGRTKPKRQPRYHVVLWDDDDHTYQY VVVMLRSLFGHPPSRGYRMAKEMDTQGRVIVLTTTREHAELKRDQIHAFGRDRLLARSKG SMKASIEAEE |
| PS1043 | 390 | MPTAASATESAIEDTPAPARPEVDGRTKPKRQPRYHVVLWDDDDHTYQYVVVMLRSLFGH PKQRGYRMAKEMDTQGRVIVLTTTREHAELKRDQIHAFGRDRLLARSKGSMKASIEAEEG |

TABLE 1-continued

Non-limiting example sequences of amino acid binding proteins.

| Name | SEQ ID NO. | Sequence |
|---|---|---|
| | | SAGSAAGSGEFMPTAASATESAIEDTPAPARPEVDGRTKPKRQPRYHVVLWDDDDHTYQY VVVMLRSLFGHPKQRGYRMAKEMDTQGRVIVLTTTREHAELKRDQIHAFGRDRLLARSKG SMKASIEAEE |
| PS1044 | 391 | MSPILGYWKIKGLVQPTRLLLEYLEEKYEEHLYERDEGDKWRNKKFELGLEFPNLPYYID |
| PS1045 | 392 | MSPILGYWKIKGLVQPTRLLLEYLEEKYEEHLYERDEGDKWRNKKFELGLEFPNLPYYID |
| PS1046 | 393 | MGGLFFNALKNCKENFTVLQTIRQQQSTLNGSWVALLQTRNTLNRAGIRYMMDQNNIGSG STVAELMESASISLKQAEKNWADYEALPRDPRQSTAAAAEIKRNYDIYHNALAELIQLLG AGKINEFFDQPTQGYQDGFEKQYVAYMEQNDRLHDIAVSDNNASYS |
| PS1047 | 394 | MGGLFFNALKNDKENFTVLQTIRQQQSTLNGSWVALLQTRNTLNRAGIRYMMDQNNIGSG STVAELMESASISLKQAEKNWADYEALPRDPRQSTAAAAEIKRNYDIYHNALAELIQLLG AGKINEFFDQPTQGYQDGFEKQYVAYMEQNDRLHDIAVSDNNASYS |
| PS1048 | 395 | MPTAASATESAIEDTPAPARPEVDGRTKPKRQPRYHVVLWDDDDHTYQYYVVMLRSLFGH PPSRGYRMAKEMDTQGRVIVLTTTREHAELKRDQIHAFGRDRLLARSKGSMKASIEAEE |
| PS1049 | 396 | MPTAASATESAIEDTPAPARPEVDGRTKPKRQPRYHVVLWDDDDHTYQYYVVMLRSLFGH PPSRGYRMAKEIDTQGRVIVLTTTREHAELKRDQIHAFGRDRLLARSKGSMKASIEAEE |
| PS1050 | 397 | MPTAASATESAIEDTPAPARPEVDGRTKPKRQPRYHVVLWEDDDETYQYIVVMLRSLFGH PPSRGYRMAKELDTQGRVIVLTTTREHAELKRDQIHAFGRDRLLARSKGSLKASIEAEE |
| PS1051 | 398 | MPTAASATESAIEDTPAPARPEVDGRTKPKRQPRYHVVLWNDDDLTYQYLVVMLRSLFGH PPSRGYRMIKEMDTQGRVIVLTTTREHAELKRDQIHAFGRDRLLARSKGSPKASIEAEE |
| PS1052 | 399 | MPTAASATESAIEDTPAPARPEVDGRTKPKRQPRYHVVLWEDDDETYQYLVVMLRSLFGH PPSRGYRMAKEIDTQGRVIVLTTTREHAELKRDQIHAFGRDRLLARSKGSMKASIEAEE |
| PS1053 | 400 | MPTAASATESAIEDTPAPARPEVDGRTKPKRQPRYHVVLWDDDDDTYQYLVVMLRSLFGH PPSRGYRMMKEIDTQGRVIVLTTTREHAELKRDQIHAFGRDRLLARSKGSLKASIEAEE |
| PS1054 | 401 | MPTAASATESAIEDTPAPARPEVDGRTKPKRQPRYHVVLWDDDDETYQYLVVMLRSLFGH PPSRGYRMVKEADTQGRVIVLTTTREHAELKRDQIHAFGRDRLLARSKGSMKASIEAEE |
| PS1055 | 402 | MPTAASATESAIEDTPAPARPEVDGRTKPKRQPRYHVVLWTDDDQTYQYMVVMLRSLFGH PPSRGYRMAKELDTQGRVIVLTTTREHAELKRDQIHAFGRDRLLARSKGSPKASIEAEE |
| PS1056 | 403 | MPTAASATESAIEDTPAPARPEVDGRTKPKRQPRYHVVLWSDDDETYQYIVVMLRSLFGH PPSRGYRMIKELDTQGRVIVLTTTREHAELKRDQIHAFGRDRLLARSKGSVKASIEAEE |
| PS1057 | 404 | MPTAASATESAIEDTPAPARPEVDGRTKPKRQPRYHVVLWDDDDDTYQYLVVMLRSLFGH PPSRGYRMAKELDTQGRVIVLTTTREHAELKRDQIHAFGRDRLLARSKGSMKASIEAEE |
| PS1058 | 405 | MPTAASATESAIEDTPAPARPEVDGRTKPKRQPRYHVVLWDDDDHTYQYVVVMLRSLFGH PPSRGYRMVKEMDTQGRVIVLTTTREHAELKRDQIHAFGRDRLLARSKGSVKASIEAEE |
| PS1059 | 406 | MPTAASATESAIEDTPAPARPEVDGRTKPKRQPRYHVVLWEDDDETYQYLVVMLRSLFGH PPSRGYRMVKEIDTQGRVIVLTTTREHAELKRDQIHAFGRDRLLARSKGSWKASIEAEE |
| PS1060 | 407 | MHHHHHHHHHHDYDIPTTENLYFQGMPTAASATESAIEDTPAPARPEVDGRTKPKRQPRY HVVLWDDDDHTYQYVVVMLRSLFGHPPSRGYRMAKEMDTQGRVIVLTTTREHAELKRDQI HAFGRDRLLARSKGSMKASIEAEE |
| PS1061 | 408 | MPTAASATESAIEDTPAPARPEVDGRTEPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1062 | 409 | MPTAASATESAIEDTPAPARSEVDGRTKPERQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1063 | 410 | MPTAASATESAIEDTPAPARPEVDGRTKPKRQPRYHVVLWDDDDHSYQYVVVMLRSLFGH PPSRGYRMAKEMDTQGRVIVLTTTREHAELKRDQIHAFGRDRLLARSKGSMKASIEAEE |
| PS1064 | 411 | MPTAASATESAIEDTPAPARPEVDGRTKPKRQPRYHVVLWDDDDHIYQYVVVMLRSLFGH PPSRGYRMAKEMDTQGRVIVLTTTREHAELKRDQIHAFGRDRLLARSKGSMKASIEAEE |
| PS1065 | 412 | MPTAASATESAIEDTPAPARPEVDGRTKPKRQPRYHVVLWDDDDHTYQYVVVMLRSLVGH PPSRGYRMAKEMDTQGRVIVLTTTREHAELKRDQIHAFGRDRLLARSKGSMKASIEAEE |
| PS1066 | 413 | MPTAASATESAIEDTPAPARPEVDGRTKPKRQPRYHVVLWDDDDHTYQYVVVMLRSLFGH SPSRGYRMAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1067 | 414 | MPTAASATESAIEDTPAPARPEVDGRTKPKRQPRYHVVLWDDDDHTYQYVVVMLRSLFGH PPSRGYRMAKEMHTQGRVIVLTTTREHAELKRDQIHAFGRDRLLARSKGSMKASIEAEE |
| PS1068 | 415 | MPTAASATESAIEDTPAPARPEVDGRTKPKRQPRYHVVLWDDDDHTYQYVVVMLRSLFGH PPSRGYRMAKEMVTQGRVIVLTTTREHAELKRDQIHAFGRDRLLARSKGSMKASIEAEE |
| PS1069 | 416 | MPTAASATESAIEDTPAPARPEVDGRTKPKRQPRYHVVLWDDDDHTYQYVVVMLRSLFGH PPSRGYRMAKEMDTLGRVIVLTTTREHAELKRDQIHAFGRDRLLARSKGSMKASIEAEE |
| PS1070 | 417 | MPTAASATESAIEDTPAPARPEVDGRTKPKRQPRYHVVLWDDDDHTYQYVVVMLRSLFGH PPSRGYRHAKTMDTQGRVIVLTTTREHAELKRDQIHALGRDRLLARSKGSMKASIEAEE |
| PS1071 | 418 | MPTAASATESAIEDTPAPARPEVDGRTKPKRQPRYHVVLWDDDRHTYQYVVVMLRSLFGH PPSRGYRMAKEMDTQGRVIVLTTTREHAELKRDQIHAFGRDRLLARSKGSMKASIEAEE |
| PS1072 | 419 | MPTAASATESAIEDTPAPARPEVDGRTKPKRQPRYHVVLWDDDDHTDQYVVVMLRSLFGH PPSRGYRMALEAHTQGRVIVLTTTREHAELKRDQIHAFGRDRLLARSKGSMKASIEAEE |
| PS1073 | 420 | MPTAASATESAIEDTPAPARPEVDGRTKPKRQPRYHVVLEDDDDHTYQYVVVMLRSLFGH PPSRGYRMAKEYDTQGRVIVLTTTREHAELKRDQIHAFGRDRLLARSKGSMKASIEAEE |
| PS1074 | 421 | MPTAASATESAIEDTPAPARPEVDGRTKPKRQPRYHVVLWDDDDHTYQYIVVMLRSLFGH PPSRGYRMARIMDTQGRVIVLTTTREHAELKRDQIHAFGRDRLLARSKGSMKASIEAEE |
| PS1075 | 422 | MPTAASATESAIEDTPAPARPEVDGRTKPKRQPRYHVVLWDDDDHTYQYVVVMLRSLFGH PRQRGYRMAKEMDTQGRVIVLTTTREHAELKRDQIHAFGRDRLLARSKGSMKASIEAEE |
| PS1076 | 423 | MAIEDTPAPARPEVDGRTKPKRQPRYHVVLWDDDDHTYQYVVVMLRSLFGHPPSRGYRMA KEMDTQGRVIVLTTTREHAELKRDQIHAFGRDRLLARSKGSMKASIEAEE |
| PS1077 | 424 | MPEVDGRTKPKRQPRYHVVLWDDDDHTYQYVVVMLRSLFGHPPSRGYRMAKEMDTQGRVI VLTTTREHAELKRDQIHAFGRDRLLARSKGSMKASIEAEE |
| PS1078 | 425 | MPRYHVVLWDDDDHTYQYVVVMLRSLFGHPPSRGYRMAKEMDTQGRVIVLTTTREHAELK RDQIHAFGRDRLLARSKGSMKASIEAEE |
| PS1079 | 426 | MPTAASATESAIEDTPAPARPEVDGRTKPKRQPRYHVVLWNDDDHTYQYVVVMLQSLFGH PPERGYRLAKEVDTQGRVIVLTTTREHAELKRDQIHAFGYDPLIDRCKGSMSASIEAEE |
| PS1080 | 427 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDPLIDRCKGSMSASIEAEE |
| PS1082 | 428 | MPTAASATESAIEDTPAPARPEVDGRTKPKRQPRYHVVLWDDDDHTYQYIVVMLRSLFGH PPSRGYRMAKEMDTQGRVIVLTTTREHAELKRDQIHAFGRDRLLARSKGSMKASIEAEE |
| PS1083 | 429 | MPTAASATESAIEDTPAPARPEVDGRTKPKRQPRYHVVLWDDDDHTYQYTVVMLRSLFGH PPSRGYRMAKELDTQGRVIVLTTTREHAELKRDQIHAFGRDRLLARSKGSMKASIEAEE |
| PS1084 | 430 | MPTAASATESAIEDTPAPARPEVDGRTKPKRQPRYHVVLWNDDDHTYQYLVVMLRSLFGH PPSRGYRMAKELDTQGRVIVLTTTREHAELKRDQIHAFGRDRLLARSKGSMKASIEAEE |
| PS1085 | 431 | MPTAASATESAIEDTPAPARPEVDGRTKPKRQPRYHVVLWEDDDHTYQYLVVMLRSLFGH PPSRGYRMAKEYDTQGRVIVLTTTREHAELKRDQIHAFGRDRLLARSKGSNKASIEAEE |
| PS1086 | 432 | MPTAASATESAIEDTPAPARPEVDGRTKPKRQPRYHVVLWDDDDHTYQYVVVMLRSLFGH PTERGYRLAKEMDTQGRVIVLTTTREHAELKRDQIHAFGRDRLLARSKGSMKASIEAEE |
| PS1087 | 433 | MPTAASATESAIEDTPAPARPEVDGRTKPKRQPRYHVVLWDDDDHTYQYVVVMLRSLFGH PTERGYRMAKEMDTQGRVIVLTTTREHAELKRDQIHAFGRDRLLARSKGSMKASIEAEE |
| PS1088 | 434 | MPTAASATESAIEDTPAPARPEVDGRTKPKRQPRYHVVLWDDDDHTYQYVVVMLRSLFGH PPWRGYRLAREMDTQGRVIVLTTTREHAELKRDQIHAFGYDRLLARSKGSMKASIEAEE |
| PS1089 | 435 | MPTAASATESAIEDTPAPARPEVDGRTKPKRQPRYHVVLWDDDDHTYQYVVVMLRSLFGH PPWRGYRLAREMDTQGRVIVLTTTREHAELKRDQIHAFGRDRLLARSKGSMKASIEAEE |
| PS1090 | 436 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSLEASIEAEE |
| PS1091 | 437 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSLEASIEAEE |
| PS1092 | 438 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHASGRDRLLARSKGSYKASIEAEE |

TABLE 1-continued

Non-limiting example sequences of amino acid binding proteins.

| Name | SEQ ID NO. | Sequence |
|---|---|---|
| PS1093 | 439 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHASGRDRLLAHSKGSKKASIEAEE |
| PS1094 | 440 | MPTAASATESAIEDTPAPARPEVDGCTKPKRQPRYHVVLWDDDDHTYQYVVVMLQSLFGH PPERGYRLAKEMDTQGCVIVLTTTREHAELKRDQIYAFGYDRLLARSKGSMKASIEAEE |
| PS1095 | 441 | MPTAASATESAIEDTPAPARPEVDGRTKPKRQPRYHVVLWDDDDHTYQYVVEMLRTLFGH PPERGYRLAKEMDTQGRVIVLTTTREHAELKRDQIHAFGRDRLLARSKGSMKACIEAEE |
| PS1096 | 442 | MPTAASATESAIEDTPAPARPEVDGRAKPKRQPRYHVVLWNDDDHTYQYVVVVLQSLFSH PRERGYRLAKEMDTQGRVIVLTTTREHAELKRDQIHAFGYDRLLARSKGSMKASIEAEE |
| PS1097 | 443 | MPTAASATESAIGDTPAPARPKMDGRTKPKRQPRYHVVLWNDDDHTYQYAVVMLQSLFGH PPERGYRQAKEVDTQGRVIVLTTTREHAELKRDQIHAFGYDRLLARSKGSMKASIEAEE |
| PS1098 | 444 | MPTAASATESAIGDTPAPARPEVDGRTKPKRQPRYHVVLWDDDDHTYQYVVVMLRDLFGH PPERGYHMAKEMDTQGRVIVLTTTREHAELKRDQIHAFGRDRLLARSKGSMKASIEAEE |
| PS1099 | 445 | MGSSHHHHHHSSGENLYFQGHMPTAASATESAIEDTPAPARPEVDGRTKPKRQPRYHVVL WDDDDHTYQYVVVMLRSLFGHPPSRGYRMAKEMDTQGRVIVLTTTREHAELKRDQIHAFG RDRLLARSKGSMKASIEAEE |
| PS1100 | 446 | MGSSHHHHHHSSGENLYFQGHMQPRYHVVLWDDDDHTYQYVVVMLRSLFGHPPSRGYRMA KEMDTQGRVIVLTTTREHAELKRDQIHAFGRDRLLARSKGSMKASIEAEE |
| PS1101 | 447 | MHSKFSHAGRICGAKFKVREPIYRCKECSFDDTCVLCVNCFNPKDHTGHHVYTTICTEFN NGICDCGDKEAWNHTLFCKAEEG |
| PS1102 | 448 | MHSKFSHAGRICGAKFKVGEPIYRCKECQFDDTCVLCVNCFNPKDHTGHHVYTTICTEFN NGICDCGDKEAWNHTLFCKAEEG |
| PS1103 | 449 | MHSKFSHAGRICGAKFKVGEPIYRCKECSFDYTCVLCVNCFNPKDHTGHHVYTTICTEFN NGICDCGDKEAWNHTLFCKAEEG |
| PS1104 | 450 | MHSKFSHAGRICGAKFKVGEPIYRCKECSFDDTCVLCVNCFNPKDHRGHHVYTTICTEFN NGICDCGDKEAWNHTLFCKAEEG |
| PS1105 | 451 | MHSKFSHAGRICGAKFKVGEPIYRCKECSFDDTCVLCVNCFNPKDHTRHHVYTTICTEFN NGICDCGDKEAWNHTLFCKAEEG |
| PS1106 | 452 | MHSKFSHAGRICGAKFKVGEPIYRCKECSFDDTCVLCVNCFNPKDHTGHHVYVTICTEFN NGICDCGDKEAWNHTLFCKAEEG |
| PS1107 | 453 | MHSKFSHAGRICGAKFKVGEPIYRCKECSFDDTCVLCVNCFNPKDHTGHHVYTTICREFN NGICDCGDKEAWNHTLFCKAEEG |
| PS1108 | 454 | MHSKFSHAGRICGAKFKVGEPIYRCKECSFDDTCVLCVNCFNPKDHTGHHVYTTICTERN NGICDCGDKEAWNHTLFCKAEEG |
| PS1109 | 455 | MHSKFSHAGRICGAKFKVGEPIYRCKECSFDDTCVLCVNCFNPKDHTGHHVYTTICTEFN KGICDCGDKEAWNHTLFCKAEEG |
| PS1110 | 456 | MHSKFSHAGRICGAKFKVGEPIYRCKECSFDDTCVLCVNCFNPKDHTGHHVYTTICTEFN NGECDCGDKEAWNHTLFCKAEEG |
| PS1111 | 457 | MHSKFSHAGRICGAKFKVGEPIYRCKECSFDDTCVLCVNCFNPKDHTGHHVYTTICTEFN NGICDCGDKSAWNHTLFCKAEEG |
| PS1112 | 458 | MHSKFSHAGRICGAKFKVGEPIYRCKECSFDDTCVLCVNCFNPKDHTGHHVYTTICTEFN NGICDCGDKTAWNHTLFCKAEEG |
| PS1113 | 459 | MHSKFSHAGRICGAKFKVGEPIYRCKECSFDDTCVLCVNCFNPKDHTGHHVYTTICTEFN NGICDCGDKEAWNKTLFCKAEEG |
| PS1114 | 460 | MHSKFSHAGRICGAKFKVGEPIYRCKECSFDDTCVLCVNCFNPKDHRGHHVYTTICTERN NGICDCGDKEAWNHTLFCKAEEG |
| PS1115 | 461 | MHSKFSHAGRICGAKFKVGEPIYRCKECSFDDTCVLCVNCFNPKDHRGHHVYTTICTERN NGICDCGDKEAWNHELFCKAEEG |
| PS1116 | 462 | MHSKFSHAGRICGAKFKVGEPIYRCKECSFDDTCVLCVNCFNPKDHTYHHVYTTICTEFN NGICDCGDKEAWNHTLFCKAEEG |
| PS1117 | 463 | MHSKFSHAGRICGAKFKVGEPIYRCKECSFDDTCVLCVNCFNPKDHLGHHVYTTICTEFN NGICDCGDKEAWNHTLFCKAEEG |

TABLE 1-continued

Non-limiting example sequences of amino acid binding proteins.

| Name | SEQ ID NO. | Sequence |
|---|---|---|
| PS1118 | 464 | MHSKFSHAGRICGAKFKVGEPIYRCKECSFDDTCVLCVNCFNPKDHTGHHVYTTICTKFN NGICDCGDKEAWNHTLFCKAEEG |
| PS1119 | 465 | MHSKFSHAGRICGAKFKVGEPIYRCKECSFDDTCVLCVNCFNPKDHTGHHVYTTICKEFN NGICDCGDKEAWNHTLFCKAEEG |
| PS1120 | 466 | MHSKFSHAGRICGAKFKVGEPIYRCKECSFDDTCVLCVNCFNPKDHTGHHVYTKICTEFN NGICDCGDKEAWNHTLFCKAEEG |
| PS1121 | 467 | MHSKFSHAGRICGAKFKVGEPIYRCKECSFDDTCVLCVNCFNPKDHKGHHVYTTICTEFN NGICDCGDKEAWNHTLFCKAEEG |
| PS1122 | 468 | MHSKFSHAGRICGAKFKVGEPIYRCKECSFDDTCVLCVNCFNPKDHLGHHVYTTICTEFN NGECDCGDKTAWNHTLFCKAEEG |
| PS1123 | 469 | PLYQVVLLDDDDHTYDYIIEMLQQIFIFTMVEGYRRAEELERKGRSVLIVCELSEAEFAR DQIPSYGSDWRLPHSQGSMSAVIEPAE |
| PS1124 | 470 | MPTAASATESAIEDTPAPARPEVDGRTKPKRQPRYHVVLWDDSDHTRQYAVVMLRSLFGH PPSRGYRMAKEMATQGRVIVLTTTREHAELKRDQIHAFGRDRLLARSKGSMKASIEAEE |
| PS1125 | 471 | MPTAASATESAIEDTPAPARPEVDGRTKPKRQPRYHVVLWDDRDHTRQYAVVMLRSLFGH PPSRGYRMAKEIRTQGRVIVLTTTREHAELKRDQIHAFGRDRLLARSKGSMKASIEAEE |
| PS1126 | 472 | MPTAASATESAIEDTPAPARPEVDGRTKPKRQPRYHVVLWNDRDHTSQYIVVMLRSLFGH PPSRGYRMAKEMDTQGRVIVLTTTREHAELKRDQIHAFGRDRLLARSKGSMKASIEAEE |
| PS1127 | 473 | MPTAASATESAIEDTPAPARPEVDGRTKPKRQPRYHVVLWNDRDHTSQYIIVMLRSLFGH PPSRGYRMAKELQTQGRVIVLTTTREHAELKRDQIHAFGRDRLLARSKGSMKASIEAEE |
| PS1128 | 474 | MPTAASATESAIEDTPAPARPEVDGRTKPKRQPRYHVVFWDDDDHTYQYVVVMLRSLFGH PPSRGYRMAHEMCTQGRVIVLTTTREHAELKRDQIHAFGRDRLLARSKGSMKASIEAEE |
| PS1129 | 475 | MPTAASATESAIEDTPAPARPEVDGRTKPKRQPRYHVVLWDDDDHTYQYVVVMLRSLFYH PPSRGYRMAKEMDTQGRVIVLTTTREHAELKRDQIHAFGRDRLLARSKGSMKASIEAEE |
| PS1130 | 476 | MPTAASATESAIEDTPAPARPEVDGRTKPKRQPRYHVVLWDDDDHTYQYVVVMLRSLFYH PPSRGYRMAHEMDTQGRVIVLTTTREHAELKRDQIHAFGRDRLLARSKGSMKASIEAEE |
| PS1131 | 477 | MPTAASATESAIEDTPAPARPEVDGRTKPKRQPRYHVVQWDDDDHTYQYFVVMLRSLFGH PPSRGYRMAKEMDTQGRVIVLTTTREHAELKRDQIHAFGRDRLLARSKGSMKASIEAEE |
| PS1132 | 478 | MPTAASATESAIEDTPAPARPEVDGRTKPKRQPRYHVVQIDDDDHTYQYVVVMLRSLFYH PPSRGYRMAKEMDTQGRVIVLTTTREHAELKRDQIHAFGRDRLLARSKGSMKASIEAEE |
| PS1133 | 479 | MPTAASATESAIEDTPAPARPEVDGRTVPQRQPRYHVVLWDDDDHTYQYVVGMLRSLFGH PPSRGYRMAKEMDTQGRVIVLTTTREHAELKRDQIHAFGRDRLLARSKGSMKASIEAEE |
| PS1134 | 480 | MPTAASATESAIEDIPAPARPEVDGRTKPKHQPRYHVVLWDDDDHTYQYVVVMLRSLFGH PPSRGYRMASEMDTQGRVIVLTTTREHAELKRDQIHAFGRDRLLARSKGSMKASIEAEE |
| PS1135 | 481 | MPTAASATESAIEDTPAPARTEVDGRTVPKRQPRYHVVLWDDDDHTYQYVVEMLRSLFGH PPSRGYRMAKEMDTQGRVIVLTTTREHAELKRDQIHAFGRDRLLARSKGSMKASIEAEE |
| PS1136 | 482 | MPTAASATESAIEDTPAPARPEVDGRTRPKRQPRYHVVLWDDDDHTYQYVVVMLRKLFGH PPSRGYRMAKEMDTQGRVIVLTTTREHAELKRDQIHAFGRDRLLARSKGSMKASIEAEE |
| PS1137 | 483 | MPTAASATESAIEDTPAPARSEVDGYTVPKRQPRYHVVLWDDDDHTYQYVVVMLRSLFGH PPSRGYRMAKEMDTQGRVIVLTTTREHAELKRDQIRAFGRDRLLARSKGSMKASIEAEE |
| PS1138 | 484 | MSGSKFRGHQKSKGNSYDVEVVLQHVDTGNSYLCGYLKIKGLTEEYPTLTVFFEGEIISK KHPFLTRKWDADEDVDRKHWGKFLAFYQYAKSFNSDDFDYEELKNGDYVFMRWKEQFLVP DHTIKDISGLSFAGFYYICFQKSAASIEGYYYHRSSEWYQSLNLTHV |
| PS1139 | 485 | MSGSKFRGHQKSKGNSYDVEVVLQHVDTGNSYLCGYLKIKGLTEEYPTLTVFFEGEIISK KHPFLTRKWDADEDVDRKHWGKFLAFYQYAKSFNSDDFDYEELKNGDYVFMRWKEQFLVP DHTIKDISGASFAGFYYICFQKSAASIEGYYYHRSSEWYQSLNLTHV |
| PS1140 | 486 | MSGSKFRGHQKSKGNSYDVEVVLQHVDTGNSYLCGYLKIKGLTEEYPTLTAFFEGEIISK KHPFLTRKWDADEDVDRKHWGKFLAFYQYAKSFNSDDFDYEELKNGDYVFMRWKEQFLVP DHTIKDISGLSFAGFYYICFQKSAASIEGYYYHRSSEWYQSLNLTHV |
| PS1141 | 487 | MPTAASATESAIEDTPAPARPEVDGRTKPKRQPRYHVVLWDDDDHTYQYVVVMLRSLFGH PPSRGYRMAHEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1142 | 488 | MPTAASATESAIEDTPAPARPEVDGRTKPKRQPRYHVVLISDDDHTYQYTVVMLRSLFGH PPSRGYRMAHEMDTQGRVIVLTTTREHAELKRDQIHAFGRDRLLARSKGSMKASIEAEE |
| PS1143 | 489 | MPTAASATESAIEDTPAPARPEVDGRTKPKRQPRYHVVFWDDDDHTYQYTVVMLRSLFYH PPSRGYRMAHEMCTQGRVIVLTTTREHAELKRDQIHAFGRDRLLARSKGSMKASIEAEE |
| PS1144 | 490 | MPTAASATESAIEDTPAPARPEVDGRTKPKRQPRYHVVFWDDDDHTYQYTVVMLRSLFYH PPSRGYRMAHEMDTQGRVIVLTTTREHAELKRDQIHAFGRDRLLARSKGSMKASIEAEE |
| PS1145 | 491 | MPTAASATESAIEDTPAPARPEVDGRTKPKRQPRYHVVLWDDDDHTYQYVVVMLRSLFGH PPSRGYRMAKEMDTQGRFIVLTTTREHAELKRDQIHAFGRDRLLARSKGSMKASIEAEE |
| PS1146 | 492 | MPTAASATESAIEDTPAPARPEVDGRTKPKRQPRYHVVEWDDDSHTYQYVVVMLRSLFGH PPSRGYRMDKEMDTQGRVIVLTTTREHAELKRDQIHAFGRDRLLARSKGSEKASIEAEE |
| PS1147 | 493 | MPTAASATESAIEDTPAPARPEVDGRTKPKRQPRYHVVLWDDVDHTYQYTVVMLRSLFGY PPSRGYRMAKEVDTQGRVIVLTTTREHAELKRDQIHAFGRDRLLARSKGSMKASIEAEE |
| PS1148 | 494 | MPTAASATESAIEDTPAPARPEVDGRTKPKRQPRYHVVLWDDDDRTYQYVVVMLRSLFGH PPSRGYRMDKEMDTQGRVIVLTTTREHAELKRDQIHAFGRDRLLARSKGSMKASIEAEE |
| PS1149 | 495 | MPTAASATESAIEDTPAPARPEVDGRTKPKRQPRYHVVLWDDKDHTPQYVVVMLRSLFGH PPSRGYRMAKEMDTQGRVIVLTTTREHAELKRDQIHAFGRDRLLARSKGSMKASIEAEE |
| PS1150 | 496 | MPTAASATESAIEDTPAPARPEVDGRTKPKRQPRYHVVLWPDDDHTYQYVVVMLRSLFGH PPSRGYRLAKEMDTQGRVIVLTTTREHAELKRDQIHAFGRDRLLARSKGSMKASIEAEE |
| PS1151 | 497 | MPTAASATESAIEDTPAPARPEVDGRTKPKRQPRYHVVLWDDDDCTYQYLVVMLRSLFGH PPSRGYREAKEMDTQGRRIVLTTTREHAELKRDQIHAFGRDRLLARSKGSMKASIEAEE |
| PS1152 | 498 | MPTAASATESAIEDTPAPARPEVDGRTKPKRQPRYHVVLWDDDDHTYQYVVVMLRSLFGH PPSRGYRMIKEMDTQGRVIVLTTTREHAELKRDQIHAFGRDRLLARSKGSMKASIEAEE |
| PS1153 | 499 | MPTAASATESAIEDTPAPARPEVDGRTKPKRQPRYHVVLWDDDDHTYQYVVVMLRSLFGI PPSRGYRMAKEMDTQGRVIVLTTTREHAELKRDQIHAFGRDRLLARSKGSMKASIEAEE |
| PS1154 | 500 | MPTAASATESAIEDTPAPARPEVDGRTKPKRQPRYHVVLWDDDDHTYQYVVEMLRSLFGI PPSRGYRMAKEMDTQGRVIVLTTTREHAELKRDQIHAFGRDRLLARSKGSMKASIEAEE |
| PS1155 | 501 | MPTAASATESAIKDTPAPARSEVDGRTKPERQPRYHVVLWDDDDHTYQYVVVMLRSLFGH PTSRGYRMAKEMDTQGRVIVLTTTREHAELKRDQIHAFGRDRLLARSKGSMKASIEAEE |
| PS1156 | 502 | MPTAASATGSAIEDTPAPARPEVDGRTKPKRQPRYHVVLWDDDDHTYQYVVVMLRYLFGH PPERGYRMAKEMDTQGRVIVLTTTREHAELKRDQIHAFGRDRLLARSKGSMKASIEAEE |
| PS1157 | 503 | MPTAASATESAIEDTPAPARPEVDGRTKPKRQPRYHVVLWSDEDNTKQYIVVMLRSLFGH PPSRGYRMVEELDTQGRVIVLTTTREHAELKRDQIHAFGRDRLLARSKGSIKASIEAEE |
| PS1158 | 504 | MPTAASATESAIEDTPAPARPEVDGRTKPKRQPRYHVVVWDDDDNDEDYVVVMLRSLFGH PPSRGYRMAKEMHTQGRVIVLTTTREHAELKRDQIHAFGRDRLLARSKGSLKASIEAEE |
| PS1159 | 505 | MPTAASATESAIEDTPAPARPEVDGRTKPKRQPRYHVVLWDDEDHTYDYIVVMLRSLFGH PPSRGYRMAKELDTQGRVIVLTTTREHAELKRDQIHAFGRDRLLARSKGSVKASIEAEE |
| PS1160 | 506 | MPTAASATESAIEDTPAPARPEVDGRTKPKRQPRYHVVLWDDDDHTRQYLVVMLRSLFGH PPSRGYRMTEEADTQGRVIVLTTTREHAELKRDQIHAFGRDRLLARSKGSMKASIEAEE |
| PS1161 | 507 | MPTAASATESAIEDTPAPARPEVDGRTKPKRQPRYHVVIWDDEDHTHDYWVVMLRSLFGH PPSRGYRMSEELDTQGRVIVLTTTREHAELKRDQIHAFGRDRLLARSKGSMKASIEAEE |
| PS1162 | 508 | MGDVQPETCRPSAASGNYFPQYPEYAIETARLRTFEAWPRNLKQKPHQLAEAGFFYTGVG DRVRCFSCGGGLMDWNDNDEPWEQHARHLSQCRFVKLMKGQLYIDTVAAKPVLAEEKEES TSIGGD |
| PS1163 | 509 | MGSDAVSSDRNFPNSTNLPRNPSMADYEARIFTFGTWIYSVNKEQLARAGFYALGEGDKV KCFHCGGGLTDWKPSEDPWEQHAKWYPGCKYLLEQKGQEYINNIHLTHSLEECLVR |
| PS1164 | 510 | MGSDAVSSDRNFPNSTNLPRNPSMADYEARIFTFGTWIYSVNKEQLARAGFYALGEGDKV KCFHCGGGLTDWKPSEDPWEQHARHYPGCKYLLEQKGQEYINNIHLTHSLEECLVR |
| PS1165 | 511 | MGLENSLETLRFSISNLSMQTHAARMRTFMYWPSSVPVQPEQLASAGFYYVGRNDDVKCF CCDGGLRCWESGDDPWVEHAKWFPRCEFLIRMKGQEFVDEIQGRYPHLLEQLLS |

TABLE 1-continued

Non-limiting example sequences of amino acid binding proteins.

| Name | SEQ ID NO. | Sequence |
|---|---|---|
| PS1166 | 512 | MGLENSLETLRFSISNLSMQTHAARMRTFMYWPSSVPVQPEQLASAGFYYVGRNDDVKCF CCDGGLRCWESGDDPWVEHARHFPRCEFLIRMKGQEFVDEIQGRYPHLLEQLLS |
| PS1167 | 513 | MGSMRYTVSNLSMQTHAARFKTFFNWPSSVLVNPEQLASAGFYYVGNSDDVKCFCCDGGL RCWESGDDPWVQHAKWFPRCEYLIRIKGQEFIRQVQAS |
| PS1168 | 514 | MGSMRYTVSNLSMQTHAARFKTFFNWPSSVLVNPEQLASAGFYYVGNSDDVKCFCCDGGL RCWESGDDPWVQHARHFPRCEYLIRIKGQEFIRQVQAS |
| PS1169 | 515 | MGSHMLETEEEEEEGAGATLSRGPAFPGMGSEELRLASFYDWPLTAEVPPELLAAAGFFH TGHQDKVRCFFCYGGLQSWKRGDDPWTEHAKWFPSCQFLLRSKGRDFVHSVQETHSQLLG SWDP |
| PS1170 | 516 | MGSHMLETEEEEEEGAGATLSRGPAFPGMGSEELRLASFYDWPLTAEVPPELLAAAGFFH TGHQDKVRCFFCYGGLQSWKRGDDPWTEHARHFPSCQFLLRSKGRDFVHSVQETHSQLLG SWDP |
| PS1171 | 517 | MGSHMSTNLPRNPSMTGYEARLITFGTWMYSVNKEQLARAGFYAIGQEDKVQCFHCGGGL ANWKPKEDPWEQHAKWYPGCKYLLEEKGHEYINNIHLTRSLEGALVQTT |
| PS1172 | 518 | MGSHMSTNLPRNPSMTGYEARLITFGTWMYSVNKEQLARAGFYAIGQEDKVQCFHCGGGL ANWKPKEDPWEQHARHYPGCKYLLEEKGHEYINNIHLTRSLEGALVQTT |
| PS1173 | 519 | MGSHMRYQEEEARLASFRNWPFYVQGISPCVLSEAGFVFTGKQDTVQCFSCGGCLGNWEE GDDPWKEHAKWFPKCEFLRSKKSSEEITQYIQSYK |
| PS1174 | 520 | MGSHMRYQEEEARLASFRNWPFYVQGISPCVLSEAGFVFTGKQDTVQCFSCGGCLGNWEE GDDPWKEHARHFPKCEFLRSKKSSEEITQYIQSYK |
| PS1175 | 521 | MPTAASATESAIEDTPAPARPEVDGRTKPKRQPRYHVVLWDDDDHTVQYIVVMLRSLFGH PPSRGYRMAKEMHTQGRVIVLTTTREHAELKRDQIHAFGRDRLLARSKGSLKASIEAEE |
| PS1176 | 522 | MPTAASATESAIEDTPAPARPEVDGRTKPKRQPRYHVVLWDDDDHTVQYIVVMLRSLFGH PPSRGYRMAKEATTQGRVIVLTTTREHAELKRDQIHAFGRDRLLARSKGSAKASIEAEE |
| PS1177 | 523 | MPTAASATESAIEDTPAPARPEVDGRTKPKRQPRYHVVLWDDEDHTMQYIVVMLRSLFGH PPSRGYRMAKEMHTQGRVIVLTTTREHAELKRDQIHAFGRDRLLARSKGSAKASIEAEE |
| PS1178 | 524 | MPTAASATESAIEDTPAPARPEVDGRTKPKRQPRYHVVLWDDDDHTVQYIVVMLRSLFGH PPSRGYRMAKEIGTQGRVIVLTTTREHAELKRDQIHAFGHDRLLARSKGSAKASIEAEE |
| PS1179 | 525 | MPTAASATESAIEDTPAPARPEVDGRTKPKRQPRYHVVLWDDDDHTVQYIVVMLRSLFGH PPSRGYRMAKEMHTQGRVIVLTTTREHAELKRDQIHAFGHDRLLARSKGSAKASIEAEE |
| PS1180 | 526 | MPTAASATESAIEDTPAPARPEVDGRTKPKRQPRYHVVLWDDDDHTVQYIVVMLRSLFGH PPSRGYRMAKEIYTQGRVIVLTTTREHAELKRDQIHAFGRDRLLARSKGSAKASIEAEE |
| PS1181 | 527 | MPTAASATESAIEDTPAPARPEVDGRTKPKRQPRYHVVLWDDDDHTVQYIVVMLRSLFGH PPSRGYRMAKEMHTQGRVIVLTTTREHAELKRDQIHAFGRDRLLARSKGSAKASIEAEE |
| PS1182 | 528 | MPTAASATESAIEDTPAPARPEVDGRTKPKRQPRYHVVLWDDRDHTYQYIVVMLRSLFGH PPSRGYRMAKEAYTQGRVIVLTTTREHAELKRDQIHAFGRDRLLARSKGSLKASIEAEE |
| PS1183 | 529 | MPTAASATESAIEDTPAPARPEVDGRTKPKRQPRYHVVLWDDRDHTAQYAVVMLRSLFGH PPSRGYRMAKEIYTQGRVIVLTTTREHAELKRDQIHAFGHDRLLARSKGSAKASIEAEE |
| PS1184 | 530 | MPTAASATESAIEDTPAPARPEVDGRTKPKRQPRYHVVLWDDNDHTLQYIVVMLRSLFGH PPSRGYRMAKEVDTQGRVIVLTTTREHAELKRDQIHAFGRDRLLARSKGSMKASIEAEE |
| PS1185 | 531 | MPTAASATESAIEDTPAPARPEVDGRTKPKRQPRYHVVLWDDDDHTVQYIVVMLRSLFGH PPSRGYRMAKELDTQGRVIVLTTTREHAELKRDQIHAFGRDRLLARSKGSMKASIEAEE |
| PS1186 | 532 | MPTAASATESAIEDTPAPARPEVDGRTKPKRQPRYHVVLWDDGDHTWQYIVVMLRSLFGH PPSRGYRMAKELTTQGRVIVLTTTREHAELKRDQIHAFGRDRLLARSKGSMKASIEAEE |
| PS1187 | 533 | MPTAASATESAIEDTPAPARPEVDGRTKPKRQPRYHVVLWDDSDHTFQYIVVMLRSLFGH PPSRGYRMAKELHTQGRVIVLTTTREHAELKRDQIHAFGRDRLLARSKGSMKASIEAEE |
| PS1188 | 534 | MPTAASATESAIEDTPAPARPEVDGRTKPKRQPRYHVVLWDDADHTYQYIVVMLRSLFGH PPSRGYRMAKEMHTQGRVIVLTTTREHAELKRDQIHAFGRDRLLARSKGSMKASIEAEE |
| PS1189 | 535 | MPTAASATESAIEDTPAPARPEVDGRTKPKRQPRYHVVLWDDDDHTMQYIVVMLRSLFGH PPSRGYRMAKEVTTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1190 | 536 | MPTAASATESAIEDTPAPARPEVDGRTKPKRQPRYHVVLWDDSDHTIQYIVVMLRSLFGH<br>PPSRGYRMAKEADTQGRVIVLTTTREHAELKRDQIHAFGRDRLLARSKGSMKASIEAEE |
| PS1191 | 537 | MPTAASATESAIEDTPAPARPEVDGRTKPKRQPRYHVVLWDDDDHTWQYIVVMLRSLFGH<br>PPSRGYRMAKEMHTQGRVIVLTTTREHAELKRDQIHAFGRDRLLARSKGSMKASIEAEE |
| PS1192 | 538 | MPTAASATESAIEDTPAPARPEVDGRTKPKRQPRYHVVLWDDDDHTVQYIVVMLRSLFGH<br>PPSRGYRMAKEMHTQGRVIVLTTTREHAELKRDQIHAFGRDRLLARSKGSMKASIEAEE |
| PS1193 | 539 | MPTAASATESAIEDTPAPARPEVDGRTKPKRQPRYHVVLWDDNDHTLQYIVVMLRSLFGH<br>PPSRGYRMAKEMHTQGRVIVLTTTREHAELKRDQIHAFGRDRLLARSKGSMKASIEAEE |
| PS1194 | 540 | MPTAASATESAIEDTPAPARPEVDGRTKPKRQPRYHVVLWDDDDHTVQYIVVMLRSLFGH<br>PPSRGYRMAKEISTQGRVIVLTTTREHAELKRDQIHAFGRDRLLARSKGSMKASIEAEE |
| PS1195 | 541 | MPTAASATESAIEDTPAPARPEVDGRTKPKRQPRYHVVLWDDGDHTLQYIVVMLRSLFGH<br>PPSRGYRMAKEMHTQGRVIVLTTTREHAELKRDQIHAFGRDRLLARSKGSMKASIEAEE |
| PS1196 | 542 | MPTAASATESAIEDTPAPARPEVDGRTKPKRQPRYHVVLWDDDDHTIQYIVVMLRSLFGH<br>PPSRGYRMAKEMHTQGRVIVLTTTREHAELKRDQIHAFGRDRLLARSKGSMKASIEAEE |
| PS1197 | 543 | MPTAASATESAIEDTPAPARPEVDGRTKPKRQPRYHVVLWDDEDHTMQYIVVMLRSLFGH<br>PPSRGYRMAKEMHTQGRVIVLTTTREHAELKRDQIHAFGRDRLLARSKGSLKASIEAEE |
| PS1198 | 544 | MPTAASATESAIEDTPAPARPEVDGRTKPKRQPRYHVVLWDDDDHTYQYVVVMLRSLFGH<br>PPSRGYRMAKEMDTQGRVIVLTTTREHAELKRDQIHAFGRDRLLARSKGSMKASIEAEEG<br>SAGSAAGSGEFMDKDCEMKRTTLDSPLGKLELSGCEQGLHEIKLLGKGTSAADAVEVPAP<br>AAVLGGPEPLMQATAWLNAYFHQPEAIEEFPVPALHHPVFQQESFTRQVLWKLLKVVKFG<br>EVISYQQLAALAGNPAATAAVKTALSGNPVPILIPCHRVVSSSGAVGGYEGGLAVKEWLL<br>AHEGHRLGKPGLG |
| PS1199 | 545 | MPTAASATESAIEDTPAPARPEVDGRTKPKRQPRYHVVLWDDDDHTYQYVVVMLRSLFGH<br>PPSRGYRMAKEMDTQGRVIVLTTTREHAELKRDQIHAFGRDRLLARSKGSMKASIEAEEG<br>SAGSAAGSGEFMPTAASATESAIEDTPAPARPEVDGRTKPKRQPRYHVVLWDDDDHTYQY<br>VVVMLRSLFGHPPSRGYRMAKEMDTQGRVIVLTTTREHAELKRDQIHAFGRDRLLARSKG<br>SMKASIEAEEGSAGSAAGSGEFMDKDCEMKRTTLDSPLGKLELSGCEQGLHEIKLLGKGT<br>SAADAVEVPAPAAVLGGPEPLMQATAWLNAYFHQPEAIEEFPVPALHHPVFQQESFTRQV<br>LWKLLKVVKFGEVISYQQLAALAGNPAATAAVKTALSGNPVPILIPCHRVVSSSGAVGGY<br>EGGLAVKEWLLAHEGHRLGKPGLG |
| PS1200 | 546 | MSDSPVDLKPKPKVKPKLERPKLYKVMLLNDDYTPMSFVTVVLKAVFRMSEDTGRRVMMT<br>AHRFGSAVVVVCERDIAETKAKEATDLGKEAGFPLMFTTEPEEGSAGSAAGSGEFMSDSP<br>VDLKPKPKVKPKLERPKLYKVMLLNDDYTPMSFVTVVLKAVFRMSEDTGRRVMMTAHRFG<br>SAVVVVCERDIAETKAKEATDLGKEAGFPLMFTTEPEEGHHHHHHHHHHGGGSGGGSGGG<br>SGLNDFFEAQKIEWHEGGGSGGGSGGGSGLNDFFEAQKIEWHEGSAGSAAGSGEFMDKDC<br>EMKRTTLDSPLGKLELSGCEQGLHEIKLLGKGTSAADAVEVPAPAAVLGGPEPLMQATAW<br>LNAYFHQPEAIEEFPVPALHHPVFQQESFTRQVLWKLLKVVKFGEVISYQQLAALAGNPA<br>ATAAVKTALSGNPVPILIPCHRVVSSSGAVGGYEGGLAVKEWLLAHEGHRLGKPGLG |
| PS1201 | 547 | MHSKFSHAGRICGAKFKVGEPIYRCKECSFDDTCVLCVNCFNPKDHTGHHVYTTICTEFN<br>NGICDCGDKEAWNHTLFCKAEEGGSAGSAAGSGEFMDKDCEMKRTTLDSPLGKLELSGCE<br>QGLHEIKLLGKGTSAADAVEVPAPAAVLGGPEPLMQATAWLNAYFHQPEAIEEFPVPALH<br>HPVFQQESFTRQVLWKLLKVVKFGEVISYQQLAALAGNPAATAAVKTALSGNPVPILIPC<br>HRVVSSSGAVGGYEGGLAVKEWLLAHEGHRLGKPGLG |
| PS1202 | 548 | MHSKFSHAGRICGAKFKVGEPIYRCKECSFDDTCVLCVNCFNPKDHTGHHVYTTICTEFN<br>NGICDCGDKEAWNHTLFCKAEEGGSAGSAAGSGEFMHSKFSHAGRICGAKFKVGEPIYRC<br>KECSFDDTCVLCVNCFNPKDHTGHHVYTTICTEFNNGICDCGDKEAWNHTLFCKAEEGGS<br>AGSAAGSGEFMDKDCEMKRTTLDSPLGKLELSGCEQGLHEIKLLGKGTSAADAVEVPAPA<br>AVLGGPEPLMQATAWLNAYFHQPEAIEEFPVPALHHPVFQQESFTRQVLWKLLKVVKFGE<br>VISYQQLAALAGNPAATAAVKTALSGNPVPILIPCHRVVSSSGAVGGYEGGLAVKEWLLA<br>HEGHRLGKPGLG |
| PS1203 | 549 | MPTAASATESAIEDTPAPARPEVDGRTKPKRQPRYHVVLLDDDDHTSQYVVVMLRSLFGH<br>PPSRGYRMSKEMDTQGRAIVLTTTREHAELKRDQIHAFGRDRLLARSKGSMKASIEAEE |
| PS1204 | 550 | MPTAASATESAIEDTPAPARPEVDGRTKPKRQPRYHVVLLDDPDHTYQYVVVMLRSLFGH<br>PPSRGYRMAKEMDTQGRVIVLTTTREHAELKRDQIHAFGRDRLLARSKGSMKASIEAEE |
| PS1205 | 551 | MPTAASATESAIEDTPAPARPEVDGRTKPKRQPRYHVVQWDDDDHTYQYVVVMLRSLFYH<br>PPSRGYRMAHEMDTQGRVIVLTTTREHAELKRDQIHAFGRDRLLARSKGSMKASIEAEE |
| PS1206 | 552 | MPTAASATESAIEDTPAPARPEVDGRTKPKRQPRYHVVLWDDDDHTYQYVVVMLRSLFGH<br>PPSRGYRMAKPMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1207 | 553 | MPTAASATESAIEDTPAPARPEVDGRTKPKRQPRYHVVLWDDDDHTYQYVVVMLRSLFGH PPSRGYRMAKEMKTQGRVIVLTTTREHAELKRDQIHAFGRDRLLARSKGSMKASIEAEE |
| PS1208 | 554 | MPTAASATESAIEDTPAPARPEVDGRTKPKRQPRYHVVLYDDDDHTYQYVVVMLRSLFGH PPSRGYRMAKEMDTQGRVIVLTTTREHAELKRDQIHAFGRDRLLARSKGSMKASIEAEE |
| PS1209 | 555 | MPTAASATESAIEDTPAPARPEVDGRTKPKRQPRYHVVLQDDDDHTYQYVVVMLRSLFGH PPSRGYRMAKEMDTQGRVIVLTTTREHAELKRDQIHAFGRDRLLARSKGSMKASIEAEE |
| PS1210 | 556 | MPTAASATESAIEDTPAPARPEVDGRTKPKRQPRYHVVLWDDGDHTSQYVVVMLRSLFGH PPSRGYRMAKEMDTQGRVIVLTTTREHAELKRDQIHAFGRDRLLARSKGSMKASIEAEE |
| PS1211 | 557 | MPTAASATESAIEDTPAPARPEVDGRTKPKRQPRYHVVLWDDDTHTYQYVVVMLRSLFGH PPSRGYRMAKEMDTQGRVIVLTTTREHAELKRDQIHAFGRDRLLARSKGSMKASIEAEE |
| PS1212 | 558 | MPTAASATESAIEDTPAPARPEVDGRTKPKRQPRYHVVLWNDSDHTGQYIVVMLRSLFGH PPSRGYRMAKEKDTQGRVIVLTTTREHAELKRDQIHAFGRDRLLARSKGSMKASIEAEE |
| PS1213 | 559 | MPTAASATESAIEDTPAPARPEVDGRTKPKRQPRYHVVLWNDLDHTYQYIVVMLRSLFGH PPSRGYRMAKEMHTQGRVIVLTTTREHAELKRDQIHAFGRDRLLARSKGSMKASIEAEE |
| PS1214 | 560 | MPTAASATESAIEDTPAPARPEVDGRTKPKRQPRYHVVLWNDGDHTWQYIVVMLRSLFGH PPSRGYRMAKEMHTQGRVIVLTTTREHAELKRDQIHAFGRDRLLARSKGSMKASIEAEE |
| PS1215 | 561 | MPTAASATESAIEDTPAPARPEVDGRTKPKRQPRYHVVLWNDGDHTWQYIVVMLRSLFGH PPSRGYRMAKEAKTQGRVIVLTTTREHAELKRDQIHAFGRDRLLARSKGSMKASIEAEE |
| PS1216 | 562 | MPTAASATESAIEDTPAPARPEVDGRTKPKRQPRYHVVLWDDGDHTVQYIVVMLRSLFGH PPSRGYRMAKEMHTQGRVIVLTTTREHAELKRDQIHAFGRDRLLARSKGSMKASIEAEE |
| PS1217 | 563 | MPTAASATESAIEDTPAPARPEVDGRTKPKRQPRYHVVLWDDQDHTWQYIVVMLRSLFGH PPSRGYRMAKEMHTQGRVIVLTTTREHAELKRDQIHAFGRDRLLARSKGSMKASIEAEE |
| PS1218 | 564 | MHSKFSHAGRICGAKFKVGEPIYRCKECSFDDTCVLCVNCFNPKDHRGHHVYTTICTERN NGICDCGDKEAWNHELFCKAEEGSAGSAAGSGEFMHSKFSHAGRICGAKFKVGEPIYRCK ECSFDDTCVLCVNCFNPKDHRGHHVYTTICTERNNGICDCGDKEAWNHELFCKAEEG |
| PS1219 | 565 | MHSKFSHAGRICGAKFKVGEPIYRCKECSFDDTCVLCVNCFNPKDHLGHHVYTTICTEFN NGECDCGDKTAWNHTLFCKAEEGGGSGGGSGGGSGMHSKFSHAGRICGAKFKVGEPIYRC KECSFDDTCVLCVNCFNPKDHLGHHVYTTICTEFNNGECDCGDKTAWNHTLFCKAEEG |
| PS1220 | 566 | MHSKFSHAGRICGAKFKVGEPIYRCKECSFDDTCVLCVNCFNPKDHLGHHVYTTICTEFN NGECDCGDKTAWNHTLFCKAEEGSAGSAAGSGEFMHSKFSHAGRICGAKFKVGEPIYRCK ECSFDDTCVLCVNCFNPKDHLGHHVYTTICTEFNNGECDCGDKTAWNHTLFCKAEEG |
| PS1221 | 567 | MHSKFSHAGRICGAKFKVGEPIYRCKECSFDDTCVLCVNCFNPKDHLGHHVYTTICTEFN NGECDCGDKTAWNHTLFCKAEEGSAGSAAGSGEFGSAGSAAGSGEFGSAGSAAGSGEFMH SKFSHAGRICGAKFKVGEPIYRCKECSFDDTCVLCVNCFNPKDHLGHHVYTTICTEFNNG ECDCGDKTAWNHTLFCKAEEG |
| PS1222 | 568 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEEG GGSGGGSGGGSGMPTAASATESAIEDTPAPARPEVDGRTKPKRQPRYHVVLWDDDDHTYQ YVVVMLRSLFGHPPSRGYRMAKEMDTQGRVIVLTTTREHAELKRDQIHAFGRDRLLARSK GSMKASIEAEE |
| PS1223 | 569 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEEG SAGSAAGSGEFGSAGSAAGSGEFGSAGSAAGSGEFMPTAASATESAIEDTPAPARPEVDG RTKPKRQPRYHVVLWDDDDHTYQYVVVMLRSLFGHPPSRGYRMAKEMDTQGRVIVLTTTR EHAELKRDQIHAFGRDRLLARSKGSMKASIEAEE |
| PS1224 | 570 | MPTAASATESAIEDTPAPARPEVDGRTKPKRQPRYHVVLHDDDDHTYQYVVVMLRSLFGH PPSRGYRMAKEMDTQGRVIVLTTTREHAELKRDQIHAFGRDRLLARSKGSMKASIEAEE |
| PS1225 | 571 | MPTAASATESAIEDTPAPARPEVDGRTKPKRQPRYHVVLWDDDDHTYQYVVVMLRSLFGI PPSRGYRMAKEMDTQGRVIVLTTTREHAELKRDQIHAFGRDRLLARSKGSMKASIEAEE |
| PS1226 | 572 | MPTAASATESAIEDTPAPARPEVDGRTKPKRQPRYHVVLWDDDDHTAQYVVVMLRSLFGH PPSRGYRMAKEMDTQGRVIVLTTTREHAELKRDQIHAFGRDRLLARSKGSMKASIEAEE |
| PS1227 | 573 | MPTAASATESAIEDTPAPARPEVDGRTKPKRQPRYHVVLWDDNDHTYQYVVVMLRSLFGH PPSRGYRMAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1228 | 574 | MPTAASATESAIEDTPAPARPEVDGRTKPKRQPRYHVVLWNDDDHTYQYVVVMLRSLFGH PPSRGYRMAKEMDTQGRVIVLTTTREHAELKRDQIHAFGRDRLLARSKGSMKASIEAEE |
| PS1229 | 575 | MPTAASATESAIEDTPAPARPEVDGRTKPKRQPRYHVVLWDDDDHTWQYVVVMLRSLFGH PPSRGYRMAKEMDTQGRVIVLTTTREHAELKRDQIHAFGRDRLLARSKGSMKASIEAEE |
| PS1230 | 576 | MPTAASATESAIEDTPAPARPEVDGRTKPKRQPRYHVVLWDDDDHTYQYVVVMLRSLFGH PPSRGYRMAKELDTQGRVIVLTTTREHAELKRDQIHAFGRDRLLARSKGSMKASIEAEE |
| PS1231 | 577 | MPTAASATESAIEDTPAPARPEVDGRTKPKRQPRYHVVLWDDDDHTYQYVVVMLRSLFGY PPSRGYRMAKEMDTQGRVIVLTTTREHAELKRDQIHAFGRDRLLARSKGSMKASIEAEE |
| PS1232 | 578 | MPTAASATESAIEDTPAPARPEVDGRTKPKRQPRYHVVLWDDDDHTLQYVVVMLRSLFGH PPSRGYRMAKEMDTQGRVIVLTTTREHAELKRDQIHAFGRDRLLARSKGSMKASIEAEE |
| PS1233 | 579 | MPTAASATESAIEDTPAPARPEVDGRTKPKRQPRYHVVLWDDDDHTIQYVVVMLRSLFGH PPSRGYRMAKEMDTQGRVIVLTTTREHAELKRDQIHAFGRDRLLARSKGSMKASIEAEE |
| PS1234 | 580 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHASGRDRLLARSKGSMKASIEAEE |
| PS1235 | 581 | MPTAASATESAIEDTPAPARPEVDGRTKPKRQPRYHVVLWDDDDHTYQYVVVMLRSLFGH PLSRGYRMAKEMDTQGRVIVLTTTREHAELKRDQIHAFGRDRLLARSKGSMKASIEAEE |
| PS1236 | 582 | MPTAASATESAIEDTPAPARPEVDGRTKPKRQPRYHVVLWDDDQHTYQYVVVMLRSLFGH PPSRGYRMAKEMDTQGRVIVLTTTREHAELKRDQIHAFGRDRLLARSKGSMKASIEAEE |
| PS1237 | 583 | MPTAASATESAIEDTPAPARPEVDGRTKPKRQPRYHVVLWDDDDHTYQYVVVMLRSLFGH PPSRGYRMAKEMDTQGRTIVLTTTREHAELKRDQIHAFGRDRLLARSKGSMKASIEAEE |
| PS1238 | 584 | MPTAASATESAIEDTPAPARPEVDGRTKPKRQPRYHVVLFDDDDHTYQYVVVMLRSLFGH PPSRGYRMAKEMDTQGRVIVLTTTREHAELKRDQIHAFGRDRLLARSKGSMKASIEAEE |
| PS1239 | 585 | MPTAASATESAIEDTPAPARPEVDGRTKPKRQPRYHVVLWDDDDHTYQYVVVMLRSLFGH PPSRGYRMTKEMDTQGRVIVLTTTREHAELKRDQIHAFGRDRLLARSKGSMKASIEAEE |
| PS1240 | 586 | MPTAASATESAIEDTPAPARPEVDGRTKPKRQPRYHVVLWDDDDHTYQYVVVMLRSLFGS PPSRGYRMAKEMDTQGRLIVLTTTREHAELKRDQIHAFGRDRLLARSKGSMKASIEAEE |
| PS1241 | 587 | MPTAASATESAIEDTPAPARPEVDGRTKPKRQPRYHVVLWDDDDHTYQYVVVMLRSLFGV PPSRGYRMAKELDTQGRVIVLTTTREHAELKRDQIHAFGRDRLLARSKGSMKASIEAEE |
| PS1242 | 588 | MPTAASATESAIEDTPAPARPEVDGRTKPKRQPRYHVVLWDDDDHTYQYVVVMLRSLFGL PPSRGYRMAHEMDTQGRVIVLTTTREHAELKRDQIHAFGRDRLLARSKGSMKASIEAEE |
| PS1243 | 589 | MPTAASATESAIEDTPAPARPEVDGRTKPKRQPRYHVVLYDDDDHTDQYVVVMLRSLFGH PPSRGYRLAEEMDTQGRVIVLTTTREHAELKRDQIHAFGRDRLLARSKGSMKASIEAEE |
| PS1244 | 590 | MPTAASATESAIEDTPAPARPEVDGRTKPKRQPRYHVVLLDDDSHTYQYVVVMLRSLFGV PPSRGYRMAAEMDTQGRVIVLTTTREHAELKRDQIHAFGRDRLLARSKGSMKASIEAEE |
| PS1245 | 591 | MPTAASATESAIEDTPAPARPEVDGRTKPKRQPRYHVVLWDDHDHTYQYVVVMLRSLFGH PPSRGYRMAKELHTQGRVIVLTTTREHAELKRDQIHAFGRDRLLARSKGSMKASIEAEE |
| PS1246 | 592 | MEGNGPAAVHYQPASPPRDACVYSSCYCEENVWKLCEYIKNHDQYPLEECYAVFISNERK MIPIWKQQARPGDGPVIWDYHVVLLHVSSGGQSFIYDLDTVLPFPCLFDTYVEDAIKSDD DIHPQFRRKFRVICADSYLKNFASDRSHMKDSSGNWREPPPPYPCIETGDSKMNLNDFIS MDPKVGWGAVYTLSEFTHRFGSKN |
| PS1247 | 593 | MEGNGPAAVHYQPASPPRDACVYSSCYSEENVWKLCEYIKNHDQYPLEECYAVFISNERK MIPIWKQQARPGDGPVIWDYHVVLLHVSSGGQSFIYDLDTVLPFPCLFDTYVEDAIKSDD DIHPQFRRKFRVICADSYLKNFASDRSHMKDSSGNWREPPPPYPCIETGDSKMNLNDFIS MDPKVGWGAVYTLSEFTHRFGSKN |
| PS1248 | 594 | MEGNGPAAVHYQPASPPRDACVYSSCYSEENVWKLCEYIKNHDQYPLEECYAVFISNERK MIPIWKQQARPGDGPVIWDYQVVLLHVSSGGQSFIYDLDTVLPFPCLFDTYVEDAIKSDD DIHPQFRRKFRVICADSYLKNFASDRSHMKDSSGNWREPPPPYPCIETGDSKMNLNDFIS MDPKVGWGAVYTLSEFTHRFGSKN |
| PS1249 | 595 | MEGNGPAAVHYQPASPPRDACVYSSCYSEENVWKLCEYIKNHDQYPLEECYAVFISNERK MIPIWKQQARPGDGPVIWDYQVVLLHVSSGGQSFIYDLDTVLPFPCLFDTYVEDAIKSDD DIHPQFRRKFRVICADSYLKNFASDRSHEKDSSGNWREPPPPYPCIETGDSKMNLNDFIS MDPKVGWGAVYTLSEFTHRFGSKN |

TABLE 1-continued

| Name | SEQ ID NO. | Sequence |
|---|---|---|
| Non-limiting example sequences of amino acid binding proteins. | | |
| PS1250 | 596 | MGPAATAPQYQPVCPTRDACVYNSCYSEENIWKLCEYIKTHNQYLLEECYAVFISNEKKM VPIWKQQARPENGPVIWDYHVVLLHVSREGQSFIYDLDTILPFPCPFDIYIEDALKSDDD IHLQFRRKFRVVRADSYLKHFASDRSHMKDSSGNWREPPPEYPCIETGDSKMNLNDFISM DPAVGWGAVYTLPEFVHRFSSKTY |
| PS1251 | 597 | MGPAATAPQYQPVCPTRDACVYNSCYSEENIWKLCEYIKTHNQYLLEECYAVFISNEKKM VPIWKQQARPENGPVIWDYQVVLLHVSREGQSFIYDLDTILPFPCPFDIYIEDALKSDDD IHLQFRRKFRVVRADSYLKHFASDRSHMKDSSGNWREPPPEYPCIETGDSKMNLNDFISM DPAVGWGAVYTLPEFVHRFSSKTY |
| PS1252 | 598 | MGPAATAPQYQPVCPTRDACVYNSCYSEENIWKLCEYIKTHNQYLLEECYAVFISNEKKM VPIWKQQARPENGPVIWDYQVVLLHVSREGQSFIYDLDTILPFPCPFDIYIEDALKSDDD IHLQFRRKFRVVRADSYLKHFASDRSHEKDSSGNWREPPPEYPCIETGDSKMNLNDFISM DPAVGWGAVYTLPEFVHRFSSKTY |
| PS1253 | 599 | MVPAAAAARYQPASPPRDACVYNSCYSEENIWKLCEYIKNHDQYPLEECYAVFISNERKM IPIWKQQARPGDGPVIWYYFFLLVRYHVKSIGFSFTFQAIPLVNTLEDILAQLFKFCIHM HACVLWKFRVIRADSYLKNFASDRSHMKDSSGNWREPPPSYPCIETGDSKMNLNDFISMD PEVGWGAVYSLSEFVHRFGSQNY |
| PS1254 | 600 | MVPAAAAARYQPASPPRDACVYNSCYSEENIWKLCEYIKNHDQYPLEECYAVFISNERKM IPIWKQQARPGDGPVIWYYFFLLVRYHVKSIGFSFTFQAIPLVNTLEDILAQLFKFCIHM HACVLWKFRVIRADSYLKNFASDRSHEKDSSGNWREPPPSYPCIETGDSKMNLNDFISMD PEVGWGAVYSLSEFVHRFGSQNY |
| PS1255 | 601 | MAAGEPSPFLVRSDCLYTSCYSEENVWKLCEYIRDHRPCLLEQFSAVFISNENKMIPIWK QKSAKGDGPVIWDYHVILLHESARDGNFVYDLDTILPFPSPCNTYIREALKCDSNIHCDF RRKLRVVGAHEFLQTFASDRSHMRDSSSNWTKPPPPYPCIQTAESTMNLDDFISMNPEVG WGTVYSLAAFIERFGDTTL |
| PS1256 | 602 | MAAGEPSPFLVRSDCLYTSCYSEENVWKLCEYIRDHRPCLLEQFSAVFISNENKMIPIWK QKSAKGDGPVIWDYQVILLHESARDGNFVYDLDTILPFPSPCNTYIREALKCDSNIHCDF RRKLRVVGAHEFLQTFASDRSHMRDSSSNWTKPPPPYPCIQTAESTMNLDDFISMNPEVG WGTVYSLAAFIERFGDTTL |
| PS1257 | 603 | MAAGEPSPFLVRSDCLYTSCYSEENVWKLCEYIRDHRPCLLEQFSAVFISNENKMIPIWK QKSAKGDGPVIWDYQVILLHESARDGNFVYDLDTILPFPSPCNTYIREALKCDSNIHCDF RRKLRVVGAHEFLQTFASDRSHERDSSSNWTKPPPPYPCIQTAESTMNLDDFISMNPEVG WGTVYSLAAFIERFGDTTL |
| PS1258 | 604 | MNGLSAQHERIAPARHECVYTSCYSEENVWKLCEHIKTSKRCPLGDVYAVFISNERKMVP IWKQKSGRGEEPVIWDYHVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKT |
| PS1259 | 605 | MNGLSAQHERIAPARHECVYTSCYSEENVWKLCEHIKTSKRCPLGDVYAVFISNERKMVP IWKQKSGRGEEPVIWDYQVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKT |
| PS1260 | 606 | MNGLSAQHERIAPARHECVYTSCYSEENVWKLCEHIKTSKRCPLGDVYAVFISNERKMVP IWKQKSGRGEEPVIWDYQVILLHDCHKEQTFIYDLDTTLPFPCPFDTYVKEAFKSDNYIN PAFWRKLRVVPADVFLQNFASDRSHEKDASGGWRMPPPPYPCIETAESRMNLDDFISMNP SVGWGHVYTLEEFVQHFGKT |
| PS1261 | 607 | MESASSEYKVITPSGNQCVYTSCYSEENVWKLCEYIKNQRHCPLEEVYAVFISNERKKIP IWKQKSSRGDEPVIWDYHVILLHASKQGPSFIYDLDTILPFPCSLDVYSMEAFQSDKHLK PAYWRKLRVIPGDTYLKEFASDRSHMKDSDGNWRMPPPAYPCLETPESKMNLDDFICMDP RVGYGEVYSLSDFVKHFGVK |
| PS1262 | 608 | MESASSEYKVITPSGNQCVYTSCYSEENVWKLCEYIKNQRHCPLEEVYAVFISNERKKIP IWKQKSSRGDEPVIWDYQVILLHASKQGPSFIYDLDTILPFPCSLDVYSMEAFQSDKHLK PAYWRKLRVIPGDTYLKEFASDRSHMKDSDGNWRMPPPAYPCLETPESKMNLDDFICMDP RVGYGEVYSLSDFVKHFGVK |
| PS1263 | 609 | MESASSEYKVITPSGNQCVYTSCYSEENVWKLCEYIKNQRHCPLEEVYAVFISNERKKIP IWKQKSSRGDEPVIWDYQVILLHASKQGPSFIYDLDTILPFPCSLDVYSMEAFQSDKHLK PAYWRKLRVIPGDTYLKEFASDRSHEKDSDGNWRMPPPAYPCLETPESKMNLDDFICMDP RVGYGEVYSLSDFVKHFGVK |
| PS1264 | 610 | MEHVSSKYVNITPSRDECVYTSCYSEENVWKLCEHIKTQTQIHLDEVYAVFISNERKMIP IWKQKSSRGDEPVVWDYHVVLLHQNQQGQSFIYDQDTVLPFSCPFHVYTTEAFHTDHGLK PAFWRKLRVIPADTYLKNFASDRSHMKNADGTWRMPPPLYPCIETTDSKMNLDDFISMDS KVGCGHVYSLSEFVKHFAEK |

TABLE 1-continued

Non-limiting example sequences of amino acid binding proteins.

| Name | SEQ ID NO. | Sequence |
|---|---|---|
| PS1265 | 611 | MEHVSSKYVNITPSRDECVYTSCYSEENVWKLCEHIKTQTQIHLDEVYAVFISNERKMIP IWKQKSSRGDEPVVWDYQVVLLHQNQQGQSFIYDQDTVLPFSCPFHVYTTEAFHTDHGLK PAFWRKLRVIPADTYLKNFASDRSHMKNADGTWRMPPPLYPCIETTDSKMNLDDFISMDS KVGCGHVYSLSEFVKHFAEK |
| PS1266 | 612 | MEHVSSKYVNITPSRDECVYTSCYSEENVWKLCEHIKTQTQIHLDEVYAVFISNERKMIP IWKQKSSRGDEPVVWDYQVVLLHQNQQGQSFIYDQDTVLPFSCPFHVYTTEAFHTDHGLK PAFWRKLRVIPADTYLKNFASDRSHEKNADGTWRMPPPLYPCIETTDSKMNLDDFISMDS KVGCGHVYSLSEFVKHFAEK |
| PS1267 | 613 | MGLENSLETLRFSISNLSMQTHAARMRTFMYWPSSVPVQPEQLASAGFYYLGRNDIVICF CCDGGLHCWQSGDDPWVEHALFFPRCEFLIRMKGQEFVDEIQGRYPHLLEQLLS |
| PS1268 | 614 | MHHHHHHHHHHDYDIPTTENLYFQGMHSKFSHAGRICGAKFKVGEPIYRCKECSFDDTCV LCVNCFNPKDHLGHHVYTTICTEFNNGECDCGDKTAWNHTLFCKAEE |
| PS1270 | 615 | MHHHHHHHHHHDYDIPTTENLYFQGRFSISNLSMQTHAARMRTFMYWPSS VPVQPEQLASAGFYYVGRNDDVKCFCCDGGLRCWESGDDPWVEHAKWFPR CEFLIRMKGQEFVDEIQGRY |
| PS1271 | 616 | MGDVQPETCRPSAASGNYFPQYPEYAIETARLRTFEAWPRNLKQKPHQLAEAGFFYTGVG DRVRCFSCGGGLMDWNDNDEPWEQHARHLSQCRFVKLMKGQLYIDTVAAKPVLAEEKEES TSIGGDGSAGSAAGSGEFMGDVQPETCRPSAASGNYFPQYPEYAIETARLRTFEAWPRNL KQKPHQLAEAGFFYTGVGDRVRCFSCGGGLMDWNDNDEPWEQHARHLSQCRFVKLMKGQL YIDTVAAKPVLAEEKEESTSIGGD |
| PS1272 | 617 | MGLENSLETLRFSISNLSMQTHAARMRTFMYWPSSVPVQPEQLASAGFYYVGRNDDVKCF CCDGGLRCWESGDDPWVEHAKWFPRCEFLIRMKGQEFVDEIQGRYPHLLEQLLSGSAGSA AGSGEFMGLENSLETLRFSISNLSMQTHAARMRTFMYWPSSVPVQPEQLASAGFYYVGRN DDVKCFCCDGGLRCWESGDDPWVEHAKWFPRCEFLIRMKGQEFVDEIQGRYPHLLEQLLS GGSHHHHHHHHHHGGGSGGGSGGGSGLNDFFEAQKIEWHEGGGSGGGSGGGSGLNDFFEA QKIEWHE |
| PS1273 | 618 | MGLENSLETLRFSISNLSMQTHAARMRTFMYWPSSVPVQPEQLASAGFYYVGRNDDVKCF CCDGGLRCWESGDDPWVEHARHFPRCEFLIRMKGQEFVDEIQGRYPHLLEQLLSGSAGSA AGSGEFMGLENSLETLRFSISNLSMQTHAARMRTFMYWPSSVPVQPEQLASAGFYYVGRN DDVKCFCCDGGLRCWESGDDPWVEHARHFPRCEFLIRMKGQEFVDEIQGRYPHLLEQLLS |
| PS1274 | 619 | MGDVQPETCRPSAASGNYFPQYPEYAIETARLRTFEAWPRNLKQKPHQLAEAGFFYTG VGDRVRCFSCGGGLMDWNDNDEPWEQHALWLSQCRFVKLMKGQLYIDTVAAKPVL AEEKEESTSIGGDTGSAGSAAGSGEFMGDVQPETCRPSAASGNYFPQYPEYAIETARLR TFEAWPRNLKQKPHQLAEAGFFYTGVGDRVRCFSCGGGLMDWNDNDEPWEQHAL WLSQCRFVKLMKGQLYIDTVAAKPVLAEEKEESTSIGGDTGHHHHHHHHHHGGGSGG GSGGGSGLNDFFEAQKIEWHEGGGSGGGSGGGSGLNDFFEAQKIEWHE* |
| PS1275 | 620 | MGLENSLETLRFSISNLSMQTHAARMRTFMYWPSSVPVQPEQLASAGFYYVGRNDDVKCF CCDGGLRCWESGDDPWVEHAKWFPRCEFLIRMKGQEFVDEIQGRYPHLLEQLLSGGGSGG GSGGGSGMGLENSLETLRFSISNLSMQTHAARMRTFMYWPSSVPVQPEQLASAGFYYVGR NDDVKCFCCDGGLRCWESGDDPWVEHAKWFPRCEFLIRMKGQEFVDEIQGRYPHLLEQLL S |
| PS1276 | 621 | MGLENSLETLRFSISNLSMQTHAARMRTFMYWPSSVPVQPEQLASAGFYYVGRNDDVKCF CCDGGLRCWESGDDPWVEHAKWFPRCEFLIRMKGQEFVDEIQGRYPHLLEQLLSGSAGSA AGSGEFGSAGSAAGSGEFGSAGSAAGSGEFMGLENSLETLRFSISNLSMQTHAARMRTFM YWPSSVPVQPEQLASAGFYYVGRNDDVKCFCCDGGLRCWESGDDPWVEHAKWFPRCEFLI RMKGQEFVDEIQGRYPHLLEQLLS |
| PS1277 | 622 | MPTAASATESAIEDTPAPARPEVDGRTKPKRQPRYHVVLWDDEDHTYQYVVVMLRSLFGH PPSRGYRMAKEMDTQGRVIVLTTTREHAELKRDQIHAFGRDRLLARSKGSMKASIEAEE |
| PS1278 | 623 | MPTAASATESAIEDTPAPARPEVDGRTKPKRQPRYHVVLWDDDDHTYQYVVVMLRSLFGH PPSRGYRMAREMDTQGRVIVLTTTREHAELKRDQIHAFGRDRLLARSKGSMKASIEAEE |
| PS1279 | 624 | MPTAASATESAIEDTPAPARPEVDGRTKPKRQPRYHVVLWDDDDHTYQYVVVMLRSLFGH PPSRGYRMAKEMTTQGRVIVLTTTREHAELKRDQIHAFGRDRLLARSKGSMKASIEAEE |
| PS1280 | 625 | MPTAASATESAIEDTPAPARPEVDGRTKPKRQPRYHVVLWDDQDHTYQYVVVMLRSLFGH PPSRGYRMAKEMDTQGRVIVLTTTREHAELKRDQIHAFGRDRLLARSKGSMKASIEAEE |
| PS1281 | 626 | MPTAASATESAIEDTPAPARPEVDGRTKPKRQPRYHVVLWDDDEHTYQYVVVMLRSLFGH PPSRGYRMAKEMDTQGRVIVLTTTREHAELKRDQIHAFGRDRLLARSKGSMKASIEAEE |
| PS1282 | 627 | MPTAASATESAIEDTPAPARPEVDGRTKPKRQPRYHVVLWDDDDHTMQYVVVMLRSLFGH PPSRGYRMAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1283 | 628 | MPTAASATESAIEDTPAPARPEVDGRTKPKRQPRYHVVLWDDDDHTFQYVVVMLRSLFGH PPSRGYRMAKEMDTQGRVIVLTTTREHAELKRDQIHAFGRDRLLARSKGSMKASIEAEE |
| PS1284 | 629 | MPTAASATESAIEDTPAPARPEVDGRTKPKRQPRYHVVLWDDDDHTVQYVVVMLRSLFGH PPSRGYRMAKEMDTQGRVIVLTTTREHAELKRDQIHAFGRDRLLARSKGSMKASIEAEE |
| PS1285 | 630 | MPTAASATESAIEDTPAPARPEVDGRTKPKRQPRYHVVLYDDDTHTYQYVVVMLRSLFGH PPSRGYRMAKEMDTQGRVIVLTTTREHAELKRDQIHAFGRDRLLARSKGSMKASIEAEE |
| PS1286 | 631 | MPTAASATESAIEDTPAPARPEVDGRTKPKRQPRYHVVLYDDEDHTYQYVVVMLRSLFGH PPSRGYRMAKEMDTQGRVIVLTTTREHAELKRDQIHAFGRDRLLARSKGSMKASIEAEE |
| PS1287 | 632 | MPTAASATESAIEDTPAPARPEVDGRTKPKRQPRYHVVLYDDDDHTFQYVVVMLRSLFGH PPSRGYRMAKEMDTQGRVIVLTTTREHAELKRDQIHAFGRDRLLARSKGSMKASIEAEE |
| PS1288 | 633 | MPTAASATESAIEDTPAPARPEVDGRTKPKRQPRYHVVLYDDDDHTYQYVVVMLRSLFGH PPSRGYRMAREMDTQGRVIVLTTTREHAELKRDQIHAFGRDRLLARSKGSMKASIEAEE |
| PS1289 | 634 | MPTAASATESAIEDTPAPARPEVDGRTKPKRQPRYHVVLYDDDDHTYQYVVVMLRSLFGH PPSRGYRMAKEMTTQGRVIVLTTTREHAELKRDQIHAFGRDRLLARSKGSMKASIEAEE |
| PS1290 | 635 | MPTAASATESAIEDTPAPARPEVDGRTKPKRQPRYHVVLWDDEDHTYQYVVVMLRSLFGH PPSRGYRMAKEMTTQGRVIVLTTTREHAELKRDQIHAFGRDRLLARSKGSMKASIEAEE |
| PS1291 | 636 | MPTAASATESAIEDTPAPARPEVDGRTKPKRQPRYHVVLYDDEDHTFQYVVVMLRSLFGH PPSRGYRMAKEMDTQGRVIVLTTTREHAELKRDQIHAFGRDRLLARSKGSMKASIEAEE |
| PS1292 | 637 | MPTAASATESAIEDTPAPARPEVDGRTKPKRQPRYHVVLYDDDDHTYQYVVVMLRSLFGH PPSRGYRMAREMTTQGRVIVLTTTREHAELKRDQIHAFGRDRLLARSKGSMKASIEAEE |
| PS1293 | 638 | MPTAASATESAIEDTPAPARPEVDGRTKPKRQPRYHVVLWDDEDHTYQYVVVMLRSLFGH PPSRGYRMAREMTTQGRVIVLTTTREHAELKRDQIHAFGRDRLLARSKGSMKASIEAEE |
| PS1294 | 639 | MPTAASATESAIEDTPAPARPEVDGRTKPKRQPRYHVVLYDDEDHTFQYVVVMLRSLFGH PPSRGYRMAKEMTTQGRVIVLTTTREHAELKRDQIHAFGRDRLLARSKGSMKASIEAEE |
| PS1295 | 640 | MPTAASATESAIEDTPAPARPEVDGRTKPKRQPRYHVVLWDDEDHTFQYVVVMLRSLFGH PPSRGYRMAREMTTQGRVIVLTTTREHAELKRDQIHAFGRDRLLARSKGSMKASIEAEE |
| PS1296 | 641 | MPTAASATESAIEDTPAPARPEVDGRTKPKRQPRYHVVLYDDEDHTFQYVVVMLRSLFGH PPSRGYRMAREMTTQGRVIVLTTTREHAELKRDQIHAFGRDRLLARSKGSMKASIEAEE |
| PS1297 | 642 | MPTAASATESAIEDTPAPARPEVDGRTKPKRQPRYHVVLWSDEDHTHQYVVVMLRSLFGH PPSRGYRMAKEIDTQGRVIVLTTTREHAELKRDQIHAFGRDRLLARSKGSMKASIEAEE |
| PS1298 | 643 | MPTAASATESAIEDTPAPARPEVDGRTKPKRQPRYHVVIWEDDDHTYQYWVVMLRSLFGH PPSRGYRMAKEAHTQGRVIVLTTTREHAELKRDQIHAFGRDRLLARSKGSLKASIEAEE |
| PS1299 | 644 | MPTAASATESAIEDTPAPARPEVDGRTKPKRQPRYHVVIWSDDDHTHDYVVVMLRSLFGH PPSRGYRMTKELHTQGRVIVLTTTREHAELKRDQIHAFGRDRLLARSKGSMKASIEAEE |
| PS1300 | 645 | MPTAASATESAIEDTPAPARPEVDGRTKPKRQPRYHVVMWDDQDNTDQYWVVMLRSLFGH PPSRGYRMSEELHTQGRVIVLTTTREHAELKRDQIHAFGRDRLLARSKGSVKASIEAEE |
| PS1301 | 646 | MPTAASATESAIEDTPAPARPEVDGRTKPKRQPRYHVVVWDDEDHTHQYWVVMLRSLFGH PPSRGYRMAKEAHTQGRVIVLTTTREHAELKRDQIHAFGRDRLLARSKGSLKASIEAEE |
| PS1302 | 647 | MPTAASATESAIEDTPAPARPEVDGRTKPKRQPRYHVVLWDDDDHTSQYVVVMLHSLFGH PPSRGYRLAKEMDTQGRVIVLTTTREHAELKRDQIHAFGRDRLLARSKGSMKASIEAEE |
| PS1303 | 648 | MPTAASATESAIEDTPAPARPEVDGRTKPKRQPRYHVVLWSDEDHTHQYIVVMLRSLFGH PPSRGYRMAKEIDTQGRVIVLTTTREHAELKRDQIHAFGRDRLLARSKGSMKASIEAEE |
| PS1304 | 649 | MPTAASATESAIEDTPAPARPEVDGRTKPKRQPRYHVVLWDDDDHTKQYIVVMLRSLFGH PPSRGYRMAKEMHTQGRVIVLTTTREHAELKRDQIHAFGRDRLLARSKGSVKASIEAEE |
| PS1305 | 650 | MPTAASATESAIEDTPAPARPEVDGRTKPKRQPRYHVVMWEDEDHTFQYVVVMLRSLFGH PPSRGYRMVKEMHTQGRVIVLTTTREHAELKRDQIHAFGRDRLLARSKGSMKASIEAEE |
| PS1306 | 651 | MASDTPESLMALCTDFCLRNLDGTLGYLLDKETLRLHPDIFLPSEICDRLVNEYVELVNA ACNFEPHESFFSLFSDPRSTRLTRIHLREDLVQDQDLEAIRKQDLVELYLTNCEKLSAKS LQTLRSFSHTLVSLSLFGCTNIFYEEENPGGCEDEYLVNPTCQVLVKDFTFEGFSRLRFL NLGRMIDWVPVESLLRPLNSLAALDLSGIQTSDAAFLTQWKDSLVSLVLYNMDLSDDHIR VIVQLHKLRHLDISRDRLSSYYKFKLTREVLSLFVQKLGNLMSLDISGHMILENCSISKM EEEAGQTSIEPSKSSIIPFRALKRPLQFLGLFENSLCRLTHIPAYKVSGDKNEEQVLNAI |

TABLE 1-continued

Non-limiting example sequences of amino acid binding proteins.

| Name | SEQ ID NO. | Sequence |
|---|---|---|
| | | EAYTEHRPEITSRAINLLFDIARIERCNQLLRALKLVITALKCHKYDRNIQVTGSAALFY<br>LTNSEYRSEQSVKLRRQVIQVVLNGMESYQEVTVQRNCCLTLCNFSIPEELEFQYRRVNE<br>LLLSILNPTRQDESIQRIAVHLCNALVCQVDNDHKEAVGKMGFVVTMLKLIQKKLLDKTC<br>DQVMEFSWSALWNITDETPDNCEMFLNFNGMKLFLDCLKEFPEKQELHRNMLGLLGNVAE<br>VKELRPQLMTSQFISVFSNLLESKADGIEVSYNACGVLSHIMFDGPEAWGVCEPQREEVE<br>ERMWAAIQSWDINSRRNINYRSFEPILRLLPQGISPVSQHWATWALYNLVSVYPDKYCPL<br>LIKEGGMPLLRDIIKMATARQETKEMARKVIEHCSNFKEENMDTSR |
| PS1307 | 652 | MLTNSEYRSEQSVKLRRQVIQVVLNGMESYQEVTVQRNCCLTLCNFSIPEELEFQYRRVN<br>ELLLSILNPTRQDESIQRIAVHLCNALVCQVDNDHKEAVGKMGFVVTMLKLIQKKLLDKT<br>CDQVMEFSWSALWNITDETPDNCEMFLNFNGMKLFLDCLKEFPEKQELHRNMLGLLGNVA<br>EVKELRPQLMTSQFISVFSNLLESKADGIEVSYNACGVLSHIMFDGPEAWGVCEPQREEV<br>EERMWAAIQSWDINSRRNINYRSFEPILRLLPQGISPVSQHWATWALYNLVSVYPDKYCP<br>LLIKEGGMPLLRDIIKMATARQETKEMARKVIEHCSNFKEENMDTSR |
| PS1308 | 653 | MLTNSEYRMEQSIKLRRQVIQVVLNGMESYQEVTVQRNCCLTLCNFSIPEELEFQYRRVN<br>ELLLSILNQSRQDESIQRIAVHLCNALVCQVDNDHKEAVGKMGFVMTMLKLIQKKLADKT<br>CDQVMEFSWSALWNITDETPDNCEMFLNYSGMKLFLECLKEFPEKQELHRNMLGLLGNVA<br>EVRELRPQLMTSQFISVFSNLLESKADGIEVSYNACGVLSHIMFDGPEAWGICEPHREEV<br>VKRMWAAIQSWDINSRRNINYRSFEPILRLLPQGISPVSQHWATWALYNLVSVYPDKYCP<br>LLIKEGGIPLLKDMIKMASARQETKEMAWKVIEHCSNFKEENMDTSR |
| PS1309 | 654 | MTGSAALFYLTNTEYRGEQSVRLRRQVIQVVLNGMEHYQEVTVQRNCCLTLCNFSIPEEL<br>EFQYRRVNLLLLKILEPLRQDESIQRIAVHLCNALVCQVDNDHKEAVGKMGFVKTMLNLI<br>QKKLQDRMCDQVMEFSWSALWNITDETPDNCQMFLECNGMNLFLECLKEFPDKQELHRNM<br>LGLLGNVAEVKALRPQLLTRQFITVFSDLLDSKADGIEVSYNACGVLSHIMFDGPGVWSM<br>EEPSRTHVMDKMWTAIQSWDVSSRRNINYRSFEPILRLLPQSGAPVSQHWATWALYNLVS<br>VYPSKYCPLLIKEGGVSLLQAVLELQTSHVETKDMARKVMEQCESFKEDPMDTSR |
| PS1310 | 655 | MPEDQAGAAMEEASPYSLLDICLNFLTTHLEKFCSARQDGTLCLQEPGVFPQEVADRLLR<br>TMAFHGLLNDGTVGIFRGNQMRLKRACIRKAKISAVAFRKAFCHHKLVELDATGVNADIT<br>ITDIISGLGSNKWIQQNLQCLVLNSLTLSLEDPYERCFSRLSGLRALSITNVLFYNEDLA<br>EVASLPRLESLDISNTSITDITALLACKDRLKSLTMHHLKCLKMTTTQILDVVRELKHLN<br>HLDISDDKQFTSDIALRLLEQKDILPNLVSLDVSGRKHVTDKAVEAFIQQRPSMQFVGLL<br>ATDAGYSEFLTGEGHLKVSGEANETQIAEALKRYSERAFFVREALFHLFSLTHVMEKTKP<br>EILKLVVTGMRNHPMNLPVQLAASACVFNLTKQDLAAGMPVRLLADVTHLLLKAMEHFPN<br>HQQLQKNCLLSLCSDRILQDVPFNRFEAAKLVMQWLCNHEDQNMQRMAVAIISILAAKLS<br>TEQTAQLGTELFIVRQLLQIVKQKTNQNSVDTTLKFTLSALWNLTDESPTTCRHFIENQG<br>LELFMRVLESFPTESSIQQKVLGLLNNIAEVQELHSELMWKDFIDHISSLLHSVEVEVSY<br>FAAGIIAHLISRGEQAWTLSRSQRNSLLDDLHSAILKWPTPECEMVAYRSFNPFFPLLGC<br>FTTPGVQLWAVWAMQHVCSKNPSRYCSMLIEEGGLQHLYNIKDHEHTDPHVQQIAVAILD<br>SLEKHIVRHGRPPPCKKQPQARLN |
| PS1311 | 656 | MVFNLTKQDLAAGMPVRLLADVTHLLLKAMEHFPNHQQLQKNCLLSLCSDRILQDVPFNR<br>FEAAKLVMQWLCNHEDQNMQRMAVAIISILAAKLSTEQTAQLGTELFIVRQLLQIVKQKT<br>NQNSVDTTLKFTLSALWNLTDESPTTCRHFIENQGLELFMRVLESFPTESSIQQKVLGLL<br>NNIAEVQELHSELMWKDFIDHISSLLHSVEVEVSYFAAGIIAHLISRGEQAWTLSRSQRN<br>SLLDDLHSAILKWPTPECEMVAYRSFNPFFPLLGCFTTPGVQLWAVWAMQHVCSKNPSRY<br>CSMLIEEGGLQHLYNIKDHEHTDPHVQQIAVAILDSLEKHIVRHGRPPPCKKQPQARLN |
| PS1312 | 657 | MPEMLKLVVIGMRNHPTNLPVQLAASACVFNLTKQDLAAGMPVKLLADVTHLLLEAMKHF<br>PNHQQLQKNCLLSLCSDRILQDVPFNRFDAAKLVMQWLCNHEDQNMQRMAVAIISILAAK<br>LSTEQTAQLGAELFIVRQLLQIVRQKTSQNMVDTTLKFTLSALWNLTDESPTTCRHFIEN<br>QGLELFMKVLETFPSESSIQQKVLGLLNNIAEVKELHSELMCKDFIDQISKLLHSVEVEV<br>SYFAAGIIAHLVSRGEESWTLSSSLRETLLEQLHSAILSWPTPECEMVAYRSFNPFFPLL<br>ACFRTPGVQLWAVWAMQHVCSKNPVRYCSMLIEEGGLVRLHRIRDHMCADPDVLRITIAI<br>LDNLDRHLRKHGNPPCPKPPFAK |
| PS1313 | 658 | MLTHAIEKPRPDILKLVALGMKNHPTTLNVQLAASACVFNLTKQELAFGIPVRLLGNVTQ<br>QLLEAMKTFPNHQQLQKNCLLSLCSDRILQEVPFNRFEAAKLVMQWLCNHEDQNMQRMAV<br>AIISILAAKLSTEQTAQLGAELFIVKQLLHIVRQKTCQSTVDATLKFTLSALWNLTDESP<br>TTCRHFIENQGLELFIKVLESFPSESSIQQKVLGLLNNIAEVSELHGELMVQSFLDHIRT<br>LLHSPEVEVSYFAAGILAHLTSRGEKVWTLELTLRNTLLQQLHSAILKWPTPECEMVAYR<br>SFNPFFPLLECFQTPGVQLWAAWAMQHVCSKNAGRYCSMLLEEGGLQHLEAITSHPKTHS<br>DVRRLTESILDGLQRHRARTGYTAIPKTQAHREKCNP |
| PS1314 | 659 | MEGNGPAAVHYQPASPPRDACVYSSCYSEENVWKLCEYIKNHDQYPLEECYAVFISNERK<br>MIPIWKQQARPGDGPVIWDYQVVLLHVSSGGQSFIYDLDTVLPFPCLFDTYVEDAIKSDD<br>DIHPQFRRKFRVICADSYLKNFASDRSHMKDSSGNWREPPPPYPCIETGDSKMNLNDFIS<br>MDPKVGWGAVYTLSEFTHRFGSKNGSAGSAAGSGEFMEGNGPAAVHYQPASPPRDACVYS<br>SCYSEENVWKLCEYIKNHDQYPLEECYAVFISNERKMIPIWKQQARPGDGPVIWDYQVVL<br>LHVSSGGQSFIYDLDTVLPFPCLFDTYVEDAIKSDDDIHPQFRRKFRVICADSYLKNFAS<br>DRSHMKDSSGNWREPPPPYPCIETGDSKMNLNDFISMDPKVGWGAVYTLSEFTHRFGSKN |

TABLE 1-continued

Non-limiting example sequences of amino acid binding proteins.

| Name | SEQ ID NO. | Sequence |
|---|---|---|
| PS1315 | 660 | MNGLSAQHERIAPARHECVYTSCYSEENVWKLCEHIKTSKRCPLGDVYAVFISNERKMVP IWKQKSGRGEEPVIWDYHVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKTGSAGSAAGSGEFMNGLSAQHERIAPARHECVYTSCYSEEN VWKLCEHIKTSKRCPLGDVYAVFISNERKMVPIWKQKSGRGEEPVIWDYHVILLHDCHKE QTFIYDLDTTLPFPCPFDTYVKEAFKSDNYINPAFWRKLRVVPADVFLQNFASDRSHMKD ASGGWRMPPPPYPCIETAESRMNLDDFISMNPSVGWGHVYTLEEFVQHFGKT |
| PS1316 | 661 | MNGLSAQHERIAPARHECVYTSCYSEENVWKLCEHIKTSKRCPLGDVYAVFISNERKMVP IWKQKSGRGEEPVIWDYQVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKTGGGSGGGSGGGSGMNGLSAQHERIAPARHECVYTSCYSEE NVWKLCEHIKTSKRCPLGDVYAVFISNERKMVPIWKQKSGRGEEPVIWDYQVILLHDCHK EQTFIYDLDTTLPFPCPFDTYVKEAFKSDNYINPAFWRKLRVVPADVFLQNFASDRSHMK DASGGWRMPPPPYPCIETAESRMNLDDFISMNPSVGWGHVYTLEEFVQHFGKT |
| PS1317 | 662 | MNGLSAQHERIAPARHECVYTSCYSEENVWKLCEHIKTSKRCPLGDVYAVFISNERKMVP IWKQKSGRGEEPVIWDYQVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKTGSAGSAAGSGEFMNGLSAQHERIAPARHECVYTSCYSEEN VWKLCEHIKTSKRCPLGDVYAVFISNERKMVPIWKQKSGRGEEPVIWDYQVILLHDCHKE QTFIYDLDTTLPFPCPFDTYVKEAFKSDNYINPAFWRKLRVVPADVFLQNFASDRSHMKD ASGGWRMPPPPYPCIETAESRMNLDDFISMNPSVGWGHVYTLEEFVQHFGKT |
| PS1318 | 663 | MNGLSAQHERIAPARHECVYTSCYSEENVWKLCEHIKTSKRCPLGDVYAVFISNERKMVP IWKQKSGRGEEPVIWDYQVILLHDCHKEQTFIYDLDTTLPFPCPFDTYVKEAFKSDNYIN PAFWRKLRVVPADVFLQNFASDRSHMKDASGGWRMPPPPYPCIETAESRMNLDDFISMNP SVGWGHVYTLEEFVQHFGKTGSAGSAAGSGEFGSAGSAAGSGEFGSAGSAAGSGEFMNGL SAQHERIAPARHECVYTSCYSEENVWKLCEHIKTSKRCPLGDVYAVFISNERKMVPIWKQ KSGRGEEPVIWDYQVILLHDCHKEQTFIYDLDTTLPFPCPFDTYVKEAFKSDNYINPAFW RKLRVVPADVFLQNFASDRSHMKDASGGWRMPPPPYPCIETAESRMNLDDFISMNPSVGW GHVYTLEEFVQHFGKT |
| PS1321 | 664 | MPTAASATESAIEDTPAPARPEVDGRTKPKRQPRYHVVLWDDDDHTYQYVVAMLRSLFGH PPSRGYRMAKEMDTQGRVIVLTTTREHAELKRDQIHAFGRDRLLARSKGSMKASIEAEE |
| PS1322 | 665 | MPTAASATESAIEDTPAPARPEVDGRTKPKRQPRYHVVLWDDDDHTYQYVVMMLRSLFGH PPSRGYRMAKEMDTQGRVIVLTTTREHAELKRDQIHAFGRDRLLARSKGSMKASIEAEE |
| PS1323 | 666 | MPTAASATESAIEDTPAPARTEVDGRTKPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1324 | 667 | MPTAASATESAIEDTPAPARPEVDGRTKPKRQPRYHVVLWDDDDHTYQYVVAMLRSLFGI PPSRGYRMAKEMDTQGRVIVLTTTREHAELKRDQIHAFGRDRLLARSKGSMKASIEAEE |
| PS1325 | 668 | MPTAASATESAIEDTPAPARPEVDGRTKPKRQPRYHVVLWDDDDHTYQYVVMMLRSLFGI PPSRGYRMAKEMDTQGRVIVLTTTREHAELKRDQIHAFGRDRLLARSKGSMKASIEAEE |
| PS1326 | 669 | MPTAASATESAIEDTPAPARPEVDGRTKPKRQPRYHVVLWDDDDHTYQYVVMMLRSLFGY PPSRGYRMAKEMDTQGRVIVLTTTREHAELKRDQIHAFGRDRLLARSKGSMKASIEAEE |
| PS1327 | 670 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAWGRDRLLARSKGSMKASIEAEE |
| PS1328 | 671 | MPTAASATESAIEDTPAPARPEVDGRTKPKRQPRYHVVLWDDDDHTYQYVVVMLRSLFGH PKSRGYRMAKEMDTQGRVIVLTTTREHAELKRDQIHAFGRDRLLARSKGSMKASIEAEE |
| PS1329 | 672 | MPTAASATESAIEDTPAPARPEVDGRTKPKRQPRYHVVLWDDDDHTYQYVVVMLQSLFGH PPSRGYRMAKEMDTQGRVIVLTTTREHAELKRDQIHAFGRDRLLARSKGSMKASIEAEE |
| PS1330 | 673 | MPTAASATESAIEDTPAPARPEVDGRTKPKRQPRYHVVLWDDDDHTYQYVVVMLKSLFGH PPSRGYRMAKEMDTQGRVIVLTTTREHAELKRDQIHAFGRDRLLARSKGSMKASIEAEE |
| PS1331 | 674 | MPTAASATESAIEDTPAPARPEVDGRTKPKRQPRYHVVLWDDDDHTYQYVVVMLASLFGH PPSRGYRMAKEMDTQGRVIVLTTTREHAELKRDQIHAFGRDRLLARSKGSMKASIEAEE |
| PS1332 | 675 | MPTAASATESAIEDTPAPARPEVDGRTKPKRQPRYHVVLWDDDDHTYQYVVVMLSSLFGH PPSRGYRMAKEMDTQGRVIVLTTTREHAELKRDQIHAFGRDRLLARSKGSMKASIEAEE |
| PS1333 | 676 | MPTAASATESAIEDTPAPARPEVDGRTKPKRQPRYHVVLWDDDDHTYQYVVVMLRSLFGH PPQRGYRMAKEMDTQGRVIVLTTTREHAELKRDQIHAFGRDRLLARSKGSMKASIEAEE |
| PS1334 | 677 | MPTAASATESAIEDTPAPARPEVDGRTKPKRQPRYHVVLWDDDDHTYQYVVHMLRSLFGH PPSRGYRMAKEMDTQGRVIVLTTTREHAELKRDQIHAFGRDRLLARSKGSMKASIEAEE |

TABLE 1-continued

Non-limiting example sequences of amino acid binding proteins.

| Name | SEQ ID NO. | Sequence |
|---|---|---|
| PS1335 | 678 | MPTAASATESAIEDTPAPARPEVDGRTKPKRQPRYHVVLWDDDDHTYQYVVVMLRSVFGH PPSRGYRMAKEMDTQGRVIVLTTTREHAELKRDQIHAFGRDRLLARSKGSMKASIEAEE |
| PS1336 | 679 | MPTAASATESAIEDTPAPARPEVDGKTKPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1337 | 680 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAYGRDRLLARSKGSMKASIEAEE |
| PS1338 | 681 | MPTAASATESAIEDTPAPARSEVDGYTVPKRQQRYHVVLWDDDDHTYQYVVYMLRSVFGH PPSRGYRMAKEMDTQGRVIVLTTTREHAELKRDQIHAFGRDRLLARSKGSMKASIEAEE |
| PS1339 | 682 | MPTAASATESAIEDTPAPARPEVDGRTKPKRQPRYHVVLWDDDDHTYQYVVYMLRSVFGH PPSRGYRMAKEMDTQGRVIVLTTTREHAELKRDQIHAFGRDRLLARSKGSMKASIEAEE |
| PS1340 | 683 | MPTAASATESAIEDTPAPARPEVDGRTKPKHQPRYHVVLWDDDDHTLQYVVVMLRSLFGH PPSRGYRMAQEMETQGRVIVLTTTREHAELKRDQIHAFGRDRLLARSKGSMKASIEAEE |
| PS1341 | 684 | MPTAASATESAIEDTPAPARPEVDGRTKPKRQPRYHVVLWDDDDHTYQYVVEMLRHLFGH PPSRGYRMAKEMDTQGRVIVLTTTREHAELKRDQIHAFGRDRLLARSKGSMKASIEAEE |
| PS1342 | 685 | MPTAASATESAIEDTPAPARPEVDGRTKPKRQPRYHVVLWDDDDHTYQYVVSMLRSVFGH PPSRGYRMAKEMDTQGRVIVLTTTREHAELKRDQIRARGRDPLLARSKGSMKASIEAEE |
| PS1343 | 686 | MPTAASATESAIEDTPAPARPEVDGRTKPKRQPRYHVVLWDDDDHTYQYVVAMLRSIFGH PPSRGYRMAKEMDTQGRVIVLTTTREHAELKRDQIHAFGRDRLLARSKGSMSASIEAEE |
| PS1344 | 687 | MPTAASATESAIEDTPAPARPEVDGRTKPKRQPRYHVVLWDDDDHTYQYVVVMLRSLFGH PPSRGYRMAKELETQGRLIVLTTTREHAELKRDQIHAFGRDRLLARSKGSMKASIEAEE |
| PS1345 | 688 | MPTAASATESAIEDTPAPARPEVDGRTKPKHQPRYHVVLWDDDDHTDQYVVVMLRSLFGH PPSRGYRMAKEMDTQGRVIVLTTTREHAELKRDQIHAFGRDRLLARSKGSMSASIEAEE |
| PS1346 | 689 | MPTAASATESAIEDTPAPARPEVDGRTKPKRQPRYHVVLWDDDDHTDQYVVVMLRSLFGH PPSRGYRMAKEMDTQGRVIVLTTTREHAELKRDQIHAFGRDRLLARSKGSMSASIEAEE |
| PS1347 | 690 | MPTAASATESAIEDTPAPARPEVDGYTVPKRQPRYHVVLWDDDDHTYQYVVVMLRSLFGH PPSRGYRMAKEMDTQGRVIVLTTTREHAELKRDQIHAYGRDRLLARSKGSMKASIEAEE |
| PS1348 | 691 | MPTAASATESAIEDTPAPARPEVDGRTKPKRQPRYHVVLWDDDDHTYQYVVTMLRSVFGH PPSRGYRMAKEMDTQGRVIVLTTTREHAELKRDQIHAFGRDRLLARSKGSMKASIEAEE |
| PS1349 | 692 | MPTAASATESAIEDTPAPARSEVDGYTVPKRQPRYHVVLWDDDDHTYQYVVIMLRSLFGH PPSRGYRMAKEMDTQGRVTVLTTTREHAELKRDQIHAFGRDRLLARSKGSMKASIEAEE |
| PS1350 | 693 | MPTAASATESAIEDTPAPARPEVDGRTKPKRQPRYHVVLWDDDDHTYQYVVIMLRSLFGH PPSRGYRMAKEMDTQGRVTVLTTTREHAELKRDQIHAFGRDRLLARSKGSMKASIEAEE |
| PS1351 | 694 | MHSKFSHAGRICGAKFKVGERIYRCKECSFDDTCVLCVNCFNPKDHLGHHVYTTICTEFN NGECDCGDKTAWNHTLFCKAEEG |
| PS1352 | 695 | MHSKFSHAGRICGAKFKVGEPIYRCRECSFDDTCVLCVNCFNPKDHLGHHVYTTICTEFN NGECDCGDKTAWNHTLFCKAEEG |
| PS1353 | 696 | MHSKFSHAGRICGAKFKVGEPIYRCKLCSFDDTCVLCVNCFNPKDHLGHHVYTTICTEFN NGECDCGDKTAWNHTLFCKAEEG |
| PS1354 | 697 | MHSKFSHAGRICGAKFKVGEPIYRCKECSFDATCVLCVNCFNPKDHLGHHVYTTICTEFN NGECDCGDKTAWNHTLFCKAEEG |
| PS1355 | 698 | MHSKFSHAGRICGAKFKVGEPIYRCKECSFDCTCVLCVNCFNPKDHLGHHVYTTICTEFN NGECDCGDKTAWNHTLFCKAEEG |
| PS1356 | 699 | MHSKFSHAGRICGAKFKVGEPIYRCKECSFDGTCVLCVNCFNPKDHLGHHVYTTICTEFN NGECDCGDKTAWNHTLFCKAEEG |
| PS1357 | 700 | MHSKFSHAGRICGAKFKVGEPIYRCKECSFDHTCVLCVNCFNPKDHLGHHVYTTICTEFN NGECDCGDKTAWNHTLFCKAEEG |
| PS1358 | 701 | MHSKFSHAGRICGAKFKVGEPIYRCKECSFDKTCVLCVNCFNPKDHLGHHVYTTICTEFN NGECDCGDKTAWNHTLFCKAEEG |
| PS1359 | 702 | MHSKFSHAGRICGAKFKVGEPIYRCKECSFDPTCVLCVNCFNPKDHLGHHVYTTICTEFN NGECDCGDKTAWNHTLFCKAEEG |

TABLE 1-continued

Non-limiting example sequences of amino acid binding proteins.

| Name | SEQ ID NO. | Sequence |
|---|---|---|
| PS1360 | 703 | MHSKFSHAGRICGAKFKVGEPIYRCKECSFDQTCVLCVNCFNPKDHLGHHVYTTICTEFN NGECDCGDKTAWNHTLFCKAEEG |
| PS1361 | 704 | MHSKFSHAGRICGAKFKVGEPIYRCKECSFDRTCVLCVNCFNPKDHLGHHVYTTICTEFN NGECDCGDKTAWNHTLFCKAEEG |
| PS1362 | 705 | MHSKFSHAGRICGAKFKVGEPIYRCKECSFDSTCVLCVNCFNPKDHLGHHVYTTICTEFN NGECDCGDKTAWNHTLFCKAEEG |
| PS1363 | 706 | MHSKFSHAGRICGAKFKVGEPIYRCKECSFDVTCVLCVNCFNPKDHLGHHVYTTICTEFN NGECDCGDKTAWNHTLFCKAEEG |
| PS1364 | 707 | MHSKFSHAGRICGAKFKVGEPIYRCKECSFDDTCVLCVNCFNPKDHIGHHVYTTICTEFN NGECDCGDKTAWNHTLFCKAEEG |
| PS1365 | 708 | MHSKFSHAGRICGAKFKVGEPIYRCKECSFDDTCVLCVNCFNPKDHLGHHVYTTIRTEFN NGECDCGDKTAWNHTLFCKAEEG |
| PS1366 | 709 | MHSKFSHAGRICGAKFKVGEPIYRCKECSFDDTCVLCVNCFNPKDHLGHHVYTTICTCFN NGECDCGDKTAWNHTLFCKAEEG |
| PS1367 | 710 | MHSKFSHAGRICGAKFKVGEPIYRCKECSFDDTCVLCVNCFNPKDHLGHHVYTTICTDFN NGECDCGDKTAWNHTLFCKAEEG |
| PS1368 | 711 | MHSKFSHAGRICGAKFKVGEPIYRCKECSFDDTCVLCVNCFNPKDHLGHHVYTTICTIFN NGECDCGDKTAWNHTLFCKAEEG |
| PS1369 | 712 | MHSKFSHAGRICGAKFKVGEPIYRCKECSFDDTCVLCVNCFNPKDHLGHHVYTTICTNFN NGECDCGDKTAWNHTLFCKAEEG |
| PS1370 | 713 | MHSKFSHAGRICGAKFKVGEPIYRCKECSFDDTCVLCVNCFNPKDHLGHHVYTTICTQFN NGECDCGDKTAWNHTLFCKAEEG |
| PS1371 | 714 | MHSKFSHAGRICGAKFKVGEPIYRCKECSFDDTCVLCVNCFNPKDHLGHHVYTTICTSFN NGECDCGDKTAWNHTLFCKAEEG |
| PS1372 | 715 | MHSKFSHAGRICGAKFKVGEPIYRCKECSFDDTCVLCVNCFNPKDHLGHHVYTTICTWFN NGECDCGDKTAWNHTLFCKAEEG |
| PS1373 | 716 | MHSKFSHAGRICGAKFKVGEPIYRCKECSFDDTCVLCVNCFNPKDHLGHHVYTTICTEKN NGECDCGDKTAWNHTLFCKAEEG |
| PS1374 | 717 | MHSKFSHAGRICGAKFKVGEPIYRCKECSFDKTCVLCVNCFNPKDHIGHHVYTTICTEFN NGECDCGDKTAWNHTLFCKAEEG |
| PS1375 | 718 | MHSKFSHAGRICGAKFKVGEPIYRCKECSFDVTCVLCVNCFNPKDHLGHHVYTTIRTCKN NGECDCGDKTAWNHTLFCKAEEG |
| PS1376 | 719 | MHSKFSHAGRICGAKFKVGERIYRCKECSFDDTCVLCVNCFNPKDHLGHHVYTTIRTEFN NGECDCGDKTAWNHTLFCKAEEG |
| PS1377 | 720 | MHSKFSHAGRICGAKFKVGERIYRCKECSFDDTCVLCVNCFNPKDHLGHHVYTTIRTEKN NGECDCGDKTAWNHTLFCKAEEG |
| PS1378 | 721 | MHSKFSHAGRICGAKFKVGEPIYRCRECSFDDTCVLCVNCFNPKDHIGHHVYTTICTEFN NGECDCGDKTAWNHTLFCKAEEG |
| PS1379 | 722 | MHSKFSHAGRICGAKFKVGEPIYRCRECSFDVTCVLCVNCFNPKDHLGHHVYTTICTEFN NGECDCGDKTAWNHTLFCKAEEG |
| PS1380 | 723 | MHSKFSHAGRICGAKFKVGEPIYRCRECSFDVTCVLCVNCFNPKDHIGHHVYTTICTEFN NGECDCGDKTAWNHTLFCKAEEG |
| PS1381 | 724 | MHSKFSHAGRICGAKFKVGEPIYRCRECSFDVTCVLCVNCFNPKDHIGHHVYTTICTEFN NGECDCGDKTAWNHTLFCKAEEG |
| PS1382 | 725 | MHSKFSHAGRICGAKFKVGEPIYRCRECSFDRTCVLCVNCFNPKDHIGHHVYTTICTEFN NGECDCGDKTAWNHTLFCKAEEG |
| PS1383 | 726 | MHSKFSHAGRICGAKFKVGEPIYRCRECSFDRTCVLCVNCFNPKDHLGHHVYTTICTQKN NGECDCGDKTAWNHTLFCKAEEG |
| PS1384 | 727 | MHSKFSHAGRICGAKFKVGEPIYRCRECSFDHTCVLCVNCFNPKDHLGHHVYTTICTEFN NGECDCGDKTAWNHTLFCKAEEG |

TABLE 1-continued

Non-limiting example sequences of amino acid binding proteins.

| Name | SEQ ID NO. | Sequence |
|---|---|---|
| PS1385 | 728 | MHSKFSHAGRICGAKFKVGEPIYRCRECSFDHTCVLCVNCFNPKDHIGHHVYTTICTEFN NGECDCGDKTAWNHTLFCKAEEG |
| PS1386 | 729 | MHSKFSHAGRICGAKFKVGEPIYRCRECSFDQTCVLCVNCFNPKDHLGHHVYTTICTEKN NGECDCGDKTAWNHTLFCKAEEG |
| PS1387 | 730 | MHSKFSHAGRICGAKFKVGEPIYRCRLCSFDVTCVLCVNCFNPKDHLGHHVYTTIRTEFN NGECDCGDKTAWNHTLFCKAEEG |
| PS1388 | 731 | MHSKFSHAGRICGAKFKVGEPIYRCRLCSFDVTCVLCVNCFNPKDHLGHHVYTTIRTEKN NGECDCGDKTAWNHTLFCKAEEG |
| PS1389 | 732 | MHSKFSHAGRICGAKFKVGEPIYRCRLCSFDQTCVLCVNCFNPKDHLGHHVYTTIRTSFN NGECDCGDKTAWNHTLFCKAEEG |
| PS1390 | 733 | MHSKFSHAGRICGAKFKVGEPIYRCKLCSFDVTCVLCVNCFNPKDHLGHHVYTTIRTSKN NGECDCGDKTAWNHTLFCKAEEG |
| PS1391 | 734 | MHSKFSHAGRICGAKFKVGEPIYRCKECSFDVTCVLCVNCFNPKDHLGHHVYTTIRTEFN NGECDCGDKTAWNHTLFCKAEEG |
| PS1392 | 735 | MHSKFSHAGRICGAKFKVGEPIYRCKECSFDDTCVLCVNCFNPKDHLGHHVYTTIRTEKN NGECDCGDKTAWNHTLFCKAEEG |
| PS1393 | 736 | MHSKFSHAGRICGAKFKVGEPIYRCKLCSFDDTCVLCVNCFNPKDHLGHHVYTTIRTEFN NGECDCGDKTAWNHTLFCKAEEG |
| PS1394 | 737 | MHSKFSHAGRICGAKFKVGEPIYRCRECSFDQTCVLCVNCFNPKDHLGHHVYTTICTEFN NGECDCGDKTAWNHTLFCKAEEG |
| PS1395 | 738 | MHSKFSHAGRICGAKFKVGEPIYRCKECSFDVTCVLCVNCFNPKDHLGHHVYTTIRTEKN NGECDCGDKTAWNHTLFCKAEEG |
| PS1396 | 739 | MHSKFSHAGRICGAKFKVGEPIYRCRLCSFDDTCVLCVNCFNPKDHLGHHVYTTIRTEFN NGECDCGDKTAWNHTLFCKAEEG |
| PS1397 | 740 | MHSKFSHAGRICGAKFKVGEPIYRCKLCSFDVTCVLCVNCFNPKDHLGHHVYTTIRTEFN NGECDCGDKTAWNHTLFCKAEEG |
| PS1398 | 741 | MHSKFSHAGRICGAKFKVGEPIYRCRECSFDHTCVLCVNCFNPKDHLGHHVYTTIRTDKN NGECDCGDKTAWNHTLFCKAEEG |
| PS1399 | 742 | MGLENSLETLRFSISNLSMQTHAARMRTFMYWPSSVPVQPEQLASAGFYYLGRNDDVCCF CCDGALRCWQSGDDPWVEHALWFPRCEFLIRMKGQEFVDEIQGRYPHLLEQLLS |
| PS1400 | 743 | MGLENSLETLRFSISNLSMQTHAARMRTFMYWPSSVPVQPEQLASAGFYYVGRNDIVRCF CCDGALWCWESGDDPWVEHAKWFPRCEFLIRMKGQEFVDEIQGRYPHLLEQLLS |
| PS1401 | 744 | MGLENSLETLRFSISNLSMQTHAARMRTFMYWPSSVPVQPEQLASAGFYYLGRNDEVRCF CCDGGLHCWQSGDDPWVEHALWFPRCEFLIRMKGQEFVDEIQGRYPHLLEQLLS |
| PS1402 | 745 | MGLENSLETLRFSISNLSMQTHAARMRTFMYWPSSVPVQPEQLASAGFYYSGRNDEVRCF CCDGVLHCWESGDDPWVEHAKHFPRCEFLIRMKGQEFVDEIQGRYPHLLEQLLS |
| PS1403 | 746 | MGLENSLETLRFSISNLSMQTHAARMRTFMYWPSSVPVQPEQLASAGFYYSGRNDLVACF CCDGGLTCWESGDDPWVEHAKHFPRCEFLIRMKGQEFVDEIQGRYPHLLEQLLS |
| PS1404 | 747 | MGLENSLETLRFSISNLSMQTHAARMRTFMYWPSSVPVQPEQLASAGFYYLGRNDIVRCF CCDGVLGCWESGDDPWVEHARHFPRCEFLIRMKGQEFVDEIQGRYPHLLEQLLS |
| PS1405 | 748 | MGLENSLETLRFSISNLSMQTHAARMRTFMYWPSSVPVQPEQLASAGFYYLGRNDEVRCF CCDGGLHCWQSGDDPWVEHARWFPRCEFLIRMKGQEFVDEIQGRYPHLLEQLLS |
| PS1406 | 749 | MGLENSLETLRFSISNLSMQTHAARMRTFMYWPSSVPVQPEQLASAGFYYVGRNDIVRCF CCDGALHCWKSGDDPWVEHARHFPRCEFLIRMKGQEFVDEIQGRYPHLLEQLLS |
| PS1407 | 750 | MGLENSLETLRFSISNLSMQTHAARMRTKMYWESSVPVQWEQLASYGFQFVGRNDDVKCQ CCDGGLRCWESGDDVAVEHSKRFIRCEFLIRMKGQEFVDEIQGRYPHLLEQLLS |
| PS1408 | 751 | MGLENSLETLRFSISNLSMQTHAARMRTFMYWPSSVPVQPEQLASAGFYYLGRNDLVKCF CCDGVLHCWQSGDDPWVEHARHFPRCEFLIRMKGQEFVDEIQGRYPHLLEQLLS |
| PS1409 | 752 | MGLENSLETLRFSISNLSMQTHAARMRTFMYWPSSVPVQPEQLASAGFYYLGRNDIVKCF CCDGVLHCWQSGDDPWVEHAKHFPRCEFLIRMKGQEFVDEIQGRYPHLLEQLLS |

TABLE 1-continued

Non-limiting example sequences of amino acid binding proteins.

| Name | SEQ ID NO. | Sequence |
|---|---|---|
| PS1410 | 753 | MGLENSLETLRFSISNLSMQTHAARMRTFMYWPSSVPVQPEQLASAGFYYLGRNDEVRCF CCDGVLHCWESGDDPWVEHARWFPRCEFLIRMNGQEFVDEIQGRYPHLLEQLLS |
| PS1411 | 754 | MGLENSLETLRFSISNLSMQTHAARMRTFMYWPSSVPVQPEQLASAGFYYSGRNDIVRCF CCDGDLHCWESGDDPWVEHAKWFPRCEFLIRMKGQEFVDEIQGRYPHLLEQLLS |
| PS1412 | 755 | MGLENSLETLRFSISNLSMQTHAARMRTFMYWPSSVPVQPEQLASAGFYYAGRNDEVKCF CCDGGLHCWESGDDPWVEHARHFPRCEFLIRMNGQEFVDEIQGRYPHLLEQLLS |
| PS1413 | 756 | MGLENSLETLRFSISNLSMQTHAARMRTFMYWPSSVPVQPEQLASAGFYYLGRNDIVKCF CCDGVLHCWQSGDDPWVEHARHFPRCEFLIRMKGQEFVDEIQGRYPHLLEQLLS |
| PS1414 | 757 | MGLENSLETLRFSISNLSMQTHAARMRTFMYWPSSVPVQPEQLASAGFYYLGRNDLVKCF CCDGVLHCWQSGDDPWVEHAKHFPRCEFLIRMKGQEFVDEIQGRYPHLLEQLLS |
| PS1415 | 758 | MGLENSLETLRFSISNLSMQTHAARMRTFMYWPSSVPVQPEQLASAGFYYLGRNDLVKCF CCDGVLHCWQSGDDPWVEHAKWFPRCEFLIRMKGQEFVDEIQGRYPHLLEQLLS |
| PS1416 | 759 | MGLENSLETLRFSISNLSMQTHAARMRTFMYWPSSVPVQPEQLASAGFYYLGRNDLVKCF CCDGVLHCWESGDDPWVEHARHFPRCEFLIRMKGQEFVDEIQGRYPHLLEQLLS |
| PS1417 | 760 | MGLENSLETLRFSISNLSMQTHAARMRTFMYWPSSVPVQPEQLASAGFYYLGRNDIVKCF CCDGVLHCWQSGDDPWVEHAKWFPRCEFLIRMKGQEFVDEIQGRYPHLLEQLLS |
| PS1418 | 761 | MGLENSLETLRFSISNLSMQTHAARMRTFMYWPSSVPVQPEQLASAGFYYLGRNDLVKCF CCDGALHCWQSGDDPWVEHARHFPRCEFLIRMKGQEFVDEIQGRYPHLLEQLLS |
| PS1419 | 762 | MGLENSLETLRFSISNLSMQTHAARMRTFMYWPSSVPVQPEQLASAGFYYLGRNDLVKCF CCDGVLHCWQSGDDPWVEHARHFPRCEFLIRMKGQEFVDEVQGRYPHLLEQLLS |
| PS1420 | 763 | MGLENSLETLRFSISNLSMQTHAARMRTFMYWPSSVPVQPEQLASAGFYYLGRNDLVKCF CCDGVLHCWQSGDDPWVEHARHFPRCEFLIRMKGQEFVDEIQGRYPHLLEQLPS |
| PS1421 | 764 | MGLENSLETLRFSISNLSMQTHAARMRTFMYWPSSVPVQPEQLASAGFYYLGRNDLVKCF CCDGVLRCWESGDDPWVEHAKHFPRCEFLIRMKGQEFVDEIQGRYPHLLEQLLS |
| PS1422 | 765 | MGLENSLETLRFSISNLSMQTHAARMRTFMYWPSSVPVQPEQLASAGFYYLGRNDLVKCF CCDGVLHCWQSGDDPWVEHATWFPRCEFLIRMKGQEFVDEIQGRYPHLLEQLLS |
| PS1423 | 766 | MGLENSLETLRFSISNLSMQTHAARMRTFMYWPSSVPVQPEQLASAGFYYGGRNDLVKCF CCDGVLHCWQSGDDPWVEHARHFPRCEFLIRMKGQEFVDEIQGRYPHLLEQLLS |
| PS1424 | 767 | MGLENSLETLRFSISNLSMQTHAARMRTFMYWPSSVPVQPEQLASAGFYYLGRNDLVKCF CCDGVLHCWQGGDDPWVEHARHFPRCEFLIRMKGQEFVDEIQGRYPHLLEQLLS |
| PS1425 | 768 | MPTAASATESAIEDTPAPARPEVDGRTKPKRQPRYHVVLWDDDDHTYAYVVVMLVSLFGH PPSRGYRMAKEMDVQGRVIVLTTTRAHAELKRDQIHAFGRDRLLARSKGSMKASIEAEE |
| PS1426 | 769 | MPTAASATESAIEDTPAPARPEVDGRTKPKRQPRYHVVLWDDDDHTYAYVVVMLRSLFGH PPSRGYRMAKEMDVQGRVIVLTTTRAHAELKRDQIHAFGRDRLLARSKGSMKASIEAEE |
| PS1427 | 770 | MPTAASATESAIEDTPAPARPEVDGRTKPKRQPRYHVVLWDDDDHTYQYVVTMLRSLFGH PPSRGYRMAKEMDTQGRVIVLTTTREHAELKRDQIHAFGRDRLLARSKGSMKASIEAEE |
| PS1428 | 771 | MPTAASATESAIEDTPAPARPEVDGRTKPKRQPRYHVVLWDDDDHTYQYVVVMLRSLFGH PPGRGYRMAKEMDTQGRVIVLTTTREHAELKRDQIHAFGRDRLLARSKGSMKASIEAEE |
| PS1429 | 772 | MPTAASATESAIEDTPAPARPEVDGRTKPKRQPRYHVVLWDDDDHTYQYVVVMLRSLFGH PPSRGYRIAKEMDTQGRVIVLTTTREHAELKRDQIHAFGRDRLLARSKGSMKASIEAEE |
| PS1430 | 773 | MPTAASATESAIEDTPAPARPEVDGRTKPKRQPRYHVVLWDDDDHTYQYVVVMLRSLFGH PPSRGYRMAKEVDTQGRVIVLTTTREHAELKRDQIHAFGRDRLLARSKGSMKASIEAEE |
| PS1431 | 774 | MPTAASATESAIEDTPAPARPEVDGRTKPKRQPRYHVVLWDDDDHTYQYVVVMLRSLFGH PPSRGYRMAKEMDTQGRVIVLTTTREHAEFKRDQIHAFGRDRLLARSKGSMKASIEAEE |
| PS1432 | 775 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQINAFGRDRLLARSKGSMKASIEAEE |
| PS1433 | 776 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDSLLARSKGSMKASIEAEE |
| PS1434 | 777 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDGLLARSKGSMKASIEAEE |

TABLE 1-continued

Non-limiting example sequences of amino acid binding proteins.

| Name | SEQ ID NO. | Sequence |
|---|---|---|
| PS1435 | 778 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGRDRLLARSKGSMTASIEAEE |
| PS1436 | 779 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAWGRDSLLARSKGSMKASIEAEE |
| PS1437 | 780 | MPTAASATESAIEDTPAPARSEVDGYTVPKRQPRYHVVLWDDDDHTYQYVVGMLRSVFGH PPSRGYRMAKEMDTQGRVIVLTTTREHAELKRDQIHAFGRDRLLARSKGSMKASIEAEE |
| PS1438 | 781 | MPTAASATESAIEDTPAPVRPEVDGYTVPKRQPRYHVVLWDDDDHTYQYVVTMLRSLFGH PPGRGYRMAKEMDTQGRVIVLTTTREHAELKRDQIHAFGRDRLLARSKGSMKASIEAEE |
| PS1439 | 782 | MPTAASATESAMEDTPAPARPEVDGRTKPKRQPRYHVVLWNDDDHTYQYVVVMLQSLFGH PPKRGYRMAKEMDTQGRVIVLTTTREHAELKRDQIHAFGRDRLLARCKGSMKASIEAEE |
| PS1440 | 783 | MPTAASATESAIEDTPAPARPEVDGRTKPKRQPRYHVVLWDDDDHTYQYVVVMLQSLFGH PPNRGYRMAKEMDTQGRVIVLTTTREHAELKRDQIHAFGCDRLLARCKGSMKASIEAEE |
| PS1441 | 784 | MPTAASATESAIEDPPAPARPEVDGRTKPKRQPRYHVVMWEDDDHTYQYVVVMLRSLFGH PPNRGYRMAKEMDTQGRVIVLTTTREHAELKRDQIHAFGCDRLLARSKGSMKASIEAEE |
| PS1442 | 785 | MPTAASATESAIEDTPAPARPEVDGRTKPKRQPRYHVVLWDDDDHTYQYVVVMLRSLFGH PPSRGYRMAKELDTQGRVIVLTTTREHAELKRDQIRAYGRDGLLARSKGSMKASIEAEE |
| PS1443 | 786 | MPTAASATESAIEDTPAPARSEVDGRTEPKRQPRYHVVLWDDDDHTYQYVVAMLRSLFGH PPSRGYRMAKEMDTQGRVIVLTTTREHAELKRDQIHAFGRDSLLARSKGSMKASIEAEE |
| PS1444 | 787 | MPTAASATESAIEDTPAPARPEVDGRTKPKRQPRYHVVLWDDDDHTYQYVVVMLRSLFGH SASRGYRMAKEMDTQGRVIVLTTTREHAELKRDQIHAFGRDRLLARSKGSMKASIEAEE |
| PS1445 | 788 | MPTAASATESAIEDTPAPARSEVDGYTVPKRQPRYHVVLWDDDDHTYQYVVVMLRSLFGH PPSRGYRMAKEMDTQGRVIVLTTTREHAELKRDQIHAFGRDRLLARSKGSMKASIEAEE |
| PS1446 | 789 | MPTAASATESAIEDTPAPARPEVDGRTKPKRQPRYHVVLWDDDDHTYQYVVHMLRSIFGH PPSRGYRMAKEMDTQGRVIVLTTTREYAELKRDQIHAFGRDRLLARSKGSMKASIEAEE |
| PS1447 | 790 | MPTAASATESAIEDTPAPARPEVDGRTKPKRQPRYHVVLWDDDDHTYQYVVVMLRSLFGH PPERGYRMAKEMDTQGRVIVLTTTREHAELKRDQIHAFGRDRLLARSKGSMKASIEAEE |
| PS1448 | 791 | MPTAASATESAIEDTPAPARPEVDGRTKPKRQPRYHVVLWDDDDHTYQYVVVMLRSLFGH PPSRGYRMAKEMDTQGRVIVLTTTREHAELKRDQIHAFGYDRLLARSKGSMKASIEAEE |

EXAMPLES

Example 1. Real-Time Dynamic Single-Molecule Protein Sequencing on an Integrated Semiconductor Device In this example, a dynamic sequencing-by-degradation approach in which single surface-immobilized peptide molecules are probed in real time by a mixture of dye-labeled N-terminal amino acid recognizers was demonstrated. By measuring fluorescence intensity, lifetime, and intermolecular kinetics of recognizers on a semiconductor chip, the ability to annotate amino acids and collectively identify the peptide sequence was shown. Leveraging the kinetics of binding allows each recognizer to uniquely identify multiple amino acids. Also described here are the principles and processes to expand the number of recognizable amino acids. Furthermore, it was shown that this method is compatible with both synthetic peptides and natural peptides isolated from recombinant human proteins, and capable of detecting single amino acid changes and post-translational modifications. The results demonstrated a robust core technology that can serve as an accurate, sensitive, and scalable next-generation sequencing platform for proteins.

Measurements of the proteome provide deep and valuable insight into biological processes. However, methods with higher sensitivity are needed to fully understand the complex and dynamic states of the proteome in cells and changes to the proteome that occur in disease states, and to make this information more accessible. The complex nature of the proteome and the chemical properties of proteins present several fundamental challenges to achieving comprehensive sensitivity, throughput, and adoption on par with DNA sequencing technologies. These challenges include the large number of different proteins per cell (>10,000) and yet larger number of proteoforms; the very wide dynamic range of protein abundance in cells and biological fluids and lack of correlation with transcript levels; the costs and high detection limits of current mass spectrometry methods; and the inability to copy or amplify proteins. Methods to directly sequence single protein molecules offer the maximum possible detection sensitivity, with the potential to enable single-cell inputs, digital quantification based on read counts, detection of post-translational modifications (PTMs) and low-abundance or aberrant proteoforms, and cost and throughput levels that favor broad adoption.

Figure 6A:
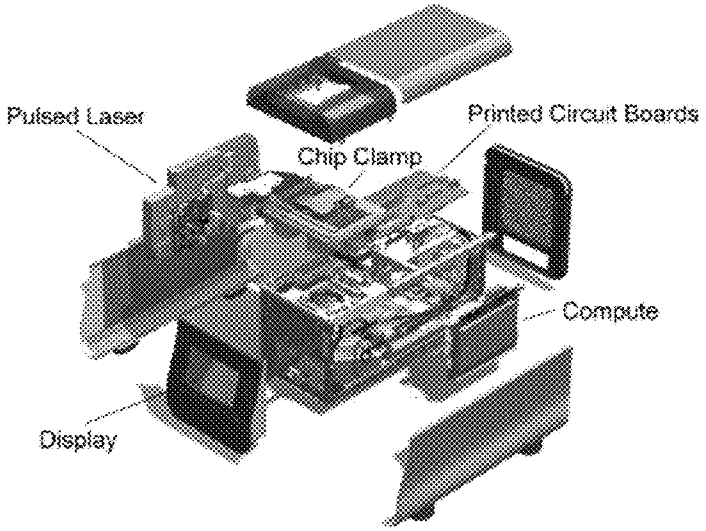
FIGS. 6A-6F show an example of chip operation.

Here, a single-molecule protein sequencing approach and integrated system for massively parallel proteomic studies was demonstrated. In this approach, peptides are immobilized in nanoscale reaction chambers on a semiconductor chip and N-terminal amino acids (NAAs) with dye-labeled NAA recognizers are detected in real time. Aminopeptidases sequentially remove individual NAAs to expose subsequent amino acids for recognition, eliminating the need for complex chemistry and fluidics (FIG. 1). A benchtop device with a 532 nm pulsed laser source for fluorescence excitation and electronics for signal processing was built (FIG. 6A). The semiconductor chip uses intensity and fluorescence lifetime, rather than emission wavelength, for discrimination of dye labels. The recognizers detect one or more types of NAAs and provide information for peptide identification based on the temporal order of NAA recognition and the kinetics of on-off binding.

CMOS fabrication technology was used to build a custom time-domain-sensitive semiconductor chip with nanosecond precision, containing fully-integrated components for single-molecule detection, including photosensors, optical waveguide circuitry, and reaction chambers for biomolecule immobilization (FIG. 1). Observation volumes less than 5 attoliters were achieved through evanescent illumination at reaction chamber bottoms from the nearby waveguide, enabling sensitive single-molecule detection in the context of high freely-diffusing dye concentrations (>1 μM).

The semiconductor chip uses a filterless system that excludes excitation light on the basis of photon arrival time, achieving greater than 10,000-fold attenuation of incident excitation light. Elimination of the need for an integrated optical filter layer increases the efficiency of fluorescence collection and enables scalable manufacturing of the chip. To enable discrimination of fluorescent dye labels attached to NAA recognizers by fluorescence lifetime and intensity, the chip rapidly alternates between early and late signal collection windows associated with each laser pulse, thereby collecting different portions of the exponential fluorescence lifetime decay curve. The relative signal in these collection windows (termed “bin ratio”) provides a reliable indication of fluorescence lifetime (FIGS. 6B-6F, and Materials and Methods).

Figure 2A:
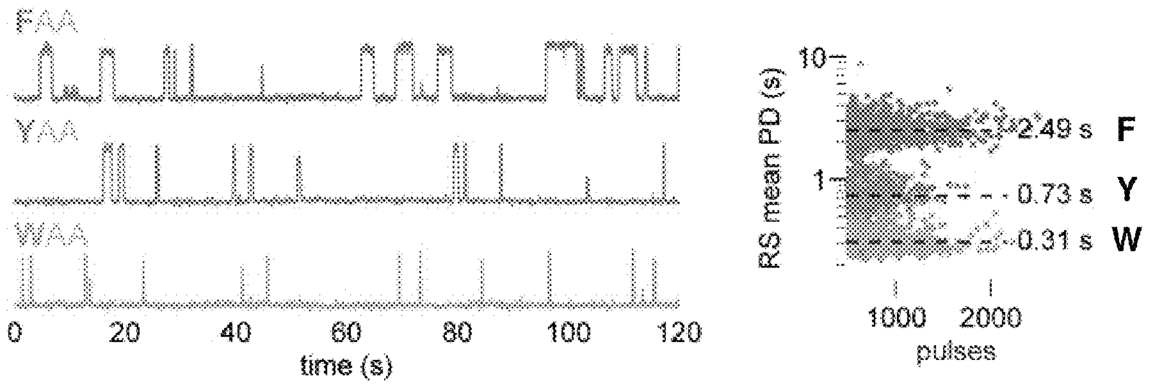
FIGS. 2A-2G show an example of NAA recognition and dynamic sequencing.
Figure 7D:
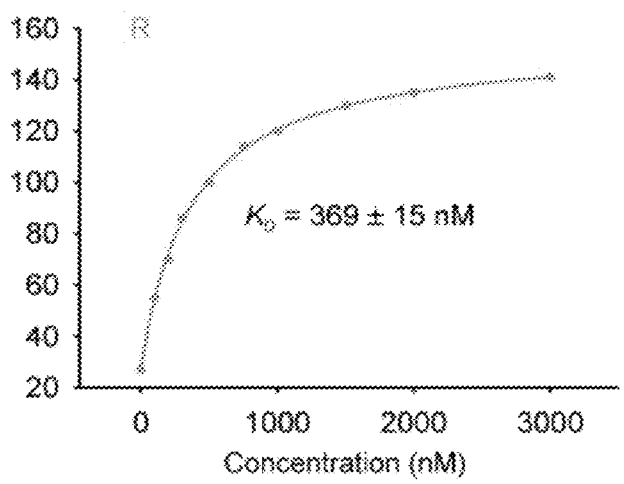

In order for NAA binding proteins to function as recognizers in this approach, the average lifetime of the bound recognizer-peptide complex should be long enough (typically >120 ms) to generate detectable single-molecule binding events. Proteins from the N-end rule adapter family ClpS that natively bind to N-terminal phenylalanine, tyrosine, and tryptophan were evaluated. Using PS610, a recognizer derived from ClpS2 from *A. tumefaciens*, it was established that this recognizer binds detectably to immobilized peptides with these NAAs. Importantly, it was also determined that the kinetics of binding differ for each NAA. To demonstrate these properties, immobilized peptides containing the initial N-terminal sequences FAA, YAA, or WAA were incubated on separate chips with PS610 and data collected for 10 hours (Methods). NAA recognition was observed by PS610, characterized by continuous on-off binding during the incubation period, with distinct pulse duration (PD) for each peptide (FIG. 2A). Median PDs were 2.51, 0.73, and 0.31 s for FAA, YAA, and WAA, respectively. These values reflect differences in binding affinity driven by different dissociation rates for each type of protein-NAA interaction (FIGS. 7A-7B).

Figure 2B:
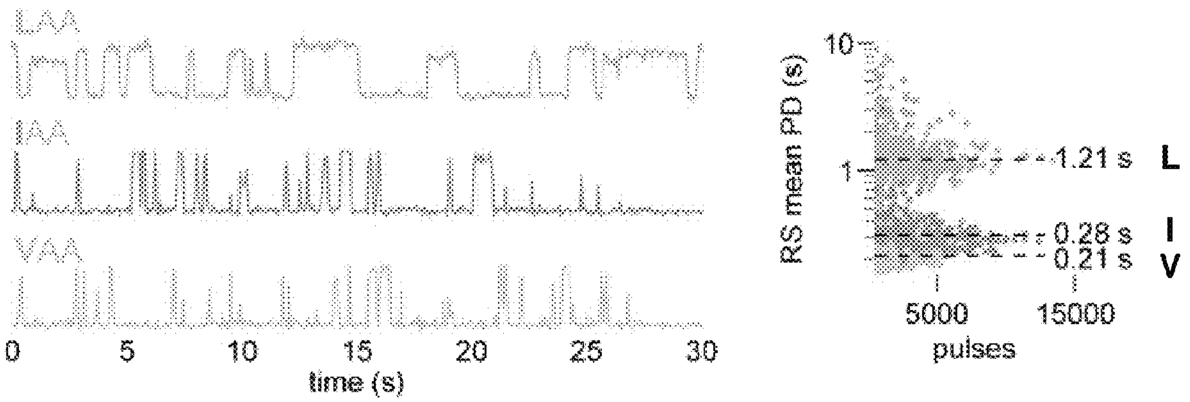

To expand the set of recognizable NAAs, N-end rule pathway proteins were investigated as a source of additional recognizers. In a comprehensive screen of diverse ClpS family proteins, a group of ClpS proteins from the bacterial phylum Planctomycetes with native binding to N-terminal leucine, isoleucine, and valine was discovered. Directed evolution techniques were applied to generate a Planctomycetes ClpS variant—P5961—with sub-micromolar affinity to N-terminal leucine, isoleucine, and valine, and recognition of these NAAs was demonstrated (FIG. 2B). The median PD of binding to peptides with N-terminal LAA, IAA, and VAA was 1.21, 0.28, and 0.21 s, respectively, in agreement with bulk characterization (FIG. 7C).

Figure 2C:
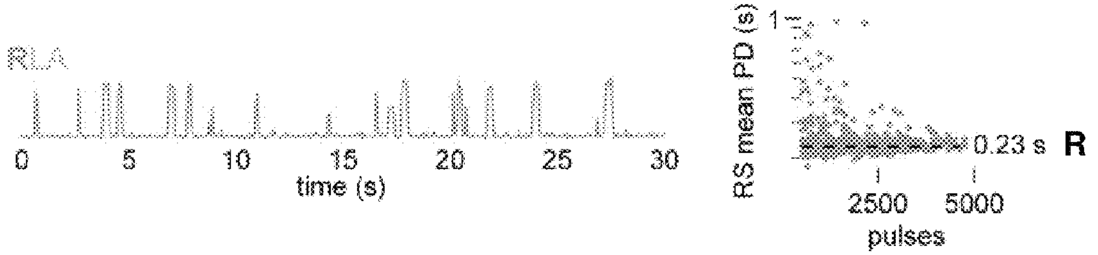
Figure 7E:
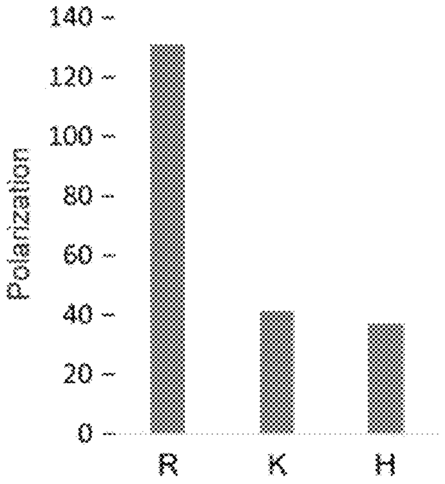

In a separate screen, a diverse set of UBR-box domains from the UBR family of ubiquitin ligases that natively bind N-terminal arginine, lysine, and histidine were investigated. The UBR-box domain from the yeast *K. lactis* UBR1 protein exhibited the highest affinity for N-terminal arginine, and this protein was used to generate an arginine recognizer, PS691. PS691 recognized arginine in a peptide with N-terminal RLA with a median PD of 0.23 s (FIG. 2C). Lower affinity binding to N-terminal lysine and histidine (FIGS. 7D-7E) was insufficient for single-molecule detection.

Figure 2D:
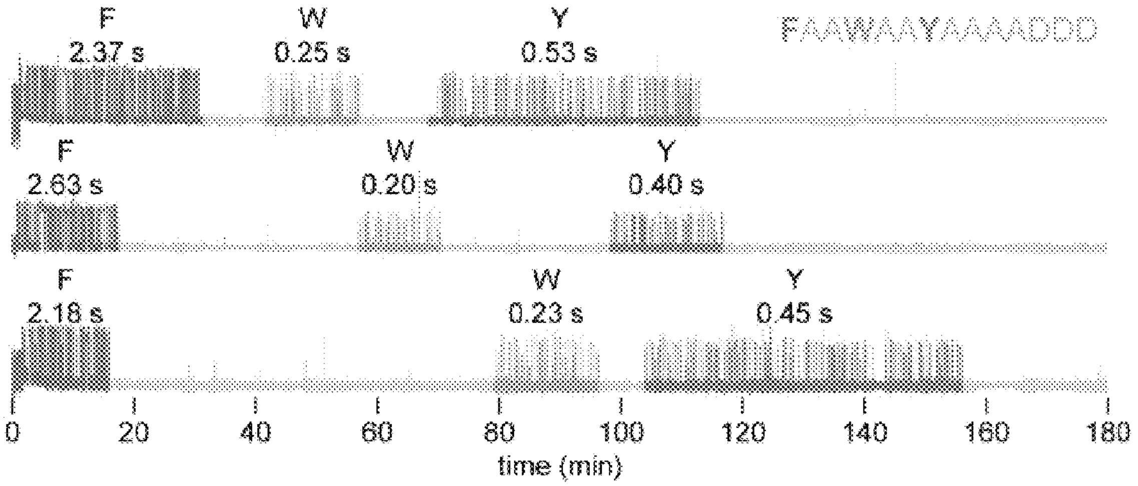

To demonstrate that amino acids in a single peptide molecule can be sequentially exposed by aminopeptidases and recognized in real time with distinguishable kinetics, an immobilized peptide containing the initial sequence FAAWAAYAA (SEQ ID NO: 832) was incubated with PS610 for 15 minutes, followed by addition of PhTET3, an aminopeptidase from *P. horikoshii*. The collected traces consisted of regions of distinct pulsing, which were referred to as recognition segments (RSs), separated by regions lacking recognition pulsing (non-recognition segments, NRSs). Analysis software was developed to automatically identify pulsing regions and transition points within traces (Methods). Traces began with recognition of phenylalanine with a median PD of 2.36 s (FIG. 2D), in agreement with the PD observed for FAA in recognition-only assays. This pattern terminated after aminopeptidase addition (on average 11 min after addition), and was followed by the ordered appearance of two RSs with median PDs of 0.25 s and 0.49 s (FIG. 2D), corresponding to the short and medium PDs obtained in YAA and WAA recognition-only assays. Thus, the introduction of aminopeptidase activity to the reaction resulted in the sequential appearance of discrete RSs with the expected kinetic properties in the correct order.

Figure 2E:
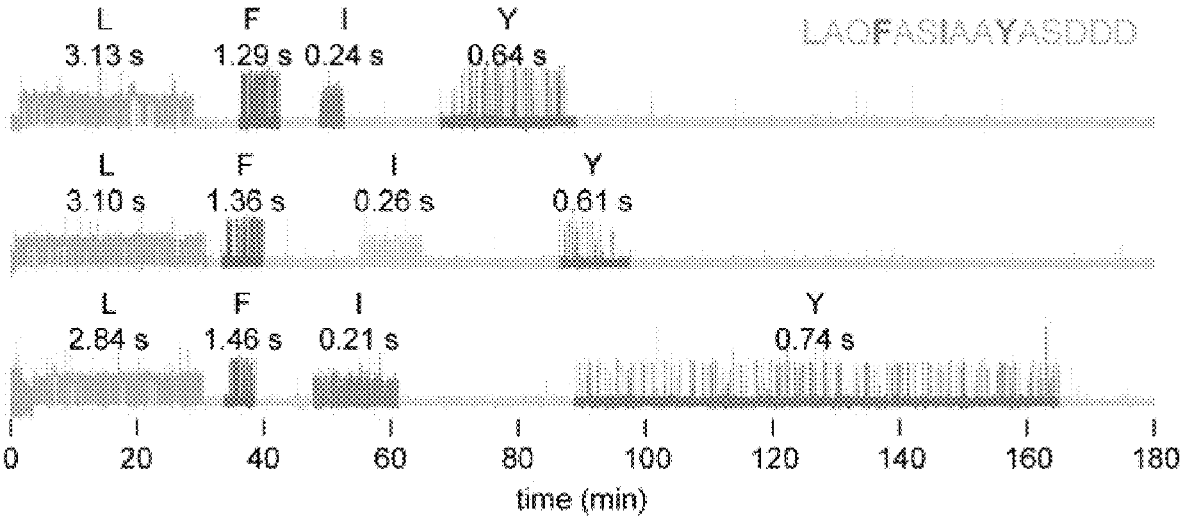
Figure 2F:
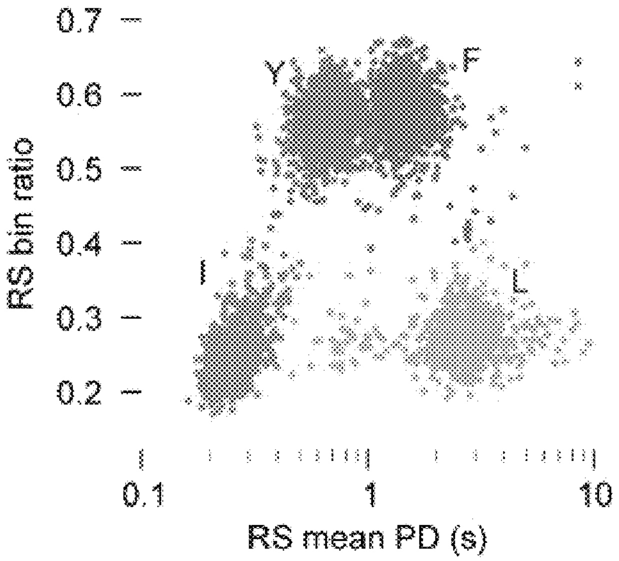
Figure 2G:
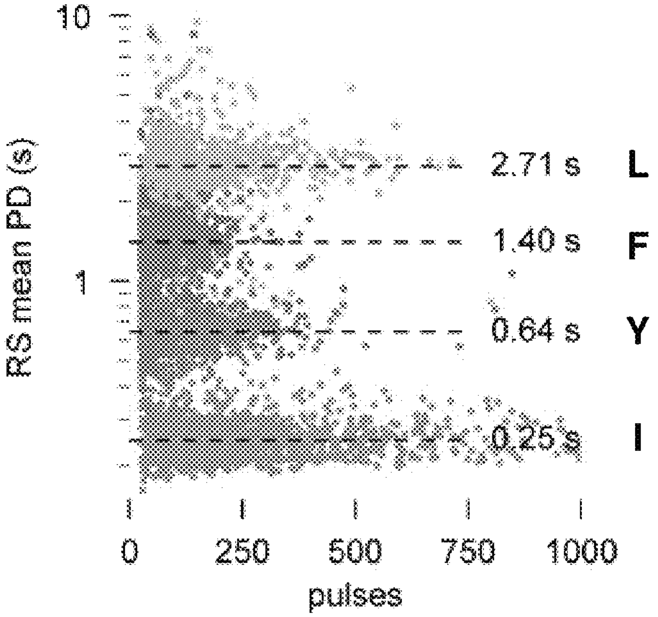

To demonstrate dynamic sequencing with two NAA recognizers, PS610 and PS961 were labeled with the distinguishable dyes atto-Rho6G and Cy3, respectively, and an immobilized peptide of sequence LAQFASIAAYASDDD (SEQ ID NO: 793) was exposed to a solution containing both recognizers. After 15 minutes, two *P. horikoshii* aminopeptidases with complementary activity covering all 20 amino acids were added—PhTET2 and PhTET3. The collected traces displayed discrete segments of pulsing alternating between PS961 and PS610 according to the order of recognizable amino acids in the peptide sequence (FIG. 2E). The average bin ratio and average PD associated with each RS readily distinguished the two dye labels and four types of recognized NAAs (FIG. 2F). Median PDs were 2.70, 1.43, 0.25, and 0.66 s for N-terminal LAQ, FAS, IAA, and YAS, respectively (FIG. 2G).

Figure 7F:
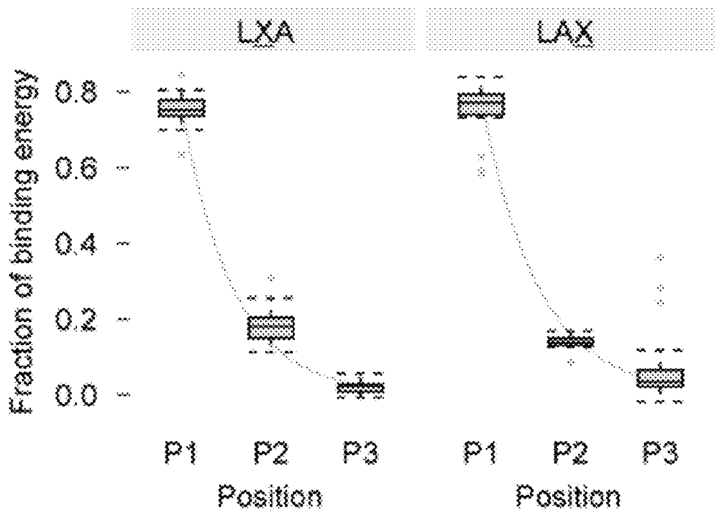
Figure 7G:
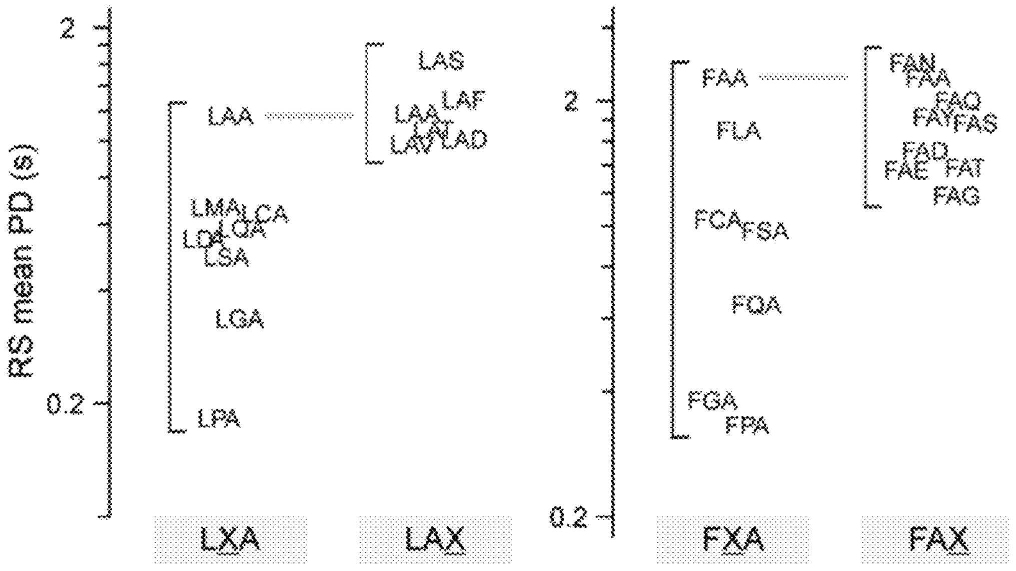
Figure 7H:
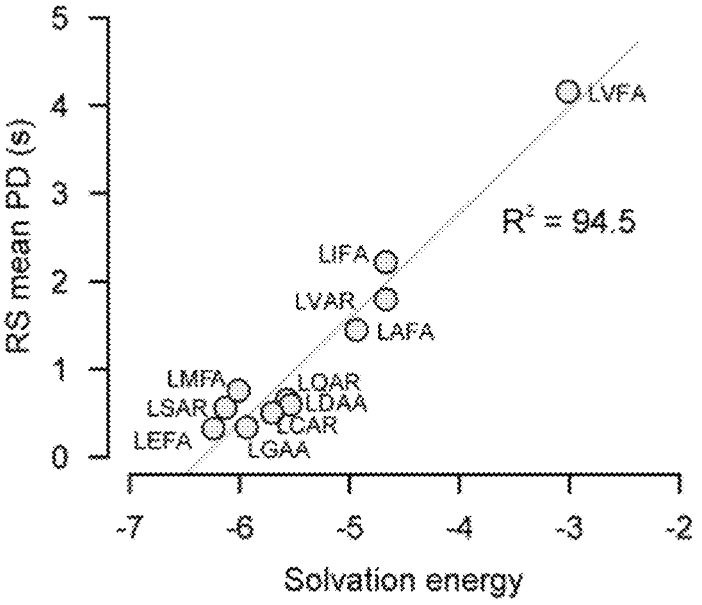

NAA-bound ClpS and UBR proteins also make contacts with the residues at position 2 (P2) and position 3 (P3) from the N-terminus that influence binding affinity. These influences are reflected in the modulation of PD depending on the downstream P2 and P3 residues, as observed above for LAA (1.21 s) compared to LAQ (2.70 s). It was found that these influences on PD vary within informatically advantageous ranges and can be determined empirically or approximated in silico to model peptide sequencing behavior a priori (FIGS. 7F-7H). A powerful feature of this recognition behavior in regards to peptide identification is that each RS contains information about potential downstream P2 and P3 residues or PTMs, whether or not these positions are the targets of an NAA recognizer.

Figure 3A:
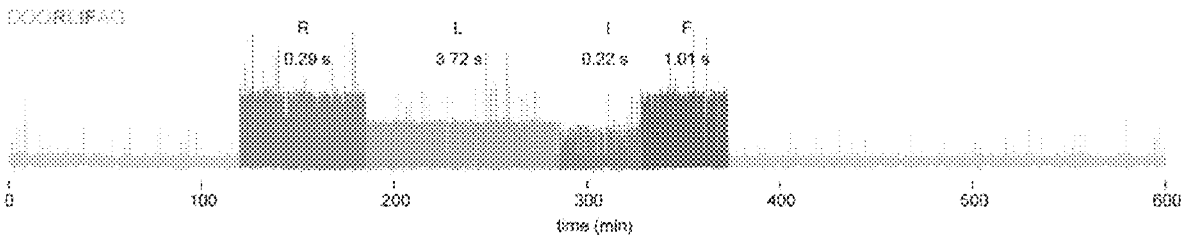
FIGS. 3A-3G show an example of dynamic sequencing of diverse peptides with high-precision kinetic outputs.
Figure 3B:
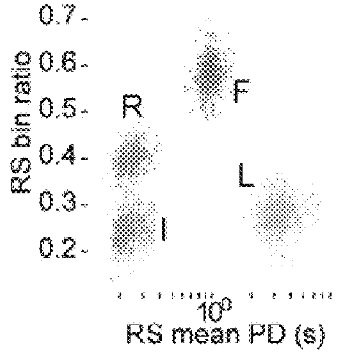
Figure 3C:
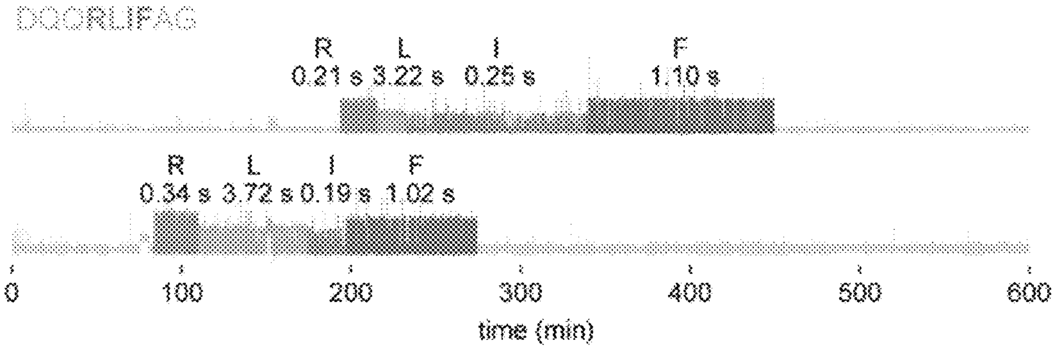

To evaluate the kinetic principles of the dynamic sequencing method when applied to diverse sequences, the synthetic peptide DQQRLIFAG (SEQ ID NO: 794), corresponding to a segment of human ubiquitin, was characterized (FIGS. 3A-3D). Sequencing reactions were performed using a combination of three differentially-labeled recognizers—PS610, PS961, and PS691—and two aminopeptidases—PhTET2 and PhTET3 (Materials and Methods). The example trace in FIG. 3A starts with an NRS that corresponds to the time interval during which residues in the initial DQQ motif are present at the N-terminus. The first RS starts at 120 min, upon exposure of N-terminal arginine to recognition by PS691. Subsequent cleavage events sequentially expose N-terminal leucine, isoleucine, and phenylalanine to their corresponding recognizers, with fast transitions (average <10 s) from one RS to the next. The transition from leucine to isoleucine recognition by PS961 is readily identified as a sharp change in average PD. This overall pattern is replicated across many instances of sequencing of the same peptide, with similar PD statistics across traces, as each peptide molecule follows the same reaction pathway over the course of the sequencing run (FIGS. 3B-3C). Due to the stochastic timing of cleavage events, each trace displays distinct start times and durations for each RS (FIG. 3C).

Figure 6B:
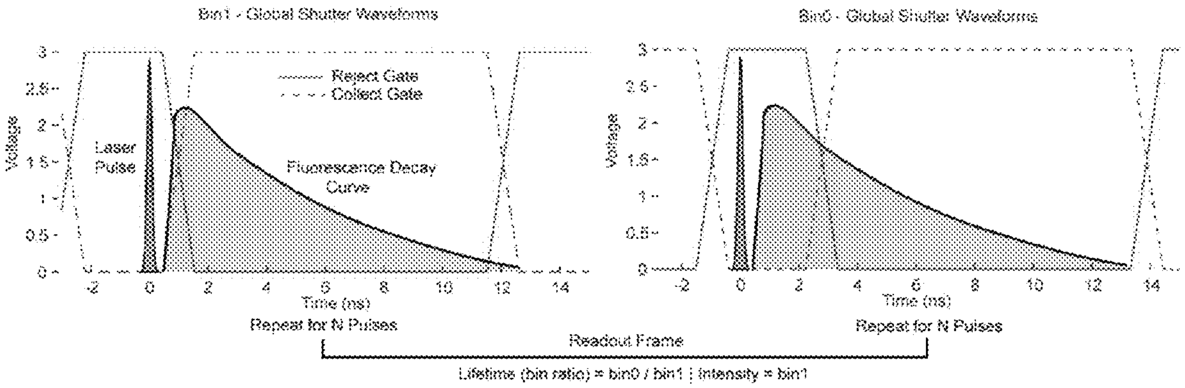
Figure 6C:
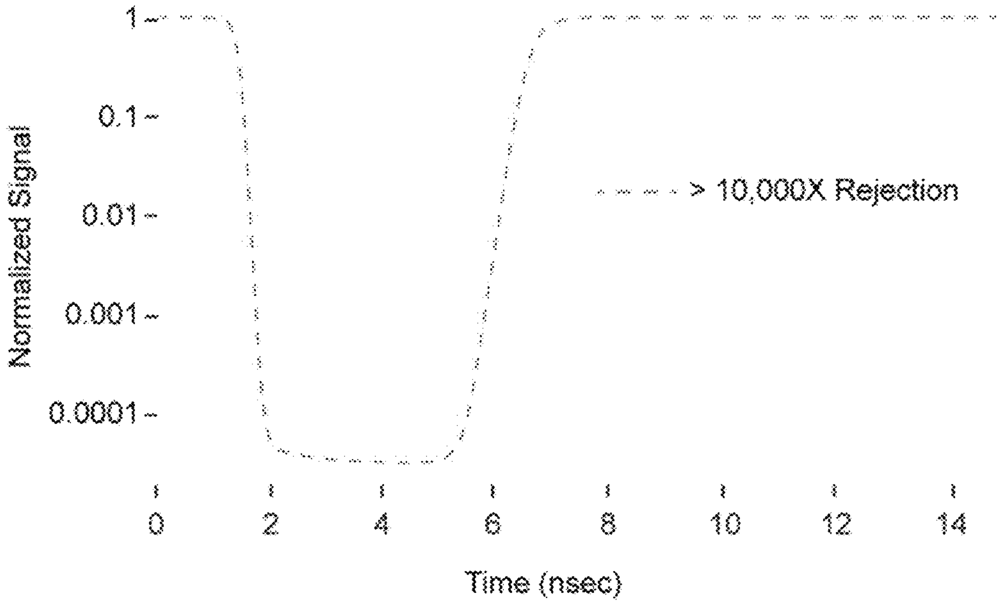
Figure 6D:
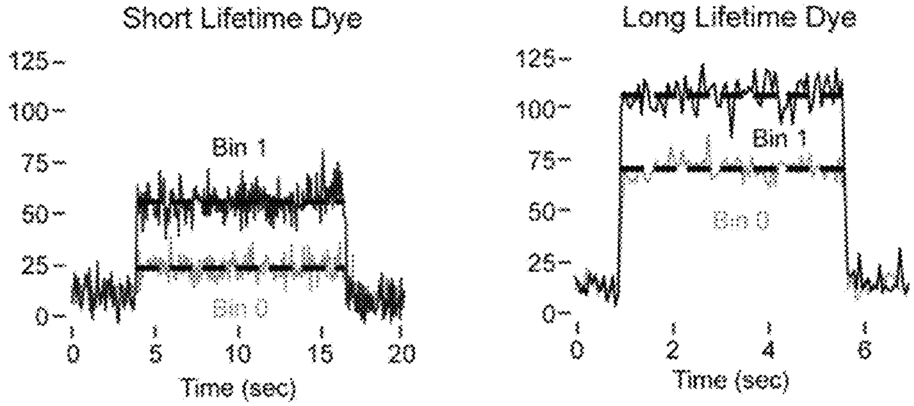
Figure 6E:
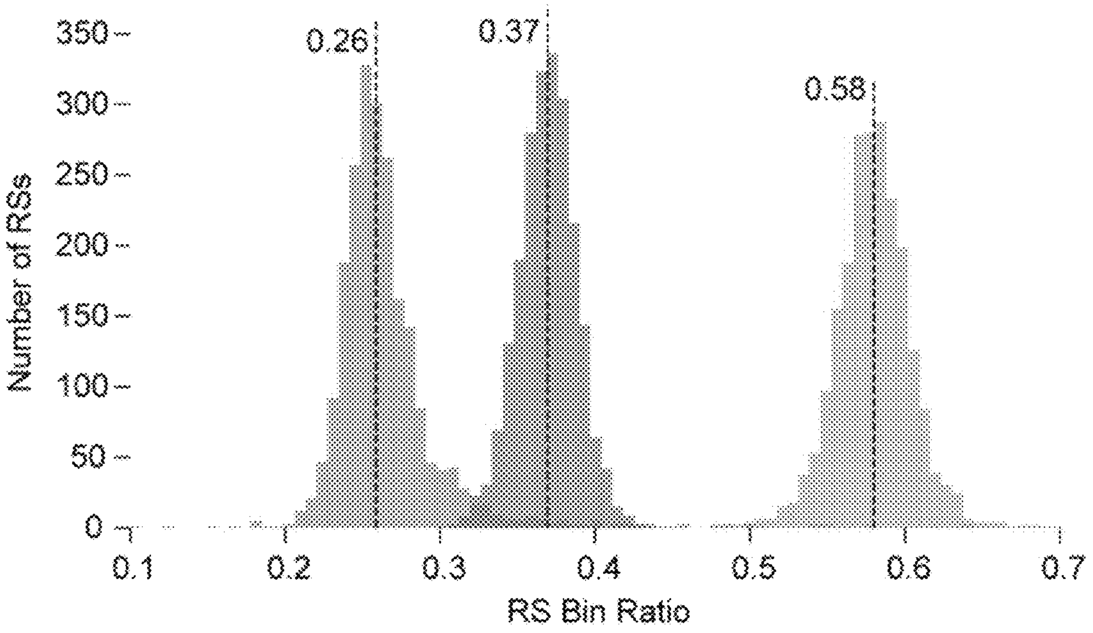
Figure 6F:
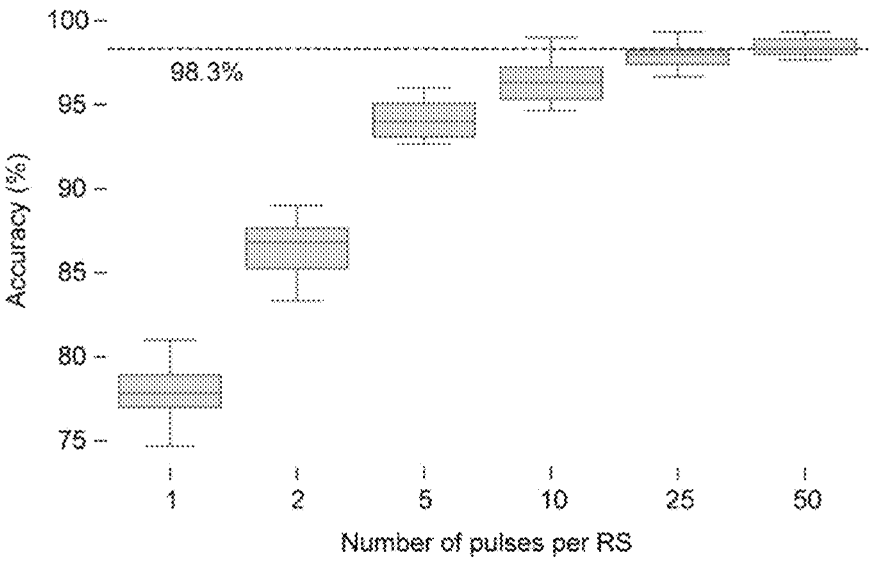
Figure 8A:
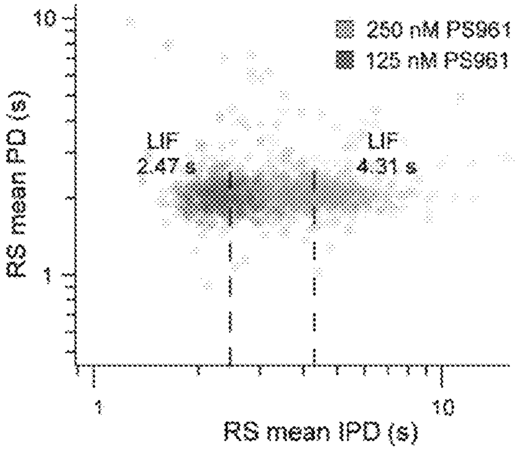
FIGS. 8A-8E show an example of binding and cleavage rates.
Figure 8B:
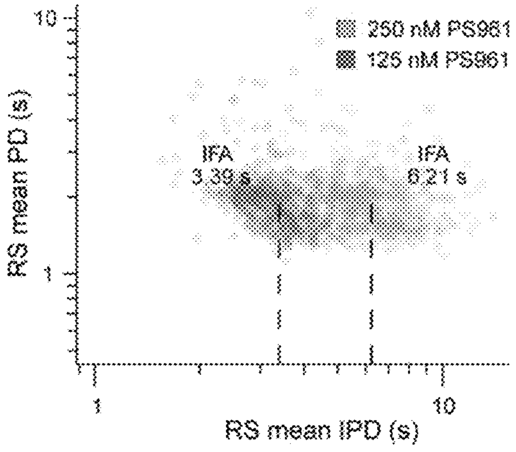

This approach reports the binding kinetics at each recognizable amino acid position and the kinetics of aminopeptidase cleavage along the peptide sequence. High-precision kinetic information on binding is obtained from a single trace, since each RS typically contains tens to hundreds of on-off binding events, resulting in a distribution of PD and interpulse duration (IPD) measurements that can be analyzed statistically. The repetitive probing of each NAA also provides accurate recognizer calling, since calls are not based on the error-prone detection of a single event associated with one fluorophore molecule (FIG. 6F). Recognizer concentration governs IPD for each RS; higher recognizer concentrations result in shorter average IPDs and faster rates of pulsing (FIGS. 8A-8B). Higher recognizer concentrations, however, increase the fluorescence background from freely diffusing recognizers, resulting in lower pulse signal-to-noise, and can compete with aminopeptidases for N-terminal access. In practice, IPDs in the range of approximately 2 to 10 s provide a favorable balance among these factors.

Figure 3D:
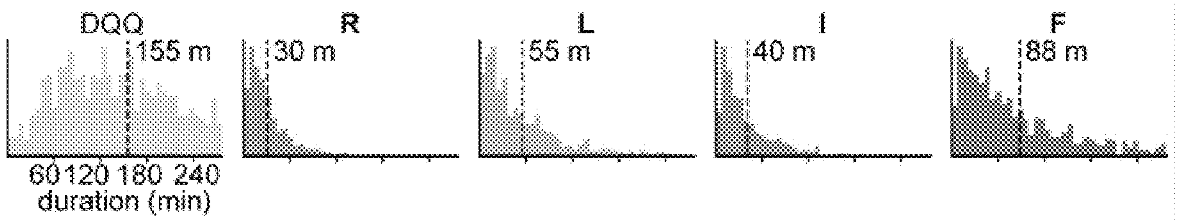
Figure 3E:
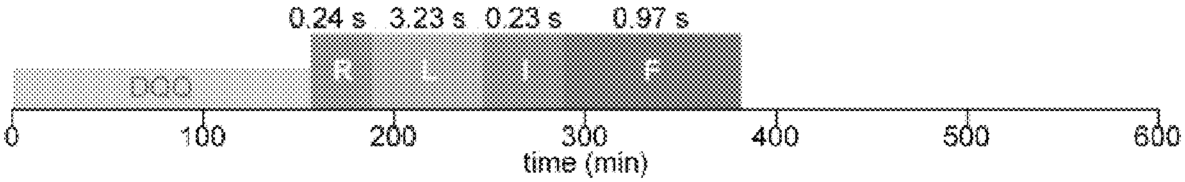
Figure 8C:
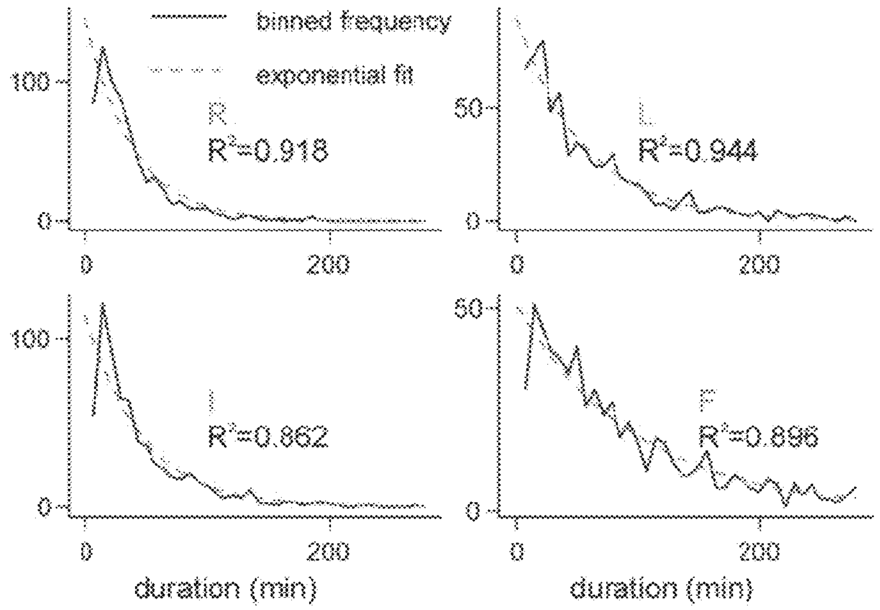
Figure 8D:
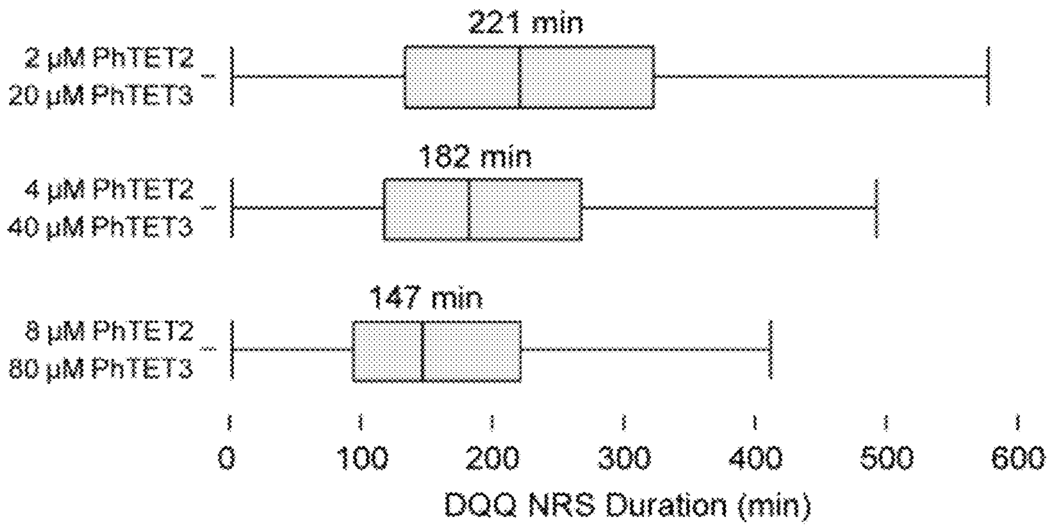
Figure 8E:
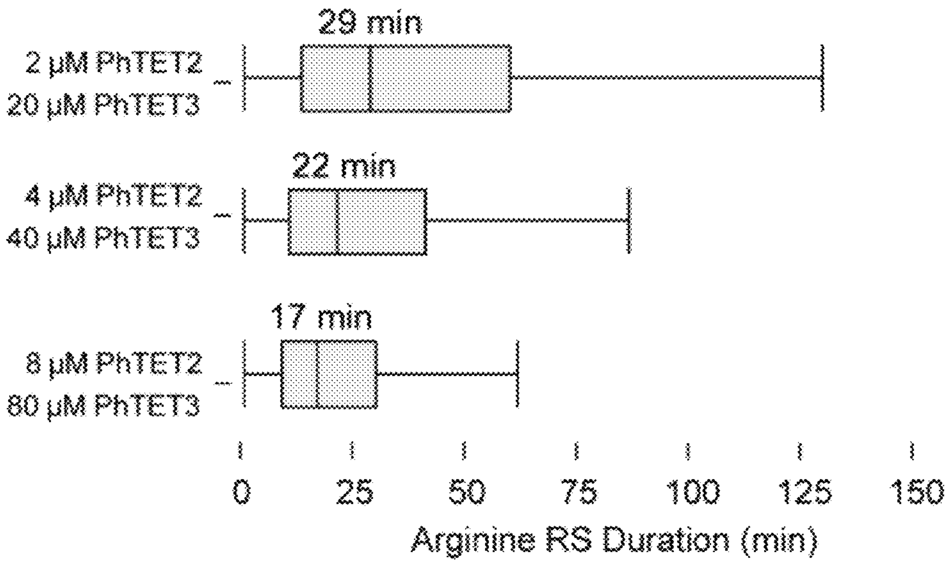

The distribution of RS durations across an ensemble of replicate traces defines the rate of cleavage of each recognizable NAA. For DQQRLIFAG (SEQ ID NO: 794) peptide, average cleavage times of 31, 54, 39, and 86 min were observed for N-terminal arginine, leucine, isoleucine, and phenylalanine, respectively, with approximate single-exponential decay statistics for each position (FIG. 3D, FIG. 8C). The distribution of NRS durations reports the cleavage rate of a run of one or more non-recognized NAAs. The average NRS duration for the initial DQQ motif was 153 min (FIG. 3D). Average cleavage rates are a key parameter and are controlled by the aminopeptidase concentration in the assay (FIGS. 8D-8E). Given the exponential behavior, average RS durations of 10 to 40 min were targeted to provide sufficient time for pulsing data collection, avoid missed RSs due to rapid cleavage, and minimize excessively long RS durations. It was found helpful to visualize the sequencing profiles of peptides as kinetic signature plots—simplified trace-like representations of the time course of complete peptide sequencing containing the median PD for each RS, and the average duration of each RS and NRS (FIG. 3E). These highly characteristic features provide a wealth of sequence-dependent information for mapping traces from peptides to their proteins of origin.

Figure 3F:
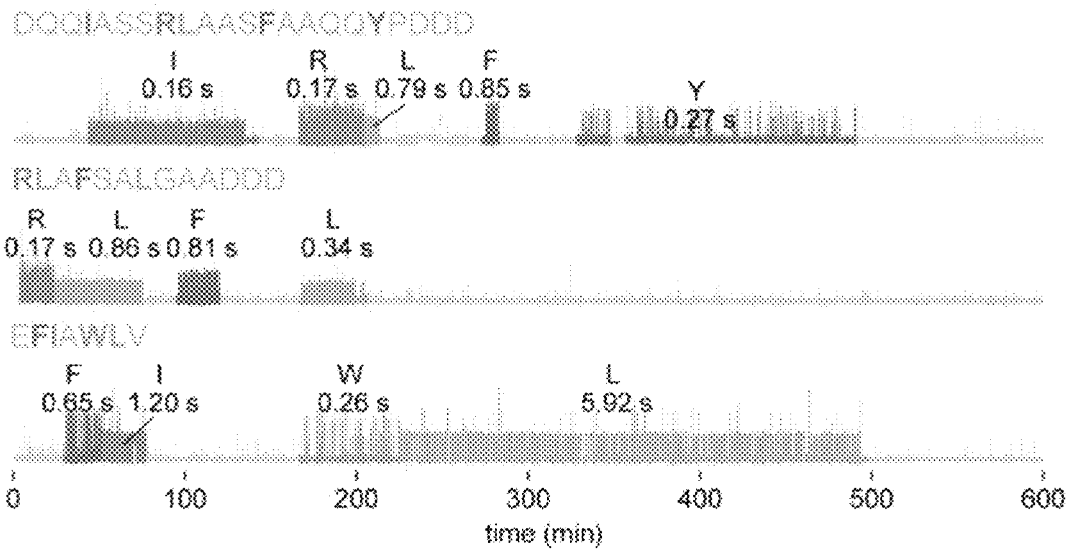
Figure 3G:
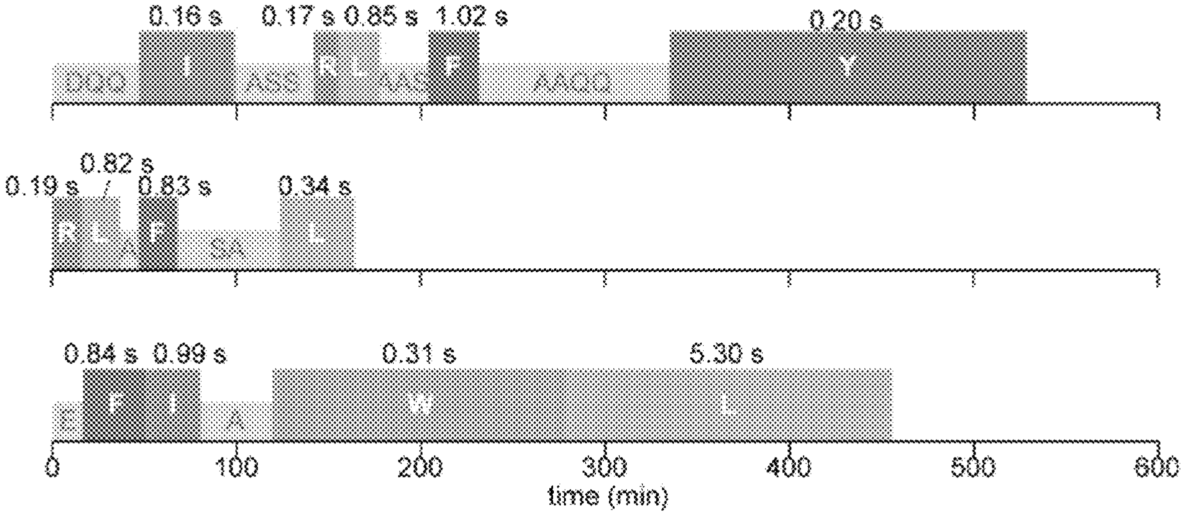

To demonstrate that this core methodology and its kinetic principles apply to a wide range of peptide sequences, the synthetic peptides DQQIASSRLAASFAAQQYPDDD (SEQ ID NO: 795), RLAFSALGAADDD (SEQ ID NO: 796), and EFIAWLV (SEQ ID NO: 797) (a segment of human GLP-1) were sequenced under the same sequencing conditions used for DQQRLIFAG (SEQ ID NO: 794) (FIG. 3F). Each peptide generated a characteristic kinetic signature in accordance with its sequence (FIG. 3G). Readouts as far as position 18 (the furthest recognizable amino acid) in the peptide DQQIASSRLAASFAAQQYPDDD (SEQ ID NO: 795) were obtained, illustrating that the method is compatible with long peptides and capable of deep access to sequence information in peptides of lengths found in typical protein digests.

Figure 4A:
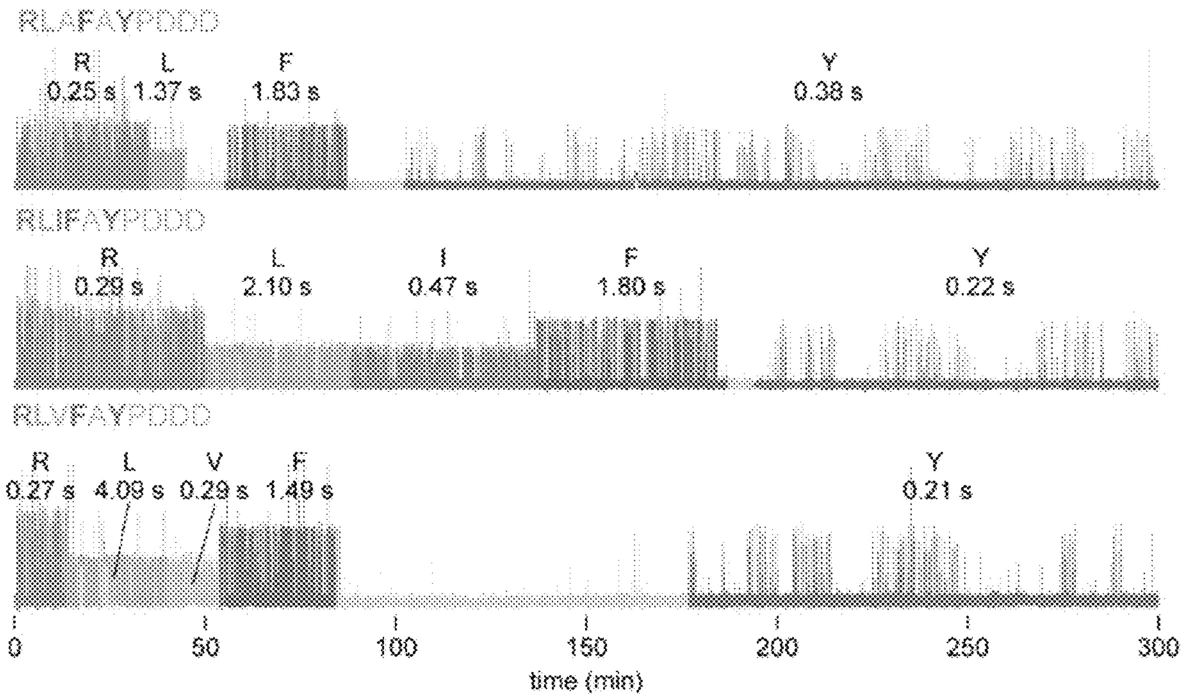
FIGS. 4A-4E show an example of detection of single amino acid changes and PTMs.
Figure 4B:
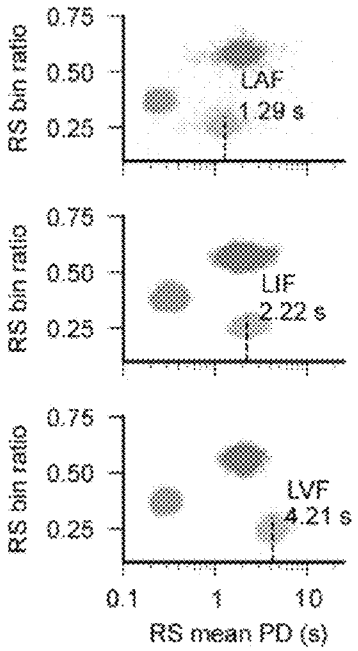
Figure 9A:
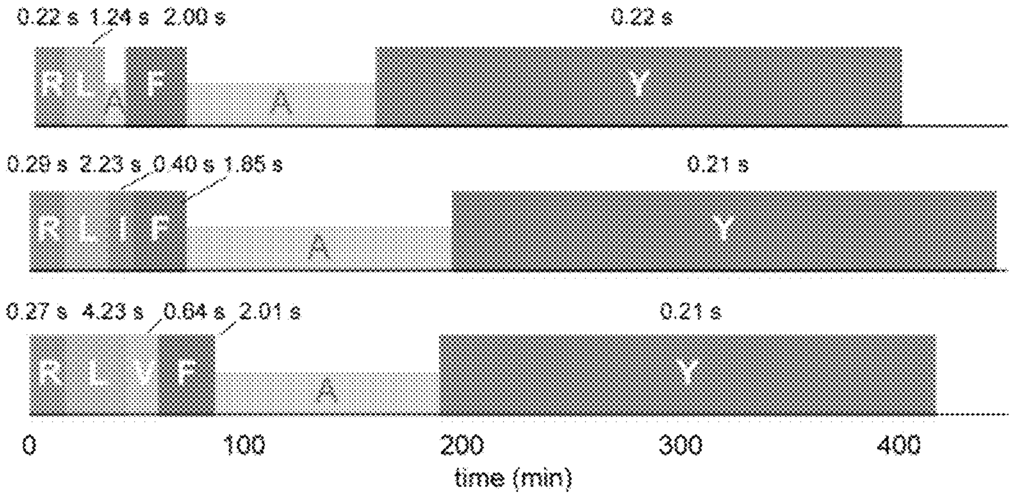
FIGS. 9A-9G show an example of kinetic signatures from single amino acid changes and PTMs.

To illustrate how the kinetic parameters acquired from sequencing are sensitive to changes in sequence composition, sequencing was performed with a set of three peptides RLAFAYPDDD (SEQ ID NO: 798), RLIFAYPDDD (SEQ ID NO: 799), and RLVFAYPDDD (SEQ ID NO: 800)—that differ only at a single position, located immediately downstream from the PS961 N-terminal target leucine. Each type of amino acid at this position had a distinct effect on the PD acquired during recognition of N-terminal leucine by PS961. Median PDs of 1.29 s, 2.22 s, and 4.21 s were observed for LAF, LIF, and LVF, respectively (FIG. 4B). In addition to differences in PD for leucine, each peptide displayed a characteristic RS or NRS in the interval between leucine and phenylalanine recognition (FIG. 4A, FIG. 9A). These results demonstrate the sensitivity of the sequencing readout to variation at a single position and illustrate that both directly recognized NAAs and adjacent residues can influence the full kinetic signature obtained from sequencing.

Figure 9B:
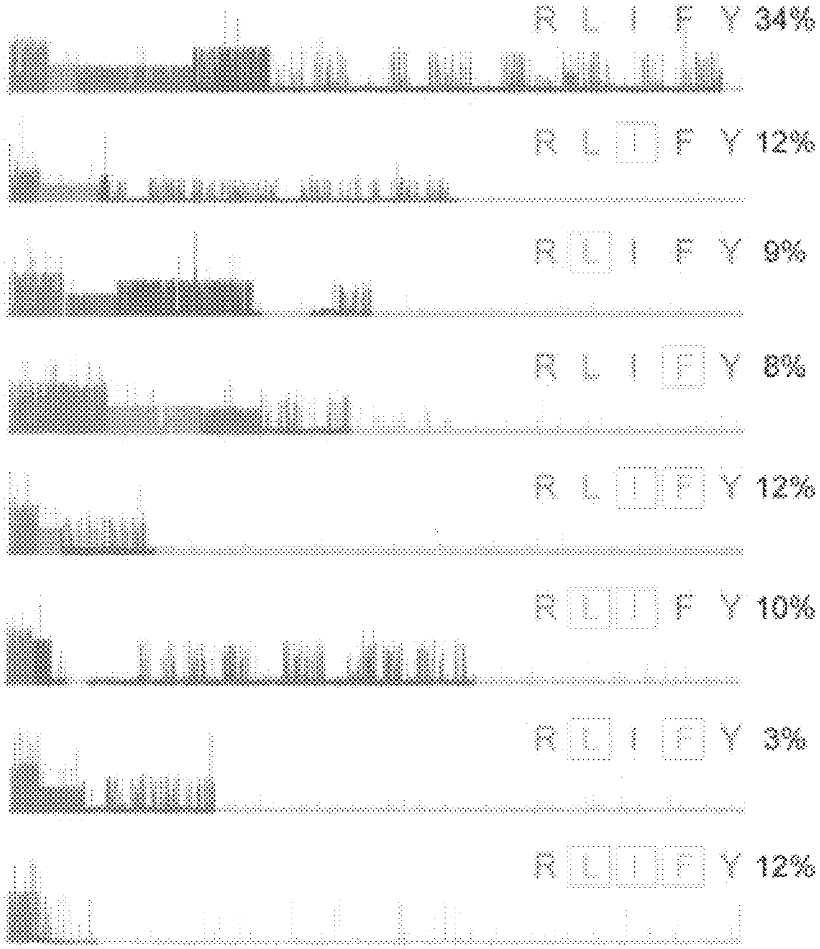
Figure 9C:

Since the aminoacyl-proline bond of the YP motif in peptides such as RLIFAYPDDD (SEQ ID NO: 799) cannot be cleaved by the PhTET aminopeptidases, observation of YP pulsing at the end of a trace ensures that cleavage progressed completely from the first to last recognizable amino acid. The sequencing output from RLIFAYPDDD (SEQ ID NO: 799), therefore, provided a convenient dataset for examining biochemical sources of non-ideal behavior that could lead to errors in peptide identification. The main sources of incomplete information in traces were deletions of expected RSs due to the stochastic occurrence of rapid sequential cleavage events (FIG. 9B) and early termination of reads resulting from photodamage or surface detachment (FIG. 9C).

Figure 4C:
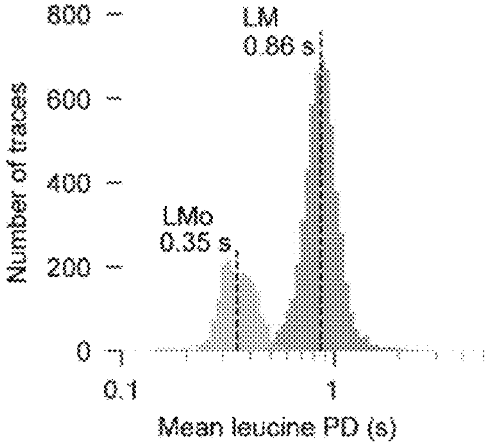
Figure 4D:
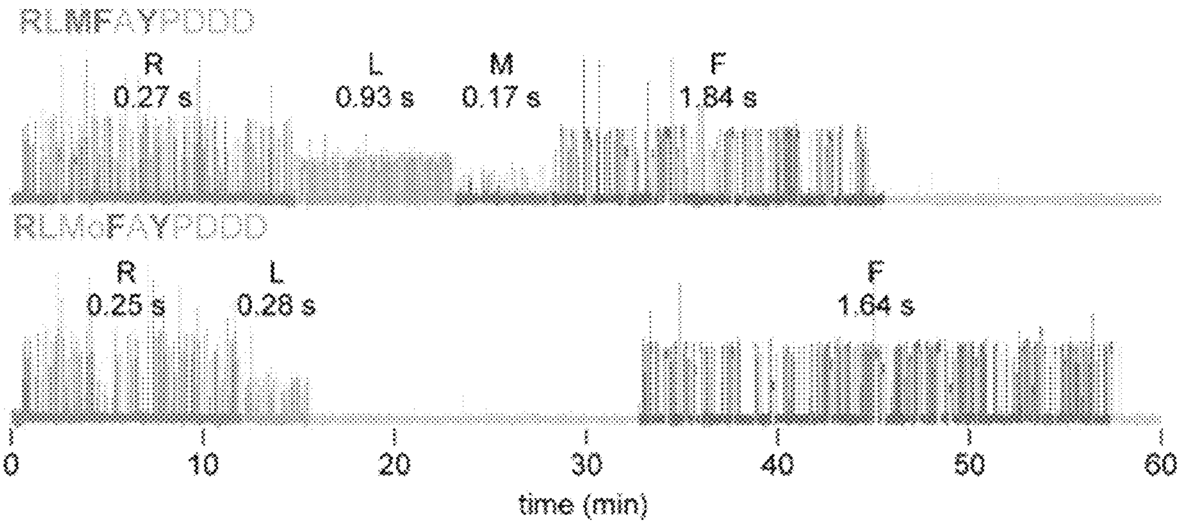
Figure 4E:
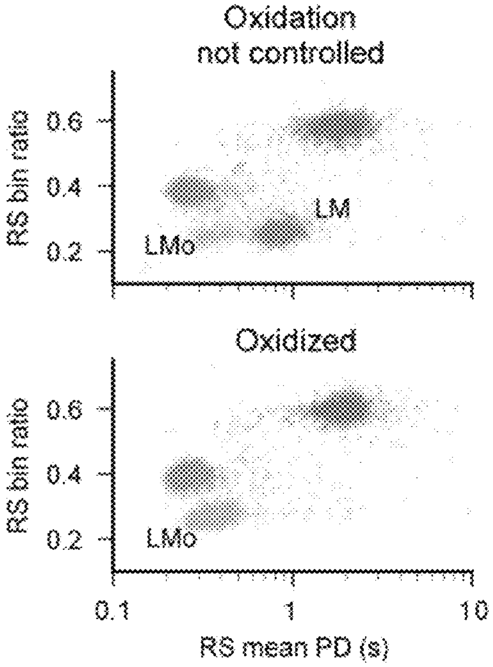
Figure 9D:
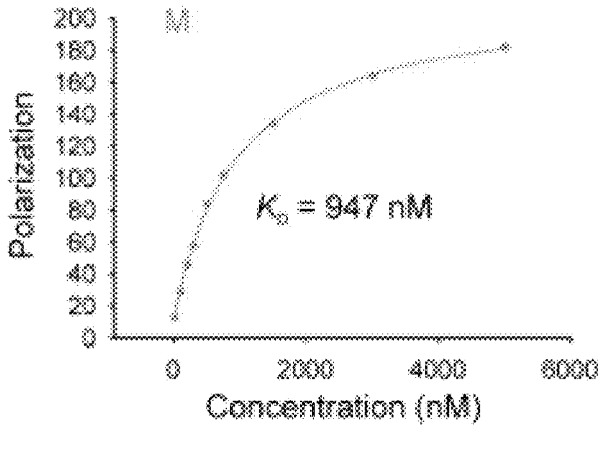
Figure 9E:
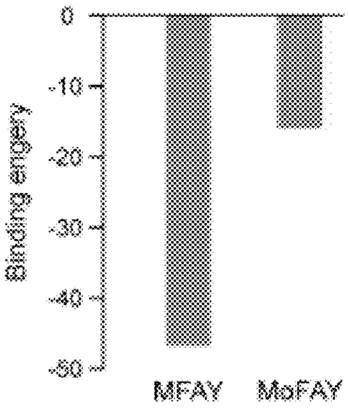

In addition to changes in amino acid sequence composition, sequencing readouts are sensitive to changes due to PTMs. As an example, methionine oxidation was examined. The thioether moiety of the methionine side chain is susceptible to oxidation during peptide synthesis and sequencing. It was determined that PS961 binds a peptide with N-terminal methionine with a $K_D$ of 947 nM (FIG. 9D) and it was hypothesized that oxidation, resulting in a polar methionine sulfoxide side chain, would eliminate binding and reduce NAA binding affinity when located at P2. It was determined computationally that methionine sulfoxide is highly unfavorable in the PS961 NAA binding pocket and that non-polar residues are preferred at P2 (FIG. 9E). The synthetic peptide RLMFAYPDDD (SEQ ID NO: 801) was sequenced, and two populations of traces with distinct kinetic signatures were observed—a first population containing leucine recognition with median PD of 0.86 s, and a second population with median PD of 0.35 s (FIG. 4C). Traces from the first population also displayed methionine recognition with short PD in the time interval between leucine and phenylalanine recognition (FIG. 4E). Methionine recognition was absent in traces from the second population (FIG. 4D), indicating that the methionine side chain in these peptides was not capable of recognition by PS961. When methionine was fully oxidized by preincubation with hydrogen peroxide (Materials and Methods), elimination of both methionine recognition and of the leucine recognition cluster was observed with long median PD, as expected (FIG. 4E). These results demonstrate the capability for extremely sensitive detection of PTMs due to their kinetic effects on recognition.

Figure 5A:
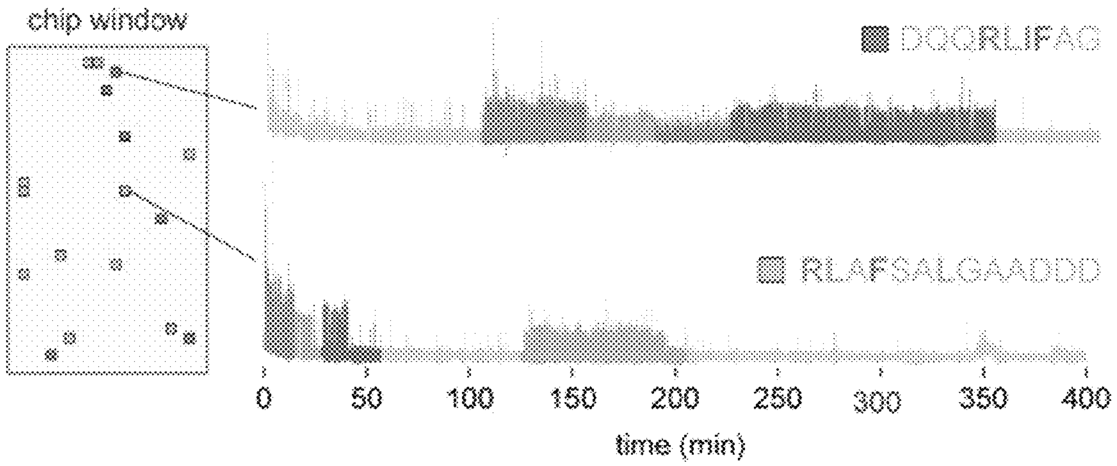
FIGS. 5A-5C show an example of discrimination of peptides in mixtures and mapping peptides to the human proteome.
Figure 5B:
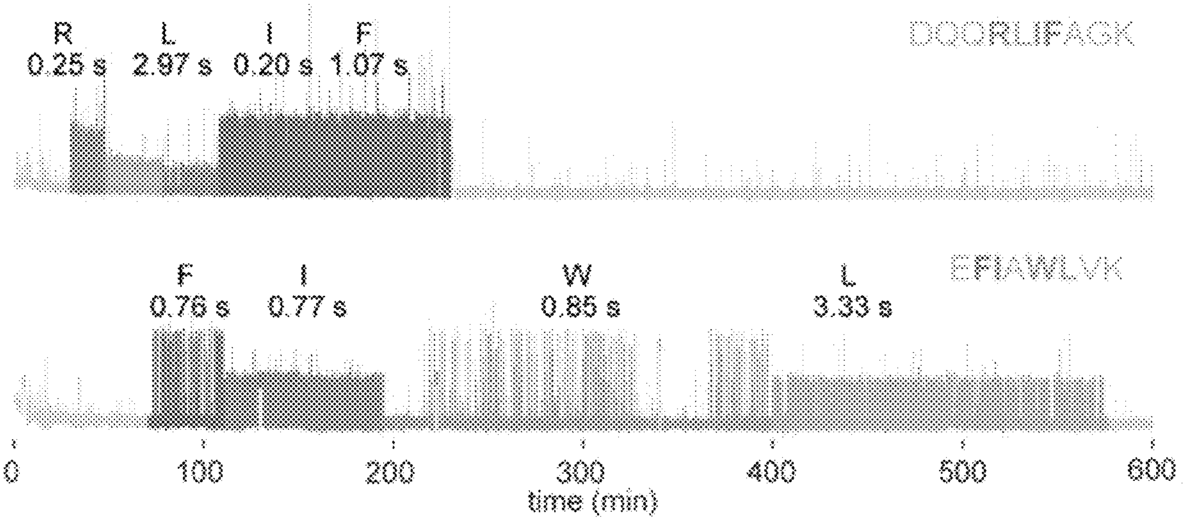
Figure 5C:
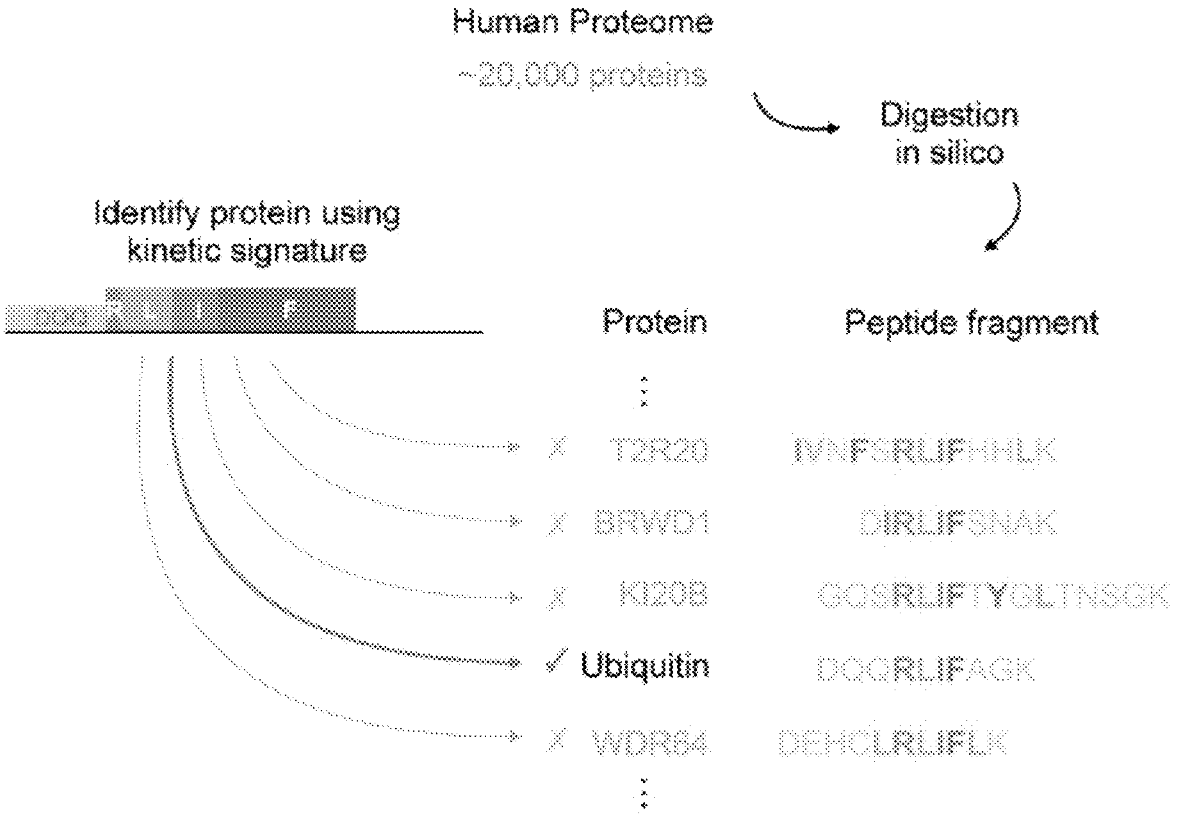
Figure 9F:
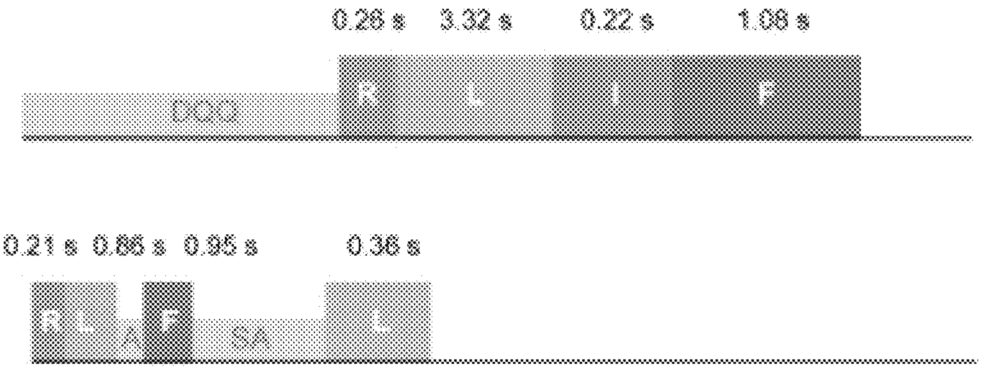
Figure 9G:
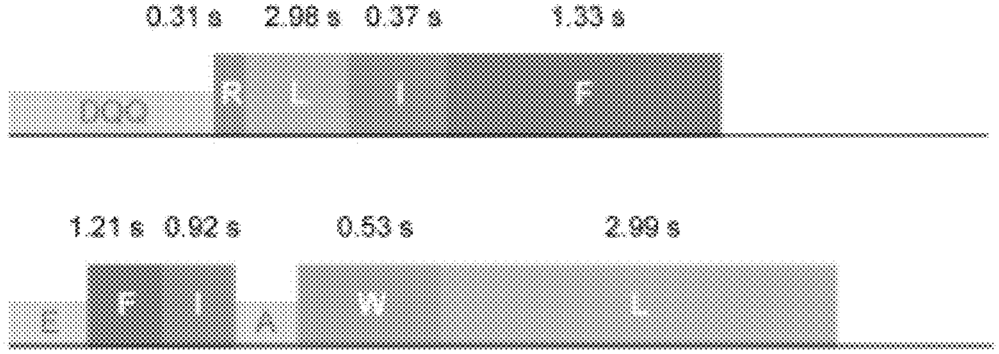

Proteomics applications require identification of peptides in mixtures derived from biological sources. To extend the results to peptide mixtures and biologically-derived peptides, two experiments were performed. First, DQQRLIFAG (SEQ ID NO: 794) and RLAFSALGAADDD (SEQ ID NO: 796) peptides were mixed, immobilized on the same chip, and a sequencing run was performed. Data analysis (Materials and Methods) identified two populations of traces corresponding to each peptide, with kinetic signatures in close agreement with those identified in runs with individual peptides (FIG. 5A, FIG. 9F). Second, to demonstrate that the method extends to biologically derived peptides, sequencing runs were performed with peptide libraries generated using a simple workflow from recombinant human ubiquitin (76 amino acids) and GLP-1 (37 amino acids) proteins digested with AspN/LysC and trypsin, respectively (Materials and Methods). For both libraries, data analysis readily identified traces matching the expected recognition pattern for the protease cleavage products DQQRLIFAGK (SEQ ID NO: 802) and EFIAWLVK (SEQ ID NO: 803) for ubiquitin and GLP-1, respectively, and produced kinetic signatures in agreement with synthetic versions of these peptides (FIG. 5B, FIG. 9G). Matches to the kinetic signature of the ubiquitin peptide DQQRLIFAGK (SEQ ID NO: 802) were identified across the human proteome, taking advantage of simple sequence constraints provided by kinetic information (Materials and Methods). Only one protein other than ubiquitin was found containing a peptide that could potentially match this signature; thus even short signatures can exhibit proteome abundance of less than one in $10^4$ proteins. These results illustrate the potential of the full kinetic output from sequencing to enable digital mapping of peptides to their proteins of origin.

Discussion

The simple, real-time dynamic approach differs markedly from other recently described single-molecule approaches that rely on complex, iterative methods involving stepwise Edman chemistry or hundreds of cycles of epitope probing. Nanopore approaches offer the potential for real-time readouts and simplicity, but face substantial challenges related to the size and biophysical complexity of polypeptides. The sequencing technology described herein is readily expanded in its capabilities, and there are multiple areas for improvement. Expansion of proteome coverage can be achieved through directed evolution and engineering of recognizers. The NAA targets demonstrated here comprise approximately 35.6% of the human proteome, but lower-affinity NAA targets require longer PD to enable detection in all sequence contexts.

Recognizers for new amino acids or PTMs can be evolved from current recognizers or identified in screens of other scaffolds, such as other types of NAA- or PTM-binding proteins or aptamers. Overall, scaling to detection of all 20 natural amino acids and multiple PTMs is feasible for de novo sequencing; however partial sequences are sufficient for most proteomics applications, which rely on mapping to pre-defined sets of candidate proteins. Aminopeptidases can be engineered to optimize cleavage rates and minimize RS deletions from rapid sequential cleavage. It is envisioned that the dynamic range of samples and the applications most suitable for the system will tend to scale with the number of reaction chambers on the chip, and that compression of dynamic range will be necessary for certain applications.

It is anticipated that the sequencing technology demonstrated here will increase the accessibility of proteomics studies, enable new discoveries in biological and clinical research, and help power a new generation of precision medicine.

Materials and Methods

Semiconductor Device Operation and Bin Ratio Calculation

Experiments were performed on pre-production semiconductor chips with 296K active wells, taking into account some loss to flow cell occlusion of the sensor array. A dual chamber flow cell allows for two independent samples to be sequenced in parallel, each utilizing 148K active wells. Initial production devices have 2M active wells, scaling to tens of millions of active wells using standard CMOS processing for the first product line. Pulsed 532 nm excitation light from a 67 MHz mode-locked laser is coupled into a grating coupler at the edge of the semiconductor chip. The use of a single laser wavelength—in combination with fluorescent dye discrimination by fluorescence intensity and lifetime—reduces size, cost, and complexity, contributing to the scalability of the platform. A network of optical waveguides divides the excitation light and routes it to the sensor array to illuminate each reaction chamber. Each CMOS pixel contains a single light-sensitive photodiode with two high-speed global shutters (a reject gate and a collect gate) that discard and collect photoelectrons (chip photonic structures reduce pixel-to-pixel crosstalk to less than 2%). Control waveforms are applied to the collect and reject gates synchronously with the incident pulsed light source (FIG. 6B). Approximately 1 ns before the excitation pulse, the reject gate is charged to >3 volts and the collect gate is discharged below 1 volt. Scattered 532 nm excitation photons generate photoelectrons in the photodiode. The photoelectrons are quickly transferred to a high voltage drain by built-in potential fields within the photodiode and the reject gate potential. Between 1 and 3 ns after excitation, the collect gate is charged to >3 volts, the reject gate is discharged to <1 volt. Photoelectrons generated from emitted photons that arrive in the photodiode after the collect gate is opened are transferred to a storage node within each pixel. Photoelectrons are accumulated for 7.5 to 30 ms, configurable, within each pixel across approximately 500,000 to 2,000,000 laser pulses (FIG. 6B). The accumulated charge in the storage node is measured with the standard transfer gate, floating diffusion, source follower, row select, and on-chip analog-to-digital converters common to all CMOS image sensors, enabling scaling to large array sizes with small pixels. Fluorescence lifetime information is obtained by alternating the timing of the collect and reject gate waveforms between subsequent measurements. In the first measurement, only emission photoelectrons that arrive >3 ns after the excitation pulse (bin 0) are collected. In the second measurement, emission photoelectrons that arrive >1 ns after the excitation pulse (bin 1) are collected. Signal measured from the pixel as the phase relationship between the excitation source and the gate waveforms is adjusted throughout the entire excitation cycle demonstrates the pixel transitioning from 100% collection of photons during the collect phase to extinction of greater than 99.99% of photons during the rejection phase in less than lns (FIG. 6C). The ratio of these two measurements (bin ratio) provides an estimate of the fluorescence lifetime (FIG. 6D). We have demonstrated the ability to differentiate multiple dyes based on bin ratio alone (FIG. 6E).

Peptide Synthesis and Labeling

Peptides were synthesized on Rink Amide Resin on a PurePrep Chorus Solid-phase peptide synthesizer (Gyros Protein Technology) using Standard Fmoc chemistry. All synthetic peptides contained C-terminal Fmoc-azidolysine. The resin was deprotected in a mixture of TFA/TIPS/$H_2O$ (2.5%/2.5%/95%) at room temperature for 1.5 h. The deprotection mixture was concentrated under an argon stream. The peptides were precipitated from cold diethyl ether, resuspended in 1:1 water-acetonitrile, and purified on reverse phase HPLC (X-bridge C18, Waters) with a gradient of 10-70% acetonitrile (0.05% TFA) over 20 min. The residue was dried under high vacuum to generate white pellets. Into a solution of DBCO-DNA-biotin (2 nmol in 100 uL PBS) was added the peptide stock solution (4 uL, 5 mM) at room temperature. The reaction progress was monitored on LC-MS (Thermo UltiMate 3000 Executive Plus). After the reaction was completed, the mixture was conjugated to an excess of streptavidin. The peptide-DNA-streptavidin complex was purified on an ion exchange HPLC (DNAPac 200, Thermo). Gradient, buffer A, 20 mM sodium phosphate buffer, pH 8.5, buffer B, 1 M NaBr, 20 mM sodium phosphate buffer, pH 8.5, 20-60% B over 15 min. The purified complex was buffer-exchanged to a solution containing 50 mM MOPS (pH 8.0) and 60 mM potassium acetate on a 30K MWCO spin filter before use. The peptide containing fully oxidized methionine was prepared by mixing 3% hydrogen peroxide with the methionine peptide in 1:1 water-methanol at room temperature for 20 minutes. The product was immediately purified on a reverse-phase HPLC using the same peptide purification method described above, the purity was verified by reverse-phase HPLC (Thermo UltiMate 3000) on an analytical column (Zorbax SB-Aq, 5 μm, 4.6×250 mm), and the correct mass of the oxidized product was verified by LC-MS (Agilent LC-MSD-iQ, positive mode).

Protein Digestion and Labeling

GLP-1 7-37, GLP-2, and Ubiquitin (1-76) recombinant proteins were purchased from RnD Systems as lyophilized powder. Each protein was reconstituted in 100 mM HEPES, pH 8.0 (20% acetonitrile) to a final concentration of 200 μM. When necessary, cysteines were reduced and alkylated using TCEP (2 mM) and iodoacetamide (10 mM). GLP1 and GLP2 were digested using 1 μg of Trypsin (LCMS grade, Pierce) at 37° C. overnight. Ubiquitin was digested using 1 μg of LysC (LCMS grade, Pierce) and 1 μg of rAspN (LCMS grade, Promega). After protease digestion, pH of peptide mixtures was adjusted to pH 10.5 using potassium carbonate (57 mM), and lysines were converted to azidolysines using imidazole-1-sulfonyl azide (ISA, 2 mM) and copper sulfate catalyst (0.5 mM). ISA was quenched using polyurethane beads bearing an amine functionality (Oligo Factory). The mixture was then filtered and adjusted to pH 7-8 using 1 M acetic acid. The solution was diluted in 50% (v/v) of 10 mM MOPS, 10 mM KOAc, pH 7.5, added to DNA-streptavidin-DBCO complex, and incubated at 37° C. for 12-16 h. When required, the detergent Cetrimonium bromide was added to the reaction at a final concentration of 0.25 mM.

Recognizer Purification, Labeling, and Characterization

Expression vectors (with pET30 a+ backbone) for recognizers and Biotin ligase were co-transformed into BL21 (DE3) chemically competent *E. coli* cells. The transformed cells were plated on Luria agar plates containing carbenicillin (50 μg/mL) and kanamycin (25 μg/mL) and incubated overnight at 37° C. to obtain single colonies. The starter liquid cultures inoculated with colonies were grown in Luria broth with ampicillin (50 μg/mL) and kanamycin (25 μg/mL) and inoculated into large cultures at a starting optical density (OD600) of ~0.01. The expression cultures were incubated at 37° C. at 230 rpm until OD600 approached ~0.7. The cultures were then induced with 4 mM IPTG. The expressed recognizer was biotinylated in vivo by adding 8 mM biotin at the same time as IPTG. Cells were harvested after ~12 hrs of expression by centrifugation at 10,000 g at 4° C., and the cell pellets were washed with 1×PBS buffer pH 7.4. The cells were resuspended in Bug buster HT (Thermo Fisher Scientific) and incubated at room temperature for 30 mins on a magnetic stirrer. The cell suspension was then diluted with equal volume of 2× lysis buffer (100 mM Tris-HCl pH 7.5, 10% glycerol, 0.5 M NaCl) and incubated at room temperature for 30 mins on a magnetic stirrer. The lysate was centrifuged at 21,000 g at 4° C. to remove cell debris. Supernatant was collected and loaded on a Nickel NTA resin (Cytiva) affinity column pre-equilibrated with Buffer A (50 mM Tris-HCl pH 7.5, 10% glycerol, 0.5 M NaCl) on an AKTA Pure (Cytiva) system. The column was washed with at least ten column volumes of the buffer containing 10 mM imidazole. Elution was performed using a 10-300 mM imidazole gradient. Eluted fractions were dialyzed in a 10 kDa cassette against 4 L of dialysis buffer (50 mM Tris-HC1 pH 7.5, 0.2 M NaCl, 50% glycerol) at 4° C. overnight.

For labeling of the recognizers, equal volumes of recognizer and DNA-Dye-Streptavidin complex were mixed at 5:1 (recognizer:DNA-dye-SV) molar ratio. The mixture was incubated on ice for 30 m and dialyzed overnight against SEC buffer (25 mM HEPES pH 8.0, 150 mM KCl). The recognizer-dye conjugate was harvested from the dialysis and centrifuged at 10,000 g at 4° C. Supernatant was collected and concentrated using 10 kDa cut off concentrators. The concentrated conjugate was purified on an Agilent 1260 Infinity HPLC system using a size exclusion column (BioSEC-3 300 Å, 3 μm).

Binding affinity was measured by polarization using a labeled peptide. The polarization response and total intensity measurements were carried out at 20° C. on a microplate fluorometer with 480 nm excitation and 530 nm emission. The interaction of recognizer with labeled peptide containing a target N-terminal residue (XAKLDEESILKQK-FITC (SEQ ID NO: 833)) was performed in PBS buffer at pH 7.4 and readings were collected after 30 min. Multiple analyses were performed at increasing recognizer concentration at a fixed concentration of a target peptide to obtain a titration curve. An equilibrium polarization response at each concentration was plotted and fit to calculate the $K_D$.

The off-rate ($k_{off}$) of PS610 was measured for various peptides using a stopped flow instrument. Labeled peptide (50 nM) was mixed with PS610 in PBS buffer pH 7.4 with 0.01% Tween-20 and incubated at 30° C. After 30 min of incubation, the recognizer:peptide complex was rapidly mixed with 10-20 fold molar excess of unlabeled trap peptide and the reaction was followed in real time by measuring the fluorescence intensity. At least three-time course traces were averaged and fit to an exponential equation.

Aminopeptidase Purification

Expression vectors (with pET30 a+ backbone) for aminopeptidases PhTET2 and PhTET3 were transformed into BL21(DE3) chemically competent *E. coli* cells. The transformed cells were plated on Luria agar plates containing kanamycin (25 μg/mL) and incubated overnight at 37° C. to obtain single colonies. The starter liquid cultures inoculated with colonies were grown in Luria broth (LB) with kanamycin (25 μg/mL) and inoculated into large cultures at a starting optical density (OD600) of ~0.01. The expression cultures were incubated at 37° C. at 230 rpm until OD600 approached ~0.7. The cultures were then induced with 0.4 mM IPTG. The expressed aminopeptidase was purified as described above for recognizers. For conditioning, the aminopeptidase protein was dialyzed against 50 mM MOPS pH 8.0/60 mM potassium acetate and then exposed to cobalt acetate at a final concentration of 400 μM for 1-1.5 h at 65° C. to form the active dodecamer complex. The conditioned aminopeptidase preparation was dialyzed further against 50 mM MOPS pH 8.0/60 mM potassium acetate, aliquoted, and flash frozen.

Peptide Loading, Recognition, and Dynamic Sequencing

The semiconductor chip was placed in the sequencing device and a chip check was performed to test electronic circuit function and to optimize laser coupling alignment. The chip was then removed from the device socket and the chip was washed twice with 50 μL of 70% isopropanol, followed by four washes with 30 μL of wash buffer (50 mM MOPS pH 8.0, 60 mM potassium acetate, 50 mM glucose, 20 mM magnesium acetate, and surfactant mix) through a flow cell attached to the chip. A second chip check was then performed. The laser was then blocked via an integrated software-controlled shutter, peptide complex was added to a final concentration of 1-10 nM and mixed thoroughly, and the chip was incubated for 15 min. The chip was then washed six times with wash buffer, followed by addition of an imaging solution (wash buffer with 5 mM Trolox and an oxygen scavenging system). The laser was unblocked and the occupancy percentage (target 10-30%, Poisson distributed) was recorded by acquiring a photobleaching signal from a fluorophore attached to the peptide complex during 5 min of laser illumination. For NAA recognition-only assays, after peptide loading, labeled recognizer was added to a final concentration of 50 nM PS610, 100 nM PS691, or 250 nM PS961 (as indicated according to the experiment), and data was recorded for 10 hours. For dynamic sequencing assays, after peptide loading, a mixture of labeled recognizers was added to obtain final concentrations of 50 nM PS610, 100 nM PS691, and 250 nM PS961. Data was recorded for 15 min. The laser was then blocked briefly and aminopeptidases were added to the sequencing reaction via the flow cell and mixed thoroughly (final concentration 2-8 μM PhTET2 and/or 20-80 μM PhTET3, as indicated according to the experiment). The laser was then unblocked, and data was recorded for 10 hours. For all runs, 30 μL of mineral oil was added to fluid reservoirs at each port of the flow cell to prevent evaporation during the run.

Signal Processing and Trace Segmentation

The measured signal on-chip comprises various noise components, the most dominant one being due to fluorescent emissions from diffusing recognizers in the reaction chamber. The pulse caller algorithm for a given reaction chamber starts by estimating the statistical properties of this background noise component. Once an estimate within certain error bounds has been established, the algorithm works in an online fashion observing new frames of data as they are generated. At each point in time, the algorithm maintains state indicating whether the signal is due to the background component only or a pulse from a recognizer-NAA interaction is being observed. The state transition from background to pulse is triggered using an edge detection test where the shift in signal is expected to be significant with respect to the background component's statistical distribution. The state transition from pulse to background is triggered when a small window of the most recent frames of the signal appears to conform to the background component's distribution again. The algorithm maintains an updated model of the background component as new background frames are observed. This provides robustness against drift in the signal intensity together with a feedback control loop that maintains a stable optical coupling of the laser into the chip based on any such detected drift. As detected pulses can be due to true recognizer-to-dipeptide interaction events as well as other occasional transient noise spikes, a downstream filter layer is employed to test the significance of pulse events based on their duration, intensity, and noise patterns within the context of the full timeline of the run and the entire dataset of reaction chambers.

Initial regions are determined by performing a sliding window calculation of pulse rate along the time dimension of a series of pulses. Regions with a mean pulse rate >1 pulse/min are then subdivided according to a greedy bisection approach. Here, the pulses on the left and right of each potential split are assessed for statistically significant deviation in any of four separate pulse properties—intensity, bin ratio, pulse duration, and interpulse duration—using a Mann-Whitney U Test. To define RSs, the split point with the lowest p-value for any of the four properties is used to sub-divide the region and the process continues until no regions remain with a candidate split point with p-value $<10^{-5}$ in any comparison. In this manner, transitions from one RS to the next in a region of continuous pulsing are determined a priori on the basis of changes in fluorescence properties of pulsing kinetics. The resulting regions are called recognition segments (RSs).

Recognition Segment Classification

RS classification for reactions containing single synthetic peptides was performed using an unsupervised clustering algorithm. A subset of RSs including those with mean signal-to-noise ratio of their constituent pulses of ≥3 were used to pre-train a Gaussian mixture model (GMM) to identify approximate centroids for each of N classes of recognition, where N equals the number of expected recognizable peptide states with F, Y, W, L, I, V, or R at the N-terminus. Identified clusters were assigned to recognizable peptide states by matching the predominant order of cluster sequences observed to the expected amino acid sequence and by using prior knowledge of dye properties to identify the binders active during each RS. Subsequent rounds of GMM fitting were performed on all RSs matching the expected order of these events to refine the GMM model until no further sequences appeared in the expected order. The final model was then applied to all RSs in a given reaction.

RS classification for reactions containing library prepared peptides and mixes of peptides was performed using a random forest classifier that was pre-trained on annotated RS pulse features from prior synthetic peptide experiments. Unless otherwise noted, figures and statistics produced from classified RSs are derived from reaction chambers containing the expected sequence of RSs.

Molecular Dynamics and Binding Energy Calculation

Homology models of PS961 complexed to peptide were generated using an internal crystal structure, mutations were applied and optimized using protCAD prior to molecular dynamics. AMBER20 implicit solvent molecular dynamics simulations using the generalized Born solvation potential were performed using the ff19SB force field with no atomic distance cutoff. Minimization was performed using steepest descent, followed by conjugate gradient minimization. The system was thermalized from 0 to 300K using Langevin dynamics and a collision frequency of 3 $ps^{-1}$. Molecular dynamics simulations of the equilibrated recognizer-peptide complex, free recognizer and free peptide were independently run for 5 nanoseconds at 300 K to perform the binding energy calculation using MMPBSA. Where 125 frames, each containing 10,000 2 femtosecond steps, were used for the calculation from the three simulations. Binding energy and the decomposition of all residues contributing to the binding energy was computed in 0.15 M salt concentration.

Figure 10A:
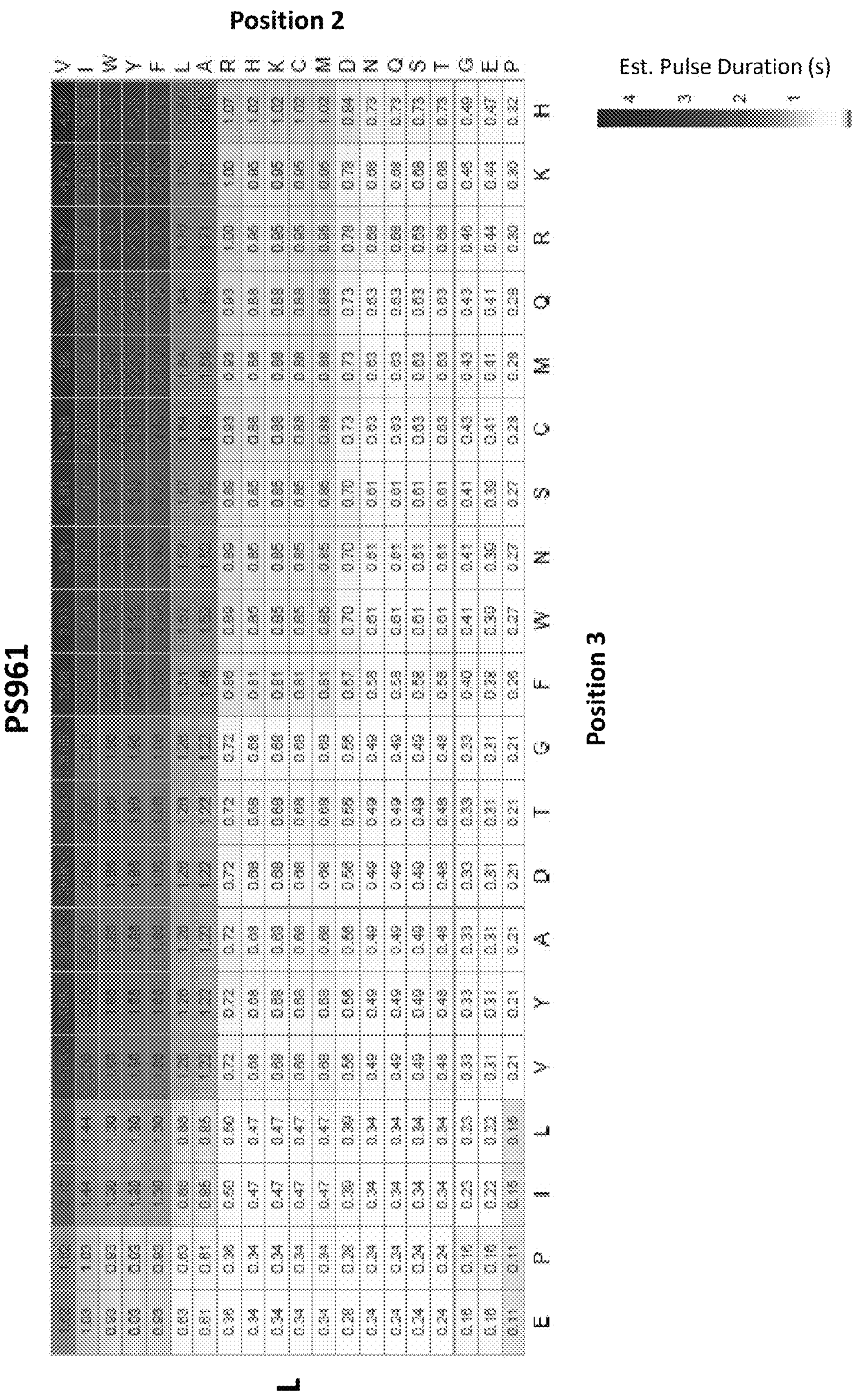
FIGS. 10A-10M show an example of peptide identification using modeled proteome-wide kinetic signatures.
Figure 10B:
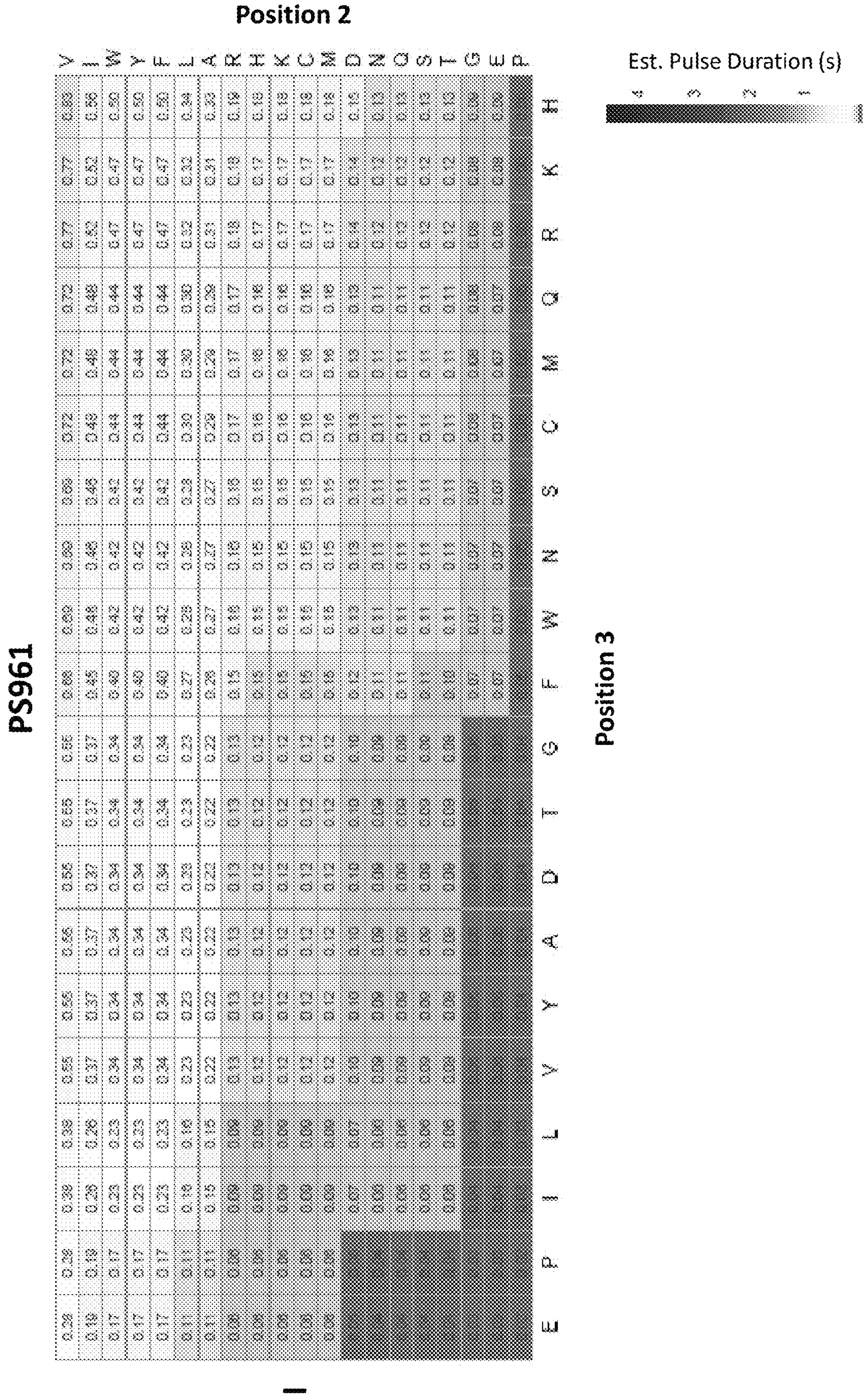
Figure 10C:
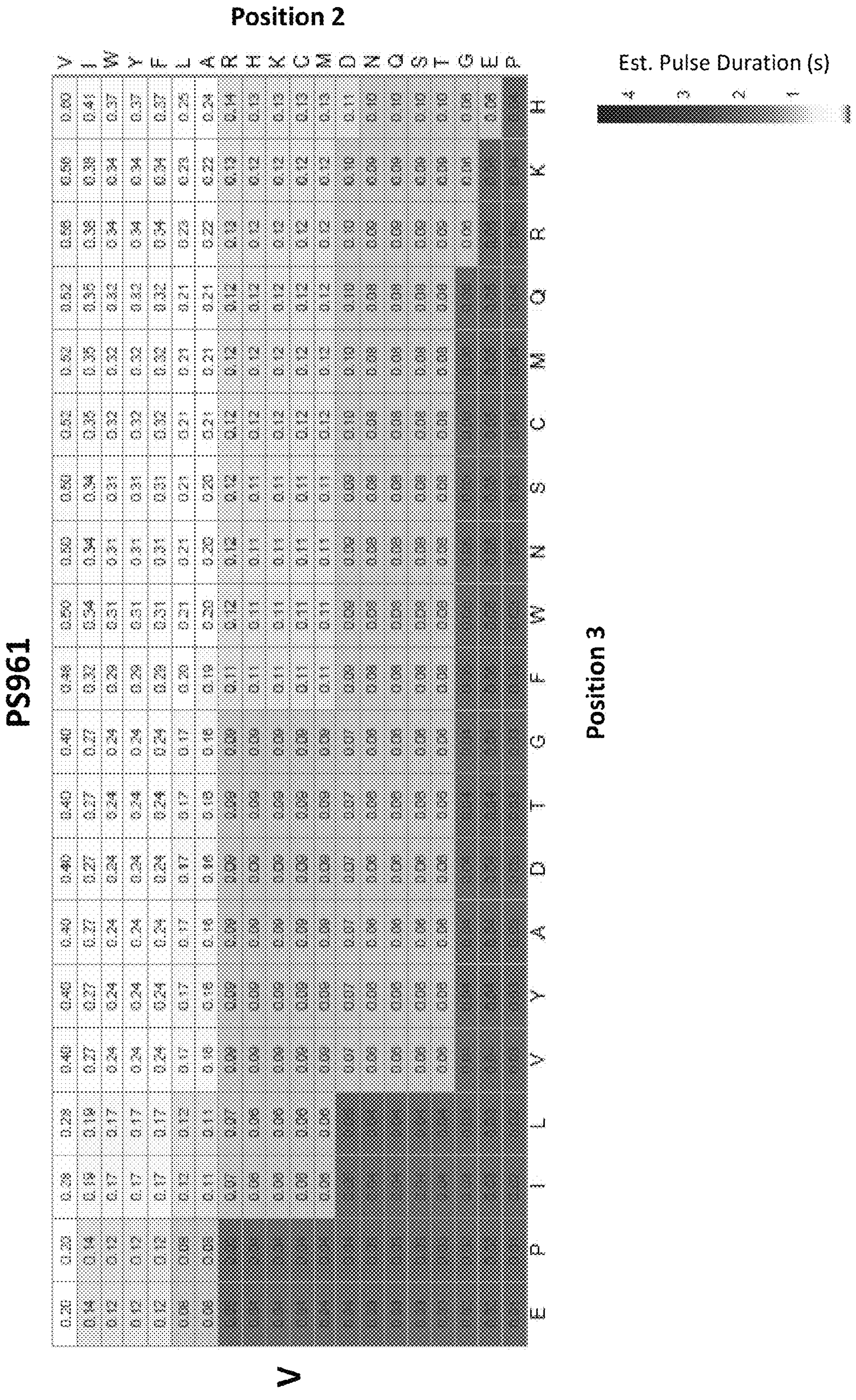
Figure 10D:
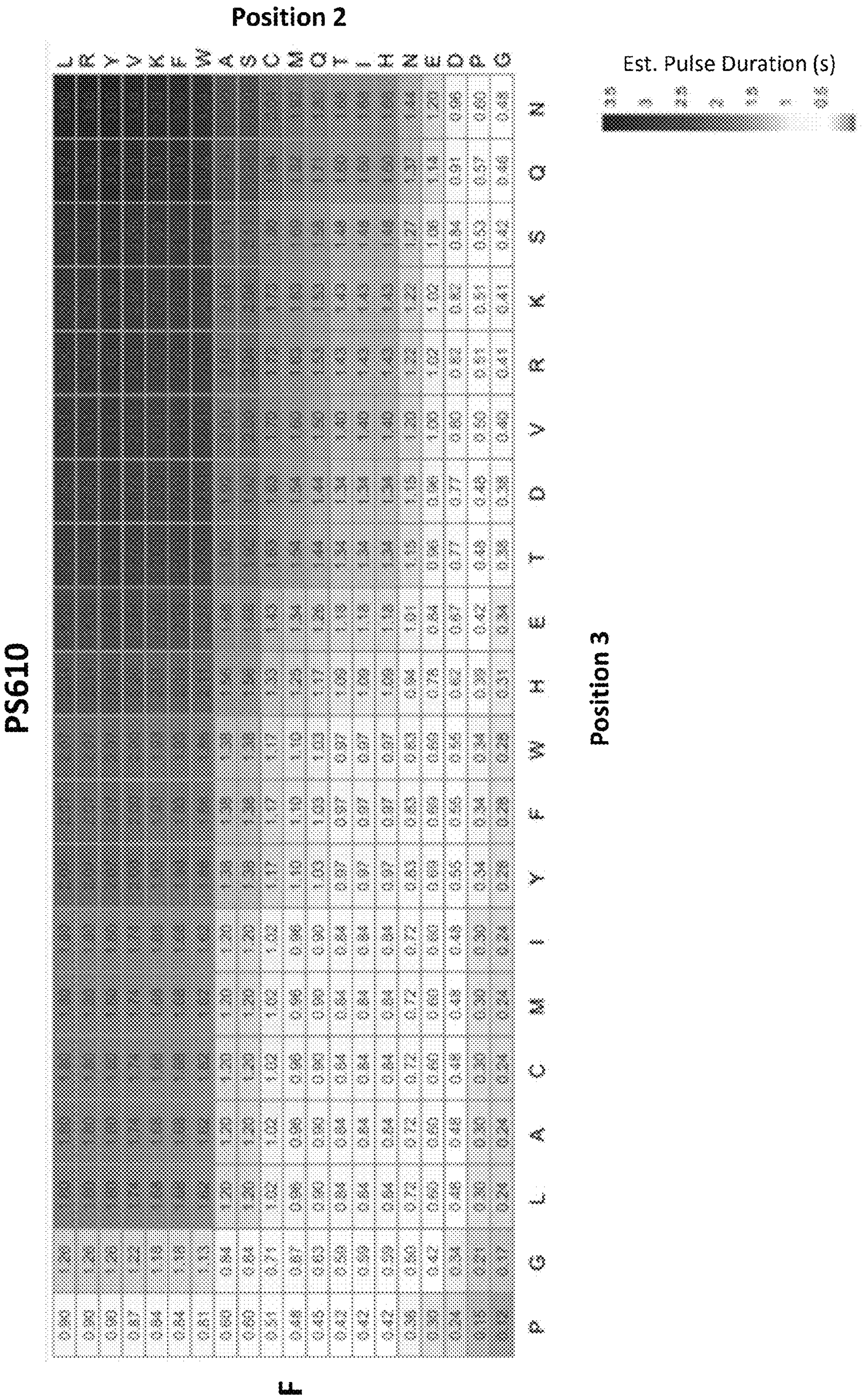
Figure 10E:
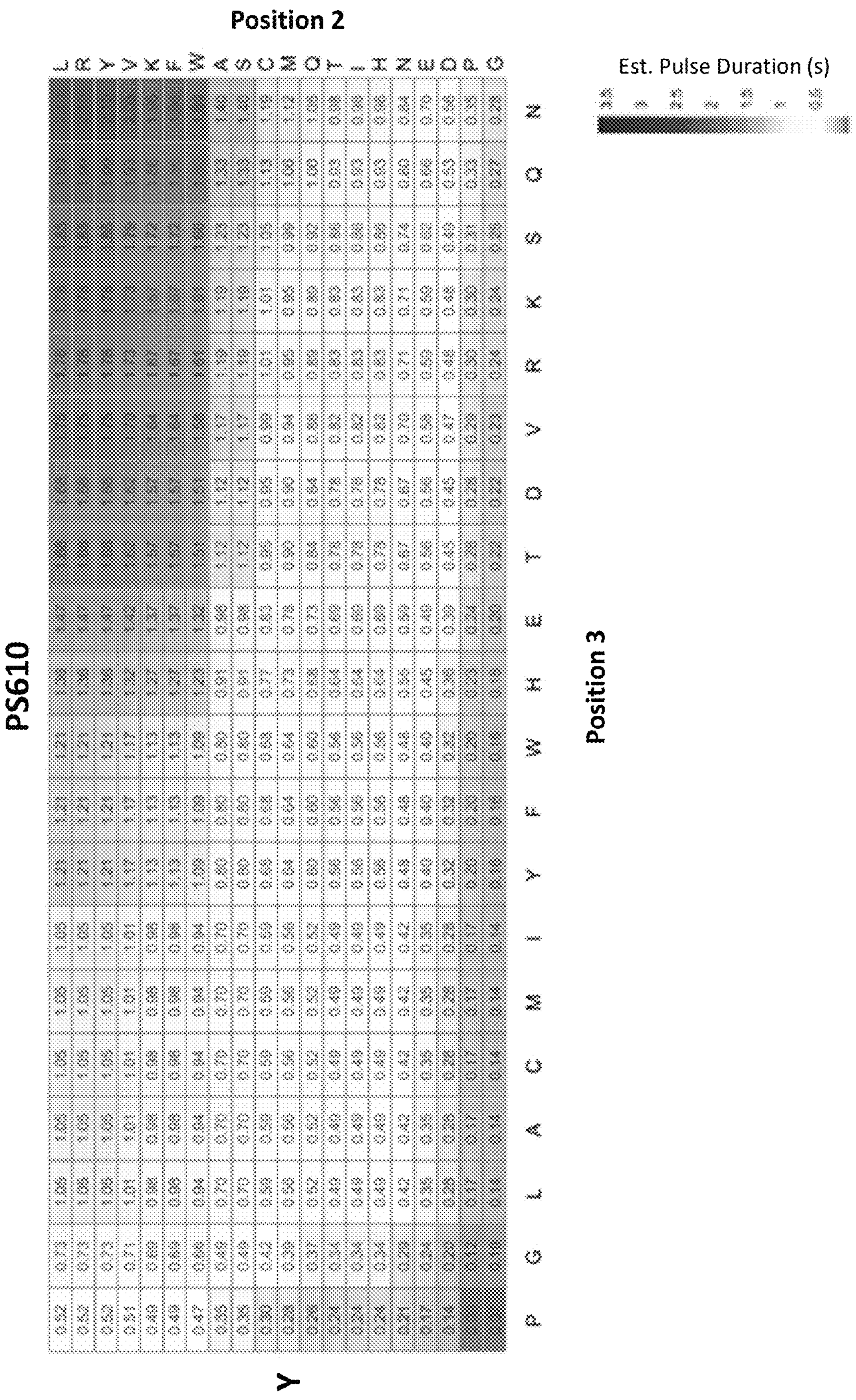
Figure 10F:
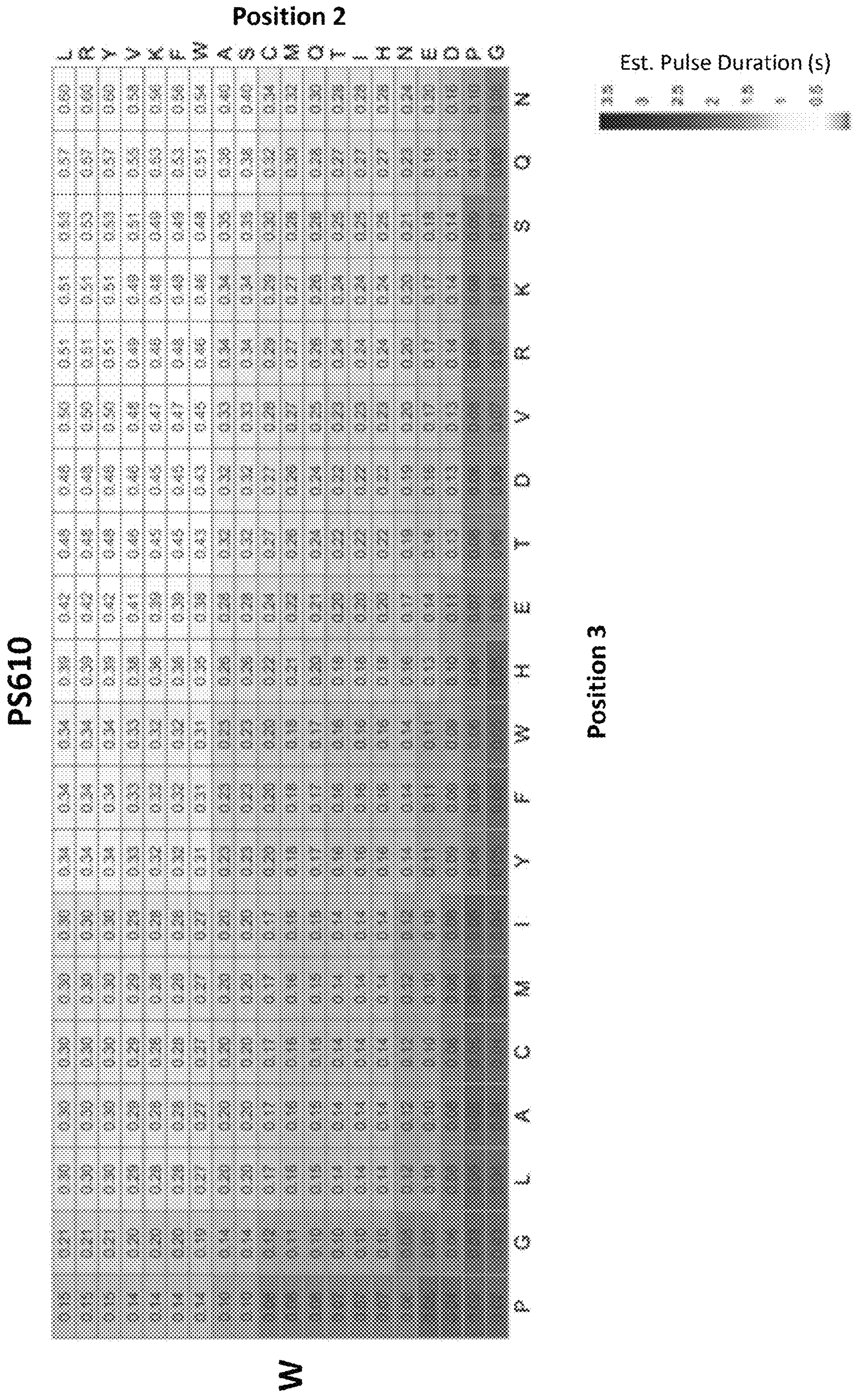
Figure 10G:
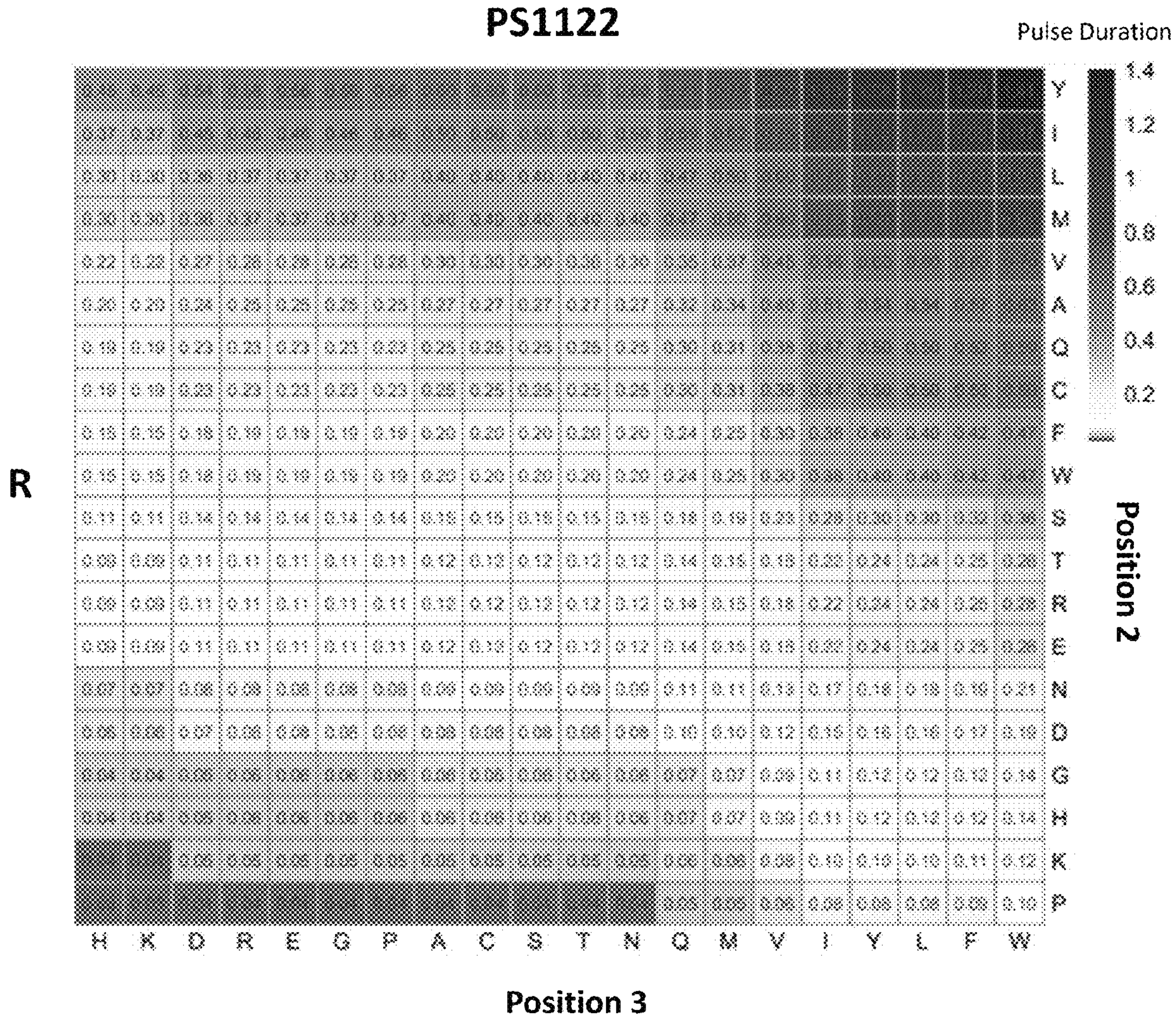
Figure 10H:
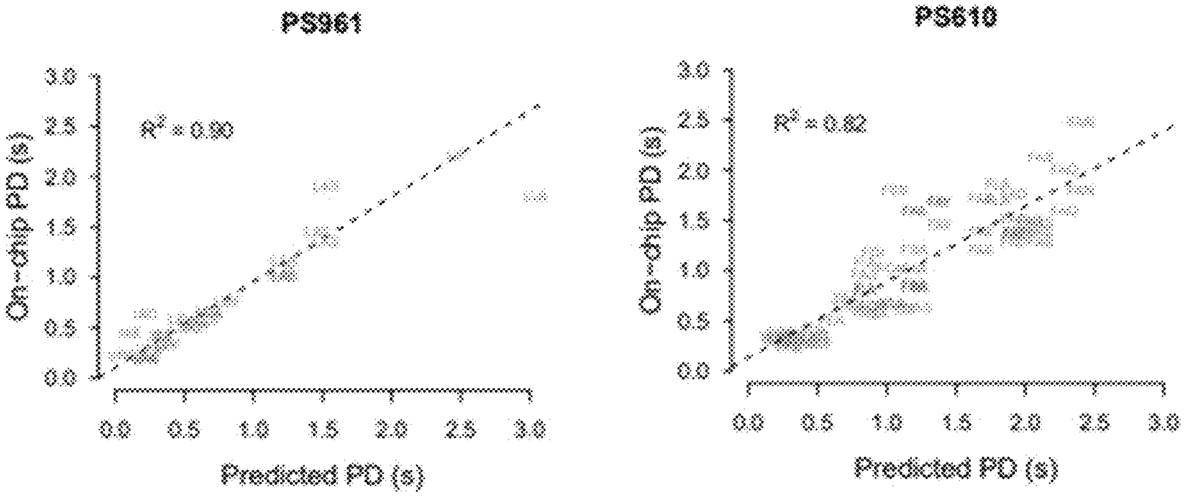

Example 2. Peptide Identification Using Modeled Proteome-Wide Kinetic Signatures Sequencing and biochemical data was used to determine predicted pulse durations for recognizers binding all possible tripeptide targets. FIGS. 10A-10C show heatmaps of predicted pulse durations for PS961 binding tripeptide targets having leucine (FIG. 10A), isoleucine (FIG. 10B), or valine (FIG. 10C) at the N-terminal position. FIGS. 10D-10F show heatmaps of predicted pulse durations for PS610 binding tripeptide targets having phenylalanine (FIG. 10D), tyrosine (FIG. 10E), or tryptophan (FIG. 10F) at the N-terminal position. FIG. 10G shows a heatmap of predicted pulse durations for PS1122 binding tripeptide targets having arginine at the N-terminal position. The predicted pulse durations displayed high correlation with actual pulse durations from on-chip experimental results for PS961 (FIG. 10H, left plot) and PS610 (FIG. 10H, right plot).

With this database of predicted tripeptide pulse durations, the expected kinetic signature of every peptide in the human proteome can be modeled, which could provide an improved understanding and utilization of the ability to identify proteins from sequencing output. A kinetic signature is an average representation of the sequencing behavior of a peptide on-chip, as detailed above in Example 1. The information in kinetic signatures derived from single-molecule traces dramatically improves the ability to map sequencing data to the proteome (e.g., compared to methods based on alignment of text strings, as in DNA sequencing). Kinetic information can include, for example, pulse duration, interpulse duration, and recognition segment (RS) duration.

To prepare a model demonstrating the ability to uniquely map peptides to the human proteome (with the recognizers PS961, PS610, and PS1122), an in silico digest of the proteome with AspN/LysC was performed, followed by a selection of all peptides that end in lysine (used for on-chip immobilization) and are greater than 7 amino acids in length. The results are shown below.

| | |
|---|---|
| Human proteins (SWISS-Prot): | 20,595 proteins |
| Peptides from AspN/LysC digest: | 1,148,192 |
| Peptides ending in lysine: | 652,225 |
| Peptides with >7 amino acids: | 273,112 |

Figure 10I:
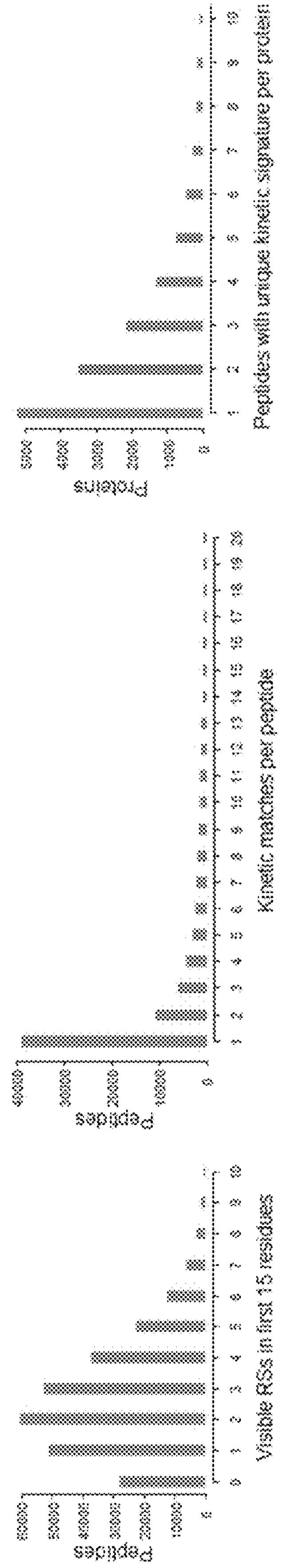

A predicted pulse duration was assigned to every visible amino acid in the set of 273,112 peptides (positions with predicted average PD of less than 0.18 s were treated as invisible). The distribution of predicted RSs in the first 15 residues is shown in FIG. 10I (left plot). 82,068 peptides contained 4 or more RSs (and thus were considered potentially informative). Kinetic signatures were created for each of these peptides.

The kinetic signature contains the expected binder and average PD at each visible position, and a gap to represent runs of one or more invisible amino acids. Next, for each peptide, the number of peptides with identical kinetic signatures was determined (signatures were considered identical if they had the same order of RSs and gaps, and the predicted PDs at each RS were somewhat similar (shorter PD not less than half the longer PD in any pairwise comparison)). According to this analysis, 38,849 out of 82,068 peptides produced a unique kinetic signature with no other matches in the human proteome. A further 10,571 peptides had only 1 other match. The distribution of kinetic matches per peptide is shown in FIG. 10I (middle plot). 14,167 proteins (69% of all proteins) contained at least one uniquely mappable peptide. On average, there were 2.5 uniquely mappable peptides per protein. The distribution of uniquely mappable peptides per protein is shown FIG. 10I (right plot).

Figure 10J:
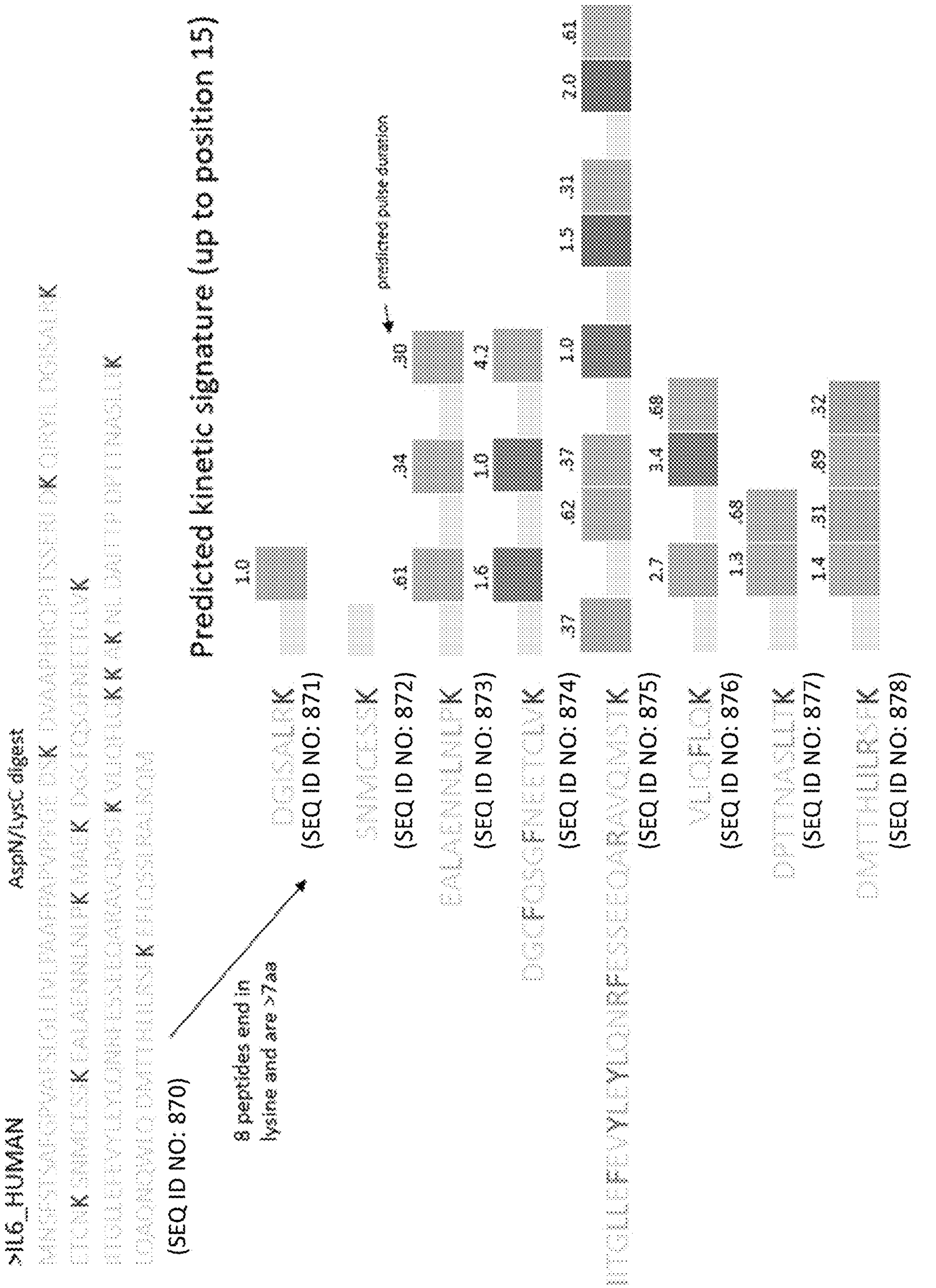
Figure 10K:
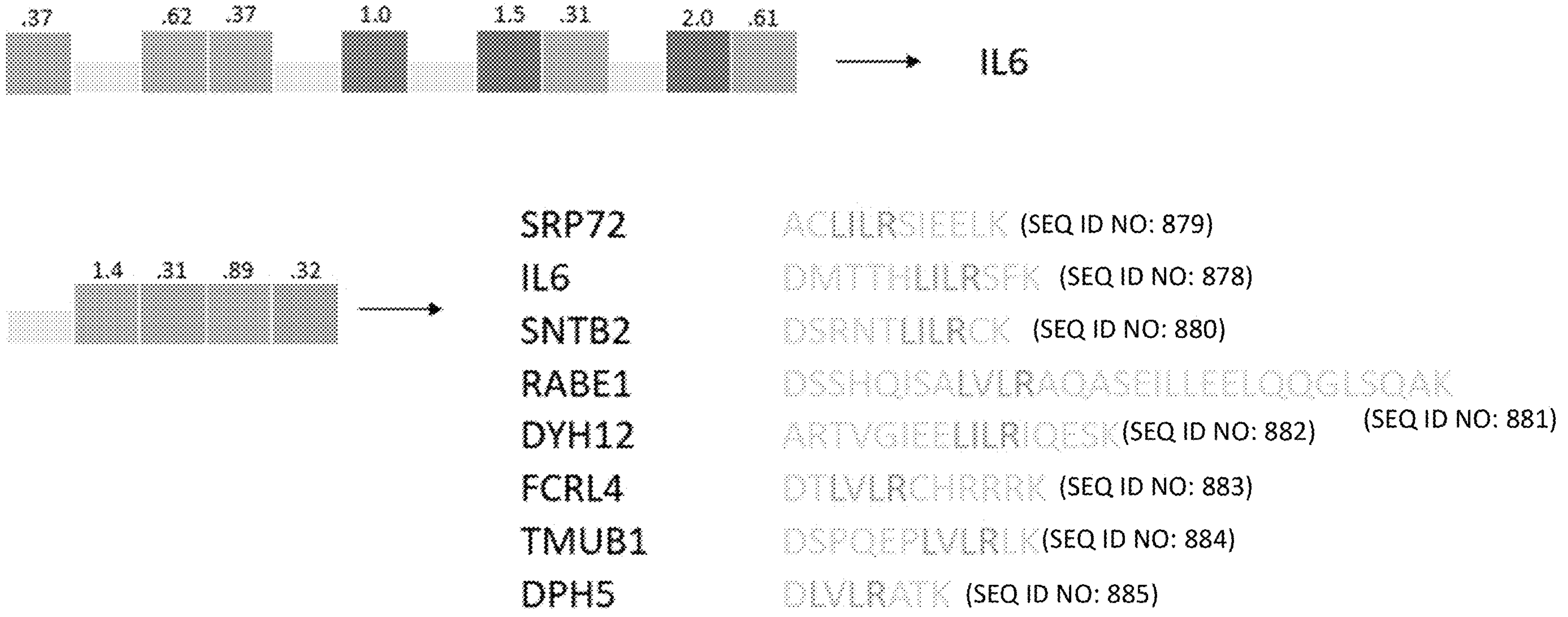

To further illustrate this data and how it might be used to model protein behavior, results with IL6 protein are shown in FIG. 10J (for simplicity, residues immediately before C-terminal lysine were treated as invisible and XP motifs were treated as cleavable). As shown in FIG. 10J, two peptides contain at least 4 RSs. As shown in FIG. 10K, one of these peptides maps uniquely to IL6, and the other peptide matches the kinetic signature of 8 different peptides from 8 proteins.

To provide an illustrative example using a smaller proteome, the *E. coli* proteome (containing only 4,392 proteins) was analyzed as described above for the human proteome. The results are shown below.

| | |
|---|---|
| *E. Coli* Proteins: | 4,392 |
| Peptides from AspN/LysC digest: | 126,439 |
| Peptides ending in lysine: | 59,697 |
| Peptides with >7 amino acids: | 28,046 |
| Peptides containing 4+ visible RSs in first 15 residues: | 9,925 |
| Peptides having unique kinetic signatures: | 7,740 (78%) |
| Proteins having at least one peptide with 4+ RSs in first 15 residues: | 3,527 |
| Proteins having at least one uniquely mappable peptide (mean 2.4 peptides): | 3,187 out of 3527 |

Figure 10L:
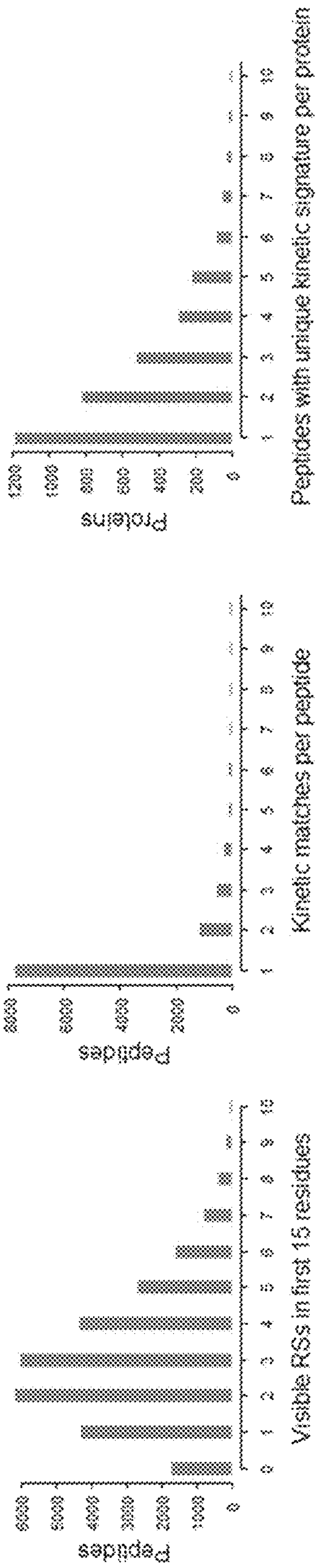
Figure 10M:
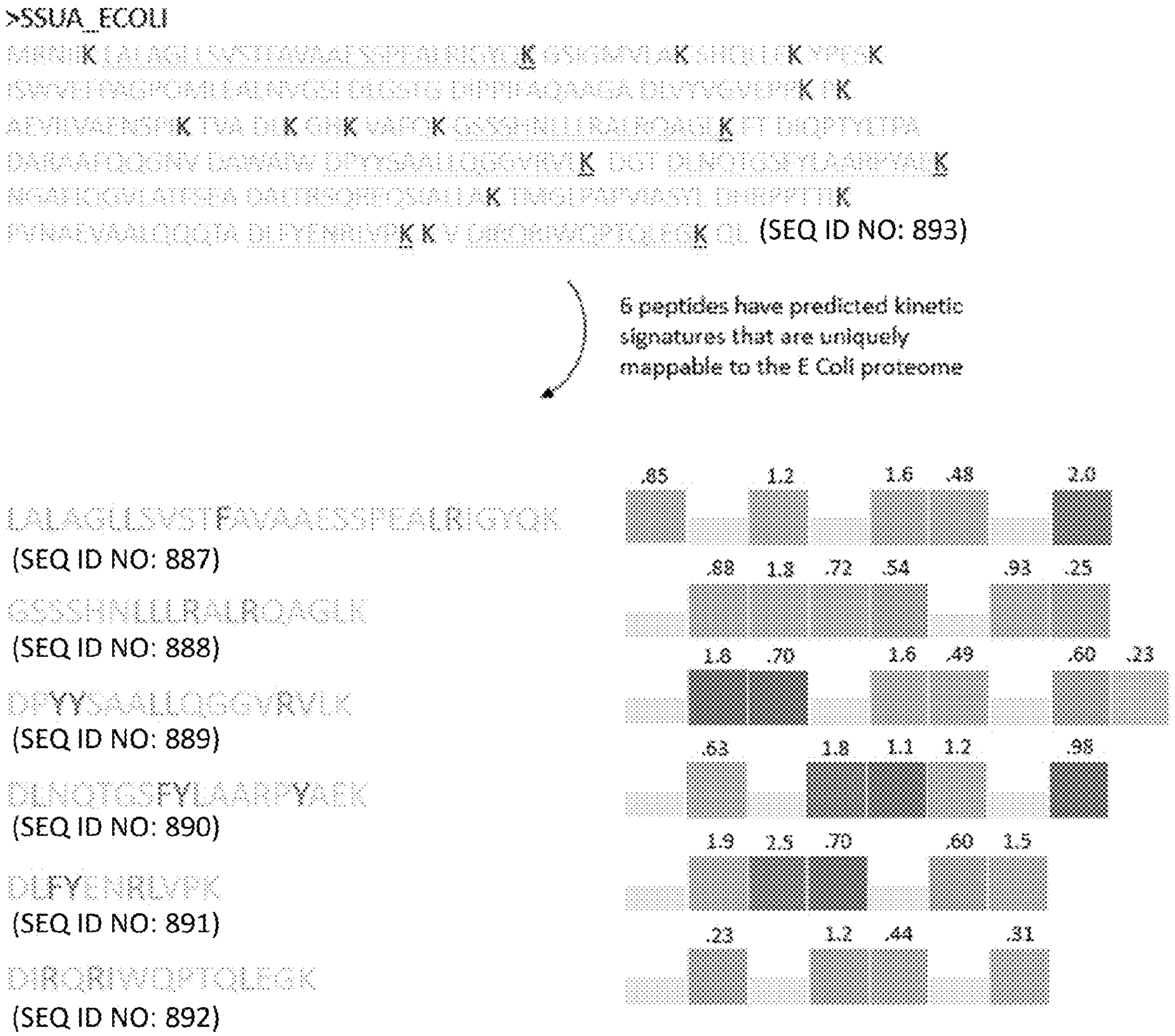

The distribution of predicted RSs in the first 15 residues is shown in FIG. 10L (left plot). 9,925 peptides contained 4 or more RSs (and thus were considered potentially informative). Kinetic signatures were created for each of these peptides. For each peptide, the number of peptides with identical kinetic signatures was determined. According to this analysis, 7,740 out of 9,925 peptides produced a unique kinetic signature with no other matches in the *E. coli* proteome. The distribution of kinetic matches per peptide is shown in FIG. 10L (middle plot). 3,187 proteins contained at least one uniquely mappable peptide. On average, there were 2.4 uniquely mappable peptides per protein. The distribution of uniquely mappable peptides per protein is shown FIG. 10L (right plot). To illustrate this data and how it might be used to model protein behavior, results with a protein from *E. coli* containing 6 peptides that are uniquely mappable are shown in FIG. 10M.

These results demonstrate the utility of a kinetics-centric view of peptide identification. This view also provides the ability to accurately model the informatic impact of changes to reaction conditions, such as the addition of new recognizers, increases in recognizer pulse duration, changes in frame rate, and addition of new dye labels.

Example 3. Direct Identification of Arginine Post-Translational Modifications

Proteins undergo a diverse array of post-translational modifications (PTMs) to their amino acid side chains that can strongly affect protein function and mediate intricate cellular events. Measuring the diversity, dynamics, and functional consequences of PTM states of proteins across the proteome is essential to understanding the role of proteins in health and disease. However, discovery and detection of PTMs and routine measurement of complex PTM states remains highly challenging and the diversity of proteoforms in the human proteome remains largely unmapped. New methods to enable sensitive detection of PTMs will greatly aid biomarker discovery, drug discovery, and the development of precision and personalized approaches to medicine.

Modifications of the arginine side chain are of particular biomedical interest. Methylation and citrullination of arginine residues in a number of human proteins have been shown to play key roles in disease states such as cardiovascular disease, autoimmune disease, and cancer. In this example, aspects of the technology described herein were applied to the detection of arginine methylation and citrullination with single-molecule resolution and sensitivity.

Figure 11A:
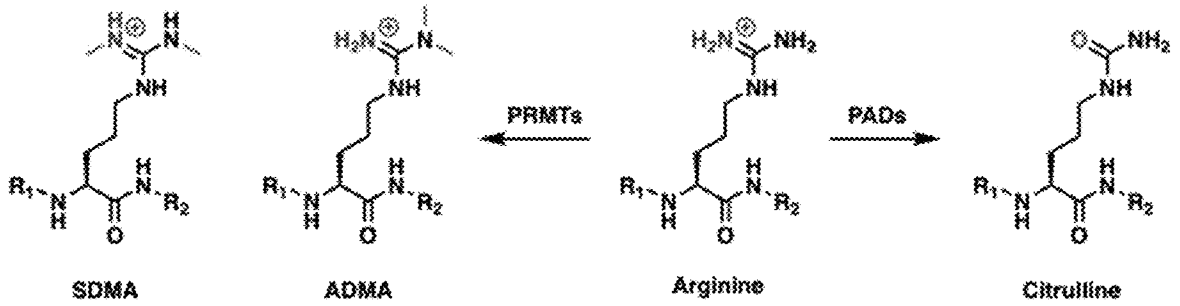
FIGS. 11A-11D show example results showing direct identification of arginine PTMs.

Arginine plays an important role in protein structure and function due to the unique properties of the guanidinium group that forms the terminus of its side chain (FIG. 11A). This group is both positively charged and capable of forming extended hydrogen bond networks and cation-n interactions with other amino acids and with nucleic acids. Arginine, therefore, often mediates key interactions between protein binding partners or between proteins and DNA.

The two most common arginine PTMs, dimethylation and citrullination, alter the arginine side chain and change its properties (FIG. 11A), potentially resulting in important downstream effects on cellular processes. Dimethylation retains arginine's positive charge but increases its size and hydrophobicity and blocks hydrogen bond formation. Citrullination eliminates arginine's positive charge, resulting in a neutral side chain with altered properties that can greatly impact protein conformation and function.

Dimethylation and citrullination of arginine are carried out by enzymes and may be part of the normal regulation of cellular processes or involved in disease states. Arginine dimethylation is catalyzed by protein arginine methyltransferases (PRMTs). PRMTs transfer two methyl groups either asymmetrically onto the same nitrogen atom, resulting in asymmetric dimethyl arginine (ADMA) or symmetrically onto opposite nitrogen atoms, resulting in symmetric dimethyl arginine (SDMA). These modifications increased size and hydrophobicity and block hydrogen bonding. Arginine citrullination is catalyzed by protein arginine deiminases (PADs). PADs carry out the hydrolysis of arginine's positively-charged guanidinium group, resulting in a neutral ureido group. This transformation results in a negligible mass increase of 0.9840 Da, but the loss of positive charge can dramatically alter protein conformation and function. FIG. 11A illustrates the structures of SDMA, ADMA, canonical arginine, and citrulline.

Arginine PTMs have emerged as important targets of biomedical research. Methylated arginine residues and their respective PRMTs have been implicated in important diseases such as cardiovascular disease and cancers. Critical involvement of arginine citrullination in immune system function, skin keratinization, myelination, and the regulation of gene expression has also been demonstrated. Notably, the removal of arginine's positive charge in some cases can cause proteins to activate the immune system, contributing to autoimmune diseases.

Challenges for the Detection of Arginine PTMs

Research into these arginine PTMs has been particularly challenging because they are difficult to detect and differentiate with current proteomic methods. Mass spectrometry is the most frequently utilized tool for detecting protein PTMs. However, mass spectrometry cannot easily distinguish ADMA and SDMA because they are constitutional isomers with identical mass. Likewise, deimination of arginine to citrulline results in a negligible mass increase of 0.9840 Da. This mass difference can easily be confused with a $^{13}C$ isotope or misinterpreted as deamidation of nearby asparagine or glutamine residues. In addition, mass spectrometry techniques for arginine PTM detection require highly specialized knowledge and training and advanced analysis methods.

Enzyme-linked immunosorbent assay (ELISA), another common method for PTM detection, uses antibodies specifically generated to detect a modified protein of interest. Although arginine PTMs are estimated to be widespread in human cells, commercially available antibodies against arginine PTMs are limited to specific sites on a few highly studied proteins. The requirement to generate new antibodies, along with complex workflows, expense, antibody reproducibility, and other challenges associated with ELISA assay development, is likely to hinder discovery and further study of novel arginine PTM sites.

Continued development toward novel methods is needed to facilitate direct detection of arginine PTMs in proteins. Single-molecule protein sequencing offers an alternative approach to the detection of ADMA, SDMA, and citrulline that is not based on mass to charge ratio or antibody specificity, but rather on the kinetic signature of binding between recognizers and N-terminal amino acids (NAAs).

Aspects of the technology described herein gain insight into these PTMs with single molecule resolution, overcoming current technological gaps, and providing direct detection of arginine PTMs. —Methodology & Workflow PTM detection involved isolating peptides and subjecting them to a real-time single-molecule protein sequencing reaction. Proteins were first digested into peptide fragments and conjugated C-terminally to macromolecular linkers. The peptide complexes were immobilized at the bottom of nanoscale wells on a semiconductor chip, resulting in single peptide molecules with exposed N-termini ready for sequencing. During the sequencing reaction, the surface-immobilized peptides were exposed to a solution containing dye-labeled NAA recognizers that bound on and off to their cognate NAAs with characteristic kinetic properties. Aminopeptidases in solution sequentially removed individual NAAs to expose subsequent amino acids for recognition. Fluorescence lifetime, intensity, and kinetic data were collected in real time and analyzed to determine amino acid sequence and PTM content.

The trace-level output included distinct pulsing regions called recognition segments (RSs); each RS corresponded to a period of time between aminopeptidase cleavage events during which an NAA recognizer bound on and off to its exposed target NAA. Chemical modifications to a target NAA or to a nearby downstream amino acid can modulate recognizer affinity, resulting in a characteristic change in the average pulse duration (PD) during an RS relative to an unmodified peptide. These modifications can also influence the rate of aminopeptidase cleavage of an NAA, resulting in a characteristic change in average duration of the corresponding RS.

Figure 11B:
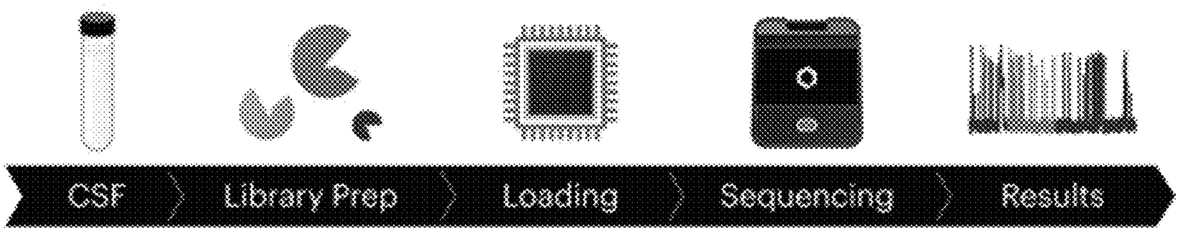

A summary of the workflow for sequencing of peptides and detection of PTMs is presented in FIG. 11B.

Results & Discussion

Detection of Arginine Dimethylation

First, the detection and differentiation of arginine, ADMA, and SDMA by single-molecule protein sequencing was demonstrated. The focus was on a key segment of the signaling protein P38MAPKa. Dimethylation of arginine residue 70 of P38MAPKa in myoblast cells by PRMT7 is a critical regulatory step in the activation of myoblast differentiation in humans.

Synthetic peptides corresponding to residues 69 to 76 of P38MAPKa were generated in three versions containing either arginine, ADMA, or SDMA at position 2: YRELRLLK (SEQ ID NO: 834), $YR_{ADMA}$ELRLLK (SEQ ID NO: 835), and $YR_{SDMA}$ELRLLK (SEQ ID NO: 836). Each peptide was sequenced using three recognizers—PS610 (F, Y, W), PS961 (L, I, V), and PS621 (R)—and data were analyzed to identify RSs, determine the mean PD of each RS, and characterize the kinetic signature of each peptide. Each peptide displayed a distinguishable pattern due to the distinct kinetic influences of arginine, ADMA, and SDMA on recognizer binding (see example traces in FIG. 11C-A).

Figure 11C:
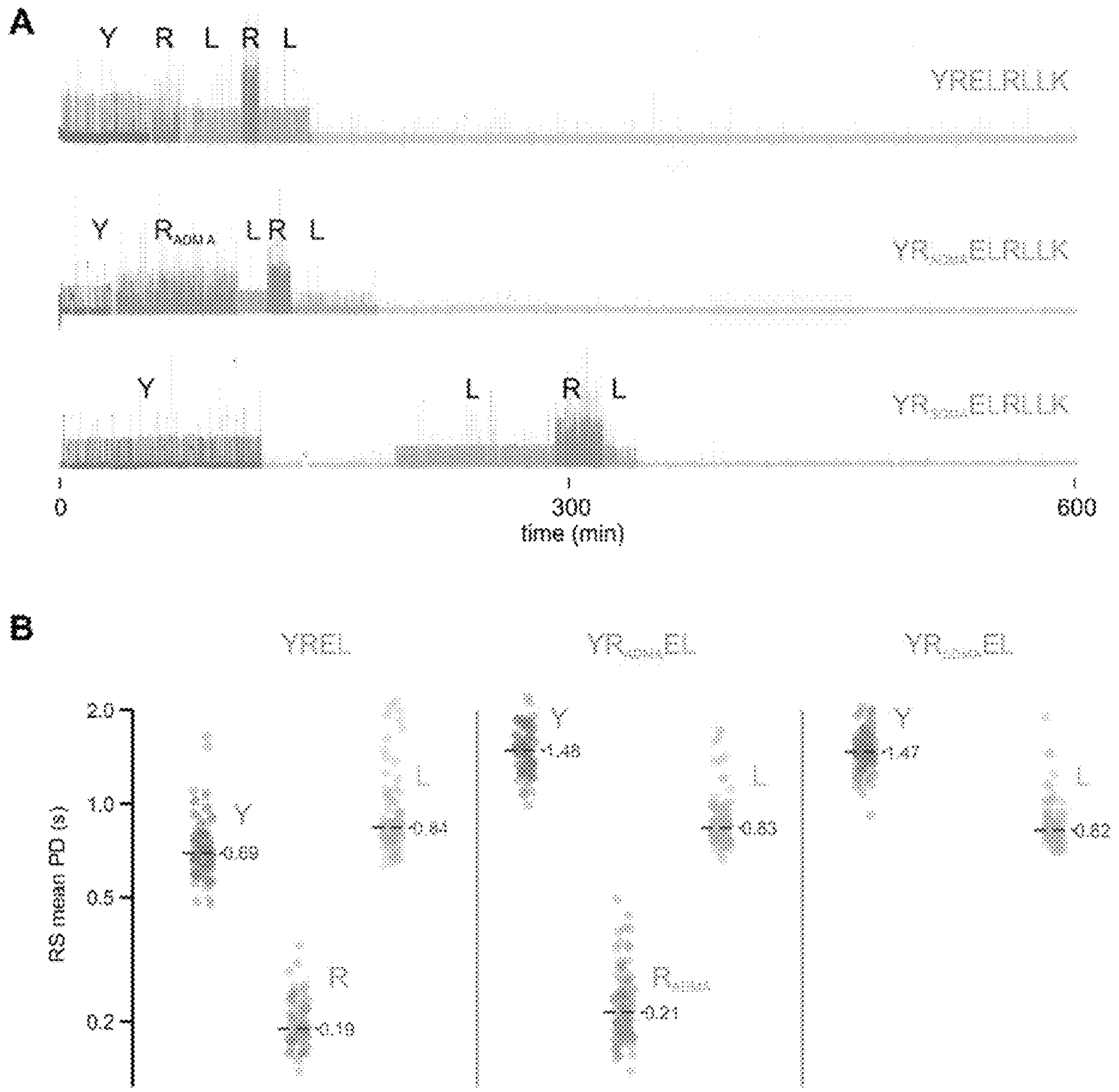
Figure 11C:
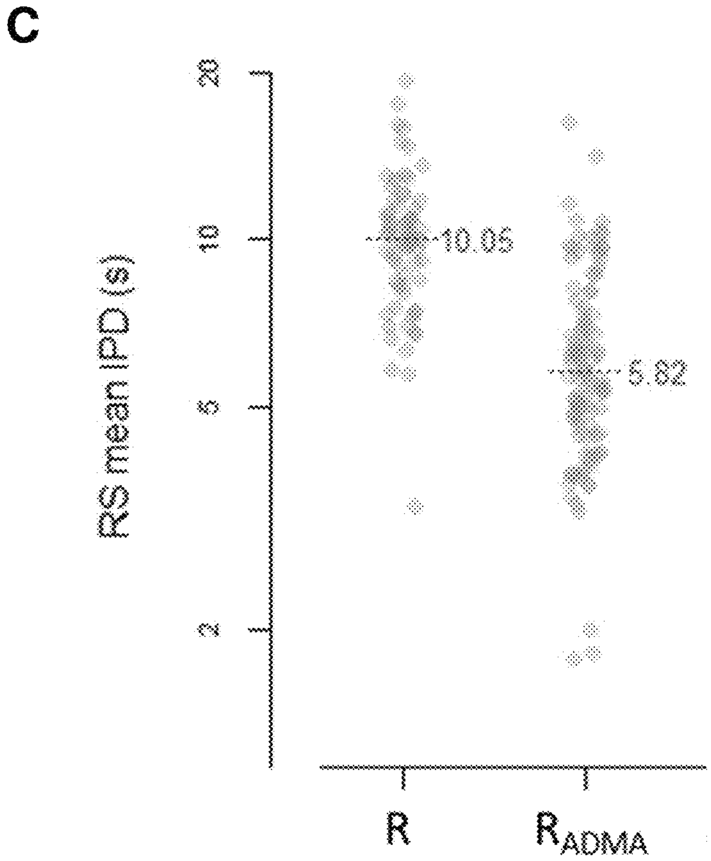

Arginine and ADMA residues exhibited binding with the recognizer PS621 with similar PD, whereas SDMA exhibited no binding (FIG. 11C-A, 11C-B). This result indicated that symmetric dimethylation of arginine—in contrast to asymmetric dimethylation—reduced the affinity of PS621 for N-terminal arginine, providing a clear kinetic difference between these isomeric arginine PTMs. The NAA recognizers used in this example contact residues at positions 2 and 3 from the N-terminus when they bind to their target NAAs; therefore, modification of these downstream residues can influence recognizer binding affinity. A strong influence of arginine dimethylation on recognition of the upstream tyrosine residue in these peptides by PS610 was observed (FIG. 11C). The median pulse duration of tyrosine recognition increased from 0.69 s for YRE to 1.47 s and 1.48 s for $YR_{ADMA}$Eand $YR_{SDMA}$ respectively (FIG. 11C-B). In addition, the median interpulse duration (IPD) of arginine recognition by PS621 decreased from 10.05 s for unmodified arginine to 5.82 s for ADMA (FIG. 11C-C).

The influence that these dimethylated arginine residues have on the recognition of preceding NAAs serves as a powerful feature of protein sequencing with single-molecule sensitivity and precision. These results demonstrate the capacity for unprecedented sensitivity in detection of arginine dimethylation using aspects of technology described herein.

Detection of Arginine Citrullination

Figure 11D:
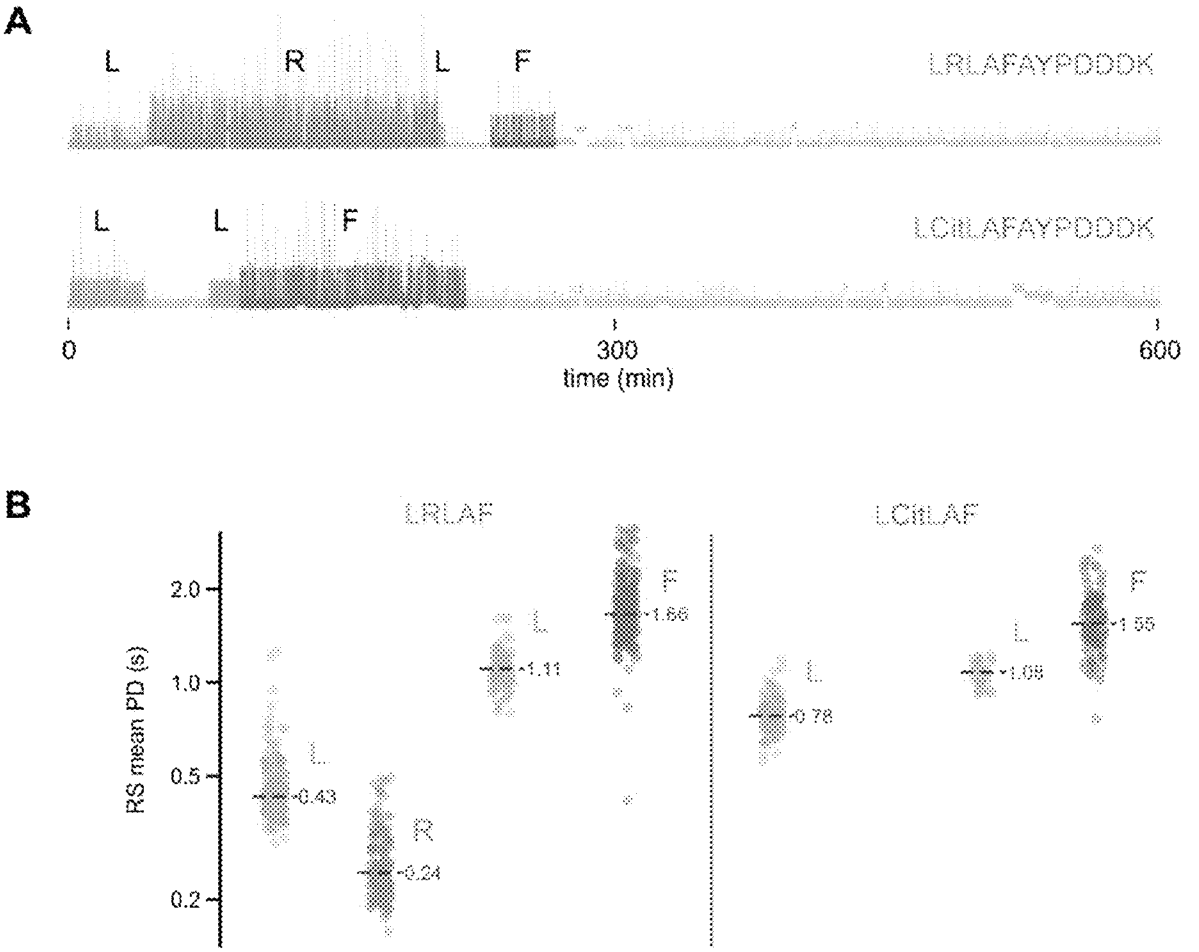

It was next demonstrated that differential binding kinetics could be used to rapidly differentiate citrullinated arginine residues from native arginine residues. Two synthetic peptide sequences containing either arginine or citrulline at position 2—LRLAFAYPDDDK (SEQ ID NO: 817) and LCitLAFAYPDDDK (SEQ ID NO: 839)—were generated and sequenced using three recognizers as described above. Each peptide displayed a highly distinguishable kinetic signature due to the influence of the different arginine and citrulline side chains on recognition (FIG. 11D-A, 11D-B). Citrullination eliminated N-terminal arginine recognition by PS621 (see example traces in FIG. 11D-A). Citrullination at position 2 also resulted in a large increase in the median PD of recognition of the N-terminal leucine located at the preceding position by PS961. Median PD was 0.43 s for LRL increased to 0.78 s for LCitL (FIG. 11D-B). These results demonstrate the capability to detect and digitally quantify arginine citrullination.

Conclusion

In this example, arginine PTMs were directly detected. Arginine PTMs play important roles in human health and disease but have been challenging to study. Current proteomic methods such as mass spectrometry and ELISA have been capable of just indirect identification of these arginine PTMs using highly specialized techniques or limited to a small set of specific proteins on the basis of antibody availability and other challenges. The ability to directly detect PTMs offers great potential for accelerated biomedical research and for a wide range of commercial applications in drug discovery and biomarker development.

Example 4. Identification of Threonine Post-Translational Modification

Figure 14A:
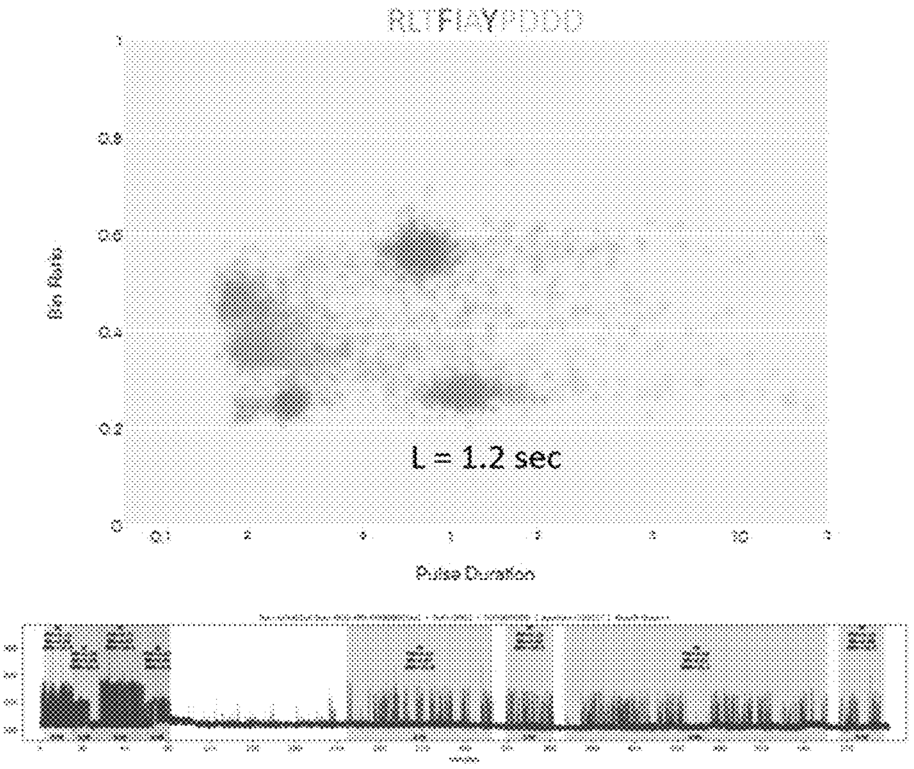
FIGS. 14A-14C show example results showing identification of a threonine PTM.
Figure 14B:
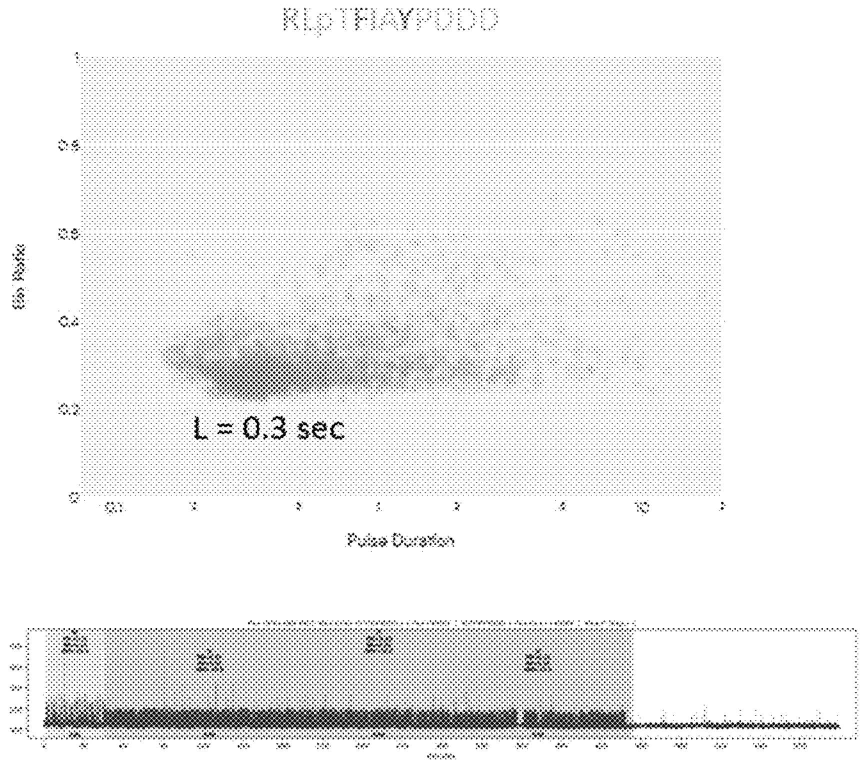
Figure 14C:
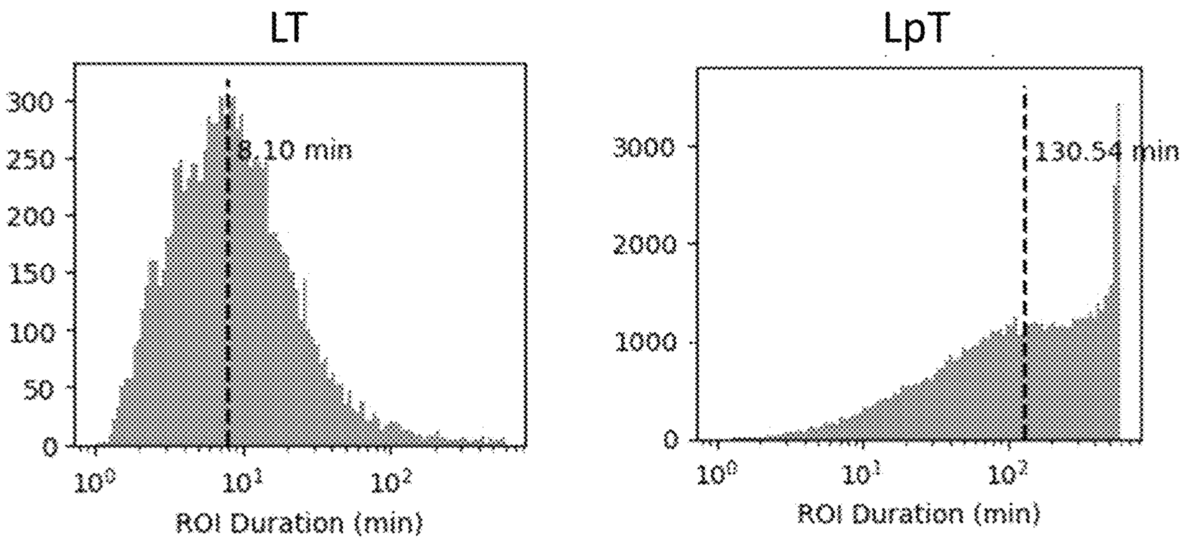

Sequencing reactions using the recognizers PS691 (R), PS610 (FYW), and PS961 (LIV) were performed separately for the peptides RLTFIAYPDDD (SEQ ID NO: 821) and RLpTFIAYPDDD (SEQ ID NO: 822) (where pT is phosphothreonine). Recognition of the N-terminal leucine preceding threonine or phosphothreonine by PS961 was observed, with distinct pulse duration for leucine followed by threonine (RS mean PD=1.2 s; FIG. 14A) compared to leucine followed by phosphothreonine (RS mean PD=0.3 sec; FIG. 14B). Moreover, recognition segment (RS) durations for leucine recognition were longer when leucine was followed by phosphothreonine (RS mean duration=130 min; FIG. 14C, right panel) compared to threonine (RS mean duration=8.1 min; FIG. 14C, left panel). These data demonstrate the ability to discriminate between unmodified and post-translationally modified threonine side chains.

Example 5. Identification of Tyrosine Post-Translational Modification

Figure 15A:
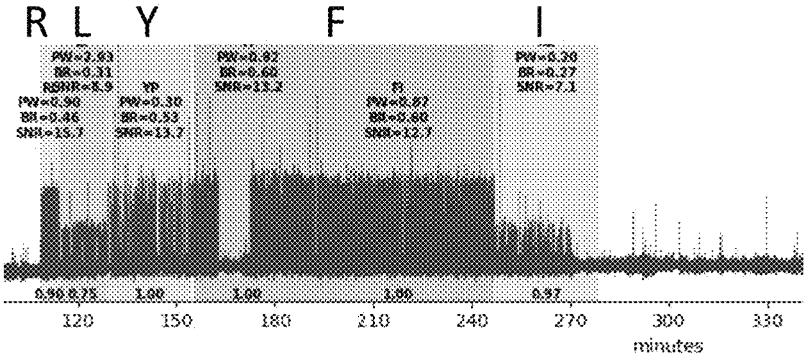
FIGS. 15A-15B show example results showing identification of a tyrosine PTM in sequencing reactions using the recognizers PS691, PS610, and PS961 for the peptides: RLYFIAYPDDD (SEQ ID NO: 823) (FIG. 15A); and RLpYFIAYPDDD (SEQ ID NO: 824), where pY is phosphotyrosine (FIG. 15B).
Figure 15B:
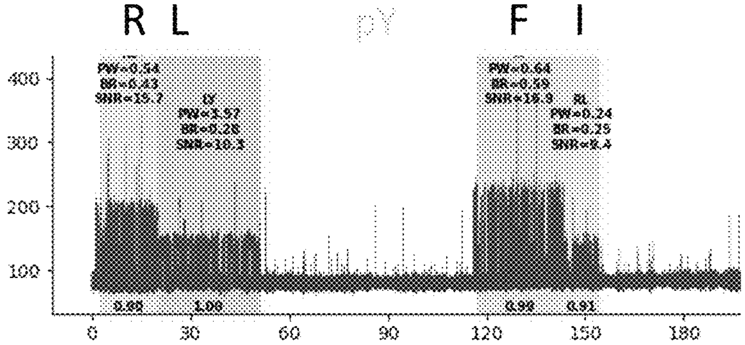

Sequencing reactions using the recognizers PS691 (R), PS610 (FYW), and PS961 (LIV) were performed separately for the peptides RLYFIAYPDDD (SEQ ID NO: 823) and RLpYFIAYPDDD (SEQ ID NO: 824) (where pY is phosphotyrosine). Recognition of the N-terminal arginine and leucine residues preceding tyrosine or phosphotyrosine by PS691 and PS961, respectively, was observed, with distinct pulse durations depending on whether the peptide contained tyrosine (FIG. 15A) or phosphotyrosine (FIG. 15B). Recognition of N-terminal arginine occurred with RS mean PD of 0.9 s for RLY and 0.45 s for RLpY. Recognition of N-terminal leucine occurred with RS mean PD of 2.45 s for LYF and 3.4 s for LpYF. Moreover, traces from the peptide RLpYFIAYPDD (SEQ ID NO: 840) contained a consensus gap between L and F, since pY was not recognized by PS610, whereas traces from the peptide RLYFIAYPDDD (SEQ ID NO: 823) contained Y recognition by PS610 during this interval. These data demonstrate the ability to discriminate between unmodified and post-translationally modified tyrosine side chains.

Example 6. Identification of Lysine Post-Translational Modification

Figure 16A:
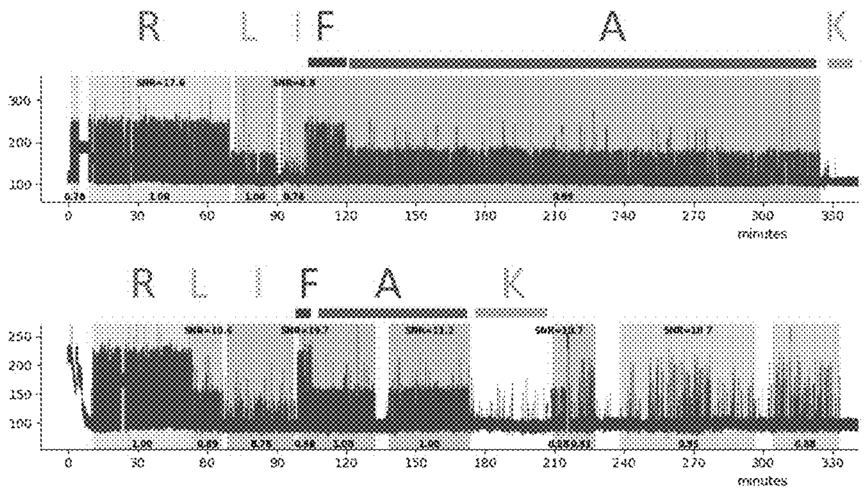
FIGS. 16A-16B show example results showing identification of a lysine PTM in sequencing reactions using the recognizers PS691, PS610, PS961, and PS1165 for the peptides: RLYFKAYPDDD (SEQ ID NO: 825) (FIG. 16A); and RLK{acetyl}FIAYPDDD (SEQ ID NO: 826), where K {acetyl} is an acetylated lysine (FIG. 16B).
Figure 16B:
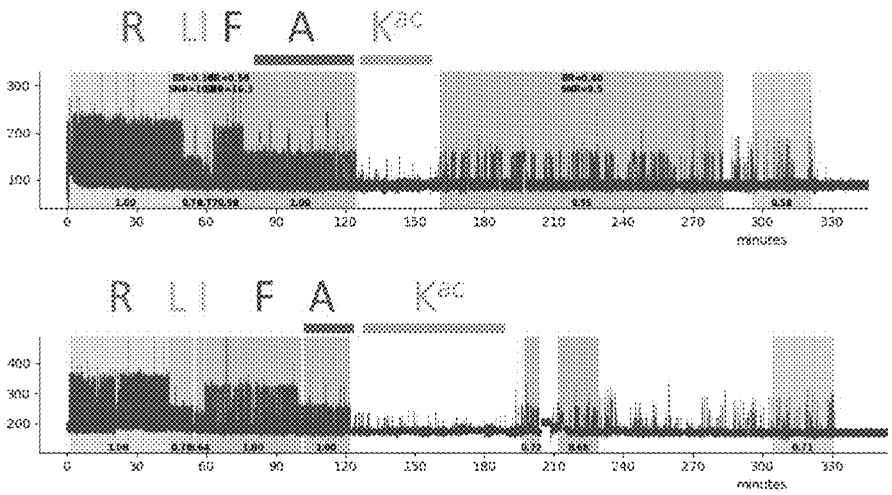

Sequencing reactions using the recognizers PS691 (R), PS610 (FYW), PS961 (LIV), and PS1165 (A) were performed separately for the peptides RLYFKAYPDDD (SEQ ID NO: 825) and RLK{acetyl}FIAYPDDD (SEQ ID NO: 826) (where K{acetyl} is an acetylated lysine). Recognition of the N-terminal phenylalanine and alanine residues preceding lysine or acetyl-lysine by PS610 and PS1165, respectively, was observed, with distinct pulse durations depending on whether the peptide contained lysine (F=1.4 s, A=1.3 s; FIG. 16A) or acetylated lysine (F=1.8 s, A=2.2 s; FIG. 16B). Recognition of N-terminal phenylalanine occurred with RS mean PD of 1.4 s for FAK and 1.8 s for FAK{acetyl}. Recognition of N-terminal alanine occurred with RS mean PD of 1.3 s for AK and 2.2 s for AK{acetyl}. These data demonstrate the ability to discriminate between unmodified and post-translationally modified lysine side chains.

Example 7. Identification of Beta-Amyloid Variants

Introduction and Significance

Alzheimer's is a neurogenerative disease that affects tens of millions of people worldwide and carries no clear genetic marker. A hallmark of Alzheimer's is the accumulation of mutated beta-amyloid proteins, creating plaques around neurons that disrupt normal cell function in the brain. The technology described herein may be used to sequence and identify key β-amyloid variants that are indicative of early-onset Alzheimer's, which enables understanding of the underlying disease's pathway to further optimize treatment responsiveness and identify targets with therapeutic potential.

Alzheimer's is a very complex disease and less than 1% of cases can be connected to a single inherited gene. Therefore, DNA sequencing alone can only give a limited view of the disease, its causes, and its pathways; further exploration of the disease mechanisms must occur at the protein level. There is evidence that point mutations in β-amyloid can lead to protein misfolding, which can contribute to the cause of disease or provide markers for early disease progression. Several variants of β-amyloid have been shown to induce misfolding, which exposes hydrophobic regions and causes protein deposition around neurons, then altering cellular function in the brain. The fibril forming peptides 16KLVF19 (SEQ ID NO: 843) and 17LVFF20 (SEQ ID NO: 844) have been explored for targeted drug developments via the β-sheet breaker mechanism.

Figure 17A:
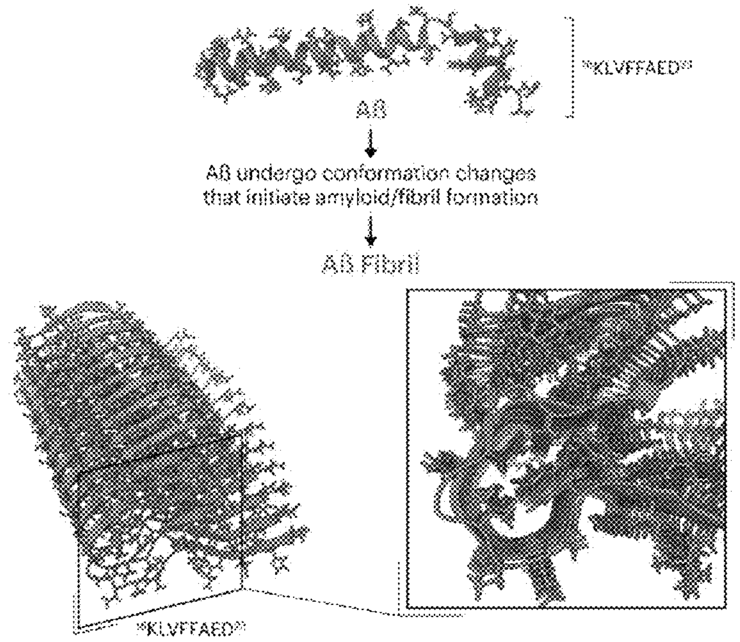
FIGS. 17A-17G illustrate aspects of an example application of the technology to identification of β-amyloid variants.

FIG. 17A illustrates an example of a β-amyloid variant. The β-amyloid variant induces misfolding of the protein, exposing hydrophobic regions, which induces aggregation. This alteration in structure morphs the β-amyloid into long filamentous chains or fibril formation, which generate insoluble deposits, which are referred to as pathological plaque.

The research around different types of recognizable proteins and potential PTMs has been largely limited in traditional proteomics. B-amyloid plaque formation is shown to be driven by a single mutation in a folded region of the protein, making their presence challenging to detect by legacy proteomic methods. Aspects of the technology described herein may be used to assess proteins at the individual amino acid level without the need for developing binding affinity assays, an invaluable tool to fully understand biological processes and monitor disease states directly.

Methodology and Workflow

Aspects of the technology described herein may be used for protein preparation, peptide library preparation, peptide sequencing and peptide profiling of synthetic samples of ß-amyloid. In this example, the wild type (LVFFAE (SEQ ID NO: 827)) and variants (17LVFFAK22 (SEQ ID NO: 828), 17LVFFGK22 (SEQ ID NO: 829), 17LVFFAG22 (SEQ ID NO: 830), and 17LVPFAE22 (SEQ ID NO: 831)) of β-amyloid were digested and labeled for further analysis. Alternatively, β-amyloid may be purified from common sources, such as cerebrospinal fluid (CSF), for downstream analysis.

Figure 17B:
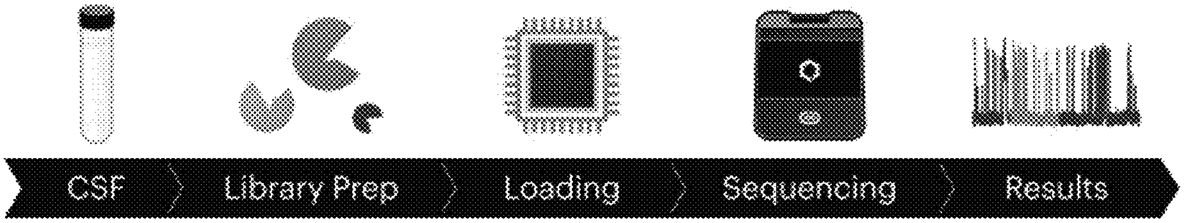
Figure 17C:
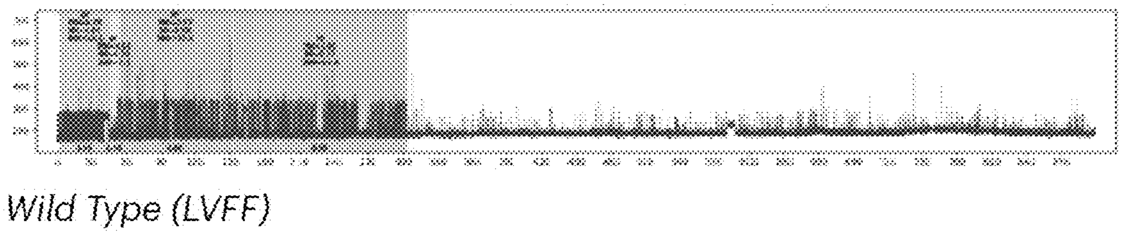
Figure 17D:
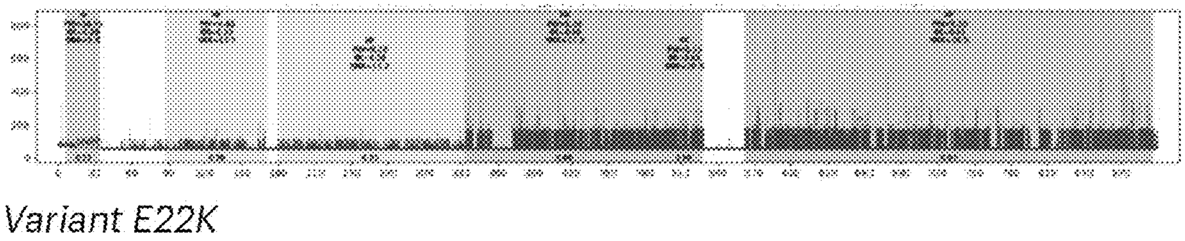
Figure 17E:
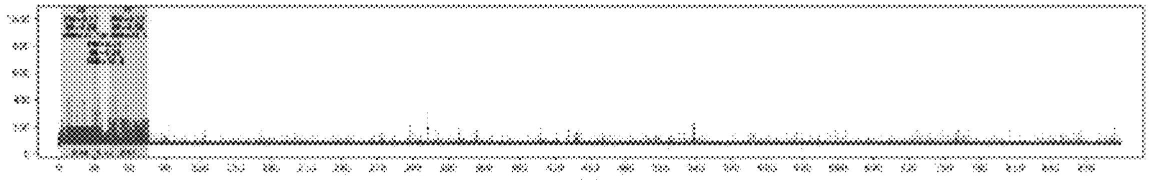
Figure 17F:
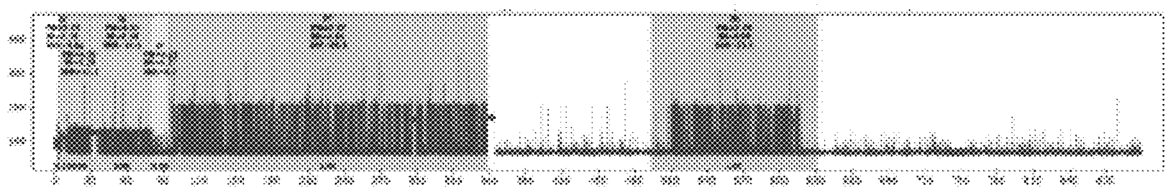
Figure 17G:
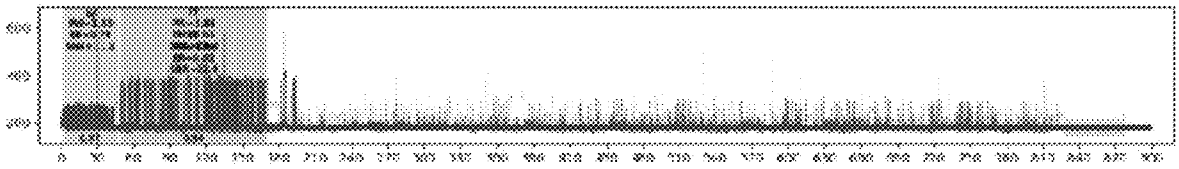

FIG. 17B illustrates an example workflow for β-amyloid variant detection. As shown in FIG. 17B, β-amyloid cerebrospinal fluid may be isolated. A peptide library may be prepared utilizing specific proteolytic enzymes. The sample may be loaded onto a chip, as described herein, and sequencing may be run. Results may include identification of amino acid sequences that demarcate potential Alzheimer's causing mutations.

A chip including aspects of the technology described herein was used for the downstream sequencing of the sample material. The chip contained millions of wells, each of which acted as an independent sequencing machine. Once the sample was loaded, cloud technology was used to set up the sequencing run and collect all the data for visualization. Once collected in the cloud, a set of proprietary algorithms, which can identify amino acids based on the specialized optical pulse patterns of each binding event, determined the sequence of the peptide and mapped that sequence back to a specific protein or protein variant.

Here, the protein sequencing technology and analysis pipeline was successfully used to distinguish a variety of clinically significant ß-amyloid point mutations. The sequencing traces containing pulse patterns of the variants, 17LVFFAK22 (SEQ ID NO: 828), 17LVFFGK22 (SEQ ID NO: 829), 17LVFFAG22 (SEQ ID NO: 830), and 17LVP-FAE22 (SEQ ID NO: 831), were compared to the wild type, 17LVFFAE22 (SEQ ID NO: 827). These patterns are shown in FIGS. 17C-17G. Software automatically identified pulses containing the same intensity, lifetime, and kinetics, which determined a recognition segment for a specific amino acid. Each recognition segment was color coded based on the N-terminal amino acid, and the collection of recognition segments provided a characteristic signature of the peptide.

Time domain sequencing functionality can observe sequence changes indirectly during peptide profiling. The specific PTMs and folding of each variant cause them to display distinctly different patterns, which can then be inferred via alterations in pulse width. For example, a point mutation in a sequence—at the N-terminal end, or at the penultimate and antepenultimate positions, of the peptide—can generate an altered pulse pattern, compared to another sequence.

TABLE 2

Average Pulse Width of Tripeptides and Variants

| Tripeptide | Variant | Average Pulse Width |
|---|---|---|
| LVX | WT | 3.26 (LVF) |
| | F19P | 1.86 (LVP) |
| FXX | WT | 2.43 (FAE) |
| | E22G | 2.99 (FAG) |
| | E22K | 2.79 (FAK) |
| | E22Q | 2.67 (FAQ) |
| | A21G | 1.31 (FGE) |

This was shown with the wild type tripeptide LVF and the tripeptide LVP from the F19P mutant. A mutation in the antepenultimate position changed the average pulse width when sequencing L from 3.26 seconds to 1.86 seconds. Likewise, the pulse width for the FAE tripeptide in the wild type changed from an average pulse width of 2.43 seconds to between 1.31 and 2.99 seconds for the mutants. Each change in pulse width provided a hint of change, and each amino acid was potentially interrogated three times when it was at the antepenultimate, penultimate, and N-terminal position. Integration of each piece of evidence can further improve the detection of mutations and PTMs.

This example demonstrates the ability to leverage aspects of the technology described herein to detect single amino acid changes known to be linked to disease progression and severity in β-amyloid. The ease of use and benchtop form factor make the technology described herein available to any lab to leverage in the analysis of other protein families to address a range of important questions related to cell and tissue function in regular and disease scenarios.

Example 8. Using Kinetic Signature Approach to Differentiate Disease-Relevant Peptides This example demonstrates use of the kinetic signature approach to differentiate citrullinated and non-citrullinated peptide fragments of vimentin protein. The presence of citrullinated vimentin in a sample from a subject (e.g., a human subject) may indicate that the subject has rheumatoid arthritis and/or a cancer.

In this example, two peptide fragments of vimentin, QP706 and QP1073, were obtained. The sequences of QP706 and QP1073 are shown in Table 3 (where Cit indicates citrulline). The two sequences are identical except that the arginine residue of QP706 is citrullinated in QP1073.

TABLE 3

Sequences of Vimentin Peptide Fragments

| Peptide | SEQ ID NO | Sequence |
|---|---|---|
| QP706 | 841 | VRFLEQQNK |
| QP1073 | 842 | VCitFLEQQNK |

Figure 18A:
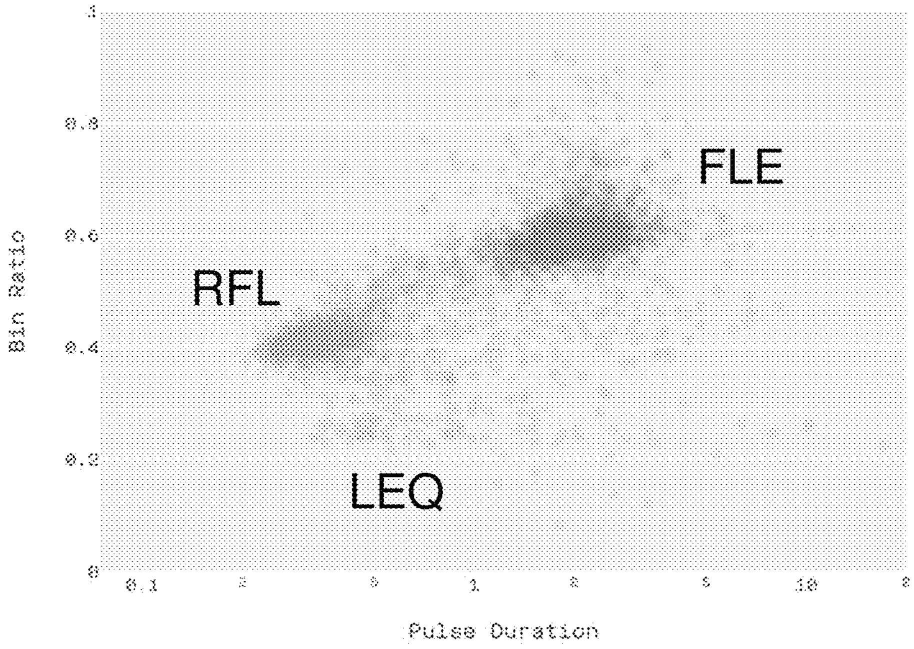
FIGS. 18A-18B show example results from sequencing reactions using the recognizers PS610, PS1220, and PS1223 for peptide fragments comprising unmodified arginine or citrulline.
Figure 18B:
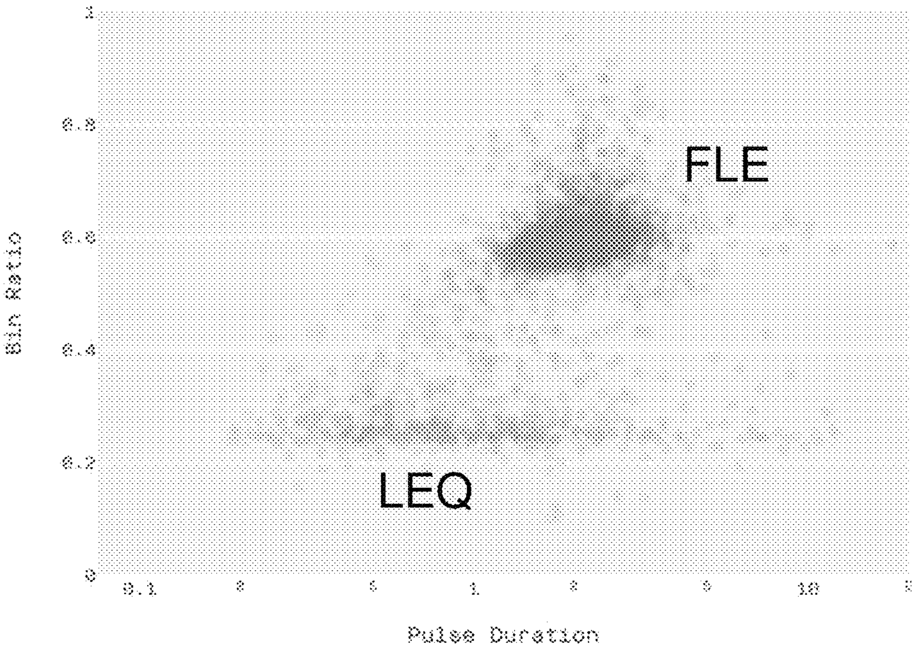

Sequencing reactions using the recognizers PS610 (FYW), PS1220 (R), and PS1223 (LIV) were performed separately for the QP706 and QP1073 peptide fragments. Each recognizer was labeled with a unique dye and/or unique number of dyes. A scatter plot of bin ratio v. pulse duration is shown for the QP706 peptide fragment in FIG. 18A and for the QP1073 peptide fragment in FIG. 18B. In the plot of FIG. 18A, three clusters corresponding to FLE, LEQ, and RFL segments are visible. The presence of these three clusters indicates that PS610 recognized the phenylalanine (F) residue, PS1223 recognized the leucine (L) residue, and PS1220 recognized the arginine (R) residue of QP706. In the plot of FIG. 18B, two clusters corresponding to FLE and LEQ segments are visible, but there is no cluster corresponding to RFL. This indicates that PS1220, which recognized the arginine (R) residue of QP706, did not recognize citrulline.

Figure 19A:
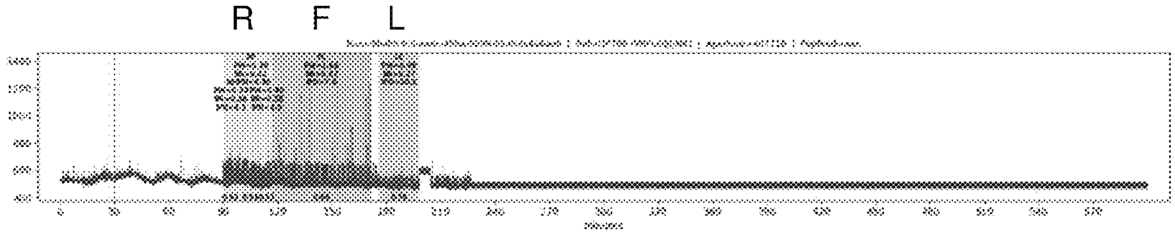
FIGS. 19A-19D show example results from sequencing reactions using the recognizers PS610, PS1220, and PS1223 for the peptide fragment VRFLEQQNK (SEQ ID NO: 841).
Figure 19B:
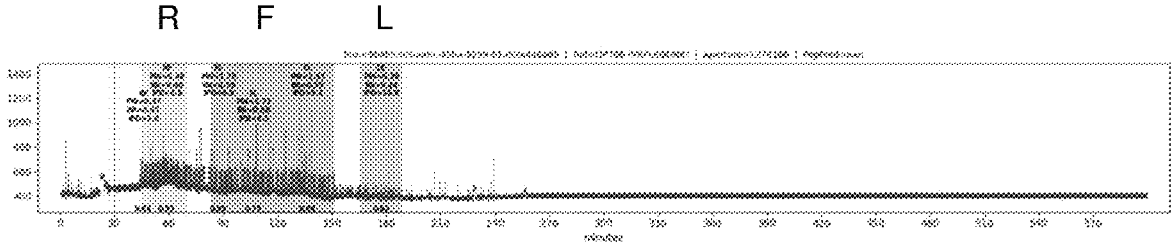
Figure 19C:
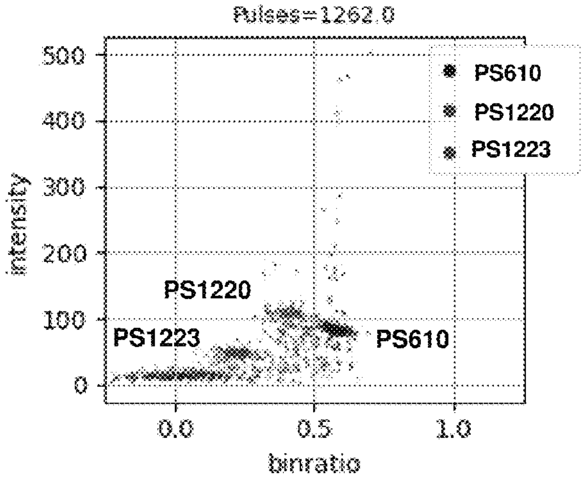
Figure 19D:
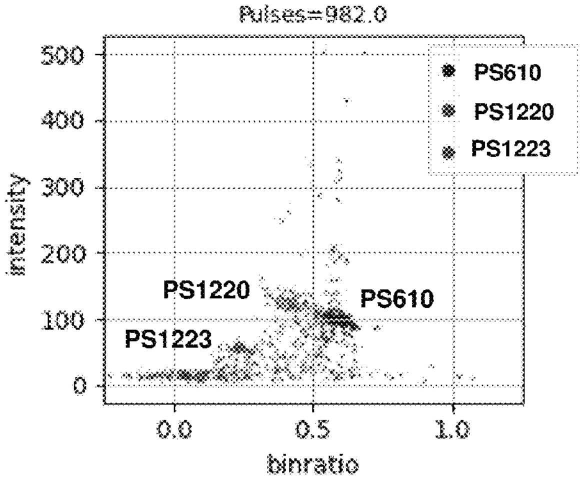
Figure 20A:
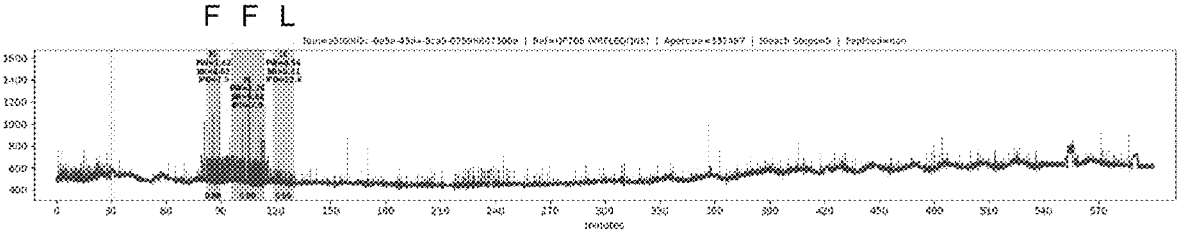
FIGS. 20A-20D show example results from sequencing reactions using the recognizers PS610, PS1220, and PS1223 for the peptide fragment VCitFLEQQNK (SEQ ID NO: 842), where Cit is citrulline.
Figure 20B:
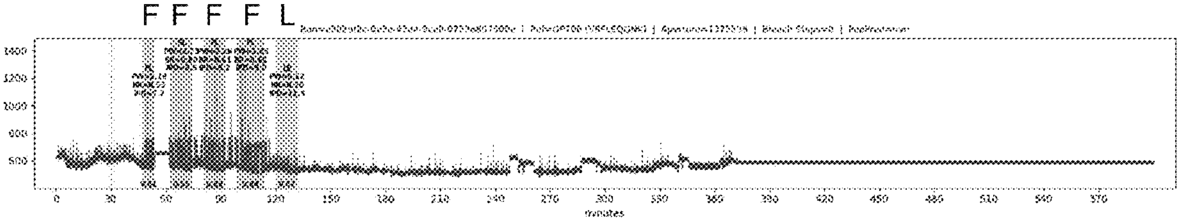
Figure 20C:
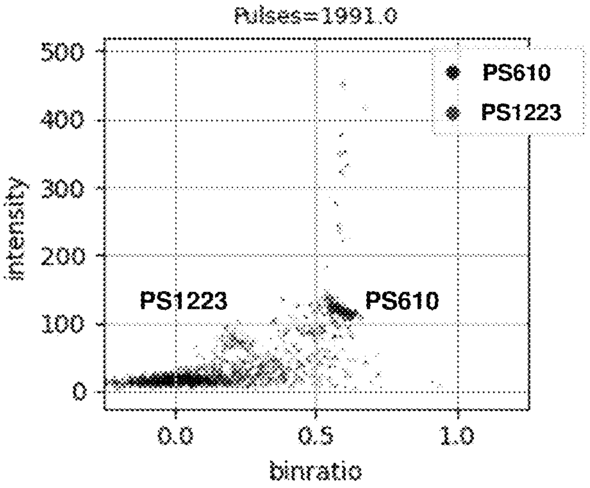
Figure 20D:
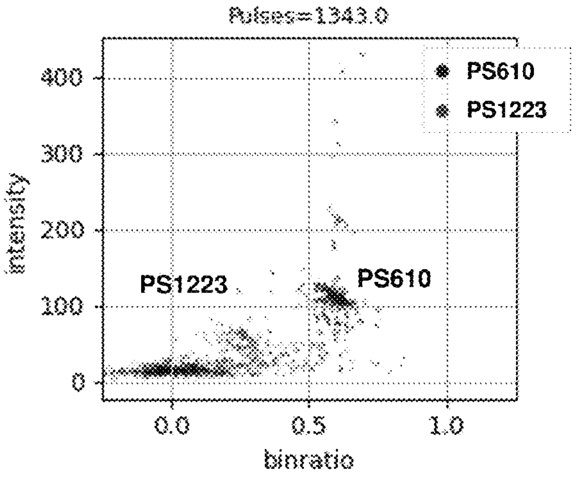

Results from additional sequencing reactions performed using the recognizers PS610 (FYW), PS1220 (R), and PS1223 (LIV) and the QP706 and QP1073 peptide fragments are shown in FIGS. 19A-19D and 20A-20D. Traces from the QP706 reactions are shown in FIGS. 19A-19B, and corresponding scatter plots of intensity v. bin ratio are shown in FIGS. 19C-19D. The traces shown in FIGS. 19A and 19B include recognition segments corresponding to arginine (R), phenylalanine (F), and leucine (L), and each of the plots of FIGS. 19C and 19D shows three separate clusters corresponding to PS610, PS1220, and PS1223. These results demonstrate recognition of the arginine (R) residue by PS1220, recognition of the phenylalanine (F) residue by PS610, and recognition of the leucine (L) residue by PS1223 for the QP706 peptide fragment. Traces from the QP1073 reactions are shown in FIGS. 20A-20B, and the corresponding scatter plots of intensity v. bin ratio are shown in FIGS. 20C-20D. The traces shown in FIGS. 20A and 20B include recognition segments corresponding to phenylalanine (F) and leucine (L) but do not include any recognition segments corresponding to arginine (R). Similarly, each of the plots of FIGS. 20C and 20D shows two separate clusters corresponding to PS610 and PS1223 but does not show a cluster corresponding to PS1220. These results demonstrate that PS1220 does not recognize the citrulline residue of the QP1073 peptide fragment.

Thus, the results of this example suggest that the absence of signal pulses from an arginine recognizer (e.g., PS1220) in a reaction with a peptide expected to contain arginine may indicate the presence of citrulline (i.e., citrullination of an arginine residue). These results demonstrate the ability to discriminate between unmodified and post-translationally modified arginine residues based on the absence of pulses from arginine recognizers. As demonstrated in this example, this ability to discriminate between unmodified and post-translationally modified arginine residues may be used to detect a disease-relevant peptide, such as a fragment of citrullinated vimentin. Detection of the disease-relevant peptide may be used as a clinical diagnostic tool to diagnose a disease, such as rheumatoid arthritis and/or a cancer, in a subject from which the disease-relevant peptide was obtained.

Example 9. Pulsing Characterization of Citrulline-Containing Peptides

This example demonstrates that signal pulse characteristics (e.g., pulse width) associated with recognition of an N-terminal acid of a peptide may be affected by the presence of a penultimate citrulline residue. In this example, sequencing reactions were conducted for 4 pairs of unmodified and citrullinated peptides: QP1028 & QP1029, QP1030 & QP1031, QP1032 & QP1033, and QP707 & QP789. The sequences of each peptide are shown in Table 4. The sequences of each pair of peptides were identical except that one peptide had an unmodified arginine residue and one peptide had a corresponding citrulline residue. For the QP1028 & QP1029 and QP1030 & QP1031 pairs, sequencing reactions were conducted using the PS610 (FYW) recognizer. For the QP1032 & QP1033 and QP707 & QP789 pairs, sequencing reactions were conducted using the PS1223 (LIV) recognizer.

Pulse widths associated with recognition of the N-terminal amino acid of each peptide are shown in Table 4. In each pair of peptides, an N-terminal amino acid (X) was followed by either unmodified arginine (X-R) or citrulline (X-Cit). Table 4 shows that presence of a citrulline residue in the penultimate position (i.e., immediately adjacent to the N-terminal amino acid) may affect (e.g., increase) pulse width. For example, Table 4 shows that the pulse width associated with recognition of phenylalanine (F) followed by unmodified arginine (R) in QP1028 was 4.94 seconds, while the pulse width associated with recognition of phenylalanine (F) followed by citrulline (Cit) in QP1029 was 5.24 seconds. Similarly, Table 4 shows that the pulse width associated with recognition of tyrosine (Y) followed by unmodified arginine (R) in QP1030 was 0.77 seconds, while the pulse width associated with recognition of tyrosine (Y) followed by citrulline (Cit) in QP1031 was 1.12 seconds. As shown in Table 4, it was found that the pulse width was longer for an N-terminal amino acid followed by citrulline compared to an N-terminal amino acid followed by an unmodified arginine. This trend was observed for both PS610 and PS1223. Thus, these results demonstrate the ability to discriminate between peptides containing unmodified arginine and citrulline residues based on pulse width associated with recognition of the immediately upstream amino acid. These results also demonstrate that recognizers provide information concerning the presence and configuration of residues beyond the subset of terminal amino acids with which the recognizers are associated. For example, PS610 (associated with N-terminal FYW) and PS1223 (associated with N-terminal LIV), which are not recognizers for N-terminal arginine, nonetheless exhibit binding kinetics that provide valuable information about arginine (modified or unmodified) when arginine is situated adjacent to the N-terminal end of a peptide.

TABLE 4

Pulse Widths of Unmodified and Citrullinated Peptides

| Peptide | SEQ ID NO | Sequence | Recognizer | Pulse Width (s) |
|---|---|---|---|---|
| QP1028 | 845 | FRLAFAYPDDDK | PS610 | 4.94 |
| QP1029 | 846 | FCitLAFAYPDDDK | PS610 | 5.24 |
| QP1030 | 847 | YRIAFAYPDDDK | PS610 | 0.77 |
| QP1031 | 848 | YCitIAFAYPDDDK | PS610 | 1.12 |
| QP1032 | 849 | IRLAFAYPDDDK | PS1223 | 0.58 |
| QP1033 | 850 | ICitLAFAYPDDDK | PS1223 | 0.84 |
| QP707 | 817 | LRLAFAYPDDDK | PS1223 | 0.42 |
| QP789 | 839 | LCitLAFAYPDDDK | PS1223 | 0.92 |

Example 10. Kinetic Differential Between ADMA and Arginine

This example demonstrates that signal pulse characteristics (e.g., pulse width, recognition segment duration) may be affected by modification of an arginine residue to asymmetric dimethyl arginine (ADMA). In this example, sequencing reactions were performed using PS621 (R), PS610 (FYW), and PS961 (LIV) recognizers for 9 pairs of peptides. Each pair comprised one peptide comprising an unmodified arginine residue followed by a non-arginine amino acid (referred to as an R-X peptide) and one peptide having an identical sequence except that the unmodified arginine was modified to be ADMA (referred to as an ADMA-X peptide). The sequences of the R-X and ADMA-X peptides are shown in Table 5.

TABLE 5

Sequences of ADMA and Unmodified Arginine Peptides

| Peptide | SEQ ID NO | Sequence |
|---|---|---|
| QP707 | 817 | LRLAFAYPDDDK |
| QP729 | 910 | LR$_{ADMA}$LAFAYPDDDK |
| QP749 | 911 | LRIAFAYPDDDK |
| QP745 | 912 | LR$_{ADMA}$IAFAYPDDDK |
| QP746 | 913 | LRYAFAYPDDDK |
| QP742 | 914 | LR$_{ADMA}$YAFAYPDDDK |
| QP748 | 915 | LRSAFAYPDDDK |
| QP744 | 916 | LR$_{ADMA}$SAFAYPDDDK |
| QP747 | 917 | LRAAFAYPDDDK |
| QP743 | 918 | LR$_{ADMA}$AAFAYPDDDK |
| QP938 | 919 | LREAFAYPDDDK |
| QP939 | 920 | LR$_{ADMA}$EAFAYPDDDK |
| QP942 | 921 | LRTAFAYPDDDK |
| QP945 | 922 | LR$_{ADMA}$TAFAYPDDDK |
| QP941 | 923 | LRQAFAYPDDDK |
| QP944 | 924 | LR$_{ADMA}$QAFAYPDDDK |
| QP943 | 925 | LRVAFAYPDDDK |
| QP946 | 926 | LR$_{ADMA}$VAFAYPDDDK |

Pulse widths and RS durations for R-X and ADMA-X peptides were obtained. For each peptide, pulse width and RS duration values were obtained by averaging results from 10 sequencing reactions. Table 6 shows the identity of X for each pair of peptides, along with the corresponding pulse width and RS duration values. As shown in Table 6, pulse widths were longer for almost all ADMA-X peptides relative to corresponding R-X peptides. In almost all cases where the pulse width of the R-X peptide was short (e.g. less than 0.12 s or 0.06 s), the pulse width of the corresponding ADMA-X peptide was longer. Additionally, RS durations were longer for ADMA-X peptides relative to corresponding R-X peptides. These results suggest that ADMA may be a better binder (e.g., bind more strongly to an arginine recognizer) than unmodified arginine, and they demonstrate the ability to discriminate between peptides comprising unmodified arginine and ADMA.

TABLE 6

Kinetic Information for Peptides Comprising ADMA or Unmodified Arginine

| Peptide Pairs | X | PW of R-X (s) | PW of ADMA-X (s) | RS R-X (min) | RS ADMA-X (min) |
|---|---|---|---|---|---|
| QP707/QP729 | L | 0.47 | 0.48 | 17.3 | 48.5 |
| QP749/QP745 | I | 0.28 | 0.32 | 15.4 | 46.9 |
| QP746/QP742 | Y | 0.18 | 0.25 | 9.6 | 39.2 |
| QP748/QP744 | S | <0.12 | 0.55 | — | — |
| QP747/QP743 | A | <0.12 | 0.19 | — | — |
| QP938/QP939 | E | <0.06 | 0.34 | — | — |
| QP942/QP945 | T | <0.06 | <0.06 | — | — |
| QP941/QP944 | Q | <0.06 | 0.21 | — | — |
| QP943/QP946 | V | 0.41 | 0.32 | 25.5 | 33.8 |

Example 11. Protein Identification Via Next-Generation Protein Sequencing and Proteome-Wide Mapping In this example, proteins were sequenced using real-time dynamic sequencing. Briefly, proteins were digested into peptide fragments and conjugated to macromolecular linkers. The conjugated peptides were then immobilized on a semiconductor chip with exposed N-termini for sequencing. Dye-labeled recognizers bound on and off to N-terminal amino acids (NAAs), generating pulsing patterns with characteristic fluorescence and kinetic properties. Aminopeptidases in solution sequentially removed individual NAAs to expose subsequent amino acids for recognition. Fluorescence lifetime, intensity, and kinetic data were collected in real time and analyzed to determine amino acid sequence. The sequencing profiles of peptides were visualized as kinetic signature plots—simplified trace-like representations of the time course of complete peptide sequencing containing the median pulse duration (PD) for each RS and the average duration of each RS and non-recognition segment (NRS).

A kinetic model that accurately predicts the PD for every possible 4-amino-acid sequence that starts with an N-terminal recognizer target was developed. The kinetic model allowed prediction of the kinetic signature for every peptide in a protein database of interest, for example the entire human proteome. Analysis software that automatically identified clusters of traces with highly similar patterns and generated an empirical kinetic signature for each cluster was also developed. With the kinetic model and clustering software, empirical kinetic signatures were generated from protein sequencing data and the protein of origin in the proteome was pinpointed by identifying peptides with matching predicted kinetic signatures.

The human protein cerebral dopamine neurotrophic factor (CDNF, 161 amino acids) was used to demonstrate protein identification from sequencing data based on the kinetic model and proteome mapping software. Recombinant CDNF was sequenced using a set of four recognizers—a recognizer recognizing N-terminal arginine (R), a recognizer recognizing N-terminal L, I, and V, a recognizer recognizing F, Y, and W, and PS1259, which recognizes N-terminal glutamine (Q) and asparagine (N) amino acids. This set of four recognizers recognized a total of 9 NAAs. CDNF was digested using the endopeptidase Lys-C and prepared a peptide library for on-chip sequencing. Sequencing analysis indicated that five peptides were expected to be readily observed on-chip because they were predicted to produce informative kinetic signatures with four or more RSs.

TABLE 7

Sequences of CDNF Peptides

| Peptide | SEQ ID NO | Sequence |
|---|---|---|
| 1 | 851 | EFLNRFYK |
| 2 | 852 | SLIDRGVNFSLDTIEK |
| 3 | 853 | ELISFCLDTK |
| 4 | 854 | ENRLCYYLGATK |
| 5 | 855 | TDYVNLIQELAPK |

Figure 21A:
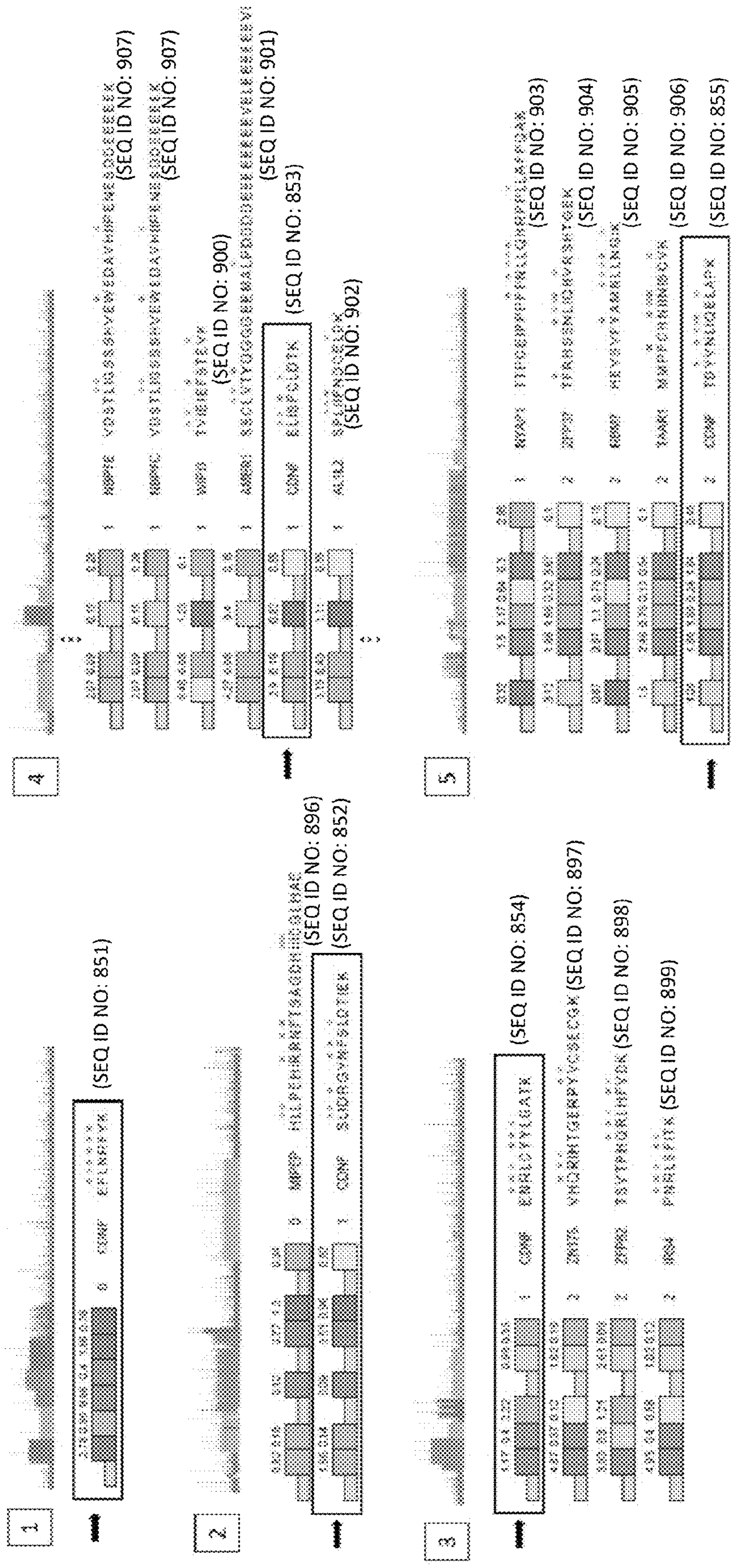
FIGS. 21A-21B show example results of mapping kinetic signatures to the human proteome.

Five main clusters of traces were identified in the sequencing output based on similarity of the pattern and kinetics of recognition using analysis software. The analysis software produced a characteristic kinetic signature summarizing the pattern of recognition and average PD for the traces grouped in each cluster. These kinetic signatures were then used as input into a mapping algorithm to identify potential matches across the entire human proteome. The database of candidate peptides consisted of over 300,000 peptides of 8 or more amino acids in length derived from an in silico digest of the human proteome, representing roughly 20,000 human proteins. FIG. 21A shows the results of proteome-wide mapping. Candidate matching peptides are shown for each cluster, with candidates corresponding to CDNF peptides outlined. The number to the right of each predicted kinetic signature indicates the number of RS s with predicted average PD that were not very close matches to the observed PD, which can be used as a ranking metric.

Figure 21B:
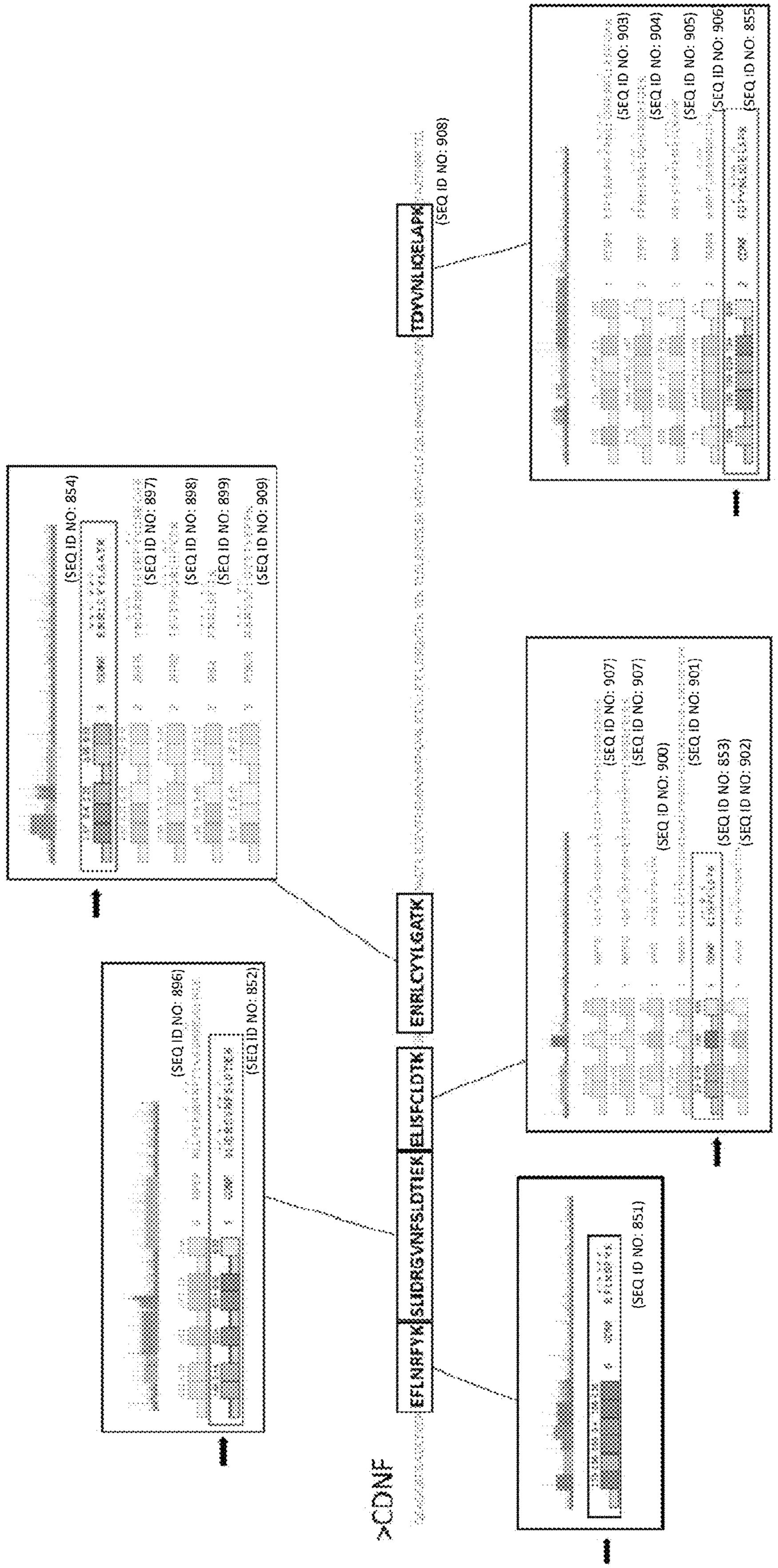

Each of the 5 kinetic signatures mapped to a set of candidate proteins that included CDNF as a top match or as the only match. Signatures containing 5 or more RSs were particularly successful at pinpointing CDNF, generating sets with 5 or fewer matching candidate proteins. Taken together, these results identified CDNF as the only human protein capable of generating the complete observed sequencing output with extremely high confidence, as shown in FIG. 21B.

In this example, sequencing data was matched with the human proteome for protein identification. It was shown that sequencing data from multiple peptide fragments can be used to generate highly characteristic kinetic signatures and identify a protein by mapping to the human proteome based on the predicted kinetic signatures of human peptides. These results demonstrate the ability to identify known or unknown proteins in biological samples via proteome-wide mapping with high accuracy.

EQUIVALENTS AND SCOPE

In the claims articles such as “a,” “an,” and “the” may mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the application describes "a composition comprising A and B," the application also contemplates the alternative embodiments "a composition consisting of A and B" and "a composition consisting essentially of A and B."

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

What is claimed is:

1. A method for determining chemical characteristics of a polypeptide, comprising:

contacting a polypeptide with one or more amino acid recognizers, wherein the one or more amino acid recognizers comprise a first set of one or more amino acid recognizers that bind to the polypeptide;

detecting a first series of signal pulses indicative of a first series of binding events between a first type of amino acid recognizer of the first set of one or more amino acid recognizers and the polypeptide, wherein the first series of binding events occur while the same terminal amino acid is present at a terminus of the polypeptide; and determining at least one chemical characteristic of a first set of at least two amino acids of the polypeptide based on at least one characteristic of the first series of signal pulses.

2. The method of claim 1, wherein the first series of binding events is between the first set of one or more amino acid recognizers and a first amino acid of the polypeptide.

3. The method of claim 2, wherein the first amino acid is a terminal amino acid of the polypeptide.

4. The method of claim 2, wherein the first amino acid is an internal amino acid of the polypeptide.

5. The method of claim 2, wherein the first set of at least two amino acids of the polypeptide comprises the first amino acid of the polypeptide.

6. The method of claim 5, wherein the first set of at least two amino acids comprises a second amino acid, and wherein the first amino acid and the second amino acid are separated by at least one other amino acid in the polypeptide.

7. The method of claim 1, wherein the first set of at least two amino acids comprises at least three amino acids.

8. The method of claim 1, wherein the first set of at least two amino acids does not consist of the terminal amino acid and a penultimate amino acid of the polypeptide.

9. The method of any claim 1, wherein at least one amino acid recognizer of the first set of one or more amino acid recognizers comprises a detectable label.

10. The method of claim 1, wherein the at least one characteristic of the first series of signal pulses comprises a first pulse duration, a first interpulse duration, and/or a first recognition segment duration.

11. The method of claim 1, further comprising:

detecting a second series of signal pulses indicative of a second series of binding events between a second type of amino acid recognizer of a second set of one or more amino acid recognizers that bind to the polypeptide, wherein the second series of binding events occur while a second same terminal amino acid is present at the terminus of the polypeptide; and determining at least one chemical characteristic of a second set of at least two amino acids of the polypeptide based on at least one characteristic of the second series of signal pulses.

12. The method of claim 11, wherein the second set of at least two amino acids of the polypeptide comprises at least one amino acid of the first set of at least two amino acids.

13. The method of claim 1, wherein determining at least one chemical characteristic of the first set of at least two amino acids comprises identifying a modification of at least one amino acid of the first set of at least two amino acids.

14. The method of claim 13, wherein the modification comprises methylation, citrullination, acetylation, phosphorylation, a covalent or non-covalent bond between the at least one amino acid and a binding component, and/or a mutation relative to a wild type protein.

15. The method of claim 14, wherein the modification comprises methylation and/or citrullination, and wherein at least one amino acid comprises an arginine.

16. The method of any claim 13, wherein the modification affects the at least one characteristic of the first series of signal pulses.

17. The method of claim 1, further comprising identifying the polypeptide based on the determined at least one chemical characteristic of the first set of at least two amino acids.

18. The method of claim 1, further comprising:

loading a sample onto a device, wherein the sample comprises a mixture of the polypeptide and a second polypeptide;

detecting a second series of signal pulses indicative of a second series of binding events between a second type of amino acid recognizer of a second set of one or more amino acid recognizers and the second polypeptide, wherein the second series of binding events occur while a second same amino acid is present at a terminus of the second polypeptide, and the first series of signal pulses and the second series of signal pulses are detected while the polypeptide and the second polypeptide are disposed in different chambers of the device; and determining at least one chemical characteristic of at least two amino acids of the second polypeptide based on at least one characteristic of the second series of signal pulses.

* * * * *

SEQUENCE LISTING

```
Sequence total quantity: 926
SEQ ID NO: 1            moltype = AA  length = 119
FEATURE                 Location/Qualifiers
```

```
source                  1..119
                        mol_type = protein
                        organism = synthetic construct
SEQUENCE: 1
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DRLLARSKGS MKASIEAEE   119

SEQ ID NO: 2            moltype = AA  length = 83
FEATURE                 Location/Qualifiers
source                  1..83
                        mol_type = protein
                        organism = synthetic construct
SEQUENCE: 2
MHSKFSHAGR ICGAKFKVGE PIYRCKECSF DDTCVLCVNC FNPKDHTGHH VYTTICTEFN  60
NGICDCGDKE AWNHTLFCKA EEG                                          83

SEQ ID NO: 3            moltype = AA  length = 200
FEATURE                 Location/Qualifiers
source                  1..200
                        mol_type = protein
                        organism = synthetic construct
SEQUENCE: 3
MNGLSAQHER IAPARHECVY TSCYCEENVW KLCEHIKTSK RCPLGDVYAV FISNERKMVP  60
IWKQKSGRGE EPVIWDYHVI LLHDCHKEQT FIYDLDTTLP FPCPFDTYVK EAFKSDNYIN  120
PAFWRKLRVV PADVFLQNFA SDRSHMKDAS GGWRMPPPPY PCIETAESRM NLDDFISMNP  180
SVGWGHVYTL EEFVQHFGKT                                              200

SEQ ID NO: 4            moltype = AA  length = 103
FEATURE                 Location/Qualifiers
source                  1..103
                        mol_type = protein
                        organism = synthetic construct
SEQUENCE: 4
MSDSPVDLKP KPKVKPKLER PKLYKVMLLN DDYTTAFFVT KVLKAVFRMS EDTGRRVMMT  60
AHRFGSAVVV VCERDIAETK AKEATDLGKE AGFPLMFTTE PEE                    103

SEQ ID NO: 5            moltype = AA  length = 103
FEATURE                 Location/Qualifiers
source                  1..103
                        mol_type = protein
                        organism = synthetic construct
SEQUENCE: 5
MSDSPVDLKP KPKVKPKLER PKLYKVMLLN DDYTTMRFVT LVLKAVFRMS EDTGRRVMMT  60
AHRFGSAVVV VCERDIAETK AKEATDLGKE AGFPLMFTTE PEE                    103

SEQ ID NO: 6            moltype = AA  length = 233
FEATURE                 Location/Qualifiers
source                  1..233
                        mol_type = protein
                        organism = synthetic construct
SEQUENCE: 6
MLSATRRALQ LFHSLFPIPR MGDSAAKIVS PQEALPGRKE PLVVAAKHHV NGNRTVEPFP  60
EGTQMAVFGM GCFWGAERKF WTLKGVYSTQ VGFAGGYTPN PTYKEVCSGK TGHAEVVRVV  120
FQPEHISFEE LLKVFWENHD PTQGMRQGND HGSQYRSAIY PTSAEHVGAA LKSKEDYQKV  180
LSEHGFGLIT TDIREGQTFY YAEDYHQQYL SKDPDGYCGL GGTGVSCPLG IKK         233

SEQ ID NO: 7            moltype = AA  length = 233
FEATURE                 Location/Qualifiers
source                  1..233
                        mol_type = protein
                        organism = synthetic construct
SEQUENCE: 7
MLSATRRALQ LFHSLFPIPR MGDSAAKIVS PQEALPGRKE PLVVAAKHHV NGNRTVEPFP  60
EGTQMAVFGM GSFWGAERKF WTLKGVYSTQ VGFAGGYTPN PTYKEVCSGK TGHAEVVRVV  120
FQPEHISFEE LLKVFWENHD PTQGMRQGND HGSQYRSAIY PTSAEHVGAA LKSKEDYQKV  180
LSEHGFGLIT TDIREGQTFY YAEDYHQQYL SKDPDGYCGL GGTGVSCPLG IKK         233

SEQ ID NO: 8            moltype = AA  length = 106
FEATURE                 Location/Qualifiers
source                  1..106
                        mol_type = protein
                        organism = synthetic construct
SEQUENCE: 8
MAFPARGKTA PKNEVRRQPP YNVILLNDDD TTYRYVIEML QKIFGFPPEK GFQIAEEVDR  60
TGRVILLTTS KEHAELKQDQ VHSYGPDPYL GRPCSGSMTC VIEPAV                 106

SEQ ID NO: 9            moltype = AA  length = 106
FEATURE                 Location/Qualifiers
source                  1..106
```

```
                        mol_type = protein
                        organism = synthetic construct
SEQUENCE: 9
MAFPARGKTA PKNEVRRQPP YNVILLDDDD HTYRYVIEML QKIFGFPPEK GFQIAEEVDR  60
TGRVILLTTS KEHAELKQDQ VHSYGPDPYL GRPCSGSMTC VIEPAV                106

SEQ ID NO: 10           moltype = AA  length = 106
FEATURE                 Location/Qualifiers
source                  1..106
                        mol_type = protein
                        organism = synthetic construct
SEQUENCE: 10
MAFPARGKTA PKNEVRRQPP YNVILLKDDD HTYRYVIEML QKIFGFPPEK GFQIAEEVDR  60
TGRVILLTTS KEHAELKQDQ VHSYGPDPYL GRPCSGSMTC VIEPAV                106

SEQ ID NO: 11           moltype = AA  length = 106
FEATURE                 Location/Qualifiers
source                  1..106
                        mol_type = protein
                        organism = synthetic construct
SEQUENCE: 11
MAFPARGKTA PKNEVRRQPP YNVILLNKDD HTYRYVIEML QKIFGFPPEK GFQIAEEVDR  60
TGRVILLTTS KEHAELKQDQ VHSYGPDPYL GRPCSGSMTC VIEPAV                106

SEQ ID NO: 12           moltype = AA  length = 106
FEATURE                 Location/Qualifiers
source                  1..106
                        mol_type = protein
                        organism = synthetic construct
SEQUENCE: 12
MAFPARGKTA PKNEVRRQPP YNVILLNDDD HTYRYVIEML QKIFGFPPEK GFQIAEEVHR  60
TGRVILLTTS KEHAELKQDQ VHSYGPDPYL GRPCSGSMTC VIEPAV                106

SEQ ID NO: 13           moltype = AA  length = 106
FEATURE                 Location/Qualifiers
source                  1..106
                        mol_type = protein
                        organism = synthetic construct
SEQUENCE: 13
MAFPARGKTA PKNEVRRQPP YNVILLNDDN HTYRYVIEML QKIFGFPPEK GFQIAEEVDR  60
TGRVILLTTS KEHAELKQDQ VHSYGPDPYL GRPCSGSMTC VIEPAV                106

SEQ ID NO: 14           moltype = AA  length = 83
FEATURE                 Location/Qualifiers
source                  1..83
                        mol_type = protein
                        organism = synthetic construct
SEQUENCE: 14
MGSVHKHTGR NCGRKFKIGE PLYRCHECGC DDTCVLCIHC FNPKDHVKHH VCTDICTEFT  60
SGICDCGDEE AWNSPLHCKA EEQ                                         83

SEQ ID NO: 15           moltype = AA  length = 292
FEATURE                 Location/Qualifiers
source                  1..292
                        mol_type = protein
                        organism = synthetic construct
SEQUENCE: 15
MTSLNIMGRK FILERAKRND NIEEIYTSAY VSLPSSTDTR LPHFKAKEED CDVYEEGTNL  60
VGKNAKYTYR SLGRHLDFLR PGLRFGGSQS SKYTYYTVEV KIDTVNLPLY KDSRSLDPHV  120
TGTFTIKNLT PVLDKVVTLF EGYVINYNQF PLCSLHWPAE ETLDPYMAQR ESDCSHWKRF  180
GHFGSDNWSL TERNFGQYNH ESAEFMNQRY IYLKWKERFL LDDEEQENQM LDDNHHLEGA  240
SFEGFYYVCL DQLTGSVEGY YYHPACELFQ KLELVPTNCD ALNTYSSGFE IA         292

SEQ ID NO: 16           moltype = AA  length = 609
FEATURE                 Location/Qualifiers
source                  1..609
                        mol_type = protein
                        organism = synthetic construct
SEQUENCE: 16
MGSSHHHHHH HHHHSSGLVP RGSHMQIFVK TLTGKTITLE VEPSDTIENV KAKIQDKEGI  60
PPDQQRLIFA GKQLEDGRTL SDYNIQKEST LHLVLRLRGG MASVVEYKGL KAGYYCGYCE  120
SREGKTSCGM WAHSMTVQDY QDLIDRGWRR SGKYVYKPVM DQTCCPQYTI RCHPLQFQPS  180
KSHKKVLKKM LKFLAKGEIS KGNCEDEPMD STVEDAVDGD FALINKLDIK CDLKTLSDLK  240
GSIESEEKEK EKSIKKEGSK EFIHPQSIEE KLGSGEPSHP IKVHIGPKPG KGADLSKPPC  300
RKAREMRKER QRLKRMQQAS AAASEAQGQP VCLLPKAKSN QPKSLEDLIF QSLPENASHK  360
LEVRLVPASF EDPEFNSSFN QSFSLYTKYQ VAIHQEAPEI CEKSEFTRFL CSSPLEAEHP  420
ADGPECGYGS FHQQYWLDGK IIAVGVLDIL PYCVSSVYLY YDPDYSFLSL GVYSALREIA  480
FTRQLHEKTS QLSYYYMGFY IHSCPKMRYK GQYRPSDLLC PETYVWVPIE QCLPSLDNSK  540
YCRFNQDPEA EDEGRSKELD RLRVFHRRSA MPYGVYKNHQ EDPSEEAGVL EYANLVGQKC  600
```

```
SERMLLFRH                                                       609

SEQ ID NO: 17          moltype = AA  length = 109
FEATURE                Location/Qualifiers
source                 1..109
                       mol_type = protein
                       organism = synthetic construct
SEQUENCE: 17
MSEPMTLPAI PQPRLKERTQ RQPPYNVILL NDDDKSYEYV AAMLQVLFGY PPEKGYQMAK  60
EVDSTGRVIL LTTTREHAEL KQEQIHAFGP DPNQARNSGS MKAVIEPAV             109

SEQ ID NO: 18          moltype = AA  length = 109
FEATURE                Location/Qualifiers
source                 1..109
                       mol_type = protein
                       organism = synthetic construct
SEQUENCE: 18
MSEPMTLPAI PQPRLKERTQ RQPPYNVILL NDDDKSYEYV IAMLQVLFGY PPEKGYQMAK  60
EVDSTGRVIL LTTTREHAEL KQEQIHAFGP DPNQARNSGS MKAVIEPAV             109

SEQ ID NO: 19          moltype = AA  length = 109
FEATURE                Location/Qualifiers
source                 1..109
                       mol_type = protein
                       organism = synthetic construct
SEQUENCE: 19
MSEPMTLPAI PQPRLKERTQ RQPPYNVIIL NDDDKSFEYV AAMLQVLFGY PPEKGYQMAK  60
EIDSTGRVIM LTTTREHAEL KQEQIHAFGP DPNQARNSGS MKAVIEPAV             109

SEQ ID NO: 20          moltype = AA  length = 109
FEATURE                Location/Qualifiers
source                 1..109
                       mol_type = protein
                       organism = synthetic construct
SEQUENCE: 20
MSEPMTLPAI PQPRLKERTQ RQPPYNVIIL NDDDKSFEYV AALLQVLFGY PPEKGYQMAK  60
EIDSTGRVIM LTTTREHAEL KQEQIHAFGP DPNQARNSGS MKAVIEPAV             109

SEQ ID NO: 21          moltype = AA  length = 109
FEATURE                Location/Qualifiers
source                 1..109
                       mol_type = protein
                       organism = synthetic construct
SEQUENCE: 21
MSEPMTLPAI PQPRLKERTQ RQPPYNVIVL NDDDKSFEYV AAMLQVLFGY PPEKGYQVAK  60
EIDSTGRVIT LTTTREHAEL KQEQIHAFGP DPNQARNSGS MKAVIEPAV             109

SEQ ID NO: 22          moltype = AA  length = 119
FEATURE                Location/Qualifiers
source                 1..119
                       mol_type = protein
                       organism = synthetic construct
SEQUENCE: 22
MPTAASATES AIEDTPAPAR PEVDGRTKPK RQPRYHVVQW NDDRHTYQYT VVMFQSLFGH  60
PPERGYRLAK ESDTQGRIIV LTTTREHAEL KRDQIHAFGY DRLLARDKGS YKASIEAEE   119

SEQ ID NO: 23          moltype = AA  length = 143
FEATURE                Location/Qualifiers
source                 1..143
                       mol_type = protein
                       organism = synthetic construct
SEQUENCE: 23
HHHHHHHHHH DYDIPTTENL YFQGMPTAAS ATESAIEDTP APARPEVDGR TKPKRQPRYH  60
VVLWNDDDHT YQYVVVMLQS LFGHPPERGY RLAKEVDTQG RVIVLTTTRE HAELKRDQIH  120
AFGYDRLLAR SKGSMKASIE AEE                                         143

SEQ ID NO: 24          moltype = AA  length = 119
FEATURE                Location/Qualifiers
source                 1..119
                       mol_type = protein
                       organism = synthetic construct
SEQUENCE: 24
MPTAASATES AIEDTPAPAR PEVDGRTKPK RQPRYHVVQW NDDRHTYQYT VVMFQSLFGH  60
PPERGYRLAK ESDTQGRIIV LTTTREHAEL KRDQIHAFGY DPLQSGDKGS YKASIEAEE   119

SEQ ID NO: 25          moltype = AA  length = 119
FEATURE                Location/Qualifiers
source                 1..119
                       mol_type = protein
```

```
                         organism = synthetic construct
SEQUENCE: 25
MPTAASATES AIEDTPAPAR PEVDGRTKPK RQPRYHVVAW NDDRHTYQYT VVMFQSLFGH  60
PPERGYRLAK EQDTQGRIIV LTTTREHAEL KRDQIHAFGY DPLQSGDKGS YKASIEAEE   119

SEQ ID NO: 26            moltype = AA  length = 119
FEATURE                  Location/Qualifiers
source                   1..119
                         mol_type = protein
                         organism = synthetic construct
SEQUENCE: 26
MPTAASATES AIEDTPAPAR PEVDGRTKPK RQPRYHVVAW NDDRHTYQYT VVMFQSLFGH  60
PPERGYRLAK EQDTQGRIIV LTTTREHAEL KRDQIHAFGY DPLQSGDKGS YKASIEAEE   119

SEQ ID NO: 27            moltype = AA  length = 119
FEATURE                  Location/Qualifiers
source                   1..119
                         mol_type = protein
                         organism = synthetic construct
SEQUENCE: 27
MPTAASATES AIEDTPAPAR PEVDGRTKPK RQPRYHVVSW NDDKHTYQWT VVMFQSLFGH  60
PPERGYRLAK ERDTQGRIIV LTTTREHAEL KRDQIHAFGY DPLQSGDKGS MKASIEAEE   119

SEQ ID NO: 28            moltype = AA  length = 91
FEATURE                  Location/Qualifiers
source                   1..91
                         mol_type = protein
                         organism = synthetic construct
SEQUENCE: 28
MKMYNIPTPT MAQVIMVDDP ITTTEFVISA LRDFFDKSLE EAKALTSSIH RDGEGVCGVY  60
PYDIARHRAA WVRDKAKALE FPLKLLVEEI K                                 91

SEQ ID NO: 29            moltype = AA  length = 91
FEATURE                  Location/Qualifiers
source                   1..91
                         mol_type = protein
                         organism = synthetic construct
SEQUENCE: 29
MKMYNIPTPT MAQVIMVDDP INTYEFTISA LRDFFDKSLE EAKALASSID RDGEGVCGVY  60
PYDIARHRAA WVRDKAKALE FPEKLLVEEI K                                 91

SEQ ID NO: 30            moltype = AA  length = 91
FEATURE                  Location/Qualifiers
source                   1..91
                         mol_type = protein
                         organism = synthetic construct
SEQUENCE: 30
MKMYNIPTPT MAQVIMVDDP INTKEFTISA LRDFFDKSLE EAKALASSID RDGEGVCGVY  60
PYDIARHRAA WVRDKAKALE FPEKLLVEEI K                                 91

SEQ ID NO: 31            moltype = AA  length = 91
FEATURE                  Location/Qualifiers
source                   1..91
                         mol_type = protein
                         organism = synthetic construct
SEQUENCE: 31
MKMYNIPTPT MAQVIRVDDP SMTNEFGISA LRDFFDKSLE EAKALASSID RDGEGVCGVY  60
PYDIARHRAA WVRDKAKALE FPSKLLVEEI K                                 91

SEQ ID NO: 32            moltype = AA  length = 91
FEATURE                  Location/Qualifiers
source                   1..91
                         mol_type = protein
                         organism = synthetic construct
SEQUENCE: 32
MKMYNIPTPT MAQVIRVDDP SMTYEFGISA LRDFFDKSLE EAKALASSID RDGEGVCGVY  60
PYDIARHRAA WVRDKAKALE FPSKLLVEEI K                                 91

SEQ ID NO: 33            moltype = AA  length = 90
FEATURE                  Location/Qualifiers
source                   1..90
                         mol_type = protein
                         organism = synthetic construct
SEQUENCE: 33
MPQERQQVTR KHYPNYKVIF LNSDFYTFQH LVALMMKYIP NMTSDRAWEI SNQIHYEGQA  60
IVWVGPQEQA ELYHEQFLRA GLTMAPLEPE                                   90

SEQ ID NO: 34            moltype = AA  length = 97
FEATURE                  Location/Qualifiers
```

```
source                  1..97
                        mol_type = protein
                        organism = synthetic construct
SEQUENCE: 34
MTSTLRARPA RDTDLQHRPY PHYRIITLDD DVMTFQHMAN SYVTFLPGMT RDQMWAMSQQ  60
DDGEGSMVVW TGPQEQAELY HVQLGNHGQT NIPLEPV                           97

SEQ ID NO: 35           moltype = AA  length = 97
FEATURE                 Location/Qualifiers
source                  1..97
                        mol_type = protein
                        organism = synthetic construct
SEQUENCE: 35
MTSTLRARPA RDTDLQHRPY PHYRIIVLDD DVMTFQHMAN SFVTFLPGMT RDQMWAMSQQ  60
DEGEGSMVVW TGPQEQAELY HVQLGNHGQT NIPLEPV                           97

SEQ ID NO: 36           moltype = AA  length = 97
FEATURE                 Location/Qualifiers
source                  1..97
                        mol_type = protein
                        organism = synthetic construct
SEQUENCE: 36
MTSTLRARPA RDTDLQHRPY PHYRIIVLDD DVMTFQHLAN SFVTFLPGMT RDQMWAMSQQ  60
DDGEGSMVVW TGPQEQAELY HVQLGNHGQT NIPLEPV                           97

SEQ ID NO: 37           moltype = AA  length = 97
FEATURE                 Location/Qualifiers
source                  1..97
                        mol_type = protein
                        organism = synthetic construct
SEQUENCE: 37
MTSTLRARPA RDTDLQHRPY PHYRIIVLDD DVMTFQHMAN SFVTFLPGMT RDQMWAMSQQ  60
DDGEGSMVVW TGPQEQAELY HVQLGNHGQT NIPLEPV                           97

SEQ ID NO: 38           moltype = AA  length = 97
FEATURE                 Location/Qualifiers
source                  1..97
                        mol_type = protein
                        organism = synthetic construct
SEQUENCE: 38
MTSTLRARPA RDTDLQHRPY PHYRIILLDS DVITFQLTAN AFVTFLPGMT RDQMWAKIQQ  60
SDGEGSCVVW TGPQEQAELY HVQLGNQGLT EIPLEPV                           97

SEQ ID NO: 39           moltype = AA  length = 128
FEATURE                 Location/Qualifiers
source                  1..128
                        mol_type = protein
                        organism = synthetic construct
SEQUENCE: 39
MVSIGAATVA CAEGRPIFSG YFDWLAAMPE TVTVPRTRLR PKTERPKLHK VIEVNQDYIP  60
WEFWVTFFKG EFHMSEDQAQ RKMIAGDRRG VYVVAVFTRD VAETKATRFS DHGRAKGYPT  120
QMTTEPEE                                                           128

SEQ ID NO: 40           moltype = AA  length = 95
FEATURE                 Location/Qualifiers
source                  1..95
                        mol_type = protein
                        organism = synthetic construct
SEQUENCE: 40
MGQTVEKPRV EGPGTGLGGS WRVITRNNDH YTRDHWARTI ARFIPGVSLE RAHEWSKVIH  60
TTGRKVVYTG HKEAAEHYWQ QFKGSGLESM PLEQG                             95

SEQ ID NO: 41           moltype = AA  length = 126
FEATURE                 Location/Qualifiers
source                  1..126
                        mol_type = protein
                        organism = synthetic construct
SEQUENCE: 41
MTLSVALGPD TQESTQTGTA VSTDTLTAPD IPWNLVDWND PVNLMSYISY VFQSYFGYSE  60
TKANKLMMEQ DKKGRSIVAH GSKEQVEQHA VALHGYGNWA TVEKATGGNS GGGKSGGPGK  120
GKGKRG                                                             126

SEQ ID NO: 42           moltype = AA  length = 99
FEATURE                 Location/Qualifiers
source                  1..99
                        mol_type = protein
                        organism = synthetic construct
SEQUENCE: 42
MSGTVVESKP RNSTQLAPRW KVIYHDNPVT TFDFTTGMFR RVFAKPPGEA RRMTREAHDT  60
```

```
GSVLVDVLAL EQAEFRRDQM HSLARAEGFP QTLTLEPAD                          99

SEQ ID NO: 43           moltype = AA  length = 99
FEATURE                 Location/Qualifiers
source                  1..99
                        mol_type = protein
                        organism = synthetic construct
SEQUENCE: 43
MSGTVVESKP RNSTQLAPRW KVIYHDQPVT TFDFTTGLFR RVFAKPPGEA RRMTREAHDT  60
GSVLVDVLAL EQAEFRRDQM HSLARAEGFP QTLTLEPAD                          99

SEQ ID NO: 44           moltype = AA  length = 103
FEATURE                 Location/Qualifiers
source                  1..103
                        mol_type = protein
                        organism = synthetic construct
SEQUENCE: 44
MSDSPVDLKP KPKVKPKLER PSMYKVITVN DDYTPMEFTI DHLQKFFSYD VERATQLMLA  60
SDYQGKAICG VFTAEVAETK VAMMNKSARE NEHPELCTLE KAE                     103

SEQ ID NO: 45           moltype = AA  length = 103
FEATURE                 Location/Qualifiers
source                  1..103
                        mol_type = protein
                        organism = synthetic construct
SEQUENCE: 45
MSDSPVDLKP KPKVKPKLER PSMYKVITVN DDYTPMEFTI DHLQKFFSYD VERATQLMLA  60
SEYQGKAICG VFTAEVAETK VAMMNKSARE NEHPELCTLE KAE                     103

SEQ ID NO: 46           moltype = AA  length = 83
FEATURE                 Location/Qualifiers
source                  1..83
                        mol_type = protein
                        organism = synthetic construct
SEQUENCE: 46
MHSKFNHAGR ICGAKHRVGE PMYRCKECSF DDTCTLCVNC FNPKDHVGHH VYTSICTEFK  60
NGICDCGDKE AWNHELNCKG AED                                           83

SEQ ID NO: 47           moltype = AA  length = 83
FEATURE                 Location/Qualifiers
source                  1..83
                        mol_type = protein
                        organism = synthetic construct
SEQUENCE: 47
MHSKFNHAGR ICGAKFRVGE PLYRCKECSF DDTCVLCVNC FNPKDHVGHH VYTSICTEFL  60
NGICDCGDKE AWNHELNCKG AED                                           83

SEQ ID NO: 48           moltype = AA  length = 83
FEATURE                 Location/Qualifiers
source                  1..83
                        mol_type = protein
                        organism = synthetic construct
SEQUENCE: 48
MHSKFNHAGR ICGAKFRVGE PLYKCKECSF DDTCVLCVNC FNPKDHVGHH VYTMICTEFL  60
NGICDCGDKE AWNHELNCKG AED                                           83

SEQ ID NO: 49           moltype = AA  length = 106
FEATURE                 Location/Qualifiers
source                  1..106
                        mol_type = protein
                        organism = synthetic construct
SEQUENCE: 49
MAFPARGKTA PKNEVRRQPP YNVIMLNDDD HTWRYAMELF QKIFGFPPEK GFQIVEEMDR  60
TGRVILLTTS KEHAELKQDQ MHSYGPDPYL GRPCSGSMTC VIEPAV                  106

SEQ ID NO: 50           moltype = AA  length = 106
FEATURE                 Location/Qualifiers
source                  1..106
                        mol_type = protein
                        organism = synthetic construct
SEQUENCE: 50
MAFPARGKTA PKNEVRRQPP YNVIILNDDD HTWRYLMEMF QKIFGFPPEK GFQIIEEIDR  60
TGRAILLTTS KEHAELKQDQ LHSYGPDPYL GRPCSGSMTV VIEPAV                  106

SEQ ID NO: 51           moltype = AA  length = 106
FEATURE                 Location/Qualifiers
source                  1..106
                        mol_type = protein
                        organism = synthetic construct
```

```
SEQUENCE: 51
MAFPARGKTA PKNEVRRQPP YNVILLNDDD HTWRYIMEMF QKIFGFPPEK GFQITEEIDR  60
TGRAILLTTS KEHAELKQDQ THSYGPDPYL GRPCSGSMTM VIEPAV                106

SEQ ID NO: 52          moltype = AA  length = 106
FEATURE                Location/Qualifiers
source                 1..106
                       mol_type = protein
                       organism = synthetic construct
SEQUENCE: 52
MAFPARGKTA PKNEVRRQPP YNVIILNDDD MTWRYLMEAF QKIFGFPPEK GFQIIEEIDR  60
TGRAILLTTS KEHAELKQDQ MHSYGPDPYL GRPCSGSMTM VIEPAV                106

SEQ ID NO: 53          moltype = AA  length = 99
FEATURE                Location/Qualifiers
source                 1..99
                       mol_type = protein
                       organism = synthetic construct
SEQUENCE: 53
MSGTVVESKP RNSTQLAPRW KVIMHDQPVI TFDFTLGMFR RVFAKPPGEA RRITREAHDT  60
GSVLVDVLAL EQAEFRRDQM HSLARAEGFP LTMTLEPAD                         99

SEQ ID NO: 54          moltype = AA  length = 106
FEATURE                Location/Qualifiers
source                 1..106
                       mol_type = protein
                       organism = synthetic construct
SEQUENCE: 54
MAFPARGKTA PKNEVRRQPP YNVIILNDDD HTYRYFIEMF QKIFGFPPEK GFQYTEEMDR  60
TGRLILLTTS KEHAELKQDQ LHSYGPDPYL GRPCSGSVTV VIEPAV                106

SEQ ID NO: 55          moltype = AA  length = 106
FEATURE                Location/Qualifiers
source                 1..106
                       mol_type = protein
                       organism = synthetic construct
SEQUENCE: 55
MAFPARGKTA PKNEVRRQPP YNVIILNDDD HTYRYFLEMF QKIFGFPPEK GFQYAEEIDR  60
TGRLILLTTS KEHAELKQDQ MHSYGPDPYL GRPCSGSITC VIEPAV                106

SEQ ID NO: 56          moltype = AA  length = 106
FEATURE                Location/Qualifiers
source                 1..106
                       mol_type = protein
                       organism = synthetic construct
SEQUENCE: 56
MAFPARGKTA PKNEVRRQPP YNVIILNDDD HTYRYFIEMF QKIFGFPPEK GFQIVEEIDR  60
TGRYILLTTS KEHAELKQDQ LHSYGPDPYL GRPCSGSITC VIEPAV                106

SEQ ID NO: 57          moltype = AA  length = 106
FEATURE                Location/Qualifiers
source                 1..106
                       mol_type = protein
                       organism = synthetic construct
SEQUENCE: 57
MAFPARGKTA PKNEVRRQPP YNVIMLNDDD HTYRYFIELF QKIFGFPPEK GFQIIEEIDR  60
TGRAILLTTS KEHAELKQDQ IHSYGPDPYL GRPCSGSITC VIEPAV                106

SEQ ID NO: 58          moltype = AA  length = 106
FEATURE                Location/Qualifiers
source                 1..106
                       mol_type = protein
                       organism = synthetic construct
SEQUENCE: 58
MAFPARGKTA PKNEVRRQPP YNVIILNDDD HTYRYFLEMF QKIFGFPPEK GFQYVEEIDR  60
TGRIILLTTS KEHAELKQDQ MHSYGPDPYL GRPCSGSITC VIEPAV                106

SEQ ID NO: 59          moltype = AA  length = 119
FEATURE                Location/Qualifiers
source                 1..119
                       mol_type = protein
                       organism = synthetic construct
SEQUENCE: 59
MPTAASATES AIEDTPAPAR PEVDGRTKPK RQPRYHVVIW NDDDHTYQYF VVMFQSLFGH  60
PPERGYRIVK EIDTQGRYIV LTTTREHAEL KRDQLHAFGY DRLLARSKGS IKASIEAEE  119

SEQ ID NO: 60          moltype = AA  length = 119
FEATURE                Location/Qualifiers
source                 1..119
```

```
                         mol_type = protein
                         organism = synthetic construct
SEQUENCE: 60
MPTAASATES AIEDTPAPAR PEVDGRTKPK RQPRYHVVYW NDDDHTYQYF VVLFQSLFGH  60
PPERGYRIVK EIDTQGRYIV LTTTREHAEL KRDQTHAFGY DRLLARSKGS IKISIEAEE   119

SEQ ID NO: 61            moltype = AA  length = 119
FEATURE                  Location/Qualifiers
source                   1..119
                         mol_type = protein
                         organism = synthetic construct
SEQUENCE: 61
MPTAASATES AIEDTPAPAR PEVDGRTKPK RQPRYHVVMW NDDDHTYQYF VVLLQSLFGH  60
PPERGYRIVK EIDTQGRYIV LTTTREHAEL KRDQIHAFGY DRLLARSKGS IKVSIEAEE   119

SEQ ID NO: 62            moltype = AA  length = 119
FEATURE                  Location/Qualifiers
source                   1..119
                         mol_type = protein
                         organism = synthetic construct
SEQUENCE: 62
MPTAASATES AIEDTPAPAR PEVDGRTKPK RQPRYHVVFW NDDDHTYQYF VVLFQSLFGH  60
PPERGYRIAK EIDTQGRYIV LTTTREHAEL KRDQVHAFGY DRLLARSKGS IKISIEAEE   119

SEQ ID NO: 63            moltype = AA  length = 119
FEATURE                  Location/Qualifiers
source                   1..119
                         mol_type = protein
                         organism = synthetic construct
SEQUENCE: 63
MPTAASATES AIEDTPAPAR PEVDGRTKPK RQPRYHVVIW NDDDHTYQYF VVTFQSLFGH  60
PPERGYRIAK EIDTQGRYIV LTTTREHAEL KRDQWHAFGY DRLLARSKGS IKCSIEAEE   119

SEQ ID NO: 64            moltype = AA  length = 83
FEATURE                  Location/Qualifiers
source                   1..83
                         mol_type = protein
                         organism = synthetic construct
SEQUENCE: 64
MHSKFSHAGR ICGAKFKVGE PAYRCKECSF DDTCILCVNC FNPKDHTGHH VYTMICTEFL  60
NGICDCGDKE AWNHTLFCKA EEG                                          83

SEQ ID NO: 65            moltype = AA  length = 83
FEATURE                  Location/Qualifiers
source                   1..83
                         mol_type = protein
                         organism = synthetic construct
SEQUENCE: 65
MHSKFSHAGR ICGAKFKVGE PAYLCKECSF DDTCILCVNC FNPKDHTGHH VYTMICTEFL  60
NGICDCGDKE AWNHTLFCKA EEG                                          83

SEQ ID NO: 66            moltype = AA  length = 103
FEATURE                  Location/Qualifiers
source                   1..103
                         mol_type = protein
                         organism = synthetic construct
SEQUENCE: 66
MSDSPVDLKP KPKVKPKLER PKLYKVMFLN DDYTPMSYII VFFKAVFRMS EDTGRRKMMT  60
AHRFGSMVVV VCERDIAETK AKEFTDHGKE AGFPIMMTTE PEE                    103

SEQ ID NO: 67            moltype = AA  length = 103
FEATURE                  Location/Qualifiers
source                   1..103
                         mol_type = protein
                         organism = synthetic construct
SEQUENCE: 67
MSDSPVDLKP KPKVKPKLER PKLYKVMFLD DDYTPMSYII VFFKAVFRMS EDTGRRKMMT  60
AHRFGSMVVV VCERDIAETK AKEFTDHGKE AGFPIQMTTE PEE                    103

SEQ ID NO: 68            moltype = AA  length = 117
FEATURE                  Location/Qualifiers
source                   1..117
                         mol_type = protein
                         organism = synthetic construct
SEQUENCE: 68
MIAEPICMQG EGDGEDGGTN RGTSVITRVK PKTKRPNLYR VLTLDDDYTP MEFMIHMFER  60
FFQKDREAAT RLMLLVHQHG VAECGVFTYE VAETKVSQMM DWARQHQHPF QMVMEKK     117

SEQ ID NO: 69            moltype = AA  length = 90
```

```
FEATURE                 Location/Qualifiers
source                  1..90
                        mol_type = protein
                        organism = synthetic construct
SEQUENCE: 69
MPQERQQVTR KHYPNYKVIL LDMDFMTFAF MSAVLMKYIP NMTSDRSTEL IRQAHYEGQT  60
IVWVGPQEQA ELYHEQFLRS GLQNMPLEPE                                   90

SEQ ID NO: 70           moltype = AA  length = 97
FEATURE                 Location/Qualifiers
source                  1..97
                        mol_type = protein
                        organism = synthetic construct
SEQUENCE: 70
MASAPSTTLD KSTQVVKKTY PNYKVIFLDS DLLTMDFLAN VMIKYIPDMT TDRAWEKAYQ  60
MHYQGQFIVW TGPQEQAELY HQQFRREGLE NIPLEAA                           97

SEQ ID NO: 71           moltype = AA  length = 97
FEATURE                 Location/Qualifiers
source                  1..97
                        mol_type = protein
                        organism = synthetic construct
SEQUENCE: 71
MTSTLRARPA RDTDLQHRPY PHYRIITLDN DVNTFQKIAN VHVTFLPGMT RDQMWAKMQQ  60
VDGEGSVVVW TGPQEQAELY HVQFGNQGLK NIPLEPV                           97

SEQ ID NO: 72           moltype = AA  length = 96
FEATURE                 Location/Qualifiers
source                  1..96
                        mol_type = protein
                        organism = synthetic construct
SEQUENCE: 72
MATETIERPR TRDPGSGLGG HWLVIMLDND HMTFDLISKV LARVIPGVTV DDAYRFTYQM  60
HQRGQVIIWR GPKEPAEHYW EQLQDVGLDN APLERH                            96

SEQ ID NO: 73           moltype = AA  length = 106
FEATURE                 Location/Qualifiers
source                  1..106
                        mol_type = protein
                        organism = synthetic construct
SEQUENCE: 73
MAFPARGKTA PKNEVRRQPP YNVIILNSDD HTYRYFMEMF QKIFGFPPEK GFQYMEEIDR  60
TGRIILLTTS KEHAELKQDQ SHSYGPDPYL GRPCSGSITM VIEPAV                 106

SEQ ID NO: 74           moltype = AA  length = 95
FEATURE                 Location/Qualifiers
source                  1..95
                        mol_type = protein
                        organism = synthetic construct
SEQUENCE: 74
MGQTVEKPRV EGPGTGLGGS WRVISRDNDH YTFDEWVRII ARFIPGVSLE RAHEWMKVLH  60
TTGRMVVYTG HKEAAEHYWQ QLKGAGFQSV PLEQG                             95

SEQ ID NO: 75           moltype = AA  length = 128
FEATURE                 Location/Qualifiers
source                  1..128
                        mol_type = protein
                        organism = synthetic construct
SEQUENCE: 75
MVSIGAATVA CAEGRPIFSG YFDWLAAMPE TVTVPRTRLR PKTERPKLYK VIFVDDDFVP  60
FEFIIRMFKA EFRMSEDQAA EKMMRAHQRG VQVVAVFTRD VAETKATRFT DWGRAKGYPL  120
IMTTEPEE                                                           128

SEQ ID NO: 76           moltype = AA  length = 128
FEATURE                 Location/Qualifiers
source                  1..128
                        mol_type = protein
                        organism = synthetic construct
SEQUENCE: 76
MVSIGAATVA CAEGRPIFSG YFDWLAAMPE TVTVPRTRLR PKTERPKLHK VIFVDQDYIP  60
FEFIITMFKG EFHMSEDQAQ RKLITAHRRG VYVVAVFTRD VAETKATRFS DAGRAKGYPL  120
QVTTEPEE                                                           128

SEQ ID NO: 77           moltype = AA  length = 126
FEATURE                 Location/Qualifiers
source                  1..126
                        mol_type = protein
                        organism = synthetic construct
SEQUENCE: 77
```

```
MTLSVALGPD TQESTQTGTA VSTDTLTAPD IPWNLVFWDD PVTLMSRIIY FFQSYFGYSE  60
TKAYKIVMEA HKKGRSIVAH GSKEQVEQHA VAFHGLGLWT TVEKATGGNS GGGKSGGPGK  120
GKGKRG                                                            126

SEQ ID NO: 78          moltype = AA  length = 110
FEATURE                Location/Qualifiers
source                 1..110
                       mol_type = protein
                       organism = synthetic construct
SEQUENCE: 78
MSDTITLPGR PEVERDERTR RQPPYNVITH DKDDITFAYF IVMYNQLFGY PPEKGYEKLK  60
EIHLNGRAIV LTTSKEHAEL KRDQMHAWGP DPFSSKDCKG SISASIEPAY            110

SEQ ID NO: 79          moltype = AA  length = 119
FEATURE                Location/Qualifiers
source                 1..119
                       mol_type = protein
                       organism = synthetic construct
SEQUENCE: 79
MPTAASATES AIEDTPAPAR PEVDGRTKPK RQPRYHVVIW NDDDWTYQYY VVMFQSLFGH  60
PPERGYRLMK ELDTQGRFIV LTTTREHAEL KRDQIHAFGY DRLLARSKGS IKASIEAEE  119

SEQ ID NO: 80          moltype = AA  length = 116
FEATURE                Location/Qualifiers
source                 1..116
                       mol_type = protein
                       organism = synthetic construct
SEQUENCE: 80
MSSPSSLDDV QVSTSRAKPA NETRTRKQPP YAVIFEDQDH VTHLWFYEMF MKVCGHAPEK  60
GFVKSQQIHT QGKVMVWSGT LELAELKRDQ FRGFGPDNYA PAPVTFPPGM TIEPLP     116

SEQ ID NO: 81          moltype = AA  length = 99
FEATURE                Location/Qualifiers
source                 1..99
                       mol_type = protein
                       organism = synthetic construct
SEQUENCE: 81
MSGTVVESKP RNSTQLAPRW KVIFHDNPVT TFAFIIGMFR RVFAKPPGEA REMLRRAHDT  60
GSVLVDVLAL EQAEFRRDQF HSEARAEGFP STMTLEPAD                        99

SEQ ID NO: 82          moltype = AA  length = 107
FEATURE                Location/Qualifiers
source                 1..107
                       mol_type = protein
                       organism = synthetic construct
SEQUENCE: 82
MHHHHHHHHH HDYDIPTTEN LYFQGMHSKF SHAGRICGAK FKVGEPIYRC KECSFDDTCV  60
LCVNCFNPKD HTGHHVYTTI CTEFNNGICD CGDKEAWNHT LFCKAEE               107

SEQ ID NO: 83          moltype = AA  length = 103
FEATURE                Location/Qualifiers
source                 1..103
                       mol_type = protein
                       organism = synthetic construct
SEQUENCE: 83
MSDSPVDLKP KPKVKPKLER PKLYKVMFLN QDYVPMSFIV VMFKAVFRMS EDTGRKKMMH  60
AHRFGSVVVV VCERDIAETK AKEFTDYGKE AGFPVMMTTE PEE                   103

SEQ ID NO: 84          moltype = AA  length = 126
FEATURE                Location/Qualifiers
source                 1..126
                       mol_type = protein
                       organism = synthetic construct
SEQUENCE: 84
MTLSVALGPD TQESTQTGTA VSTDTLTAPD IPWNLVMWNQ PVLLWSYMVY LFQSYFGYSE  60
TKTNKMVMEA HKKGRSIVAH GSKEQVEQHA VAMHGRGLWA TVEKATGGNS GGGKSGGPGK  120
GKGKRG                                                            126

SEQ ID NO: 85          moltype = AA  length = 110
FEATURE                Location/Qualifiers
source                 1..110
                       mol_type = protein
                       organism = synthetic construct
SEQUENCE: 85
MSDTITLPGR PEVERDERTR RQPPYNVITH NQDDITWEYF RVMYNQLFGY PPEKGYEKLK  60
EIHLNGRIIV LTTSKEHAEL KRDQMHAWGP DPFSSKDCKG SVSNSIEPAY            110

SEQ ID NO: 86          moltype = AA  length = 110
FEATURE                Location/Qualifiers
```

```
source                  1..110
                        mol_type = protein
                        organism = synthetic construct
SEQUENCE: 86
MSDTITLPGR PEVERDERTR RQPPYNVIIH NTDDLTWEYF KVMFNQLFGY PPEKGYEKLK  60
EIHLNGRAIV LTTSKEHAEL KRDQMHAWGP DPFSSKDCKG SVSASIEPAY             110

SEQ ID NO: 87           moltype = AA  length = 119
FEATURE                 Location/Qualifiers
source                  1..119
                        mol_type = protein
                        organism = synthetic construct
SEQUENCE: 87
MPTAASATES AIEDTPAPAR PEVDGRTKPK RQPRYHVVTW NTDDWTHQYY VVMYQSLFGH  60
PPERGYRLTK EMDTQGRCIV LTTTREHAEL KRDQMHAFGY DRLLARSKGS TKVSIEAEE   119

SEQ ID NO: 88           moltype = AA  length = 119
FEATURE                 Location/Qualifiers
source                  1..119
                        mol_type = protein
                        organism = synthetic construct
SEQUENCE: 88
MPTAASATES AIEDTPAPAR PEVDGRTKPK RQPRYHVVMW NTDDWTYQYI IVMMQSLFGH  60
PPERGYRMVK EMDTQGRTIV LTTTREHAEL KRDQMHAFGY DRLLARSKGS IKNSIEAEE   119

SEQ ID NO: 89           moltype = AA  length = 116
FEATURE                 Location/Qualifiers
source                  1..116
                        mol_type = protein
                        organism = synthetic construct
SEQUENCE: 89
MSSPSSLDDV QVSTSRAKPA NETRTRKQPP YAVIFENQDH VTILWFWEMF MKVCGHAPEK  60
GFVKSQQIHT QGKVMVWSGT LELAELKRDQ FRGFGPDNYA PRPVTFPPGM TIEPLP      116

SEQ ID NO: 90           moltype = AA  length = 116
FEATURE                 Location/Qualifiers
source                  1..116
                        mol_type = protein
                        organism = synthetic construct
SEQUENCE: 90
MSSPSSLDDV QVSTSRAKPA NETRTRKQPP YAVIMENLDH ITLLWMWEMF MKVCGHAPEK  60
GFVKSQQNHT QGKVMVWSGT LELAELKRDQ MRGWGPDNYA PRPVTFPPGF TIEPLP      116

SEQ ID NO: 91           moltype = AA  length = 99
FEATURE                 Location/Qualifiers
source                  1..99
                        mol_type = protein
                        organism = synthetic construct
SEQUENCE: 91
MSGTVVESKP RNSTQLAPRW KVIYHDQPVT TFDFIIGMFR RVFAKPPGEA REMTRRAHDT  60
GSVLVDVLAL EQAEFRRDQF HSEARAEGFP STMTLEPAD                         99

SEQ ID NO: 92           moltype = AA  length = 99
FEATURE                 Location/Qualifiers
source                  1..99
                        mol_type = protein
                        organism = synthetic construct
SEQUENCE: 92
MSGTVVESKP RNSTQLAPRW KVIYHDQPVM TFDFIIGLFR RVFAKPPGEA RTITRIAHDT  60
GSVLVDVLAL EQAEFRRDQF HSEARAEGFP ATMTLEPAD                         99

SEQ ID NO: 93           moltype = AA  length = 103
FEATURE                 Location/Qualifiers
source                  1..103
                        mol_type = protein
                        organism = synthetic construct
SEQUENCE: 93
MSDSPVDLKP KPKVKPKLER PKLYKVMFLN QDYTPMSFIV VMFKAVFRMS EDTGRKKMMH  60
AHRFGSVVVV VCERDIAETK AKEFTDYGKE AGFPSMMTTE PEE                    103

SEQ ID NO: 94           moltype = AA  length = 117
FEATURE                 Location/Qualifiers
source                  1..117
                        mol_type = protein
                        organism = synthetic construct
SEQUENCE: 94
MIAEPICMQG EGDGEDGGTN RGTSVITRVK PKTKRPNLYR VLWLNHDYIP MEFMVHMFER  60
FFQKDREAAT RYMLLVHQHG VAECGVFTYE VAETKVSQLM DWARQHQHPF QVVMEKK     117
```

```
SEQ ID NO: 95          moltype = AA  length = 117
FEATURE                Location/Qualifiers
source                 1..117
                       mol_type = protein
                       organism = synthetic construct
SEQUENCE: 95
MIAEPICMQG EGDGEDGGTN RGTSVITRVK PKTKRPNLYR VLWLNHDYIP MEFMVHMFER  60
FFQKDREAAT RIMLEVHQHG VSECGVFTYE VAETKVSQLM DFARQHQHPF QVVMEKK     117

SEQ ID NO: 96          moltype = AA  length = 90
FEATURE                Location/Qualifiers
source                 1..90
                       mol_type = protein
                       organism = synthetic construct
SEQUENCE: 96
MPQERQQVTR KHYPNYKVIM LNNDFHTFQF MSAVMMKYIP NMTSDRSWEK VNQVHYEGQT  60
IVWVGPQEQA ELYHEQFLRS GLTNMPLEPE                                  90

SEQ ID NO: 97          moltype = AA  length = 90
FEATURE                Location/Qualifiers
source                 1..90
                       mol_type = protein
                       organism = synthetic construct
SEQUENCE: 97
MPQERQQVTR KHYPNYKVIM LNDDFWTFQF LAAVIMKYIP NMTSDRVWEI TNQVHYEGQS  60
IVWVGPQEQA ELYHEQFLRE GFLHVPLEPE                                  90

SEQ ID NO: 98          moltype = AA  length = 97
FEATURE                Location/Qualifiers
source                 1..97
                       mol_type = protein
                       organism = synthetic construct
SEQUENCE: 98
MASAPSTTLD KSTQVVKKTY PNYKVILLNN DLITRDKLAN VLIKYIPDMT TDRAWERINQ  60
MHYQGQFIVW TGPQEQAELY HQQFRREGMQ NIPLEAA                          97

SEQ ID NO: 99          moltype = AA  length = 97
FEATURE                Location/Qualifiers
source                 1..97
                       mol_type = protein
                       organism = synthetic construct
SEQUENCE: 99
MASAPSTTLD KSTQVVKKTY PNYKVIMLNN DLLTRDEIAN VFIKYIPDMT TDRMWEMTNQ  60
MHYQGQLIVW TGPQEQAELY HQQFRREGLL NVPLEAA                          97

SEQ ID NO: 100         moltype = AA  length = 97
FEATURE                Location/Qualifiers
source                 1..97
                       mol_type = protein
                       organism = synthetic construct
SEQUENCE: 100
MTSTLRARPA RDTDLQHRPY PHYRIITLDN DVITFQELVN YYVTFLPGMT RDQIWAKMQQ  60
VDGEGSAVVW TGPQEQAELY HVQLGNQGLF NCPLEPV                          97

SEQ ID NO: 101         moltype = AA  length = 97
FEATURE                Location/Qualifiers
source                 1..97
                       mol_type = protein
                       organism = synthetic construct
SEQUENCE: 101
MTSTLRARPA RDTDLQHRPY PHYRIITLDM DVNTFQEIAN YYVTFLPGMT RDQMWAWMQQ  60
VDGEGSVVVW TGPQEQAELY HVQLGNQGLY NIPLEPV                          97

SEQ ID NO: 102         moltype = AA  length = 96
FEATURE                Location/Qualifiers
source                 1..96
                       mol_type = protein
                       organism = synthetic construct
SEQUENCE: 102
MATETIERPR TRDPGSGLGG HWLVIHLNSD HFTFDEHAKW LARVIPGVTV DDAYRFTDQM  60
HQRGQMIVWR GPKEPAEHYW EQLQDVGLSQ SPLERH                           96

SEQ ID NO: 103         moltype = AA  length = 96
FEATURE                Location/Qualifiers
source                 1..96
                       mol_type = protein
                       organism = synthetic construct
SEQUENCE: 103
MATETIERPR TRDPGSGLGG HWLVIMLNSD HFTFDEFSKW LARVIPGVTV DDAYRFTDQM  60
```

```
HQRGQVIVWR GPKEPAEHYW EQFQDIGLSQ VPLERH                        96

SEQ ID NO: 104         moltype = AA  length = 106
FEATURE                Location/Qualifiers
source                 1..106
                       mol_type = protein
                       organism = synthetic construct
SEQUENCE: 104
MAFPARGKTA PKNEVRRQPP YNVIILNSDD HTYRYYMEMF QKIFGFPPEK GFQYMEEIDR  60
TGRIILLTTS KEHAELKQDQ LHSYGPDPYL GRPCSGSITC VIEPAV                 106

SEQ ID NO: 105         moltype = AA  length = 106
FEATURE                Location/Qualifiers
source                 1..106
                       mol_type = protein
                       organism = synthetic construct
SEQUENCE: 105
MAFPARGKTA PKNEVRRQPP YNVIILNSDD HTYRYFMEMF QKIFGFPPEK GFQYMEEIDR  60
TGRIILLTTS KEHAELKQDQ LHSYGPDPYL GRPCSGSITC VIEPAV                 106

SEQ ID NO: 106         moltype = AA  length = 95
FEATURE                Location/Qualifiers
source                 1..95
                       mol_type = protein
                       organism = synthetic construct
SEQUENCE: 106
MGQTVEKPRV EGPGTGLGGS WRVIMRNTDH ITKDEFARSI ARFIPGVSLE RAHEKIKVMH  60
TTGRFVVYTG HKEAAEHYWQ QFKGSGVQVM PLEQG                             95

SEQ ID NO: 107         moltype = AA  length = 95
FEATURE                Location/Qualifiers
source                 1..95
                       mol_type = protein
                       organism = synthetic construct
SEQUENCE: 107
MGQTVEKPRV EGPGTGLGGS WRVIMRNDDH HTKDKFARMI ARFIPGVSLE RAHEKIKVLH  60
TTGRMVVYTG HKEAAEHYWQ QMKGAGVQNV PLEQG                             95

SEQ ID NO: 108         moltype = AA  length = 128
FEATURE                Location/Qualifiers
source                 1..128
                       mol_type = protein
                       organism = synthetic construct
SEQUENCE: 108
MVSIGAATVA CAEGRPIFSG YFDWLAAMPE TVTVPRTRLR PKTERPKLYK VIFVNRDFIP  60
MEFIIRMFKA EFRMSEDQAA RKMMYAHQRG VYVVAVFTRD VAETKATRFT DWGRAKGYPL  120
LMTTEPEE                                                           128

SEQ ID NO: 109         moltype = AA  length = 128
FEATURE                Location/Qualifiers
source                 1..128
                       mol_type = protein
                       organism = synthetic construct
SEQUENCE: 109
MVSIGAATVA CAEGRPIFSG YFDWLAAMPE TVTVPRTRLR PKTERPKLYK VIFVNRDFIP  60
MEFIIRMFKA EFRMSEDQAA TKMMLAHQRG VQVVAVFTRD VAETKATRFT DWGRAKGYPL  120
LMTTEPEE                                                           128

SEQ ID NO: 110         moltype = AA  length = 128
FEATURE                Location/Qualifiers
source                 1..128
                       mol_type = protein
                       organism = synthetic construct
SEQUENCE: 110
MVSIGAATVA CAEGRPIFSG YFDWLAAMPE TVTVPRTRLR PKTERPKLHK VIFVNQDYIP  60
WEFIVTLFKG EFHMSEDQAQ RKMIIAHRRG VYVVAVFTRD VAETKATRTS DWGRAKGYPL  120
QFTTEPEE                                                           128

SEQ ID NO: 111         moltype = AA  length = 128
FEATURE                Location/Qualifiers
source                 1..128
                       mol_type = protein
                       organism = synthetic construct
SEQUENCE: 111
MVSIGAATVA CAEGRPIFSG YFDWLAAMPE TVTVPRTRLR PKTERPKLHK VIFVNKDYIP  60
WEFIVTMFKG EFHMSEDQAQ RKMIIAHRRG VYVVAVFTRD VAETKATRFS DWGRAKGYPL  120
QMTTEPEE                                                           128

SEQ ID NO: 112         moltype = AA  length = 128
```

```
FEATURE                 Location/Qualifiers
source                  1..128
                        mol_type = protein
                        organism = synthetic construct
SEQUENCE: 112
MVSIGAATVA CAEGRPIFSG YFDWLAAMPE TVTVPRTRLR PKTERPPLHK VILVNRDFIP  60
MEFIIRMLKA EFRTTGDEAQ RKMIYAHMKG SYVVAVFTRE IAESKATRFT EWARAEGFPM  120
LMTTEPEE                                                           128

SEQ ID NO: 113          moltype = AA  length = 128
FEATURE                 Location/Qualifiers
source                  1..128
                        mol_type = protein
                        organism = synthetic construct
SEQUENCE: 113
MVSIGAATVA CAEGRPIFSG YFDWLAAMPE TVTVPRTRLR PKTERPPLHK VILVNQDFIP  60
WEFMIRFLKA EFRTTGDEAQ KKMISAHMKG SHVVAVFTRE IAESKATRMT EWARAEGFPL  120
LFTTEPEE                                                           128

SEQ ID NO: 114          moltype = AA  length = 126
FEATURE                 Location/Qualifiers
source                  1..126
                        mol_type = protein
                        organism = synthetic construct
SEQUENCE: 114
MTLSVALGPD TQESTQTGTA VSTDTLTAPD IPWNLVIWNL PVLLWSFIVY LFQSYFGYSE  60
TKANKIVMEM HKKGRSIVAH GSKEQVEQHA VAFHGRGLWT TVEKATGGNS GGGKSGGPGK  120
GKGKRG                                                             126

SEQ ID NO: 115          moltype = AA  length = 119
FEATURE                 Location/Qualifiers
source                  1..119
                        mol_type = protein
                        organism = synthetic construct
SEQUENCE: 115
MPTAASATES AIEDTPAPAR PEVDGRTKPK RQPRYHVVLW NDDDHTHQYV VVMLQSLFGH  60
PPERGYRLAK EVDTQGRVIV LTTTREHAEL KRDQIHAFGY DRLLARSKGS MKASIEAEE   119

SEQ ID NO: 116          moltype = AA  length = 119
FEATURE                 Location/Qualifiers
source                  1..119
                        mol_type = protein
                        organism = synthetic construct
SEQUENCE: 116
MPTAASATES AIEDTPAPAR PEVDGRTKPK RQPRYHVVLW NDDDHTYQYV VMMLQSLFGH  60
PPERGYRLAK EVDTQGRVIV LTTTREHAEL KRDQIHAFGY DRLLARSKGS MKASIEAEE   119

SEQ ID NO: 117          moltype = AA  length = 119
FEATURE                 Location/Qualifiers
source                  1..119
                        mol_type = protein
                        organism = synthetic construct
SEQUENCE: 117
MPTAASATES AIEDTPAPAR PEVDGRTKPK RQPRYHVVLW NDDDHTHQYV VMMLQSLFGH  60
PPERGYRLAK EVDTQGRVIV LTTTREHAEL KRDQIHAFGY DRLLARSKGS MKASIEAEE   119

SEQ ID NO: 118          moltype = AA  length = 119
FEATURE                 Location/Qualifiers
source                  1..119
                        mol_type = protein
                        organism = synthetic construct
SEQUENCE: 118
MPTAASATES AIEDTPAPAR PEVDGRTKPK RQPRYHVVLW DDDDHTYQYV VVMLQSLFGH  60
PPERGYRLAK EVDTQGRVIV LTTTREHAEL KRDQIHAFGY DRLLARSKGS MKASIEAEE   119

SEQ ID NO: 119          moltype = AA  length = 119
FEATURE                 Location/Qualifiers
source                  1..119
                        mol_type = protein
                        organism = synthetic construct
SEQUENCE: 119
MPTAASATES AIEDTPAPAR PEVDGRTKPK RQPRYHVVLW DYDDHTYQYV VVMLQSLFGH  60
PPERGYRLAK EVDTQGRVIV LTTTREHAEL KRDQIHAFGY DRLLARSKGS MKASIEAEE   119

SEQ ID NO: 120          moltype = AA  length = 119
FEATURE                 Location/Qualifiers
source                  1..119
                        mol_type = protein
                        organism = synthetic construct
```

```
SEQUENCE: 120
MPTAASATES AIEDTPAPAR PEVDGRTKPK RQPRYHVVLW DYDDHTYQYV VVMLQSLFGH  60
PPERGYRLAK ELDTQGRVIV LTTTREHAEL KRDQIHAFGY DRLLARSKGS MKASIEAEE   119

SEQ ID NO: 121         moltype = AA  length = 119
FEATURE                Location/Qualifiers
source                 1..119
                       mol_type = protein
                       organism = synthetic construct
SEQUENCE: 121
MPTAASATES AIEDTPAPAR PEVDGRTKPK RQPRYHVVLW NDEDHTYQYV VVMLQSLFGH  60
PPERGYRLAK EVDTQGRVIV LTTTREHAEL KRDQIHAFGY DRLLARSKGS MKASIEAEE   119

SEQ ID NO: 122         moltype = AA  length = 119
FEATURE                Location/Qualifiers
source                 1..119
                       mol_type = protein
                       organism = synthetic construct
SEQUENCE: 122
MPTAASATES AIEDTPAPAR PEVDGRTKPK RQPRYHVVLW NYDDHTYQYV VVMLQSLFGH  60
PPERGYRLAK EVDTQGRVIV LTTTREHAEL KRDQIHAFGY DRLLARSKGS MKASIEAEE   119

SEQ ID NO: 123         moltype = AA  length = 126
FEATURE                Location/Qualifiers
source                 1..126
                       mol_type = protein
                       organism = synthetic construct
SEQUENCE: 123
MTLSVALGPD TQESTQTGTA VSTDTLTAPD IPWNLVIWDD PVNLMSYVSY VFQSYFGYSE  60
TKANKLMMEV HKKGRSIVAH GSKEQVEQHA VAMHGYGLWA TVEKATGGNS GGGKSGGPGK  120
GKGKRG                                                             126

SEQ ID NO: 124         moltype = AA  length = 110
FEATURE                Location/Qualifiers
source                 1..110
                       mol_type = protein
                       organism = synthetic construct
SEQUENCE: 124
MSDTITLPGR PEVERDERTR RQPPYNVILH DDDDHTFEYV IVMLNQLFGY PPEKGYEMAK  60
EVHLNGRVIV LTTSKEHAEL KRDQIHAFGP DPFSSKDCKG SMSASIEPAY             110

SEQ ID NO: 125         moltype = AA  length = 119
FEATURE                Location/Qualifiers
source                 1..119
                       mol_type = protein
                       organism = synthetic construct
SEQUENCE: 125
MPTAASATES AIEDTPAPAR PEVDGRTKPK RQPRYHVVLW DDDDHTYQYV VVMLQSLFGH  60
PPERGYRLAK EVDTQGRVIV LTTTREHAEL KRDQIHAFGY DRLLARSKGS MKASIEAEE   119

SEQ ID NO: 126         moltype = AA  length = 116
FEATURE                Location/Qualifiers
source                 1..116
                       mol_type = protein
                       organism = synthetic construct
SEQUENCE: 126
MSSPSSLDDV QVSTSRAKPA NETRTRKQPP YAVIVEDDDH HTFLYVIEAL MKVCGHAPEK  60
GFVLAQQIHT QGKAMVWSGT LELAELKRDQ LRGFGPDNYA PRPVTFPLGV TIEPLP      116

SEQ ID NO: 127         moltype = AA  length = 99
FEATURE                Location/Qualifiers
source                 1..99
                       mol_type = protein
                       organism = synthetic construct
SEQUENCE: 127
MSGTVVESKP RNSTQLAPRW KVIVHDDPVT TFDFVLGVLR RVFAKPPGEA RRITREAHDT  60
GSALVDVLAL EQAEFRRDQA HSLARAEGFP LTLTLEPAD                         99

SEQ ID NO: 128         moltype = AA  length = 103
FEATURE                Location/Qualifiers
source                 1..103
                       mol_type = protein
                       organism = synthetic construct
SEQUENCE: 128
MSDSPVDLKP KPKVKPKLER PKLYKVMLLD DDYTPMSFVT VVLKAVFRMS EDTGRRVMMT  60
AHRFGSAVVV VCERDIAETK AKEATDLGKE AGFPLMFTTE PEE                    103

SEQ ID NO: 129         moltype = AA  length = 117
FEATURE                Location/Qualifiers
```

```
source                  1..117
                        mol_type = protein
                        organism = synthetic construct
SEQUENCE: 129
MIAEPICMQG EGDGEDGGTN RGTSVITRVK PKTKRPNLYR VLLLDDDYTP MEFVIHILER  60
FFQKDREAAT RIMLHVHQHG VGECGVFTYE VAETKVSQVM DFARQHQHPL QCVMEKK     117

SEQ ID NO: 130          moltype = AA  length = 90
FEATURE                 Location/Qualifiers
source                  1..90
                        mol_type = protein
                        organism = synthetic construct
SEQUENCE: 130
MPQERQQVTR KHYPNYKVIV LDDDFNTFQH VAACLMKYIP NMTSDRAWEL TNQVHYEGQA  60
IVWVGPQEQA ELYHEQLLRA GLTMAPLEPE                                   90

SEQ ID NO: 131          moltype = AA  length = 97
FEATURE                 Location/Qualifiers
source                  1..97
                        mol_type = protein
                        organism = synthetic construct
SEQUENCE: 131
MASAPSTTLD KSTQVVKKTY PNYKVIVLDD DLNTFDHVAN CLIKYIPDMT TDRAWELTNQ  60
VHYQGQAIVW TGPQEQAELY HQQLRREGLT MAPLEAA                           97

SEQ ID NO: 132          moltype = AA  length = 96
FEATURE                 Location/Qualifiers
source                  1..96
                        mol_type = protein
                        organism = synthetic construct
SEQUENCE: 132
MATETIERPR TRDPGSGLGG HWLVIVLDDD HNTFDHVAKT LARVIPGVTV DDGYRFADQI  60
HQRGQAIVWR GPKEPAEHYW EQLQDAGLSM APLERH                            96

SEQ ID NO: 133          moltype = AA  length = 106
FEATURE                 Location/Qualifiers
source                  1..106
                        mol_type = protein
                        organism = synthetic construct
SEQUENCE: 133
MAFPARGKTA PKNEVRRQPP YNVILLDDDD HTYRYVIEML QKIFGFPPEK GFQIAEEVDR  60
TGRVILLTTS KEHAELKQDQ VHSYGPDPYL GRPCSGSMTC VIEPAV                 106

SEQ ID NO: 134          moltype = AA  length = 95
FEATURE                 Location/Qualifiers
source                  1..95
                        mol_type = protein
                        organism = synthetic construct
SEQUENCE: 134
MGQTVEKPRV EGPGTGLGGS WRVIVRDDDH NTFDHVARTL ARFIPGVSLE RGHEIAKVIH  60
TTGRAVVYTG HKEAAEHYWQ QLKGAGLTMA PLEQG                             95

SEQ ID NO: 135          moltype = AA  length = 128
FEATURE                 Location/Qualifiers
source                  1..128
                        mol_type = protein
                        organism = synthetic construct
SEQUENCE: 135
MVSIGAATVA CAEGRPIFSG YFDWLAAMPE TVTVPRTRLR PKTERPKLYK VILVDDDFTP  60
REFVVRVLKA EFRMSEDQAA KVMMTAHQRG VCVVAVFTRD VAETKATRAT DAGRAKGYPL  120
LFTTEPEE                                                           128

SEQ ID NO: 136          moltype = AA  length = 128
FEATURE                 Location/Qualifiers
source                  1..128
                        mol_type = protein
                        organism = synthetic construct
SEQUENCE: 136
MVSIGAATVA CAEGRPIFSG YFDWLAAMPE TVTVPRTRLR PKTERPKLHK VILVDDDYTP  60
REFVVTVLKG EFHMSEDQAQ RVMITAHRRG VCVVAVFTRD VAETKATRAS DAGRAKGYPL  120
QFTTEPEE                                                           128

SEQ ID NO: 137          moltype = AA  length = 128
FEATURE                 Location/Qualifiers
source                  1..128
                        mol_type = protein
                        organism = synthetic construct
SEQUENCE: 137
MVSIGAATVA CAEGRPIFSG YFDWLAAMPE TVTVPRTRLR PKTERPPLHK VILVDDDFTP  60
```

```
REFVVRLLKA EFRTTGDEAQ RIMITAHMKG SCVVAVFTRE IAESKATRAT ETARAEGFPL  120
LFTTEPEE                                                           128

SEQ ID NO: 138          moltype = AA  length = 126
FEATURE                 Location/Qualifiers
source                  1..126
                        mol_type = protein
                        organism = synthetic construct
SEQUENCE: 138
MTLSVALGPD TQESTQTGTA VSTDTLTAPD IPWNLVIWDD PVNLMSYVSY VFQSYFGYSE  60
TKANKLMMEV DKKGRSIVAH GSKEQVEQHA VAMHGYGLWA TVEKATGGNS GGGKSGGPGK  120
GKGKRG                                                             126

SEQ ID NO: 139          moltype = AA  length = 110
FEATURE                 Location/Qualifiers
source                  1..110
                        mol_type = protein
                        organism = synthetic construct
SEQUENCE: 139
MSDTITLPGR PEVERDERTR RQPPYNVILH DDDDHTFEYV IVMLNQLFGY PPEKGYEMAK  60
EVDLNGRVIV LTTSKEHAEL KRDQIHAFGP DPFSSKDCKG SMSASIEPAY             110

SEQ ID NO: 140          moltype = AA  length = 116
FEATURE                 Location/Qualifiers
source                  1..116
                        mol_type = protein
                        organism = synthetic construct
SEQUENCE: 140
MSSPSSLDDV QVSTSRAKPA NETRTRKQPP YAVIVEDDDH HTFLYVIEAL MKVCGHAPEK  60
GFVLAQQIDT QGKAMVWSGT LELAELKRDQ LRGFGPDNYA PRPVTFPLGV TIEPLP      116

SEQ ID NO: 141          moltype = AA  length = 99
FEATURE                 Location/Qualifiers
source                  1..99
                        mol_type = protein
                        organism = synthetic construct
SEQUENCE: 141
MSGTVVESKP RNSTQLAPRW KVIVHDDPVT TFDFVLGVLR RVFAKPPGEA RRITREADDT  60
GSALVDVLAL EQAEFRRDQA HSLARAEGFP LTLTLEPAD                         99

SEQ ID NO: 142          moltype = AA  length = 103
FEATURE                 Location/Qualifiers
source                  1..103
                        mol_type = protein
                        organism = synthetic construct
SEQUENCE: 142
MSDSPVDLKP KPKVKPKLER PKLYKVMLLD DDYTPMSFVT VVLKAVFRMS EDTGRRVMMT  60
ADRFGSAVVV VCERDIAETK AKEATDLGKE AGFPLMFTTE PEE                    103

SEQ ID NO: 143          moltype = AA  length = 117
FEATURE                 Location/Qualifiers
source                  1..117
                        mol_type = protein
                        organism = synthetic construct
SEQUENCE: 143
MIAEPICMQG EGDGEDGGTN RGTSVITRVK PKTKRPNLYR VLLLDDDYTP MEFVIHILER  60
FFQKDREAAT RIMLHVDQHG VGECGVFTYE VAETKVSQVM DFARQHQHPL QCVMEKK      117

SEQ ID NO: 144          moltype = AA  length = 90
FEATURE                 Location/Qualifiers
source                  1..90
                        mol_type = protein
                        organism = synthetic construct
SEQUENCE: 144
MPQERQQVTR KHYPNYKVIV LDDDFNTFQH VAACLMKYIP NMTSDRAWEL TNQVDYEGQA  60
IVWVGPQEQA ELYHEQLLRA GLTMAPLEPE                                   90

SEQ ID NO: 145          moltype = AA  length = 97
FEATURE                 Location/Qualifiers
source                  1..97
                        mol_type = protein
                        organism = synthetic construct
SEQUENCE: 145
MASAPSTTLD KSTQVVKKTY PNYKVIVLDD DLNTFDHVAN CLIKYIPDMT TDRAWELTNQ  60
VDYQGQAIVW TGPQEQAELY HQQLRREGLT MAPLEAA                           97

SEQ ID NO: 146          moltype = AA  length = 96
FEATURE                 Location/Qualifiers
source                  1..96
```

```
                        mol_type = protein
                        organism = synthetic construct
SEQUENCE: 146
MATETIERPR TRDPGSGLGG HWLVIVLDDD HNTFDHVAKT LARVIPGVTV DDGYRFADQI  60
DQRGQAIVWR GPKEPAEHYW EQLQDAGLSM APLERH                            96

SEQ ID NO: 147          moltype = AA  length = 95
FEATURE                 Location/Qualifiers
source                  1..95
                        mol_type = protein
                        organism = synthetic construct
SEQUENCE: 147
MGQTVEKPRV EGPGTGLGGS WRVIVRDDDH NTFDHVARTL ARFIPGVSLE RGHEIAKVID  60
TTGRAVVYTG HKEAAEHYWQ QLKGAGLTMA PLEQG                             95

SEQ ID NO: 148          moltype = AA  length = 128
FEATURE                 Location/Qualifiers
source                  1..128
                        mol_type = protein
                        organism = synthetic construct
SEQUENCE: 148
MVSIGAATVA CAEGRPIFSG YFDWLAAMPE TVTVPRTRLR PKTERPKLYK VILVDDDFTP  60
REFVVRVLKA EFRMSEDQAA KVMMTADQRG VCVVAVFTRD VAETKATRAT DAGRAKGYPL  120
LFTTEPEE                                                           128

SEQ ID NO: 149          moltype = AA  length = 128
FEATURE                 Location/Qualifiers
source                  1..128
                        mol_type = protein
                        organism = synthetic construct
SEQUENCE: 149
MVSIGAATVA CAEGRPIFSG YFDWLAAMPE TVTVPRTRLR PKTERPKLHK VILVDDDYTP  60
REFVVTVLKG EFHMSEDQAQ RVMITADRRG VCVVAVFTRD VAETKATRAS DAGRAKGYPL  120
QFTTEPEE                                                           128

SEQ ID NO: 150          moltype = AA  length = 128
FEATURE                 Location/Qualifiers
source                  1..128
                        mol_type = protein
                        organism = synthetic construct
SEQUENCE: 150
MVSIGAATVA CAEGRPIFSG YFDWLAAMPE TVTVPRTRLR PKTERPPLHK VILVDDDFTP  60
REFVVRLLKA EFRTTGDEAQ RIMITADMKG SCVVAVFTRE IAESKATRAT ETARAEGFPL  120
LFTTEPEE                                                           128

SEQ ID NO: 151          moltype = AA  length = 119
FEATURE                 Location/Qualifiers
source                  1..119
                        mol_type = protein
                        organism = synthetic construct
SEQUENCE: 151
MPTAASATES AIEDTPAPAR PEVDGRTKPK RQPRYHVVLW DDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 152          moltype = AA  length = 119
FEATURE                 Location/Qualifiers
source                  1..119
                        mol_type = protein
                        organism = synthetic construct
SEQUENCE: 152
MPTAASATES AIEDTPAPAR PEVDGRTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 153          moltype = AA  length = 119
FEATURE                 Location/Qualifiers
source                  1..119
                        mol_type = protein
                        organism = synthetic construct
SEQUENCE: 153
MPTAASATES AIEDTPAPAR PEVDGRTKPK RQPRYHVVLW DDDDHTYQYV VVMLQSLFGH  60
PPERGYRLAK EMDTLGRVIV LTTTREHAEL KRDQIHAFGY DRLLARSKGS MKASIEAEE   119

SEQ ID NO: 154          moltype = AA  length = 119
FEATURE                 Location/Qualifiers
source                  1..119
                        mol_type = protein
                        organism = synthetic construct
SEQUENCE: 154
MPTAASATES AIEDTPAPAR PEVDGRTKPK RQPRYHVVLW NDDDHTYQYV VVMLQSLFGH  60
```

```
PPERGYRLAK EMDTLGRVIV LTTTREHAEL KRDQIHAFGY DRLLARSKGS MKASIEAEE   119

SEQ ID NO: 155         moltype = AA  length = 119
FEATURE                Location/Qualifiers
source                 1..119
                       mol_type = protein
                       organism = synthetic construct
SEQUENCE: 155
MPTAASATES AIEDTPAPAR PEVDGRTKPK RQPRYHVVLW NDDYHTYQYV VVMLQSLFGH  60
PPERGYRLAK EVDTQGRVIV LTTTREHAEL KRDQIHAFGY DRLLARSKGS MKASIEAEE   119

SEQ ID NO: 156         moltype = AA  length = 119
FEATURE                Location/Qualifiers
source                 1..119
                       mol_type = protein
                       organism = synthetic construct
SEQUENCE: 156
MPTAASATES AIEDTPAPAR PEVDGRTKPK RQPRYHVVLW NDNYHTYQYV VVMLQSLFGH  60
PPERGYRLAK EVDTQGRVIV LTTTREHAEL KRDQIHAFGY DRLLARSKGS MKASIEAEE   119

SEQ ID NO: 157         moltype = AA  length = 119
FEATURE                Location/Qualifiers
source                 1..119
                       mol_type = protein
                       organism = synthetic construct
SEQUENCE: 157
MPTAASATES AIEDTPAPAR PEVDGRTKPK RQPRYHVVLW NDDDHTYQYV VVMLQSLFGH  60
PPKRGYRLAK EVDTQGRVIV LTTTREHAEL KRDQIHAFGY DRLLARSKGS MKASIEAEE   119

SEQ ID NO: 158         moltype = AA  length = 119
FEATURE                Location/Qualifiers
source                 1..119
                       mol_type = protein
                       organism = synthetic construct
SEQUENCE: 158
MPTAASATES AIEDTPAPAR PEVDGRTKPK RQPRYHVVLW NDDDHTYQYV VVMLQSLFGH  60
SPERGYRLAK EVDTQGRVIV LTTTREHAEL KRDQIHAFGY DRLLARSKGS MKASIEAEE   119

SEQ ID NO: 159         moltype = AA  length = 119
FEATURE                Location/Qualifiers
source                 1..119
                       mol_type = protein
                       organism = synthetic construct
SEQUENCE: 159
MPTAASATES AIEDTPAPAR PEVDGRTKPK RQPRYHVVLW NDDDHTYQYV VVMLQSLFGH  60
PRERGYRLAK EVDTQGRVIV LTTTREHAEL KRDQIHAFGY DRLLARSKGS MKASIEAEE   119

SEQ ID NO: 160         moltype = AA  length = 119
FEATURE                Location/Qualifiers
source                 1..119
                       mol_type = protein
                       organism = synthetic construct
SEQUENCE: 160
MPTAASATES AIEDTPAPAR PEVDGRTKPK RQPRYHVVLW NDADHTYQYV VVMLQSLFGH  60
PPERGYRLAK EVDTQGRVIV LTTTREHAEL KRDQIHAFGY DRLLARSKGS MKASIEAEE   119

SEQ ID NO: 161         moltype = AA  length = 119
FEATURE                Location/Qualifiers
source                 1..119
                       mol_type = protein
                       organism = synthetic construct
SEQUENCE: 161
MPTAASATES AIEDTPAPAR PEVDGRTKPK RQPRYHVVLW NDDDHTYQYV VVMLQSLFGH  60
PPERGFRLAK EVDTQGRVIV LTTTREHAEL KRDQIHAFGY DRLLARSKGS MKASIEAEE   119

SEQ ID NO: 162         moltype = AA  length = 119
FEATURE                Location/Qualifiers
source                 1..119
                       mol_type = protein
                       organism = synthetic construct
SEQUENCE: 162
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DRLLAHSKGS MKASIEAEE   119

SEQ ID NO: 163         moltype = AA  length = 119
FEATURE                Location/Qualifiers
source                 1..119
                       mol_type = protein
                       organism = synthetic construct
```

```
SEQUENCE: 163
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DRLLAGSKGS MKASIEAEE   119

SEQ ID NO: 164         moltype = AA  length = 119
FEATURE                Location/Qualifiers
source                 1..119
                       mol_type = protein
                       organism = synthetic construct
SEQUENCE: 164
MPTAASATES AIEDTPAPAR PEVDGRTKPK RQPRYHVVLW NDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 165         moltype = AA  length = 119
FEATURE                Location/Qualifiers
source                 1..119
                       mol_type = protein
                       organism = synthetic construct
SEQUENCE: 165
MPTAASATES AIEDTPAPAR PEVDGRTKPK RQPRYHVVLW NDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 166         moltype = AA  length = 119
FEATURE                Location/Qualifiers
source                 1..119
                       mol_type = protein
                       organism = synthetic construct
SEQUENCE: 166
MPTAASATES AIEDTPAPAR PEVDSRTKPK RQPRYHVVNW NDDDLTCQYL VVMLQSLFGH  60
PPERGYRLAK EVDTQGRVIV LTTTREHAEL KRDQIHAFGY DRLLARSKGS IKASIEAEE   119

SEQ ID NO: 167         moltype = AA  length = 119
FEATURE                Location/Qualifiers
source                 1..119
                       mol_type = protein
                       organism = synthetic construct
SEQUENCE: 167
MPTAASATES AIEDTPAPAR PEVDSRTKPK RQPRYHVVNW NDDDLTCQYM VVMLQSLFGH  60
PPERGYRLAK EVDTQGRVIV LTTTREHAEL KRDQIHAFGY DRLLARSKGS TKASIEAEE   119

SEQ ID NO: 168         moltype = AA  length = 119
FEATURE                Location/Qualifiers
source                 1..119
                       mol_type = protein
                       organism = synthetic construct
SEQUENCE: 168
MPTAASATES AIEDTPAPAR PEVDGRTKPK RQPRYHVVNW NDDDPTRQYM VVMLQSLFGH  60
PPERGYRLAK ETDTQGRVIV LTTTREHAEL KRDQIHAFGY DRLLARSKGS TKASIEAEE   119

SEQ ID NO: 169         moltype = AA  length = 119
FEATURE                Location/Qualifiers
source                 1..119
                       mol_type = protein
                       organism = synthetic construct
SEQUENCE: 169
MPTAASATES AIEDTPAPAR PEVDGRTKPK RQPRYHVVNW NDDDPTRQYL VVMLQSLFGH  60
PPERGYRLAK ETDTQGRVIV LTTTREHAEL KRDQIHAFGY DRLLARSKGS TKASIEAEE   119

SEQ ID NO: 170         moltype = AA  length = 119
FEATURE                Location/Qualifiers
source                 1..119
                       mol_type = protein
                       organism = synthetic construct
SEQUENCE: 170
MPTAASATES AIEDTPAPAR PEVDGRTKPK RQPRYHVVLW NDDDHTYQYV VVMLQSLFGH  60
PPKRGYRLAK EVDTQGRVIV LTTTREHAEL KRDQIHAFGY DRLLARSKGS MKASIEAEE   119

SEQ ID NO: 171         moltype = AA  length = 119
FEATURE                Location/Qualifiers
source                 1..119
                       mol_type = protein
                       organism = synthetic construct
SEQUENCE: 171
MPTAASATES AIEDTPAPAR PEVDGRTKPK RQPRYHVVLW NDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 172         moltype = AA  length = 119
FEATURE                Location/Qualifiers
source                 1..119
```

```
                         mol_type = protein
                         organism = synthetic construct
SEQUENCE: 172
MPTAASATES AIEDTPAPAR PEVDGRTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 173           moltype = AA  length = 119
FEATURE                  Location/Qualifiers
source                   1..119
                         mol_type = protein
                         organism = synthetic construct
SEQUENCE: 173
MPTAASATES AIEDTPAPAR PEVDGRTKPK RQPRYHVVLW DDDDHTYQYV VVMLQSLFGH  60
PPKRGYRLAK EVDTQGRVIV LTTTREHAEL KRDQIHAFGY DRLLARSKGS MKASIEAEE   119

SEQ ID NO: 174           moltype = AA  length = 119
FEATURE                  Location/Qualifiers
source                   1..119
                         mol_type = protein
                         organism = synthetic construct
SEQUENCE: 174
MPTAASATES AIEDTPAPAR PEVDGRTKPK RQPRYHVVLW NDDDHTYQYV VVMLQSLFGH  60
PPKRGYRLAK EMDTQGRVIV LTTTREHAEL KRDQIHAFGY DRLLARSKGS MKASIEAEE   119

SEQ ID NO: 175           moltype = AA  length = 119
FEATURE                  Location/Qualifiers
source                   1..119
                         mol_type = protein
                         organism = synthetic construct
SEQUENCE: 175
MPTAASATES AIEDTPAPAR PEVDGRTKPK RQPRYHVVLW DDDDHTYQYV VVMLQSLFGH  60
PPKRGYRLAK EMDTQGRVIV LTTTREHAEL KRDQIHAFGY DRLLARSKGS MKASIEAEE   119

SEQ ID NO: 176           moltype = AA  length = 119
FEATURE                  Location/Qualifiers
source                   1..119
                         mol_type = protein
                         organism = synthetic construct
SEQUENCE: 176
MPTAASGTES AIEDTPAPAR PEVDGRTKPK RQPRYHVVLW DDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 177           moltype = AA  length = 119
FEATURE                  Location/Qualifiers
source                   1..119
                         mol_type = protein
                         organism = synthetic construct
SEQUENCE: 177
MPTAASGTES AIEDTPAPAR PEVDGRTKPK RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 178           moltype = AA  length = 119
FEATURE                  Location/Qualifiers
source                   1..119
                         mol_type = protein
                         organism = synthetic construct
SEQUENCE: 178
MPTAASGTES AIEDTPAPAR PEVDGRTKPK RQPRYHVVLW DDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 179           moltype = AA  length = 119
FEATURE                  Location/Qualifiers
source                   1..119
                         mol_type = protein
                         organism = synthetic construct
SEQUENCE: 179
MPTAASATES AFEDTPAPAR PEVDGRTKPK RQPRYHVVLW DDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 180           moltype = AA  length = 119
FEATURE                  Location/Qualifiers
source                   1..119
                         mol_type = protein
                         organism = synthetic construct
SEQUENCE: 180
MPTAASATES AFEDTPAPAR PEVDGRTKPK RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 181           moltype = AA  length = 119
```

```
FEATURE                 Location/Qualifiers
source                  1..119
                        mol_type = protein
                        organism = synthetic construct
SEQUENCE: 181
MPTAASATES AFEDTPAPAR PEVDGRTKPK RQPRYHVVLW DDDDHTYQYV VVMLRSLFGH  60
PPKRGYRLAK EVDTQGRVIV LTTTREHAEL KRDQIHAFGY DRLLARSKGS MKASIEAEE   119

SEQ ID NO: 182          moltype = AA  length = 119
FEATURE                 Location/Qualifiers
source                  1..119
                        mol_type = protein
                        organism = synthetic construct
SEQUENCE: 182
MPTAASATES AFEDTPAPAR PEVDGRTKPK RQPRYHVVLW DDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 183          moltype = AA  length = 119
FEATURE                 Location/Qualifiers
source                  1..119
                        mol_type = protein
                        organism = synthetic construct
SEQUENCE: 183
MPTAASATES AIEDTPAPAR PEVDGRTKPK RQPRYHVVLW NDDDHTYQYV VVMLQSLFGH  60
PRERGYRLAK EVDTLGRVIV LTTTREHAEL KRDQIHAFGY DRLLARSKGS MKASIEAEE   119

SEQ ID NO: 184          moltype = AA  length = 119
FEATURE                 Location/Qualifiers
source                  1..119
                        mol_type = protein
                        organism = synthetic construct
SEQUENCE: 184
MPTAASATES AIEDTPAPAR PEVDGRTKPK RQPRYHVVLW DDDDHTYQYV VVMLQSLFGH  60
PRERGYRLAK EVDTLGRVIV LTTTREHAEL KRDQIHAFGY DRLLARSKGS MKASIEAEE   119

SEQ ID NO: 185          moltype = AA  length = 119
FEATURE                 Location/Qualifiers
source                  1..119
                        mol_type = protein
                        organism = synthetic construct
SEQUENCE: 185
MPTAASATES AIEDTPAPAR PEVDGRTKPK RQPRYHVVLW DDDDHTYQYV VVMLQSLFGH  60
PRERGYRLAK EMDTLGRVIV LTTTREHAEL KRDQIHAFGY DRLLARSKGS MKASIEAEE   119

SEQ ID NO: 186          moltype = AA  length = 119
FEATURE                 Location/Qualifiers
source                  1..119
                        mol_type = protein
                        organism = synthetic construct
SEQUENCE: 186
MPTAASATES AIEDTPAPAR PEVDGRTKPK RQPRYHVVLW DDDDHTYQYV VVMLQSLFGH  60
PRKRGYRLAK EMDTLGRVIV LTTTREHAEL KRDQIHAFGY DRLLARSKGS MKASIEAEE   119

SEQ ID NO: 187          moltype = AA  length = 119
FEATURE                 Location/Qualifiers
source                  1..119
                        mol_type = protein
                        organism = synthetic construct
SEQUENCE: 187
MPTAASATES AIEDTPAPAR PEVDGRTKPK RQPRYHVVLW NDDDHTYQYV VVMLQSLFGH  60
PRKRGYRLAK EMDTLGRVIV LTTTREHAEL KRDQIHAFGY DRLLARSKGS MKASIEAEE   119

SEQ ID NO: 188          moltype = AA  length = 119
FEATURE                 Location/Qualifiers
source                  1..119
                        mol_type = protein
                        organism = synthetic construct
SEQUENCE: 188
MPTAASATES AIEDTPAPAR PVVDGRTKPK RQPRYHVVLW DDDDHTYQYV VVMLQSLFGH  60
PPERGYRLAK EVDTQGRVIV LTTTREHAEL KRDQIHAFGY DRLLARSKGS MKASIEAEE   119

SEQ ID NO: 189          moltype = AA  length = 119
FEATURE                 Location/Qualifiers
source                  1..119
                        mol_type = protein
                        organism = synthetic construct
SEQUENCE: 189
MPTAASATES AIEDTPAPAR PVVDGRTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119
```

```
SEQ ID NO: 190          moltype = AA  length = 119
FEATURE                 Location/Qualifiers
source                  1..119
                        mol_type = protein
                        organism = synthetic construct
SEQUENCE: 190
MPTAASATES AIEDTPAPAR PVVDGRTKPK RQPRYHVVLW DDDDHTYQYV VVMLQSLFGH  60
PPKRGYRLAK EMDTQGRVIV LTTTREHAEL KRDQIHAFGY DRLLARSKGS MKASIEAEE   119

SEQ ID NO: 191          moltype = AA  length = 119
FEATURE                 Location/Qualifiers
source                  1..119
                        mol_type = protein
                        organism = synthetic construct
SEQUENCE: 191
MPTAASATES AIEDTPAPAR PVVDGRTKPK RQPRYHVVLW DDDDHTYQYV VVMLQSLFGH  60
PPKRGYRLAK EVDTQGRVIV LTTTREHAEL KRDQIHAFGY DRLLARSKGS MKASIEAEE   119

SEQ ID NO: 192          moltype = AA  length = 119
FEATURE                 Location/Qualifiers
source                  1..119
                        mol_type = protein
                        organism = synthetic construct
SEQUENCE: 192
MPTAASATES AIEDTPAPAR PEVDGRTKPK RQPRYHVVLW NDDDHTYQYV VVMLQSLFGH  60
PRERGYRLAK EVDTQGRVIV LTTTREHAEL KRDQIHAFGY DRLLARSKGS MKASIEAEE   119

SEQ ID NO: 193          moltype = AA  length = 119
FEATURE                 Location/Qualifiers
source                  1..119
                        mol_type = protein
                        organism = synthetic construct
SEQUENCE: 193
MPTAASATES AIEDTPAPAR PEVDGRTKPK RQPRYHVVLW DDDDHTYQYV VVMLQSLFGH  60
PRERGYRLAK EVDTQGRVIV LTTTREHAEL KRDQIHAFGY DRLLARSKGS MKASIEAEE   119

SEQ ID NO: 194          moltype = AA  length = 119
FEATURE                 Location/Qualifiers
source                  1..119
                        mol_type = protein
                        organism = synthetic construct
SEQUENCE: 194
MPTAASATES AIEDTPAPAR PEVDGRTKPK RQPRYHVVLW DDDDHTYQYV VVMLQSLFGH  60
PRERGYRLAK EMDTQGRVIV LTTTREHAEL KRDQIHAFGY DRLLARSKGS MKASIEAEE   119

SEQ ID NO: 195          moltype = AA  length = 119
FEATURE                 Location/Qualifiers
source                  1..119
                        mol_type = protein
                        organism = synthetic construct
SEQUENCE: 195
MPTAASATES AIEDTPAPAR PEVDGRTKPK RQPRYHVVLW DDDDHTYQYV VVMLQSLFGH  60
PRKRGYRLAK EMDTQGRVIV LTTTREHAEL KRDQIHAFGY DRLLARSKGS MKASIEAEE   119

SEQ ID NO: 196          moltype = AA  length = 120
FEATURE                 Location/Qualifiers
source                  1..120
                        mol_type = protein
                        organism = synthetic construct
SEQUENCE: 196
MPTAASATES AIEDTPAPAR PEVDGRTKPK RQPRYHVVLW NDDDHTYQYV VVMLQSLFGH  60
PRKRGYRLAK EVMDTQGRVI VLTTTREHAE LKRDQIHAFG YDRLLARSKG SMKASIEAEE  120

SEQ ID NO: 197          moltype = AA  length = 119
FEATURE                 Location/Qualifiers
source                  1..119
                        mol_type = protein
                        organism = synthetic construct
SEQUENCE: 197
MPTAASATES AIEDTPAPAR PEVDGRTKPK RQPRYHVVLW NDDDHTYQYV VVMLQSLFGH  60
SPKRGYRLAK EVDTQGRVIV LTTTREHAEL KRDQIHAFGY DRLLARSKGS MKASIEAEE   119

SEQ ID NO: 198          moltype = AA  length = 119
FEATURE                 Location/Qualifiers
source                  1..119
                        mol_type = protein
                        organism = synthetic construct
SEQUENCE: 198
```

```
MPTAASATES AIEDTPAPAR PEVDGRTKPK RQPRYHVVLW DDDDHTYQYV VVMLQSLFGH  60
SPKRGYRLAK EVDTQGRVIV LTTTREHAEL KRDQIHAFGY DRLLARSKGS MKASIEAEE   119

SEQ ID NO: 199         moltype = AA  length = 119
FEATURE                Location/Qualifiers
source                 1..119
                       mol_type = protein
                       organism = synthetic construct
SEQUENCE: 199
MPTAASATES AIEDTPAPAR PEVDGRTKPK RQPRYHVVLW DDDDHTYQYV VVMLQSLFGH  60
SPKRGYRLAK EMDTQGRVIV LTTTREHAEL KRDQIHAFGY DRLLARSKGS MKASIEAEE   119

SEQ ID NO: 200         moltype = AA  length = 119
FEATURE                Location/Qualifiers
source                 1..119
                       mol_type = protein
                       organism = synthetic construct
SEQUENCE: 200
MPTAASATES AIEDTPAPAR PEVDGRTKPK RQPRYHVVLW NDDDHTYQYV VVMLQSLFGH  60
SPKRGYRLAK EMDTQGRVIV LTTTREHAEL KRDQIHAFGY DRLLARSKGS MKASIEAEE   119

SEQ ID NO: 201         moltype = AA  length = 119
FEATURE                Location/Qualifiers
source                 1..119
                       mol_type = protein
                       organism = synthetic construct
SEQUENCE: 201
MPTAASATES AIEDTPAPAR PEVDGRTKPK RQPRYHVVLW NDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 202         moltype = AA  length = 119
FEATURE                Location/Qualifiers
source                 1..119
                       mol_type = protein
                       organism = synthetic construct
SEQUENCE: 202
MPTAASATES AIEDTPAPAR PEVDGRTKPK RQPRYHVVLW DDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 203         moltype = AA  length = 119
FEATURE                Location/Qualifiers
source                 1..119
                       mol_type = protein
                       organism = synthetic construct
SEQUENCE: 203
MPTAASATES AIEDTPAPAR PEVDGRTKPK RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 204         moltype = AA  length = 119
FEATURE                Location/Qualifiers
source                 1..119
                       mol_type = protein
                       organism = synthetic construct
SEQUENCE: 204
MPTAASATES AIEDTPAPAR PEVDGRTKPK RQPRYHVVLW DDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 205         moltype = AA  length = 119
FEATURE                Location/Qualifiers
source                 1..119
                       mol_type = protein
                       organism = synthetic construct
SEQUENCE: 205
MPTAASATES AIEDTPAPAR PEVDGRTKPK RQPRYHVVLW NDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 206         moltype = AA  length = 119
FEATURE                Location/Qualifiers
source                 1..119
                       mol_type = protein
                       organism = synthetic construct
SEQUENCE: 206
MPTAASATES AIEDTPAPAR PEVDGRTKPK HQPRYHVVLW NDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 207         moltype = AA  length = 119
FEATURE                Location/Qualifiers
source                 1..119
                       mol_type = protein
```

```
                        organism = synthetic construct
SEQUENCE: 207
MPTAASATES AIEDTPAPAR PEVDGRTKPK HQPRYHVVLW DDDDHTYQYV VVMLRSLFGH  60
PPERGYRLAK EVDTQGRVIV LTTTREHAEL KRDQIHAFGY DRLLARSKGS MKASIEAEE   119

SEQ ID NO: 208          moltype = AA  length = 119
FEATURE                 Location/Qualifiers
source                  1..119
                        mol_type = protein
                        organism = synthetic construct
SEQUENCE: 208
MPTAASATES AIEDTPAPAR PEVDGRTKPK HQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 209          moltype = AA  length = 119
FEATURE                 Location/Qualifiers
source                  1..119
                        mol_type = protein
                        organism = synthetic construct
SEQUENCE: 209
MPTAASATES AIEDTPAPAR PEVDGRTKPK HQPRYHVVLW DDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 210          moltype = AA  length = 119
FEATURE                 Location/Qualifiers
source                  1..119
                        mol_type = protein
                        organism = synthetic construct
SEQUENCE: 210
MPTAASATES AIEDTPAPAR PEVDGRTKPK HQPRYHVVLW NDDDHTYQYV VVMLRSLFGH  60
PPKRGYRLAK EMDTQGRVIV LTTTREHAEL KRDQIHAFGY DRLLARSKGS MKASIEAEE   119

SEQ ID NO: 211          moltype = AA  length = 119
FEATURE                 Location/Qualifiers
source                  1..119
                        mol_type = protein
                        organism = synthetic construct
SEQUENCE: 211
MPTAASATES AIEDTPAPAR PEVDGRTKPK RQPRYHVVLW NDDDHTYQYV VVMLQSLFGH  60
PPERGYRMAK EVDTQGRVIV LTTTREHAEL KRDQIHAFGY DRLLARSKGS MKASIEAEE   119

SEQ ID NO: 212          moltype = AA  length = 119
FEATURE                 Location/Qualifiers
source                  1..119
                        mol_type = protein
                        organism = synthetic construct
SEQUENCE: 212
MPTAASATES AIEDTPAPAR PEVDGRTKPK RQPRYHVVLW DDDDHTYQYV VVMLQSLFGH  60
PPERGYRMAK EVDTQGRVIV LTTTREHAEL KRDQIHAFGY DRLLARSKGS MKASIEAEE   119

SEQ ID NO: 213          moltype = AA  length = 119
FEATURE                 Location/Qualifiers
source                  1..119
                        mol_type = protein
                        organism = synthetic construct
SEQUENCE: 213
MPTAASATES AIEDTPAPAR PEVDGRTKPK RQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 214          moltype = AA  length = 119
FEATURE                 Location/Qualifiers
source                  1..119
                        mol_type = protein
                        organism = synthetic construct
SEQUENCE: 214
MPTAASATES AIEDTPAPAR PEVDGRTKPK RQPRYHVVLW DDDDHTYQYV VVMLQSLFGH  60
PPKRGYRMAK EMDTQGRVIV LTTTREHAEL KRDQIHAFGY DRLLARSKGS MKASIEAEE   119

SEQ ID NO: 215          moltype = AA  length = 119
FEATURE                 Location/Qualifiers
source                  1..119
                        mol_type = protein
                        organism = synthetic construct
SEQUENCE: 215
MPTAASATES AIEDTPAPAR PEVDGRTKPK RQPRYHVVLW NDDDHTYQYV VVMLQSLFGH  60
PPKRGYRMAK EMDTQGRVIV LTTTREHAEL KRDQIHAFGY DRLLARSKGS MKASIEAEE   119

SEQ ID NO: 216          moltype = AA  length = 119
FEATURE                 Location/Qualifiers
```

```
source                  1..119
                        mol_type = protein
                        organism = synthetic construct
SEQUENCE: 216
MPTAASATES AIEDTPAPAR PEVDGRTKPK RQPRYHVVLW NDDDHTYQYV VVMLQSLLGH  60
PPERGYRLAK EMDTQGRVIV LTTTREHAEL KRDQIHAFGY DRLLARSKGS MKASIEAEE   119

SEQ ID NO: 217          moltype = AA  length = 119
FEATURE                 Location/Qualifiers
source                  1..119
                        mol_type = protein
                        organism = synthetic construct
SEQUENCE: 217
MPTAASATES AIEDTPAPAR PEVDGRTKPK RQPRYHVVLW DDDDHTYQYV VVMLQSLLGH  60
PPERGYRLAK EMDTQGRVIV LTTTREHAEL KRDQIHAFGY DRLLARSKGS MKASIEAEE   119

SEQ ID NO: 218          moltype = AA  length = 119
FEATURE                 Location/Qualifiers
source                  1..119
                        mol_type = protein
                        organism = synthetic construct
SEQUENCE: 218
MPTAASATES AIEDTPAPAR PEVDGRTKPK RQPRYHVVLW DDDDHTYQYV VVMLQSLLGH  60
PPKRGYRLAK EMDTQGRVIV LTTTREHAEL KRDQIHAFGY DRLLARSKGS MKASIEAEE   119

SEQ ID NO: 219          moltype = AA  length = 119
FEATURE                 Location/Qualifiers
source                  1..119
                        mol_type = protein
                        organism = synthetic construct
SEQUENCE: 219
MPTAASATES AIEDTPAPAR PEVDGRTKPK RQPRYHVVLW NDDDHTYQYV VVMLQSLLGH  60
PPKRGYRLAK EMDTQGRVIV LTTTREHAEL KRDQIHAFGY DRLLARSKGS MKASIEAEE   119

SEQ ID NO: 220          moltype = AA  length = 119
FEATURE                 Location/Qualifiers
source                  1..119
                        mol_type = protein
                        organism = synthetic construct
SEQUENCE: 220
MPTAASATES AIEDTPAPAR PEVDGRTKPK RQPRYHVVLW NDDDHTYQYV VVMLQSLFGH  60
PPGRGYRLAK EVDTQGRVIV LTTTREHAEL KRDQIHAFGY DRLLARSKGS MKASIEAEE   119

SEQ ID NO: 221          moltype = AA  length = 119
FEATURE                 Location/Qualifiers
source                  1..119
                        mol_type = protein
                        organism = synthetic construct
SEQUENCE: 221
MPTAASATES AIEDTPAPAR PEVDGRTKPK RQPRYHVVLW DDDDHTYQYV VVMLQSLFGH  60
PPGRGYRLAK EVDTQGRVIV LTTTREHAEL KRDQIHAFGY DRLLARSKGS MKASIEAEE   119

SEQ ID NO: 222          moltype = AA  length = 119
FEATURE                 Location/Qualifiers
source                  1..119
                        mol_type = protein
                        organism = synthetic construct
SEQUENCE: 222
MPTAASATES AIEDTPAPAR PEVDGRTKPK RQPRYHVVLW DDDDHTYQYV VVMLQSLFGH  60
PPGRGYRLAK EMDTQGRVIV LTTTREHAEL KRDQIHAFGY DRLLARSKGS MKASIEAEE   119

SEQ ID NO: 223          moltype = AA  length = 119
FEATURE                 Location/Qualifiers
source                  1..119
                        mol_type = protein
                        organism = synthetic construct
SEQUENCE: 223
MPTAASATES AIEDTPAPAR PEVDGRTKPK RQPRYHVVLW NDDDHTYQYV VVMLQSLFGH  60
PPGRGYRLAK EMDTQGRVIV LTTTREHAEL KRDQIHAFGY DRLLARSKGS MKASIEAEE   119

SEQ ID NO: 224          moltype = AA  length = 119
FEATURE                 Location/Qualifiers
source                  1..119
                        mol_type = protein
                        organism = synthetic construct
SEQUENCE: 224
MPTAASATES AIEDTPAPAR PEVDGRTKPK RQPRYHVVLW NDDDHTYQYV VVMLQSLFGH  60
PPGRGYRLAK EVDTQGRVIV LTTTREHAEL KRDQIHAFGY DRLLARSKGS MKASIEAEE   119
```

```
SEQ ID NO: 225          moltype = AA  length = 119
FEATURE                 Location/Qualifiers
source                  1..119
                        mol_type = protein
                        organism = synthetic construct
SEQUENCE: 225
MPTAASATES AIEDTPAPAR PEVDGRTKPK RQPRYHVVLW DDDDHTYQYV VVMLQSLFGH  60
PPGRGYRLAK EVDTQGRVIV LTTTREHAEL KRDQIHAFGY DRLLAHSKGS MKASIEAEE   119

SEQ ID NO: 226          moltype = AA  length = 119
FEATURE                 Location/Qualifiers
source                  1..119
                        mol_type = protein
                        organism = synthetic construct
SEQUENCE: 226
MPTAASATES AIEDTPAPAR PEVDGRTKPK RQPRYHVVLW DDDDHTYQYV VVMLQSLFGH  60
PPGRGYRLAK EMDTQGRVIV LTTTREHAEL KRDQIHAFGY DRLLAHSKGS MKASIEAEE   119

SEQ ID NO: 227          moltype = AA  length = 107
FEATURE                 Location/Qualifiers
source                  1..107
                        mol_type = protein
                        organism = synthetic construct
SEQUENCE: 227
MPSAAPAKPK TKRQSRTQGM PPYNVVLLDD DDHTYGYVIE MLRKVFGHPP EKGFELATEV  60
DKNGRVIVMT TNLEVAELKR DEVHAFGPDP LMPRSKGSMS AVVERAG                107

SEQ ID NO: 228          moltype = AA  length = 107
FEATURE                 Location/Qualifiers
source                  1..107
                        mol_type = protein
                        organism = synthetic construct
SEQUENCE: 228
MPSAAPAKPK TKRQSRTQGM PPYNVVLLDD DDHTYGYVIE MLNKVFGHPP EKGFELATEM  60
DKNGRVIVMT TNLEVAELKR DEVHAFGPDP LMPRSKGSMS AVVERAG                107

SEQ ID NO: 229          moltype = AA  length = 107
FEATURE                 Location/Qualifiers
source                  1..107
                        mol_type = protein
                        organism = synthetic construct
SEQUENCE: 229
MPSAAPAKPK TKRQSRTQGM PPYNVVLLDD DDHTYGYVIE MLRKVFGHPP EKGFELATEM  60
DKNGRVIVMT TNLEVAELKR DEVHAFGPDP LMPRSKGSMS AVVERAG                107

SEQ ID NO: 230          moltype = AA  length = 107
FEATURE                 Location/Qualifiers
source                  1..107
                        mol_type = protein
                        organism = synthetic construct
SEQUENCE: 230
MPSAAPAKPK TKRQSRTQGM PPYNVVLLDD DDHTYGYVIE MLNKVFGHPR EKGFELATEV  60
DKLGRVIVMT TNLEVAELKR DEVHAFGPDP LMPRSKGSMS AVVERAG                107

SEQ ID NO: 231          moltype = AA  length = 107
FEATURE                 Location/Qualifiers
source                  1..107
                        mol_type = protein
                        organism = synthetic construct
SEQUENCE: 231
MPSAAPAKPK TKRQSRTQGM PPYNVVLLDD DDHTYGYVIE MLRKVFGHPR EKGFELATEM  60
DKLGRVIVMT TNLEVAELKR DEVHAFGPDP LMPRSKGSMS AVVERAG                107

SEQ ID NO: 232          moltype = AA  length = 107
FEATURE                 Location/Qualifiers
source                  1..107
                        mol_type = protein
                        organism = synthetic construct
SEQUENCE: 232
MPSAAPAKPV TKRQSRTQGM PPYNVVLLDD DDHTYGYVIE MLNKVFGHPP EKGFELATEV  60
DKNGRVIVMT TNLEVAELKR DEVHAFGPDP LMPRSKGSMS AVVERAG                107

SEQ ID NO: 233          moltype = AA  length = 107
FEATURE                 Location/Qualifiers
source                  1..107
                        mol_type = protein
                        organism = synthetic construct
SEQUENCE: 233
MPSAAPAKPV TKRQSRTQGM PPYNVVLLDD DDHTYGYVIE MLRKVFGHPP EKGFELATEM  60
```

```
DKNGRVIVMT TNLEVAELKR DEVHAFGPDP LMPRSKGSMS AVVERAG                107

SEQ ID NO: 234         moltype = AA  length = 107
FEATURE                Location/Qualifiers
source                 1..107
                       mol_type = protein
                       organism = synthetic construct
SEQUENCE: 234
MPSAAPAKPK TKRQSRTQGM PPYNVVLLDD DDHTYGYVIE MLNKVFGHPR EKGFELATEV  60
DKNGRVIVMT TNLEVAELKR DEVHAFGPDP LMPRSKGSMS AVVERAG                107

SEQ ID NO: 235         moltype = AA  length = 107
FEATURE                Location/Qualifiers
source                 1..107
                       mol_type = protein
                       organism = synthetic construct
SEQUENCE: 235
MPSAAPAKPK TKRQSRTQGM PPYNVVLLDD DDHTYGYVIE MLRKVFGHPR EKGFELATEV  60
DKNGRVIVMT TNLEVAELKR DEVHAFGPDP LMPRSKGSMS AVVERAG                107

SEQ ID NO: 236         moltype = AA  length = 107
FEATURE                Location/Qualifiers
source                 1..107
                       mol_type = protein
                       organism = synthetic construct
SEQUENCE: 236
MPSAAPAKPK TKRQSRTQGM PPYNVVLLDD DDHTYGYVIE MLRKVFGHPR EKGFELATEM  60
DKNGRVIVMT TNLEVAELKR DEVHAFGPDP LMPRSKGSMS AVVERAG                107

SEQ ID NO: 237         moltype = AA  length = 107
FEATURE                Location/Qualifiers
source                 1..107
                       mol_type = protein
                       organism = synthetic construct
SEQUENCE: 237
MPSAAPAKPK TKRQSRTQGM PPYNVVLLDD DDHTYGYVIE MLNKVFGHSP EKGFELATEV  60
DKNGRVIVMT TNLEVAELKR DEVHAFGPDP LMPRSKGSMS AVVERAG                107

SEQ ID NO: 238         moltype = AA  length = 107
FEATURE                Location/Qualifiers
source                 1..107
                       mol_type = protein
                       organism = synthetic construct
SEQUENCE: 238
MPSAAPAKPK TKRQSRTQGM PPYNVVLLDD DDHTYGYVIE MLRKVFGHSP EKGFELATEM  60
DKNGRVIVMT TNLEVAELKR DEVHAFGPDP LMPRSKGSMS AVVERAG                107

SEQ ID NO: 239         moltype = AA  length = 107
FEATURE                Location/Qualifiers
source                 1..107
                       mol_type = protein
                       organism = synthetic construct
SEQUENCE: 239
MPSAAPAKPK TKRQSRTQHM PPYNVVLLDD DDHTYGYVIE MLRKVFGHPP EKGFELATEV  60
DKNGRVIVMT TNLEVAELKR DEVHAFGPDP LMPRSKGSMS AVVERAG                107

SEQ ID NO: 240         moltype = AA  length = 107
FEATURE                Location/Qualifiers
source                 1..107
                       mol_type = protein
                       organism = synthetic construct
SEQUENCE: 240
MPSAAPAKPK TKRQSRTQHM PPYNVVLLDD DDHTYGYVIE MLRKVFGHPP EKGFELATEM  60
DKNGRVIVMT TNLEVAELKR DEVHAFGPDP LMPRSKGSMS AVVERAG                107

SEQ ID NO: 241         moltype = AA  length = 107
FEATURE                Location/Qualifiers
source                 1..107
                       mol_type = protein
                       organism = synthetic construct
SEQUENCE: 241
MPSAAPAKPK TKRQSRTQGM PPYNVVLLDD DDHTYGYVIE MLNKVFGHPP EKGFEMATEV  60
DKNGRVIVMT TNLEVAELKR DEVHAFGPDP LMPRSKGSMS AVVERAG                107

SEQ ID NO: 242         moltype = AA  length = 107
FEATURE                Location/Qualifiers
source                 1..107
                       mol_type = protein
                       organism = synthetic construct
```

```
SEQUENCE: 242
MPSAAPAKPK TKRQSRTQGM PPYNVVLLDD DDHTYGYVIE MLRKVFGHPP EKGFEMATEM  60
DKNGRVIVMT TNLEVAELKR DEVHAFGPDP LMPRSKGSMS AVVERAG               107

SEQ ID NO: 243         moltype = AA  length = 107
FEATURE                Location/Qualifiers
source                 1..107
                       mol_type = protein
                       organism = synthetic construct
SEQUENCE: 243
MPSAAPAKPK TKRQSRTQGM PPYNVVLLDD DDHTYGYVIE MLNKVLGHPP EKGFELATEM  60
DKNGRVIVMT TNLEVAELKR DEVHAFGPDP LMPRSKGSMS AVVERAG               107

SEQ ID NO: 244         moltype = AA  length = 107
FEATURE                Location/Qualifiers
source                 1..107
                       mol_type = protein
                       organism = synthetic construct
SEQUENCE: 244
MPSAAPAKPK TKRQSRTQGM PPYNVVLLDD DDHTYGYVIE MLRKVLGHPP EKGFELATEM  60
DKNGRVIVMT TNLEVAELKR DEVHAFGPDP LMPRSKGSMS AVVERAG               107

SEQ ID NO: 245         moltype = AA  length = 107
FEATURE                Location/Qualifiers
source                 1..107
                       mol_type = protein
                       organism = synthetic construct
SEQUENCE: 245
MPSAAPAKPK TKRQSRTQGM PPYNVVLLDD DDHTYGYVIE MLNKVFGHPP GKGFELATEV  60
DKNGRVIVMT TNLEVAELKR DEVHAFGPDP LMPRSKGSMS AVVERAG               107

SEQ ID NO: 246         moltype = AA  length = 107
FEATURE                Location/Qualifiers
source                 1..107
                       mol_type = protein
                       organism = synthetic construct
SEQUENCE: 246
MPSAAPAKPK TKRQSRTQGM PPYNVVLLDD DDHTYGYVIE MLRKVFGHPP GKGFELATEM  60
DKNGRVIVMT TNLEVAELKR DEVHAFGPDP LMPRSKGSMS AVVERAG               107

SEQ ID NO: 247         moltype = AA  length = 107
FEATURE                Location/Qualifiers
source                 1..107
                       mol_type = protein
                       organism = synthetic construct
SEQUENCE: 247
MPSAAPAKPK TKRQSRTQGM PPYNVVLLDD DDHTYGYVIE MLNKVFGHPP GKGFELATEV  60
DKNGRVIVMT TNLEVAELKR DEVHAFGPDP LMPHSKGSMS AVVERAG               107

SEQ ID NO: 248         moltype = AA  length = 107
FEATURE                Location/Qualifiers
source                 1..107
                       mol_type = protein
                       organism = synthetic construct
SEQUENCE: 248
MPSAAPAKPK TKRQSRTQGM PPYNVVLLDD DDHTYGYVIE MLRKVFGHPP GKGFELATEM  60
DKNGRVIVMT TNLEVAELKR DEVHAFGPDP LMPHSKGSMS AVVERAG               107

SEQ ID NO: 249         moltype = AA  length = 119
FEATURE                Location/Qualifiers
source                 1..119
                       mol_type = protein
                       organism = synthetic construct
SEQUENCE: 249
MPTAASATES AIEDTPAPAR PEVDGRTKPK RQPRYHVVLW DDDDHTYQYV VVMLQSLFGH  60
PPKRGYRLAK EMDTLGRVIV LTTTREHAEL KRDQIHAFGY DRLLARSKGS MKASIEAEE  119

SEQ ID NO: 250         moltype = AA  length = 119
FEATURE                Location/Qualifiers
source                 1..119
                       mol_type = protein
                       organism = synthetic construct
SEQUENCE: 250
MPTAASATES AIEDTPAPAR PEVDGRTKPK RQPRYHVVNW NDDDPTRQYT VVMLQSLFGH  60
PPERGYRLAK ETRTQGRVIV LTTTREHAEL KRDQIHAFGY DRLLARSKGS TKASIEAEE  119

SEQ ID NO: 251         moltype = AA  length = 119
FEATURE                Location/Qualifiers
source                 1..119
```

```
                        mol_type = protein
                        organism = synthetic construct
SEQUENCE: 251
MPTAASATES AIEDTPAPAR PEVDSRTKPK RQPRYHVVNW NDDDLTCQYT VVMLQSLFGH  60
PPERGYRLAK EVDTQGRVIV LTTTREHAEL KRDQIHAFGY DRLLARSKGS HKASIEAEE   119

SEQ ID NO: 252          moltype = AA  length = 119
FEATURE                 Location/Qualifiers
source                  1..119
                        mol_type = protein
                        organism = synthetic construct
SEQUENCE: 252
MPTAASATES AIEDTPAPAR PEVDGRTKPK RQPRYHVVSW NDDDHTSQYT VVMLQSLFGH  60
PPERGYRLAK ELHTQGRVIV LTTTREHAEL KRDQIHAFGY DRLLARSKGS PKASIEAEE   119

SEQ ID NO: 253          moltype = AA  length = 119
FEATURE                 Location/Qualifiers
source                  1..119
                        mol_type = protein
                        organism = synthetic construct
SEQUENCE: 253
MPTAASATES AIEDTPAPAR PEVDGRTKPK RQPRYHVVLW NDDDHTYQYV VVMLQSLFGH  60
PPKRGYRMAK EVDTQGRVIV LTTTREHAEL KRDQIHAFGY DRLLARSKGS MKASIEAEE   119

SEQ ID NO: 254          moltype = AA  length = 119
FEATURE                 Location/Qualifiers
source                  1..119
                        mol_type = protein
                        organism = synthetic construct
SEQUENCE: 254
MPTAASATES AIEDTPAPAR PEVDGRTKPK RQPRYHVVLW NDDDHTYQYV VVMLQSLFGH  60
PRKRGYRLAK EVDTQGRVIV LTTTREHAEL KRDQIHAFGY DRLLARSKGS MKASIEAEE   119

SEQ ID NO: 255          moltype = AA  length = 119
FEATURE                 Location/Qualifiers
source                  1..119
                        mol_type = protein
                        organism = synthetic construct
SEQUENCE: 255
MPTAASATES AIEDTPAPAR PEVDGRTKPK RQPRYHVVLW NDDDHTYQYV VVMLQSLFGH  60
PPGRGYRLAK EVDTQGRVIV LTTTREHAEL KRDQIHAFGY DRLLAHSKGS MKASIEAEE   119

SEQ ID NO: 256          moltype = AA  length = 119
FEATURE                 Location/Qualifiers
source                  1..119
                        mol_type = protein
                        organism = synthetic construct
SEQUENCE: 256
MPTAASATES AIEDTPAPAR PEVDGRTKPK RQPRYHVVLW NDDDHTYQYV VVMLQSLFGH  60
PPKRGYRLAK EVDTQGRVIV LTTTREHAEL KRDQIHAFGY DRLLAHSKGS MKASIEAEE   119

SEQ ID NO: 257          moltype = AA  length = 119
FEATURE                 Location/Qualifiers
source                  1..119
                        mol_type = protein
                        organism = synthetic construct
SEQUENCE: 257
MPTAASATES AIEDTPAPAR PEVDGRTKPK RQPRYHVVLW NDDDHTYQYV VVMLQSLFGH  60
PPRRGYRLAK EVDTQGRVIV LTTTREHAEL KRDQIHAFGY DRLLARSKGS MKASIEAEE   119

SEQ ID NO: 258          moltype = AA  length = 119
FEATURE                 Location/Qualifiers
source                  1..119
                        mol_type = protein
                        organism = synthetic construct
SEQUENCE: 258
MPTAASATES AIEDTPAPAR PEVDGRTKPK RQPRYHVVLW NDDDHTYQYV VVMLQSLFGH  60
PPDRGYRLAK EVDTQGRVIV LTTTREHAEL KRDQIHAFGY DRLLARSKGS MKASIEAEE   119

SEQ ID NO: 259          moltype = AA  length = 119
FEATURE                 Location/Qualifiers
source                  1..119
                        mol_type = protein
                        organism = synthetic construct
SEQUENCE: 259
MPTAASATES AIEDTPAPAR PEVDGRTKPK RQPRYHVVLW DDDDHTYQYV VVMLQSLFGH  60
PPKRGYRLAK EVDTQGRVIV LTTTREHAEL KRDQIHAFGY DRLLAHSKGS MKASIEAEE   119

SEQ ID NO: 260          moltype = AA  length = 119
```

```
FEATURE                Location/Qualifiers
source                 1..119
                       mol_type = protein
                       organism = synthetic construct
SEQUENCE: 260
MPTAASATES AIEDTPAPAR PEVDGRTKPK RQPRYHVVLW DDDDHTYQYV VVMLQSLFGH  60
PPKRGYRLAK EMDTQGRVIV LTTTREHAEL KRDQIHAFGY DRLLAHSKGS MKASIEAEE   119

SEQ ID NO: 261         moltype = AA  length = 119
FEATURE                Location/Qualifiers
source                 1..119
                       mol_type = protein
                       organism = synthetic construct
SEQUENCE: 261
MPTAASATES AIEDTPAPAR PEVDGRTKPK RQPRYHVVLW NDDDHTYQYV VVMLRSLFGH  60
PPERGYRLAK EVDTQGRVIV LTTTREHAEL KRDQIHAFGY DRLLAHSKGS MKASIEAEE   119

SEQ ID NO: 262         moltype = AA  length = 119
FEATURE                Location/Qualifiers
source                 1..119
                       mol_type = protein
                       organism = synthetic construct
SEQUENCE: 262
MPTAASATES AIEDTPAPAR PEVDGRTKPK RQPRYHVVLW NDNYHTYQYV VVMLQSLFGH  60
PPERGYRLAK EVDTQGRVIV LTTTREHAEL KRDQIHAFGY DRLLAHSKGS MKASIEAEE   119

SEQ ID NO: 263         moltype = AA  length = 119
FEATURE                Location/Qualifiers
source                 1..119
                       mol_type = protein
                       organism = synthetic construct
SEQUENCE: 263
MPTAASATES AIEDTPAPAR PEVDGRTKPK RQPRYHVVLW NDNDHTYQYV VVMLQSLFGH  60
PPERGYRLAK EVDTQGRVIV LTTTREHAEL KRDQIHAFGY DRLLAHSKGS MKASIEAEE   119

SEQ ID NO: 264         moltype = AA  length = 119
FEATURE                Location/Qualifiers
source                 1..119
                       mol_type = protein
                       organism = synthetic construct
SEQUENCE: 264
MPTAASATES AIEDTPAPAR PEVDGRTKPK RQPRYHVVLW DDNYHTYQYV VVMLQSLFGH  60
PPERGYRLAK EVDTQGRVIV LTTTREHAEL KRDQIHAFGY DRLLAHSKGS MKASIEAEE   119

SEQ ID NO: 265         moltype = AA  length = 119
FEATURE                Location/Qualifiers
source                 1..119
                       mol_type = protein
                       organism = synthetic construct
SEQUENCE: 265
MPTAASATES AIEDTPAPAR PEVDGRTKPK RQPRYHVVLW DDDDHTYQYV VVMLQSLFGH  60
PPERGYRLAK EVDTQGRVIV LTTTREHAEL KRDQIHAFGY DRLLAHSKGS MKASIEAEE   119

SEQ ID NO: 266         moltype = AA  length = 107
FEATURE                Location/Qualifiers
source                 1..107
                       mol_type = protein
                       organism = synthetic construct
SEQUENCE: 266
MPSAAPAKPK TKRQSRTQGM PPYNVVLLDD DDHTYGYVIE MLNKVFGHPP KKGFELATEV  60
DKNGRVIVMT TNLEVAELKR DEVHAFGPDP LMPRSKGSMS AVVERAG                107

SEQ ID NO: 267         moltype = AA  length = 107
FEATURE                Location/Qualifiers
source                 1..107
                       mol_type = protein
                       organism = synthetic construct
SEQUENCE: 267
MPSAAPAKPK TKRQSRTQGM PPYNVVLLDD DDHTYGYVIE MLNKVFGHPP EKGFELATEV  60
DKNGRVIVMT TNLEVAELKR DEVHAFGPDP LMPHSKGSMS AVVERAG                107

SEQ ID NO: 268         moltype = AA  length = 107
FEATURE                Location/Qualifiers
source                 1..107
                       mol_type = protein
                       organism = synthetic construct
SEQUENCE: 268
MPSAAPAKPK TKRQSRTQGM PPYNVVLLDD DDHTYGYVIE MLNKVFGHPP KKGFELATEV  60
DKNGRVIVMT TNLEVAELKR DEVHAFGPDP LMPHSKGSMS AVVERAG                107
```

```
SEQ ID NO: 269          moltype = AA  length = 107
FEATURE                 Location/Qualifiers
source                  1..107
                        mol_type = protein
                        organism = synthetic construct
SEQUENCE: 269
MPSAAPAKPK TKRQSRTQGM PPYNVVLLDD DDHTYGYVIE MLNKVFGHPP EKGFELATEM  60
DKLGRVIVMT TNLEVAELKR DEVHAFGPDP LMPRSKGSMS AVVERAG                107

SEQ ID NO: 270          moltype = AA  length = 107
FEATURE                 Location/Qualifiers
source                  1..107
                        mol_type = protein
                        organism = synthetic construct
SEQUENCE: 270
MPSAAPAKPK TKRQSRTQGM PPYNVVLLDD NYHTYGYVIE MLNKVFGHPP EKGFELATEV  60
DKNGRVIVMT TNLEVAELKR DEVHAFGPDP LMPRSKGSMS AVVERAG                107

SEQ ID NO: 271          moltype = AA  length = 119
FEATURE                 Location/Qualifiers
source                  1..119
                        mol_type = protein
                        organism = synthetic construct
SEQUENCE: 271
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DPLMPRSKGS MSAVVEAEE   119

SEQ ID NO: 272          moltype = AA  length = 119
FEATURE                 Location/Qualifiers
source                  1..119
                        mol_type = protein
                        organism = synthetic construct
SEQUENCE: 272
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DPLMPRSKGS MSASIEAEE   119

SEQ ID NO: 273          moltype = AA  length = 119
FEATURE                 Location/Qualifiers
source                  1..119
                        mol_type = protein
                        organism = synthetic construct
SEQUENCE: 273
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGP DPLMPRSKGS MSAVVERAG   119

SEQ ID NO: 274          moltype = AA  length = 119
FEATURE                 Location/Qualifiers
source                  1..119
                        mol_type = protein
                        organism = synthetic construct
SEQUENCE: 274
MPTAASATES AFEDTPAPAR PVVDGRTKPK HQPRYHVVLW DDDDHTYQYV VVMLRSLFGH  60
PRERGYRMAK EMDTLGRVIV LTTTREHAEL KRDQIHAFGY DRLLARSKGS MKASIEAEE   119

SEQ ID NO: 275          moltype = AA  length = 119
FEATURE                 Location/Qualifiers
source                  1..119
                        mol_type = protein
                        organism = synthetic construct
SEQUENCE: 275
MPTAASATES AFEDTPAPAR PVVDGRTKPK RQPRYHVVLW DDDDHTYQYV VVMLRSLFGH  60
PRERGYRMAK EMDTLGRVIV LTTTREHAEL KRDQIHAFGY DRLLARSKGS MKASIEAEE   119

SEQ ID NO: 276          moltype = AA  length = 119
FEATURE                 Location/Qualifiers
source                  1..119
                        mol_type = protein
                        organism = synthetic construct
SEQUENCE: 276
MPTAASATES AFEDTPAPAR PEVDGRTKPK RQPRYHVVLW DDDDHTYQYV VVMLRSLFGH  60
PRERGYRMAK EMDTLGRVIV LTTTREHAEL KRDQIHAFGY DRLLARSKGS MKASIEAEE   119

SEQ ID NO: 277          moltype = AA  length = 119
FEATURE                 Location/Qualifiers
source                  1..119
                        mol_type = protein
                        organism = synthetic construct
SEQUENCE: 277
```

```
MPTAASATES AFEDTPAPAR PEVDGRTKPK RQPRYHVVLW DDDDHTYQYV VVMLRSLFGH  60
PRERGYRMAK EMDTQGRVIV LTTTREHAEL KRDQIHAFGY DRLLARSKGS MKASIEAEE   119

SEQ ID NO: 278          moltype = AA  length = 119
FEATURE                 Location/Qualifiers
source                  1..119
                        mol_type = protein
                        organism = synthetic construct
SEQUENCE: 278
MPTAASATES AIEDTPAPAR PVVDGRTKPK HQPRYHVVLW DDDDHTYQYV VVMLRSLFGH  60
PRERGYRMAK EMDTLGRVIV LTTTREHAEL KRDQIHAFGY DRLLARSKGS MKASIEAEE   119

SEQ ID NO: 279          moltype = AA  length = 119
FEATURE                 Location/Qualifiers
source                  1..119
                        mol_type = protein
                        organism = synthetic construct
SEQUENCE: 279
MPTAASATES AIEDTPAPAR PVVDGRTKPK HQPRYHVVLW DDDDHTYQYV VVMLQSLFGH  60
PRERGYRMAK EMDTLGRVIV LTTTREHAEL KRDQIHAFGY DRLLARSKGS MKASIEAEE   119

SEQ ID NO: 280          moltype = AA  length = 119
FEATURE                 Location/Qualifiers
source                  1..119
                        mol_type = protein
                        organism = synthetic construct
SEQUENCE: 280
MPTAASATES AIEDTPAPAR PVVDGRTKPK HQPRYHVVLW DDDDHTYQYV VVMLQSLFGH  60
PPERGYRMAK EMDTLGRVIV LTTTREHAEL KRDQIHAFGY DRLLARSKGS MKASIEAEE   119

SEQ ID NO: 281          moltype = AA  length = 119
FEATURE                 Location/Qualifiers
source                  1..119
                        mol_type = protein
                        organism = synthetic construct
SEQUENCE: 281
MPTAASATES AFEDTPAPAR PEVDGRTKPK RQPRYHVVLW DDDDHTYQYV VVMLRSLFGH  60
PPERGYRMAK EMDTQGRVIV LTTTREHAEL KRDQIHAFGY DRLLARSKGS MKASIEAEE   119

SEQ ID NO: 282          moltype = AA  length = 119
FEATURE                 Location/Qualifiers
source                  1..119
                        mol_type = protein
                        organism = synthetic construct
SEQUENCE: 282
MPTAASATES AIEDTPAPAR PEVDGRTKPK RQPRYHVVLW DDDDHTYQYV VVMLQSLFGH  60
PRERGYRMAK EMDTLGRVIV LTTTREHAEL KRDQIHAFGY DRLLARSKGS MKASIEAEE   119

SEQ ID NO: 283          moltype = AA  length = 119
FEATURE                 Location/Qualifiers
source                  1..119
                        mol_type = protein
                        organism = synthetic construct
SEQUENCE: 283
MPTAASATES AIEDTPAPAR PEVDGRTKPK HQPRYHVVLW DDDDHTYQYV VVMLRSLFGH  60
PPERGYRMAK EMDTQGRVIV LTTTREHAEL KRDQIHAFGY DRLLARSKGS MKASIEAEE   119

SEQ ID NO: 284          moltype = AA  length = 119
FEATURE                 Location/Qualifiers
source                  1..119
                        mol_type = protein
                        organism = synthetic construct
SEQUENCE: 284
MPTAASATES AIEDTPAPAR PVVDGRTKPK HQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 285          moltype = AA  length = 119
FEATURE                 Location/Qualifiers
source                  1..119
                        mol_type = protein
                        organism = synthetic construct
SEQUENCE: 285
MPTAASATES AIEDTPAPAR PVVDGRTKPK RQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 286          moltype = AA  length = 119
FEATURE                 Location/Qualifiers
source                  1..119
                        mol_type = protein
```

```
                         organism = synthetic construct
SEQUENCE: 286
MPTAASATES AIEDTPAPAR PEVDGRTKPK RQPRYHVVLW DDDDHTYQYV VVMLRSLFGH  60
PPERGYRMAK EMDTQGRVIV LTTTREHAEL KRDQIHAFGY DRLLARSKGS MKASIEAEE   119

SEQ ID NO: 287           moltype = AA  length = 119
FEATURE                  Location/Qualifiers
source                   1..119
                         mol_type = protein
                         organism = synthetic construct
SEQUENCE: 287
MPTAASATES AIEDTPAPAR PEVDGRTKPK RQPRYHVVLW DDDDHTYQYV VVMLQSLFGH  60
PRERGYRMAK EMDTQGRVIV LTTTREHAEL KRDQIHAFGY DRLLARSKGS MKASIEAEE   119

SEQ ID NO: 288           moltype = AA  length = 119
FEATURE                  Location/Qualifiers
source                   1..119
                         mol_type = protein
                         organism = synthetic construct
SEQUENCE: 288
MPTAASATES AIEDTPAPAR PEVDGRTKPK RQPRYHVVLW DDDDHTYQYV VVMLQSLFGH  60
PPERGYRMAK EMDTLGRVIV LTTTREHAEL KRDQIHAFGY DRLLARSKGS MKASIEAEE   119

SEQ ID NO: 289           moltype = AA  length = 119
FEATURE                  Location/Qualifiers
source                   1..119
                         mol_type = protein
                         organism = synthetic construct
SEQUENCE: 289
MPTAASATES AIEDTPAPAR PEVDGRTKPK RQPRYHVVLW DDDDHTYQYV VVMLRSLFGH  60
PPERGYRMAK EMDTQGRVIV LTTTREHAEL KRDQIHAFGY DRLLARSKGS MKASIEAEE   119

SEQ ID NO: 290           moltype = AA  length = 119
FEATURE                  Location/Qualifiers
source                   1..119
                         mol_type = protein
                         organism = synthetic construct
SEQUENCE: 290
MPTAASATES AFEDTPAPAR PEVDGRTKPK RQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 291           moltype = AA  length = 119
FEATURE                  Location/Qualifiers
source                   1..119
                         mol_type = protein
                         organism = synthetic construct
SEQUENCE: 291
MPTAASATES AIEDTPAPAR PEVDGRTKPK HQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 292           moltype = AA  length = 119
FEATURE                  Location/Qualifiers
source                   1..119
                         mol_type = protein
                         organism = synthetic construct
SEQUENCE: 292
MPTAASATES AFEDTPAPAR PVVDGRTKPK HQPRYHVVLW DDDDHTYQYV VVMLRSLFGH  60
PRERGYRLAK EMDTLGRVIV LTTTREHAEL KRDQIHAFGY DRLLARSKGS MKASIEAEE   119

SEQ ID NO: 293           moltype = AA  length = 119
FEATURE                  Location/Qualifiers
source                   1..119
                         mol_type = protein
                         organism = synthetic construct
SEQUENCE: 293
MPTAASATES AFEDTPAPAR PVVDGRTKPK RQPRYHVVLW DDDDHTYQYV VVMLRSLFGH  60
PRERGYRLAK EMDTLGRVIV LTTTREHAEL KRDQIHAFGY DRLLARSKGS MKASIEAEE   119

SEQ ID NO: 294           moltype = AA  length = 119
FEATURE                  Location/Qualifiers
source                   1..119
                         mol_type = protein
                         organism = synthetic construct
SEQUENCE: 294
MPTAASATES AFEDTPAPAR PEVDGRTKPK RQPRYHVVLW DDDDHTYQYV VVMLRSLFGH  60
PRERGYRLAK EMDTLGRVIV LTTTREHAEL KRDQIHAFGY DRLLARSKGS MKASIEAEE   119

SEQ ID NO: 295           moltype = AA  length = 119
FEATURE                  Location/Qualifiers
```

```
source                  1..119
                        mol_type = protein
                        organism = synthetic construct
SEQUENCE: 295
MPTAASATES AFEDTPAPAR PEVDGRTKPK RQPRYHVVLW DDDDHTYQYV VVMLRSLFGH  60
PRERGYRLAK EMDTQGRVIV LTTTREHAEL KRDQIHAFGY DRLLARSKGS MKASIEAEE   119

SEQ ID NO: 296          moltype = AA  length = 119
FEATURE                 Location/Qualifiers
source                  1..119
                        mol_type = protein
                        organism = synthetic construct
SEQUENCE: 296
MPTAASATES AIEDTPAPAR PVVDGRTKPK HQPRYHVVLW DDDDHTYQYV VVMLRSLFGH  60
PRERGYRLAK EMDTLGRVIV LTTTREHAEL KRDQIHAFGY DRLLARSKGS MKASIEAEE   119

SEQ ID NO: 297          moltype = AA  length = 119
FEATURE                 Location/Qualifiers
source                  1..119
                        mol_type = protein
                        organism = synthetic construct
SEQUENCE: 297
MPTAASATES AIEDTPAPAR PVVDGRTKPK HQPRYHVVLW DDDDHTYQYV VVMLQSLFGH  60
PRERGYRLAK EMDTLGRVIV LTTTREHAEL KRDQIHAFGY DRLLARSKGS MKASIEAEE   119

SEQ ID NO: 298          moltype = AA  length = 119
FEATURE                 Location/Qualifiers
source                  1..119
                        mol_type = protein
                        organism = synthetic construct
SEQUENCE: 298
MPTAASATES AIEDTPAPAR PVVDGRTKPK HQPRYHVVLW DDDDHTYQYV VVMLQSLFGH  60
PPERGYRLAK EMDTLGRVIV LTTTREHAEL KRDQIHAFGY DRLLARSKGS MKASIEAEE   119

SEQ ID NO: 299          moltype = AA  length = 119
FEATURE                 Location/Qualifiers
source                  1..119
                        mol_type = protein
                        organism = synthetic construct
SEQUENCE: 299
MPTAASATES AIEDTPAPAR PVVDGRTKPK HQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 300          moltype = AA  length = 119
FEATURE                 Location/Qualifiers
source                  1..119
                        mol_type = protein
                        organism = synthetic construct
SEQUENCE: 300
MPTAASATES AFEDTPAPAR PEVDGRTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 301          moltype = AA  length = 119
FEATURE                 Location/Qualifiers
source                  1..119
                        mol_type = protein
                        organism = synthetic construct
SEQUENCE: 301
MPTAASATES AIEDTPAPAR PEVDGRTKPK HQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 302          moltype = AA  length = 119
FEATURE                 Location/Qualifiers
source                  1..119
                        mol_type = protein
                        organism = synthetic construct
SEQUENCE: 302
MPTAASATES AFEDTPAPAR PVVDGRTKPK HQPRYHVVLW DDNYHTYQYV VVMLRSLFGH  60
PRERGYRMAK EMDTLGRVIV LTTTREHAEL KRDQIHAFGY DRLLAHSKGS MKASIEAEE   119

SEQ ID NO: 303          moltype = AA  length = 119
FEATURE                 Location/Qualifiers
source                  1..119
                        mol_type = protein
                        organism = synthetic construct
SEQUENCE: 303
MPTAASATES AIEDTPAPAR PEVDGRTKPK RQPRYHVVLW DDNYHTYQYV VVMLQSLFGH  60
PPERGYRMAK EMDTQGRVIV LTTTREHAEL KRDQIHAFGY DRLLAHSKGS MKASIEAEE   119
```

```
SEQ ID NO: 304         moltype = AA  length = 119
FEATURE                Location/Qualifiers
source                 1..119
                       mol_type = protein
                       organism = synthetic construct
SEQUENCE: 304
MPTAASATES AIEDTPAPAR PEVDGRTKPK RQPRYHVVLW DDDYHTYQYV VVMLQSLFGH  60
PPERGYRMAK EMDTQGRVIV LTTTREHAEL KRDQIHAFGY DRLLAHSKGS MKASIEAEE   119

SEQ ID NO: 305         moltype = AA  length = 119
FEATURE                Location/Qualifiers
source                 1..119
                       mol_type = protein
                       organism = synthetic construct
SEQUENCE: 305
MPTAASATES AIEDTPAPAR PEVDGRTKPK RQPRYHVVLW DDDDHTYQYV VVMLQSLFGH  60
PPERGYRMAK EMDTQGRVIV LTTTREHAEL KRDQIHAFGY DRLLAHSKGS MKASIEAEE   119

SEQ ID NO: 306         moltype = AA  length = 119
FEATURE                Location/Qualifiers
source                 1..119
                       mol_type = protein
                       organism = synthetic construct
SEQUENCE: 306
MPTAASATES AIEDTPAPAR PEVDGRTKPK RQPRYHVVLW DDDYHTYQYV VVMLQSLFGH  60
PPERGYRMAK EMDTQGRVIV LTTTREHAEL KRDQIHAFGY DRLLARSKGS MKASIEAEE   119

SEQ ID NO: 307         moltype = AA  length = 119
FEATURE                Location/Qualifiers
source                 1..119
                       mol_type = protein
                       organism = synthetic construct
SEQUENCE: 307
MPTAASATES AIEDTPAPAR PEVDGRTKPK RQPRYHVVLW DDNDHTYQYV VVMLQSLFGH  60
PPERGYRMAK EMDTQGRVIV LTTTREHAEL KRDQIHAFGY DRLLARSKGS MKASIEAEE   119

SEQ ID NO: 308         moltype = AA  length = 119
FEATURE                Location/Qualifiers
source                 1..119
                       mol_type = protein
                       organism = synthetic construct
SEQUENCE: 308
MPTAASATES AFEDTPAPAR PVVDGRTKPK HQPRYHVVLW DDDDHTYQYV VVMLRSLFGH  60
PRERGYRLAK EMDTLGRVIV LTTTREHAEL KRDQIHAFGY DRLLARSKGS MKASIEAEE   119

SEQ ID NO: 309         moltype = AA  length = 119
FEATURE                Location/Qualifiers
source                 1..119
                       mol_type = protein
                       organism = synthetic construct
SEQUENCE: 309
MPTAASATES AIEDTPAPAR PEVDGRTKPK HQPRYHVVLW DDDDHTYQYV VVMLRSLFGH  60
PPERGYRLAK EMDTLGRVIV LTTTREHAEL KRDQIHAFGY DRLLARSKGS MKASIEAEE   119

SEQ ID NO: 310         moltype = AA  length = 119
FEATURE                Location/Qualifiers
source                 1..119
                       mol_type = protein
                       organism = synthetic construct
SEQUENCE: 310
MPTAASATES AIEDTPAPAR PEVDGRTKPK HQPRYHVVLW DDDDHTYQYV VVMLRSLFGH  60
PRERGYRLAK EMDTQGRVIV LTTTREHAEL KRDQIHAFGY DRLLARSKGS MKASIEAEE   119

SEQ ID NO: 311         moltype = AA  length = 119
FEATURE                Location/Qualifiers
source                 1..119
                       mol_type = protein
                       organism = synthetic construct
SEQUENCE: 311
MPTAASATES AIEDTPAPAR PVVDGRTKPK HQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 312         moltype = AA  length = 144
FEATURE                Location/Qualifiers
source                 1..144
                       mol_type = protein
                       organism = synthetic construct
SEQUENCE: 312
MHHHHHHHHH HDYDIPTTEN LYFQGMPTAA SATESAIEDT PAPARPEVDG RTKPKHQPRY  60
```

```
HVVLWDDDDH TYQYVVVMLR SLFGHPPERG YRLAKEMDTQ GRVIVLTTTR EHAELKRDQI  120
HAFGYDRLLA RSKGSMKASI EAEE                                         144

SEQ ID NO: 313          moltype = AA  length = 119
FEATURE                 Location/Qualifiers
source                  1..119
                        mol_type = protein
                        organism = synthetic construct
SEQUENCE: 313
MPTAASATES AIEDTPAPAR PEVDGRTKPK RQPRYHVVLW DDDDHTYQYV VVMLRSLFGI  60
PPERGYRLAK EMDTQGRVIV LTTTREHAEL KRDQIHAFGY DRLLARSKGS MKASIEAEE   119

SEQ ID NO: 314          moltype = AA  length = 119
FEATURE                 Location/Qualifiers
source                  1..119
                        mol_type = protein
                        organism = synthetic construct
SEQUENCE: 314
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 315          moltype = AA  length = 119
FEATURE                 Location/Qualifiers
source                  1..119
                        mol_type = protein
                        organism = synthetic construct
SEQUENCE: 315
MPTAASATES AIEDTPAPAR PEVDGRTKPK RQPRYHVVLW DDDDHTYQYV VVMLRSLFGH  60
PYARGYRLAK EMDTQGRVIV LTTTREHAEL KRDQIHAFGR DRLLARSKGS MKASIEAEE   119

SEQ ID NO: 316          moltype = AA  length = 119
FEATURE                 Location/Qualifiers
source                  1..119
                        mol_type = protein
                        organism = synthetic construct
SEQUENCE: 316
MPTAASATES AIEDTPAPAR PEVDGRTKPK RQPRYHVVLW DDDDHTYQYV VVMLRSLFGH  60
PPARGYRLAK EMDTQGRVIV LTTTREHAEL KRDQIHAFGR DRLLARSKGS MKASIEAEE   119

SEQ ID NO: 317          moltype = AA  length = 119
FEATURE                 Location/Qualifiers
source                  1..119
                        mol_type = protein
                        organism = synthetic construct
SEQUENCE: 317
MPTAASATES AIEDTPAPAR PEVDGRTKPK RQPRYHVVLW DDDDHTYQYV VVMLRSLFGH  60
PPWRGYRLAK EMDTQGRVIV LTTTREHAEL KRDQIHAFGY DRLLAHSKGS MKASIEAEE   119

SEQ ID NO: 318          moltype = AA  length = 119
FEATURE                 Location/Qualifiers
source                  1..119
                        mol_type = protein
                        organism = synthetic construct
SEQUENCE: 318
MPTAASATES AIEDTPAPAR PEVDGRTKPK RQPRYHVVLW DDDDHTYQYV VVMLQSLFGH  60
PPSRGYRMAK EMDTQGRVIV LTTTREHAEL KRDQIHAFGY DRLLAHSKGS MKASIEAEE   119

SEQ ID NO: 319          moltype = AA  length = 119
FEATURE                 Location/Qualifiers
source                  1..119
                        mol_type = protein
                        organism = synthetic construct
SEQUENCE: 319
MPTAASATES AIEDTPAPAR PEVDGRTKPK RQPRYHVVLW DDDDHTYQYV VVMLQSLFGH  60
PPARGYRLAK EMDTQGRVIV LTTTREHAEL KRDQIHAFGY DRLLAHSKGS MKASIEAEE   119

SEQ ID NO: 320          moltype = AA  length = 119
FEATURE                 Location/Qualifiers
source                  1..119
                        mol_type = protein
                        organism = synthetic construct
SEQUENCE: 320
MPTAASATES AIEDTPAPAR PEVDGRTKPK RQPRYHVVLW DDDDHTYQYV VVMLRSLFGH  60
PPARGYRLAK EMDTQGRVIV LTTTREHAEL KRDQIHAFGR DRLLARSKGS MKASIEAEE   119

SEQ ID NO: 321          moltype = AA  length = 119
FEATURE                 Location/Qualifiers
source                  1..119
                        mol_type = protein
```

```
                         organism = synthetic construct
SEQUENCE: 321
MPTAASATES AIEDTPAPAR PEVDGRTKPK RQPRYHVVLW NDDDHTYQYV VVMLRSLFGH  60
PPERGYRLAK EMDTQGRVIV LTTTREHAEL KRDQIHAFGR DRLLARSKGS MKASIEAEE   119

SEQ ID NO: 322           moltype = AA  length = 119
FEATURE                  Location/Qualifiers
source                   1..119
                         mol_type = protein
                         organism = synthetic construct
SEQUENCE: 322
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLAHSKGS MKASIEAEE   119

SEQ ID NO: 323           moltype = AA  length = 119
FEATURE                  Location/Qualifiers
source                   1..119
                         mol_type = protein
                         organism = synthetic construct
SEQUENCE: 323
MPTAASATES AIEDTPAPAR PEVDGRTKPK RQPRYHVVLW NDDDHTYQYV VVMLRSLFGH  60
PPSRGYRLAK EMDTQGRVIV LTTTREHAEL KRDQIHAFGY DRLLARSKGS MKASIEAEE   119

SEQ ID NO: 324           moltype = AA  length = 119
FEATURE                  Location/Qualifiers
source                   1..119
                         mol_type = protein
                         organism = synthetic construct
SEQUENCE: 324
MPTAASATES AIEDTPAPAR PEVDGRTKPK HQPRYHVVLW DDDDHTYQYV VVMLRSLFGH  60
PPERGYRLAK EMDTQGRVIV LTTTREHAEL KRDQIHAFGY DRLLAHSKGS MKASIEAEE   119

SEQ ID NO: 325           moltype = AA  length = 119
FEATURE                  Location/Qualifiers
source                   1..119
                         mol_type = protein
                         organism = synthetic construct
SEQUENCE: 325
MPTAASATES AIEDTPAPAR PEVDGRTKPK HQPRYHVVLW DDDDHTYQYV VVMLHSLFGH  60
PPERGYRLAK EMDTQGRVIV LTTTREHAEL KRDQIHAFGY DRLLAHSKGS MKASIEAEE   119

SEQ ID NO: 326           moltype = AA  length = 119
FEATURE                  Location/Qualifiers
source                   1..119
                         mol_type = protein
                         organism = synthetic construct
SEQUENCE: 326
MPTAASATES AIEDTPAPAR PEVDGRTKPK HQPRYHVVLW DDDDHTYQYL VVMLRSLFGH  60
PPERGYRLAK EMDTQGRVIV LTTTREHAEL KRDQIHAFGY DRLLARSKGS MKASIEAEE   119

SEQ ID NO: 327           moltype = AA  length = 119
FEATURE                  Location/Qualifiers
source                   1..119
                         mol_type = protein
                         organism = synthetic construct
SEQUENCE: 327
MPTAASATES AIEDTPAPAR PEVDGRTKPK HQPRYHVVLW DDDDHTYQYI VVMLRSLFGH  60
PPERGYRLAK EMDTQGRVIV LTTTREHAEL KRDQIHAFGY DRLLARSKGS MKASIEAEE   119

SEQ ID NO: 328           moltype = AA  length = 119
FEATURE                  Location/Qualifiers
source                   1..119
                         mol_type = protein
                         organism = synthetic construct
SEQUENCE: 328
MPTAASATES AIEDTPAPAR PEVDGRTKPK HQPRYHVVLW DDDDHTYQYV VVMLRSLFGH  60
PPERGYRLAK EFDTQGRVIV LTTTREHAEL KRDQIHAFGY DRLLARSKGS MKASIEAEE   119

SEQ ID NO: 329           moltype = AA  length = 119
FEATURE                  Location/Qualifiers
source                   1..119
                         mol_type = protein
                         organism = synthetic construct
SEQUENCE: 329
MPTAASATES AIEDTPAPAR PEVDGRTKPK HQPRYHVVLW DDNYHTYQYV VVMLRSLFGH  60
PPERGYRLAK EMDTQGRVIV LTTTREHAEL KRDQIHAFGY DRLLARSKGS MKASIEAEE   119

SEQ ID NO: 330           moltype = AA  length = 119
FEATURE                  Location/Qualifiers
```

```
source                  1..119
                        mol_type = protein
                        organism = synthetic construct
SEQUENCE: 330
MPTAASATES AIEDTPAPAR PEVDGRTKPK RQPRYHVVLW DDDDHTYQYV VVMLHSLFGH  60
PPERGYRLAK EMDTQGRVIV LTTTREHAEL KRDQIHAFGY DRLLARSKGS MKASIEAEE   119

SEQ ID NO: 331          moltype = AA  length = 119
FEATURE                 Location/Qualifiers
source                  1..119
                        mol_type = protein
                        organism = synthetic construct
SEQUENCE: 331
MPTAASGTES AIEDTPAPAR PEVDGRTKPK RQPRYHVVLW DDDDHTYQYV VEMLRSLFGH  60
PPERGYRLAK EMDTQGRVIV LTTTREHAEL KRDQIHAFGY DRLLARSKGS MKASIEAEE   119

SEQ ID NO: 332          moltype = AA  length = 119
FEATURE                 Location/Qualifiers
source                  1..119
                        mol_type = protein
                        organism = synthetic construct
SEQUENCE: 332
MPTAASATES AFEDTPAPAR PEVDGRTKPK RQPRYHVVLW DDDDHTYQYV VVMLRSLFGH  60
PTERGYRLAK EMDTQGRVIV LTTTREHAEL KRDQIHAFGY DRLLARSKGS MKASIEAEE   119

SEQ ID NO: 333          moltype = AA  length = 119
FEATURE                 Location/Qualifiers
source                  1..119
                        mol_type = protein
                        organism = synthetic construct
SEQUENCE: 333
MPTAASATES AIEDTPAPAR PEVDGRTKPK RQPRYHVVLW DDDDHTYQYV VVMLRSLFGH  60
PPDRGYRLAK EMDTQGRVIV LTTTREHAEL KRDQIHAFGY DRLLARSKGS MKASIEAEE   119

SEQ ID NO: 334          moltype = AA  length = 119
FEATURE                 Location/Qualifiers
source                  1..119
                        mol_type = protein
                        organism = synthetic construct
SEQUENCE: 334
MPTAASATES AIEDTPAPAR PEVDGRTKPK RQPRYHVVLW DDDDHTYQYV VVMLQSLLGH  60
PPERGYRLAK EMDTQGRVIV LTTTREHAEL KRDQIHAFGY DRLLARSKGS MKASIEAEE   119

SEQ ID NO: 335          moltype = AA  length = 119
FEATURE                 Location/Qualifiers
source                  1..119
                        mol_type = protein
                        organism = synthetic construct
SEQUENCE: 335
MPTAASATES AIEDTPAPAR PEMDGRTKPK RQPRYHVVLW DDDDHTYQYV VVMLRSLFGH  60
PPERGYRLAK EMDTQGRVIV LTTTREHAEL KRGQIHAFGY DRLLARSKGS MKASIEAEE   119

SEQ ID NO: 336          moltype = AA  length = 119
FEATURE                 Location/Qualifiers
source                  1..119
                        mol_type = protein
                        organism = synthetic construct
SEQUENCE: 336
MPTAASATES AIEDTPAPAR PEVDGRTKPK RQPRYYVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 337          moltype = AA  length = 119
FEATURE                 Location/Qualifiers
source                  1..119
                        mol_type = protein
                        organism = synthetic construct
SEQUENCE: 337
MPTAASATES AIEDTPAPAR PEVDGRTKPK RQTRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 338          moltype = AA  length = 119
FEATURE                 Location/Qualifiers
source                  1..119
                        mol_type = protein
                        organism = synthetic construct
SEQUENCE: 338
MPTAASATES AIEDTPAPAR PEVDGRTVPK RQPRYHVVLW DDDDHTYQYV VVMLQSLFGH  60
PPERGYHLAK EMDTQGRVIV LTTTREHAEL KRDQIHAFGY DRLLARSKGS MKASIEAEE   119
```

```
SEQ ID NO: 339         moltype = AA  length = 119
FEATURE                Location/Qualifiers
source                 1..119
                       mol_type = protein
                       organism = synthetic construct
SEQUENCE: 339
MPTAASATES AIEDTPAPAR PEVDGRTKPK RQPRYHVVLW DDDDHTYQYV VVMLQSLFGH  60
PPERGYRLAK EMDTQGRVVV LTTTREHAEL KRDQIHAFGY DRLLARSKGS MKASIEAEE   119

SEQ ID NO: 340         moltype = AA  length = 119
FEATURE                Location/Qualifiers
source                 1..119
                       mol_type = protein
                       organism = synthetic construct
SEQUENCE: 340
MPTAASATES AIEDTPAPAR PEVDGRTVPK RQPRYHVVLW DDDDHTYQYV VVMLQSLFGH  60
PPERGYRMAK EMDTQGRVIV LTTTREHAEL KRDQIHAFGY DRLLARSKGS MKASIEAEE   119

SEQ ID NO: 341         moltype = AA  length = 119
FEATURE                Location/Qualifiers
source                 1..119
                       mol_type = protein
                       organism = synthetic construct
SEQUENCE: 341
MPTAASATES AIEDTPAPAR PEVDGRTKPR RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 342         moltype = AA  length = 119
FEATURE                Location/Qualifiers
source                 1..119
                       mol_type = protein
                       organism = synthetic construct
SEQUENCE: 342
MPTAASATES AIEDTPAPAR PEVDGRTVPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 343         moltype = AA  length = 119
FEATURE                Location/Qualifiers
source                 1..119
                       mol_type = protein
                       organism = synthetic construct
SEQUENCE: 343
MPTAASATES AFEDTPAPAR PEVDGRTKPI RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 344         moltype = AA  length = 119
FEATURE                Location/Qualifiers
source                 1..119
                       mol_type = protein
                       organism = synthetic construct
SEQUENCE: 344
MPTAASATES AIEDTPAPAR PEVDGRTKPK RQPRCHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 345         moltype = AA  length = 119
FEATURE                Location/Qualifiers
source                 1..119
                       mol_type = protein
                       organism = synthetic construct
SEQUENCE: 345
MPTAASATES AIEDTPAPAR SEVDGRTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 346         moltype = AA  length = 119
FEATURE                Location/Qualifiers
source                 1..119
                       mol_type = protein
                       organism = synthetic construct
SEQUENCE: 346
MPTAASATES AIEDTPAPAR PEVDGRTKPE RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 347         moltype = AA  length = 119
FEATURE                Location/Qualifiers
source                 1..119
                       mol_type = protein
                       organism = synthetic construct
SEQUENCE: 347
MPTAASATES AIEDTPAPAR PEVDGCTKPK RQPRYHVVLW DDDDHTYQYV VVMLQSLFGH  60
```

```
PPERGYRLAK EMDTQGRVIV LTTTREHAEL KRDQIHAFGY DRLLARSKGS MKASIEAEE   119

SEQ ID NO: 348         moltype = AA  length = 119
FEATURE                Location/Qualifiers
source                 1..119
                       mol_type = protein
                       organism = synthetic construct
SEQUENCE: 348
MPTAASATES AIEDTPAPAR PEVDGSTKPK RQPRYHVVLW DDDDHTYQYV VVMLQSLFGH  60
PPERGYRLAK EMDTQGRVIV LTTTREHAEL KRDQIHAFGY DRLLARSKGS MKASIEAEE   119

SEQ ID NO: 349         moltype = AA  length = 119
FEATURE                Location/Qualifiers
source                 1..119
                       mol_type = protein
                       organism = synthetic construct
SEQUENCE: 349
MPTAASATES AIEDTPAPAR PEMDGRTKPK RQPRYHVVLW DDDDHTYQYV VVMLRSLFGH  60
PPERGYRLAK EMDTQGRVIV LTTTREHAEL KRDQIHAVGY DRLLARSKGS MKASIEAEE   119

SEQ ID NO: 350         moltype = AA  length = 119
FEATURE                Location/Qualifiers
source                 1..119
                       mol_type = protein
                       organism = synthetic construct
SEQUENCE: 350
MPTAASATES AIEDTPAPAR PEVDGRTKPK RHPRYHVVLW DDDDHTYQYV VVMLQSLFGH  60
SPKRGYCLAK EMDTQGRVIV LTTTREHAEL KRDQIHAFGY DRLLARSKGS MKASIEAEE   119

SEQ ID NO: 351         moltype = AA  length = 119
FEATURE                Location/Qualifiers
source                 1..119
                       mol_type = protein
                       organism = synthetic construct
SEQUENCE: 351
MPTAASATES AFEDTPAPAR PEVDGRTKPK RQPRYHVVLW DDDDHTYQYV VVMLRSLFGY  60
PPERGYRLAK EMDTQGRVIV LTTTREHAEL KRDQIHAFGY DRLLARSKGS MKASIEAEE   119

SEQ ID NO: 352         moltype = AA  length = 119
FEATURE                Location/Qualifiers
source                 1..119
                       mol_type = protein
                       organism = synthetic construct
SEQUENCE: 352
MPTAASATES AIEDTPAPAR PVVDGRTKPK RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 353         moltype = AA  length = 119
FEATURE                Location/Qualifiers
source                 1..119
                       mol_type = protein
                       organism = synthetic construct
SEQUENCE: 353
MPTAASATES AFEDTPAPAR PEVDGRTKPK RQPRYHVVLW DDDDHTYQYV VVMLRTLFGH  60
PPERGYRLAK EMDTQGRVIV LTTTREHAEL KRDQIHAFGY DRLLARSKGS MKASIEAEE   119

SEQ ID NO: 354         moltype = AA  length = 119
FEATURE                Location/Qualifiers
source                 1..119
                       mol_type = protein
                       organism = synthetic construct
SEQUENCE: 354
MPTAASATES AIEDTPAPAR PEVDGRTKPK HQPRYHVVLW DDDDHTYQYV VVMLRDLFGH  60
PPERGYRLAK EMDTQGRVIV LTTTREHAEL KRDQIHAFGY DRLLARSKGS MKASIEAEE   119

SEQ ID NO: 355         moltype = AA  length = 119
FEATURE                Location/Qualifiers
source                 1..119
                       mol_type = protein
                       organism = synthetic construct
SEQUENCE: 355
MPTAASATES AIEDTPAPAR PEVDGRTKPK HQPRYHVVLW DDDDHTYQYV VVMLRSLFGH  60
PKQRGYRLAK EMDTQGRVIV LTTTREHAEL KRDQIHAFGY DRLLARSKGS MKASIEAEE   119

SEQ ID NO: 356         moltype = AA  length = 119
FEATURE                Location/Qualifiers
source                 1..119
                       mol_type = protein
                       organism = synthetic construct
```

```
SEQUENCE: 356
MPTAASATES AIEDTPAPAR PVVDGRTKPK HQPRYHVVLW DDDDHTYQYV VVMLRSLFGH  60
PQRRGYRLAK EMDTQGRVIV LTTTREHAEL KRDQIHAFGY DRLLARSKGS MKASIEAEE   119

SEQ ID NO: 357         moltype = AA  length = 119
FEATURE                Location/Qualifiers
source                 1..119
                       mol_type = protein
                       organism = synthetic construct
SEQUENCE: 357
MPTAASATES AIEDTPAPAR PVVDGRTKPK RQPRYHVVLW DDDDHTYQYV VVMLLSLFGH  60
PSERGYRLAK EMDTQGRVIV LTTTREHAEL KRDQIHAFGY DRLLARSKGS MKASIEAEE   119

SEQ ID NO: 358         moltype = AA  length = 119
FEATURE                Location/Qualifiers
source                 1..119
                       mol_type = protein
                       organism = synthetic construct
SEQUENCE: 358
MPTAASATES AFEDTPAPAR PEVDGRTKPK HQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 359         moltype = AA  length = 119
FEATURE                Location/Qualifiers
source                 1..119
                       mol_type = protein
                       organism = synthetic construct
SEQUENCE: 359
MPTAASATES AIEDTPAPAR PEVDGRTKPK HQPRYHVVLW DDDDHTYQYV VVMLRYLFGH  60
PPERGYRLAK EMDTQGRVIV LTTTREHAEL KRDQIHAFGY DRLLARSKGS MKASIEAEE   119

SEQ ID NO: 360         moltype = AA  length = 119
FEATURE                Location/Qualifiers
source                 1..119
                       mol_type = protein
                       organism = synthetic construct
SEQUENCE: 360
MPTAASATES AIEDTPALAR PEVDGRTKPK HQPRYHVVLW DDDDHTYQYV VVMLLSLFGH  60
PPERGYRLAK EMDTQGRVIV LTTTREHAEL KRDQIHAFGY DRLLARSKGS MKASIEAEE   119

SEQ ID NO: 361         moltype = AA  length = 119
FEATURE                Location/Qualifiers
source                 1..119
                       mol_type = protein
                       organism = synthetic construct
SEQUENCE: 361
MPTAASATES AIEDTPAPAR PVVDGRTKPK RQPRYHVVLW DDHDHTYQYV VVMLRSLFGH  60
PPERGYRLAK EMDTQGRVIV LTTTREHAEL KRDQIHAFGY DRLLARSKGS MKASIEAEE   119

SEQ ID NO: 362         moltype = AA  length = 119
FEATURE                Location/Qualifiers
source                 1..119
                       mol_type = protein
                       organism = synthetic construct
SEQUENCE: 362
MPTAASATES AIEDTPAPAR PEVDGRTKPK RQPRYHVVLW DDDDHTYQYV VVMLRSLFGH  60
PPERGYRKAK ELDTQGRVIV LTTTREHAEL KRDQIHAFGY DRLLARSKGS MKASIEAEE   119

SEQ ID NO: 363         moltype = AA  length = 119
FEATURE                Location/Qualifiers
source                 1..119
                       mol_type = protein
                       organism = synthetic construct
SEQUENCE: 363
MPTAASATES AIEDTPAPAR PEVDGRTKPK RQPRYHVVLW DDDDHTYQYV VVMLRSLFGH  60
PPERGYRLAK ELVTQGRVIV LTTTREHAEL KRDQIHAFGY DRLLARSKGS MKASIEAEE   119

SEQ ID NO: 364         moltype = AA  length = 119
FEATURE                Location/Qualifiers
source                 1..119
                       mol_type = protein
                       organism = synthetic construct
SEQUENCE: 364
MPTAASATES AIEDTPAPAR PEVDGRTKPK RQPRYHVVLW DDDDHTYQYV VVMLRTLFGH  60
PPSRGYRMAK EMDTQGRVIV LTTTREHAEL KRDQIHAFGR DRLLARSKGS MKASIEAEE   119

SEQ ID NO: 365         moltype = AA  length = 119
FEATURE                Location/Qualifiers
source                 1..119
```

```
                        mol_type = protein
                        organism = synthetic construct
SEQUENCE: 365
MPTAASATES AIEDTPAPAR PEVDGRTKPK RQPRYHVVLW DDDDHTYQYV VVMLRDLFGH  60
PPSRGYRMAK EMDTQGRVIV LTTTREHAEL KRDQIHAFGR DRLLARSKGS MKASIEAEE   119

SEQ ID NO: 366          moltype = AA  length = 119
FEATURE                 Location/Qualifiers
source                  1..119
                        mol_type = protein
                        organism = synthetic construct
SEQUENCE: 366
MPTAASATES AIEDTPAPAR PEVDGRTKPK RQPRYHVVLW DDDDHTYQYV VVMLRYLFGH  60
PPSRGYRMAK EMDTQGRVIV LTTTREHAEL KRDQIHAFGR DRLLARSKGS MKASIEAEE   119

SEQ ID NO: 367          moltype = AA  length = 119
FEATURE                 Location/Qualifiers
source                  1..119
                        mol_type = protein
                        organism = synthetic construct
SEQUENCE: 367
MPTAASATES AIEDTPAPAR PEVDGRTKPK RQPRYHVVLW DDDDHTYQYV VVMLRSLFGH  60
PKQRGYRMAK EMDTQGRVIV LTTTREHAEL KRDQIHAFGR DRLLARSKGS MKASIEAEE   119

SEQ ID NO: 368          moltype = AA  length = 119
FEATURE                 Location/Qualifiers
source                  1..119
                        mol_type = protein
                        organism = synthetic construct
SEQUENCE: 368
MPTAASATES AFEDTPAPAR PEVDGRTKPK HQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 369          moltype = AA  length = 119
FEATURE                 Location/Qualifiers
source                  1..119
                        mol_type = protein
                        organism = synthetic construct
SEQUENCE: 369
MPTAASATES AIEDTPAPAR PEVDGRTKPK RQPRYHVVLW DDDDHTYQYV VVMLRSLFGH  60
PQRRGYRMAK EMDTQGRVIV LTTTREHAEL KRDQIHAFGR DRLLARSKGS MKASIEAEE   119

SEQ ID NO: 370          moltype = AA  length = 119
FEATURE                 Location/Qualifiers
source                  1..119
                        mol_type = protein
                        organism = synthetic construct
SEQUENCE: 370
MPTAASATES AIEDTPAPAR PVVDGRTKPK HQPRYHVVLW DDDDHTYQYV VVMLRSLFGH  60
PQRRGYRMAK EMDTQGRVIV LTTTREHAEL KRDQIHAFGR DRLLARSKGS MKASIEAEE   119

SEQ ID NO: 371          moltype = AA  length = 119
FEATURE                 Location/Qualifiers
source                  1..119
                        mol_type = protein
                        organism = synthetic construct
SEQUENCE: 371
MPTAASATES AIEDTPAPAR PEVDGRTKPK RQPRYHVVLW DDDDHTYQYV VVMLRSLFGH  60
PRSRGYRMAK EMDTQGRVIV LTTTREHAEL KRDQIHAFGR DRLLARSKGS MKASIEAEE   119

SEQ ID NO: 372          moltype = AA  length = 119
FEATURE                 Location/Qualifiers
source                  1..119
                        mol_type = protein
                        organism = synthetic construct
SEQUENCE: 372
MPTAASATES AFEDIPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 373          moltype = AA  length = 119
FEATURE                 Location/Qualifiers
source                  1..119
                        mol_type = protein
                        organism = synthetic construct
SEQUENCE: 373
MPTATSATES AIEDTPAPAR PEVDGRTKPK RQPHYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 374          moltype = AA  length = 119
```

```
FEATURE                Location/Qualifiers
source                 1..119
                       mol_type = protein
                       organism = synthetic construct
SEQUENCE: 374
MPTAASATES AIEDTPAPAR PEVDGRTKPK RQPRYHVVLW DDDDHTYQYV VVMLRSLFGH  60
PRERGYRLAK EMDTQGRVIV LTTTREHAEL KRDQIHAFGY DRLLARSKGS MKASIEAEE   119

SEQ ID NO: 375         moltype = AA  length = 119
FEATURE                Location/Qualifiers
source                 1..119
                       mol_type = protein
                       organism = synthetic construct
SEQUENCE: 375
MPTAASATES AFEDIPAPAR PEVDGRTKPK RQPRYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 376         moltype = AA  length = 119
FEATURE                Location/Qualifiers
source                 1..119
                       mol_type = protein
                       organism = synthetic construct
SEQUENCE: 376
MPTATSATES AIEDTPAPAR PEVDGRTKPK RQPHYHVVLW DDDDHTYQYV VVMLRSLFGH  60
PPERGYRLAK EMDTQGRVIV LTTTREHAEL KRDQIHAFGY DRLLARSKGS MKASIEAEE   119

SEQ ID NO: 377         moltype = AA  length = 119
FEATURE                Location/Qualifiers
source                 1..119
                       mol_type = protein
                       organism = synthetic construct
SEQUENCE: 377
MPTAASATES AIEDTPAPAR PEVDGRTKPK KQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 378         moltype = AA  length = 119
FEATURE                Location/Qualifiers
source                 1..119
                       mol_type = protein
                       organism = synthetic construct
SEQUENCE: 378
MPTAASATES AIEDTPAPAR PEVDGRTKPK RQPRYHVVLW DDDDHTYQYV VVMLRSLFGF  60
PPSRGYRMAK EMDTQGRVIV LTTTREHAEL KRDQIHAFGR DRLLARSKGS MKASIEAEE   119

SEQ ID NO: 379         moltype = AA  length = 119
FEATURE                Location/Qualifiers
source                 1..119
                       mol_type = protein
                       organism = synthetic construct
SEQUENCE: 379
MPTAASATES AIEDIPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 380         moltype = AA  length = 119
FEATURE                Location/Qualifiers
source                 1..119
                       mol_type = protein
                       organism = synthetic construct
SEQUENCE: 380
MPTAASATES AIEDTPAPAR PEVDGRTKPK RQPRYHVVLW DDDDHTYQYV VVMFRSLFGH  60
PPSRGYRMAK EMDTQGRVIV LTTTREHAEL KRDQIHAFGR DRLLARSKGS MKASIEAEE   119

SEQ ID NO: 381         moltype = AA  length = 119
FEATURE                Location/Qualifiers
source                 1..119
                       mol_type = protein
                       organism = synthetic construct
SEQUENCE: 381
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHALGR DRLLARSKGS MKASIEAEE   119

SEQ ID NO: 382         moltype = AA  length = 119
FEATURE                Location/Qualifiers
source                 1..119
                       mol_type = protein
                       organism = synthetic construct
SEQUENCE: 382
MPTAASATES AIEDTPAPAR PEVDGRTKPK RQPRYHVVLW DDDDHTYQYV VVMLRSLFGH  60
PPSRGYRMAK EMDTQGRVIV LTTTNEHAEL KRDQIHAFGR DRLLARSKGS MKASIEAEE   119
```

```
SEQ ID NO: 383          moltype = AA  length = 119
FEATURE                 Location/Qualifiers
source                  1..119
                        mol_type = protein
                        organism = synthetic construct
SEQUENCE: 383
MPTAASATES AIEDTPAPAR PEVDGRTKPK RQPRYHVVLW DDDDHTYQYV VVMFRSLFGH  60
PPSRGYRMAK EMDTQGRVIV LTTTREHAEL KRDQIHALGR DRLLARSKGS MKASIEAEE   119

SEQ ID NO: 384          moltype = AA  length = 119
FEATURE                 Location/Qualifiers
source                  1..119
                        mol_type = protein
                        organism = synthetic construct
SEQUENCE: 384
MPTAASATES AIEDTPAPAR PEVDGRTKPK RQPRYHVVLW DDDDHTYQYV VVMLRSLFGH  60
PPSRGYRMAK EMDTQGVVIV LTTTREHAEL KRDQIHAFGR DRLLARSKGS MKASIEAEE   119

SEQ ID NO: 385          moltype = AA  length = 119
FEATURE                 Location/Qualifiers
source                  1..119
                        mol_type = protein
                        organism = synthetic construct
SEQUENCE: 385
MPTAASATES AIEDTPAPAR PEVDGRTKPK RQPRYHVVLW DDDDHTYQYV VVMLRSLFGH  60
PPSRGYRMAK EMRTQGRVIV LTTTREHAEL KRDQIHAFGR DRLLARSKGS MKASIEAEE   119

SEQ ID NO: 386          moltype = AA  length = 119
FEATURE                 Location/Qualifiers
source                  1..119
                        mol_type = protein
                        organism = synthetic construct
SEQUENCE: 386
MPTAASATES AIEDTPAPAR PEVDGRTKPK RQPRYHVVLW DDDDHTYQYV VVMLRSLFGH  60
PPSRGYRMAK EMDTQGRVIP LTTTREHAEL KRDQIHAFGR DRLLARSKGS MKASIEAEE   119

SEQ ID NO: 387          moltype = AA  length = 119
FEATURE                 Location/Qualifiers
source                  1..119
                        mol_type = protein
                        organism = synthetic construct
SEQUENCE: 387
MPTAASATES AIEDTPAPAR PEVDGRTKPK RQPRYHVVNW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 388          moltype = AA  length = 119
FEATURE                 Location/Qualifiers
source                  1..119
                        mol_type = protein
                        organism = synthetic construct
SEQUENCE: 388
MPTAASATES AIEDTPAPAR PEVDGRTKPK RQPRYHVVLW DDDDHTYQYV VVMLRSLFGH  60
PPSRGYRMAK EMDTQGRVIV LTTTTEHAEL KRDQIHAFGR DRLLARSKGS MKASIEAEE   119

SEQ ID NO: 389          moltype = AA  length = 250
FEATURE                 Location/Qualifiers
source                  1..250
                        mol_type = protein
                        organism = synthetic construct
SEQUENCE: 389
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEEG  120
SAGSAAGSGE FMPTAASATE SAIEDTPAPA RPEVDGRTKP KRQPRYHVVL WDDDDHTYQY  180
VVVMLRSLFG HPPSRGYRMA KEMDTQGRVI VLTTTREHAE LKRDQIHAFG RDRLLARSKG  240
SMKASIEAEE                                                         250

SEQ ID NO: 390          moltype = AA  length = 250
FEATURE                 Location/Qualifiers
source                  1..250
                        mol_type = protein
                        organism = synthetic construct
SEQUENCE: 390
MPTAASATES AIEDTPAPAR PEVDGRTKPK RQPRYHVVLW DDDDHTYQYV VVMLRSLFGH  60
PKQRGYRMAK EMDTQGRVIV LTTTREHAEL KRDQIHAFGR DRLLARSKGS MKASIEAEEG  120
SAGSAAGSGE FMPTAASATE SAIEDTPAPA RPEVDGRTKP KRQPRYHVVL WDDDDHTYQY  180
VVVMLRSLFG HPKQRGYRMA KEMDTQGRVI VLTTTREHAE LKRDQIHAFG RDRLLARSKG  240
SMKASIEAEE                                                         250
```

```
SEQ ID NO: 391         moltype = AA  length = 60
FEATURE                Location/Qualifiers
source                 1..60
                       mol_type = protein
                       organism = synthetic construct
SEQUENCE: 391
MSPILGYWKI KGLVQPTRLL LEYLEEKYEE HLYERDEGDK WRNKKFELGL EFPNLPYYID  60

SEQ ID NO: 392         moltype = AA  length = 60
FEATURE                Location/Qualifiers
source                 1..60
                       mol_type = protein
                       organism = synthetic construct
SEQUENCE: 392
MSPILGYWKI KGLVQPTRLL LEYLEEKYEE HLYERDEGDK WRNKKFELGL EFPNLPYYID  60

SEQ ID NO: 393         moltype = AA  length = 166
FEATURE                Location/Qualifiers
source                 1..166
                       mol_type = protein
                       organism = synthetic construct
SEQUENCE: 393
MGGLFFNALK NCKENFTVLQ TIRQQQSTLN GSWVALLQTR NTLNRAGIRY MMDQNNIGSG  60
STVAELMESA SISLKQAEKN WADYEALPRD PRQSTAAAAE IKRNYDIYHN ALAELIQLLG  120
AGKINEFFDQ PTQGYQDGFE KQYVAYMEQN DRLHDIAVSD NNASYS                166

SEQ ID NO: 394         moltype = AA  length = 166
FEATURE                Location/Qualifiers
source                 1..166
                       mol_type = protein
                       organism = synthetic construct
SEQUENCE: 394
MGGLFFNALK NDKENFTVLQ TIRQQQSTLN GSWVALLQTR NTLNRAGIRY MMDQNNIGSG  60
STVAELMESA SISLKQAEKN WADYEALPRD PRQSTAAAAE IKRNYDIYHN ALAELIQLLG  120
AGKINEFFDQ PTQGYQDGFE KQYVAYMEQN DRLHDIAVSD NNASYS                166

SEQ ID NO: 395         moltype = AA  length = 119
FEATURE                Location/Qualifiers
source                 1..119
                       mol_type = protein
                       organism = synthetic construct
SEQUENCE: 395
MPTAASATES AIEDTPAPAR PEVDGRTKPK RQPRYHVVLW DDDDHTYQYY VVMLRSLFGH  60
PPSRGYRMAK EMDTQGRVIV LTTTREHAEL KRDQIHAFGR DRLLARSKGS MKASIEAEE   119

SEQ ID NO: 396         moltype = AA  length = 119
FEATURE                Location/Qualifiers
source                 1..119
                       mol_type = protein
                       organism = synthetic construct
SEQUENCE: 396
MPTAASATES AIEDTPAPAR PEVDGRTKPK RQPRYHVVLW DDDDHTYQYY VVMLRSLFGH  60
PPSRGYRMAK EIDTQGRVIV LTTTREHAEL KRDQIHAFGR DRLLARSKGS MKASIEAEE   119

SEQ ID NO: 397         moltype = AA  length = 119
FEATURE                Location/Qualifiers
source                 1..119
                       mol_type = protein
                       organism = synthetic construct
SEQUENCE: 397
MPTAASATES AIEDTPAPAR PEVDGRTKPK RQPRYHVVLW EDDDETYQYI VVMLRSLFGH  60
PPSRGYRMAK ELDTQGRVIV LTTTREHAEL KRDQIHAFGR DRLLARSKGS LKASIEAEE   119

SEQ ID NO: 398         moltype = AA  length = 119
FEATURE                Location/Qualifiers
source                 1..119
                       mol_type = protein
                       organism = synthetic construct
SEQUENCE: 398
MPTAASATES AIEDTPAPAR PEVDGRTKPK RQPRYHVVLW NDDDLTYQYL VVMLRSLFGH  60
PPSRGYRMIK EMDTQGRVIV LTTTREHAEL KRDQIHAFGR DRLLARSKGS PKASIEAEE   119

SEQ ID NO: 399         moltype = AA  length = 119
FEATURE                Location/Qualifiers
source                 1..119
                       mol_type = protein
                       organism = synthetic construct
SEQUENCE: 399
MPTAASATES AIEDTPAPAR PEVDGRTKPK RQPRYHVVLW EDDDETYQYL VVMLRSLFGH  60
```

```
PPSRGYRMAK EIDTQGRVIV LTTTREHAEL KRDQIHAFGR DRLLARSKGS MKASIEAEE   119

SEQ ID NO: 400          moltype = AA  length = 119
FEATURE                 Location/Qualifiers
source                  1..119
                        mol_type = protein
                        organism = synthetic construct
SEQUENCE: 400
MPTAASATES AIEDTPAPAR PEVDGRTKPK RQPRYHVVLW DDDDDTYQYL VVMLRSLFGH  60
PPSRGYRMMK EIDTQGRVIV LTTTREHAEL KRDQIHAFGR DRLLARSKGS LKASIEAEE   119

SEQ ID NO: 401          moltype = AA  length = 119
FEATURE                 Location/Qualifiers
source                  1..119
                        mol_type = protein
                        organism = synthetic construct
SEQUENCE: 401
MPTAASATES AIEDTPAPAR PEVDGRTKPK RQPRYHVVLW DDDDETYQYL VVMLRSLFGH  60
PPSRGYRMVK EADTQGRVIV LTTTREHAEL KRDQIHAFGR DRLLARSKGS MKASIEAEE   119

SEQ ID NO: 402          moltype = AA  length = 119
FEATURE                 Location/Qualifiers
source                  1..119
                        mol_type = protein
                        organism = synthetic construct
SEQUENCE: 402
MPTAASATES AIEDTPAPAR PEVDGRTKPK RQPRYHVVLW TDDDQTYQYM VVMLRSLFGH  60
PPSRGYRMAK ELDTQGRVIV LTTTREHAEL KRDQIHAFGR DRLLARSKGS PKASIEAEE   119

SEQ ID NO: 403          moltype = AA  length = 119
FEATURE                 Location/Qualifiers
source                  1..119
                        mol_type = protein
                        organism = synthetic construct
SEQUENCE: 403
MPTAASATES AIEDTPAPAR PEVDGRTKPK RQPRYHVVLW SDDDETYQYI VVMLRSLFGH  60
PPSRGYRMIK ELDTQGRVIV LTTTREHAEL KRDQIHAFGR DRLLARSKGS VKASIEAEE   119

SEQ ID NO: 404          moltype = AA  length = 119
FEATURE                 Location/Qualifiers
source                  1..119
                        mol_type = protein
                        organism = synthetic construct
SEQUENCE: 404
MPTAASATES AIEDTPAPAR PEVDGRTKPK RQPRYHVVLW DDDDDTYQYL VVMLRSLFGH  60
PPSRGYRMAK ELDTQGRVIV LTTTREHAEL KRDQIHAFGR DRLLARSKGS MKASIEAEE   119

SEQ ID NO: 405          moltype = AA  length = 119
FEATURE                 Location/Qualifiers
source                  1..119
                        mol_type = protein
                        organism = synthetic construct
SEQUENCE: 405
MPTAASATES AIEDTPAPAR PEVDGRTKPK RQPRYHVVLW DDDDHTYQYV VVMLRSLFGH  60
PPSRGYRMVK EMDTQGRVIV LTTTREHAEL KRDQIHAFGR DRLLARSKGS VKASIEAEE   119

SEQ ID NO: 406          moltype = AA  length = 119
FEATURE                 Location/Qualifiers
source                  1..119
                        mol_type = protein
                        organism = synthetic construct
SEQUENCE: 406
MPTAASATES AIEDTPAPAR PEVDGRTKPK RQPRYHVVLW EDDDETYQYL VVMLRSLFGH  60
PPSRGYRMVK EIDTQGRVIV LTTTREHAEL KRDQIHAFGR DRLLARSKGS WKASIEAEE   119

SEQ ID NO: 407          moltype = AA  length = 144
FEATURE                 Location/Qualifiers
source                  1..144
                        mol_type = protein
                        organism = synthetic construct
SEQUENCE: 407
MHHHHHHHHH HDYDIPTTEN LYFQGMPTAA SATESAIEDT PAPARPEVDG RTKPKRQPRY  60
HVVLWDDDDH TYQYVVVMLR SLFGHPPSRG YRMAKEMDTQ GRVIVLTTTR EHAELKRDQI  120
HAFGRDRLLA RSKGSMKASI EAEE                                         144

SEQ ID NO: 408          moltype = AA  length = 119
FEATURE                 Location/Qualifiers
source                  1..119
                        mol_type = protein
```

```
                         organism = synthetic construct
SEQUENCE: 408
MPTAASATES AIEDTPAPAR PEVDGRTEPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 409           moltype = AA  length = 119
FEATURE                  Location/Qualifiers
source                   1..119
                         mol_type = protein
                         organism = synthetic construct
SEQUENCE: 409
MPTAASATES AIEDTPAPAR SEVDGRTKPE RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 410           moltype = AA  length = 119
FEATURE                  Location/Qualifiers
source                   1..119
                         mol_type = protein
                         organism = synthetic construct
SEQUENCE: 410
MPTAASATES AIEDTPAPAR PEVDGRTKPK RQPRYHVVLW DDDDHSYQYV VVMLRSLFGH  60
PPSRGYRMAK EMDTQGRVIV LTTTREHAEL KRDQIHAFGR DRLLARSKGS MKASIEAEE   119

SEQ ID NO: 411           moltype = AA  length = 119
FEATURE                  Location/Qualifiers
source                   1..119
                         mol_type = protein
                         organism = synthetic construct
SEQUENCE: 411
MPTAASATES AIEDTPAPAR PEVDGRTKPK RQPRYHVVLW DDDDHIYQYV VVMLRSLFGH  60
PPSRGYRMAK EMDTQGRVIV LTTTREHAEL KRDQIHAFGR DRLLARSKGS MKASIEAEE   119

SEQ ID NO: 412           moltype = AA  length = 119
FEATURE                  Location/Qualifiers
source                   1..119
                         mol_type = protein
                         organism = synthetic construct
SEQUENCE: 412
MPTAASATES AIEDTPAPAR PEVDGRTKPK RQPRYHVVLW DDDDHTYQYV VVMLRSLVGH  60
PPSRGYRMAK EMDTQGRVIV LTTTREHAEL KRDQIHAFGR DRLLARSKGS MKASIEAEE   119

SEQ ID NO: 413           moltype = AA  length = 119
FEATURE                  Location/Qualifiers
source                   1..119
                         mol_type = protein
                         organism = synthetic construct
SEQUENCE: 413
MPTAASATES AIEDTPAPAR PEVDGRTKPK RQPRYHVVLW DDDDHTYQYV VVMLRSLFGH  60
SPSRGYRMAK EMDTQGRVIV LTTTREHAEL KRDQIHAFGR DRLLARSKGS MKASIEAEE   119

SEQ ID NO: 414           moltype = AA  length = 119
FEATURE                  Location/Qualifiers
source                   1..119
                         mol_type = protein
                         organism = synthetic construct
SEQUENCE: 414
MPTAASATES AIEDTPAPAR PEVDGRTKPK RQPRYHVVLW DDDDHTYQYV VVMLRSLFGH  60
PPSRGYRMAK EMHTQGRVIV LTTTREHAEL KRDQIHAFGR DRLLARSKGS MKASIEAEE   119

SEQ ID NO: 415           moltype = AA  length = 119
FEATURE                  Location/Qualifiers
source                   1..119
                         mol_type = protein
                         organism = synthetic construct
SEQUENCE: 415
MPTAASATES AIEDTPAPAR PEVDGRTKPK RQPRYHVVLW DDDDHTYQYV VVMLRSLFGH  60
PPSRGYRMAK EMVTQGRVIV LTTTREHAEL KRDQIHAFGR DRLLARSKGS MKASIEAEE   119

SEQ ID NO: 416           moltype = AA  length = 119
FEATURE                  Location/Qualifiers
source                   1..119
                         mol_type = protein
                         organism = synthetic construct
SEQUENCE: 416
MPTAASATES AIEDTPAPAR PEVDGRTKPK RQPRYHVVLW DDDDHTYQYV VVMLRSLFGH  60
PPSRGYRMAK EMDTLGRVIV LTTTREHAEL KRDQIHAFGR DRLLARSKGS MKASIEAEE   119

SEQ ID NO: 417           moltype = AA  length = 119
FEATURE                  Location/Qualifiers
```

```
source                  1..119
                        mol_type = protein
                        organism = synthetic construct
SEQUENCE: 417
MPTAASATES AIEDTPAPAR PEVDGRTKPK RQPRYHVVLW DDDDHTYQYV VVMLRSLFGH  60
PPSRGYRHAK TMDTQGRVIV LTTTREHAEL KRDQIHALGR DRLLARSKGS MKASIEAEE   119

SEQ ID NO: 418          moltype = AA  length = 119
FEATURE                 Location/Qualifiers
source                  1..119
                        mol_type = protein
                        organism = synthetic construct
SEQUENCE: 418
MPTAASATES AIEDTPAPAR PEVDGRTKPK RQPRYHVVLW DDDRHTYQYV VVMLRSLFGH  60
PPSRGYRMAK EMDTQGRVIV LTTTREHAEL KRDQIHAFGR DRLLARSKGS MKASIEAEE   119

SEQ ID NO: 419          moltype = AA  length = 119
FEATURE                 Location/Qualifiers
source                  1..119
                        mol_type = protein
                        organism = synthetic construct
SEQUENCE: 419
MPTAASATES AIEDTPAPAR PEVDGRTKPK RQPRYHVVLW DDDDHTDQYV VVMLRSLFGH  60
PPSRGYRMAL EAHTQGRVIV LTTTREHAEL KRDQIHAFGR DRLLARSKGS MKASIEAEE   119

SEQ ID NO: 420          moltype = AA  length = 119
FEATURE                 Location/Qualifiers
source                  1..119
                        mol_type = protein
                        organism = synthetic construct
SEQUENCE: 420
MPTAASATES AIEDTPAPAR PEVDGRTKPK RQPRYHVVLE DDDDHTYQYV VVMLRSLFGH  60
PPSRGYRMAK EYDTQGRVIV LTTTREHAEL KRDQIHAFGR DRLLARSKGS MKASIEAEE   119

SEQ ID NO: 421          moltype = AA  length = 119
FEATURE                 Location/Qualifiers
source                  1..119
                        mol_type = protein
                        organism = synthetic construct
SEQUENCE: 421
MPTAASATES AIEDTPAPAR PEVDGRTKPK RQPRYHVVLW DDDDHTYQYI VVMLRSLFGH  60
PPSRGYRMAR IMDTQGRVIV LTTTREHAEL KRDQIHAFGR DRLLARSKGS MKASIEAEE   119

SEQ ID NO: 422          moltype = AA  length = 119
FEATURE                 Location/Qualifiers
source                  1..119
                        mol_type = protein
                        organism = synthetic construct
SEQUENCE: 422
MPTAASATES AIEDTPAPAR PEVDGRTKPK RQPRYHVVLW DDDDHTYQYV VVMLRSLFGH  60
PRQRGYRMAK EMDTQGRVIV LTTTREHAEL KRDQIHAFGR DRLLARSKGS MKASIEAEE   119

SEQ ID NO: 423          moltype = AA  length = 110
FEATURE                 Location/Qualifiers
source                  1..110
                        mol_type = protein
                        organism = synthetic construct
SEQUENCE: 423
MAIEDTPAPA RPEVDGRTKP KRQPRYHVVL WDDDDHTYQY VVVMLRSLFG HPPSRGYRMA  60
KEMDTQGRVI VLTTTREHAE LKRDQIHAFG RDRLLARSKG SMKASIEAEE             110

SEQ ID NO: 424          moltype = AA  length = 100
FEATURE                 Location/Qualifiers
source                  1..100
                        mol_type = protein
                        organism = synthetic construct
SEQUENCE: 424
MPEVDGRTKP KRQPRYHVVL WDDDDHTYQY VVVMLRSLFG HPPSRGYRMA KEMDTQGRVI  60
VLTTTREHAE LKRDQIHAFG RDRLLARSKG SMKASIEAEE                        100

SEQ ID NO: 425          moltype = AA  length = 88
FEATURE                 Location/Qualifiers
source                  1..88
                        mol_type = protein
                        organism = synthetic construct
SEQUENCE: 425
MPRYHVVLWD DDDHTYQYVV VMLRSLFGHP PSRGYRMAKE MDTQGRVIVL TTTREHAELK  60
RDQIHAFGRD RLLARSKGSM KASIEAEE                                     88
```

```
SEQ ID NO: 426         moltype = AA  length = 119
FEATURE                Location/Qualifiers
source                 1..119
                       mol_type = protein
                       organism = synthetic construct
SEQUENCE: 426
MPTAASATES AIEDTPAPAR PEVDGRTKPK RQPRYHVVLW NDDDHTYQYV VVMLQSLFGH  60
PPERGYRLAK EVDTQGRVIV LTTTREHAEL KRDQIHAFGY DPLIDRCKGS MSASIEAEE   119

SEQ ID NO: 427         moltype = AA  length = 119
FEATURE                Location/Qualifiers
source                 1..119
                       mol_type = protein
                       organism = synthetic construct
SEQUENCE: 427
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DPLIDRCKGS MSASIEAEE   119

SEQ ID NO: 428         moltype = AA  length = 119
FEATURE                Location/Qualifiers
source                 1..119
                       mol_type = protein
                       organism = synthetic construct
SEQUENCE: 428
MPTAASATES AIEDTPAPAR PEVDGRTKPK RQPRYHVVLW DDDDHTYQYI VVMLRSLFGH  60
PPSRGYRMAK EMDTQGRVIV LTTTREHAEL KRDQIHAFGR DRLLARSKGS MKASIEAEE   119

SEQ ID NO: 429         moltype = AA  length = 119
FEATURE                Location/Qualifiers
source                 1..119
                       mol_type = protein
                       organism = synthetic construct
SEQUENCE: 429
MPTAASATES AIEDTPAPAR PEVDGRTKPK RQPRYHVVLW DDDDHTYQYT VVMLRSLFGH  60
PPSRGYRMAK ELDTQGRVIV LTTTREHAEL KRDQIHAFGR DRLLARSKGS MKASIEAEE   119

SEQ ID NO: 430         moltype = AA  length = 119
FEATURE                Location/Qualifiers
source                 1..119
                       mol_type = protein
                       organism = synthetic construct
SEQUENCE: 430
MPTAASATES AIEDTPAPAR PEVDGRTKPK RQPRYHVVLW NDDDHTYQYL VVMLRSLFGH  60
PPSRGYRMAK ELDTQGRVIV LTTTREHAEL KRDQIHAFGR DRLLARSKGS MKASIEAEE   119

SEQ ID NO: 431         moltype = AA  length = 119
FEATURE                Location/Qualifiers
source                 1..119
                       mol_type = protein
                       organism = synthetic construct
SEQUENCE: 431
MPTAASATES AIEDTPAPAR PEVDGRTKPK RQPRYHVVLW EDDDHTYQYL VVMLRSLFGH  60
PPSRGYRMAK EYDTQGRVIV LTTTREHAEL KRDQIHAFGR DRLLARSKGS NKASIEAEE   119

SEQ ID NO: 432         moltype = AA  length = 119
FEATURE                Location/Qualifiers
source                 1..119
                       mol_type = protein
                       organism = synthetic construct
SEQUENCE: 432
MPTAASATES AIEDTPAPAR PEVDGRTKPK RQPRYHVVLW DDDDHTYQYV VVMLRSLFGH  60
PTERGYRLAK EMDTQGRVIV LTTTREHAEL KRDQIHAFGR DRLLARSKGS MKASIEAEE   119

SEQ ID NO: 433         moltype = AA  length = 119
FEATURE                Location/Qualifiers
source                 1..119
                       mol_type = protein
                       organism = synthetic construct
SEQUENCE: 433
MPTAASATES AIEDTPAPAR PEVDGRTKPK RQPRYHVVLW DDDDHTYQYV VVMLRSLFGH  60
PTERGYRMAK EMDTQGRVIV LTTTREHAEL KRDQIHAFGR DRLLARSKGS MKASIEAEE   119

SEQ ID NO: 434         moltype = AA  length = 119
FEATURE                Location/Qualifiers
source                 1..119
                       mol_type = protein
                       organism = synthetic construct
SEQUENCE: 434
MPTAASATES AIEDTPAPAR PEVDGRTKPK RQPRYHVVLW DDDDHTYQYV VVMLRSLFGH  60
```

```
PPWRGYRLAR EMDTQGRVIV LTTTREHAEL KRDQIHAFGY DRLLARSKGS MKASIEAEE   119

SEQ ID NO: 435         moltype = AA  length = 119
FEATURE                Location/Qualifiers
source                 1..119
                       mol_type = protein
                       organism = synthetic construct
SEQUENCE: 435
MPTAASATES AIEDTPAPAR PEVDGRTKPK RQPRYHVVLW DDDDHTYQYV VVMLRSLFGH  60
PPWRGYRLAR EMDTQGRVIV LTTTREHAEL KRDQIHAFGR DRLLARSKGS MKASIEAEE   119

SEQ ID NO: 436         moltype = AA  length = 119
FEATURE                Location/Qualifiers
source                 1..119
                       mol_type = protein
                       organism = synthetic construct
SEQUENCE: 436
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS LEASIEAEE   119

SEQ ID NO: 437         moltype = AA  length = 119
FEATURE                Location/Qualifiers
source                 1..119
                       mol_type = protein
                       organism = synthetic construct
SEQUENCE: 437
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS LEASIEAEE   119

SEQ ID NO: 438         moltype = AA  length = 119
FEATURE                Location/Qualifiers
source                 1..119
                       mol_type = protein
                       organism = synthetic construct
SEQUENCE: 438
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHASGR DRLLARSKGS YKASIEAEE   119

SEQ ID NO: 439         moltype = AA  length = 119
FEATURE                Location/Qualifiers
source                 1..119
                       mol_type = protein
                       organism = synthetic construct
SEQUENCE: 439
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHASGR DRLLAHSKGS KKASIEAEE   119

SEQ ID NO: 440         moltype = AA  length = 119
FEATURE                Location/Qualifiers
source                 1..119
                       mol_type = protein
                       organism = synthetic construct
SEQUENCE: 440
MPTAASATES AIEDTPAPAR PEVDGCTKPK RQPRYHVVLW DDDDHTYQYV VVMLQSLFGH  60
PPERGYRLAK EMDTQGCVIV LTTTREHAEL KRDQIYAFGY DRLLARSKGS MKASIEAEE   119

SEQ ID NO: 441         moltype = AA  length = 119
FEATURE                Location/Qualifiers
source                 1..119
                       mol_type = protein
                       organism = synthetic construct
SEQUENCE: 441
MPTAASATES AIEDTPAPAR PEVDGRTKPK RQPRYHVVLW DDDDHTYQYV VEMLRTLFGH  60
PPERGYRLAK EMDTQGRVIV LTTTREHAEL KRDQIHAFGR DRLLARSKGS MKACIEAEE   119

SEQ ID NO: 442         moltype = AA  length = 119
FEATURE                Location/Qualifiers
source                 1..119
                       mol_type = protein
                       organism = synthetic construct
SEQUENCE: 442
MPTAASATES AIEDTPAPAR PEVDGRAKPK RQPRYHVVLW NDDDHTYQYV VVVLQSLFSH  60
PRERGYRLAK EMDTQGRVIV LTTTREHAEL KRDQIHAFGY DRLLARSKGS MKASIEAEE   119

SEQ ID NO: 443         moltype = AA  length = 119
FEATURE                Location/Qualifiers
source                 1..119
                       mol_type = protein
                       organism = synthetic construct
```

```
SEQUENCE: 443
MPTAASATES AIGDTPAPAR PKMDGRTKPK RQPRYHVVLW NDDDHTYQYA VVMLQSLFGH  60
PPERGYRQAK EVDTQGRVIV LTTTREHAEL KRDQIHAFGY DRLLARSKGS MKASIEAEE   119

SEQ ID NO: 444         moltype = AA  length = 119
FEATURE                Location/Qualifiers
source                 1..119
                       mol_type = protein
                       organism = synthetic construct
SEQUENCE: 444
MPTAASATES AIGDTPAPAR PEVDGRTKPK RQPRYHVVLW DDDDHTYQYV VVMLRDLFGH  60
PPERGYHMAK EMDTQGRVIV LTTTREHAEL KRDQIHAFGR DRLLARSKGS MKASIEAEE   119

SEQ ID NO: 445         moltype = AA  length = 140
FEATURE                Location/Qualifiers
source                 1..140
                       mol_type = protein
                       organism = synthetic construct
SEQUENCE: 445
MGSSHHHHHH SSGENLYFQG HMPTAASATE SAIEDTPAPA RPEVDGRTKP KRQPRYHVVL  60
WDDDDHTYQY VVVMLRSLFG HPPSRGYRMA KEMDTQGRVI VLTTTREHAE LKRDQIHAFG  120
RDRLLARSKG SMKASIEAEE                                              140

SEQ ID NO: 446         moltype = AA  length = 110
FEATURE                Location/Qualifiers
source                 1..110
                       mol_type = protein
                       organism = synthetic construct
SEQUENCE: 446
MGSSHHHHHH SSGENLYFQG HMQPRYHVVL WDDDDHTYQY VVVMLRSLFG HPPSRGYRMA  60
KEMDTQGRVI VLTTTREHAE LKRDQIHAFG RDRLLARSKG SMKASIEAEE             110

SEQ ID NO: 447         moltype = AA  length = 83
FEATURE                Location/Qualifiers
source                 1..83
                       mol_type = protein
                       organism = synthetic construct
SEQUENCE: 447
MHSKFSHAGR ICGAKFKVRE PIYRCKECSF DDTCVLCVNC FNPKDHTGHH VYTTICTEFN  60
NGICDCGDKE AWNHTLFCKA EEG                                          83

SEQ ID NO: 448         moltype = AA  length = 83
FEATURE                Location/Qualifiers
source                 1..83
                       mol_type = protein
                       organism = synthetic construct
SEQUENCE: 448
MHSKFSHAGR ICGAKFKVGE PIYRCKECQF DDTCVLCVNC FNPKDHTGHH VYTTICTEFN  60
NGICDCGDKE AWNHTLFCKA EEG                                          83

SEQ ID NO: 449         moltype = AA  length = 83
FEATURE                Location/Qualifiers
source                 1..83
                       mol_type = protein
                       organism = synthetic construct
SEQUENCE: 449
MHSKFSHAGR ICGAKFKVGE PIYRCKECSF DYTCVLCVNC FNPKDHTGHH VYTTICTEFN  60
NGICDCGDKE AWNHTLFCKA EEG                                          83

SEQ ID NO: 450         moltype = AA  length = 83
FEATURE                Location/Qualifiers
source                 1..83
                       mol_type = protein
                       organism = synthetic construct
SEQUENCE: 450
MHSKFSHAGR ICGAKFKVGE PIYRCKECSF DDTCVLCVNC FNPKDHRGHH VYTTICTEFN  60
NGICDCGDKE AWNHTLFCKA EEG                                          83

SEQ ID NO: 451         moltype = AA  length = 83
FEATURE                Location/Qualifiers
source                 1..83
                       mol_type = protein
                       organism = synthetic construct
SEQUENCE: 451
MHSKFSHAGR ICGAKFKVGE PIYRCKECSF DDTCVLCVNC FNPKDHTRHH VYTTICTEFN  60
NGICDCGDKE AWNHTLFCKA EEG                                          83

SEQ ID NO: 452         moltype = AA  length = 83
FEATURE                Location/Qualifiers
```

```
source                  1..83
                        mol_type = protein
                        organism = synthetic construct
SEQUENCE: 452
MHSKFSHAGR ICGAKFKVGE PIYRCKECSF DDTCVLCVNC FNPKDHTGHH VYVTICTEFN  60
NGICDCGDKE AWNHTLFCKA EEG                                          83

SEQ ID NO: 453          moltype = AA  length = 83
FEATURE                 Location/Qualifiers
source                  1..83
                        mol_type = protein
                        organism = synthetic construct
SEQUENCE: 453
MHSKFSHAGR ICGAKFKVGE PIYRCKECSF DDTCVLCVNC FNPKDHTGHH VYTTICREFN  60
NGICDCGDKE AWNHTLFCKA EEG                                          83

SEQ ID NO: 454          moltype = AA  length = 83
FEATURE                 Location/Qualifiers
source                  1..83
                        mol_type = protein
                        organism = synthetic construct
SEQUENCE: 454
MHSKFSHAGR ICGAKFKVGE PIYRCKECSF DDTCVLCVNC FNPKDHTGHH VYTTICTERN  60
NGICDCGDKE AWNHTLFCKA EEG                                          83

SEQ ID NO: 455          moltype = AA  length = 83
FEATURE                 Location/Qualifiers
source                  1..83
                        mol_type = protein
                        organism = synthetic construct
SEQUENCE: 455
MHSKFSHAGR ICGAKFKVGE PIYRCKECSF DDTCVLCVNC FNPKDHTGHH VYTTICTEFN  60
KGICDCGDKE AWNHTLFCKA EEG                                          83

SEQ ID NO: 456          moltype = AA  length = 83
FEATURE                 Location/Qualifiers
source                  1..83
                        mol_type = protein
                        organism = synthetic construct
SEQUENCE: 456
MHSKFSHAGR ICGAKFKVGE PIYRCKECSF DDTCVLCVNC FNPKDHTGHH VYTTICTEFN  60
NGECDCGDKE AWNHTLFCKA EEG                                          83

SEQ ID NO: 457          moltype = AA  length = 83
FEATURE                 Location/Qualifiers
source                  1..83
                        mol_type = protein
                        organism = synthetic construct
SEQUENCE: 457
MHSKFSHAGR ICGAKFKVGE PIYRCKECSF DDTCVLCVNC FNPKDHTGHH VYTTICTEFN  60
NGICDCGDKS AWNHTLFCKA EEG                                          83

SEQ ID NO: 458          moltype = AA  length = 83
FEATURE                 Location/Qualifiers
source                  1..83
                        mol_type = protein
                        organism = synthetic construct
SEQUENCE: 458
MHSKFSHAGR ICGAKFKVGE PIYRCKECSF DDTCVLCVNC FNPKDHTGHH VYTTICTEFN  60
NGICDCGDKT AWNHTLFCKA EEG                                          83

SEQ ID NO: 459          moltype = AA  length = 83
FEATURE                 Location/Qualifiers
source                  1..83
                        mol_type = protein
                        organism = synthetic construct
SEQUENCE: 459
MHSKFSHAGR ICGAKFKVGE PIYRCKECSF DDTCVLCVNC FNPKDHTGHH VYTTICTEFN  60
NGICDCGDKE AWNKTLFCKA EEG                                          83

SEQ ID NO: 460          moltype = AA  length = 83
FEATURE                 Location/Qualifiers
source                  1..83
                        mol_type = protein
                        organism = synthetic construct
SEQUENCE: 460
MHSKFSHAGR ICGAKFKVGE PIYRCKECSF DDTCVLCVNC FNPKDHRGHH VYTTICTERN  60
NGICDCGDKE AWNHTLFCKA EEG                                          83
```

```
SEQ ID NO: 461         moltype = AA  length = 83
FEATURE                Location/Qualifiers
source                 1..83
                       mol_type = protein
                       organism = synthetic construct
SEQUENCE: 461
MHSKFSHAGR ICGAKFKVGE PIYRCKECSF DDTCVLCVNC FNPKDHRGHH VYTTICTERN  60
NGICDCGDKE AWNHELFCKA EEG                                          83

SEQ ID NO: 462         moltype = AA  length = 83
FEATURE                Location/Qualifiers
source                 1..83
                       mol_type = protein
                       organism = synthetic construct
SEQUENCE: 462
MHSKFSHAGR ICGAKFKVGE PIYRCKECSF DDTCVLCVNC FNPKDHTYHH VYTTICTEFN  60
NGICDCGDKE AWNHTLFCKA EEG                                          83

SEQ ID NO: 463         moltype = AA  length = 83
FEATURE                Location/Qualifiers
source                 1..83
                       mol_type = protein
                       organism = synthetic construct
SEQUENCE: 463
MHSKFSHAGR ICGAKFKVGE PIYRCKECSF DDTCVLCVNC FNPKDHLGHH VYTTICTEFN  60
NGICDCGDKE AWNHTLFCKA EEG                                          83

SEQ ID NO: 464         moltype = AA  length = 83
FEATURE                Location/Qualifiers
source                 1..83
                       mol_type = protein
                       organism = synthetic construct
SEQUENCE: 464
MHSKFSHAGR ICGAKFKVGE PIYRCKECSF DDTCVLCVNC FNPKDHTGHH VYTTICTKFN  60
NGICDCGDKE AWNHTLFCKA EEG                                          83

SEQ ID NO: 465         moltype = AA  length = 83
FEATURE                Location/Qualifiers
source                 1..83
                       mol_type = protein
                       organism = synthetic construct
SEQUENCE: 465
MHSKFSHAGR ICGAKFKVGE PIYRCKECSF DDTCVLCVNC FNPKDHTGHH VYTTICKEFN  60
NGICDCGDKE AWNHTLFCKA EEG                                          83

SEQ ID NO: 466         moltype = AA  length = 83
FEATURE                Location/Qualifiers
source                 1..83
                       mol_type = protein
                       organism = synthetic construct
SEQUENCE: 466
MHSKFSHAGR ICGAKFKVGE PIYRCKECSF DDTCVLCVNC FNPKDHTGHH VYTKICTEFN  60
NGICDCGDKE AWNHTLFCKA EEG                                          83

SEQ ID NO: 467         moltype = AA  length = 83
FEATURE                Location/Qualifiers
source                 1..83
                       mol_type = protein
                       organism = synthetic construct
SEQUENCE: 467
MHSKFSHAGR ICGAKFKVGE PIYRCKECSF DDTCVLCVNC FNPKDHKGHH VYTTICTEFN  60
NGICDCGDKE AWNHTLFCKA EEG                                          83

SEQ ID NO: 468         moltype = AA  length = 83
FEATURE                Location/Qualifiers
source                 1..83
                       mol_type = protein
                       organism = synthetic construct
SEQUENCE: 468
MHSKFSHAGR ICGAKFKVGE PIYRCKECSF DDTCVLCVNC FNPKDHLGHH VYTTICTEFN  60
NGECDCGDKT AWNHTLFCKA EEG                                          83

SEQ ID NO: 469         moltype = AA  length = 87
FEATURE                Location/Qualifiers
source                 1..87
                       mol_type = protein
                       organism = synthetic construct
SEQUENCE: 469
PLYQVVLLDD DDHTYDYIIE MLQQIFIFTM VEGYRRAEEL ERKGRSVLIV CELSEAEFAR  60
```

```
DQIPSYGSDW RLPHSQGSMS AVIEPAE                                        87

SEQ ID NO: 470          moltype = AA  length = 119
FEATURE                 Location/Qualifiers
source                  1..119
                        mol_type = protein
                        organism = synthetic construct
SEQUENCE: 470
MPTAASATES AIEDTPAPAR PEVDGRTKPK RQPRYHVVLW DDSDHTRQYA VVMLRSLFGH  60
PPSRGYRMAK EMATQGRVIV LTTTREHAEL KRDQIHAFGR DRLLARSKGS MKASIEAEE   119

SEQ ID NO: 471          moltype = AA  length = 119
FEATURE                 Location/Qualifiers
source                  1..119
                        mol_type = protein
                        organism = synthetic construct
SEQUENCE: 471
MPTAASATES AIEDTPAPAR PEVDGRTKPK RQPRYHVVLW DDRDHTRQYA VVMLRSLFGH  60
PPSRGYRMAK EIRTQGRVIV LTTTREHAEL KRDQIHAFGR DRLLARSKGS MKASIEAEE   119

SEQ ID NO: 472          moltype = AA  length = 119
FEATURE                 Location/Qualifiers
source                  1..119
                        mol_type = protein
                        organism = synthetic construct
SEQUENCE: 472
MPTAASATES AIEDTPAPAR PEVDGRTKPK RQPRYHVVLW NDRDHTSQYI VVMLRSLFGH  60
PPSRGYRMAK EMDTQGRVIV LTTTREHAEL KRDQIHAFGR DRLLARSKGS MKASIEAEE   119

SEQ ID NO: 473          moltype = AA  length = 119
FEATURE                 Location/Qualifiers
source                  1..119
                        mol_type = protein
                        organism = synthetic construct
SEQUENCE: 473
MPTAASATES AIEDTPAPAR PEVDGRTKPK RQPRYHVVLW NDRDHTSQYI IVMLRSLFGH  60
PPSRGYRMAK ELQTQGRVIV LTTTREHAEL KRDQIHAFGR DRLLARSKGS MKASIEAEE   119

SEQ ID NO: 474          moltype = AA  length = 119
FEATURE                 Location/Qualifiers
source                  1..119
                        mol_type = protein
                        organism = synthetic construct
SEQUENCE: 474
MPTAASATES AIEDTPAPAR PEVDGRTKPK RQPRYHVVFW DDDDHTYQYV VVMLRSLFGH  60
PPSRGYRMAH EMCTQGRVIV LTTTREHAEL KRDQIHAFGR DRLLARSKGS MKASIEAEE   119

SEQ ID NO: 475          moltype = AA  length = 119
FEATURE                 Location/Qualifiers
source                  1..119
                        mol_type = protein
                        organism = synthetic construct
SEQUENCE: 475
MPTAASATES AIEDTPAPAR PEVDGRTKPK RQPRYHVVLW DDDDHTYQYV VVMLRSLFYH  60
PPSRGYRMAK EMDTQGRVIV LTTTREHAEL KRDQIHAFGR DRLLARSKGS MKASIEAEE   119

SEQ ID NO: 476          moltype = AA  length = 119
FEATURE                 Location/Qualifiers
source                  1..119
                        mol_type = protein
                        organism = synthetic construct
SEQUENCE: 476
MPTAASATES AIEDTPAPAR PEVDGRTKPK RQPRYHVVLW DDDDHTYQYV VVMLRSLFYH  60
PPSRGYRMAH EMDTQGRVIV LTTTREHAEL KRDQIHAFGR DRLLARSKGS MKASIEAEE   119

SEQ ID NO: 477          moltype = AA  length = 119
FEATURE                 Location/Qualifiers
source                  1..119
                        mol_type = protein
                        organism = synthetic construct
SEQUENCE: 477
MPTAASATES AIEDTPAPAR PEVDGRTKPK RQPRYHVVQW DDDDHTYQYF VVMLRSLFGH  60
PPSRGYRMAK EMDTQGRVIV LTTTREHAEL KRDQIHAFGR DRLLARSKGS MKASIEAEE   119

SEQ ID NO: 478          moltype = AA  length = 119
FEATURE                 Location/Qualifiers
source                  1..119
                        mol_type = protein
                        organism = synthetic construct
```

```
SEQUENCE: 478
MPTAASATES AIEDTPAPAR PEVDGRTKPK RQPRYHVVQI DDDDHTYQYV VVMLRSLFYH  60
PPSRGYRMAK EMDTQGRVIV LTTTREHAEL KRDQIHAFGR DRLLARSKGS MKASIEAEE   119

SEQ ID NO: 479         moltype = AA  length = 119
FEATURE                Location/Qualifiers
source                 1..119
                       mol_type = protein
                       organism = synthetic construct
SEQUENCE: 479
MPTAASATES AIEDTPAPAR PEVDGRTVPQ RQPRYHVVLW DDDDHTYQYV VGMLRSLFGH  60
PPSRGYRMAK EMDTQGRVIV LTTTREHAEL KRDQIHAFGR DRLLARSKGS MKASIEAEE   119

SEQ ID NO: 480         moltype = AA  length = 119
FEATURE                Location/Qualifiers
source                 1..119
                       mol_type = protein
                       organism = synthetic construct
SEQUENCE: 480
MPTAASATES AIEDIPAPAR PEVDGRTKPK HQPRYHVVLW DDDDHTYQYV VVMLRSLFGH  60
PPSRGYRMAS EMDTQGRVIV LTTTREHAEL KRDQIHAFGR DRLLARSKGS MKASIEAEE   119

SEQ ID NO: 481         moltype = AA  length = 119
FEATURE                Location/Qualifiers
source                 1..119
                       mol_type = protein
                       organism = synthetic construct
SEQUENCE: 481
MPTAASATES AIEDTPAPAR TEVDGRTVPK RQPRYHVVLW DDDDHTYQYV VEMLRSLFGH  60
PPSRGYRMAK EMDTQGRVIV LTTTREHAEL KRDQIHAFGR DRLLARSKGS MKASIEAEE   119

SEQ ID NO: 482         moltype = AA  length = 119
FEATURE                Location/Qualifiers
source                 1..119
                       mol_type = protein
                       organism = synthetic construct
SEQUENCE: 482
MPTAASATES AIEDTPAPAR PEVDGRTRPK RQPRYHVVLW DDDDHTYQYV VVMLRKLFGH  60
PPSRGYRMAK EMDTQGRVIV LTTTREHAEL KRDQIHAFGR DRLLARSKGS MKASIEAEE   119

SEQ ID NO: 483         moltype = AA  length = 119
FEATURE                Location/Qualifiers
source                 1..119
                       mol_type = protein
                       organism = synthetic construct
SEQUENCE: 483
MPTAASATES AIEDTPAPAR SEVDGYTVPK RQPRYHVVLW DDDDHTYQYV VVMLRSLFGH  60
PPSRGYRMAK EMDTQGRVIV LTTTREHAEL KRDQIRAFGR DRLLARSKGS MKASIEAEE   119

SEQ ID NO: 484         moltype = AA  length = 167
FEATURE                Location/Qualifiers
source                 1..167
                       mol_type = protein
                       organism = synthetic construct
SEQUENCE: 484
MSGSKFRGHQ KSKGNSYDVE VVLQHVDTGN SYLCGYLKIK GLTEEYPTLT VFFEGEIISK  60
KHPFLTRKWD ADEDVDRKHW GKFLAFYQYA KSFNSDDFDY EELKNGDYVF MRWKEQFLVP  120
DHTIKDISGL SFAGFYYICF QKSAASIEGY YYHRSSEWYQ SLNLTHV               167

SEQ ID NO: 485         moltype = AA  length = 167
FEATURE                Location/Qualifiers
source                 1..167
                       mol_type = protein
                       organism = synthetic construct
SEQUENCE: 485
MSGSKFRGHQ KSKGNSYDVE VVLQHVDTGN SYLCGYLKIK GLTEEYPTLT VFFEGEIISK  60
KHPFLTRKWD ADEDVDRKHW GKFLAFYQYA KSFNSDDFDY EELKNGDYVF MRWKEQFLVP  120
DHTIKDISGA SFAGFYYICF QKSAASIEGY YYHRSSEWYQ SLNLTHV               167

SEQ ID NO: 486         moltype = AA  length = 167
FEATURE                Location/Qualifiers
source                 1..167
                       mol_type = protein
                       organism = synthetic construct
SEQUENCE: 486
MSGSKFRGHQ KSKGNSYDVE VVLQHVDTGN SYLCGYLKIK GLTEEYPTLT AFFEGEIISK  60
KHPFLTRKWD ADEDVDRKHW GKFLAFYQYA KSFNSDDFDY EELKNGDYVF MRWKEQFLVP  120
DHTIKDISGL SFAGFYYICF QKSAASIEGY YYHRSSEWYQ SLNLTHV               167
```

```
SEQ ID NO: 487         moltype = AA  length = 119
FEATURE                Location/Qualifiers
source                 1..119
                       mol_type = protein
                       organism = synthetic construct
SEQUENCE: 487
MPTAASATES AIEDTPAPAR PEVDGRTKPK RQPRYHVVLW DDDDHTYQYV VVMLRSLFGH  60
PPSRGYRMAH EMDTQGRVIV LTTTREHAEL KRDQIHAFGR DRLLARSKGS MKASIEAEE   119

SEQ ID NO: 488         moltype = AA  length = 119
FEATURE                Location/Qualifiers
source                 1..119
                       mol_type = protein
                       organism = synthetic construct
SEQUENCE: 488
MPTAASATES AIEDTPAPAR PEVDGRTKPK RQPRYHVVLI SDDDHTYQYT VVMLRSLFGH  60
PPSRGYRMAH EMDTQGRVIV LTTTREHAEL KRDQIHAFGR DRLLARSKGS MKASIEAEE   119

SEQ ID NO: 489         moltype = AA  length = 119
FEATURE                Location/Qualifiers
source                 1..119
                       mol_type = protein
                       organism = synthetic construct
SEQUENCE: 489
MPTAASATES AIEDTPAPAR PEVDGRTKPK RQPRYHVVFW DDDDHTYQYT VVMLRSLFYH  60
PPSRGYRMAH EMCTQGRVIV LTTTREHAEL KRDQIHAFGR DRLLARSKGS MKASIEAEE   119

SEQ ID NO: 490         moltype = AA  length = 119
FEATURE                Location/Qualifiers
source                 1..119
                       mol_type = protein
                       organism = synthetic construct
SEQUENCE: 490
MPTAASATES AIEDTPAPAR PEVDGRTKPK RQPRYHVVFW DDDDHTYQYT VVMLRSLFYH  60
PPSRGYRMAH EMDTQGRVIV LTTTREHAEL KRDQIHAFGR DRLLARSKGS MKASIEAEE   119

SEQ ID NO: 491         moltype = AA  length = 119
FEATURE                Location/Qualifiers
source                 1..119
                       mol_type = protein
                       organism = synthetic construct
SEQUENCE: 491
MPTAASATES AIEDTPAPAR PEVDGRTKPK RQPRYHVVLW DDDDHTYQYV VVMLRSLFGH  60
PPSRGYRMAK EMDTQGRFIV LTTTREHAEL KRDQIHAFGR DRLLARSKGS MKASIEAEE   119

SEQ ID NO: 492         moltype = AA  length = 119
FEATURE                Location/Qualifiers
source                 1..119
                       mol_type = protein
                       organism = synthetic construct
SEQUENCE: 492
MPTAASATES AIEDTPAPAR PEVDGRTKPK RQPRYHVVEW DDDSHTYQYV VVMLRSLFGH  60
PPSRGYRMDK EMDTQGRVIV LTTTREHAEL KRDQIHAFGR DRLLARSKGS EKASIEAEE   119

SEQ ID NO: 493         moltype = AA  length = 119
FEATURE                Location/Qualifiers
source                 1..119
                       mol_type = protein
                       organism = synthetic construct
SEQUENCE: 493
MPTAASATES AIEDTPAPAR PEVDGRTKPK RQPRYHVVLW DDVDHTYQYT VVMLRSLFGY  60
PPSRGYRMAK EVDTQGRVIV LTTTREHAEL KRDQIHAFGR DRLLARSKGS MKASIEAEE   119

SEQ ID NO: 494         moltype = AA  length = 119
FEATURE                Location/Qualifiers
source                 1..119
                       mol_type = protein
                       organism = synthetic construct
SEQUENCE: 494
MPTAASATES AIEDTPAPAR PEVDGRTKPK RQPRYHVVLW DDDDRTYQYV VVMLRSLFGH  60
PPSRGYRMDK EMDTQGRVIV LTTTREHAEL KRDQIHAFGR DRLLARSKGS MKASIEAEE   119

SEQ ID NO: 495         moltype = AA  length = 119
FEATURE                Location/Qualifiers
source                 1..119
                       mol_type = protein
                       organism = synthetic construct
SEQUENCE: 495
MPTAASATES AIEDTPAPAR PEVDGRTKPK RQPRYHVVLW DDKDHTPQYV VVMLRSLFGH  60
```

```
PPSRGYRMAK EMDTQGRVIV LTTTREHAEL KRDQIHAFGR DRLLARSKGS MKASIEAEE   119

SEQ ID NO: 496         moltype = AA  length = 119
FEATURE                Location/Qualifiers
source                 1..119
                       mol_type = protein
                       organism = synthetic construct
SEQUENCE: 496
MPTAASATES AIEDTPAPAR PEVDGRTKPK RQPRYHVVLW PDDDHTYQYV VVMLRSLFGH  60
PPSRGYRLAK EMDTQGRVIV LTTTREHAEL KRDQIHAFGR DRLLARSKGS MKASIEAEE   119

SEQ ID NO: 497         moltype = AA  length = 119
FEATURE                Location/Qualifiers
source                 1..119
                       mol_type = protein
                       organism = synthetic construct
SEQUENCE: 497
MPTAASATES AIEDTPAPAR PEVDGRTKPK RQPRYHVVLW DDDDCTYQYL VVMLRSLFGH  60
PPSRGYREAK EMDTQGRRIV LTTTREHAEL KRDQIHAFGR DRLLARSKGS MKASIEAEE   119

SEQ ID NO: 498         moltype = AA  length = 119
FEATURE                Location/Qualifiers
source                 1..119
                       mol_type = protein
                       organism = synthetic construct
SEQUENCE: 498
MPTAASATES AIEDTPAPAR PEVDGRTKPK RQPRYHVVLW DDDDHTYQYV VVMLRSLFGH  60
PPSRGYRMIK EMDTQGRVIV LTTTREHAEL KRDQIHAFGR DRLLARSKGS MKASIEAEE   119

SEQ ID NO: 499         moltype = AA  length = 119
FEATURE                Location/Qualifiers
source                 1..119
                       mol_type = protein
                       organism = synthetic construct
SEQUENCE: 499
MPTAASATES AIEDTPAPAR PEVDGRTKPK RQPRYHVVLW DDDDHTYQYV VVMLRSLFGI  60
PPSRGYRMAK EMDTQGRVIV LTTTREHAEL KRDQIHAFGR DRLLARSKGS MKASIEAEE   119

SEQ ID NO: 500         moltype = AA  length = 119
FEATURE                Location/Qualifiers
source                 1..119
                       mol_type = protein
                       organism = synthetic construct
SEQUENCE: 500
MPTAASATES AIEDTPAPAR PEVDGRTKPK RQPRYHVVLW DDDDHTYQYV VEMLRSLFGI  60
PPSRGYRMAK EMDTQGRVIV LTTTREHAEL KRDQIHAFGR DRLLARSKGS MKASIEAEE   119

SEQ ID NO: 501         moltype = AA  length = 119
FEATURE                Location/Qualifiers
source                 1..119
                       mol_type = protein
                       organism = synthetic construct
SEQUENCE: 501
MPTAASATES AIKDTPAPAR SEVDGRTKPE RQPRYHVVLW DDDDHTYQYV VVMLRSLFGH  60
PTSRGYRMAK EMDTQGRVIV LTTTREHAEL KRDQIHAFGR DRLLARSKGS MKASIEAEE   119

SEQ ID NO: 502         moltype = AA  length = 119
FEATURE                Location/Qualifiers
source                 1..119
                       mol_type = protein
                       organism = synthetic construct
SEQUENCE: 502
MPTAASATGS AIEDTPAPAR PEVDGRTKPK RQPRYHVVLW DDDDHTYQYV VVMLRYLFGH  60
PPERGYRMAK EMDTQGRVIV LTTTREHAEL KRDQIHAFGR DRLLARSKGS MKASIEAEE   119

SEQ ID NO: 503         moltype = AA  length = 119
FEATURE                Location/Qualifiers
source                 1..119
                       mol_type = protein
                       organism = synthetic construct
SEQUENCE: 503
MPTAASATES AIEDTPAPAR PEVDGRTKPK RQPRYHVVLW SDEDNTKQYI VVMLRSLFGH  60
PPSRGYRMVE ELDTQGRVIV LTTTREHAEL KRDQIHAFGR DRLLARSKGS IKASIEAEE   119

SEQ ID NO: 504         moltype = AA  length = 119
FEATURE                Location/Qualifiers
source                 1..119
                       mol_type = protein
                       organism = synthetic construct
```

```
SEQUENCE: 504
MPTAASATES AIEDTPAPAR PEVDGRTKPK RQPRYHVVVW DDDDNDEDYV VVMLRSLFGH  60
PPSRGYRMAK EMHTQGRVIV LTTTREHAEL KRDQIHAFGR DRLLARSKGS LKASIEAEE   119

SEQ ID NO: 505         moltype = AA  length = 119
FEATURE                Location/Qualifiers
source                 1..119
                       mol_type = protein
                       organism = synthetic construct
SEQUENCE: 505
MPTAASATES AIEDTPAPAR PEVDGRTKPK RQPRYHVVLW DDEDHTYDYI VVMLRSLFGH  60
PPSRGYRMAK ELDTQGRVIV LTTTREHAEL KRDQIHAFGR DRLLARSKGS VKASIEAEE   119

SEQ ID NO: 506         moltype = AA  length = 119
FEATURE                Location/Qualifiers
source                 1..119
                       mol_type = protein
                       organism = synthetic construct
SEQUENCE: 506
MPTAASATES AIEDTPAPAR PEVDGRTKPK RQPRYHVVLW DDDDHTRQYL VVMLRSLFGH  60
PPSRGYRMTE EADTQGRVIV LTTTREHAEL KRDQIHAFGR DRLLARSKGS MKASIEAEE   119

SEQ ID NO: 507         moltype = AA  length = 119
FEATURE                Location/Qualifiers
source                 1..119
                       mol_type = protein
                       organism = synthetic construct
SEQUENCE: 507
MPTAASATES AIEDTPAPAR PEVDGRTKPK RQPRYHVVIW DDEDHTHDYW VVMLRSLFGH  60
PPSRGYRMSE ELDTQGRVIV LTTTREHAEL KRDQIHAFGR DRLLARSKGS MKASIEAEE   119

SEQ ID NO: 508         moltype = AA  length = 126
FEATURE                Location/Qualifiers
source                 1..126
                       mol_type = protein
                       organism = synthetic construct
SEQUENCE: 508
MGDVQPETCR PSAASGNYFP QYPEYAIETA RLRTFEAWPR NLKQKPHQLA EAGFFYTGVG  60
DRVRCFSCGG GLMDWNDNDE PWEQHARHLS QCRFVKLMKG QLYIDTVAAK PVLAEEKEES  120
TSIGGD                                                            126

SEQ ID NO: 509         moltype = AA  length = 116
FEATURE                Location/Qualifiers
source                 1..116
                       mol_type = protein
                       organism = synthetic construct
SEQUENCE: 509
MGSDAVSSDR NFPNSTNLPR NPSMADYEAR IFTFGTWIYS VNKEQLARAG FYALGEGDKV  60
KCFHCGGGLT DWKPSEDPWE QHAKWYPGCK YLLEQKGQEY INNIHLTHSL EECLVR      116

SEQ ID NO: 510         moltype = AA  length = 116
FEATURE                Location/Qualifiers
source                 1..116
                       mol_type = protein
                       organism = synthetic construct
SEQUENCE: 510
MGSDAVSSDR NFPNSTNLPR NPSMADYEAR IFTFGTWIYS VNKEQLARAG FYALGEGDKV  60
KCFHCGGGLT DWKPSEDPWE QHARHYPGCK YLLEQKGQEY INNIHLTHSL EECLVR      116

SEQ ID NO: 511         moltype = AA  length = 114
FEATURE                Location/Qualifiers
source                 1..114
                       mol_type = protein
                       organism = synthetic construct
SEQUENCE: 511
MGLENSLETL RFSISNLSMQ THAARMRTFM YWPSSVPVQP EQLASAGFYY VGRNDDVKCF  60
CCDGGLRCWE SGDDPWVEHA KWFPRCEFLI RMKGQEFVDE IQGRYPHLLE QLLS        114

SEQ ID NO: 512         moltype = AA  length = 114
FEATURE                Location/Qualifiers
source                 1..114
                       mol_type = protein
                       organism = synthetic construct
SEQUENCE: 512
MGLENSLETL RFSISNLSMQ THAARMRTFM YWPSSVPVQP EQLASAGFYY VGRNDDVKCF  60
CCDGGLRCWE SGDDPWVEHA RHFPRCEFLI RMKGQEFVDE IQGRYPHLLE QLLS        114

SEQ ID NO: 513         moltype = AA  length = 98
FEATURE                Location/Qualifiers
```

```
source                  1..98
                        mol_type = protein
                        organism = synthetic construct
SEQUENCE: 513
MGSMRYTVSN LSMQTHAARF KTFFNWPSSV LVNPEQLASA GFYYVGNSDD VKCFCCDGGL  60
RCWESGDDPW VQHAKWFPRC EYLIRIKGQE FIRQVQAS                          98

SEQ ID NO: 514          moltype = AA  length = 98
FEATURE                 Location/Qualifiers
source                  1..98
                        mol_type = protein
                        organism = synthetic construct
SEQUENCE: 514
MGSMRYTVSN LSMQTHAARF KTFFNWPSSV LVNPEQLASA GFYYVGNSDD VKCFCCDGGL  60
RCWESGDDPW VQHARHFPRC EYLIRIKGQE FIRQVQAS                          98

SEQ ID NO: 515          moltype = AA  length = 124
FEATURE                 Location/Qualifiers
source                  1..124
                        mol_type = protein
                        organism = synthetic construct
SEQUENCE: 515
MGSHMLETEE EEEEGAGATL SRGPAFPGMG SEELRLASFY DWPLTAEVPP ELLAAAGFFH  60
TGHQDKVRCF FCYGGLQSWK RGDDPWTEHA KWFPSCQFLL RSKGRDFVHS VQETHSQLLG  120
SWDP                                                               124

SEQ ID NO: 516          moltype = AA  length = 124
FEATURE                 Location/Qualifiers
source                  1..124
                        mol_type = protein
                        organism = synthetic construct
SEQUENCE: 516
MGSHMLETEE EEEEGAGATL SRGPAFPGMG SEELRLASFY DWPLTAEVPP ELLAAAGFFH  60
TGHQDKVRCF FCYGGLQSWK RGDDPWTEHA RHFPSCQFLL RSKGRDFVHS VQETHSQLLG  120
SWDP                                                               124

SEQ ID NO: 517          moltype = AA  length = 109
FEATURE                 Location/Qualifiers
source                  1..109
                        mol_type = protein
                        organism = synthetic construct
SEQUENCE: 517
MGSHMSTNLP RNPSMTGYEA RLITFGTWMY SVNKEQLARA GFYAIGQEDK VQCFHCGGGL  60
ANWKPKEDPW EQHAKWYPGC KYLLEEKGHE YINNIHLTRS LEGALVQTT              109

SEQ ID NO: 518          moltype = AA  length = 109
FEATURE                 Location/Qualifiers
source                  1..109
                        mol_type = protein
                        organism = synthetic construct
SEQUENCE: 518
MGSHMSTNLP RNPSMTGYEA RLITFGTWMY SVNKEQLARA GFYAIGQEDK VQCFHCGGGL  60
ANWKPKEDPW EQHARHYPGC KYLLEEKGHE YINNIHLTRS LEGALVQTT              109

SEQ ID NO: 519          moltype = AA  length = 95
FEATURE                 Location/Qualifiers
source                  1..95
                        mol_type = protein
                        organism = synthetic construct
SEQUENCE: 519
MGSHMRYQEE EARLASFRNW PFYVQGISPC VLSEAGFVFT GKQDTVQCFS CGGCLGNWEE  60
GDDPWKEHAK WFPKCEFLRS KKSSEEITQY IQSYK                             95

SEQ ID NO: 520          moltype = AA  length = 95
FEATURE                 Location/Qualifiers
source                  1..95
                        mol_type = protein
                        organism = synthetic construct
SEQUENCE: 520
MGSHMRYQEE EARLASFRNW PFYVQGISPC VLSEAGFVFT GKQDTVQCFS CGGCLGNWEE  60
GDDPWKEHAR HFPKCEFLRS KKSSEEITQY IQSYK                             95

SEQ ID NO: 521          moltype = AA  length = 119
FEATURE                 Location/Qualifiers
source                  1..119
                        mol_type = protein
                        organism = synthetic construct
SEQUENCE: 521
MPTAASATES AIEDTPAPAR PEVDGRTKPK RQPRYHVVLW DDDDHTVQYI VVMLRSLFGH  60
```

```
PPSRGYRMAK EMHTQGRVIV LTTTREHAEL KRDQIHAFGR DRLLARSKGS LKASIEAEE   119

SEQ ID NO: 522         moltype = AA  length = 119
FEATURE                Location/Qualifiers
source                 1..119
                       mol_type = protein
                       organism = synthetic construct
SEQUENCE: 522
MPTAASATES AIEDTPAPAR PEVDGRTKPK RQPRYHVVLW DDDDHTVQYI VVMLRSLFGH  60
PPSRGYRMAK EATTQGRVIV LTTTREHAEL KRDQIHAFGR DRLLARSKGS AKASIEAEE   119

SEQ ID NO: 523         moltype = AA  length = 119
FEATURE                Location/Qualifiers
source                 1..119
                       mol_type = protein
                       organism = synthetic construct
SEQUENCE: 523
MPTAASATES AIEDTPAPAR PEVDGRTKPK RQPRYHVVLW DDEDHTMQYI VVMLRSLFGH  60
PPSRGYRMAK EMHTQGRVIV LTTTREHAEL KRDQIHAFGR DRLLARSKGS AKASIEAEE   119

SEQ ID NO: 524         moltype = AA  length = 119
FEATURE                Location/Qualifiers
source                 1..119
                       mol_type = protein
                       organism = synthetic construct
SEQUENCE: 524
MPTAASATES AIEDTPAPAR PEVDGRTKPK RQPRYHVVLW DDDDHTVQYI VVMLRSLFGH  60
PPSRGYRMAK EIGTQGRVIV LTTTREHAEL KRDQIHAFGH DRLLARSKGS AKASIEAEE   119

SEQ ID NO: 525         moltype = AA  length = 119
FEATURE                Location/Qualifiers
source                 1..119
                       mol_type = protein
                       organism = synthetic construct
SEQUENCE: 525
MPTAASATES AIEDTPAPAR PEVDGRTKPK RQPRYHVVLW DDDDHTVQYI VVMLRSLFGH  60
PPSRGYRMAK EMHTQGRVIV LTTTREHAEL KRDQIHAFGH DRLLARSKGS AKASIEAEE   119

SEQ ID NO: 526         moltype = AA  length = 119
FEATURE                Location/Qualifiers
source                 1..119
                       mol_type = protein
                       organism = synthetic construct
SEQUENCE: 526
MPTAASATES AIEDTPAPAR PEVDGRTKPK RQPRYHVVLW DDDDHTVQYI VVMLRSLFGH  60
PPSRGYRMAK EIYTQGRVIV LTTTREHAEL KRDQIHAFGR DRLLARSKGS AKASIEAEE   119

SEQ ID NO: 527         moltype = AA  length = 119
FEATURE                Location/Qualifiers
source                 1..119
                       mol_type = protein
                       organism = synthetic construct
SEQUENCE: 527
MPTAASATES AIEDTPAPAR PEVDGRTKPK RQPRYHVVLW DDDDHTVQYI VVMLRSLFGH  60
PPSRGYRMAK EMHTQGRVIV LTTTREHAEL KRDQIHAFGR DRLLARSKGS AKASIEAEE   119

SEQ ID NO: 528         moltype = AA  length = 119
FEATURE                Location/Qualifiers
source                 1..119
                       mol_type = protein
                       organism = synthetic construct
SEQUENCE: 528
MPTAASATES AIEDTPAPAR PEVDGRTKPK RQPRYHVVLW DDRDHTYQYI VVMLRSLFGH  60
PPSRGYRMAK EAYTQGRVIV LTTTREHAEL KRDQIHAFGR DRLLARSKGS LKASIEAEE   119

SEQ ID NO: 529         moltype = AA  length = 119
FEATURE                Location/Qualifiers
source                 1..119
                       mol_type = protein
                       organism = synthetic construct
SEQUENCE: 529
MPTAASATES AIEDTPAPAR PEVDGRTKPK RQPRYHVVLW DDRDHTAQYA VVMLRSLFGH  60
PPSRGYRMAK EIYTQGRVIV LTTTREHAEL KRDQIHAFGH DRLLARSKGS AKASIEAEE   119

SEQ ID NO: 530         moltype = AA  length = 119
FEATURE                Location/Qualifiers
source                 1..119
                       mol_type = protein
                       organism = synthetic construct
```

```
SEQUENCE: 530
MPTAASATES AIEDTPAPAR PEVDGRTKPK RQPRYHVVLW DDNDHTLQYI VVMLRSLFGH  60
PPSRGYRMAK EVDTQGRVIV LTTTREHAEL KRDQIHAFGR DRLLARSKGS MKASIEAEE   119

SEQ ID NO: 531         moltype = AA  length = 119
FEATURE                Location/Qualifiers
source                 1..119
                       mol_type = protein
                       organism = synthetic construct
SEQUENCE: 531
MPTAASATES AIEDTPAPAR PEVDGRTKPK RQPRYHVVLW DDDDHTVQYI VVMLRSLFGH  60
PPSRGYRMAK ELDTQGRVIV LTTTREHAEL KRDQIHAFGR DRLLARSKGS MKASIEAEE   119

SEQ ID NO: 532         moltype = AA  length = 119
FEATURE                Location/Qualifiers
source                 1..119
                       mol_type = protein
                       organism = synthetic construct
SEQUENCE: 532
MPTAASATES AIEDTPAPAR PEVDGRTKPK RQPRYHVVLW DDGDHTWQYI VVMLRSLFGH  60
PPSRGYRMAK ELTTQGRVIV LTTTREHAEL KRDQIHAFGR DRLLARSKGS MKASIEAEE   119

SEQ ID NO: 533         moltype = AA  length = 119
FEATURE                Location/Qualifiers
source                 1..119
                       mol_type = protein
                       organism = synthetic construct
SEQUENCE: 533
MPTAASATES AIEDTPAPAR PEVDGRTKPK RQPRYHVVLW DDSDHTFQYI VVMLRSLFGH  60
PPSRGYRMAK ELHTQGRVIV LTTTREHAEL KRDQIHAFGR DRLLARSKGS MKASIEAEE   119

SEQ ID NO: 534         moltype = AA  length = 119
FEATURE                Location/Qualifiers
source                 1..119
                       mol_type = protein
                       organism = synthetic construct
SEQUENCE: 534
MPTAASATES AIEDTPAPAR PEVDGRTKPK RQPRYHVVLW DDADHTYQYI VVMLRSLFGH  60
PPSRGYRMAK EMHTQGRVIV LTTTREHAEL KRDQIHAFGR DRLLARSKGS MKASIEAEE   119

SEQ ID NO: 535         moltype = AA  length = 119
FEATURE                Location/Qualifiers
source                 1..119
                       mol_type = protein
                       organism = synthetic construct
SEQUENCE: 535
MPTAASATES AIEDTPAPAR PEVDGRTKPK RQPRYHVVLW DDDDHTMQYI VVMLRSLFGH  60
PPSRGYRMAK EVTTQGRVIV LTTTREHAEL KRDQIHAFGR DRLLARSKGS MKASIEAEE   119

SEQ ID NO: 536         moltype = AA  length = 119
FEATURE                Location/Qualifiers
source                 1..119
                       mol_type = protein
                       organism = synthetic construct
SEQUENCE: 536
MPTAASATES AIEDTPAPAR PEVDGRTKPK RQPRYHVVLW DDSDHTIQYI VVMLRSLFGH  60
PPSRGYRMAK EADTQGRVIV LTTTREHAEL KRDQIHAFGR DRLLARSKGS MKASIEAEE   119

SEQ ID NO: 537         moltype = AA  length = 119
FEATURE                Location/Qualifiers
source                 1..119
                       mol_type = protein
                       organism = synthetic construct
SEQUENCE: 537
MPTAASATES AIEDTPAPAR PEVDGRTKPK RQPRYHVVLW DDDDHTWQYI VVMLRSLFGH  60
PPSRGYRMAK EMHTQGRVIV LTTTREHAEL KRDQIHAFGR DRLLARSKGS MKASIEAEE   119

SEQ ID NO: 538         moltype = AA  length = 119
FEATURE                Location/Qualifiers
source                 1..119
                       mol_type = protein
                       organism = synthetic construct
SEQUENCE: 538
MPTAASATES AIEDTPAPAR PEVDGRTKPK RQPRYHVVLW DDDDHTVQYI VVMLRSLFGH  60
PPSRGYRMAK EMHTQGRVIV LTTTREHAEL KRDQIHAFGR DRLLARSKGS MKASIEAEE   119

SEQ ID NO: 539         moltype = AA  length = 119
FEATURE                Location/Qualifiers
source                 1..119
```

```
                         mol_type = protein
                         organism = synthetic construct
SEQUENCE: 539
MPTAASATES AIEDTPAPAR PEVDGRTKPK RQPRYHVVLW DDNDHTLQYI VVMLRSLFGH  60
PPSRGYRMAK EMHTQGRVIV LTTTREHAEL KRDQIHAFGR DRLLARSKGS MKASIEAEE   119

SEQ ID NO: 540           moltype = AA  length = 119
FEATURE                  Location/Qualifiers
source                   1..119
                         mol_type = protein
                         organism = synthetic construct
SEQUENCE: 540
MPTAASATES AIEDTPAPAR PEVDGRTKPK RQPRYHVVLW DDDDHTVQYI VVMLRSLFGH  60
PPSRGYRMAK EISTQGRVIV LTTTREHAEL KRDQIHAFGR DRLLARSKGS MKASIEAEE   119

SEQ ID NO: 541           moltype = AA  length = 119
FEATURE                  Location/Qualifiers
source                   1..119
                         mol_type = protein
                         organism = synthetic construct
SEQUENCE: 541
MPTAASATES AIEDTPAPAR PEVDGRTKPK RQPRYHVVLW DDGDHTLQYI VVMLRSLFGH  60
PPSRGYRMAK EMHTQGRVIV LTTTREHAEL KRDQIHAFGR DRLLARSKGS MKASIEAEE   119

SEQ ID NO: 542           moltype = AA  length = 119
FEATURE                  Location/Qualifiers
source                   1..119
                         mol_type = protein
                         organism = synthetic construct
SEQUENCE: 542
MPTAASATES AIEDTPAPAR PEVDGRTKPK RQPRYHVVLW DDDDHTIQYI VVMLRSLFGH  60
PPSRGYRMAK EMHTQGRVIV LTTTREHAEL KRDQIHAFGR DRLLARSKGS MKASIEAEE   119

SEQ ID NO: 543           moltype = AA  length = 119
FEATURE                  Location/Qualifiers
source                   1..119
                         mol_type = protein
                         organism = synthetic construct
SEQUENCE: 543
MPTAASATES AIEDTPAPAR PEVDGRTKPK RQPRYHVVLW DDEDHTMQYI VVMLRSLFGH  60
PPSRGYRMAK EMHTQGRVIV LTTTREHAEL KRDQIHAFGR DRLLARSKGS LKASIEAEE   119

SEQ ID NO: 544           moltype = AA  length = 313
FEATURE                  Location/Qualifiers
source                   1..313
                         mol_type = protein
                         organism = synthetic construct
SEQUENCE: 544
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEEG  120
SAGSAAGSGE FMDKDCEMKR TTLDSPLGKL ELSGCEQGLH EIKLLGKGTS AADAVEVPAP  180
AAVLGGPEPL MQATAWLNAY FHQPEAIEEF PVPALHHPVF QQESFTRQVL WKLLKVVKFG  240
EVISYQQLAA LAGNPAATAA VKTALSGNPV PILIPCHRVV SSSGAVGGYE GGLAVKEWLL  300
AHEGHRLGKP GLG                                                    313

SEQ ID NO: 545           moltype = AA  length = 444
FEATURE                  Location/Qualifiers
source                   1..444
                         mol_type = protein
                         organism = synthetic construct
SEQUENCE: 545
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEEG  120
SAGSAAGSGE FMPTAASATE SAIEDTPAPA RPEVDGRTKP KRQPRYHVVL WDDDDHTYQY  180
VVVMLRSLFG HPPSRGYRMA KEMDTQGRVI VLTTTREHAE LKRDQIHAFG RDRLLARSKG  240
SMKASIEAEE GSAGSAAGSG EFMDKDCEMK RTTLDSPLGK LELSGCEQGL HEIKLLGKGT  300
SAADAVEVPA PAAVLGGPEP LMQATAWLNA YFHQPEAIEE FPVPALHHPV FQQESFTRQV  360
LWKLLKVVKF GEVISYQQLA ALAGNPAATA AVKTALSGNP VPILIPCHRV VSSSGAVGGY  420
EGGLAVKEWL LAHEGHRLGK PGLG                                        444

SEQ ID NO: 546           moltype = AA  length = 477
FEATURE                  Location/Qualifiers
source                   1..477
                         mol_type = protein
                         organism = synthetic construct
SEQUENCE: 546
MSDSPVDLKP KPKVKPKLER PKLYKVMLLN DDYTPMSFVT VVLKAVFRMS EDTGRRVMMT  60
AHRFGSAVVV VCERDIAETK AKEATDLGKE AGFPLMFTTE PEEGSAGSAA GSGEFMSDSP  120
VDLKPKPKVK PKLERPKLYK VMLLNDDYTP MSFVTVVLKA VFRMSEDTGR RVMMTAHRFG  180
```

```
SAVVVVCERD IAETKAKEAT DLGKEAGFPL MFTTEPEEGH HHHHHHHHHG GGSGGGSGGG  240
SGLNDFFEAQ KIEWHEGGGS GGGSGGGSGL NDFFEAQKIE WHEGSAGSAA GSGEFMDKDC  300
EMKRTTLDSP LGKLELSGCE QGLHEIKLLG KGTSAADAVE VPAPAAVLGG PEPLMQATAW  360
LNAYFHQPEA IEEFPVPALH HPVFQQESFT RQVLWKLLKV VKFGEVISYQ QLAALAGNPA  420
ATAAVKTALS GNPVPILIPC HRVVSSSGAV GGYEGGLAVK EWLLAHEGHR LGKPGLG     477

SEQ ID NO: 547         moltype = AA  length = 277
FEATURE                Location/Qualifiers
source                 1..277
                       mol_type = protein
                       organism = synthetic construct
SEQUENCE: 547
MHSKFSHAGR ICGAKFKVGE PIYRCKECSF DDTCVLCVNC FNPKDHTGHH VYTTICTEFN  60
NGICDCGDKE AWNHTLFCKA EEGGSAGSAA GSGEFMDKDC EMKRTTLDSP LGKLELSGCE  120
QGLHEIKLLG KGTSAADAVE VPAPAAVLGG PEPLMQATAW LNAYFHQPEA IEEFPVPALH  180
HPVFQQESFT RQVLWKLLKV VKFGEVISYQ QLAALAGNPA ATAAVKTALS GNPVPILIPC  240
HRVVSSSGAV GGYEGGLAVK EWLLAHEGHR LGKPGLG                           277

SEQ ID NO: 548         moltype = AA  length = 372
FEATURE                Location/Qualifiers
source                 1..372
                       mol_type = protein
                       organism = synthetic construct
SEQUENCE: 548
MHSKFSHAGR ICGAKFKVGE PIYRCKECSF DDTCVLCVNC FNPKDHTGHH VYTTICTEFN  60
NGICDCGDKE AWNHTLFCKA EEGGSAGSAA GSGEFMHSKF SHAGRICGAK FKVGEPIYRC  120
KECSFDDTCV LCVNCFNPKD HTGHHVYTTI CTEFNNGICD CGDKEAWNHT LFCKAEEGGS  180
AGSAAGSGEF MDKDCEMKRT TLDSPLGKLE LSGCEQGLHE IKLLGKGTSA ADAVEVPAPA  240
AVLGGPEPLM QATAWLNAYF HQPEAIEEFP VPALHHPVFQ QESFTRQVLW KLLKVVKFGE  300
VISYQQLAAL AGNPAATAAV KTALSGNPVP ILIPCHRVVS SSGAVGGYEG GLAVKEWLLA  360
HEGHRLGKPG LG                                                      372

SEQ ID NO: 549         moltype = AA  length = 119
FEATURE                Location/Qualifiers
source                 1..119
                       mol_type = protein
                       organism = synthetic construct
SEQUENCE: 549
MPTAASATES AIEDTPAPAR PEVDGRTKPK RQPRYHVVLL DDDDHTSQYV VVMLRSLFGH  60
PPSRGYRMSK EMDTQGRAIV LTTTREHAEL KRDQIHAFGR DRLLARSKGS MKASIEAEE   119

SEQ ID NO: 550         moltype = AA  length = 119
FEATURE                Location/Qualifiers
source                 1..119
                       mol_type = protein
                       organism = synthetic construct
SEQUENCE: 550
MPTAASATES AIEDTPAPAR PEVDGRTKPK RQPRYHVVLL DDPDHTYQYV VVMLRSLFGH  60
PPSRGYRMAK EMDTQGRVIV LTTTREHAEL KRDQIHAFGR DRLLARSKGS MKASIEAEE   119

SEQ ID NO: 551         moltype = AA  length = 119
FEATURE                Location/Qualifiers
source                 1..119
                       mol_type = protein
                       organism = synthetic construct
SEQUENCE: 551
MPTAASATES AIEDTPAPAR PEVDGRTKPK RQPRYHVVQW DDDDHTYQYV VVMLRSLFYH  60
PPSRGYRMAH EMDTQGRVIV LTTTREHAEL KRDQIHAFGR DRLLARSKGS MKASIEAEE   119

SEQ ID NO: 552         moltype = AA  length = 119
FEATURE                Location/Qualifiers
source                 1..119
                       mol_type = protein
                       organism = synthetic construct
SEQUENCE: 552
MPTAASATES AIEDTPAPAR PEVDGRTKPK RQPRYHVVLW DDDDHTYQYV VVMLRSLFGH  60
PPSRGYRMAK PMDTQGRVIV LTTTREHAEL KRDQIHAFGR DRLLARSKGS MKASIEAEE   119

SEQ ID NO: 553         moltype = AA  length = 119
FEATURE                Location/Qualifiers
source                 1..119
                       mol_type = protein
                       organism = synthetic construct
SEQUENCE: 553
MPTAASATES AIEDTPAPAR PEVDGRTKPK RQPRYHVVLW DDDDHTYQYV VVMLRSLFGH  60
PPSRGYRMAK EMKTQGRVIV LTTTREHAEL KRDQIHAFGR DRLLARSKGS MKASIEAEE   119

SEQ ID NO: 554         moltype = AA  length = 119
FEATURE                Location/Qualifiers
```

```
source                  1..119
                        mol_type = protein
                        organism = synthetic construct
SEQUENCE: 554
MPTAASATES AIEDTPAPAR PEVDGRTKPK RQPRYHVVLY DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 555          moltype = AA  length = 119
FEATURE                 Location/Qualifiers
source                  1..119
                        mol_type = protein
                        organism = synthetic construct
SEQUENCE: 555
MPTAASATES AIEDTPAPAR PEVDGRTKPK RQPRYHVVLQ DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 556          moltype = AA  length = 119
FEATURE                 Location/Qualifiers
source                  1..119
                        mol_type = protein
                        organism = synthetic construct
SEQUENCE: 556
MPTAASATES AIEDTPAPAR PEVDGRTKPK RQPRYHVVLW DDGDHTSQYV VVMLRSLFGH  60
PPSRGYRMAK EMDTQGRVIV LTTTREHAEL KRDQIHAFGR DRLLARSKGS MKASIEAEE   119

SEQ ID NO: 557          moltype = AA  length = 119
FEATURE                 Location/Qualifiers
source                  1..119
                        mol_type = protein
                        organism = synthetic construct
SEQUENCE: 557
MPTAASATES AIEDTPAPAR PEVDGRTKPK RQPRYHVVLW DDDTHTYQYV VVMLRSLFGH  60
PPSRGYRMAK EMDTQGRVIV LTTTREHAEL KRDQIHAFGR DRLLARSKGS MKASIEAEE   119

SEQ ID NO: 558          moltype = AA  length = 119
FEATURE                 Location/Qualifiers
source                  1..119
                        mol_type = protein
                        organism = synthetic construct
SEQUENCE: 558
MPTAASATES AIEDTPAPAR PEVDGRTKPK RQPRYHVVLW NDSDHTGQYI VVMLRSLFGH  60
PPSRGYRMAK EKDTQGRVIV LTTTREHAEL KRDQIHAFGR DRLLARSKGS MKASIEAEE   119

SEQ ID NO: 559          moltype = AA  length = 119
FEATURE                 Location/Qualifiers
source                  1..119
                        mol_type = protein
                        organism = synthetic construct
SEQUENCE: 559
MPTAASATES AIEDTPAPAR PEVDGRTKPK RQPRYHVVLW NDLDHTYQYI VVMLRSLFGH  60
PPSRGYRMAK EMHTQGRVIV LTTTREHAEL KRDQIHAFGR DRLLARSKGS MKASIEAEE   119

SEQ ID NO: 560          moltype = AA  length = 119
FEATURE                 Location/Qualifiers
source                  1..119
                        mol_type = protein
                        organism = synthetic construct
SEQUENCE: 560
MPTAASATES AIEDTPAPAR PEVDGRTKPK RQPRYHVVLW NDGDHTWQYI VVMLRSLFGH  60
PPSRGYRMAK EMHTQGRVIV LTTTREHAEL KRDQIHAFGR DRLLARSKGS MKASIEAEE   119

SEQ ID NO: 561          moltype = AA  length = 119
FEATURE                 Location/Qualifiers
source                  1..119
                        mol_type = protein
                        organism = synthetic construct
SEQUENCE: 561
MPTAASATES AIEDTPAPAR PEVDGRTKPK RQPRYHVVLW NDGDHTWQYI VVMLRSLFGH  60
PPSRGYRMAK EAKTQGRVIV LTTTREHAEL KRDQIHAFGR DRLLARSKGS MKASIEAEE   119

SEQ ID NO: 562          moltype = AA  length = 119
FEATURE                 Location/Qualifiers
source                  1..119
                        mol_type = protein
                        organism = synthetic construct
SEQUENCE: 562
MPTAASATES AIEDTPAPAR PEVDGRTKPK RQPRYHVVLW DDGDHTVQYI VVMLRSLFGH  60
PPSRGYRMAK EMHTQGRVIV LTTTREHAEL KRDQIHAFGR DRLLARSKGS MKASIEAEE   119
```

```
SEQ ID NO: 563         moltype = AA  length = 119
FEATURE                Location/Qualifiers
source                 1..119
                       mol_type = protein
                       organism = synthetic construct
SEQUENCE: 563
MPTAASATES AIEDTPAPAR PEVDGRTKPK RQPRYHVVLW DDQDHTWQYI VVMLRSLFGH  60
PPSRGYRMAK EMHTQGRVIV LTTTREHAEL KRDQIHAFGR DRLLARSKGS MKASIEAEE   119

SEQ ID NO: 564         moltype = AA  length = 177
FEATURE                Location/Qualifiers
source                 1..177
                       mol_type = protein
                       organism = synthetic construct
SEQUENCE: 564
MHSKFSHAGR ICGAKFKVGE PIYRCKECSF DDTCVLCVNC FNPKDHRGHH VYTTICTERN  60
NGICDCGDKE AWNHELFCKA EEGSAGSAAG SGEFMHSKFS HAGRICGAKF KVGEPIYRCK  120
ECSFDDTCVL CVNCFNPKDH RGHHVYTTIC TERNNGICDC GDKEAWNHEL FCKAEEG     177

SEQ ID NO: 565         moltype = AA  length = 178
FEATURE                Location/Qualifiers
source                 1..178
                       mol_type = protein
                       organism = synthetic construct
SEQUENCE: 565
MHSKFSHAGR ICGAKFKVGE PIYRCKECSF DDTCVLCVNC FNPKDHLGHH VYTTICTEFN  60
NGECDCGDKT AWNHTLFCKA EEGGGSGGGS GGGSGMHSKF SHAGRICGAK FKVGEPIYRC  120
KECSFDDTCV LCVNCFNPKD HLGHHVYTTI CTEFNNGECD CGDKTAWNHT LFCKAEEG    178

SEQ ID NO: 566         moltype = AA  length = 177
FEATURE                Location/Qualifiers
source                 1..177
                       mol_type = protein
                       organism = synthetic construct
SEQUENCE: 566
MHSKFSHAGR ICGAKFKVGE PIYRCKECSF DDTCVLCVNC FNPKDHLGHH VYTTICTEFN  60
NGECDCGDKT AWNHTLFCKA EEGSAGSAAG SGEFMHSKFS HAGRICGAKF KVGEPIYRCK  120
ECSFDDTCVL CVNCFNPKDH LGHHVYTTIC TEFNNGECDC GDKTAWNHTL FCKAEEG     177

SEQ ID NO: 567         moltype = AA  length = 201
FEATURE                Location/Qualifiers
source                 1..201
                       mol_type = protein
                       organism = synthetic construct
SEQUENCE: 567
MHSKFSHAGR ICGAKFKVGE PIYRCKECSF DDTCVLCVNC FNPKDHLGHH VYTTICTEFN  60
NGECDCGDKT AWNHTLFCKA EEGSAGSAAG SGEFGSAGSA AGSGEFGSAG SAAGSGEFMH  120
SKFSHAGRIC GAKFKVGEPI YRCKECSFDD TCVLCVNCFN PKDHLGHHVY TTICTEFNNG  180
ECDCGDKTAW NHTLFCKAEE G                                            201

SEQ ID NO: 568         moltype = AA  length = 251
FEATURE                Location/Qualifiers
source                 1..251
                       mol_type = protein
                       organism = synthetic construct
SEQUENCE: 568
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEEG  120
GGSGGGSGGG SGMPTAASAT ESAIEDTPAP ARPEVDGRTK PKRQPRYHVV LWDDDDHTYQ  180
YVVVMLRSLF GHPPSRGYRM AKEMDTQGRV IVLTTTREHA ELKRDQIHAF GRDRLLARSK  240
GSMKASIEAE E                                                       251

SEQ ID NO: 569         moltype = AA  length = 274
FEATURE                Location/Qualifiers
source                 1..274
                       mol_type = protein
                       organism = synthetic construct
SEQUENCE: 569
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEEG  120
SAGSAAGSGE FGSAGSAAGS GEFGSAGSAA GSGEFMPTAA SATESAIEDT PAPARPEVDG  180
RTKPKRQPRY HVVLWDDDDH TYQYVVVMLR SLFGHPPSRG YRMAKEMDTQ GRVIVLTTTR  240
EHAELKRDQI HAFGRDRLLA RSKGSMKASI EAEE                              274

SEQ ID NO: 570         moltype = AA  length = 119
FEATURE                Location/Qualifiers
source                 1..119
                       mol_type = protein
                       organism = synthetic construct
```

```
SEQUENCE: 570
MPTAASATES AIEDTPAPAR PEVDGRTKPK RQPRYHVVLH DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 571         moltype = AA  length = 119
FEATURE                Location/Qualifiers
source                 1..119
                       mol_type = protein
                       organism = synthetic construct
SEQUENCE: 571
MPTAASATES AIEDTPAPAR PEVDGRTKPK RQPRYHVVLW DDDDHTYQYV VVMLRSLFGI  60
PPSRGYRMAK EMDTQGRVIV LTTTREHAEL KRDQIHAFGR DRLLARSKGS MKASIEAEE   119

SEQ ID NO: 572         moltype = AA  length = 119
FEATURE                Location/Qualifiers
source                 1..119
                       mol_type = protein
                       organism = synthetic construct
SEQUENCE: 572
MPTAASATES AIEDTPAPAR PEVDGRTKPK RQPRYHVVLW DDDDHTAQYV VVMLRSLFGH  60
PPSRGYRMAK EMDTQGRVIV LTTTREHAEL KRDQIHAFGR DRLLARSKGS MKASIEAEE   119

SEQ ID NO: 573         moltype = AA  length = 119
FEATURE                Location/Qualifiers
source                 1..119
                       mol_type = protein
                       organism = synthetic construct
SEQUENCE: 573
MPTAASATES AIEDTPAPAR PEVDGRTKPK RQPRYHVVLW DDNDHTYQYV VVMLRSLFGH  60
PPSRGYRMAK EMDTQGRVIV LTTTREHAEL KRDQIHAFGR DRLLARSKGS MKASIEAEE   119

SEQ ID NO: 574         moltype = AA  length = 119
FEATURE                Location/Qualifiers
source                 1..119
                       mol_type = protein
                       organism = synthetic construct
SEQUENCE: 574
MPTAASATES AIEDTPAPAR PEVDGRTKPK RQPRYHVVLW NDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 575         moltype = AA  length = 119
FEATURE                Location/Qualifiers
source                 1..119
                       mol_type = protein
                       organism = synthetic construct
SEQUENCE: 575
MPTAASATES AIEDTPAPAR PEVDGRTKPK RQPRYHVVLW DDDDHTWQYV VVMLRSLFGH  60
PPSRGYRMAK EMDTQGRVIV LTTTREHAEL KRDQIHAFGR DRLLARSKGS MKASIEAEE   119

SEQ ID NO: 576         moltype = AA  length = 119
FEATURE                Location/Qualifiers
source                 1..119
                       mol_type = protein
                       organism = synthetic construct
SEQUENCE: 576
MPTAASATES AIEDTPAPAR PEVDGRTKPK RQPRYHVVLW DDDDHTYQYV VVMLRSLFGH  60
PPSRGYRMAK ELDTQGRVIV LTTTREHAEL KRDQIHAFGR DRLLARSKGS MKASIEAEE   119

SEQ ID NO: 577         moltype = AA  length = 119
FEATURE                Location/Qualifiers
source                 1..119
                       mol_type = protein
                       organism = synthetic construct
SEQUENCE: 577
MPTAASATES AIEDTPAPAR PEVDGRTKPK RQPRYHVVLW DDDDHTYQYV VVMLRSLFGY  60
PPSRGYRMAK EMDTQGRVIV LTTTREHAEL KRDQIHAFGR DRLLARSKGS MKASIEAEE   119

SEQ ID NO: 578         moltype = AA  length = 119
FEATURE                Location/Qualifiers
source                 1..119
                       mol_type = protein
                       organism = synthetic construct
SEQUENCE: 578
MPTAASATES AIEDTPAPAR PEVDGRTKPK RQPRYHVVLW DDDDHTLQYV VVMLRSLFGH  60
PPSRGYRMAK EMDTQGRVIV LTTTREHAEL KRDQIHAFGR DRLLARSKGS MKASIEAEE   119

SEQ ID NO: 579         moltype = AA  length = 119
FEATURE                Location/Qualifiers
source                 1..119
```

```
                         mol_type = protein
                         organism = synthetic construct
SEQUENCE: 579
MPTAASATES AIEDTPAPAR PEVDGRTKPK RQPRYHVVLW DDDDHTIQYV VVMLRSLFGH  60
PPSRGYRMAK EMDTQGRVIV LTTTREHAEL KRDQIHAFGR DRLLARSKGS MKASIEAEE   119

SEQ ID NO: 580           moltype = AA  length = 119
FEATURE                  Location/Qualifiers
source                   1..119
                         mol_type = protein
                         organism = synthetic construct
SEQUENCE: 580
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHASGR DRLLARSKGS MKASIEAEE   119

SEQ ID NO: 581           moltype = AA  length = 119
FEATURE                  Location/Qualifiers
source                   1..119
                         mol_type = protein
                         organism = synthetic construct
SEQUENCE: 581
MPTAASATES AIEDTPAPAR PEVDGRTKPK RQPRYHVVLW DDDDHTYQYV VVMLRSLFGH  60
PLSRGYRMAK EMDTQGRVIV LTTTREHAEL KRDQIHAFGR DRLLARSKGS MKASIEAEE   119

SEQ ID NO: 582           moltype = AA  length = 119
FEATURE                  Location/Qualifiers
source                   1..119
                         mol_type = protein
                         organism = synthetic construct
SEQUENCE: 582
MPTAASATES AIEDTPAPAR PEVDGRTKPK RQPRYHVVLW DDDQHTYQYV VVMLRSLFGH  60
PPSRGYRMAK EMDTQGRVIV LTTTREHAEL KRDQIHAFGR DRLLARSKGS MKASIEAEE   119

SEQ ID NO: 583           moltype = AA  length = 119
FEATURE                  Location/Qualifiers
source                   1..119
                         mol_type = protein
                         organism = synthetic construct
SEQUENCE: 583
MPTAASATES AIEDTPAPAR PEVDGRTKPK RQPRYHVVLW DDDDHTYQYV VVMLRSLFGH  60
PPSRGYRMAK EMDTQGRTIV LTTTREHAEL KRDQIHAFGR DRLLARSKGS MKASIEAEE   119

SEQ ID NO: 584           moltype = AA  length = 119
FEATURE                  Location/Qualifiers
source                   1..119
                         mol_type = protein
                         organism = synthetic construct
SEQUENCE: 584
MPTAASATES AIEDTPAPAR PEVDGRTKPK RQPRYHVVLF DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 585           moltype = AA  length = 119
FEATURE                  Location/Qualifiers
source                   1..119
                         mol_type = protein
                         organism = synthetic construct
SEQUENCE: 585
MPTAASATES AIEDTPAPAR PEVDGRTKPK RQPRYHVVLW DDDDHTYQYV VVMLRSLFGH  60
PPSRGYRMTK EMDTQGRVIV LTTTREHAEL KRDQIHAFGR DRLLARSKGS MKASIEAEE   119

SEQ ID NO: 586           moltype = AA  length = 119
FEATURE                  Location/Qualifiers
source                   1..119
                         mol_type = protein
                         organism = synthetic construct
SEQUENCE: 586
MPTAASATES AIEDTPAPAR PEVDGRTKPK RQPRYHVVLW DDDDHTYQYV VVMLRSLFGS  60
PPSRGYRMAK EMDTQGRLIV LTTTREHAEL KRDQIHAFGR DRLLARSKGS MKASIEAEE   119

SEQ ID NO: 587           moltype = AA  length = 119
FEATURE                  Location/Qualifiers
source                   1..119
                         mol_type = protein
                         organism = synthetic construct
SEQUENCE: 587
MPTAASATES AIEDTPAPAR PEVDGRTKPK RQPRYHVVLW DDDDHTYQYV VVMLRSLFGV  60
PPSRGYRMAK ELDTQGRVIV LTTTREHAEL KRDQIHAFGR DRLLARSKGS MKASIEAEE   119

SEQ ID NO: 588           moltype = AA  length = 119
```

```
FEATURE                Location/Qualifiers
source                 1..119
                       mol_type = protein
                       organism = synthetic construct
SEQUENCE: 588
MPTAASATES AIEDTPAPAR PEVDGRTKPK RQPRYHVVLW DDDDHTYQYV VVMLRSLFGL  60
PPSRGYRMAH EMDTQGRVIV LTTTREHAEL KRDQIHAFGR DRLLARSKGS MKASIEAEE   119

SEQ ID NO: 589         moltype = AA  length = 119
FEATURE                Location/Qualifiers
source                 1..119
                       mol_type = protein
                       organism = synthetic construct
SEQUENCE: 589
MPTAASATES AIEDTPAPAR PEVDGRTKPK RQPRYHVVLY DDDDHTDQYV VVMLRSLFGH  60
PPSRGYRLAE EMDTQGRVIV LTTTREHAEL KRDQIHAFGR DRLLARSKGS MKASIEAEE   119

SEQ ID NO: 590         moltype = AA  length = 119
FEATURE                Location/Qualifiers
source                 1..119
                       mol_type = protein
                       organism = synthetic construct
SEQUENCE: 590
MPTAASATES AIEDTPAPAR PEVDGRTKPK RQPRYHVVLL DDDSHTYQYV VVMLRSLFGV  60
PPSRGYRMAA EMDTQGRVIV LTTTREHAEL KRDQIHAFGR DRLLARSKGS MKASIEAEE   119

SEQ ID NO: 591         moltype = AA  length = 119
FEATURE                Location/Qualifiers
source                 1..119
                       mol_type = protein
                       organism = synthetic construct
SEQUENCE: 591
MPTAASATES AIEDTPAPAR PEVDGRTKPK RQPRYHVVLW DDHDHTYQYV VVMLRSLFGH  60
PPSRGYRMAK ELHTQGRVIV LTTTREHAEL KRDQIHAFGR DRLLARSKGS MKASIEAEE   119

SEQ ID NO: 592         moltype = AA  length = 204
FEATURE                Location/Qualifiers
source                 1..204
                       mol_type = protein
                       organism = synthetic construct
SEQUENCE: 592
MEGNGPAAVH YQPASPPRDA CVYSSCYCEE NVWKLCEYIK NHDQYPLEEC YAVFISNERK  60
MIPIWKQQAR PGDGPVIWDY HVVLLHVSSG GQSFIYDLDT VLPFPCLFDT YVEDAIKSDD  120
DIHPQFRRKF RVICADSYLK NFASDRSHMK DSSGNWREPP PPYPCIETGD SKMNLNDFIS  180
MDPKVGWGAV YTLSEFTHRF GSKN                                         204

SEQ ID NO: 593         moltype = AA  length = 204
FEATURE                Location/Qualifiers
source                 1..204
                       mol_type = protein
                       organism = synthetic construct
SEQUENCE: 593
MEGNGPAAVH YQPASPPRDA CVYSSCYSEE NVWKLCEYIK NHDQYPLEEC YAVFISNERK  60
MIPIWKQQAR PGDGPVIWDY HVVLLHVSSG GQSFIYDLDT VLPFPCLFDT YVEDAIKSDD  120
DIHPQFRRKF RVICADSYLK NFASDRSHMK DSSGNWREPP PPYPCIETGD SKMNLNDFIS  180
MDPKVGWGAV YTLSEFTHRF GSKN                                         204

SEQ ID NO: 594         moltype = AA  length = 204
FEATURE                Location/Qualifiers
source                 1..204
                       mol_type = protein
                       organism = synthetic construct
SEQUENCE: 594
MEGNGPAAVH YQPASPPRDA CVYSSCYSEE NVWKLCEYIK NHDQYPLEEC YAVFISNERK  60
MIPIWKQQAR PGDGPVIWDY QVVLLHVSSG GQSFIYDLDT VLPFPCLFDT YVEDAIKSDD  120
DIHPQFRRKF RVICADSYLK NFASDRSHMK DSSGNWREPP PPYPCIETGD SKMNLNDFIS  180
MDPKVGWGAV YTLSEFTHRF GSKN                                         204

SEQ ID NO: 595         moltype = AA  length = 204
FEATURE                Location/Qualifiers
source                 1..204
                       mol_type = protein
                       organism = synthetic construct
SEQUENCE: 595
MEGNGPAAVH YQPASPPRDA CVYSSCYSEE NVWKLCEYIK NHDQYPLEEC YAVFISNERK  60
MIPIWKQQAR PGDGPVIWDY QVVLLHVSSG GQSFIYDLDT VLPFPCLFDT YVEDAIKSDD  120
DIHPQFRRKF RVICADSYLK NFASDRSHEK DSSGNWREPP PPYPCIETGD SKMNLNDFIS  180
MDPKVGWGAV YTLSEFTHRF GSKN                                         204
```

```
SEQ ID NO: 596          moltype = AA  length = 204
FEATURE                 Location/Qualifiers
source                  1..204
                        mol_type = protein
                        organism = synthetic construct
SEQUENCE: 596
MGPAATAPQY QPVCPTRDAC VYNSCYSEEN IWKLCEYIKT HNQYLLEECY AVFISNEKKM  60
VPIWKQQARP ENGPVIWDYH VVLLHVSREG QSFIYDLDTI LPFPCPFDIY IEDALKSDDD  120
IHLQFRRKFR VVRADSYLKH FASDRSHMKD SSGNWREPPP EYPCIETGDS KMNLNDFISM  180
DPAVGWGAVY TLPEFVHRFS SKTY                                          204

SEQ ID NO: 597          moltype = AA  length = 204
FEATURE                 Location/Qualifiers
source                  1..204
                        mol_type = protein
                        organism = synthetic construct
SEQUENCE: 597
MGPAATAPQY QPVCPTRDAC VYNSCYSEEN IWKLCEYIKT HNQYLLEECY AVFISNEKKM  60
VPIWKQQARP ENGPVIWDYQ VVLLHVSREG QSFIYDLDTI LPFPCPFDIY IEDALKSDDD  120
IHLQFRRKFR VVRADSYLKH FASDRSHMKD SSGNWREPPP EYPCIETGDS KMNLNDFISM  180
DPAVGWGAVY TLPEFVHRFS SKTY                                          204

SEQ ID NO: 598          moltype = AA  length = 204
FEATURE                 Location/Qualifiers
source                  1..204
                        mol_type = protein
                        organism = synthetic construct
SEQUENCE: 598
MGPAATAPQY QPVCPTRDAC VYNSCYSEEN IWKLCEYIKT HNQYLLEECY AVFISNEKKM  60
VPIWKQQARP ENGPVIWDYQ VVLLHVSREG QSFIYDLDTI LPFPCPFDIY IEDALKSDDD  120
IHLQFRRKFR VVRADSYLKH FASDRSHEKD SSGNWREPPP EYPCIETGDS KMNLNDFISM  180
DPAVGWGAVY TLPEFVHRFS SKTY                                          204

SEQ ID NO: 599          moltype = AA  length = 203
FEATURE                 Location/Qualifiers
source                  1..203
                        mol_type = protein
                        organism = synthetic construct
SEQUENCE: 599
MVPAAAAARY QPASPPRDAC VYNSCYSEEN IWKLCEYIKN HDQYPLEECY AVFISNERKM  60
IPIWKQQARP GDGPVIWYYF FLLVRYHVKS IGFSFTFQAI PLVNTLEDIL AQLFKFCIHM  120
HACVLWKFRV IRADSYLKNF ASDRSHMKDS SGNWREPPPS YPCIETGDSK MNLNDFISMD  180
PEVGWGAVYS LSEFVHRFGS QNY                                           203

SEQ ID NO: 600          moltype = AA  length = 203
FEATURE                 Location/Qualifiers
source                  1..203
                        mol_type = protein
                        organism = synthetic construct
SEQUENCE: 600
MVPAAAAARY QPASPPRDAC VYNSCYSEEN IWKLCEYIKN HDQYPLEECY AVFISNERKM  60
IPIWKQQARP GDGPVIWYYF FLLVRYHVKS IGFSFTFQAI PLVNTLEDIL AQLFKFCIHM  120
HACVLWKFRV IRADSYLKNF ASDRSHEKDS SGNWREPPPS YPCIETGDSK MNLNDFISMD  180
PEVGWGAVYS LSEFVHRFGS QNY                                           203

SEQ ID NO: 601          moltype = AA  length = 199
FEATURE                 Location/Qualifiers
source                  1..199
                        mol_type = protein
                        organism = synthetic construct
SEQUENCE: 601
MAAGEPSPFL VRSDCLYTSC YSEENVWKLC EYIRDHRPCL LEQFSAVFIS NENKMIPIWK  60
QKSAKGDGPV IWDYHVILLH ESARDGNFVY DLDTILPFPS PCNTYIREAL KCDSNIHCDF  120
RRKLRVVGAH EFLQTFASDR SHMRDSSSNW TKPPPPYPCI QTAESTMNLD DFISMNPEVG  180
WGTVYSLAAF IERFGDTTL                                                199

SEQ ID NO: 602          moltype = AA  length = 199
FEATURE                 Location/Qualifiers
source                  1..199
                        mol_type = protein
                        organism = synthetic construct
SEQUENCE: 602
MAAGEPSPFL VRSDCLYTSC YSEENVWKLC EYIRDHRPCL LEQFSAVFIS NENKMIPIWK  60
QKSAKGDGPV IWDYQVILLH ESARDGNFVY DLDTILPFPS PCNTYIREAL KCDSNIHCDF  120
RRKLRVVGAH EFLQTFASDR SHMRDSSSNW TKPPPPYPCI QTAESTMNLD DFISMNPEVG  180
WGTVYSLAAF IERFGDTTL                                                199

SEQ ID NO: 603          moltype = AA  length = 199
FEATURE                 Location/Qualifiers
```

```
source                  1..199
                        mol_type = protein
                        organism = synthetic construct
SEQUENCE: 603
MAAGEPSPFL VRSDCLYTSC YSEENVWKLC EYIRDHRPCL LEQFSAVFIS NENKMIPIWK  60
QKSAKGDGPV IWDYQVILLH ESARDGNFVY DLDTILPFPS PCNTYIREAL KCDSNIHCDF  120
RRKLRVVGAH EFLQTFASDR SHERDSSSNW TKPPPPYPCI QTAESTMNLD DFISMNPEVG  180
WGTVYSLAAF IERFGDTTL                                               199

SEQ ID NO: 604          moltype = AA  length = 200
FEATURE                 Location/Qualifiers
source                  1..200
                        mol_type = protein
                        organism = synthetic construct
SEQUENCE: 604
MNGLSAQHER IAPARHECVY TSCYSEENVW KLCEHIKTSK RCPLGDVYAV FISNERKMVP  60
IWKQKSGRGE EPVIWDYHVI LLHDCHKEQT FIYDLDTTLP FPCPFDTYVK EAFKSDNYIN  120
PAFWRKLRVV PADVFLQNFA SDRSHMKDAS GGWRMPPPPY PCIETAESRM NLDDFISMNP  180
SVGWGHVYTL EEFVQHFGKT                                              200

SEQ ID NO: 605          moltype = AA  length = 200
FEATURE                 Location/Qualifiers
source                  1..200
                        mol_type = protein
                        organism = synthetic construct
SEQUENCE: 605
MNGLSAQHER IAPARHECVY TSCYSEENVW KLCEHIKTSK RCPLGDVYAV FISNERKMVP  60
IWKQKSGRGE EPVIWDYQVI LLHDCHKEQT FIYDLDTTLP FPCPFDTYVK EAFKSDNYIN  120
PAFWRKLRVV PADVFLQNFA SDRSHMKDAS GGWRMPPPPY PCIETAESRM NLDDFISMNP  180
SVGWGHVYTL EEFVQHFGKT                                              200

SEQ ID NO: 606          moltype = AA  length = 200
FEATURE                 Location/Qualifiers
source                  1..200
                        mol_type = protein
                        organism = synthetic construct
SEQUENCE: 606
MNGLSAQHER IAPARHECVY TSCYSEENVW KLCEHIKTSK RCPLGDVYAV FISNERKMVP  60
IWKQKSGRGE EPVIWDYQVI LLHDCHKEQT FIYDLDTTLP FPCPFDTYVK EAFKSDNYIN  120
PAFWRKLRVV PADVFLQNFA SDRSHEKDAS GGWRMPPPPY PCIETAESRM NLDDFISMNP  180
SVGWGHVYTL EEFVQHFGKT                                              200

SEQ ID NO: 607          moltype = AA  length = 200
FEATURE                 Location/Qualifiers
source                  1..200
                        mol_type = protein
                        organism = synthetic construct
SEQUENCE: 607
MESASSEYKV ITPSGNQCVY TSCYSEENVW KLCEYIKNQR HCPLEEVYAV FISNERKKIP  60
IWKQKSSRGD EPVIWDYHVI LLHASKQGPS FIYDLDTILP FPCSLDVYSM EAFQSDKHLK  120
PAYWRKLRVI PGDTYLKEFA SDRSHMKDSD GNWRMPPPAY PCLETPESKM NLDDFICMDP  180
RVGYGEVYSL SDFVKHFGVK                                              200

SEQ ID NO: 608          moltype = AA  length = 200
FEATURE                 Location/Qualifiers
source                  1..200
                        mol_type = protein
                        organism = synthetic construct
SEQUENCE: 608
MESASSEYKV ITPSGNQCVY TSCYSEENVW KLCEYIKNQR HCPLEEVYAV FISNERKKIP  60
IWKQKSSRGD EPVIWDYQVI LLHASKQGPS FIYDLDTILP FPCSLDVYSM EAFQSDKHLK  120
PAYWRKLRVI PGDTYLKEFA SDRSHMKDSD GNWRMPPPAY PCLETPESKM NLDDFICMDP  180
RVGYGEVYSL SDFVKHFGVK                                              200

SEQ ID NO: 609          moltype = AA  length = 200
FEATURE                 Location/Qualifiers
source                  1..200
                        mol_type = protein
                        organism = synthetic construct
SEQUENCE: 609
MESASSEYKV ITPSGNQCVY TSCYSEENVW KLCEYIKNQR HCPLEEVYAV FISNERKKIP  60
IWKQKSSRGD EPVIWDYQVI LLHASKQGPS FIYDLDTILP FPCSLDVYSM EAFQSDKHLK  120
PAYWRKLRVI PGDTYLKEFA SDRSHEKDSD GNWRMPPPAY PCLETPESKM NLDDFICMDP  180
RVGYGEVYSL SDFVKHFGVK                                              200

SEQ ID NO: 610          moltype = AA  length = 200
FEATURE                 Location/Qualifiers
source                  1..200
                        mol_type = protein
```

```
                        organism = synthetic construct
SEQUENCE: 610
MEHVSSKYVN ITPSRDECVY TSCYSEENVW KLCEHIKTQT QIHLDEVYAV FISNERKMIP  60
IWKQKSSRGD EPVVWDYHVV LLHQNQQGQS FIYDQDTVLP FSCPFHVYTT EAFHTDHGLK  120
PAFWRKLRVI PADTYLKNFA SDRSHMKNAD GTWRMPPPLY PCIETTDSKM NLDDFISMDS  180
KVGCGHVYSL SEFVKHFAEK                                             200

SEQ ID NO: 611          moltype = AA  length = 200
FEATURE                 Location/Qualifiers
source                  1..200
                        mol_type = protein
                        organism = synthetic construct
SEQUENCE: 611
MEHVSSKYVN ITPSRDECVY TSCYSEENVW KLCEHIKTQT QIHLDEVYAV FISNERKMIP  60
IWKQKSSRGD EPVVWDYQVV LLHQNQQGQS FIYDQDTVLP FSCPFHVYTT EAFHTDHGLK  120
PAFWRKLRVI PADTYLKNFA SDRSHMKNAD GTWRMPPPLY PCIETTDSKM NLDDFISMDS  180
KVGCGHVYSL SEFVKHFAEK                                             200

SEQ ID NO: 612          moltype = AA  length = 200
FEATURE                 Location/Qualifiers
source                  1..200
                        mol_type = protein
                        organism = synthetic construct
SEQUENCE: 612
MEHVSSKYVN ITPSRDECVY TSCYSEENVW KLCEHIKTQT QIHLDEVYAV FISNERKMIP  60
IWKQKSSRGD EPVVWDYQVV LLHQNQQGQS FIYDQDTVLP FSCPFHVYTT EAFHTDHGLK  120
PAFWRKLRVI PADTYLKNFA SDRSHEKNAD GTWRMPPPLY PCIETTDSKM NLDDFISMDS  180
KVGCGHVYSL SEFVKHFAEK                                             200

SEQ ID NO: 613          moltype = AA  length = 114
FEATURE                 Location/Qualifiers
source                  1..114
                        mol_type = protein
                        organism = synthetic construct
SEQUENCE: 613
MGLENSLETL RFSISNLSMQ THAARMRTFM YWPSSVPVQP EQLASAGFYY LGRNDIVICF  60
CCDGGLHCWQ SGDDPWVEHA LFFPRCEFLI RMKGQEFVDE IQGRYPHLLE QLLS       114

SEQ ID NO: 614          moltype = AA  length = 107
FEATURE                 Location/Qualifiers
source                  1..107
                        mol_type = protein
                        organism = synthetic construct
SEQUENCE: 614
MHHHHHHHHH HDYDIPTTEN LYFQGMHSKF SHAGRICGAK FKVGEPIYRC KECSFDDTCV  60
LCVNCFNPKD HLGHHVYTTI CTEFNNGECD CGDKTAWNHT LFCKAEE               107

SEQ ID NO: 615          moltype = AA  length = 120
FEATURE                 Location/Qualifiers
source                  1..120
                        mol_type = protein
                        organism = synthetic construct
SEQUENCE: 615
MHHHHHHHHH HDYDIPTTEN LYFQGRFSIS NLSMQTHAAR MRTFMYWPSS VPVQPEQLAS  60
AGFYYVGRND DVKCFCCDGG LRCWESGDDP WVEHAKWFPR CEFLIRMKGQ EFVDEIQGRY  120

SEQ ID NO: 616          moltype = AA  length = 264
FEATURE                 Location/Qualifiers
source                  1..264
                        mol_type = protein
                        organism = synthetic construct
SEQUENCE: 616
MGDVQPETCR PSAASGNYFP QYPEYAIETA RLRTFEAWPR NLKQKPHQLA EAGFFYTGVG  60
DRVRCFSCGG GLMDWNDNDE PWEQHARHLS QCRFVKLMKG QLYIDTVAAK PVLAEEKEES  120
TSIGGDGSAG SAAGSGEFMG DVQPETCRPS AASGNYFPQY PEYAIETARL RTFEAWPRNL  180
KQKPHQLAEA GFFYTGVGDR VRCFSCGGGL MDWNDNDEPW EQHARHLSQC RFVKLMKGQL  240
YIDTVAAKPV LAEEKEESTS IGGD                                        264

SEQ ID NO: 617          moltype = AA  length = 307
FEATURE                 Location/Qualifiers
source                  1..307
                        mol_type = protein
                        organism = synthetic construct
SEQUENCE: 617
MGLENSLETL RFSISNLSMQ THAARMRTFM YWPSSVPVQP EQLASAGFYY VGRNDDVKCF  60
CCDGGLRCWE SGDDPWVEHA KWFPRCEFLI RMKGQEFVDE IQGRYPHLLE QLLSGSAGSA  120
AGSGEFMGLE NSLETLRFSI SNLSMQTHAA RMRTFMYWPS SVPVQPEQLA SAGFYYVGRN  180
DDVKCFCCDG GLRCWESGDD PWVEHAKWFP RCEFLIRMKG QEFVDEIQGR YPHLLEQLLS  240
GGSHHHHHHH HHHGGGSGGG SGGGSGLNDF FEAQKIEWHE GGGSGGGSGG GSGLNDFFEA  300
```

```
QKIEWHE                                                                 307

SEQ ID NO: 618         moltype = AA  length = 240
FEATURE                Location/Qualifiers
source                 1..240
                       mol_type = protein
                       organism = synthetic construct
SEQUENCE: 618
MGLENSLETL RFSISNLSMQ THAARMRTFM YWPSSVPVQP EQLASAGFYY VGRNDDVKCF  60
CCDGGLRCWE SGDDPWVEHA RHFPRCEFLI RMKGQEFVDE IQGRYPHLLE QLLSGSAGSA  120
AGSGEFMGLE NSLETLRFSI SNLSMQTHAA RMRTFMYWPS SVPVQPEQLA SAGFYYVGRN  180
DDVKCFCCDG GLRCWESGDD PWVEHARHFP RCEFLIRMKG QEFVDEIQGR YPHLLEQLLS  240

SEQ ID NO: 619         moltype = AA  length = 331
FEATURE                Location/Qualifiers
source                 1..331
                       mol_type = protein
                       organism = synthetic construct
SEQUENCE: 619
MGDVQPETCR PSAASGNYFP QYPEYAIETA RLRTFEAWPR NLKQKPHQLA EAGFFYTGVG  60
DRVRCFSCGG GLMDWNDNDE PWEQHALWLS QCRFVKLMKG QLYIDTVAAK PVLAEEKEES  120
TSIGGDTGSA GSAAGSGEFM GDVQPETCRP SAASGNYFPQ YPEYAIETAR LRTFEAWPRN  180
LKQKPHQLAE AGFFYTGVGD RVRCFSCGGG LMDWNDNDEP WEQHALWLSQ CRFVKLMKGQ  240
LYIDTVAAKP VLAEEKEEST SIGGDTGHHH HHHHHHHGGG SGGGSGGGSG LNDFFEAQKI  300
EWHEGGGSGG GSGGGSGLND FFEAQKIEWH E                                331

SEQ ID NO: 620         moltype = AA  length = 241
FEATURE                Location/Qualifiers
source                 1..241
                       mol_type = protein
                       organism = synthetic construct
SEQUENCE: 620
MGLENSLETL RFSISNLSMQ THAARMRTFM YWPSSVPVQP EQLASAGFYY VGRNDDVKCF  60
CCDGGLRCWE SGDDPWVEHA KWFPRCEFLI RMKGQEFVDE IQGRYPHLLE QLLSGGGSGG  120
GSGGGSGMGL ENSLETLRFS ISNLSMQTHA ARMRTFMYWP SSVPVQPEQL ASAGFYYVGR  180
NDDVKCFCCD GGLRCWESGD DPWVEHAKWF PRCEFLIRMK GQEFVDEIQG RYPHLLEQLL  240
S                                                                 241

SEQ ID NO: 621         moltype = AA  length = 264
FEATURE                Location/Qualifiers
source                 1..264
                       mol_type = protein
                       organism = synthetic construct
SEQUENCE: 621
MGLENSLETL RFSISNLSMQ THAARMRTFM YWPSSVPVQP EQLASAGFYY VGRNDDVKCF  60
CCDGGLRCWE SGDDPWVEHA KWFPRCEFLI RMKGQEFVDE IQGRYPHLLE QLLSGSAGSA  120
AGSGEFGSAG SAAGSGEFGS AGSAAGSGEF MGLENSLETL RFSISNLSMQ THAARMRTFM  180
YWPSSVPVQP EQLASAGFYY VGRNDDVKCF CCDGGLRCWE SGDDPWVEHA KWFPRCEFLI  240
RMKGQEFVDE IQGRYPHLLE QLLS                                        264

SEQ ID NO: 622         moltype = AA  length = 119
FEATURE                Location/Qualifiers
source                 1..119
                       mol_type = protein
                       organism = synthetic construct
SEQUENCE: 622
MPTAASATES AIEDTPAPAR PEVDGRTKPK RQPRYHVVLW DDEDHTYQYV VVMLRSLFGH  60
PPSRGYRMAK EMDTQGRVIV LTTTREHAEL KRDQIHAFGR DRLLARSKGS MKASIEAEE   119

SEQ ID NO: 623         moltype = AA  length = 119
FEATURE                Location/Qualifiers
source                 1..119
                       mol_type = protein
                       organism = synthetic construct
SEQUENCE: 623
MPTAASATES AIEDTPAPAR PEVDGRTKPK RQPRYHVVLW DDDDHTYQYV VVMLRSLFGH  60
PPSRGYRMAR EMDTQGRVIV LTTTREHAEL KRDQIHAFGR DRLLARSKGS MKASIEAEE   119

SEQ ID NO: 624         moltype = AA  length = 119
FEATURE                Location/Qualifiers
source                 1..119
                       mol_type = protein
                       organism = synthetic construct
SEQUENCE: 624
MPTAASATES AIEDTPAPAR PEVDGRTKPK RQPRYHVVLW DDDDHTYQYV VVMLRSLFGH  60
PPSRGYRMAK EMTTQGRVIV LTTTREHAEL KRDQIHAFGR DRLLARSKGS MKASIEAEE   119

SEQ ID NO: 625         moltype = AA  length = 119
FEATURE                Location/Qualifiers
```

```
source                  1..119
                        mol_type = protein
                        organism = synthetic construct
SEQUENCE: 625
MPTAASATES AIEDTPAPAR PEVDGRTKPK RQPRYHVVLW DDQDHTYQYV VVMLRSLFGH  60
PPSRGYRMAK EMDTQGRVIV LTTTREHAEL KRDQIHAFGR DRLLARSKGS MKASIEAEE   119

SEQ ID NO: 626          moltype = AA  length = 119
FEATURE                 Location/Qualifiers
source                  1..119
                        mol_type = protein
                        organism = synthetic construct
SEQUENCE: 626
MPTAASATES AIEDTPAPAR PEVDGRTKPK RQPRYHVVLW DDDEHTYQYV VVMLRSLFGH  60
PPSRGYRMAK EMDTQGRVIV LTTTREHAEL KRDQIHAFGR DRLLARSKGS MKASIEAEE   119

SEQ ID NO: 627          moltype = AA  length = 119
FEATURE                 Location/Qualifiers
source                  1..119
                        mol_type = protein
                        organism = synthetic construct
SEQUENCE: 627
MPTAASATES AIEDTPAPAR PEVDGRTKPK RQPRYHVVLW DDDDHTMQYV VVMLRSLFGH  60
PPSRGYRMAK EMDTQGRVIV LTTTREHAEL KRDQIHAFGR DRLLARSKGS MKASIEAEE   119

SEQ ID NO: 628          moltype = AA  length = 119
FEATURE                 Location/Qualifiers
source                  1..119
                        mol_type = protein
                        organism = synthetic construct
SEQUENCE: 628
MPTAASATES AIEDTPAPAR PEVDGRTKPK RQPRYHVVLW DDDDHTFQYV VVMLRSLFGH  60
PPSRGYRMAK EMDTQGRVIV LTTTREHAEL KRDQIHAFGR DRLLARSKGS MKASIEAEE   119

SEQ ID NO: 629          moltype = AA  length = 119
FEATURE                 Location/Qualifiers
source                  1..119
                        mol_type = protein
                        organism = synthetic construct
SEQUENCE: 629
MPTAASATES AIEDTPAPAR PEVDGRTKPK RQPRYHVVLW DDDDHTVQYV VVMLRSLFGH  60
PPSRGYRMAK EMDTQGRVIV LTTTREHAEL KRDQIHAFGR DRLLARSKGS MKASIEAEE   119

SEQ ID NO: 630          moltype = AA  length = 119
FEATURE                 Location/Qualifiers
source                  1..119
                        mol_type = protein
                        organism = synthetic construct
SEQUENCE: 630
MPTAASATES AIEDTPAPAR PEVDGRTKPK RQPRYHVVLY DDDTHTYQYV VVMLRSLFGH  60
PPSRGYRMAK EMDTQGRVIV LTTTREHAEL KRDQIHAFGR DRLLARSKGS MKASIEAEE   119

SEQ ID NO: 631          moltype = AA  length = 119
FEATURE                 Location/Qualifiers
source                  1..119
                        mol_type = protein
                        organism = synthetic construct
SEQUENCE: 631
MPTAASATES AIEDTPAPAR PEVDGRTKPK RQPRYHVVLY DDEDHTYQYV VVMLRSLFGH  60
PPSRGYRMAK EMDTQGRVIV LTTTREHAEL KRDQIHAFGR DRLLARSKGS MKASIEAEE   119

SEQ ID NO: 632          moltype = AA  length = 119
FEATURE                 Location/Qualifiers
source                  1..119
                        mol_type = protein
                        organism = synthetic construct
SEQUENCE: 632
MPTAASATES AIEDTPAPAR PEVDGRTKPK RQPRYHVVLY DDDDHTFQYV VVMLRSLFGH  60
PPSRGYRMAK EMDTQGRVIV LTTTREHAEL KRDQIHAFGR DRLLARSKGS MKASIEAEE   119

SEQ ID NO: 633          moltype = AA  length = 119
FEATURE                 Location/Qualifiers
source                  1..119
                        mol_type = protein
                        organism = synthetic construct
SEQUENCE: 633
MPTAASATES AIEDTPAPAR PEVDGRTKPK RQPRYHVVLY DDDDHTYQYV VVMLRSLFGH  60
PPSRGYRMAR EMDTQGRVIV LTTTREHAEL KRDQIHAFGR DRLLARSKGS MKASIEAEE   119
```

```
SEQ ID NO: 634         moltype = AA  length = 119
FEATURE                Location/Qualifiers
source                 1..119
                       mol_type = protein
                       organism = synthetic construct
SEQUENCE: 634
MPTAASATES AIEDTPAPAR PEVDGRTKPK RQPRYHVVLY DDDDHTYQYV VVMLRSLFGH  60
PPSRGYRMAK EMTTQGRVIV LTTTREHAEL KRDQIHAFGR DRLLARSKGS MKASIEAEE   119

SEQ ID NO: 635         moltype = AA  length = 119
FEATURE                Location/Qualifiers
source                 1..119
                       mol_type = protein
                       organism = synthetic construct
SEQUENCE: 635
MPTAASATES AIEDTPAPAR PEVDGRTKPK RQPRYHVVLW DDEDHTYQYV VVMLRSLFGH  60
PPSRGYRMAK EMTTQGRVIV LTTTREHAEL KRDQIHAFGR DRLLARSKGS MKASIEAEE   119

SEQ ID NO: 636         moltype = AA  length = 119
FEATURE                Location/Qualifiers
source                 1..119
                       mol_type = protein
                       organism = synthetic construct
SEQUENCE: 636
MPTAASATES AIEDTPAPAR PEVDGRTKPK RQPRYHVVLY DDEDHTFQYV VVMLRSLFGH  60
PPSRGYRMAK EMDTQGRVIV LTTTREHAEL KRDQIHAFGR DRLLARSKGS MKASIEAEE   119

SEQ ID NO: 637         moltype = AA  length = 119
FEATURE                Location/Qualifiers
source                 1..119
                       mol_type = protein
                       organism = synthetic construct
SEQUENCE: 637
MPTAASATES AIEDTPAPAR PEVDGRTKPK RQPRYHVVLY DDDDHTYQYV VVMLRSLFGH  60
PPSRGYRMAR EMTTQGRVIV LTTTREHAEL KRDQIHAFGR DRLLARSKGS MKASIEAEE   119

SEQ ID NO: 638         moltype = AA  length = 119
FEATURE                Location/Qualifiers
source                 1..119
                       mol_type = protein
                       organism = synthetic construct
SEQUENCE: 638
MPTAASATES AIEDTPAPAR PEVDGRTKPK RQPRYHVVLW DDEDHTYQYV VVMLRSLFGH  60
PPSRGYRMAR EMTTQGRVIV LTTTREHAEL KRDQIHAFGR DRLLARSKGS MKASIEAEE   119

SEQ ID NO: 639         moltype = AA  length = 119
FEATURE                Location/Qualifiers
source                 1..119
                       mol_type = protein
                       organism = synthetic construct
SEQUENCE: 639
MPTAASATES AIEDTPAPAR PEVDGRTKPK RQPRYHVVLY DDEDHTFQYV VVMLRSLFGH  60
PPSRGYRMAK EMTTQGRVIV LTTTREHAEL KRDQIHAFGR DRLLARSKGS MKASIEAEE   119

SEQ ID NO: 640         moltype = AA  length = 119
FEATURE                Location/Qualifiers
source                 1..119
                       mol_type = protein
                       organism = synthetic construct
SEQUENCE: 640
MPTAASATES AIEDTPAPAR PEVDGRTKPK RQPRYHVVLW DDEDHTFQYV VVMLRSLFGH  60
PPSRGYRMAR EMTTQGRVIV LTTTREHAEL KRDQIHAFGR DRLLARSKGS MKASIEAEE   119

SEQ ID NO: 641         moltype = AA  length = 119
FEATURE                Location/Qualifiers
source                 1..119
                       mol_type = protein
                       organism = synthetic construct
SEQUENCE: 641
MPTAASATES AIEDTPAPAR PEVDGRTKPK RQPRYHVVLY DDEDHTFQYV VVMLRSLFGH  60
PPSRGYRMAR EMTTQGRVIV LTTTREHAEL KRDQIHAFGR DRLLARSKGS MKASIEAEE   119

SEQ ID NO: 642         moltype = AA  length = 119
FEATURE                Location/Qualifiers
source                 1..119
                       mol_type = protein
                       organism = synthetic construct
SEQUENCE: 642
MPTAASATES AIEDTPAPAR PEVDGRTKPK RQPRYHVVLW SDEDHTHQYV VVMLRSLFGH  60
```

```
PPSRGYRMAK EIDTQGRVIV LTTTREHAEL KRDQIHAFGR DRLLARSKGS MKASIEAEE   119

SEQ ID NO: 643         moltype = AA  length = 119
FEATURE                Location/Qualifiers
source                 1..119
                       mol_type = protein
                       organism = synthetic construct
SEQUENCE: 643
MPTAASATES AIEDTPAPAR PEVDGRTKPK RQPRYHVVIW EDDDHTYQYW VVMLRSLFGH  60
PPSRGYRMAK EAHTQGRVIV LTTTREHAEL KRDQIHAFGR DRLLARSKGS LKASIEAEE   119

SEQ ID NO: 644         moltype = AA  length = 119
FEATURE                Location/Qualifiers
source                 1..119
                       mol_type = protein
                       organism = synthetic construct
SEQUENCE: 644
MPTAASATES AIEDTPAPAR PEVDGRTKPK RQPRYHVVIW SDDDHTHDYV VVMLRSLFGH  60
PPSRGYRMTK ELHTQGRVIV LTTTREHAEL KRDQIHAFGR DRLLARSKGS MKASIEAEE   119

SEQ ID NO: 645         moltype = AA  length = 119
FEATURE                Location/Qualifiers
source                 1..119
                       mol_type = protein
                       organism = synthetic construct
SEQUENCE: 645
MPTAASATES AIEDTPAPAR PEVDGRTKPK RQPRYHVVMW DDQDNTDQYW VVMLRSLFGH  60
PPSRGYRMSE ELHTQGRVIV LTTTREHAEL KRDQIHAFGR DRLLARSKGS VKASIEAEE   119

SEQ ID NO: 646         moltype = AA  length = 119
FEATURE                Location/Qualifiers
source                 1..119
                       mol_type = protein
                       organism = synthetic construct
SEQUENCE: 646
MPTAASATES AIEDTPAPAR PEVDGRTKPK RQPRYHVVVW DDEDHTHQYW VVMLRSLFGH  60
PPSRGYRMAK EAHTQGRVIV LTTTREHAEL KRDQIHAFGR DRLLARSKGS LKASIEAEE   119

SEQ ID NO: 647         moltype = AA  length = 119
FEATURE                Location/Qualifiers
source                 1..119
                       mol_type = protein
                       organism = synthetic construct
SEQUENCE: 647
MPTAASATES AIEDTPAPAR PEVDGRTKPK RQPRYHVVLW DDDDHTSQYV VVMLHSLFGH  60
PPSRGYRLAK EMDTQGRVIV LTTTREHAEL KRDQIHAFGR DRLLARSKGS MKASIEAEE   119

SEQ ID NO: 648         moltype = AA  length = 119
FEATURE                Location/Qualifiers
source                 1..119
                       mol_type = protein
                       organism = synthetic construct
SEQUENCE: 648
MPTAASATES AIEDTPAPAR PEVDGRTKPK RQPRYHVVLW SDEDHTHQYI VVMLRSLFGH  60
PPSRGYRMAK EIDTQGRVIV LTTTREHAEL KRDQIHAFGR DRLLARSKGS MKASIEAEE   119

SEQ ID NO: 649         moltype = AA  length = 119
FEATURE                Location/Qualifiers
source                 1..119
                       mol_type = protein
                       organism = synthetic construct
SEQUENCE: 649
MPTAASATES AIEDTPAPAR PEVDGRTKPK RQPRYHVVLW DDDDHTKQYI VVMLRSLFGH  60
PPSRGYRMAK EMHTQGRVIV LTTTREHAEL KRDQIHAFGR DRLLARSKGS VKASIEAEE   119

SEQ ID NO: 650         moltype = AA  length = 119
FEATURE                Location/Qualifiers
source                 1..119
                       mol_type = protein
                       organism = synthetic construct
SEQUENCE: 650
MPTAASATES AIEDTPAPAR PEVDGRTKPK RQPRYHVVMW EDEDHTFQYV VVMLRSLFGH  60
PPSRGYRMVK EMHTQGRVIV LTTTREHAEL KRDQIHAFGR DRLLARSKGS MKASIEAEE   119

SEQ ID NO: 651         moltype = AA  length = 766
FEATURE                Location/Qualifiers
source                 1..766
                       mol_type = protein
                       organism = synthetic construct
```

```
SEQUENCE: 651
MASDTPESLM ALCTDFCLRN LDGTLGYLLD KETLRLHPDI FLPSEICDRL VNEYVELVNA  60
ACNFEPHESF FSLFSDPRST RLTRIHLRED LVQDQDLEAI RKQDLVELYL TNCEKLSAKS  120
LQTLRSFSHT LVSLSLFGCT NIFYEEENPG GCEDEYLVNP TCQVLVKDFT FEGFSRLRFL  180
NLGRMIDWVP VESLLRPLNS LAALDLSGIQ TSDAAFLTQW KDSLVSLVLY NMDLSDDHIR  240
VIVQLHKLRH LDISRDRLSS YYKFKLTREV LSLFVQKLGN LMSLDISGHM ILENCSISKM  300
EEEAGQTSIE PSKSSIIPFR ALKRPLQFLG LFENSLCRLT HIPAYKVSGD KNEEQVLNAI  360
EAYTEHRPEI TSRAINLLFD IARIERCNQL LRALKLVITA LKCHKYDRNI QVTGSAALFY  420
LTNSEYRSEQ SVKLRRQVIQ VVLNGMESYQ EVTVQRNCCL TLCNFSIPEE LEFQYRRVNE  480
LLLSILNPTR QDESIQRIAV HLCNALVCQV DNDHKEAVGK MGFVVTMLKL IQKKLLDKTC  540
DQVMEFSWSA LWNITDETPD NCEMFLNFNG MKLFLDCLKE FPEKQELHRN MLGLLGNVAE  600
VKELRPQLMT SQFISVFSNL LESKADGIEV SYNACGVLSH IMFDGPEAWG VCEPQREEVE  660
ERMWAAIQSW DINSRRNINY RSFEPILRLL PQGISPVSQH WATWALYNLV SVYPDKYCPL  720
LIKEGGMPLL RDIIKMATAR QETKEMARKV IEHCSNFKEE NMDTSR                766

SEQ ID NO: 652         moltype = AA  length = 347
FEATURE                Location/Qualifiers
source                 1..347
                       mol_type = protein
                       organism = synthetic construct
SEQUENCE: 652
MLTNSEYRSE QSVKLRRQVI QVVLNGMESY QEVTVQRNCC LTLCNFSIPE ELEFQYRRVN  60
ELLLSILNPT RQDESIQRIA VHLCNALVCQ VDNDHKEAVG KMGFVVTMLK LIQKKLLDKT  120
CDQVMEFSWS ALWNITDETP DNCEMFLNFN GMKLFLDCLK EFPEKQELHR NMLGLLGNVA  180
EVKELRPQLM TSQFISVFSN LLESKADGIE VSYNACGVLS HIMFDGPEAW GVCEPQREEV  240
EERMWAAIQS WDINSRRNIN YRSFEPILRL LPQGISPVSQ HWATWALYNL VSVYPDKYCP  300
LLIKEGGMPL LRDIIKMATA RQETKEMARK VIEHCSNFKE ENMDTSR               347

SEQ ID NO: 653         moltype = AA  length = 347
FEATURE                Location/Qualifiers
source                 1..347
                       mol_type = protein
                       organism = synthetic construct
SEQUENCE: 653
MLTNSEYRME QSIKLRRQVI QVVLNGMESY QEVTVQRNCC LTLCNFSIPE ELEFQYRRVN  60
ELLLSILNQS RQDESIQRIA VHLCNALVCQ VDNDHKEAVG KMGFVMTMLK LIQKKLADKT  120
CDQVMEFSWS ALWNITDETP DNCEMFLNYS GMKLFLECLK EFPEKQELHR NMLGLLGNVA  180
EVRELRPQLM TSQFISVFSN LLESKADGIE VSYNACGVLS HIMFDGPEAW GICEPHREEV  240
VKRMWAAIQS WDINSRRNIN YRSFEPILRL LPQGISPVSQ HWATWALYNL VSVYPDKYCP  300
LLIKEGGIPL LKDMIKMASA RQETKEMAWK VIEHCSNFKE ENMDTSR               347

SEQ ID NO: 654         moltype = AA  length = 355
FEATURE                Location/Qualifiers
source                 1..355
                       mol_type = protein
                       organism = synthetic construct
SEQUENCE: 654
MTGSAALFYL TNTEYRGEQS VRLRRQVIQV VLNGMEHYQE VTVQRNCCLT LCNFSIPEEL  60
EFQYRRVNLL LLKILEPLRQ DESIQRIAVH LCNALVCQVD NDHKEAVGKM GFVKTMLNLI  120
QKKLQDRMCD QVMEFSWSAL WNITDETPDN CQMFLECNGM NLFLECLKEF PDKQELHRNM  180
LGLLGNVAEV KALRPQLLTR QFITVFSDLL DSKADGIEVS YNACGVLSHI MFDGPGVWSM  240
EEPSRTHVMD KMWTAIQSWD VSSRRNINYR SFEPILRLLP QSGAPVSQHW ATWALYNLVS  300
VYPSKYCPLL IKEGGVSLLQ AVLELQTSHV ETKDMARKVM EQCESFKEDP MDTSR       355

SEQ ID NO: 655         moltype = AA  length = 744
FEATURE                Location/Qualifiers
source                 1..744
                       mol_type = protein
                       organism = synthetic construct
SEQUENCE: 655
MPEDQAGAAM EEASPYSLLD ICLNFLTTHL EKFCSARQDG TLCLQEPGVF PQEVADRLLR  60
TMAFHGLLND GTVGIFRGNQ MRLKRACIRK AKISAVAFRK AFCHHKLVEL DATGVNADIT  120
ITDIISGLGS NKWIQQNLQC LVLNSLTLSL EDPYERCFSR LSGLRALSIT NVLFYNEDLA  180
EVASLPRLES LDISNTSITD ITALLACKDR LKSLTMHHLK CLKMTTTQIL DVVRELKHLN  240
HLDISDDKQF TSDIALRLLE QKDILPNLVS LDVSGRKHVT DKAVEAFIQQ RPSMQFVGLL  300
ATDAGYSEFL TGEGHLKVSG EANETQIAEA LKRYSERAFF VREALFHLFS LTHVMEKTKP  360
EILKLVVTGM RNHPMNLPVQ LAASACVFNL TKQDLAAGMP VRLLADVTHL LLKAMEHFPN  420
HQQLQKNCLL SLCSDRILQD VPFNRFEAAK LVMQWLCNHE DQNMQRMAVA IISILAAKLS  480
TEQTAQLGTE LFIVRQLLQI VKQKTNQNSV DTTLKFTLSA LWNLTDESPT TCRHFIENQG  540
LELFMRVLES FPTESSIQQK VLGLLNNIAE VQELHSELMW KDFIDHISSL LHSVEVEVSY  600
FAAGIIAHLI SRGEQAWTLS RSQRNSLLDD LHSAILKWPT PECEMVAYRS FNPFFPLLGC  660
FTTPGVQLWA VWAMQHVCSK NPSRYCSMLI EEGGLQHLYN IKDHEHTDPH VQQIAVAILD  720
SLEKHIVRHG RPPPCKKQPQ ARLN                                        744

SEQ ID NO: 656         moltype = AA  length = 359
FEATURE                Location/Qualifiers
source                 1..359
                       mol_type = protein
                       organism = synthetic construct
```

```
SEQUENCE: 656
MVFNLTKQDL AAGMPVRLLA DVTHLLLKAM EHFPNHQQLQ KNCLLSLCSD RILQDVPFNR  60
FEAAKLVMQW LCNHEDQNMQ RMAVAIISIL AAKLSTEQTA QLGTELFIVR QLLQIVKQKT 120
NQNSVDTTLK FTLSALWNLT DESPTTCRHF IENQGLELFM RVLESFPTES SIQQKVLGLL 180
NNIAEVQELH SELMWKDFID HISSLLHSVE VEVSYFAAGI IAHLISRGEQ AWTLSRSQRN 240
SLLDDLHSAI LKWPTPECEM VAYRSFNPFF PLLGCFTTPG VQLWAVWAMQ HVCSKNPSRY 300
CSMLIEEGGL QHLYNIKDHE HTDPHVQQIA VAILDSLEKH IVRHGRPPPC KKQPQARLN  359

SEQ ID NO: 657         moltype = AA  length = 383
FEATURE                Location/Qualifiers
source                 1..383
                       mol_type = protein
                       organism = synthetic construct
SEQUENCE: 657
MPEMLKLVVI GMRNHPTNLP VQLAASACVF NLTKQDLAAG MPVKLLADVT HLLLEAMKHF  60
PNHQQLQKNC LLSLCSDRIL QDVPFNRFDA AKLVMQWLCN HEDQNMQRMA VAIISILAAK 120
LSTEQTAQLG AELFIVRQLL QIVRQKTSQN MVDTTLKFTL SALWNLTDES PTTCRHFIEN 180
QGLELFMKVL ETFPSESSIQ QKVLGLLNNI AEVKELHSEL MCKDFIDQIS KLLHSVEVEV 240
SYFAAGIIAH LVSRGEESWT LSSSLRETLL EQLHSAILSW PTPECEMVAY RSFNPFFPLL 300
ACFRTPGVQL WAVWAMQHVC SKNPVRYCSM LIEEGGLVRL HRIRDHMCAD PDVLRITIAI 360
LDNLDRHLRK HGNPPCPKPP FAK                                        383

SEQ ID NO: 658         moltype = AA  length = 397
FEATURE                Location/Qualifiers
source                 1..397
                       mol_type = protein
                       organism = synthetic construct
SEQUENCE: 658
MLTHAIEKPR PDILKLVALG MKNHPTTLNV QLAASACVFN LTKQELAFGI PVRLLGNVTQ  60
QLLEAMKTFP NHQQLQKNCL LSLCSDRILQ EVPFNRFEAA KLVMQWLCNH EDQNMQRMAV 120
AIISILAAKL STEQTAQLGA ELFIVKQLLH IVRQKTCQST VDATLKFTLS ALWNLTDESP 180
TTCRHFIENQ GLELFIKVLE SFPSESSIQQ KVLGLLNNIA EVSELHGELM VQSFLDHIRT 240
LLHSPEVEVS YFAAGILAHL TSRGEKVWTL ELTLRNTLLQ QLHSAILKWP TPECEMVAYR 300
SFNPFFPLLE CFQTPGVQLW AAWAMQHVCS KNAGRYCSML LEEGGLQHLE AITSHPKTHS 360
DVRRLTESIL DGLQRHRART GYTAIPKTQA HREKCNP                         397

SEQ ID NO: 659         moltype = AA  length = 420
FEATURE                Location/Qualifiers
source                 1..420
                       mol_type = protein
                       organism = synthetic construct
SEQUENCE: 659
MEGNGPAAVH YQPASPPRDA CVYSSCYSEE NVWKLCEYIK NHDQYPLEEC YAVFISNERK  60
MIPIWKQQAR PGDGPVIWDY QVVLLHVSSG GQSFIYDLDT VLPFPCLFDT YVEDAIKSDD 120
DIHPQFRRKF RVICADSYLK NFASDRSHMK DSSGNWREPP PPYPCIETGD SKMNLNDFIS 180
MDPKVGWGAV YTLSEFTHRF GSKNGSAGSA AGSGEFMEGN GPAAVHYQPA SPPRDACVYS 240
SCYSEENVWK LCEYIKNHDQ YPLEECYAVF ISNERKMIPI WKQQARPGDG PVIWDYQVVL 300
LHVSSGGQSF IYDLDTVLPF PCLFDTYVED AIKSDDDIHP QFRRKFRVIC ADSYLKNFAS 360
DRSHMKDSSG NWREPPPPYP CIETGDSKMN LNDFISMDPK VGWGAVYTLS EFTHRFGSKN 420

SEQ ID NO: 660         moltype = AA  length = 412
FEATURE                Location/Qualifiers
source                 1..412
                       mol_type = protein
                       organism = synthetic construct
SEQUENCE: 660
MNGLSAQHER IAPARHECVY TSCYSEENVW KLCEHIKTSK RCPLGDVYAV FISNERKMVP  60
IWKQKSGRGE EPVIWDYHVI LLHDCHKEQT FIYDLDTTLP FPCPFDTYVK EAFKSDNYIN 120
PAFWRKLRVV PADVFLQNFA SDRSHMKDAS GGWRMPPPPY PCIETAESRM NLDDFISMNP 180
SVGWGHVYTL EEFVQHFGKT GSAGSAAGSG EFMNGLSAQH ERIAPARHEC VYTSCYSEEN 240
VWKLCEHIKT SKRCPLGDVY AVFISNERKM VPIWKQKSGR GEEPVIWDYH VILLHDCHKE 300
QTFIYDLDTT LPFPCPFDTY VKEAFKSDNY INPAFWRKLR VVPADVFLQN FASDRSHMKD 360
ASGGWRMPPP PYPCIETAES RMNLDDFISM NPSVGWGHVY TLEEFVQHFG KT         412

SEQ ID NO: 661         moltype = AA  length = 413
FEATURE                Location/Qualifiers
source                 1..413
                       mol_type = protein
                       organism = synthetic construct
SEQUENCE: 661
MNGLSAQHER IAPARHECVY TSCYSEENVW KLCEHIKTSK RCPLGDVYAV FISNERKMVP  60
IWKQKSGRGE EPVIWDYQVI LLHDCHKEQT FIYDLDTTLP FPCPFDTYVK EAFKSDNYIN 120
PAFWRKLRVV PADVFLQNFA SDRSHMKDAS GGWRMPPPPY PCIETAESRM NLDDFISMNP 180
SVGWGHVYTL EEFVQHFGKT GGGSGGGSGG GSGMNGLSAQ HERIAPARHE CVYTSCYSEE 240
NVWKLCEHIK TSKRCPLGDV YAVFISNERK MVPIWKQKSG RGEEPVIWDY QVILLHDCHK 300
EQTFIYDLDT TLPFPCPFDT YVKEAFKSDN YINPAFWRKL RVVPADVFLQ NFASDRSHMK 360
DASGGWRMPP PPYPCIETAE SRMNLDDFIS MNPSVGWGHV YTLEEFVQHF GKT        413

SEQ ID NO: 662         moltype = AA  length = 412
```

```
FEATURE                Location/Qualifiers
source                 1..412
                       mol_type = protein
                       organism = synthetic construct
SEQUENCE: 662
MNGLSAQHER IAPARHECVY TSCYSEENVW KLCEHIKTSK RCPLGDVYAV FISNERKMVP  60
IWKQKSGRGE EPVIWDYQVI LLHDCHKEQT FIYDLDTTLP FPCPFDTYVK EAFKSDNYIN  120
PAFWRKLRVV PADVFLQNFA SDRSHMKDAS GGWRMPPPPY PCIETAESRM NLDDFISMNP  180
SVGWGHVYTL EEFVQHFGKT GSAGSAAGSG EFMNGLSAQH ERIAPARHEC VYTSCYSEEN  240
VWKLCEHIKT SKRCPLGDVY AVFISNERKM VPIWKQKSGR GEEPVIWDYQ VILLHDCHKE  300
QTFIYDLDTT LPFPCPFDTY VKEAFKSDNY INPAFWRKLR VVPADVFLQN FASDRSHMKD  360
ASGGWRMPPP PYPCIETAES RMNLDDFISM NPSVGWGHVY TLEEFVQHFG KT          412

SEQ ID NO: 663         moltype = AA  length = 436
FEATURE                Location/Qualifiers
source                 1..436
                       mol_type = protein
                       organism = synthetic construct
SEQUENCE: 663
MNGLSAQHER IAPARHECVY TSCYSEENVW KLCEHIKTSK RCPLGDVYAV FISNERKMVP  60
IWKQKSGRGE EPVIWDYQVI LLHDCHKEQT FIYDLDTTLP FPCPFDTYVK EAFKSDNYIN  120
PAFWRKLRVV PADVFLQNFA SDRSHMKDAS GGWRMPPPPY PCIETAESRM NLDDFISMNP  180
SVGWGHVYTL EEFVQHFGKT GSAGSAAGSG EFGSAGSAAG SGEFGSAGSA AGSGEFMNGL  240
SAQHERIAPA RHECVYTSCY SEENVWKLCE HIKTSKRCPL GDVYAVFISN ERKMVPIWKQ  300
KSGRGEEPVI WDYQVILLHD CHKEQTFIYD LDTTLPFPCP FDTYVKEAFK SDNYINPAFW  360
RKLRVVPADV FLQNFASDRS HMKDASGGWR MPPPPYPCIE TAESRMNLDD FISMNPSVGW  420
GHVYTLEEFV QHFGKT                                                  436

SEQ ID NO: 664         moltype = AA  length = 119
FEATURE                Location/Qualifiers
source                 1..119
                       mol_type = protein
                       organism = synthetic construct
SEQUENCE: 664
MPTAASATES AIEDTPAPAR PEVDGRTKPK RQPRYHVVLW DDDDHTYQYV VAMLRSLFGH  60
PPSRGYRMAK EMDTQGRVIV LTTTREHAEL KRDQIHAFGR DRLLARSKGS MKASIEAEE   119

SEQ ID NO: 665         moltype = AA  length = 119
FEATURE                Location/Qualifiers
source                 1..119
                       mol_type = protein
                       organism = synthetic construct
SEQUENCE: 665
MPTAASATES AIEDTPAPAR PEVDGRTKPK RQPRYHVVLW DDDDHTYQYV VMMLRSLFGH  60
PPSRGYRMAK EMDTQGRVIV LTTTREHAEL KRDQIHAFGR DRLLARSKGS MKASIEAEE   119

SEQ ID NO: 666         moltype = AA  length = 119
FEATURE                Location/Qualifiers
source                 1..119
                       mol_type = protein
                       organism = synthetic construct
SEQUENCE: 666
MPTAASATES AIEDTPAPAR TEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 667         moltype = AA  length = 119
FEATURE                Location/Qualifiers
source                 1..119
                       mol_type = protein
                       organism = synthetic construct
SEQUENCE: 667
MPTAASATES AIEDTPAPAR PEVDGRTKPK RQPRYHVVLW DDDDHTYQYV VAMLRSLFGI  60
PPSRGYRMAK EMDTQGRVIV LTTTREHAEL KRDQIHAFGR DRLLARSKGS MKASIEAEE   119

SEQ ID NO: 668         moltype = AA  length = 119
FEATURE                Location/Qualifiers
source                 1..119
                       mol_type = protein
                       organism = synthetic construct
SEQUENCE: 668
MPTAASATES AIEDTPAPAR PEVDGRTKPK RQPRYHVVLW DDDDHTYQYV VMMLRSLFGI  60
PPSRGYRMAK EMDTQGRVIV LTTTREHAEL KRDQIHAFGR DRLLARSKGS MKASIEAEE   119

SEQ ID NO: 669         moltype = AA  length = 119
FEATURE                Location/Qualifiers
source                 1..119
                       mol_type = protein
                       organism = synthetic construct
SEQUENCE: 669
```

```
MPTAASATES AIEDTPAPAR PEVDGRTKPK RQPRYHVVLW DDDDHTYQYV VMMLRSLFGY  60
PPSRGYRMAK EMDTQGRVIV LTTTREHAEL KRDQIHAFGR DRLLARSKGS MKASIEAEE   119

SEQ ID NO: 670          moltype = AA  length = 119
FEATURE                 Location/Qualifiers
source                  1..119
                        mol_type = protein
                        organism = synthetic construct
SEQUENCE: 670
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAWGR DRLLARSKGS MKASIEAEE   119

SEQ ID NO: 671          moltype = AA  length = 119
FEATURE                 Location/Qualifiers
source                  1..119
                        mol_type = protein
                        organism = synthetic construct
SEQUENCE: 671
MPTAASATES AIEDTPAPAR PEVDGRTKPK RQPRYHVVLW DDDDHTYQYV VVMLRSLFGH  60
PKSRGYRMAK EMDTQGRVIV LTTTREHAEL KRDQIHAFGR DRLLARSKGS MKASIEAEE   119

SEQ ID NO: 672          moltype = AA  length = 119
FEATURE                 Location/Qualifiers
source                  1..119
                        mol_type = protein
                        organism = synthetic construct
SEQUENCE: 672
MPTAASATES AIEDTPAPAR PEVDGRTKPK RQPRYHVVLW DDDDHTYQYV VVMLQSLFGH  60
PPSRGYRMAK EMDTQGRVIV LTTTREHAEL KRDQIHAFGR DRLLARSKGS MKASIEAEE   119

SEQ ID NO: 673          moltype = AA  length = 119
FEATURE                 Location/Qualifiers
source                  1..119
                        mol_type = protein
                        organism = synthetic construct
SEQUENCE: 673
MPTAASATES AIEDTPAPAR PEVDGRTKPK RQPRYHVVLW DDDDHTYQYV VVMLKSLFGH  60
PPSRGYRMAK EMDTQGRVIV LTTTREHAEL KRDQIHAFGR DRLLARSKGS MKASIEAEE   119

SEQ ID NO: 674          moltype = AA  length = 119
FEATURE                 Location/Qualifiers
source                  1..119
                        mol_type = protein
                        organism = synthetic construct
SEQUENCE: 674
MPTAASATES AIEDTPAPAR PEVDGRTKPK RQPRYHVVLW DDDDHTYQYV VVMLASLFGH  60
PPSRGYRMAK EMDTQGRVIV LTTTREHAEL KRDQIHAFGR DRLLARSKGS MKASIEAEE   119

SEQ ID NO: 675          moltype = AA  length = 119
FEATURE                 Location/Qualifiers
source                  1..119
                        mol_type = protein
                        organism = synthetic construct
SEQUENCE: 675
MPTAASATES AIEDTPAPAR PEVDGRTKPK RQPRYHVVLW DDDDHTYQYV VVMLSSLFGH  60
PPSRGYRMAK EMDTQGRVIV LTTTREHAEL KRDQIHAFGR DRLLARSKGS MKASIEAEE   119

SEQ ID NO: 676          moltype = AA  length = 119
FEATURE                 Location/Qualifiers
source                  1..119
                        mol_type = protein
                        organism = synthetic construct
SEQUENCE: 676
MPTAASATES AIEDTPAPAR PEVDGRTKPK RQPRYHVVLW DDDDHTYQYV VVMLRSLFGH  60
PPQRGYRMAK EMDTQGRVIV LTTTREHAEL KRDQIHAFGR DRLLARSKGS MKASIEAEE   119

SEQ ID NO: 677          moltype = AA  length = 119
FEATURE                 Location/Qualifiers
source                  1..119
                        mol_type = protein
                        organism = synthetic construct
SEQUENCE: 677
MPTAASATES AIEDTPAPAR PEVDGRTKPK RQPRYHVVLW DDDDHTYQYV VHMLRSLFGH  60
PPSRGYRMAK EMDTQGRVIV LTTTREHAEL KRDQIHAFGR DRLLARSKGS MKASIEAEE   119

SEQ ID NO: 678          moltype = AA  length = 119
FEATURE                 Location/Qualifiers
source                  1..119
                        mol_type = protein
```

```
                      organism = synthetic construct
SEQUENCE: 678
MPTAASATES AIEDTPAPAR PEVDGRTKPK RQPRYHVVLW DDDDHTYQYV VVMLRSVFGH  60
PPSRGYRMAK EMDTQGRVIV LTTTREHAEL KRDQIHAFGR DRLLARSKGS MKASIEAEE   119

SEQ ID NO: 679        moltype = AA  length = 119
FEATURE               Location/Qualifiers
source                1..119
                      mol_type = protein
                      organism = synthetic construct
SEQUENCE: 679
MPTAASATES AIEDTPAPAR PEVDGKTKPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 680        moltype = AA  length = 119
FEATURE               Location/Qualifiers
source                1..119
                      mol_type = protein
                      organism = synthetic construct
SEQUENCE: 680
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAYGR DRLLARSKGS MKASIEAEE   119

SEQ ID NO: 681        moltype = AA  length = 119
FEATURE               Location/Qualifiers
source                1..119
                      mol_type = protein
                      organism = synthetic construct
SEQUENCE: 681
MPTAASATES AIEDTPAPAR SEVDGYTVPK RQQRYHVVLW DDDDHTYQYV VYMLRSVFGH  60
PPSRGYRMAK EMDTQGRVIV LTTTREHAEL KRDQIHAFGR DRLLARSKGS MKASIEAEE   119

SEQ ID NO: 682        moltype = AA  length = 119
FEATURE               Location/Qualifiers
source                1..119
                      mol_type = protein
                      organism = synthetic construct
SEQUENCE: 682
MPTAASATES AIEDTPAPAR PEVDGRTKPK RQPRYHVVLW DDDDHTYQYV VYMLRSVFGH  60
PPSRGYRMAK EMDTQGRVIV LTTTREHAEL KRDQIHAFGR DRLLARSKGS MKASIEAEE   119

SEQ ID NO: 683        moltype = AA  length = 119
FEATURE               Location/Qualifiers
source                1..119
                      mol_type = protein
                      organism = synthetic construct
SEQUENCE: 683
MPTAASATES AIEDTPAPAR PEVDGRTKPK HQPRYHVVLW DDDDHTLQYV VVMLRSLFGH  60
PPSRGYRMAQ EMETQGRVIV LTTTREHAEL KRDQIHAFGR DRLLARSKGS MKASIEAEE   119

SEQ ID NO: 684        moltype = AA  length = 119
FEATURE               Location/Qualifiers
source                1..119
                      mol_type = protein
                      organism = synthetic construct
SEQUENCE: 684
MPTAASATES AIEDTPAPAR PEVDGRTKPK RQPRYHVVLW DDDDHTYQYV VEMLRHLFGH  60
PPSRGYRMAK EMDTQGRVIV LTTTREHAEL KRDQIHAFGR DRLLARSKGS MKASIEAEE   119

SEQ ID NO: 685        moltype = AA  length = 119
FEATURE               Location/Qualifiers
source                1..119
                      mol_type = protein
                      organism = synthetic construct
SEQUENCE: 685
MPTAASATES AIEDTPAPAR PEVDGRTKPK RQPRYHVVLW DDDDHTYQYV VSMLRSVFGH  60
PPSRGYRMAK EMDTQGRVIV LTTTREHAEL KRDQIRARGR DPLLARSKGS MKASIEAEE   119

SEQ ID NO: 686        moltype = AA  length = 119
FEATURE               Location/Qualifiers
source                1..119
                      mol_type = protein
                      organism = synthetic construct
SEQUENCE: 686
MPTAASATES AIEDTPAPAR PEVDGRTKPK RQPRYHVVLW DDDDHTYQYV VAMLRSIFGH  60
PPSRGYRMAK EMDTQGRVIV LTTTREHAEL KRDQIHAFGR DRLLARSKGS MSASIEAEE   119

SEQ ID NO: 687        moltype = AA  length = 119
FEATURE               Location/Qualifiers
```

```
source                  1..119
                        mol_type = protein
                        organism = synthetic construct
SEQUENCE: 687
MPTAASATES AIEDTPAPAR PEVDGRTKPK RQPRYHVVLW DDDDHTYQYV VVMLRSLFGH  60
PPSRGYRMAK ELETQGRLIV LTTTREHAEL KRDQIHAFGR DRLLARSKGS MKASIEAEE   119

SEQ ID NO: 688          moltype = AA  length = 119
FEATURE                 Location/Qualifiers
source                  1..119
                        mol_type = protein
                        organism = synthetic construct
SEQUENCE: 688
MPTAASATES AIEDTPAPAR PEVDGRTKPK HQPRYHVVLW DDDDHTDQYV VVMLRSLFGH  60
PPSRGYRMAK EMDTQGRVIV LTTTREHAEL KRDQIHAFGR DRLLARSKGS MSASIEAEE   119

SEQ ID NO: 689          moltype = AA  length = 119
FEATURE                 Location/Qualifiers
source                  1..119
                        mol_type = protein
                        organism = synthetic construct
SEQUENCE: 689
MPTAASATES AIEDTPAPAR PEVDGRTKPK RQPRYHVVLW DDDDHTDQYV VVMLRSLFGH  60
PPSRGYRMAK EMDTQGRVIV LTTTREHAEL KRDQIHAFGR DRLLARSKGS MSASIEAEE   119

SEQ ID NO: 690          moltype = AA  length = 119
FEATURE                 Location/Qualifiers
source                  1..119
                        mol_type = protein
                        organism = synthetic construct
SEQUENCE: 690
MPTAASATES AIEDTPAPAR PEVDGYTVPK RQPRYHVVLW DDDDHTYQYV VVMLRSLFGH  60
PPSRGYRMAK EMDTQGRVIV LTTTREHAEL KRDQIHAYGR DRLLARSKGS MKASIEAEE   119

SEQ ID NO: 691          moltype = AA  length = 119
FEATURE                 Location/Qualifiers
source                  1..119
                        mol_type = protein
                        organism = synthetic construct
SEQUENCE: 691
MPTAASATES AIEDTPAPAR PEVDGRTKPK RQPRYHVVLW DDDDHTYQYV VTMLRSVFGH  60
PPSRGYRMAK EMDTQGRVIV LTTTREHAEL KRDQIHAFGR DRLLARSKGS MKASIEAEE   119

SEQ ID NO: 692          moltype = AA  length = 119
FEATURE                 Location/Qualifiers
source                  1..119
                        mol_type = protein
                        organism = synthetic construct
SEQUENCE: 692
MPTAASATES AIEDTPAPAR SEVDGYTVPK RQPRYHVVLW DDDDHTYQYV VIMLRSLFGH  60
PPSRGYRMAK EMDTQGRVTV LTTTREHAEL KRDQIHAFGR DRLLARSKGS MKASIEAEE   119

SEQ ID NO: 693          moltype = AA  length = 119
FEATURE                 Location/Qualifiers
source                  1..119
                        mol_type = protein
                        organism = synthetic construct
SEQUENCE: 693
MPTAASATES AIEDTPAPAR PEVDGRTKPK RQPRYHVVLW DDDDHTYQYV VIMLRSLFGH  60
PPSRGYRMAK EMDTQGRVTV LTTTREHAEL KRDQIHAFGR DRLLARSKGS MKASIEAEE   119

SEQ ID NO: 694          moltype = AA  length = 83
FEATURE                 Location/Qualifiers
source                  1..83
                        mol_type = protein
                        organism = synthetic construct
SEQUENCE: 694
MHSKFSHAGR ICGAKFKVGE RIYRCKECSF DDTCVLCVNC FNPKDHLGHH VYTTICTEFN  60
NGECDCGDKT AWNHTLFCKA EEG                                         83

SEQ ID NO: 695          moltype = AA  length = 83
FEATURE                 Location/Qualifiers
source                  1..83
                        mol_type = protein
                        organism = synthetic construct
SEQUENCE: 695
MHSKFSHAGR ICGAKFKVGE PIYRCRECSF DDTCVLCVNC FNPKDHLGHH VYTTICTEFN  60
NGECDCGDKT AWNHTLFCKA EEG                                         83
```

```
SEQ ID NO: 696          moltype = AA  length = 83
FEATURE                 Location/Qualifiers
source                  1..83
                        mol_type = protein
                        organism = synthetic construct
SEQUENCE: 696
MHSKFSHAGR ICGAKFKVGE PIYRCKLCSF DDTCVLCVNC FNPKDHLGHH VYTTICTEFN  60
NGECDCGDKT AWNHTLFCKA EEG                                          83

SEQ ID NO: 697          moltype = AA  length = 83
FEATURE                 Location/Qualifiers
source                  1..83
                        mol_type = protein
                        organism = synthetic construct
SEQUENCE: 697
MHSKFSHAGR ICGAKFKVGE PIYRCKECSF DATCVLCVNC FNPKDHLGHH VYTTICTEFN  60
NGECDCGDKT AWNHTLFCKA EEG                                          83

SEQ ID NO: 698          moltype = AA  length = 83
FEATURE                 Location/Qualifiers
source                  1..83
                        mol_type = protein
                        organism = synthetic construct
SEQUENCE: 698
MHSKFSHAGR ICGAKFKVGE PIYRCKECSF DCTCVLCVNC FNPKDHLGHH VYTTICTEFN  60
NGECDCGDKT AWNHTLFCKA EEG                                          83

SEQ ID NO: 699          moltype = AA  length = 83
FEATURE                 Location/Qualifiers
source                  1..83
                        mol_type = protein
                        organism = synthetic construct
SEQUENCE: 699
MHSKFSHAGR ICGAKFKVGE PIYRCKECSF DGTCVLCVNC FNPKDHLGHH VYTTICTEFN  60
NGECDCGDKT AWNHTLFCKA EEG                                          83

SEQ ID NO: 700          moltype = AA  length = 83
FEATURE                 Location/Qualifiers
source                  1..83
                        mol_type = protein
                        organism = synthetic construct
SEQUENCE: 700
MHSKFSHAGR ICGAKFKVGE PIYRCKECSF DHTCVLCVNC FNPKDHLGHH VYTTICTEFN  60
NGECDCGDKT AWNHTLFCKA EEG                                          83

SEQ ID NO: 701          moltype = AA  length = 83
FEATURE                 Location/Qualifiers
source                  1..83
                        mol_type = protein
                        organism = synthetic construct
SEQUENCE: 701
MHSKFSHAGR ICGAKFKVGE PIYRCKECSF DKTCVLCVNC FNPKDHLGHH VYTTICTEFN  60
NGECDCGDKT AWNHTLFCKA EEG                                          83

SEQ ID NO: 702          moltype = AA  length = 83
FEATURE                 Location/Qualifiers
source                  1..83
                        mol_type = protein
                        organism = synthetic construct
SEQUENCE: 702
MHSKFSHAGR ICGAKFKVGE PIYRCKECSF DPTCVLCVNC FNPKDHLGHH VYTTICTEFN  60
NGECDCGDKT AWNHTLFCKA EEG                                          83

SEQ ID NO: 703          moltype = AA  length = 83
FEATURE                 Location/Qualifiers
source                  1..83
                        mol_type = protein
                        organism = synthetic construct
SEQUENCE: 703
MHSKFSHAGR ICGAKFKVGE PIYRCKECSF DQTCVLCVNC FNPKDHLGHH VYTTICTEFN  60
NGECDCGDKT AWNHTLFCKA EEG                                          83

SEQ ID NO: 704          moltype = AA  length = 83
FEATURE                 Location/Qualifiers
source                  1..83
                        mol_type = protein
                        organism = synthetic construct
SEQUENCE: 704
MHSKFSHAGR ICGAKFKVGE PIYRCKECSF DRTCVLCVNC FNPKDHLGHH VYTTICTEFN  60
```

```
NGECDCGDKT AWNHTLFCKA EEG                                          83

SEQ ID NO: 705          moltype = AA  length = 83
FEATURE                 Location/Qualifiers
source                  1..83
                        mol_type = protein
                        organism = synthetic construct
SEQUENCE: 705
MHSKFSHAGR ICGAKFKVGE PIYRCKECSF DSTCVLCVNC FNPKDHLGHH VYTTICTEFN  60
NGECDCGDKT AWNHTLFCKA EEG                                          83

SEQ ID NO: 706          moltype = AA  length = 83
FEATURE                 Location/Qualifiers
source                  1..83
                        mol_type = protein
                        organism = synthetic construct
SEQUENCE: 706
MHSKFSHAGR ICGAKFKVGE PIYRCKECSF DVTCVLCVNC FNPKDHLGHH VYTTICTEFN  60
NGECDCGDKT AWNHTLFCKA EEG                                          83

SEQ ID NO: 707          moltype = AA  length = 83
FEATURE                 Location/Qualifiers
source                  1..83
                        mol_type = protein
                        organism = synthetic construct
SEQUENCE: 707
MHSKFSHAGR ICGAKFKVGE PIYRCKECSF DDTCVLCVNC FNPKDHIGHH VYTTICTEFN  60
NGECDCGDKT AWNHTLFCKA EEG                                          83

SEQ ID NO: 708          moltype = AA  length = 83
FEATURE                 Location/Qualifiers
source                  1..83
                        mol_type = protein
                        organism = synthetic construct
SEQUENCE: 708
MHSKFSHAGR ICGAKFKVGE PIYRCKECSF DDTCVLCVNC FNPKDHLGHH VYTTIRTEFN  60
NGECDCGDKT AWNHTLFCKA EEG                                          83

SEQ ID NO: 709          moltype = AA  length = 83
FEATURE                 Location/Qualifiers
source                  1..83
                        mol_type = protein
                        organism = synthetic construct
SEQUENCE: 709
MHSKFSHAGR ICGAKFKVGE PIYRCKECSF DDTCVLCVNC FNPKDHLGHH VYTTICTCFN  60
NGECDCGDKT AWNHTLFCKA EEG                                          83

SEQ ID NO: 710          moltype = AA  length = 83
FEATURE                 Location/Qualifiers
source                  1..83
                        mol_type = protein
                        organism = synthetic construct
SEQUENCE: 710
MHSKFSHAGR ICGAKFKVGE PIYRCKECSF DDTCVLCVNC FNPKDHLGHH VYTTICTDFN  60
NGECDCGDKT AWNHTLFCKA EEG                                          83

SEQ ID NO: 711          moltype = AA  length = 83
FEATURE                 Location/Qualifiers
source                  1..83
                        mol_type = protein
                        organism = synthetic construct
SEQUENCE: 711
MHSKFSHAGR ICGAKFKVGE PIYRCKECSF DDTCVLCVNC FNPKDHLGHH VYTTICTIFN  60
NGECDCGDKT AWNHTLFCKA EEG                                          83

SEQ ID NO: 712          moltype = AA  length = 83
FEATURE                 Location/Qualifiers
source                  1..83
                        mol_type = protein
                        organism = synthetic construct
SEQUENCE: 712
MHSKFSHAGR ICGAKFKVGE PIYRCKECSF DDTCVLCVNC FNPKDHLGHH VYTTICTNFN  60
NGECDCGDKT AWNHTLFCKA EEG                                          83

SEQ ID NO: 713          moltype = AA  length = 83
FEATURE                 Location/Qualifiers
source                  1..83
                        mol_type = protein
                        organism = synthetic construct
```

```
SEQUENCE: 713
MHSKFSHAGR ICGAKFKVGE PIYRCKECSF DDTCVLCVNC FNPKDHLGHH VYTTICTQFN  60
NGECDCGDKT AWNHTLFCKA EEG                                          83

SEQ ID NO: 714          moltype = AA  length = 83
FEATURE                 Location/Qualifiers
source                  1..83
                        mol_type = protein
                        organism = synthetic construct
SEQUENCE: 714
MHSKFSHAGR ICGAKFKVGE PIYRCKECSF DDTCVLCVNC FNPKDHLGHH VYTTICTSFN  60
NGECDCGDKT AWNHTLFCKA EEG                                          83

SEQ ID NO: 715          moltype = AA  length = 83
FEATURE                 Location/Qualifiers
source                  1..83
                        mol_type = protein
                        organism = synthetic construct
SEQUENCE: 715
MHSKFSHAGR ICGAKFKVGE PIYRCKECSF DDTCVLCVNC FNPKDHLGHH VYTTICTWFN  60
NGECDCGDKT AWNHTLFCKA EEG                                          83

SEQ ID NO: 716          moltype = AA  length = 83
FEATURE                 Location/Qualifiers
source                  1..83
                        mol_type = protein
                        organism = synthetic construct
SEQUENCE: 716
MHSKFSHAGR ICGAKFKVGE PIYRCKECSF DDTCVLCVNC FNPKDHLGHH VYTTICTEKN  60
NGECDCGDKT AWNHTLFCKA EEG                                          83

SEQ ID NO: 717          moltype = AA  length = 83
FEATURE                 Location/Qualifiers
source                  1..83
                        mol_type = protein
                        organism = synthetic construct
SEQUENCE: 717
MHSKFSHAGR ICGAKFKVGE PIYRCKECSF DKTCVLCVNC FNPKDHIGHH VYTTICTEFN  60
NGECDCGDKT AWNHTLFCKA EEG                                          83

SEQ ID NO: 718          moltype = AA  length = 83
FEATURE                 Location/Qualifiers
source                  1..83
                        mol_type = protein
                        organism = synthetic construct
SEQUENCE: 718
MHSKFSHAGR ICGAKFKVGE PIYRCKECSF DVTCVLCVNC FNPKDHLGHH VYTTIRTCKN  60
NGECDCGDKT AWNHTLFCKA EEG                                          83

SEQ ID NO: 719          moltype = AA  length = 83
FEATURE                 Location/Qualifiers
source                  1..83
                        mol_type = protein
                        organism = synthetic construct
SEQUENCE: 719
MHSKFSHAGR ICGAKFKVGE RIYRCKECSF DDTCVLCVNC FNPKDHLGHH VYTTIRTEFN  60
NGECDCGDKT AWNHTLFCKA EEG                                          83

SEQ ID NO: 720          moltype = AA  length = 83
FEATURE                 Location/Qualifiers
source                  1..83
                        mol_type = protein
                        organism = synthetic construct
SEQUENCE: 720
MHSKFSHAGR ICGAKFKVGE RIYRCKECSF DDTCVLCVNC FNPKDHLGHH VYTTIRTEKN  60
NGECDCGDKT AWNHTLFCKA EEG                                          83

SEQ ID NO: 721          moltype = AA  length = 83
FEATURE                 Location/Qualifiers
source                  1..83
                        mol_type = protein
                        organism = synthetic construct
SEQUENCE: 721
MHSKFSHAGR ICGAKFKVGE PIYRCRECSF DDTCVLCVNC FNPKDHIGHH VYTTICTEFN  60
NGECDCGDKT AWNHTLFCKA EEG                                          83

SEQ ID NO: 722          moltype = AA  length = 83
FEATURE                 Location/Qualifiers
source                  1..83
```

```
                         mol_type = protein
                         organism = synthetic construct
SEQUENCE: 722
MHSKFSHAGR ICGAKFKVGE PIYRCRECSF DVTCVLCVNC FNPKDHLGHH VYTTICTEFN  60
NGECDCGDKT AWNHTLFCKA EEG                                          83

SEQ ID NO: 723           moltype = AA  length = 83
FEATURE                  Location/Qualifiers
source                   1..83
                         mol_type = protein
                         organism = synthetic construct
SEQUENCE: 723
MHSKFSHAGR ICGAKFKVGE PIYRCRECSF DVTCVLCVNC FNPKDHIGHH VYTTICTEFN  60
NGECDCGDKT AWNHTLFCKA EEG                                          83

SEQ ID NO: 724           moltype = AA  length = 83
FEATURE                  Location/Qualifiers
source                   1..83
                         mol_type = protein
                         organism = synthetic construct
SEQUENCE: 724
MHSKFSHAGR ICGAKFKVGE PIYRCRECSF DVTCVLCVNC FNPKDHIGHH VYTTICTEFN  60
NGECDCGDKT AWNHTLFCKA EEG                                          83

SEQ ID NO: 725           moltype = AA  length = 83
FEATURE                  Location/Qualifiers
source                   1..83
                         mol_type = protein
                         organism = synthetic construct
SEQUENCE: 725
MHSKFSHAGR ICGAKFKVGE PIYRCRECSF DRTCVLCVNC FNPKDHIGHH VYTTICTEFN  60
NGECDCGDKT AWNHTLFCKA EEG                                          83

SEQ ID NO: 726           moltype = AA  length = 83
FEATURE                  Location/Qualifiers
source                   1..83
                         mol_type = protein
                         organism = synthetic construct
SEQUENCE: 726
MHSKFSHAGR ICGAKFKVGE PIYRCRECSF DRTCVLCVNC FNPKDHLGHH VYTTICTQKN  60
NGECDCGDKT AWNHTLFCKA EEG                                          83

SEQ ID NO: 727           moltype = AA  length = 83
FEATURE                  Location/Qualifiers
source                   1..83
                         mol_type = protein
                         organism = synthetic construct
SEQUENCE: 727
MHSKFSHAGR ICGAKFKVGE PIYRCRECSF DHTCVLCVNC FNPKDHLGHH VYTTICTEFN  60
NGECDCGDKT AWNHTLFCKA EEG                                          83

SEQ ID NO: 728           moltype = AA  length = 83
FEATURE                  Location/Qualifiers
source                   1..83
                         mol_type = protein
                         organism = synthetic construct
SEQUENCE: 728
MHSKFSHAGR ICGAKFKVGE PIYRCRECSF DHTCVLCVNC FNPKDHIGHH VYTTICTEFN  60
NGECDCGDKT AWNHTLFCKA EEG                                          83

SEQ ID NO: 729           moltype = AA  length = 83
FEATURE                  Location/Qualifiers
source                   1..83
                         mol_type = protein
                         organism = synthetic construct
SEQUENCE: 729
MHSKFSHAGR ICGAKFKVGE PIYRCRECSF DQTCVLCVNC FNPKDHLGHH VYTTICTEKN  60
NGECDCGDKT AWNHTLFCKA EEG                                          83

SEQ ID NO: 730           moltype = AA  length = 83
FEATURE                  Location/Qualifiers
source                   1..83
                         mol_type = protein
                         organism = synthetic construct
SEQUENCE: 730
MHSKFSHAGR ICGAKFKVGE PIYRCRLCSF DVTCVLCVNC FNPKDHLGHH VYTTIRTEFN  60
NGECDCGDKT AWNHTLFCKA EEG                                          83

SEQ ID NO: 731           moltype = AA  length = 83
```

```
FEATURE                Location/Qualifiers
source                 1..83
                       mol_type = protein
                       organism = synthetic construct
SEQUENCE: 731
MHSKFSHAGR ICGAKFKVGE PIYRCRLCSF DVTCVLCVNC FNPKDHLGHH VYTTIRTEKN  60
NGECDCGDKT AWNHTLFCKA EEG                                          83

SEQ ID NO: 732         moltype = AA  length = 83
FEATURE                Location/Qualifiers
source                 1..83
                       mol_type = protein
                       organism = synthetic construct
SEQUENCE: 732
MHSKFSHAGR ICGAKFKVGE PIYRCRLCSF DQTCVLCVNC FNPKDHLGHH VYTTIRTSFN  60
NGECDCGDKT AWNHTLFCKA EEG                                          83

SEQ ID NO: 733         moltype = AA  length = 83
FEATURE                Location/Qualifiers
source                 1..83
                       mol_type = protein
                       organism = synthetic construct
SEQUENCE: 733
MHSKFSHAGR ICGAKFKVGE PIYRCKLCSF DVTCVLCVNC FNPKDHLGHH VYTTIRTSKN  60
NGECDCGDKT AWNHTLFCKA EEG                                          83

SEQ ID NO: 734         moltype = AA  length = 83
FEATURE                Location/Qualifiers
source                 1..83
                       mol_type = protein
                       organism = synthetic construct
SEQUENCE: 734
MHSKFSHAGR ICGAKFKVGE PIYRCKECSF DVTCVLCVNC FNPKDHLGHH VYTTIRTEFN  60
NGECDCGDKT AWNHTLFCKA EEG                                          83

SEQ ID NO: 735         moltype = AA  length = 83
FEATURE                Location/Qualifiers
source                 1..83
                       mol_type = protein
                       organism = synthetic construct
SEQUENCE: 735
MHSKFSHAGR ICGAKFKVGE PIYRCKECSF DDTCVLCVNC FNPKDHLGHH VYTTIRTEKN  60
NGECDCGDKT AWNHTLFCKA EEG                                          83

SEQ ID NO: 736         moltype = AA  length = 83
FEATURE                Location/Qualifiers
source                 1..83
                       mol_type = protein
                       organism = synthetic construct
SEQUENCE: 736
MHSKFSHAGR ICGAKFKVGE PIYRCKLCSF DDTCVLCVNC FNPKDHLGHH VYTTIRTEFN  60
NGECDCGDKT AWNHTLFCKA EEG                                          83

SEQ ID NO: 737         moltype = AA  length = 83
FEATURE                Location/Qualifiers
source                 1..83
                       mol_type = protein
                       organism = synthetic construct
SEQUENCE: 737
MHSKFSHAGR ICGAKFKVGE PIYRCRECSF DQTCVLCVNC FNPKDHLGHH VYTTICTEFN  60
NGECDCGDKT AWNHTLFCKA EEG                                          83

SEQ ID NO: 738         moltype = AA  length = 83
FEATURE                Location/Qualifiers
source                 1..83
                       mol_type = protein
                       organism = synthetic construct
SEQUENCE: 738
MHSKFSHAGR ICGAKFKVGE PIYRCKECSF DVTCVLCVNC FNPKDHLGHH VYTTIRTEKN  60
NGECDCGDKT AWNHTLFCKA EEG                                          83

SEQ ID NO: 739         moltype = AA  length = 83
FEATURE                Location/Qualifiers
source                 1..83
                       mol_type = protein
                       organism = synthetic construct
SEQUENCE: 739
MHSKFSHAGR ICGAKFKVGE PIYRCRLCSF DDTCVLCVNC FNPKDHLGHH VYTTIRTEFN  60
NGECDCGDKT AWNHTLFCKA EEG                                          83
```

```
SEQ ID NO: 740         moltype = AA  length = 83
FEATURE                Location/Qualifiers
source                 1..83
                       mol_type = protein
                       organism = synthetic construct
SEQUENCE: 740
MHSKFSHAGR ICGAKFKVGE PIYRCKLCSF DVTCVLCVNC FNPKDHLGHH VYTTIRTEFN  60
NGECDCGDKT AWNHTLFCKA EEG                                          83

SEQ ID NO: 741         moltype = AA  length = 83
FEATURE                Location/Qualifiers
source                 1..83
                       mol_type = protein
                       organism = synthetic construct
SEQUENCE: 741
MHSKFSHAGR ICGAKFKVGE PIYRCRECSF DHTCVLCVNC FNPKDHLGHH VYTTIRTDKN  60
NGECDCGDKT AWNHTLFCKA EEG                                          83

SEQ ID NO: 742         moltype = AA  length = 114
FEATURE                Location/Qualifiers
source                 1..114
                       mol_type = protein
                       organism = synthetic construct
SEQUENCE: 742
MGLENSLETL RFSISNLSMQ THAARMRTFM YWPSSVPVQP EQLASAGFYY LGRNDDVCCF  60
CCDGALRCWQ SGDDPWVEHA LWFPRCEFLI RMKGQEFVDE IQGRYPHLLE QLLS        114

SEQ ID NO: 743         moltype = AA  length = 114
FEATURE                Location/Qualifiers
source                 1..114
                       mol_type = protein
                       organism = synthetic construct
SEQUENCE: 743
MGLENSLETL RFSISNLSMQ THAARMRTFM YWPSSVPVQP EQLASAGFYY VGRNDIVRCF  60
CCDGALWCWE SGDDPWVEHA KWFPRCEFLI RMKGQEFVDE IQGRYPHLLE QLLS        114

SEQ ID NO: 744         moltype = AA  length = 114
FEATURE                Location/Qualifiers
source                 1..114
                       mol_type = protein
                       organism = synthetic construct
SEQUENCE: 744
MGLENSLETL RFSISNLSMQ THAARMRTFM YWPSSVPVQP EQLASAGFYY LGRNDEVRCF  60
CCDGGLHCWQ SGDDPWVEHA LWFPRCEFLI RMKGQEFVDE IQGRYPHLLE QLLS        114

SEQ ID NO: 745         moltype = AA  length = 114
FEATURE                Location/Qualifiers
source                 1..114
                       mol_type = protein
                       organism = synthetic construct
SEQUENCE: 745
MGLENSLETL RFSISNLSMQ THAARMRTFM YWPSSVPVQP EQLASAGFYY SGRNDEVRCF  60
CCDGVLHCWE SGDDPWVEHA KHFPRCEFLI RMKGQEFVDE IQGRYPHLLE QLLS        114

SEQ ID NO: 746         moltype = AA  length = 114
FEATURE                Location/Qualifiers
source                 1..114
                       mol_type = protein
                       organism = synthetic construct
SEQUENCE: 746
MGLENSLETL RFSISNLSMQ THAARMRTFM YWPSSVPVQP EQLASAGFYY SGRNDLVACF  60
CCDGGLTCWE SGDDPWVEHA KHFPRCEFLI RMKGQEFVDE IQGRYPHLLE QLLS        114

SEQ ID NO: 747         moltype = AA  length = 114
FEATURE                Location/Qualifiers
source                 1..114
                       mol_type = protein
                       organism = synthetic construct
SEQUENCE: 747
MGLENSLETL RFSISNLSMQ THAARMRTFM YWPSSVPVQP EQLASAGFYY LGRNDIVRCF  60
CCDGVLGCWE SGDDPWVEHA RHFPRCEFLI RMKGQEFVDE IQGRYPHLLE QLLS        114

SEQ ID NO: 748         moltype = AA  length = 114
FEATURE                Location/Qualifiers
source                 1..114
                       mol_type = protein
                       organism = synthetic construct
SEQUENCE: 748
```

```
MGLENSLETL RFSISNLSMQ THAARMRTFM YWPSSVPVQP EQLASAGFYY LGRNDEVRCF  60
CCDGGLHCWQ SGDDPWVEHA RWFPRCEFLI RMKGQEFVDE IQGRYPHLLE QLLS        114

SEQ ID NO: 749         moltype = AA  length = 114
FEATURE                Location/Qualifiers
source                 1..114
                       mol_type = protein
                       organism = synthetic construct
SEQUENCE: 749
MGLENSLETL RFSISNLSMQ THAARMRTFM YWPSSVPVQP EQLASAGFYY VGRNDIVRCF  60
CCDGALHCWK SGDDPWVEHA RHFPRCEFLI RMKGQEFVDE IQGRYPHLLE QLLS        114

SEQ ID NO: 750         moltype = AA  length = 114
FEATURE                Location/Qualifiers
source                 1..114
                       mol_type = protein
                       organism = synthetic construct
SEQUENCE: 750
MGLENSLETL RFSISNLSMQ THAARMRTKM YWESSVPVQW EQLASYGFQF VGRNDDVKCQ  60
CCDGGLRCWE SGDDVAVEHS KRFIRCEFLI RMKGQEFVDE IQGRYPHLLE QLLS        114

SEQ ID NO: 751         moltype = AA  length = 114
FEATURE                Location/Qualifiers
source                 1..114
                       mol_type = protein
                       organism = synthetic construct
SEQUENCE: 751
MGLENSLETL RFSISNLSMQ THAARMRTFM YWPSSVPVQP EQLASAGFYY LGRNDLVKCF  60
CCDGVLHCWQ SGDDPWVEHA RHFPRCEFLI RMKGQEFVDE IQGRYPHLLE QLLS        114

SEQ ID NO: 752         moltype = AA  length = 114
FEATURE                Location/Qualifiers
source                 1..114
                       mol_type = protein
                       organism = synthetic construct
SEQUENCE: 752
MGLENSLETL RFSISNLSMQ THAARMRTFM YWPSSVPVQP EQLASAGFYY LGRNDIVKCF  60
CCDGVLHCWQ SGDDPWVEHA KHFPRCEFLI RMKGQEFVDE IQGRYPHLLE QLLS        114

SEQ ID NO: 753         moltype = AA  length = 114
FEATURE                Location/Qualifiers
source                 1..114
                       mol_type = protein
                       organism = synthetic construct
SEQUENCE: 753
MGLENSLETL RFSISNLSMQ THAARMRTFM YWPSSVPVQP EQLASAGFYY LGRNDEVRCF  60
CCDGVLHCWE SGDDPWVEHA RWFPRCEFLI RMNGQEFVDE IQGRYPHLLE QLLS        114

SEQ ID NO: 754         moltype = AA  length = 114
FEATURE                Location/Qualifiers
source                 1..114
                       mol_type = protein
                       organism = synthetic construct
SEQUENCE: 754
MGLENSLETL RFSISNLSMQ THAARMRTFM YWPSSVPVQP EQLASAGFYY SGRNDIVRCF  60
CCDGDLHCWE SGDDPWVEHA KWFPRCEFLI RMKGQEFVDE IQGRYPHLLE QLLS        114

SEQ ID NO: 755         moltype = AA  length = 114
FEATURE                Location/Qualifiers
source                 1..114
                       mol_type = protein
                       organism = synthetic construct
SEQUENCE: 755
MGLENSLETL RFSISNLSMQ THAARMRTFM YWPSSVPVQP EQLASAGFYY AGRNDEVKCF  60
CCDGGLHCWE SGDDPWVEHA RHFPRCEFLI RMNGQEFVDE IQGRYPHLLE QLLS        114

SEQ ID NO: 756         moltype = AA  length = 114
FEATURE                Location/Qualifiers
source                 1..114
                       mol_type = protein
                       organism = synthetic construct
SEQUENCE: 756
MGLENSLETL RFSISNLSMQ THAARMRTFM YWPSSVPVQP EQLASAGFYY LGRNDIVKCF  60
CCDGVLHCWQ SGDDPWVEHA RHFPRCEFLI RMKGQEFVDE IQGRYPHLLE QLLS        114

SEQ ID NO: 757         moltype = AA  length = 114
FEATURE                Location/Qualifiers
source                 1..114
                       mol_type = protein
```

```
                         organism = synthetic construct
SEQUENCE: 757
MGLENSLETL RFSISNLSMQ THAARMRTFM YWPSSVPVQP EQLASAGFYY LGRNDLVKCF  60
CCDGVLHCWQ SGDDPWVEHA KHFPRCEFLI RMKGQEFVDE IQGRYPHLLE QLLS        114

SEQ ID NO: 758           moltype = AA  length = 114
FEATURE                  Location/Qualifiers
source                   1..114
                         mol_type = protein
                         organism = synthetic construct
SEQUENCE: 758
MGLENSLETL RFSISNLSMQ THAARMRTFM YWPSSVPVQP EQLASAGFYY LGRNDLVKCF  60
CCDGVLHCWQ SGDDPWVEHA KWFPRCEFLI RMKGQEFVDE IQGRYPHLLE QLLS        114

SEQ ID NO: 759           moltype = AA  length = 114
FEATURE                  Location/Qualifiers
source                   1..114
                         mol_type = protein
                         organism = synthetic construct
SEQUENCE: 759
MGLENSLETL RFSISNLSMQ THAARMRTFM YWPSSVPVQP EQLASAGFYY LGRNDLVKCF  60
CCDGVLHCWE SGDDPWVEHA RHFPRCEFLI RMKGQEFVDE IQGRYPHLLE QLLS        114

SEQ ID NO: 760           moltype = AA  length = 114
FEATURE                  Location/Qualifiers
source                   1..114
                         mol_type = protein
                         organism = synthetic construct
SEQUENCE: 760
MGLENSLETL RFSISNLSMQ THAARMRTFM YWPSSVPVQP EQLASAGFYY LGRNDIVKCF  60
CCDGVLHCWQ SGDDPWVEHA KWFPRCEFLI RMKGQEFVDE IQGRYPHLLE QLLS        114

SEQ ID NO: 761           moltype = AA  length = 114
FEATURE                  Location/Qualifiers
source                   1..114
                         mol_type = protein
                         organism = synthetic construct
SEQUENCE: 761
MGLENSLETL RFSISNLSMQ THAARMRTFM YWPSSVPVQP EQLASAGFYY LGRNDLVKCF  60
CCDGALHCWQ SGDDPWVEHA RHFPRCEFLI RMKGQEFVDE IQGRYPHLLE QLLS        114

SEQ ID NO: 762           moltype = AA  length = 114
FEATURE                  Location/Qualifiers
source                   1..114
                         mol_type = protein
                         organism = synthetic construct
SEQUENCE: 762
MGLENSLETL RFSISNLSMQ THAARMRTFM YWPSSVPVQP EQLASAGFYY LGRNDLVKCF  60
CCDGVLHCWQ SGDDPWVEHA RHFPRCEFLI RMKGQEFVDE VQGRYPHLLE QLLS        114

SEQ ID NO: 763           moltype = AA  length = 114
FEATURE                  Location/Qualifiers
source                   1..114
                         mol_type = protein
                         organism = synthetic construct
SEQUENCE: 763
MGLENSLETL RFSISNLSMQ THAARMRTFM YWPSSVPVQP EQLASAGFYY LGRNDLVKCF  60
CCDGVLHCWQ SGDDPWVEHA RHFPRCEFLI RMKGQEFVDE IQGRYPHLLE QLPS        114

SEQ ID NO: 764           moltype = AA  length = 114
FEATURE                  Location/Qualifiers
source                   1..114
                         mol_type = protein
                         organism = synthetic construct
SEQUENCE: 764
MGLENSLETL RFSISNLSMQ THAARMRTFM YWPSSVPVQP EQLASAGFYY LGRNDLVKCF  60
CCDGVLRCWE SGDDPWVEHA KHFPRCEFLI RMKGQEFVDE IQGRYPHLLE QLLS        114

SEQ ID NO: 765           moltype = AA  length = 114
FEATURE                  Location/Qualifiers
source                   1..114
                         mol_type = protein
                         organism = synthetic construct
SEQUENCE: 765
MGLENSLETL RFSISNLSMQ THAARMRTFM YWPSSVPVQP EQLASAGFYY LGRNDLVKCF  60
CCDGVLHCWQ SGDDPWVEHA TWFPRCEFLI RMKGQEFVDE IQGRYPHLLE QLLS        114

SEQ ID NO: 766           moltype = AA  length = 114
FEATURE                  Location/Qualifiers
```

```
source                  1..114
                        mol_type = protein
                        organism = synthetic construct
SEQUENCE: 766
MGLENSLETL RFSISNLSMQ THAARMRTFM YWPSSVPVQP EQLASAGFYY GGRNDLVKCF  60
CCDGVLHCWQ SGDDPWVEHA RHFPRCEFLI RMKGQEFVDE IQGRYPHLLE QLLS        114

SEQ ID NO: 767          moltype = AA  length = 114
FEATURE                 Location/Qualifiers
source                  1..114
                        mol_type = protein
                        organism = synthetic construct
SEQUENCE: 767
MGLENSLETL RFSISNLSMQ THAARMRTFM YWPSSVPVQP EQLASAGFYY LGRNDLVKCF  60
CCDGVLHCWQ GGDDPWVEHA RHFPRCEFLI RMKGQEFVDE IQGRYPHLLE QLLS        114

SEQ ID NO: 768          moltype = AA  length = 119
FEATURE                 Location/Qualifiers
source                  1..119
                        mol_type = protein
                        organism = synthetic construct
SEQUENCE: 768
MPTAASATES AIEDTPAPAR PEVDGRTKPK RQPRYHVVLW DDDDHTYAYV VVMLVSLFGH  60
PPSRGYRMAK EMDVQGRVIV LTTTRAHAEL KRDQIHAFGR DRLLARSKGS MKASIEAEE   119

SEQ ID NO: 769          moltype = AA  length = 119
FEATURE                 Location/Qualifiers
source                  1..119
                        mol_type = protein
                        organism = synthetic construct
SEQUENCE: 769
MPTAASATES AIEDTPAPAR PEVDGRTKPK RQPRYHVVLW DDDDHTYAYV VVMLRSLFGH  60
PPSRGYRMAK EMDVQGRVIV LTTTRAHAEL KRDQIHAFGR DRLLARSKGS MKASIEAEE   119

SEQ ID NO: 770          moltype = AA  length = 119
FEATURE                 Location/Qualifiers
source                  1..119
                        mol_type = protein
                        organism = synthetic construct
SEQUENCE: 770
MPTAASATES AIEDTPAPAR PEVDGRTKPK RQPRYHVVLW DDDDHTYQYV VTMLRSLFGH  60
PPSRGYRMAK EMDTQGRVIV LTTTREHAEL KRDQIHAFGR DRLLARSKGS MKASIEAEE   119

SEQ ID NO: 771          moltype = AA  length = 119
FEATURE                 Location/Qualifiers
source                  1..119
                        mol_type = protein
                        organism = synthetic construct
SEQUENCE: 771
MPTAASATES AIEDTPAPAR PEVDGRTKPK RQPRYHVVLW DDDDHTYQYV VVMLRSLFGH  60
PPGRGYRMAK EMDTQGRVIV LTTTREHAEL KRDQIHAFGR DRLLARSKGS MKASIEAEE   119

SEQ ID NO: 772          moltype = AA  length = 119
FEATURE                 Location/Qualifiers
source                  1..119
                        mol_type = protein
                        organism = synthetic construct
SEQUENCE: 772
MPTAASATES AIEDTPAPAR PEVDGRTKPK RQPRYHVVLW DDDDHTYQYV VVMLRSLFGH  60
PPSRGYRIAK EMDTQGRVIV LTTTREHAEL KRDQIHAFGR DRLLARSKGS MKASIEAEE   119

SEQ ID NO: 773          moltype = AA  length = 119
FEATURE                 Location/Qualifiers
source                  1..119
                        mol_type = protein
                        organism = synthetic construct
SEQUENCE: 773
MPTAASATES AIEDTPAPAR PEVDGRTKPK RQPRYHVVLW DDDDHTYQYV VVMLRSLFGH  60
PPSRGYRMAK EVDTQGRVIV LTTTREHAEL KRDQIHAFGR DRLLARSKGS MKASIEAEE   119

SEQ ID NO: 774          moltype = AA  length = 119
FEATURE                 Location/Qualifiers
source                  1..119
                        mol_type = protein
                        organism = synthetic construct
SEQUENCE: 774
MPTAASATES AIEDTPAPAR PEVDGRTKPK RQPRYHVVLW DDDDHTYQYV VVMLRSLFGH  60
PPSRGYRMAK EMDTQGRVIV LTTTREHAEF KRDQIHAFGR DRLLARSKGS MKASIEAEE   119
```

```
SEQ ID NO: 775          moltype = AA  length = 119
FEATURE                 Location/Qualifiers
source                  1..119
                        mol_type = protein
                        organism = synthetic construct
SEQUENCE: 775
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQINAFGR DRLLARSKGS MKASIEAEE   119

SEQ ID NO: 776          moltype = AA  length = 119
FEATURE                 Location/Qualifiers
source                  1..119
                        mol_type = protein
                        organism = synthetic construct
SEQUENCE: 776
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DSLLARSKGS MKASIEAEE   119

SEQ ID NO: 777          moltype = AA  length = 119
FEATURE                 Location/Qualifiers
source                  1..119
                        mol_type = protein
                        organism = synthetic construct
SEQUENCE: 777
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DGLLARSKGS MKASIEAEE   119

SEQ ID NO: 778          moltype = AA  length = 119
FEATURE                 Location/Qualifiers
source                  1..119
                        mol_type = protein
                        organism = synthetic construct
SEQUENCE: 778
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGR DRLLARSKGS MTASIEAEE   119

SEQ ID NO: 779          moltype = AA  length = 119
FEATURE                 Location/Qualifiers
source                  1..119
                        mol_type = protein
                        organism = synthetic construct
SEQUENCE: 779
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAWGR DSLLARSKGS MKASIEAEE   119

SEQ ID NO: 780          moltype = AA  length = 119
FEATURE                 Location/Qualifiers
source                  1..119
                        mol_type = protein
                        organism = synthetic construct
SEQUENCE: 780
MPTAASATES AIEDTPAPAR SEVDGYTVPK RQPRYHVVLW DDDDHTYQYV VGMLRSVFGH  60
PPSRGYRMAK EMDTQGRVIV LTTTREHAEL KRDQIHAFGR DRLLARSKGS MKASIEAEE   119

SEQ ID NO: 781          moltype = AA  length = 119
FEATURE                 Location/Qualifiers
source                  1..119
                        mol_type = protein
                        organism = synthetic construct
SEQUENCE: 781
MPTAASATES AIEDTPAPVR PEVDGYTVPK RQPRYHVVLW DDDDHTYQYV VTMLRSLFGH  60
PPGRGYRMAK EMDTQGRVIV LTTTREHAEL KRDQIHAFGR DRLLARSKGS MKASIEAEE   119

SEQ ID NO: 782          moltype = AA  length = 119
FEATURE                 Location/Qualifiers
source                  1..119
                        mol_type = protein
                        organism = synthetic construct
SEQUENCE: 782
MPTAASATES AMEDTPAPAR PEVDGRTKPK RQPRYHVVLW NDDDHTYQYV VVMLQSLFGH  60
PPKRGYRMAK EMDTQGRVIV LTTTREHAEL KRDQIHAFGR DRLLARCKGS MKASIEAEE   119

SEQ ID NO: 783          moltype = AA  length = 119
FEATURE                 Location/Qualifiers
source                  1..119
                        mol_type = protein
                        organism = synthetic construct
SEQUENCE: 783
MPTAASATES AIEDTPAPAR PEVDGRTKPK RQPRYHVVLW DDDDHTYQYV VVMLQSLFGH  60
```

-continued

```
PPNRGYRMAK EMDTQGRVIV LTTTREHAEL KRDQIHAFGC DRLLARCKGS MKASIEAEE   119

SEQ ID NO: 784          moltype = AA  length = 119
FEATURE                 Location/Qualifiers
source                  1..119
                        mol_type = protein
                        organism = synthetic construct
SEQUENCE: 784
MPTAASATES AIEDPPAPAR PEVDGRTKPK RQPRYHVVMW EDDDHTYQYV VVMLRSLFGH  60
PPNRGYRMAK EMDTQGRVIV LTTTREHAEL KRDQIHAFGC DRLLARSKGS MKASIEAEE   119

SEQ ID NO: 785          moltype = AA  length = 119
FEATURE                 Location/Qualifiers
source                  1..119
                        mol_type = protein
                        organism = synthetic construct
SEQUENCE: 785
MPTAASATES AIEDTPAPAR PEVDGRTKPK RQPRYHVVLW DDDDHTYQYV VVMLRSLFGH  60
PPSRGYRMAK ELDTQGRVIV LTTTREHAEL KRDQIRAYGR DGLLARSKGS MKASIEAEE   119

SEQ ID NO: 786          moltype = AA  length = 119
FEATURE                 Location/Qualifiers
source                  1..119
                        mol_type = protein
                        organism = synthetic construct
SEQUENCE: 786
MPTAASATES AIEDTPAPAR SEVDGRTEPK RQPRYHVVLW DDDDHTYQYV VAMLRSLFGH  60
PPSRGYRMAK EMDTQGRVIV LTTTREHAEL KRDQIHAFGR DSLLARSKGS MKASIEAEE   119

SEQ ID NO: 787          moltype = AA  length = 119
FEATURE                 Location/Qualifiers
source                  1..119
                        mol_type = protein
                        organism = synthetic construct
SEQUENCE: 787
MPTAASATES AIEDTPAPAR PEVDGRTKPK RQPRYHVVLW DDDDHTYQYV VVMLRSLFGH  60
SASRGYRMAK EMDTQGRVIV LTTTREHAEL KRDQIHAFGR DRLLARSKGS MKASIEAEE   119

SEQ ID NO: 788          moltype = AA  length = 119
FEATURE                 Location/Qualifiers
source                  1..119
                        mol_type = protein
                        organism = synthetic construct
SEQUENCE: 788
MPTAASATES AIEDTPAPAR SEVDGYTVPK RQPRYHVVLW DDDDHTYQYV VVMLRSLFGH  60
PPSRGYRMAK EMDTQGRVIV LTTTREHAEL KRDQIHAFGR DRLLARSKGS MKASIEAEE   119

SEQ ID NO: 789          moltype = AA  length = 119
FEATURE                 Location/Qualifiers
source                  1..119
                        mol_type = protein
                        organism = synthetic construct
SEQUENCE: 789
MPTAASATES AIEDTPAPAR PEVDGRTKPK RQPRYHVVLW DDDDHTYQYV VHMLRSIFGH  60
PPSRGYRMAK EMDTQGRVIV LTTTREYAEL KRDQIHAFGR DRLLARSKGS MKASIEAEE   119

SEQ ID NO: 790          moltype = AA  length = 119
FEATURE                 Location/Qualifiers
source                  1..119
                        mol_type = protein
                        organism = synthetic construct
SEQUENCE: 790
MPTAASATES AIEDTPAPAR PEVDGRTKPK RQPRYHVVLW DDDDHTYQYV VVMLRSLFGH  60
PPERGYRMAK EMDTQGRVIV LTTTREHAEL KRDQIHAFGR DRLLARSKGS MKASIEAEE   119

SEQ ID NO: 791          moltype = AA  length = 119
FEATURE                 Location/Qualifiers
source                  1..119
                        mol_type = protein
                        organism = synthetic construct
SEQUENCE: 791
MPTAASATES AIEDTPAPAR PEVDGRTKPK RQPRYHVVLW DDDDHTYQYV VVMLRSLFGH  60
PPSRGYRMAK EMDTQGRVIV LTTTREHAEL KRDQIHAFGY DRLLARSKGS MKASIEAEE   119

SEQ ID NO: 792          moltype = AA  length = 13
FEATURE                 Location/Qualifiers
source                  1..13
                        mol_type = protein
                        organism = synthetic construct
```

```
SEQUENCE: 792
FAAWAAYAAA DDD                                                    13

SEQ ID NO: 793          moltype = AA  length = 15
FEATURE                 Location/Qualifiers
source                  1..15
                        mol_type = protein
                        organism = synthetic construct
SEQUENCE: 793
LAQFASIAAY ASDDD                                                  15

SEQ ID NO: 794          moltype = AA  length = 9
FEATURE                 Location/Qualifiers
source                  1..9
                        mol_type = protein
                        organism = synthetic construct
SEQUENCE: 794
DQQRLIFAG                                                         9

SEQ ID NO: 795          moltype = AA  length = 22
FEATURE                 Location/Qualifiers
source                  1..22
                        mol_type = protein
                        organism = synthetic construct
SEQUENCE: 795
DQQIASSRLA ASFAAQQYPD DD                                          22

SEQ ID NO: 796          moltype = AA  length = 13
FEATURE                 Location/Qualifiers
source                  1..13
                        mol_type = protein
                        organism = synthetic construct
SEQUENCE: 796
RLAFSALGAA DDD                                                    13

SEQ ID NO: 797          moltype = AA  length = 7
FEATURE                 Location/Qualifiers
source                  1..7
                        mol_type = protein
                        organism = synthetic construct
SEQUENCE: 797
EFIAWLV                                                           7

SEQ ID NO: 798          moltype = AA  length = 10
FEATURE                 Location/Qualifiers
source                  1..10
                        mol_type = protein
                        organism = synthetic construct
SEQUENCE: 798
RLAFAYPDDD                                                        10

SEQ ID NO: 799          moltype = AA  length = 10
FEATURE                 Location/Qualifiers
source                  1..10
                        mol_type = protein
                        organism = synthetic construct
SEQUENCE: 799
RLIFAYPDDD                                                        10

SEQ ID NO: 800          moltype = AA  length = 10
FEATURE                 Location/Qualifiers
source                  1..10
                        mol_type = protein
                        organism = synthetic construct
SEQUENCE: 800
RLVFAYPDDD                                                        10

SEQ ID NO: 801          moltype = AA  length = 10
FEATURE                 Location/Qualifiers
source                  1..10
                        mol_type = protein
                        organism = synthetic construct
SEQUENCE: 801
RLMFAYPDDD                                                        10

SEQ ID NO: 802          moltype = AA  length = 10
FEATURE                 Location/Qualifiers
source                  1..10
                        mol_type = protein
```

```
                        organism = synthetic construct
SEQUENCE: 802
DQQRLIFAGK                                                      10

SEQ ID NO: 803          moltype = AA  length = 8
FEATURE                 Location/Qualifiers
source                  1..8
                        mol_type = protein
                        organism = synthetic construct
SEQUENCE: 803
EFIAWLVK                                                        8

SEQ ID NO: 804          moltype = AA  length = 13
FEATURE                 Location/Qualifiers
source                  1..13
                        mol_type = protein
                        organism = synthetic construct
SEQUENCE: 804
IVNFSRLIFH HLK                                                  13

SEQ ID NO: 805          moltype = AA  length = 10
FEATURE                 Location/Qualifiers
source                  1..10
                        mol_type = protein
                        organism = synthetic construct
SEQUENCE: 805
DIRLIFSNAK                                                      10

SEQ ID NO: 806          moltype = AA  length = 16
FEATURE                 Location/Qualifiers
source                  1..16
                        mol_type = protein
                        organism = synthetic construct
SEQUENCE: 806
GQSRLIFTYG LTNSGK                                               16

SEQ ID NO: 807          moltype = AA  length = 11
FEATURE                 Location/Qualifiers
source                  1..11
                        mol_type = protein
                        organism = synthetic construct
SEQUENCE: 807
DQQRLLIFAG K                                                    11

SEQ ID NO: 808          moltype = AA  length = 11
FEATURE                 Location/Qualifiers
source                  1..11
                        mol_type = protein
                        organism = synthetic construct
SEQUENCE: 808
DEHCLRLIFL K                                                    11

SEQ ID NO: 809          moltype = AA  length = 13
FEATURE                 Location/Qualifiers
source                  1..13
                        mol_type = protein
                        organism = synthetic construct
SITE                    5
                        note = FITC label
SEQUENCE: 809
FAKLKDEESI LKQ                                                  13

SEQ ID NO: 810          moltype = AA  length = 13
FEATURE                 Location/Qualifiers
source                  1..13
                        mol_type = protein
                        organism = synthetic construct
SITE                    5
                        note = FITC Label
SEQUENCE: 810
YAKLKDEESI LKQ                                                  13

SEQ ID NO: 811          moltype = AA  length = 13
FEATURE                 Location/Qualifiers
source                  1..13
                        mol_type = protein
                        organism = synthetic construct
SITE                    5
                        note = FITC Label
```

```
SEQUENCE: 811
WAKLKDEESI LKQ                                                13

SEQ ID NO: 812         moltype = AA  length = 5
FEATURE                Location/Qualifiers
source                 1..5
                       mol_type = protein
                       organism = synthetic construct
SEQUENCE: 812
RLIFY                                                         5

SEQ ID NO: 813         moltype = AA  length = 14
FEATURE                Location/Qualifiers
source                 1..14
                       mol_type = protein
                       organism = synthetic construct
SEQUENCE: 813
FAAWAAYAAA ADDD                                               14

SEQ ID NO: 814         moltype = AA  length = 4
FEATURE                Location/Qualifiers
source                 1..4
                       mol_type = protein
                       organism = synthetic construct
SEQUENCE: 814
YREL                                                          4

SEQ ID NO: 815         moltype = AA  length = 4
FEATURE                Location/Qualifiers
source                 1..4
                       mol_type = protein
                       organism = synthetic construct
MOD_RES                2
                       note = asymmetric dimethylarginine
SEQUENCE: 815
YREL                                                          4

SEQ ID NO: 816         moltype = AA  length = 4
FEATURE                Location/Qualifiers
source                 1..4
                       mol_type = protein
                       organism = synthetic construct
MOD_RES                2
                       note = symmetric dimethylarginine
SEQUENCE: 816
YREL                                                          4

SEQ ID NO: 817         moltype = AA  length = 12
FEATURE                Location/Qualifiers
source                 1..12
                       mol_type = protein
                       organism = synthetic construct
SEQUENCE: 817
LRLAFAYPDD DK                                                 12

SEQ ID NO: 818         moltype = AA  length = 12
FEATURE                Location/Qualifiers
source                 1..12
                       mol_type = protein
                       organism = synthetic construct
MOD_RES                2
                       note = citrullinated arginine
SEQUENCE: 818
LRLAFAYPDD DK                                                 12

SEQ ID NO: 819         moltype = AA  length = 5
FEATURE                Location/Qualifiers
source                 1..5
                       mol_type = protein
                       organism = synthetic construct
SEQUENCE: 819
LRLAF                                                         5

SEQ ID NO: 820         moltype = AA  length = 5
FEATURE                Location/Qualifiers
source                 1..5
                       mol_type = protein
                       organism = synthetic construct
MOD_RES                2
```

```
                        note = citrullinated arginine
SEQUENCE: 820
LRLAF                                                                       5

SEQ ID NO: 821          moltype = AA  length = 11
FEATURE                 Location/Qualifiers
source                  1..11
                        mol_type = protein
                        organism = synthetic construct
SEQUENCE: 821
RLTFIAYPDD D                                                                11

SEQ ID NO: 822          moltype = AA  length = 11
FEATURE                 Location/Qualifiers
source                  1..11
                        mol_type = protein
                        organism = synthetic construct
MOD_RES                 3
                        note = phosphothreonine
SEQUENCE: 822
RLTFIAYPDD D                                                                11

SEQ ID NO: 823          moltype = AA  length = 11
FEATURE                 Location/Qualifiers
source                  1..11
                        mol_type = protein
                        organism = synthetic construct
SEQUENCE: 823
RLYFIAYPDD D                                                                11

SEQ ID NO: 824          moltype = AA  length = 11
FEATURE                 Location/Qualifiers
source                  1..11
                        mol_type = protein
                        organism = synthetic construct
MOD_RES                 3
                        note = phosphotyrosine
SEQUENCE: 824
RLYFIAYPDD D                                                                11

SEQ ID NO: 825          moltype = AA  length = 11
FEATURE                 Location/Qualifiers
source                  1..11
                        mol_type = protein
                        organism = synthetic construct
SEQUENCE: 825
RLYFKAYPDD D                                                                11

SEQ ID NO: 826          moltype = AA  length = 11
FEATURE                 Location/Qualifiers
source                  1..11
                        mol_type = protein
                        organism = synthetic construct
MOD_RES                 3
                        note = acetylated lysine
SEQUENCE: 826
RLKFIAYPDD D                                                                11

SEQ ID NO: 827          moltype = AA  length = 6
FEATURE                 Location/Qualifiers
source                  1..6
                        mol_type = protein
                        organism = synthetic construct
SEQUENCE: 827
LVFFAE                                                                      6

SEQ ID NO: 828          moltype = AA  length = 6
FEATURE                 Location/Qualifiers
source                  1..6
                        mol_type = protein
                        organism = synthetic construct
SEQUENCE: 828
LVFFAK                                                                      6

SEQ ID NO: 829          moltype = AA  length = 6
FEATURE                 Location/Qualifiers
source                  1..6
                        mol_type = protein
                        organism = synthetic construct
```

```
SEQUENCE: 829
LVFFGK                                                                 6

SEQ ID NO: 830          moltype = AA  length = 6
FEATURE                 Location/Qualifiers
source                  1..6
                        mol_type = protein
                        organism = synthetic construct
SEQUENCE: 830
LVFFAG                                                                 6

SEQ ID NO: 831          moltype = AA  length = 6
FEATURE                 Location/Qualifiers
source                  1..6
                        mol_type = protein
                        organism = synthetic construct
SEQUENCE: 831
LVPFAE                                                                 6

SEQ ID NO: 832          moltype = AA  length = 9
FEATURE                 Location/Qualifiers
source                  1..9
                        mol_type = protein
                        organism = synthetic construct
SEQUENCE: 832
FAAWAAYAA                                                              9

SEQ ID NO: 833          moltype = AA  length = 13
FEATURE                 Location/Qualifiers
source                  1..13
                        mol_type = protein
                        organism = synthetic construct
SEQUENCE: 833
XAKLDEESIL KQK                                                         13

SEQ ID NO: 834          moltype = AA  length = 8
FEATURE                 Location/Qualifiers
source                  1..8
                        mol_type = protein
                        organism = synthetic construct
SEQUENCE: 834
YRELRLLK                                                               8

SEQ ID NO: 835          moltype = AA  length = 8
FEATURE                 Location/Qualifiers
source                  1..8
                        mol_type = protein
                        organism = synthetic construct
MOD_RES                 2
                        note = asymmetric dimethylarginine
SEQUENCE: 835
YRELRLLK                                                               8

SEQ ID NO: 836          moltype = AA  length = 8
FEATURE                 Location/Qualifiers
source                  1..8
                        mol_type = protein
                        organism = synthetic construct
MOD_RES                 2
                        note = symmetric dimethylarginine
SEQUENCE: 836
YRELRLLK                                                               8

SEQ ID NO: 837          moltype =   length =
SEQUENCE: 837
000

SEQ ID NO: 838          moltype =   length =
SEQUENCE: 838
000

SEQ ID NO: 839          moltype = AA  length = 12
FEATURE                 Location/Qualifiers
source                  1..12
                        mol_type = protein
                        organism = synthetic construct
MOD_RES                 2
                        note = citrullinated arginine
SEQUENCE: 839
```

```
LRLAFAYPDD DK                                                    12

SEQ ID NO: 840          moltype = AA  length = 10
FEATURE                 Location/Qualifiers
source                  1..10
                        mol_type = protein
                        organism = synthetic construct
MOD_RES                 3
                        note = phosphotyrosine
SEQUENCE: 840
RLYFIAYPDD                                                       10

SEQ ID NO: 841          moltype = AA  length = 9
FEATURE                 Location/Qualifiers
source                  1..9
                        mol_type = protein
                        organism = synthetic construct
SEQUENCE: 841
VRFLEQQNK                                                        9

SEQ ID NO: 842          moltype = AA  length = 9
FEATURE                 Location/Qualifiers
source                  1..9
                        mol_type = protein
                        organism = synthetic construct
MOD_RES                 2
                        note = citrullinated arginine
SEQUENCE: 842
VRFLEQQNK                                                        9

SEQ ID NO: 843          moltype = AA  length = 4
FEATURE                 Location/Qualifiers
source                  1..4
                        mol_type = protein
                        organism = synthetic construct
SEQUENCE: 843
KLVF                                                             4

SEQ ID NO: 844          moltype = AA  length = 4
FEATURE                 Location/Qualifiers
source                  1..4
                        mol_type = protein
                        organism = synthetic construct
SEQUENCE: 844
LVFF                                                             4

SEQ ID NO: 845          moltype = AA  length = 12
FEATURE                 Location/Qualifiers
source                  1..12
                        mol_type = protein
                        organism = synthetic construct
SEQUENCE: 845
FRLAFAYPDD DK                                                    12

SEQ ID NO: 846          moltype = AA  length = 12
FEATURE                 Location/Qualifiers
source                  1..12
                        mol_type = protein
                        organism = synthetic construct
MOD_RES                 2
                        note = citrullinated arginine
SEQUENCE: 846
FRLAFAYPDD DK                                                    12

SEQ ID NO: 847          moltype = AA  length = 12
FEATURE                 Location/Qualifiers
source                  1..12
                        mol_type = protein
                        organism = synthetic construct
SEQUENCE: 847
YRIAFAYPDD DK                                                    12

SEQ ID NO: 848          moltype = AA  length = 12
FEATURE                 Location/Qualifiers
source                  1..12
                        mol_type = protein
                        organism = synthetic construct
MOD_RES                 2
                        note = citrullinated arginine
```

```
SEQUENCE: 848
YRIAFAYPDD DK                                                    12

SEQ ID NO: 849          moltype = AA  length = 12
FEATURE                 Location/Qualifiers
source                  1..12
                        mol_type = protein
                        organism = synthetic construct
SEQUENCE: 849
IRLAFAYPDD DK                                                    12

SEQ ID NO: 850          moltype = AA  length = 12
FEATURE                 Location/Qualifiers
source                  1..12
                        mol_type = protein
                        organism = synthetic construct
MOD_RES                 2
                        note = citrullinated arginine
SEQUENCE: 850
IRLAFAYPDD DK                                                    12

SEQ ID NO: 851          moltype = AA  length = 8
FEATURE                 Location/Qualifiers
source                  1..8
                        mol_type = protein
                        organism = synthetic construct
SEQUENCE: 851
EFLNRFYK                                                         8

SEQ ID NO: 852          moltype = AA  length = 16
FEATURE                 Location/Qualifiers
source                  1..16
                        mol_type = protein
                        organism = synthetic construct
SEQUENCE: 852
SLIDRGVNFS LDTIEK                                                16

SEQ ID NO: 853          moltype = AA  length = 10
FEATURE                 Location/Qualifiers
source                  1..10
                        mol_type = protein
                        organism = synthetic construct
SEQUENCE: 853
ELISFCLDTK                                                       10

SEQ ID NO: 854          moltype = AA  length = 12
FEATURE                 Location/Qualifiers
source                  1..12
                        mol_type = protein
                        organism = synthetic construct
SEQUENCE: 854
ENRLCYYLGA TK                                                    12

SEQ ID NO: 855          moltype = AA  length = 13
FEATURE                 Location/Qualifiers
source                  1..13
                        mol_type = protein
                        organism = synthetic construct
SEQUENCE: 855
TDYVNLIQEL APK                                                   13

SEQ ID NO: 856          moltype = AA  length = 18
FEATURE                 Location/Qualifiers
source                  1..18
                        mol_type = protein
                        organism = synthetic construct
SEQUENCE: 856
DQQIASSRLA ASFAAQQY                                              18

SEQ ID NO: 857          moltype = AA  length = 7
FEATURE                 Location/Qualifiers
source                  1..7
                        mol_type = protein
                        organism = synthetic construct
SEQUENCE: 857
RLAFSAL                                                          7

SEQ ID NO: 858          moltype = AA  length = 10
FEATURE                 Location/Qualifiers
```

```
source                1..10
                      mol_type = protein
                      organism = synthetic construct
MOD_RES               3
                      note = methionine sulfoxide
SEQUENCE: 858
RLMFAYPDDD                                                  10

SEQ ID NO: 859        moltype = AA  length = 4
FEATURE               Location/Qualifiers
source                1..4
                      mol_type = protein
                      organism = synthetic construct
SEQUENCE: 859
LVFA                                                        4

SEQ ID NO: 860        moltype = AA  length = 4
FEATURE               Location/Qualifiers
source                1..4
                      mol_type = protein
                      organism = synthetic construct
SEQUENCE: 860
LIFA                                                        4

SEQ ID NO: 861        moltype = AA  length = 4
FEATURE               Location/Qualifiers
source                1..4
                      mol_type = protein
                      organism = synthetic construct
SEQUENCE: 861
LVAR                                                        4

SEQ ID NO: 862        moltype = AA  length = 4
FEATURE               Location/Qualifiers
source                1..4
                      mol_type = protein
                      organism = synthetic construct
SEQUENCE: 862
LAFA                                                        4

SEQ ID NO: 863        moltype = AA  length = 4
FEATURE               Location/Qualifiers
source                1..4
                      mol_type = protein
                      organism = synthetic construct
SEQUENCE: 863
LQAR                                                        4

SEQ ID NO: 864        moltype = AA  length = 4
FEATURE               Location/Qualifiers
source                1..4
                      mol_type = protein
                      organism = synthetic construct
SEQUENCE: 864
LDAA                                                        4

SEQ ID NO: 865        moltype = AA  length = 4
FEATURE               Location/Qualifiers
source                1..4
                      mol_type = protein
                      organism = synthetic construct
SEQUENCE: 865
LCAR                                                        4

SEQ ID NO: 866        moltype = AA  length = 4
FEATURE               Location/Qualifiers
source                1..4
                      mol_type = protein
                      organism = synthetic construct
SEQUENCE: 866
LGAA                                                        4

SEQ ID NO: 867        moltype = AA  length = 4
FEATURE               Location/Qualifiers
source                1..4
                      mol_type = protein
                      organism = synthetic construct
SEQUENCE: 867
LMFA                                                        4
```

```
SEQ ID NO: 868         moltype = AA  length = 4
FEATURE                Location/Qualifiers
source                 1..4
                       mol_type = protein
                       organism = synthetic construct
SEQUENCE: 868
LSAR                                                                4

SEQ ID NO: 869         moltype = AA  length = 4
FEATURE                Location/Qualifiers
source                 1..4
                       mol_type = protein
                       organism = synthetic construct
SEQUENCE: 869
LEFA                                                                4

SEQ ID NO: 870         moltype = AA  length = 212
FEATURE                Location/Qualifiers
source                 1..212
                       mol_type = protein
                       organism = Homo sapiens
SEQUENCE: 870
MNSFSTSAFG PVAFSLGLLL VLPAAFPAPV PPGEDSKDVA APHRQPLTSS ERIDKQIRYI  60
LDGISALRKE TCNKSNMCES SKEALAENNL NLPKMAEKDG CFQSGFNEET CLVKIITGLL  120
EFEVYLEYLQ NRFESSEEQA RAVQMSTKVL IQFLQKKAKN LDAITTPDPT TNASLLTKLQ  180
AQNQWLQDMT THLILRSFKE FLQSSLRALR QM                                 212

SEQ ID NO: 871         moltype = AA  length = 8
FEATURE                Location/Qualifiers
source                 1..8
                       mol_type = protein
                       organism = synthetic construct
SEQUENCE: 871
DGISALRK                                                            8

SEQ ID NO: 872         moltype = AA  length = 8
FEATURE                Location/Qualifiers
source                 1..8
                       mol_type = protein
                       organism = synthetic construct
SEQUENCE: 872
SNMCESSK                                                            8

SEQ ID NO: 873         moltype = AA  length = 12
FEATURE                Location/Qualifiers
source                 1..12
                       mol_type = protein
                       organism = synthetic construct
SEQUENCE: 873
EALAENNLNL PK                                                       12

SEQ ID NO: 874         moltype = AA  length = 16
FEATURE                Location/Qualifiers
source                 1..16
                       mol_type = protein
                       organism = synthetic construct
SEQUENCE: 874
DGCFQSGFNE ETCLVK                                                   16

SEQ ID NO: 875         moltype = AA  length = 34
FEATURE                Location/Qualifiers
source                 1..34
                       mol_type = protein
                       organism = synthetic construct
SEQUENCE: 875
IITGLLEFEV YLEYLQNRFE SSEEQARAVQ MSTK                               34

SEQ ID NO: 876         moltype = AA  length = 8
FEATURE                Location/Qualifiers
source                 1..8
                       mol_type = protein
                       organism = synthetic construct
SEQUENCE: 876
VLIQFLQK                                                            8

SEQ ID NO: 877         moltype = AA  length = 11
FEATURE                Location/Qualifiers
source                 1..11
```

```
                        mol_type = protein
                        organism = synthetic construct
SEQUENCE: 877
DPTTNASLLT K                                              11

SEQ ID NO: 878          moltype = AA  length = 12
FEATURE                 Location/Qualifiers
source                  1..12
                        mol_type = protein
                        organism = synthetic construct
SEQUENCE: 878
DMTTHLILRS FK                                             12

SEQ ID NO: 879          moltype = AA  length = 12
FEATURE                 Location/Qualifiers
source                  1..12
                        mol_type = protein
                        organism = synthetic construct
SEQUENCE: 879
ACLILRSIEE LK                                             12

SEQ ID NO: 880          moltype = AA  length = 11
FEATURE                 Location/Qualifiers
source                  1..11
                        mol_type = protein
                        organism = synthetic construct
SEQUENCE: 880
DSRNTLILRC K                                              11

SEQ ID NO: 881          moltype = AA  length = 31
FEATURE                 Location/Qualifiers
source                  1..31
                        mol_type = protein
                        organism = synthetic construct
SEQUENCE: 881
DSSHQISALV LRAQASEILL EELQQGLSQA K                        31

SEQ ID NO: 882          moltype = AA  length = 17
FEATURE                 Location/Qualifiers
source                  1..17
                        mol_type = protein
                        organism = synthetic construct
SEQUENCE: 882
ARTVGIEELI LRIQESK                                        17

SEQ ID NO: 883          moltype = AA  length = 12
FEATURE                 Location/Qualifiers
source                  1..12
                        mol_type = protein
                        organism = synthetic construct
SEQUENCE: 883
DTLVLRCHRR RK                                             12

SEQ ID NO: 884          moltype = AA  length = 12
FEATURE                 Location/Qualifiers
source                  1..12
                        mol_type = protein
                        organism = synthetic construct
SEQUENCE: 884
DSPQEPLVLR LK                                             12

SEQ ID NO: 885          moltype = AA  length = 8
FEATURE                 Location/Qualifiers
source                  1..8
                        mol_type = protein
                        organism = synthetic construct
SEQUENCE: 885
DLVLRATK                                                  8

SEQ ID NO: 886          moltype = AA  length = 318
FEATURE                 Location/Qualifiers
source                  1..318
                        mol_type = protein
                        organism = synthetic construct
SEQUENCE: 886
MRNIIKLALG LLSVSTFAVA AESSPEALRI GYQKGSIGMV LAKSHQLLEK YPESKISWVE  60
FPAGPAQMLE ALNVGSIDLG STGDIPPIFA WAAGADLVYV GVEPPKPKAE VILVAENSPI  120
KTVADLKGHK VAFQKGSSSH NLLLRALRQA GLKFTDIQPT YLTPADARAA FQQGNVDAWA  180
IWDPYYSAAL LQGGVRVLKD GTDLNQTGSF YLAARPYAEK NGAFIQGVLA TFSEADALTR  240
```

```
SQREQSIALL AKTMGLPAPV IASYLDHRPP TTIKPVNAEV AALQQQTADL FYENRLVPKK  300
VDIRQRIWQP TQLEGKQL                                                318

SEQ ID NO: 887         moltype = AA  length = 29
FEATURE                Location/Qualifiers
source                 1..29
                       mol_type = protein
                       organism = synthetic construct
SEQUENCE: 887
LALAGLLSVS TFAVAAESSP EALRIGYQK                                    29

SEQ ID NO: 888         moltype = AA  length = 18
FEATURE                Location/Qualifiers
source                 1..18
                       mol_type = protein
                       organism = synthetic construct
SEQUENCE: 888
GSSSHNLLLR ALRQAGLK                                                18

SEQ ID NO: 889         moltype = AA  length = 17
FEATURE                Location/Qualifiers
source                 1..17
                       mol_type = protein
                       organism = synthetic construct
SEQUENCE: 889
DPYYSAALLQ GGVRVLK                                                 17

SEQ ID NO: 890         moltype = AA  length = 18
FEATURE                Location/Qualifiers
source                 1..18
                       mol_type = protein
                       organism = synthetic construct
SEQUENCE: 890
DLNQTGSFYL AARPYAEK                                                18

SEQ ID NO: 891         moltype = AA  length = 11
FEATURE                Location/Qualifiers
source                 1..11
                       mol_type = protein
                       organism = synthetic construct
SEQUENCE: 891
DLFYENRLVP K                                                       11

SEQ ID NO: 892         moltype = AA  length = 15
FEATURE                Location/Qualifiers
source                 1..15
                       mol_type = protein
                       organism = synthetic construct
SEQUENCE: 892
DIRQRIWQPT QLEGK                                                   15

SEQ ID NO: 893         moltype = AA  length = 318
FEATURE                Location/Qualifiers
source                 1..318
                       mol_type = protein
                       organism = Escherichia coli
SEQUENCE: 893
MRNIIKLALG LLSVSTFAVA AESSPEALRI GYQKGSIGMV LAKSHQLLEK YPESKISWVE  60
FPAGPAQMLE ALNVGSIDLG STGDIPPIFA WAAGADLVYV GVEPPKPKAE VILVAENSPI  120
KTVADLKGHK VAFQKGSSSH NLLLRALRQA GLKFTDIQPT YLTPADARAA FQQGNVDAWA  180
IWDPYYSAAL LQGGVRVLKD GTDLNQTGSF YLAARPYAEK NGAFIQGVLA TFSEADALTR  240
SQREQSIALL AKTMGLPAPV IASYLDHRPP TTIKPVNAEV AALQQQTADL FYENRLVPKK  300
VDIRQRIWQP TQLEGKQL                                                318

SEQ ID NO: 894         moltype = AA  length = 8
FEATURE                Location/Qualifiers
source                 1..8
                       mol_type = protein
                       organism = synthetic construct
MOD_RES                2
                       note = asymmetric dimethylarginine
SEQUENCE: 894
YRELRKKL                                                           8

SEQ ID NO: 895         moltype = AA  length = 8
FEATURE                Location/Qualifiers
source                 1..8
                       mol_type = protein
                       organism = synthetic construct
```

```
MOD_RES                 2
                        note = symmetric dimethylarginine
SEQUENCE: 895
YRELRLLK                                                                    8

SEQ ID NO: 896          moltype = AA  length = 26
FEATURE                 Location/Qualifiers
source                  1..26
                        mol_type = protein
                        organism = synthetic construct
SEQUENCE: 896
HLLPEHIRRN FTSAGDHIII DGLHAE                                                26

SEQ ID NO: 897          moltype = AA  length = 19
FEATURE                 Location/Qualifiers
source                  1..19
                        mol_type = protein
                        organism = synthetic construct
SEQUENCE: 897
VHQRIHTGER PYVCSECGK                                                        19

SEQ ID NO: 898          moltype = AA  length = 14
FEATURE                 Location/Qualifiers
source                  1..14
                        mol_type = protein
                        organism = synthetic construct
SEQUENCE: 898
TSVTPHQRLH FVDK                                                             14

SEQ ID NO: 899          moltype = AA  length = 9
FEATURE                 Location/Qualifiers
source                  1..9
                        mol_type = protein
                        organism = synthetic construct
SEQUENCE: 899
PNRLSFITK                                                                   9

SEQ ID NO: 900          moltype = AA  length = 12
FEATURE                 Location/Qualifiers
source                  1..12
                        mol_type = protein
                        organism = synthetic construct
SEQUENCE: 900
TVIEIEFSTE VK                                                               12

SEQ ID NO: 901          moltype = AA  length = 39
FEATURE                 Location/Qualifiers
source                  1..39
                        mol_type = protein
                        organism = synthetic construct
SEQUENCE: 901
SSCLVTYQGG EEMALPDDDD EEEEEEEEVE LEEEEEEVI                                  39

SEQ ID NO: 902          moltype = AA  length = 13
FEATURE                 Location/Qualifiers
source                  1..13
                        mol_type = protein
                        organism = synthetic construct
SEQUENCE: 902
SPLIIFNDCE LDK                                                              13

SEQ ID NO: 903          moltype = AA  length = 27
FEATURE                 Location/Qualifiers
source                  1..27
                        mol_type = protein
                        organism = synthetic construct
SEQUENCE: 903
TTPCEIPPPF PNLLQHRPPL LAFPQAK                                               27

SEQ ID NO: 904          moltype = AA  length = 19
FEATURE                 Location/Qualifiers
source                  1..19
                        mol_type = protein
                        organism = synthetic construct
SEQUENCE: 904
TFRHSSNLIQ HVRSHTGEK                                                        19

SEQ ID NO: 905          moltype = AA  length = 16
FEATURE                 Location/Qualifiers
```

```
source                1..16
                      mol_type = protein
                      organism = synthetic construct
SEQUENCE: 905
HEVSVPYAMN LLNGIK                                             16

SEQ ID NO: 906        moltype = AA  length = 15
FEATURE               Location/Qualifiers
source                1..15
                      mol_type = protein
                      organism = synthetic construct
SEQUENCE: 906
MMPFCHNIIN ISCVK                                              15

SEQ ID NO: 907        moltype = AA  length = 34
FEATURE               Location/Qualifiers
source                1..34
                      mol_type = protein
                      organism = synthetic construct
SEQUENCE: 907
VDSTLIGSSS HVEWEDAVHI IPENESDDEE EEEK                         34

SEQ ID NO: 908        moltype = AA  length = 162
FEATURE               Location/Qualifiers
source                1..162
                      mol_type = protein
                      organism = synthetic construct
SEQUENCE: 908
QEAGGRPGAD CEVCHEFLNR FYKSLIDRGV NFSLDTIEKE LISFCLDTKG KENRLCYYLG  60
ATKDAATKIL SEVTRPMSVV HMPAMKICEK LKKLDSQICE LKYEKTLDLA SVDLRKMRVA  120
ELKQILHSWG EECRACAEKT DYVNLIQWLA PKYAATHPKT EL                162

SEQ ID NO: 909        moltype = AA  length = 16
FEATURE               Location/Qualifiers
source                1..16
                      mol_type = protein
                      organism = synthetic construct
SEQUENCE: 909
RNRVSFLGVT TVEPPK                                             16

SEQ ID NO: 910        moltype = AA  length = 12
FEATURE               Location/Qualifiers
source                1..12
                      mol_type = protein
                      organism = synthetic construct
MOD_RES               2
                      note = asymmetric dimethylarginine
SEQUENCE: 910
LRLAFAYPDD DK                                                 12

SEQ ID NO: 911        moltype = AA  length = 12
FEATURE               Location/Qualifiers
source                1..12
                      mol_type = protein
                      organism = synthetic construct
SEQUENCE: 911
LRIAFAYPDD DK                                                 12

SEQ ID NO: 912        moltype = AA  length = 12
FEATURE               Location/Qualifiers
source                1..12
                      mol_type = protein
                      organism = synthetic construct
MOD_RES               2
                      note = asymmetric dimethylarginine
SEQUENCE: 912
LRIAFAYPDD DK                                                 12

SEQ ID NO: 913        moltype = AA  length = 12
FEATURE               Location/Qualifiers
source                1..12
                      mol_type = protein
                      organism = synthetic construct
SEQUENCE: 913
LRYAFAYPDD DK                                                 12

SEQ ID NO: 914        moltype = AA  length = 12
FEATURE               Location/Qualifiers
source                1..12
```

```
                        mol_type = protein
                        organism = synthetic construct
MOD_RES                 2
                        note = asymmetric dimethylarginine
SEQUENCE: 914
LRYAFAYPDD DK                                                        12

SEQ ID NO: 915          moltype = AA  length = 12
FEATURE                 Location/Qualifiers
source                  1..12
                        mol_type = protein
                        organism = synthetic construct
SEQUENCE: 915
LRSAFAYPDD DK                                                        12

SEQ ID NO: 916          moltype = AA  length = 12
FEATURE                 Location/Qualifiers
source                  1..12
                        mol_type = protein
                        organism = synthetic construct
MOD_RES                 2
                        note = asymmetric dimethylarginine
SEQUENCE: 916
LRSAFAYPDD DK                                                        12

SEQ ID NO: 917          moltype = AA  length = 12
FEATURE                 Location/Qualifiers
source                  1..12
                        mol_type = protein
                        organism = synthetic construct
SEQUENCE: 917
LRAAFAYPDD DK                                                        12

SEQ ID NO: 918          moltype = AA  length = 12
FEATURE                 Location/Qualifiers
source                  1..12
                        mol_type = protein
                        organism = synthetic construct
MOD_RES                 2
                        note = asymmetric dimethylarginine
SEQUENCE: 918
LRAAFAYPDD DK                                                        12

SEQ ID NO: 919          moltype = AA  length = 12
FEATURE                 Location/Qualifiers
source                  1..12
                        mol_type = protein
                        organism = synthetic construct
SEQUENCE: 919
LREAFAYPDD DK                                                        12

SEQ ID NO: 920          moltype = AA  length = 12
FEATURE                 Location/Qualifiers
source                  1..12
                        mol_type = protein
                        organism = synthetic construct
MOD_RES                 2
                        note = asymmetric dimethylarginine
SEQUENCE: 920
LREAFAYPDD DK                                                        12

SEQ ID NO: 921          moltype = AA  length = 12
FEATURE                 Location/Qualifiers
source                  1..12
                        mol_type = protein
                        organism = synthetic construct
SEQUENCE: 921
LRTAFAYPDD DK                                                        12

SEQ ID NO: 922          moltype = AA  length = 12
FEATURE                 Location/Qualifiers
source                  1..12
                        mol_type = protein
                        organism = synthetic construct
SEQUENCE: 922
LRTAFAYPDD DK                                                        12

SEQ ID NO: 923          moltype = AA  length = 12
FEATURE                 Location/Qualifiers
```

-continued

```
source                  1..12
                        mol_type = protein
                        organism = synthetic construct
SEQUENCE: 923
LRQAFAYPDD DK                                                         12

SEQ ID NO: 924          moltype = AA  length = 12
FEATURE                 Location/Qualifiers
source                  1..12
                        mol_type = protein
                        organism = synthetic construct
MOD_RES                 2
                        note = asymmetric dimethylarginine
SEQUENCE: 924
LRQAFAYPDD DK                                                         12

SEQ ID NO: 925          moltype = AA  length = 12
FEATURE                 Location/Qualifiers
source                  1..12
                        mol_type = protein
                        organism = synthetic construct
SEQUENCE: 925
LRVAFAYPDD DK                                                         12

SEQ ID NO: 926          moltype = AA  length = 12
FEATURE                 Location/Qualifiers
source                  1..12
                        mol_type = protein
                        organism = synthetic construct
MOD_RES                 2
                        note = asymmetric dimethylarginine
SEQUENCE: 926
LRVAFAYPDD DK                                                         12
```